(12) United States Patent
Park et al.

(10) Patent No.: US 11,847,755 B2
(45) Date of Patent: Dec. 19, 2023

(54) SYSTEM AND METHOD FOR IMAGE SEGMENTATION, BONE MODEL GENERATION AND MODIFICATION, AND SURGICAL PLANNING

(71) Applicant: Howmedica Osteonics Corporation, Mahwah, NJ (US)

(72) Inventors: Ilwhan Park, Walnut Creek, CA (US); Charlie W. Chi, Milpitas, CA (US); Venkata Surya Sarva, Fremont, CA (US); Irene Min Choi, Emeryville, CA (US); Elena Pavlovskaia, San Francisco, CA (US); Oleg Mishin, Foster City, CA (US); Boris E. Shpungin, Pleasanton, CA (US)

(73) Assignee: HOWMEDICA OSTEONICS CORPORATION, Mahwah, NJ (US)

( * ) Notice: Subject to any disclaimer, the term of this patent is extended or adjusted under 35 U.S.C. 154(b) by 16 days.

(21) Appl. No.: 17/326,069

(22) Filed: May 20, 2021

(65) Prior Publication Data
US 2021/0275227 A1 Sep. 9, 2021

Related U.S. Application Data

(60) Continuation of application No. 16/865,998, filed on May 4, 2020, now Pat. No. 11,045,227, which is a
(Continued)

(51) Int. Cl.
G06T 19/20 (2011.01)
A61B 17/70 (2006.01)
(Continued)

(52) U.S. Cl.
CPC .............. *G06T 19/20* (2013.01); *A61B 5/055* (2013.01); *A61B 6/032* (2013.01); *A61B 17/1675* (2013.01); *A61B 17/1703* (2013.01); *A61B 17/7013* (2013.01); *A61B 34/10* (2016.02); *A61B 90/37* (2016.02); *B33Y 10/00* (2014.12); *B33Y 50/00* (2014.12); *B33Y 50/02* (2014.12); *B33Y 80/00* (2014.12); *G06F 30/00* (2020.01); *G06F 30/20* (2020.01); *G06T 7/0012* (2013.01);
(Continued)

(58) Field of Classification Search
None
See application file for complete search history.

(56) References Cited

U.S. PATENT DOCUMENTS

| 8,160,345 | B2 * | 4/2012 | Pavlovskaia | G06T 7/12 |
| | | | | 382/131 |
| 10,575,875 | B2 | 3/2020 | Pavlovskaia et al. | |
| 10,687,856 | B2 * | 6/2020 | Park | G16H 30/20 |

* cited by examiner

*Primary Examiner* — Rodney E Fuller
(74) *Attorney, Agent, or Firm* — Polsinelli PC

(57) ABSTRACT

A computer-implemented method of preoperatively planning a surgical procedure on a knee of a patient including determining femoral condyle vectors and tibial plateau vectors based on image data of the knee, the femoral condyle vectors and the tibial plateau vectors corresponding to motion vectors of the femoral condyles and the tibial plateau as they move relative to each other. The method may also include modifying a bone model representative of at least one of the femur and the tibia into a modified bone model based on the femoral condyle vectors and the tibial plateau vectors. And the method may further include determining coordinate locations for a resection of the modified bone model.

28 Claims, 184 Drawing Sheets

Related U.S. Application Data continuation of application No. 16/376,362, filed on Apr. 5, 2019, now Pat. No. 10,687,856, which is a continuation-in-part of application No. 16/229,997, filed on Dec. 21, 2018, now Pat. No. 10,675,063, and a continuation-in-part of application No. 16/211,735, filed on Dec. 6, 2018, now Pat. No. 11,033,334, said application No. 16/229,997 is a continuation of application No. 15/581,974, filed on Apr. 28, 2017, now Pat. No. 10,159,513, said application No. 16/376,362 is a continuation-in-part of application No. 15/477,952, filed on Apr. 3, 2017, now Pat. No. 10,251,707, said application No. 16/211,735 is a continuation of application No. 15/167,710, filed on May 27, 2016, now Pat. No. 10,182,870, said application No. 15/581,974 is a continuation of application No. 14/946,106, filed on Nov. 19, 2015, now Pat. No. 9,687,259, said application No. 15/167,710 is a continuation-in-part of application No. 14/084,255, filed on Nov. 19, 2013, now Pat. No. 9,782,226, said application No. 15/477,952 is a continuation of application No. 13/923,093, filed on Jun. 20, 2013, now Pat. No. 9,646,113, said application No. 14/946,106 is a continuation of application No. 13/731,697, filed on Dec. 31, 2012, now Pat. No. 9,208,263, which is a continuation of application No. 13/374,960, filed on Jan. 25, 2012, now Pat. No. 8,532,361, which is a continuation of application No. 13/066,568, filed on Apr. 18, 2011, now Pat. No. 8,160,345, said application No. 14/084,255 is a continuation of application No. 13/086,275, filed on Apr. 13, 2011, now Pat. No. 8,617,171, which is a continuation-in-part of application No. 12/760,388, filed on Apr. 14, 2010, now Pat. No. 8,737,700, which is a continuation-in-part of application No. 12/563,809, filed on Sep. 21, 2009, now Pat. No. 8,545,509, and a continuation-in-part of application No. 12/546,545, filed on Aug. 24, 2009, now Pat. No. 8,715,291, and a continuation-in-part of application No. 12/505,056, filed on Jul. 17, 2009, now Pat. No. 8,777,875, said application No. 12/563,809 is a continuation-in-part of application No. 12/505,056, filed on Jul. 17, 2009, now Pat. No. 8,777,875, said application No. 13/066,568 is a continuation-in-part of application No. 12/386,105, filed on Apr. 14, 2009, now Pat. No. 8,311,306, said application No. 12/563,809 is a continuation-in-part of application No. 12/111,924, filed on Apr. 29, 2008, now Pat. No. 8,480,679, said application No. 13/923,093 is a division of application No. 12/111,924, filed on Apr. 29, 2008, now Pat. No. 8,480,679, said application No. 12/760,388 is a continuation-in-part of application No. 12/111,924, filed on Apr. 29, 2008, now Pat. No. 8,480,679, and a continuation-in-part of application No. 11/959,344, filed on Dec. 18, 2007, now Pat. No. 8,221,430, said application No. 12/546,545 is a continuation-in-part of application No. 11/959,344, filed on Dec. 18, 2007, now Pat. No. 8,221,430, said application No. 12/563,809 is a continuation-in-part of application No. 11/959,344, filed on Dec. 18, 2007, now Pat. No. 8,221,430.

(60) Provisional application No. 61/102,692, filed on Oct. 3, 2008, provisional application No. 61/083,053, filed on Jul. 23, 2008, provisional application No. 61/126,102, filed on Apr. 30, 2008.

(51) Int. Cl.

| | |
|---|---|
| *B33Y 80/00* | (2015.01) |
| *G06T 17/00* | (2006.01) |
| *A61B 34/10* | (2016.01) |
| *A61B 17/16* | (2006.01) |
| *A61B 6/03* | (2006.01) |
| *G06T 17/20* | (2006.01) |
| *A61B 5/055* | (2006.01) |
| *G06T 7/12* | (2017.01) |
| *G06T 7/13* | (2017.01) |
| *A61B 90/00* | (2016.01) |
| *A61B 17/17* | (2006.01) |
| *B33Y 50/02* | (2015.01) |
| *G16H 50/50* | (2018.01) |
| *B33Y 10/00* | (2015.01) |
| *G06T 7/00* | (2017.01) |
| *B33Y 50/00* | (2015.01) |
| *G06F 30/00* | (2020.01) |
| *G06F 30/20* | (2020.01) |
| *G06V 10/46* | (2022.01) |
| *G06V 10/22* | (2022.01) |
| *G06T 7/70* | (2017.01) |
| *A61B 17/15* | (2006.01) |

(52) U.S. Cl.
CPC .................. *G06T 7/12* (2017.01); *G06T 7/13* (2017.01); *G06T 17/00* (2013.01); *G06T 17/20* (2013.01); *G06V 10/225* (2022.01); *G06V 10/46* (2022.01); *G16H 50/50* (2018.01); *A61B 17/155* (2013.01); *A61B 17/157* (2013.01); *A61B 2017/1602* (2013.01); *A61B 2034/105* (2016.02); *A61B 2034/107* (2016.02); *A61B 2034/108* (2016.02); *A61B 2090/374* (2016.02); *A61B 2090/3762* (2016.02); *G06T 7/70* (2017.01); *G06T 2200/08* (2013.01); *G06T 2207/30008* (2013.01); *G06T 2210/41* (2013.01); *G06T 2219/2021* (2013.01); *G06V 10/471* (2022.01); *G06V 2201/033* (2022.01); *Y10T 29/49826* (2015.01)

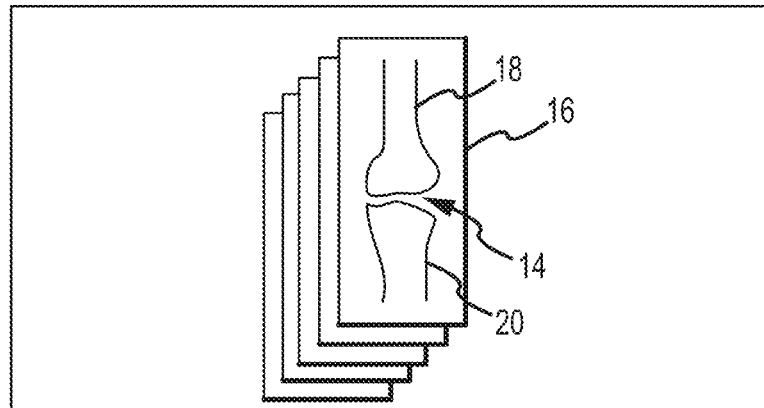
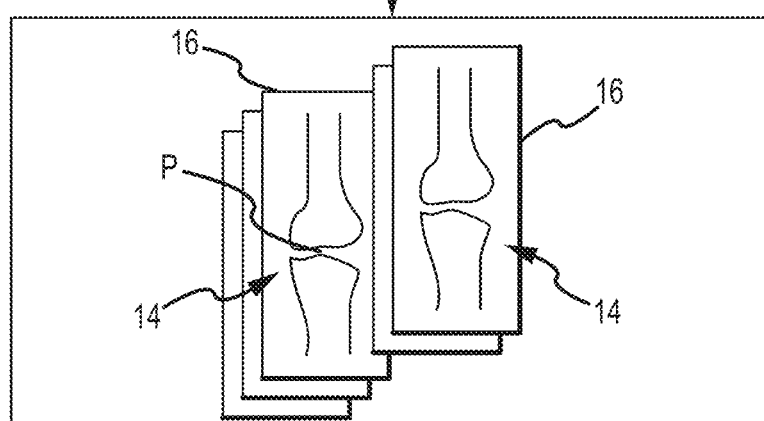
FIG.1B

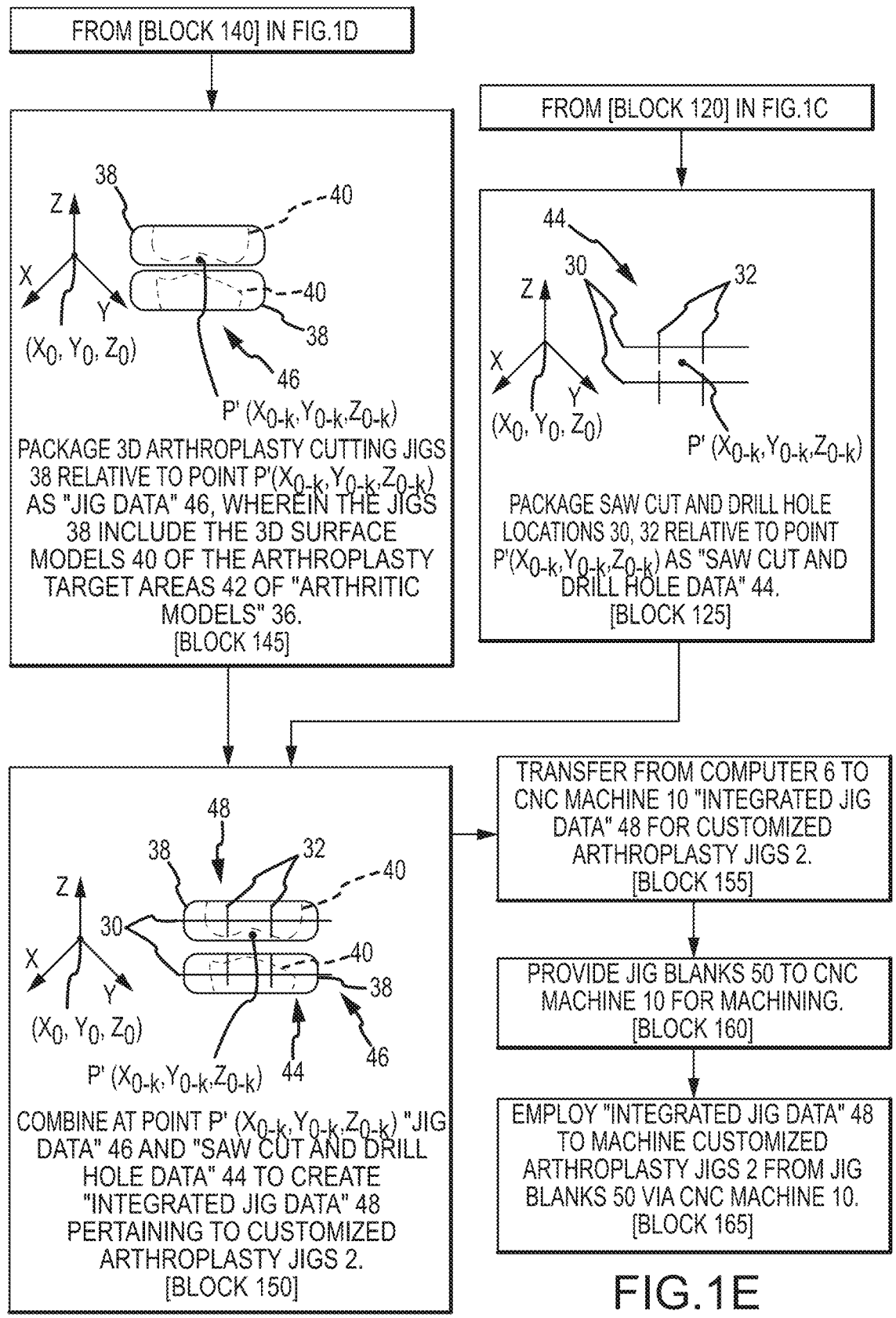

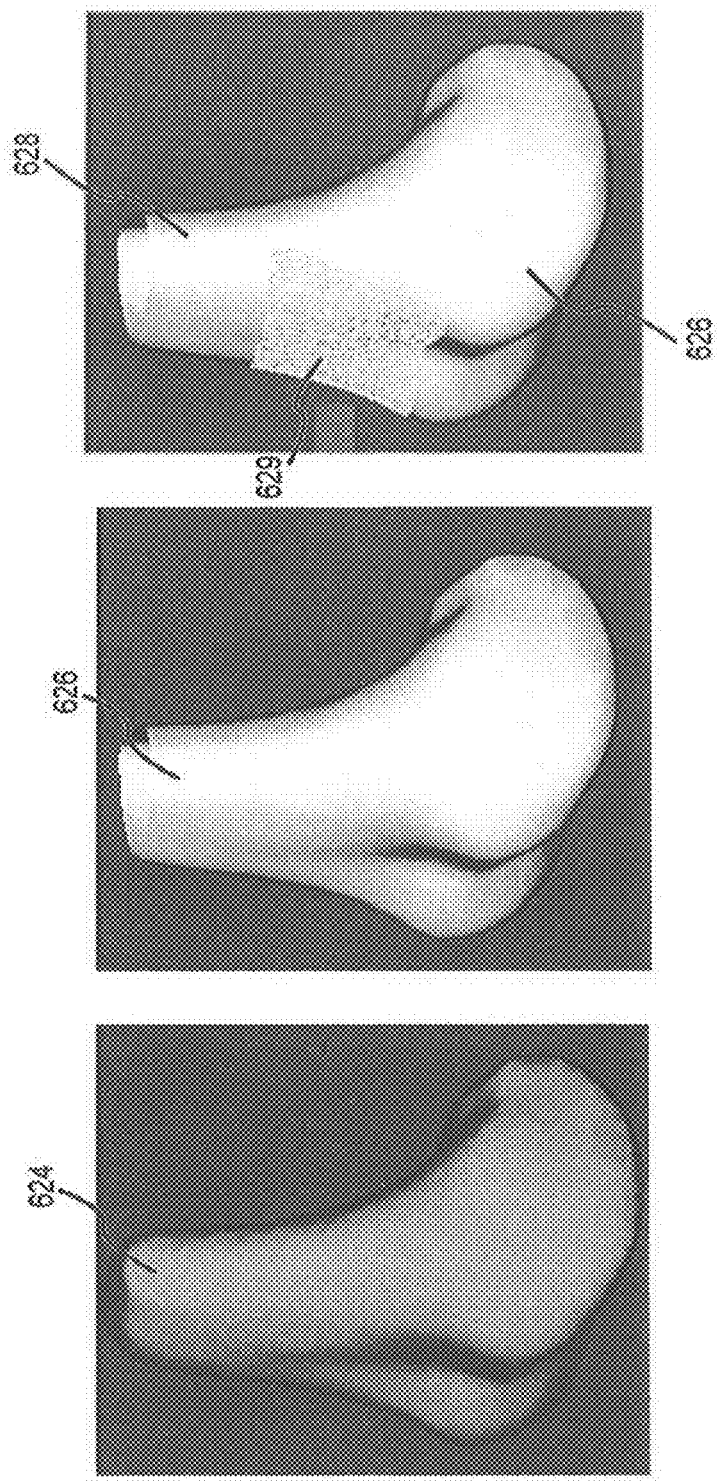

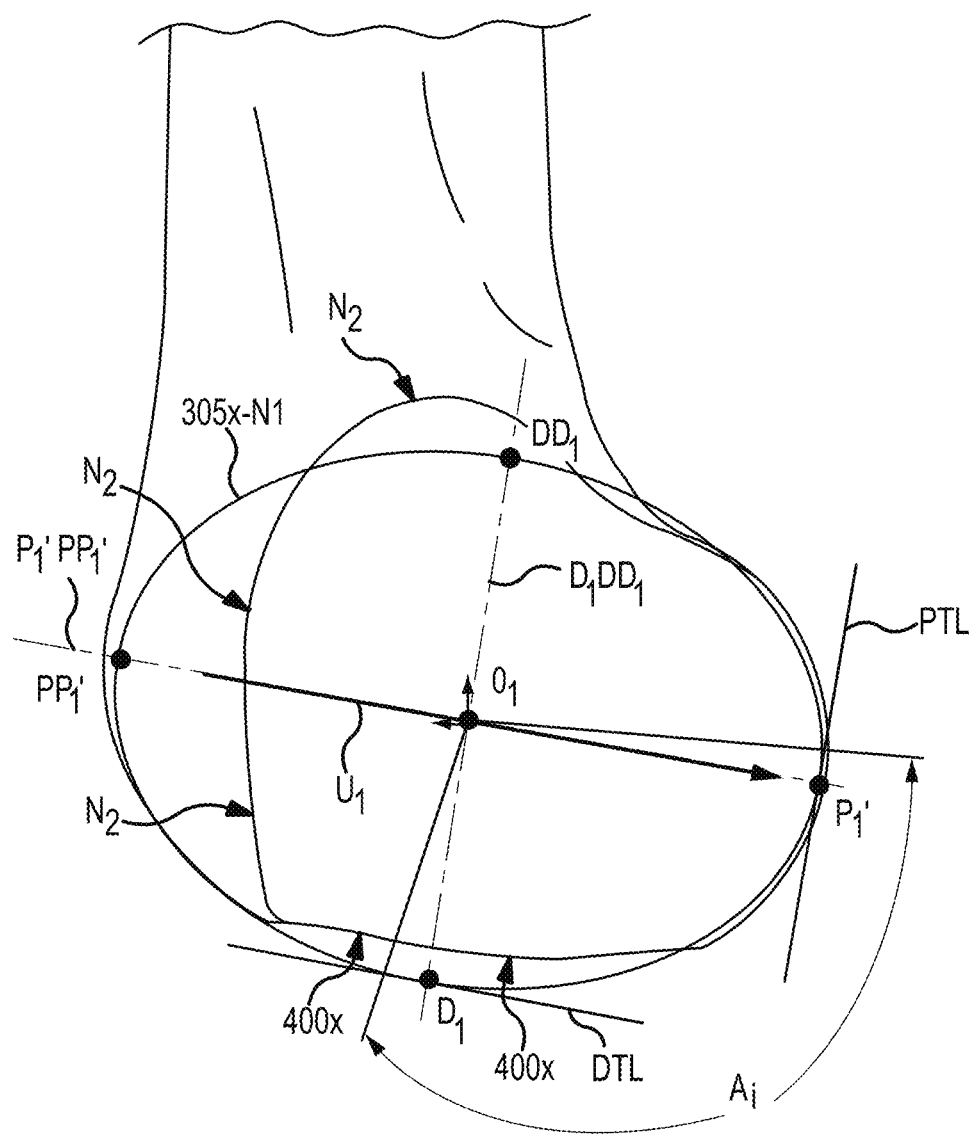
FIG.44C1

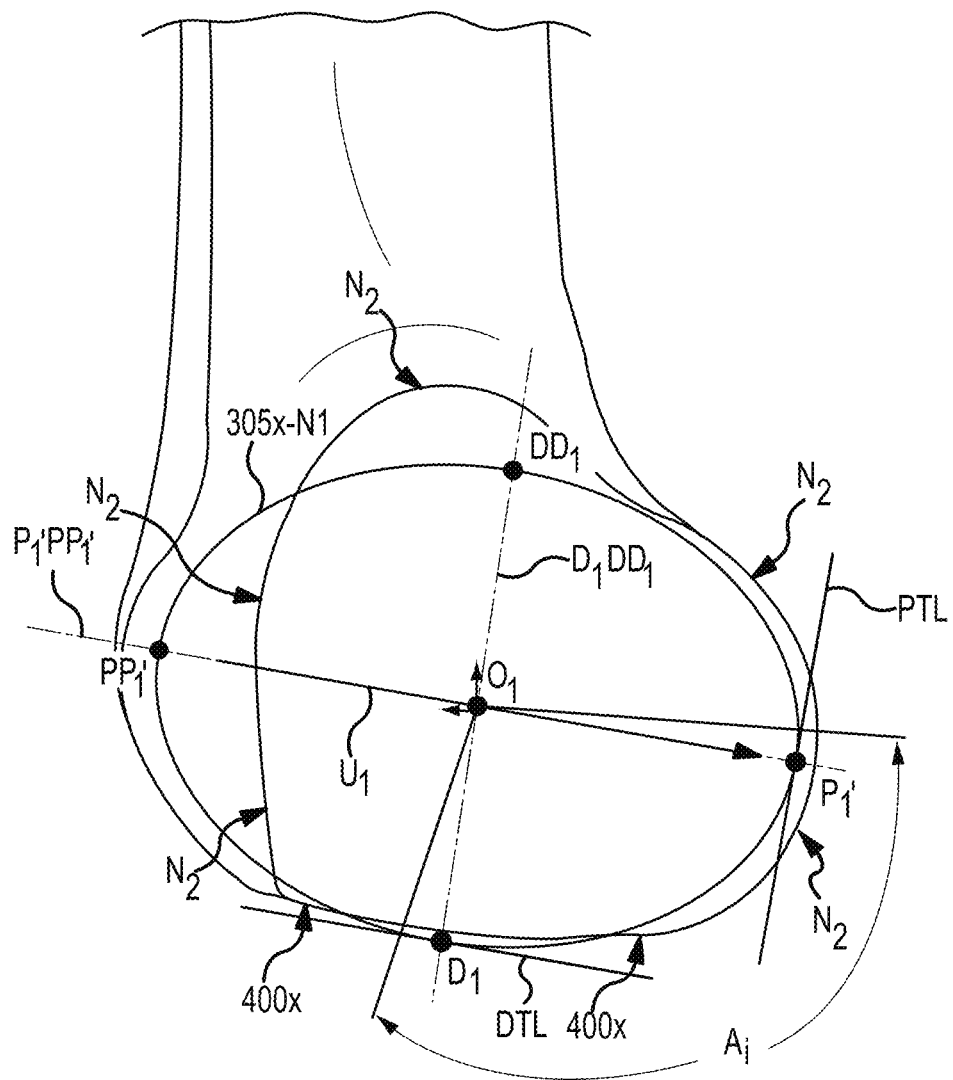
FIG.44C2

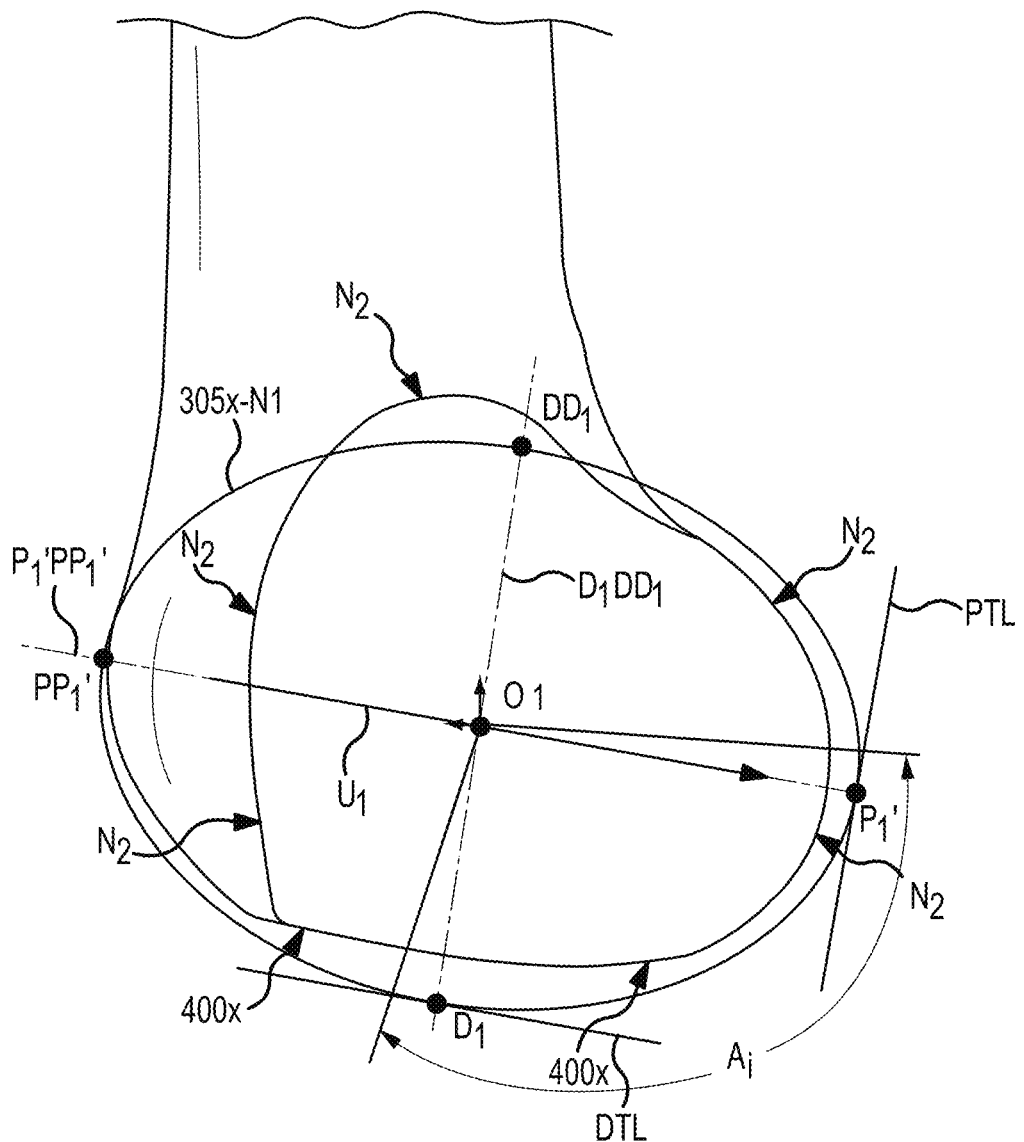
FIG.44C3

OSTEO ARTHRITIS KNEE BONE DAMAGE CRITERIA

| MEDIAL KNEE | | | LATERAL KNEE | | | RESTORATION (YES/NO) |
|---|---|---|---|---|---|---|
| SEVERE | MEDIUM | LIGHT | SEVERE | MEDIUM | LIGHT | |
|  |  | X |  |  | X | YES |
|  | X | X |  | X |  | YES |
|  | X | X | X |  |  | YES |
|  | X |  |  |  | X | YES |
|  |  |  |  | X |  | YES |
|  |  |  | X |  |  | NO |
| X |  |  |  |  | X | YES |
| X |  |  |  | X |  | NO |
| X |  |  | X |  |  | NO |

LIGHT: NO BONE DAMAGE OR BONE DAMAGE << 1mm
MEDIUM: BONE DAMAGE ≈1mm
SEVERE: BONE DAMAGE >>1mm

FIG.46

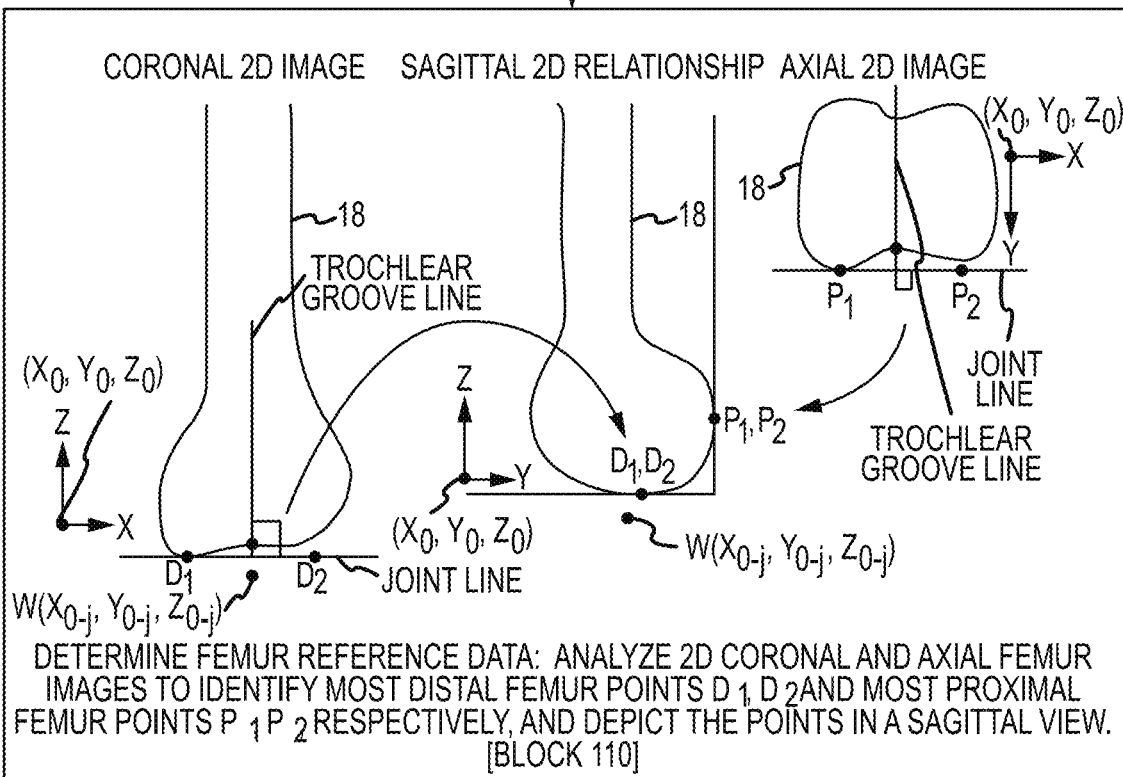
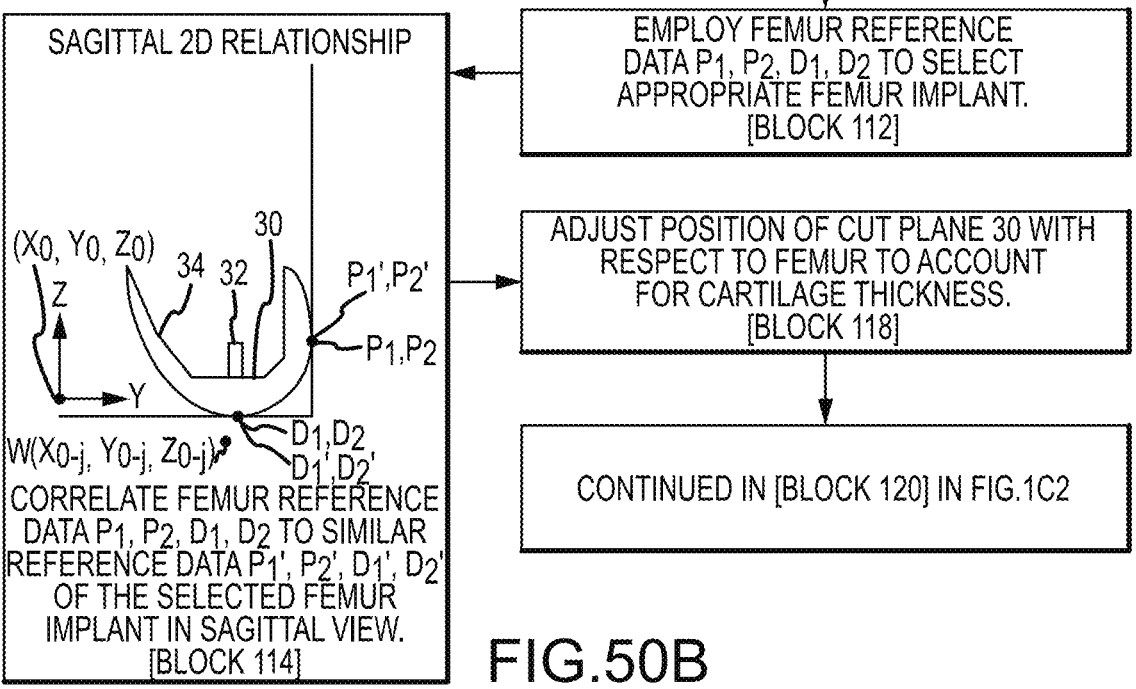
FIG.50B

FROM [BLOCK 118] IN FIG. 1C1

REPEAT PROCESS OF BLOCK 110 FOR TIBIA IN SIMILAR MANNER, EXCEPT SAGITTAL AND CORONAL IMAGE SLICES OF TIBIA ARE ANALYZED TO IDENTIFY THE LOWEST AND MOST ANTERIOR AND POSTERIOR POINTS OF THE TIBIA RECESSED CONDYLAR SURFACES, THIS TIBIA REFERENCE DATA THEN BEING PROJECTED ON TO AN AXIAL VIEW.
[BLOCK 120]

EMPLOY TIBIA REFERENCE DATA TO SELECT APPROPRIATE TIBIA IMPLANT.
[BLOCK 121]

REPEAT PROCESS OF BLOCK 114 FOR TIBIA IN SIMILAR MANNER, EXCEPT IN AN AXIAL VIEW CORRELATE TIBIA REFERENCE DATA TO SIMILAR REFERENCE DATA OF THE SELECTED TIBIA IMPLANT.
[BLOCK 122]

ADJUST POSITION OF CUT PLANE 30 WITH RESPECT TO TIBIA TO ACCOUNT FOR CARTILAGE THICKNESS.
[BLOCK 123]

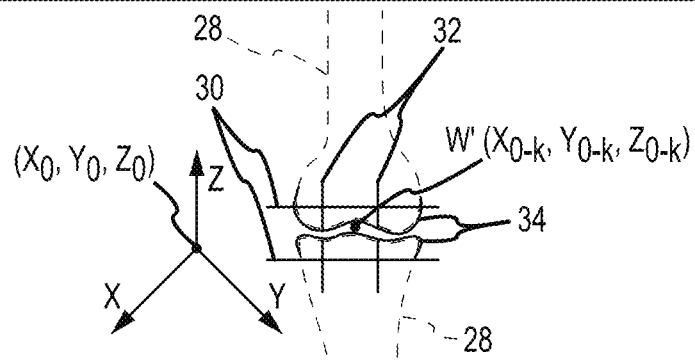

PACKAGE SAW CUT LOCATION 30 AND DRILL HOLE LOCATIONS 32 ASSOCIATED WITH PRE-OPERATIVE PLANNING ("POP") OF FEMUR AND TIBIA IMPLANTS 34 RELATIVE TO THE FEMUR AND TIBIA DATA 28 AND THE UPDATED POINT $W'(X_{0-k}, Y_{0-k}, Z_{0-k})$, WHICH MAY BE DIFFERENT FROM ORIGINAL POINT $W(X_{0-j}, Y_{0-j}, Z_{0-j})$ DUE TO ADJUSTMENTS TO DATA POSITIONS DURING ANY ONE OR MORE OF THE PROCESSES OF BLOCKS 110-124.
[BLOCK 124]

CONTINUED IN [BLOCK 125] IN FIG.1E

FIG.50C

```
┌─────────────────────────────────────────────────┐
│   MEASURE THE MINIMUM CARTILAGE THICKNESS FOR   │
│  THE UNDAMAGED AND DAMAGED FEMORAL CONDYLES.    │
│                  [BLOCK 1170]                   │
└─────────────────────────────────────────────────┘
                         │
                         ▼
┌─────────────────────────────────────────────────┐
│ USE THE CARTILAGE THICKNESS MEASURED FOR THE LEAST │
│  DAMAGED CONDYLE CARTILAGE AS THE CARTILAGE     │
│         THICKNESS REFERENCE FOR POP.            │
│                  [BLOCK 1175]                   │
└─────────────────────────────────────────────────┘
```

FIG.63E

SYSTEM AND METHOD FOR IMAGE SEGMENTATION, BONE MODEL GENERATION AND MODIFICATION, AND SURGICAL PLANNING

CROSS REFERENCE TO RELATED APPLICATION

The present application is a continuation of U.S. application Ser. No. 16/865,998 filed May 4, 2020, which application is a continuation of U.S. application Ser. No. 16/376,362 filed Apr. 5, 2019, now U.S. Pat. No. 10,687,856, which application is a continuation-in-part application of U.S. patent application Ser. No. 16/229,997 filed Dec. 21, 2018, now U.S. Pat. No. 10,675,063, which is a continuation application of U.S. application Ser. No. 15/581,974 filed Apr. 28, 2017, now U.S. Pat. No. 10,159,513, which application is a continuation of U.S. application Ser. No. 14/946,106 filed Nov. 19, 2015, now U.S. Pat. No. 9,687,259, which application is a continuation of U.S. application Ser. No. 13/731,697 filed Dec. 31, 2012, now U.S. Pat. No. 9,208,263, which application is a continuation of U.S. application Ser. No. 13/374,960 filed Jan. 25, 2012, now U.S. Pat. No. 8,532,361, which application is a continuation of U.S. patent application Ser. No. 13/066,568, filed Apr. 18, 2011, now U.S. Pat. No. 8,160,345, which application is a continuation-in-part application of U.S. patent application Ser. No. 12/386,105 filed Apr. 14, 2009, now U.S. Pat. No. 8,311,306. U.S. application Ser. No. 12/386,105 claims the benefit under 35 U.S.C. § 119(e) of U.S. Provisional Patent Application No. 61/126,102, entitled "System and Method For Image Segmentation in Generating Computer Models of a Joint to Undergo Arthroplasty" filed on Apr. 30, 2008.

Application Ser. No. 16/376,362 is also a continuation-in-part of U.S. patent application Ser. No. 15/477,952 filed Apr. 3, 2017, now U.S. Pat. No. 10,251,707, which is a continuation application of U.S. application Ser. No. 13/923,093 filed Jun. 20, 2013, now U.S. Pat. No. 9,646,113, which application is a divisional application of U.S. application Ser. No. 12/111,924 filed Apr. 29, 2008, now U.S. Pat. No. 8,480,679.

Application Ser. No. 16/376,362 is also a continuation-in-part of U.S. patent application Ser. No. 16/211,735, filed Dec. 6, 2018, which is a continuation of U.S. application Ser. No. 15/167,710 filed May 27, 2016, now U.S. Pat. No. 10,182,870, which application is a continuation-in-part of U.S. application Ser. No. 14/084,255 filed Nov. 19, 2013, now U.S. Pat. No. 9,782,226, which application is a continuation of U.S. application Ser. No. 13/086,275 ("the '275 application"), filed Apr. 13, 2011, and titled "Preoperatively Planning an Arthroplasty Procedure and Generating a Corresponding Patient Specific Arthroplasty Resection Guide," now U.S. Pat. No. 8,617,171. The '275 application is a continuation-in-part ("CIP") of U.S. patent application Ser. No. 12/760,388 ("the '388 application"), filed Apr. 14, 2010, now U.S. Pat. No. 8,737,700. The '388 application is a CIP application of U.S. patent application Ser. No. 12/563,809 ("the '809 application), filed Sep. 21, 2009, and titled "Arthroplasty System and Related Methods," now U.S. Pat. No. 8,545,509, which claims priority to U.S. patent application 61/102,692 ("the '692 application"), filed Oct. 3, 2008, and titled "Arthroplasty System and Related Methods." The '388 application is also a CIP application of U.S. patent application Ser. No. 12/546,545 ("the 545 application"), filed Aug. 24, 2009, and titled "Arthroplasty System and Related Methods," now U.S. Pat. No. 8,715,291, which claims priority to the '692 application. The '809 application is also a CIP application of U.S. patent application Ser. No. 12/111,924 ("the '924 application"), filed Apr. 29, 2008, and titled "Generation of a Computerized Bone Model Representative of a Pre-Degenerated State and Useable in the Design and Manufacture of Arthroplasty Devices," now U.S. Pat. No. 8,480,679. The '545 application is also a CIP application of U.S. patent application Ser. No. 11/959,344 ("the '344 application), filed Dec. 18, 2007, and titled "System and Method for Manufacturing Arthroplasty Jigs," now U.S. Pat. No. 8,221,430. The '809 application is a CIP application of U.S. patent application Ser. No. 12/505,056 ("the '056 application"), filed Jul. 17, 2009, and titled "System and Method for Manufacturing Arthroplasty Jigs Having Improved Mating Accuracy," now U.S. Pat. No. 8,777,875. The '056 application claims priority to U.S. patent application 61/083,053, filed Jul. 23, 2008, and titled "System and Method for Manufacturing Arthroplasty Jigs Having Improved Mating Accuracy." The '809 application is also a CIP application of the '344 application. The '388 application is also a CIP of the '344 application. The '388 application is also a CIP of the '924 application. And the '388 application is also a CIP of the '056 application.

The present application claims priority to all of the above mentioned applications and hereby incorporates by reference all of the above-mentioned applications in their entireties into the present application.

FIELD OF THE INVENTION

The present invention relates to image segmentation, morphing bone models to pre-degenerated states, and planning surgeries.

BACKGROUND OF THE INVENTION

Over time and through repeated use, bones and joints can become damaged or worn. For example, repetitive strain on bones and joints (e.g., through athletic activity), traumatic events, and certain diseases (e.g., arthritis) can cause cartilage in joint areas, which normally provides a cushioning effect, to wear down. Cartilage wearing down can result in fluid accumulating in the joint areas, pain, stiffness, and decreased mobility.

Arthroplasty procedures can be used to repair damaged joints. During a typical arthroplasty procedure, an arthritic or otherwise dysfunctional joint can be remodeled or realigned, or an implant can be implanted into the damaged region. Arthroplasty procedures may take place in any of a number of different regions of the body, such as a knee, a hip, a shoulder, or an elbow.

One type of arthroplasty procedure is a total knee arthroplasty ("TKA"), in which a damaged knee joint is replaced with prosthetic implants. The knee joint may have been damaged by, for example, arthritis (e.g., severe osteoarthritis or degenerative arthritis), trauma, or a rare destructive joint disease. During a TKA procedure, a damaged portion in the distal region of the femur may be removed and replaced with a metal shell, and a damaged portion in the proximal region of the tibia may be removed and replaced with a channeled piece of plastic having a metal stem. In some TKA procedures, a plastic button may also be added under the surface of the patella, depending on the condition of the patella.

Implants that are implanted into a damaged region may provide support and structure to the damaged region, and may help to restore the damaged region, thereby enhancing its functionality. Prior to implantation of an implant in a damaged region, the damaged region may be prepared to receive the implant. For example, in a knee arthroplasty procedure, one or more of the bones in the knee area, such as the femur and/or the tibia, may be treated (e.g., cut, drilled, reamed, and/or resurfaced) to provide one or more surfaces that can align with the implant and thereby accommodate the implant.

Accuracy in implant alignment is an important factor to the success of a TKA procedure. A one- to two-millimeter translational misalignment, or a one- to two-degree rotational misalignment, may result in imbalanced ligaments, and may thereby significantly affect the outcome of the TKA procedure. For example, implant misalignment may result in intolerable post-surgery pain, and also may prevent the patient from having full leg extension and stable leg flexion.

To achieve accurate implant alignment, prior to treating (e.g., cutting, drilling, reaming, and/or resurfacing) any regions of a bone, it is important to correctly determine the location at which the treatment will take place and how the treatment will be oriented. In some methods, an arthroplasty jig may be used to accurately position and orient a finishing instrument, such as a cutting, drilling, reaming, or resurfacing instrument on the regions of the bone. The arthroplasty jig may, for example, include one or more apertures and/or slots that are configured to accept such an instrument.

A system and method has been developed for producing customized arthroplasty jigs configured to allow a surgeon to accurately and quickly perform an arthroplasty procedure that restores the pre-deterioration alignment of the joint, thereby improving the success rate of such procedures. Specifically, the customized arthroplasty jigs are indexed such that they matingly receive the regions of the bone to be subjected to a treatment (e.g., cutting, drilling, reaming, and/or resurfacing). The customized arthroplasty jigs are also indexed to provide the proper location and orientation of the treatment relative to the regions of the bone. The indexing aspect of the customized arthroplasty jigs allows the treatment of the bone regions to be done quickly and with a high degree of accuracy that will allow the implants to restore the patient's joint to a generally pre-deteriorated state. However, the system and method for generating the customized jigs often relies on a human to "eyeball" bone models on a computer screen to determine configurations needed for the generation of the customized jigs. This "eyeballing" or manual manipulation of the bone modes on the computer screen is inefficient and unnecessarily raises the time, manpower and costs associated with producing the customized arthroplasty jigs. Furthermore, a less manual approach may improve the accuracy of the resulting jigs.

There is a need in the art for a system and method for reducing the labor associated with generating customized arthroplasty jigs. There is also a need in the art for a system and method for increasing the accuracy of customized arthroplasty jigs.

SUMMARY

Systems and methods for image segmentation in generating computer models of a joint to undergo arthroplasty are disclosed. Some embodiments may include a method of partitioning an image of a bone into a plurality of regions, where the method of partitioning may include obtaining a plurality of volumetric image slices of the bone, generating a plurality of spline curves associated with the bone, verifying that at least one of the plurality of spline curves follow a surface of the bone, and creating a three dimensional (3D) mesh representation based upon the at least one of the plurality of spline curves.

Aspects of the present disclosure may involve a computer-implemented method of preoperatively planning a surgical procedure on a knee of a patient, where the knee joins together a femur having femoral condyles and a tibia having a tibial plateau. The surgical procedure may include implanting an implant on at least one of the femur and the tibia as part of the procedure. The method may include determining femoral condyle vectors and tibial plateau vectors based on image data of the knee. The femoral condyle vectors and the tibial plateau vectors may correspond to motion vectors of the femoral condyles and the tibial plateau as they move relative to each other. The method may further include modifying a bone model representative of at least one of the femur and the tibia into a modified bone model based on the femoral condyle vectors and the tibial plateau vectors. And the method may further include determining coordinate locations for a resection of the modified bone model.

In certain instances, modifying the bone model may include modifying a shape of femoral condyles of the bone model. In certain instances, modifying the bone model may include modifying a shape of a tibial plateau of the bone model. In certain instances, modifying the bone model may include restoring a surface of the bone model to a less degenerated state.

In certain instances, the bone model is a femoral bone model and a tibial bone model.

In certain instances, the modified bone model may include a modification to a surface profile of the bone model.

In certain instances, the modified bone model is a restored bone model with the surface profile being modified from a degenerated state to a less degenerated state.

In certain instances, the image data of the knee may include preoperatively generated medical images.

In certain instances, the image data of the knee may include two dimensional image views of the knee, and the femoral condyle vectors and tibial plateau vectors are determined based on an analysis of geometric features of the femoral condyles and tibial plateau in the two dimensional image views of the knee.

In certain instances, determining coordinate locations for a resection of the modified bone model may include: aligning points on an implant model with corresponding points on the modified bone model, the implant model is positioned and oriented relative to the modified bone model in a coordinate system that is reflective of the implant being implanted on the femur.

In certain instances, the points on the modified bone model may include a first point at a most distal location on a condylar surface of the modified bone model and a second point on a location on the condylar surface of the modified bone model that is proximal to the first point.

In certain instances, the points on the implant model may include a third point at a most distal location on a condylar surface of the implant model and a fourth point on a location on the condylar surface of the implant model that is proximal to the third point.

In certain instances, determining coordinate locations for a resection of the modified bone model may include: aligning a point on an implant model with a corresponding point on the modified bone model, the implant model is positioned and oriented relative to the modified bone model in a coordinate system that is reflective of the implant being implanted on the tibia.

In certain instances, the point on the modified bone model may include a first point at a most distally recessed location on a condylar surface of the modified bone model.

In certain instances, the point on the implant model may include a second point at a most distally recessed location on a condylar surface of the implant model.

In certain instances, determining coordinate locations for a resection of the modified bone model may include automatically identifying a preliminary position and orientation of the resection.

Aspects of the present disclosure may involve a method of planning and performing a surgical procedure on a knee of a patient where the knee joins together a femur having femoral condyles and a tibia having a tibial plateau. The method may include performing a motion analysis of the knee, whereby a 3D bone model representing at least one of the femur and tibia is modified into a modified 3D bone model based on the motion analysis of the knee. And the method may include determining coordinate locations for a resection of the modified bone model.

In certain instances, performing the motion analysis of the knee may include using a computer to determine femoral condyle vectors and tibial plateau vectors corresponding to motion vectors of the femoral condyles and the tibial plateau as they move relative to each other.

In certain instances, the bone model is modified into the modified bone model based on femoral condyle vectors and tibial plateau vectors.

In certain instances, further may include performing the surgical procedure including cutting a physical resection on the patient at the knee at a location that corresponds to the resection of the modified bone model.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIGS. 1B-1E are flow chart diagrams outlining the jig production method disclosed herein.

FIG. 7I is another sagittal plane image slice of a segmented femur and tibia.

FIG. 31A is an isometric view of a closed golden femur mesh.

FIG. 31B is an isometric view of an open golden femur mesh created from the closed golden femur mesh of FIG. 31A.

FIG. 31C is the open femur mesh of FIG. 31B with regions of a different precision indicated.

FIG. 44C1 is an $N_2$ image slice of the medial condyle as taken along the $N_2$ line in FIG. 44A.

FIG. 44C2 is the same view as FIG. 44C1, except illustrating the need to increase the size of the reference information prior to restoring the contour line of the $N_2$ image slice.

FIG. 44C3 is the same view as FIG. 44C1, except illustrating the need to reduce the size of the reference information prior to restoring the contour line of the $N_2$ image slice.

FIG. 46 is a table illustrating how OA knee conditions may impact the likelihood of successful bone restoration.

FIGS. 50A-50E are flow chart diagrams outlining the jig production method disclosed herein.

FIG. 55B is an axial imaging slice taken along section lines of the femur of FIG. 54A, wherein the trochlear groove bisector line is shown.

FIG. 55C is an axial imaging slice taken along section lines of the femur of FIG. 54A, wherein the femur reference data is shown.

FIG. 55D is the axial imaging slices taken along section lines of the femur in FIG. 54A.

FIG. 56A is a coronal slice taken along section lines of the femur of FIG. 54A, wherein the femur reference data is shown FIG. 56B is the coronal imaging slices taken along section lines of the femur in FIG. 54A.

FIG. 56C is a sagittal imaging slice of the femur in FIG. 54A.

FIG. 56D is an axial imaging slice taken along section lines of the femur of FIG. 54A, wherein the femur reference data is shown.

FIG. 56E is a coronal imaging slice taken along section lines of the femur of FIG. 54A, wherein the femur reference data is shown.

FIG. 57 is a posterior view of a 3D model of a distal femur.

FIG. 58 depicts a y-z coordinate system wherein the femur reference data is shown.

FIG. 59 is a perspective view of a femoral implant model, wherein the femur implant reference data is shown.

FIG. 60 is another perspective view of a femoral implant model, wherein the femur implant reference data is shown.

FIG. 61 is a y-z coordinate system wherein some of the femur implant reference data is shown.

Figure 62:
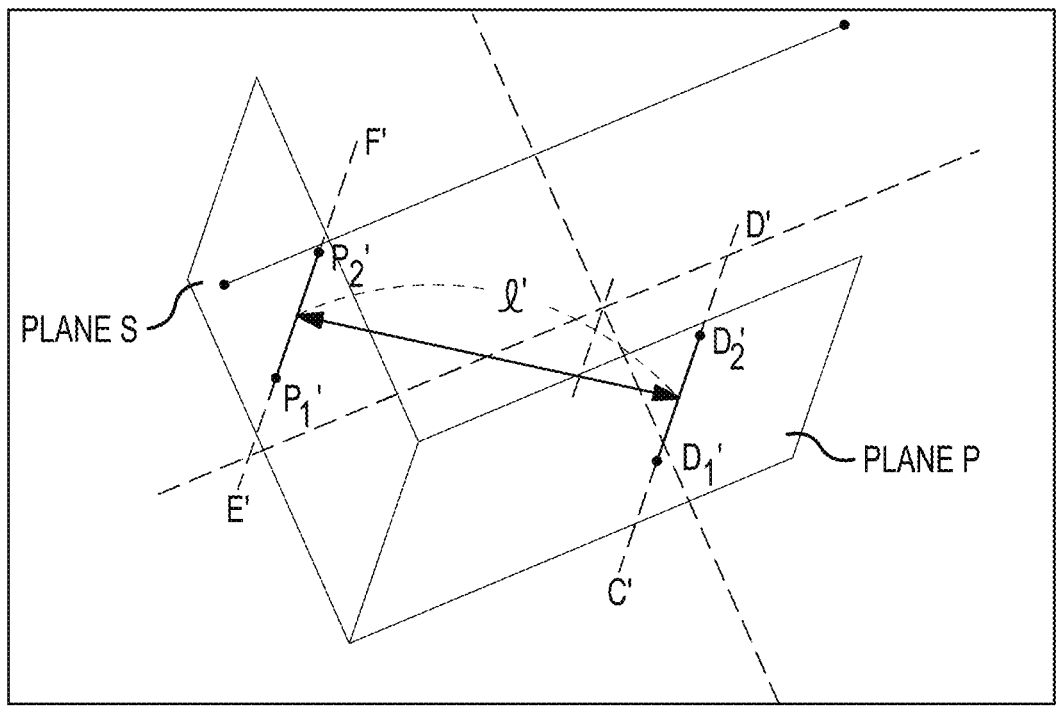

FIG. 62 is an x-y-z coordinate system wherein the femur implant reference data is shown.

Figure 63A:
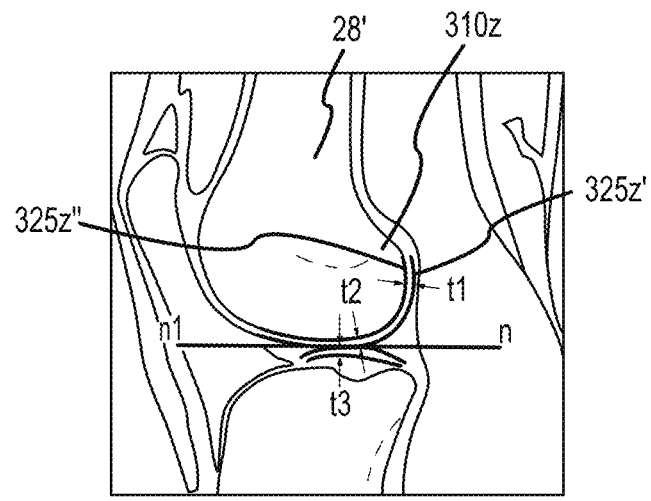

FIG. 63A shows the femoral condyle and the proximal tibia of the knee in a sagittal view MRI image slice.

Figure 63B:
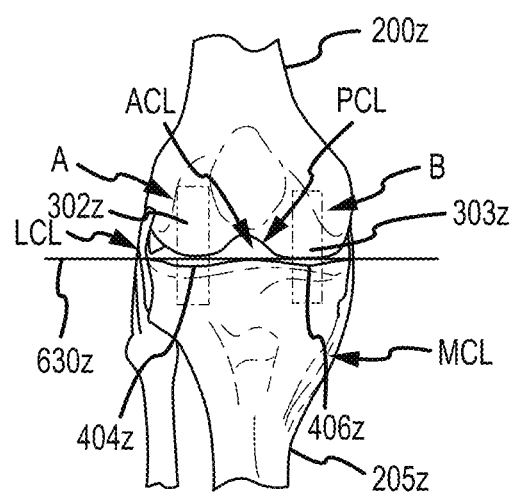

FIG. 63B is a coronal view of a knee model in extension.

Figure 63C:
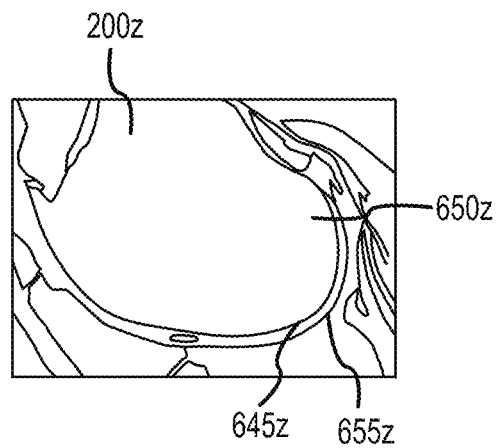
Figure 63D:
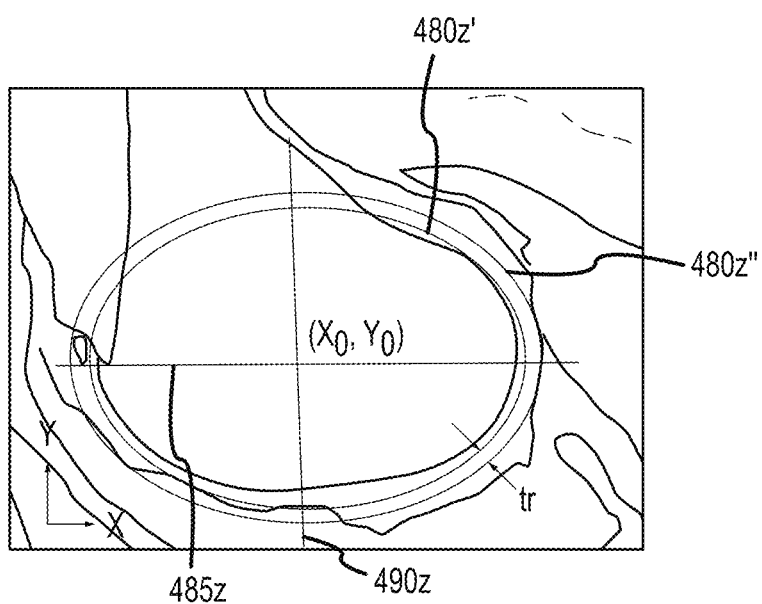

FIGS. 63C and 63D illustrate MRI segmentation slices for joint line assessment.

FIG. 63E is a flow chart illustrating the method for determining cartilage thickness used to determine proper joint line.

Figure 63F:
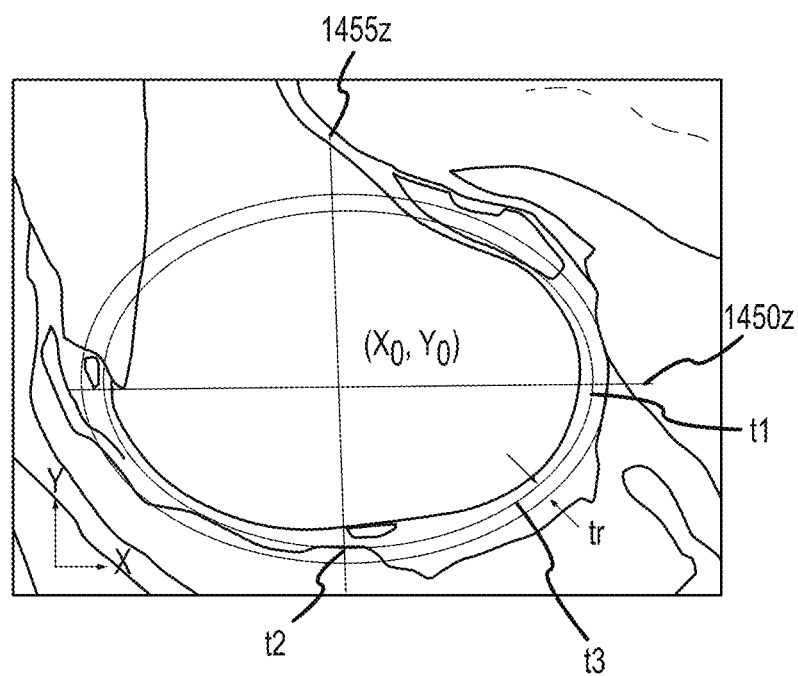

FIG. 63F illustrates a MRI segmentation slice for joint line assessment.

Figure 63G:
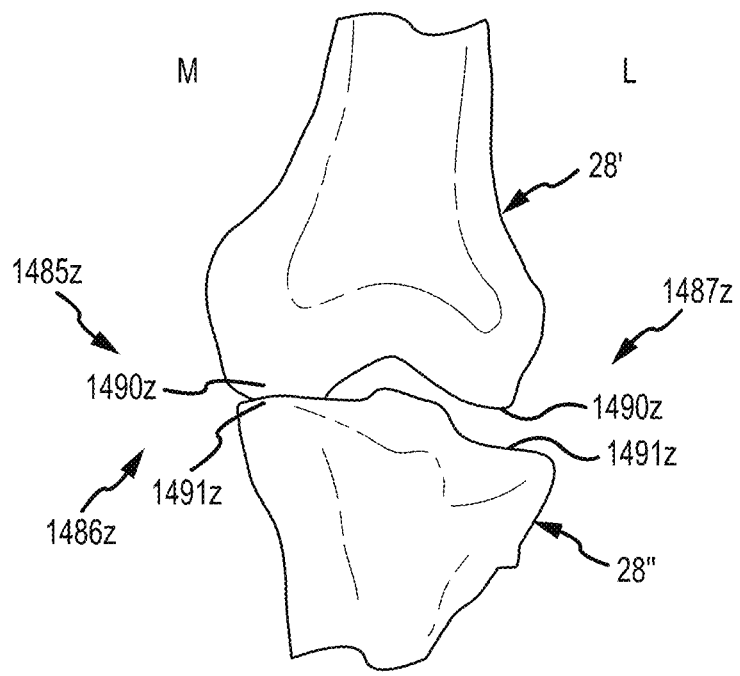
Figure 63H:
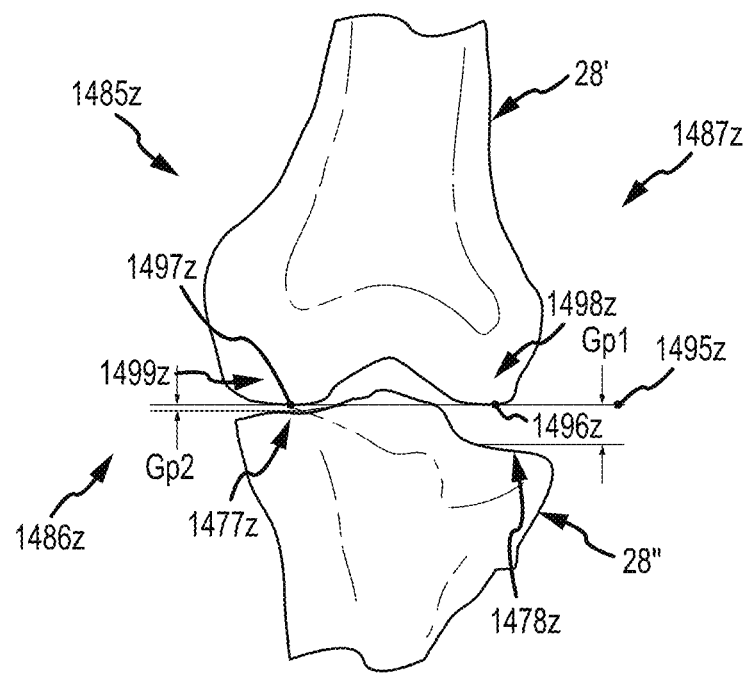

FIGS. 63G and 63H illustrate coronal views of the bone images in their alignment relative to each as a result of OA.

Figure 63I:
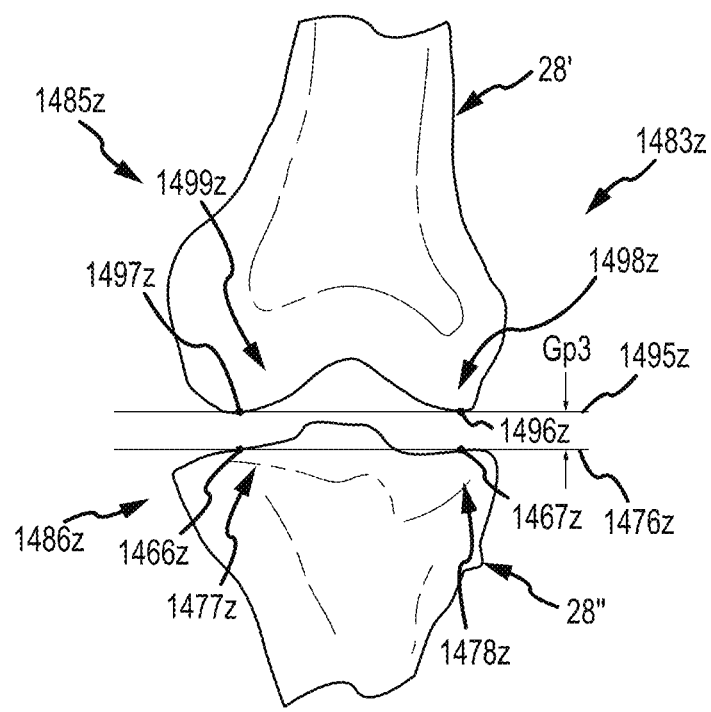

FIG. 63I illustrates a coronal view of the bone images with a restored gap Gp3.

Figure 63J:
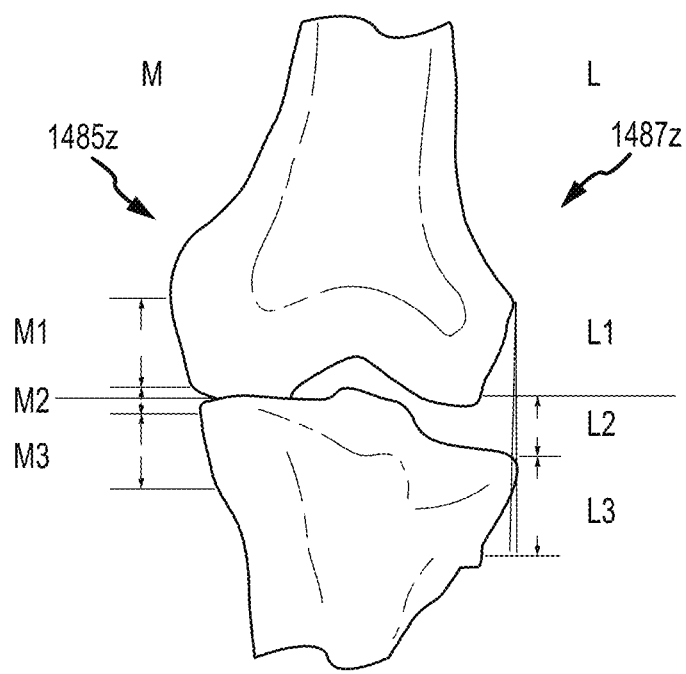

FIG. 63J is a coronal view of bone images oriented relative to each other in a deteriorated state orientation.

Figure 64:
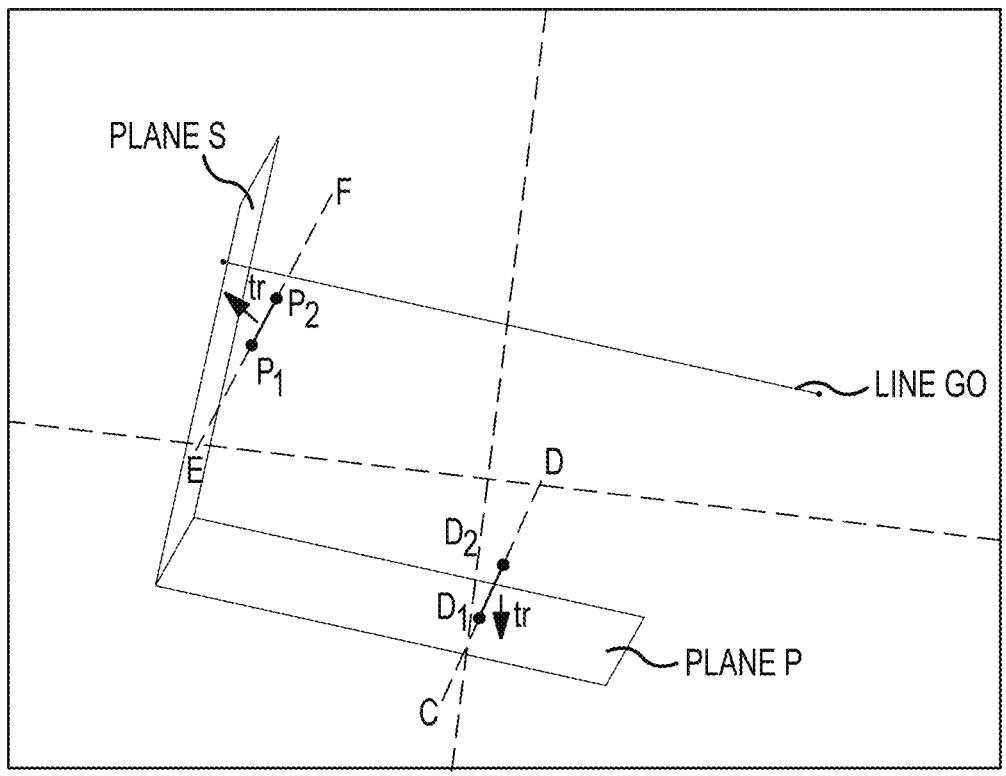

FIG. 64 is a 3D coordinate system wherein the femur reference data is shown.

Figure 65:
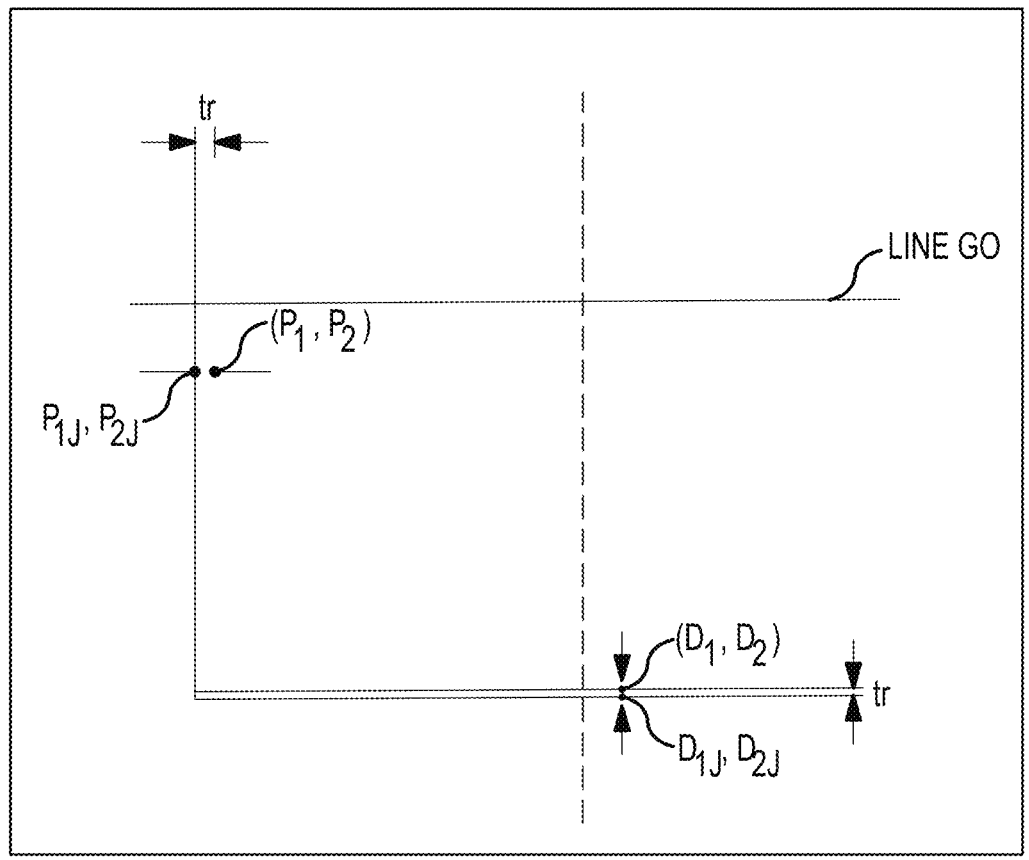

FIG. 65 is a y-z plane wherein the joint compensation points are shown.

Figure 66:
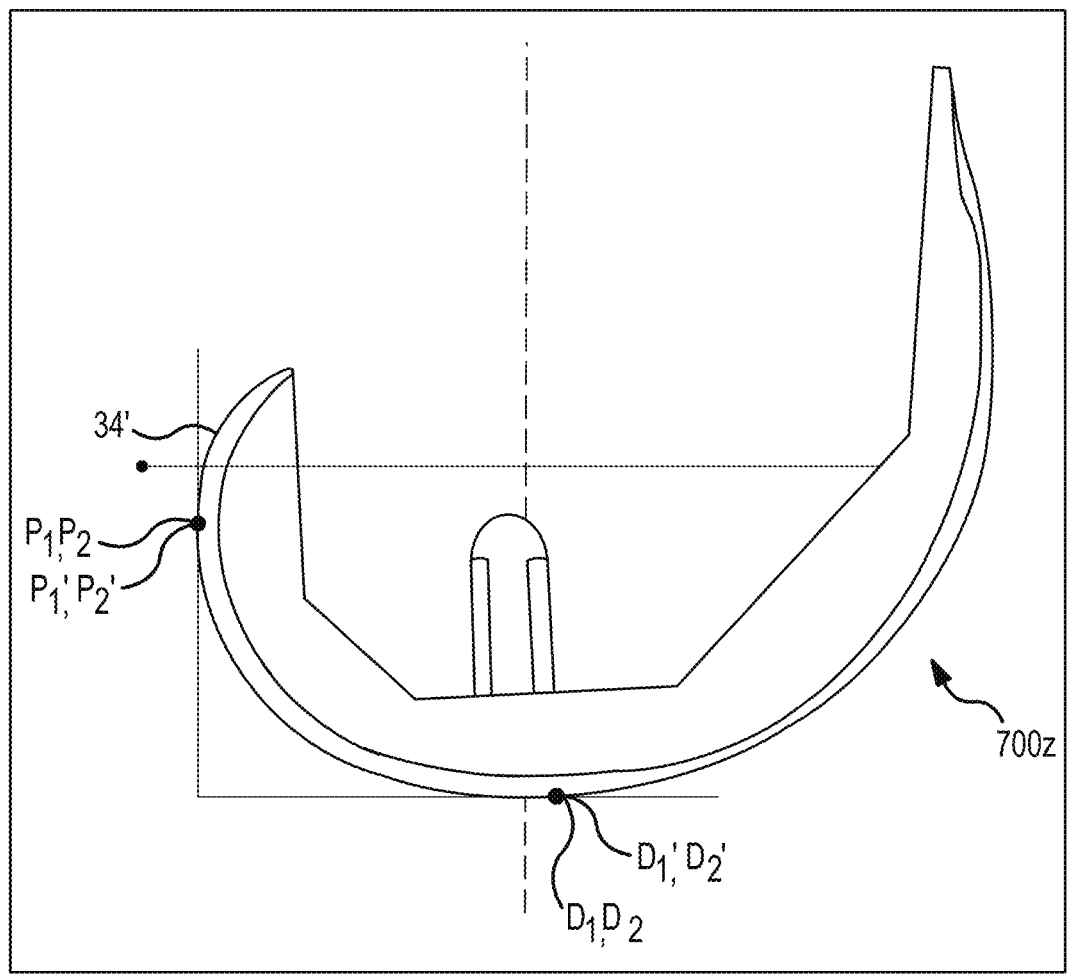

FIG. 66 illustrates the implant model 34' placed onto the same coordinate plane with the femur reference data.

Figure 52A:
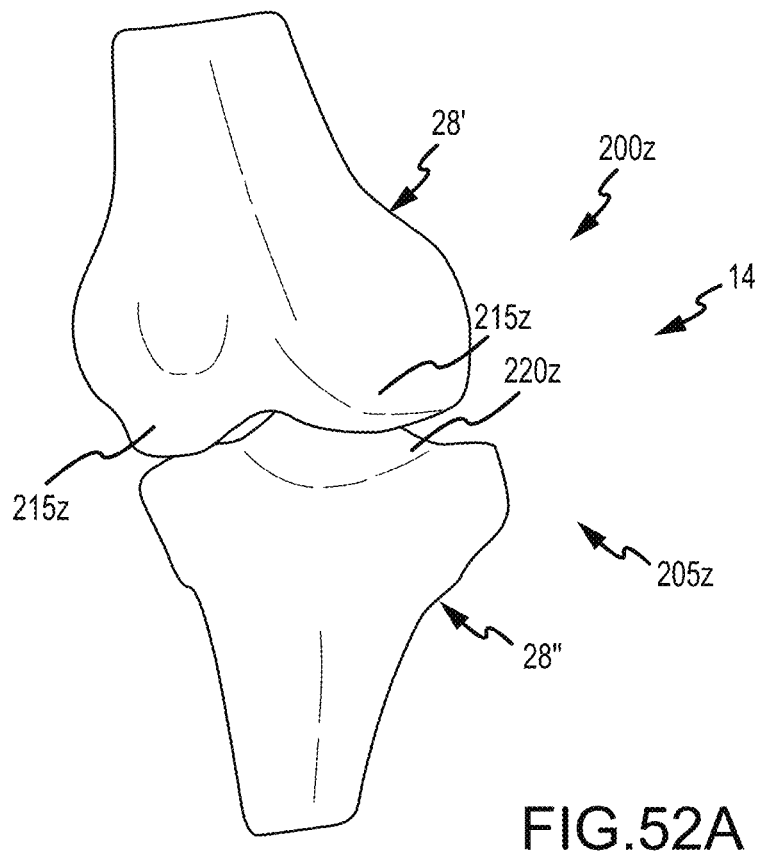
FIG. 52A is an isometric view of a 3D computer model of a femur lower end and a 3D computer model of a tibia upper end in position relative to each to form a knee joint and representative of the femur and tibia in a non-degenerated state.
Figure 52B:
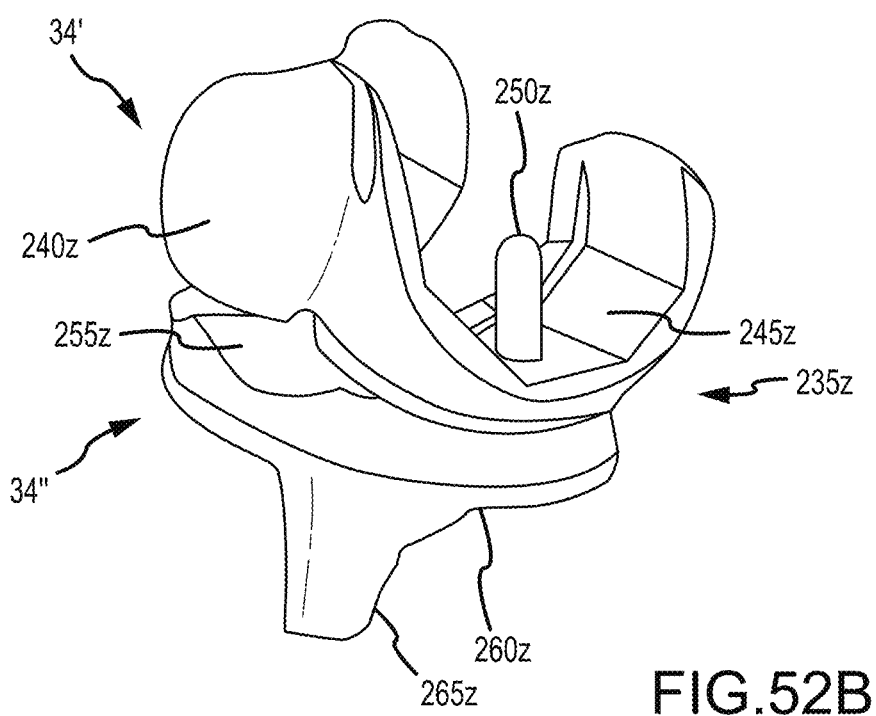
FIG. 52B is an isometric view of a 3D computer model of a femur implant and a 3D computer model of a tibia implant in position relative to each to form an artificial knee joint.
Figures 67A, 67B:
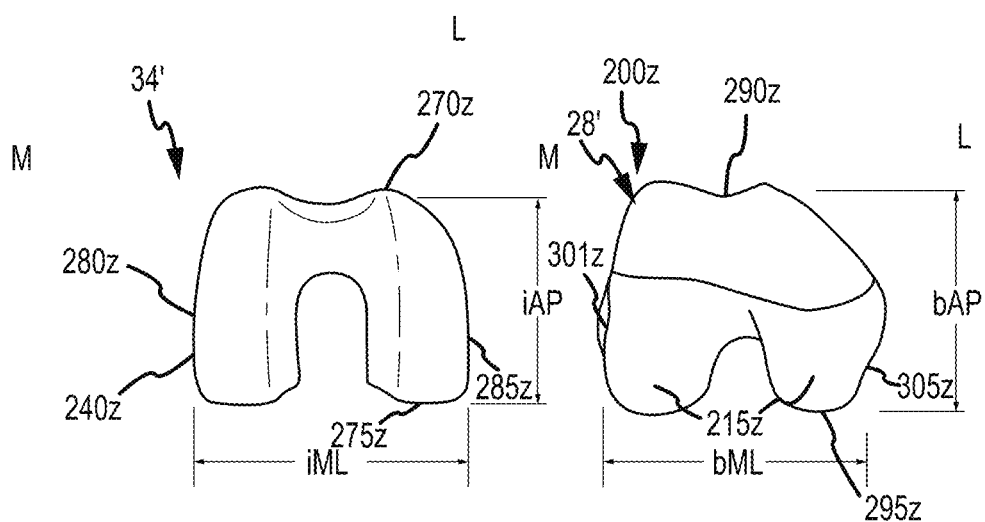

FIG. 67A is a plan view of the joint side of the femur implant model depicted in FIG. 52B.

FIG. 67B is an axial end view of the femur lower end of the femur bone model depicted in FIG. 52A.

Figure 67C:
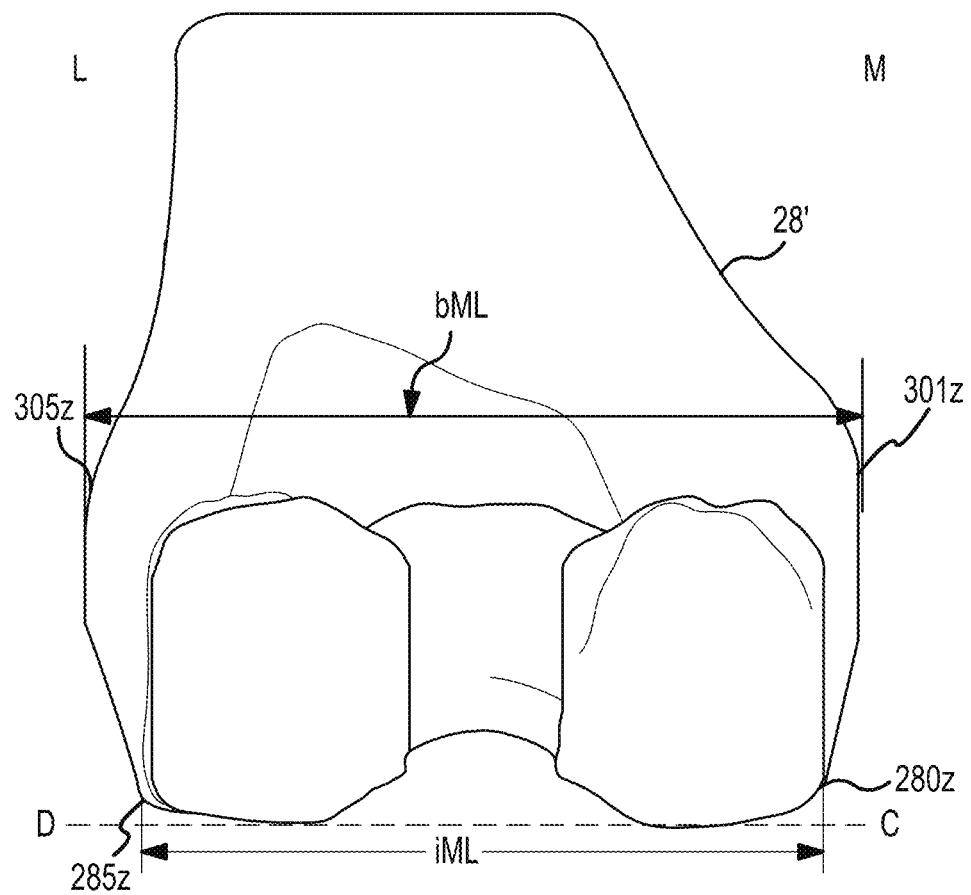

FIG. 67C illustrates the implant extents iAP and iML and the femur extents bAP, bML as they may be aligned for proper implant placement.

Figure 68A:
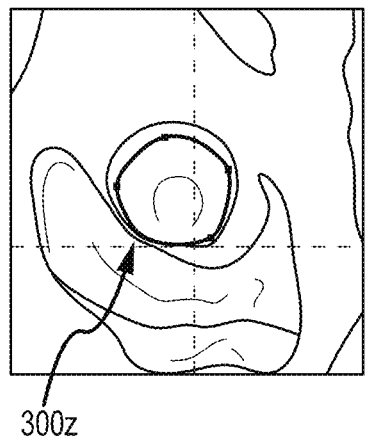

FIG. 68A shows the most medial edge of the femur in a 2D sagittal imaging slice.

Figure 68B:
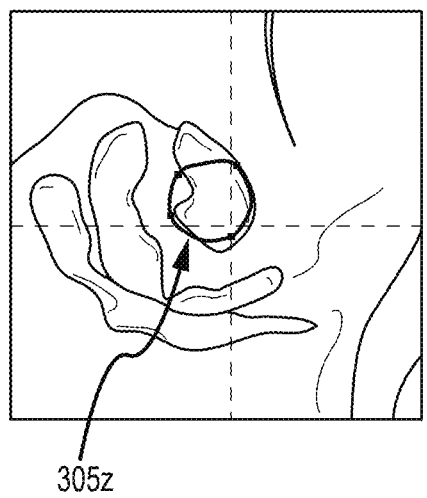

FIG. 68B, illustrates the most lateral edge of the femur in a 2D sagittal imaging slice.

Figure 68C:
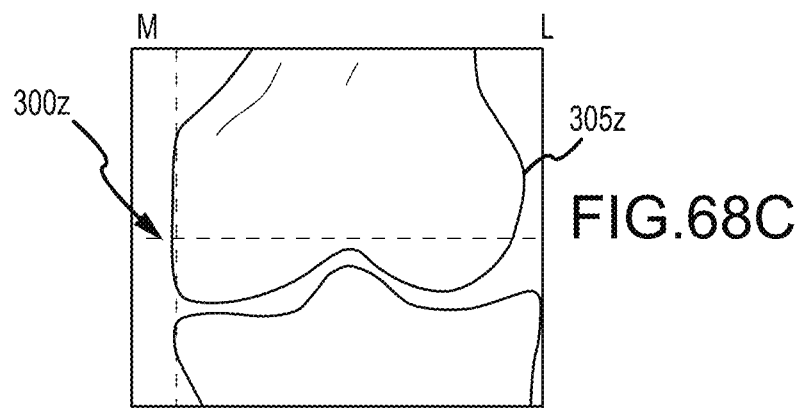

FIG. 68C is a 2D imaging slice in coronal view showing the medial and lateral edges.

Figure 69A:
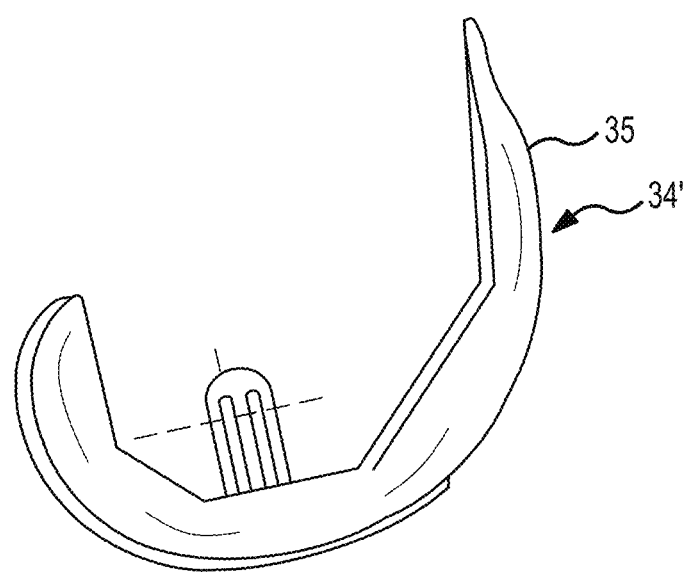

FIG. 69A is a candidate implant model mapped onto a y-z plane.

Figure 69B:
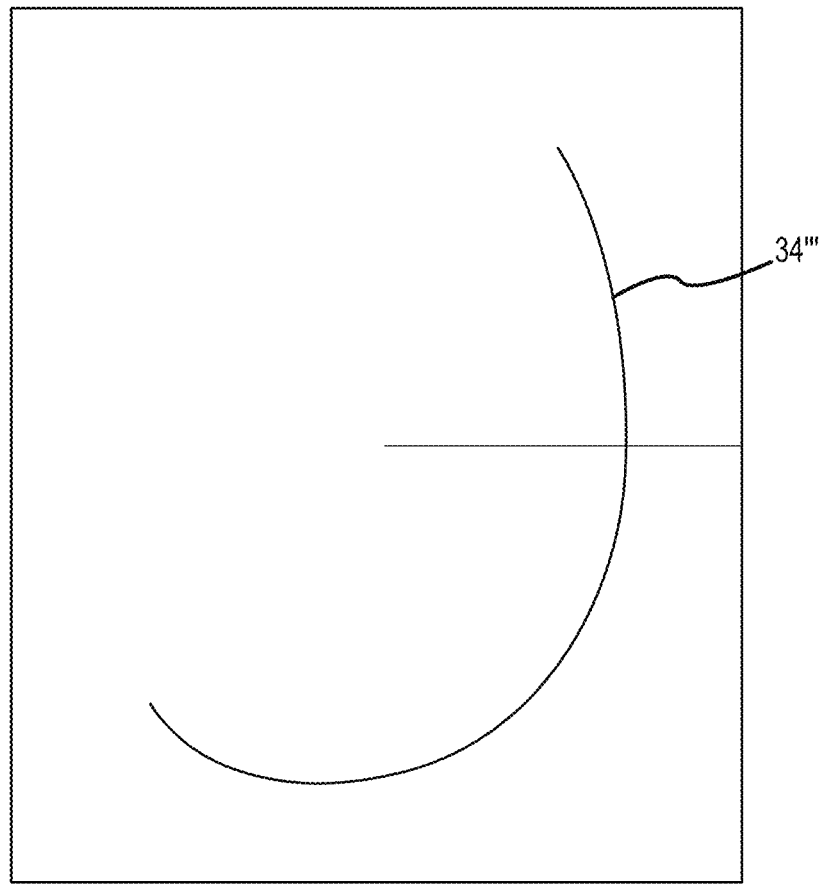

FIG. 69B is the silhouette curve of the articular surface of the candidate implant model.

Figure 69C:
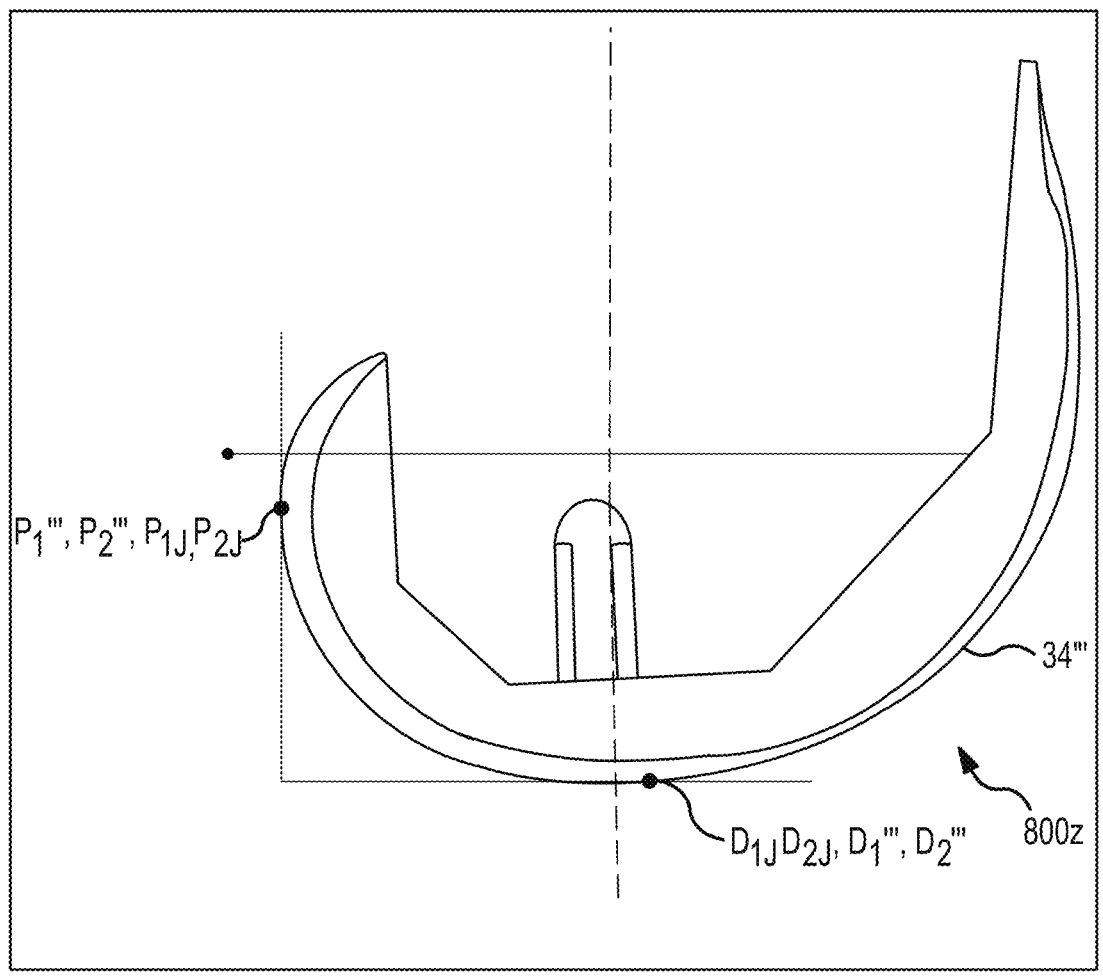

FIG. 69C is the silhouette curve of the candidate implant model aligned with the joint spacing compensation points $D_{1J}D_{2J}$ and $P_{1J}P_{2J}$.

Figure 70A:
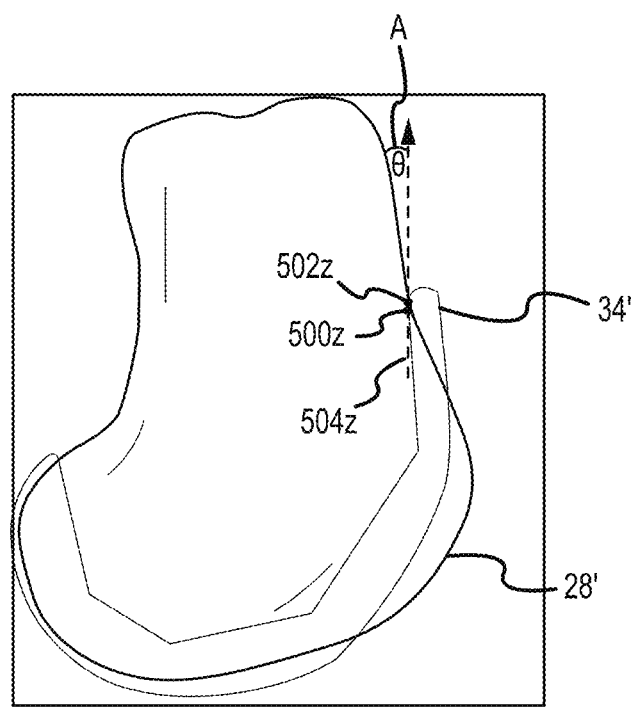

FIG. 70A illustrates a sagittal imaging slice of a distal femur with an implant model.

Figure 70B:
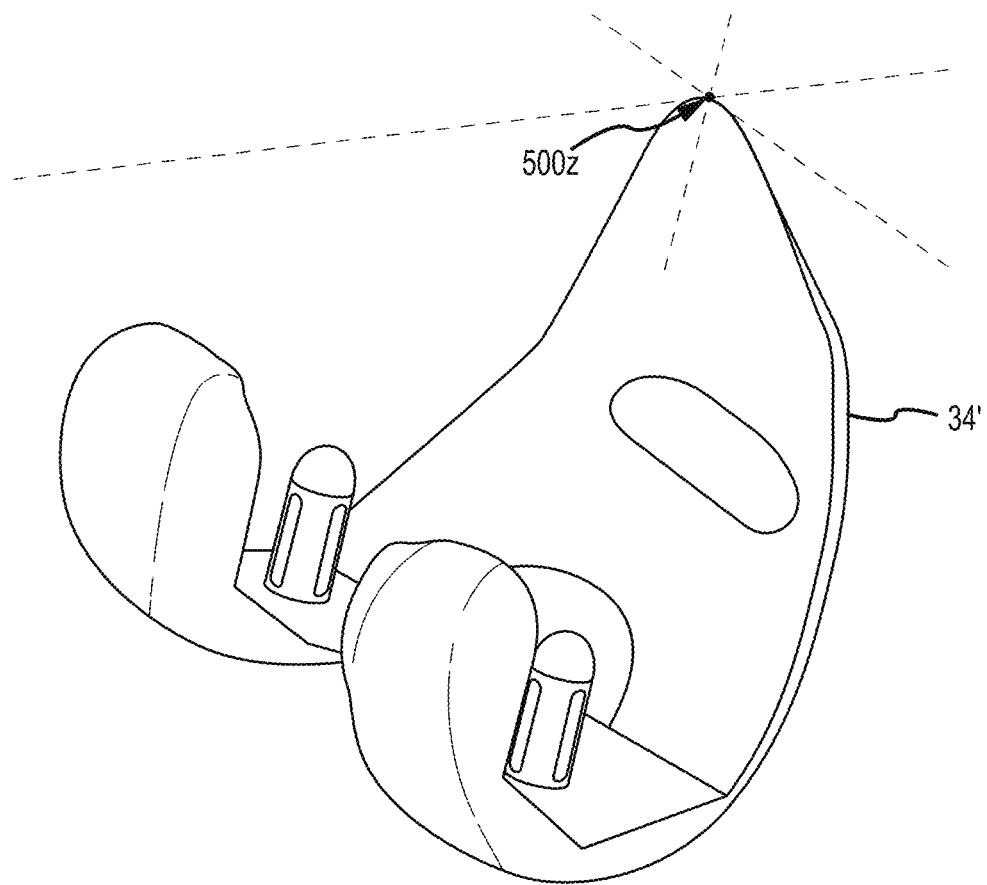

FIG. 70B depicts a femur implant model wherein the flange point on the implant is shown.

Figure 70C:
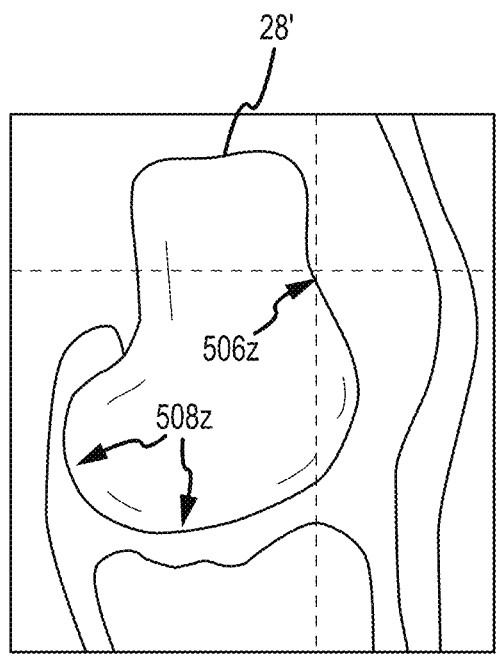

FIG. 70C shows an imaging slice of the distal femur in the sagittal view, wherein the inflection point located on the anterior shaft of the spline is shown.

Figure 70D:
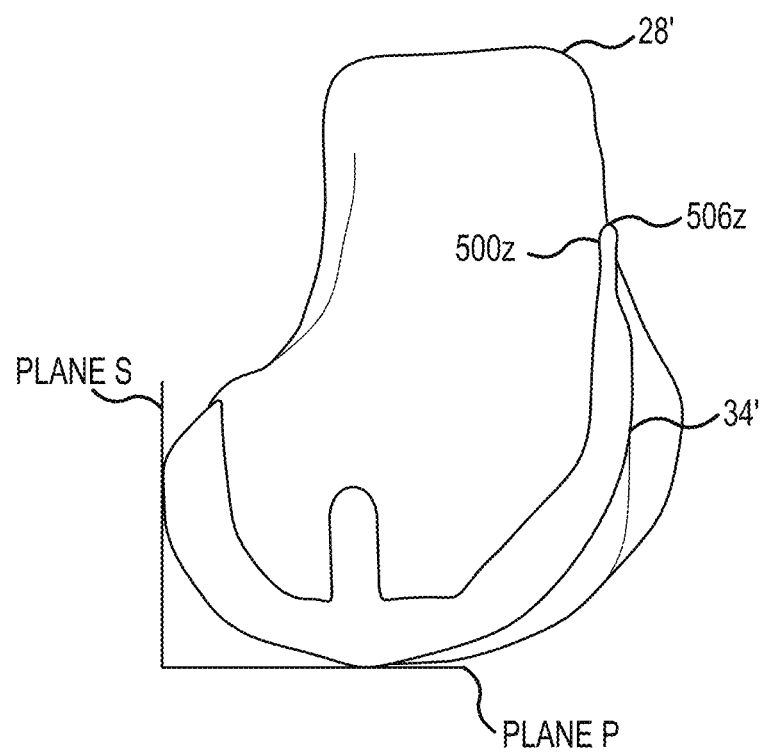

FIG. 70D illustrates the 2D implant model properly positioned on the 2D femur image, as depicted in a sagittal view.

Figure 71A:
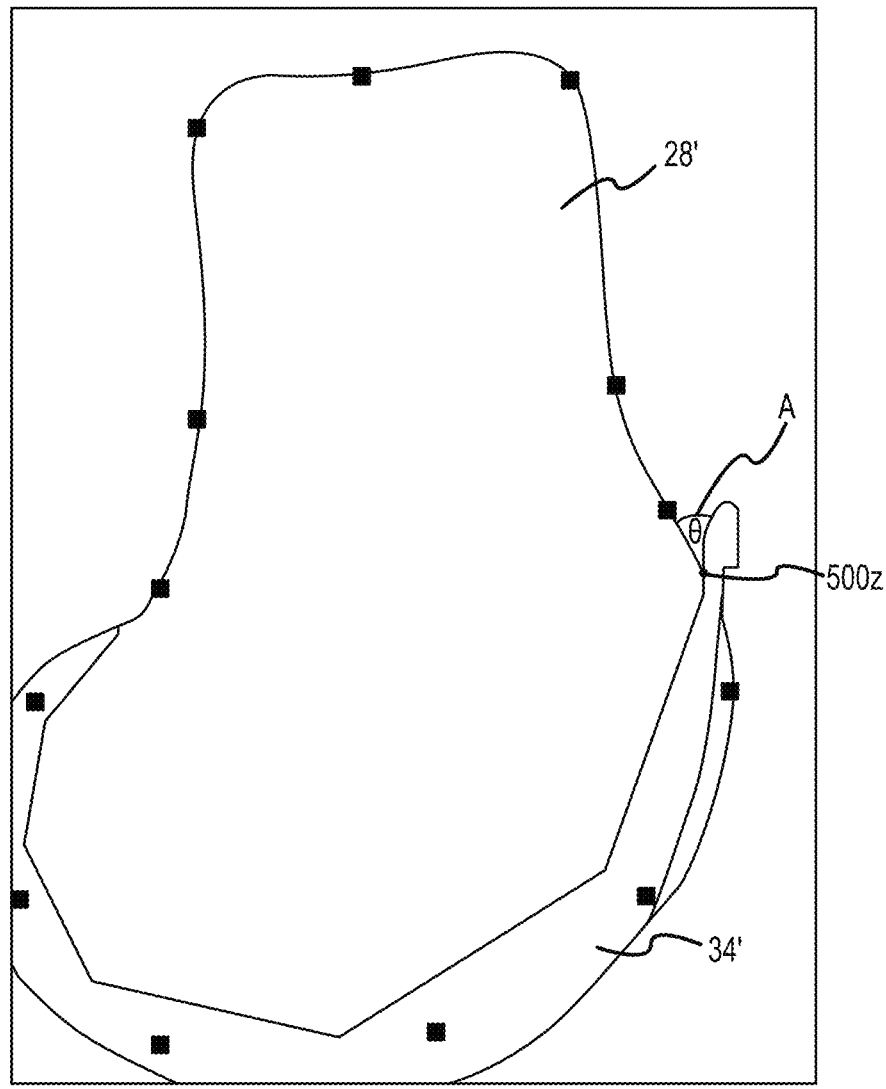

FIG. 71A depicts an implant model that is improperly aligned on a 2D femur image, as depicted in a sagittal view.

Figure 71B:
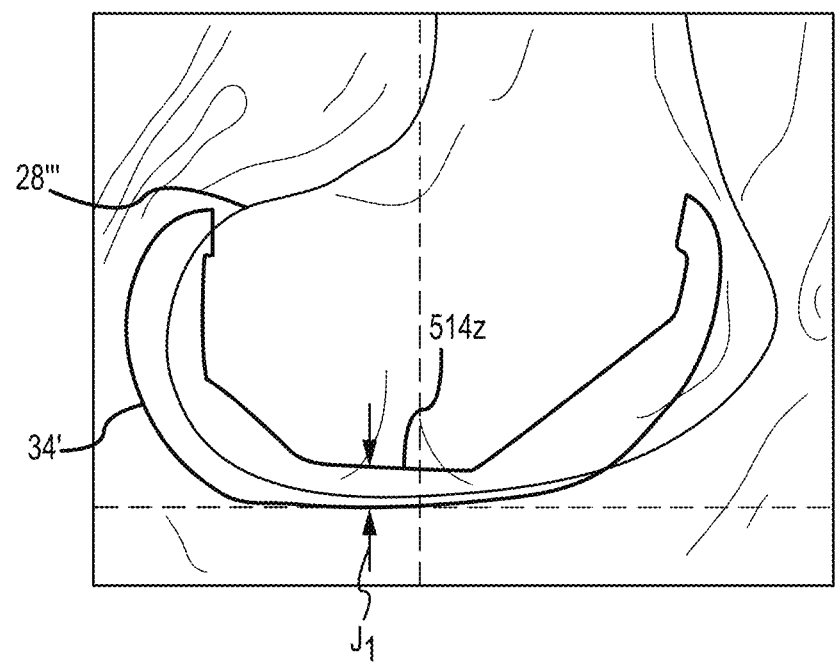

FIG. 71B illustrates the implant positioned on a femur transform wherein a femur cut plane is shown, as depicted in a sagittal view.

Figure 72:
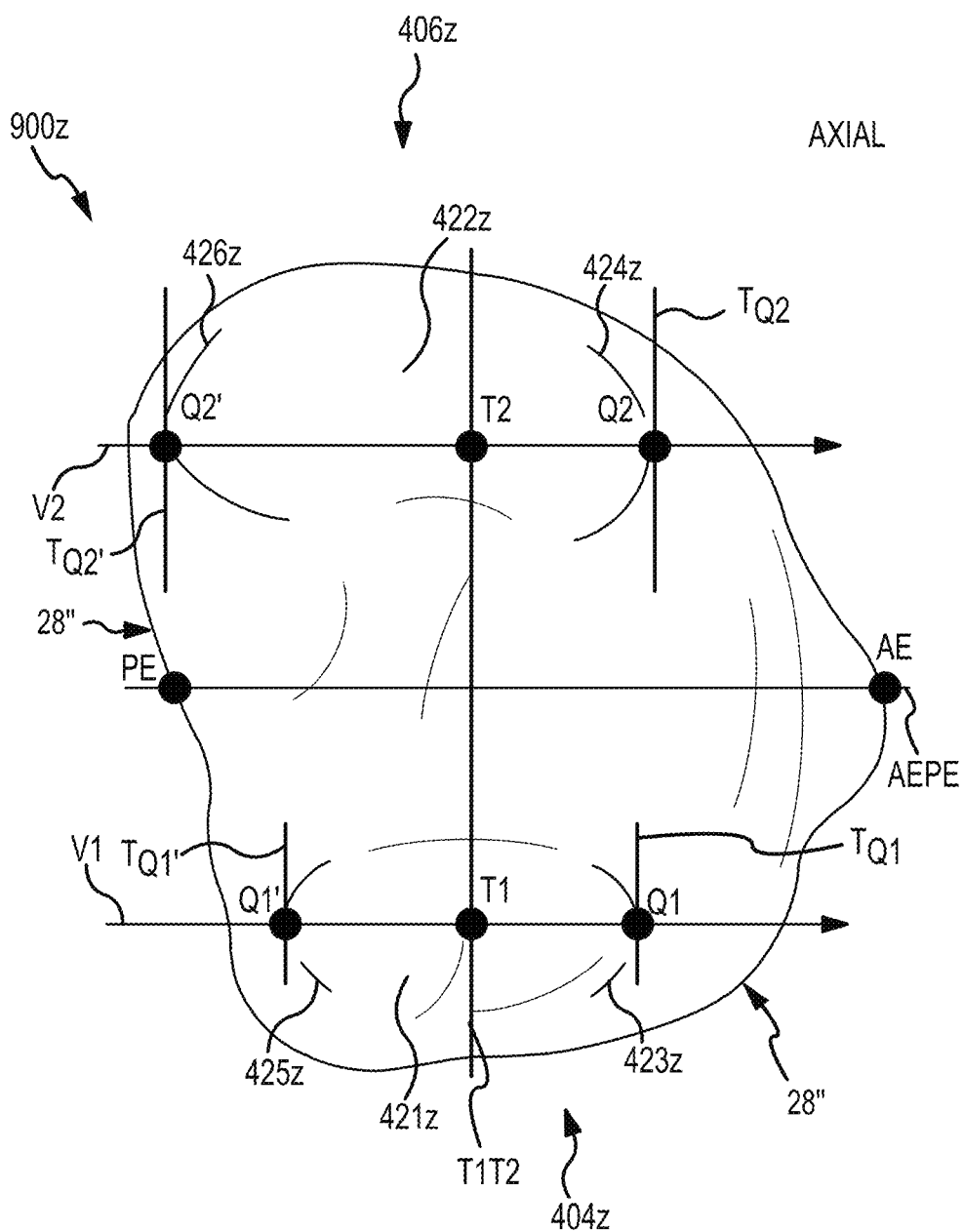

FIG. 72 is a top view of the tibia plateaus of a tibia bone image or model.

Figure 73A:
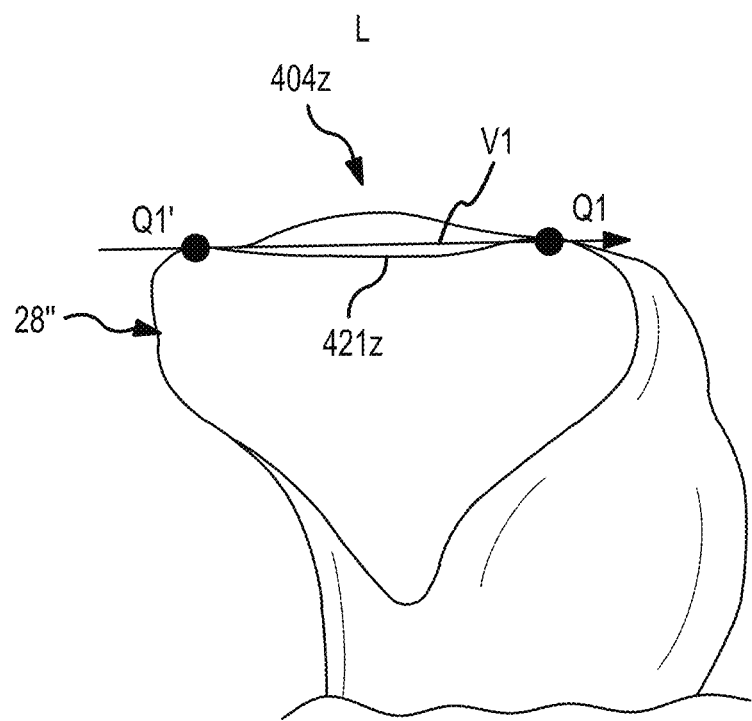

FIG. 73A is a sagittal cross section through a lateral tibia plateau of the 2D tibia bone model or image.

Figure 73B:
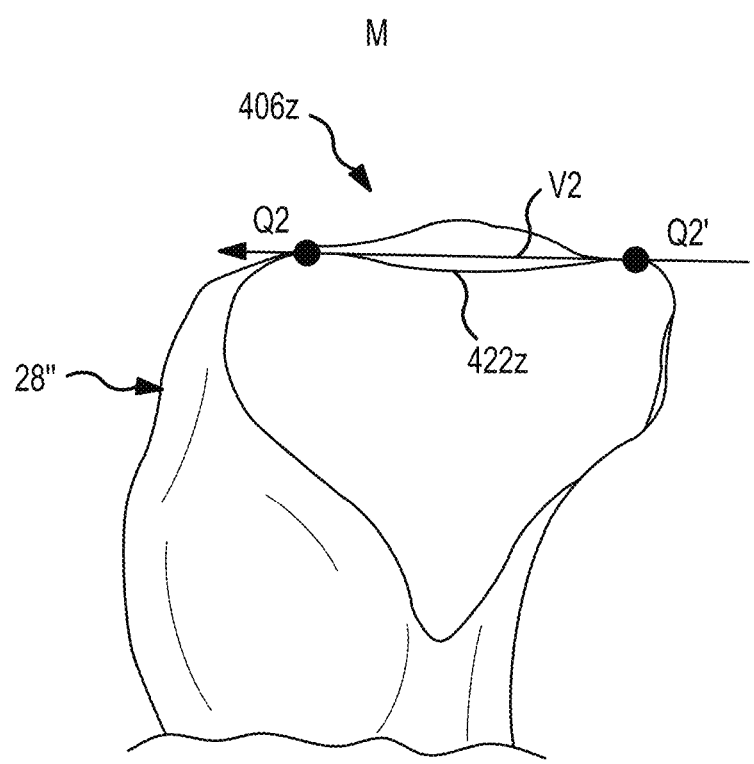

FIG. 73B is a sagittal cross section through a medial tibia plateau of the 2D tibia bone model or image.

Figure 73C:
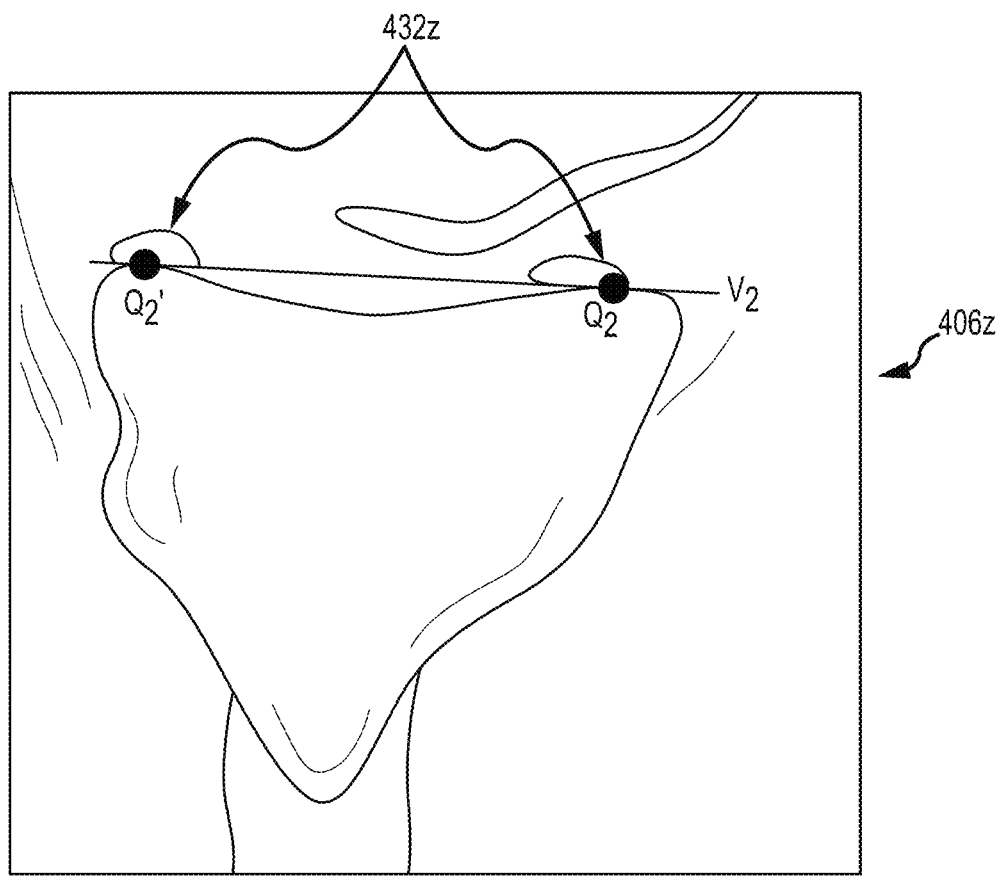

FIG. 73C depicts a sagittal cross section through an undamaged or little damaged medial tibia plateau of the 2D tibia model, wherein osteophytes are also shown.

Figure 73D:
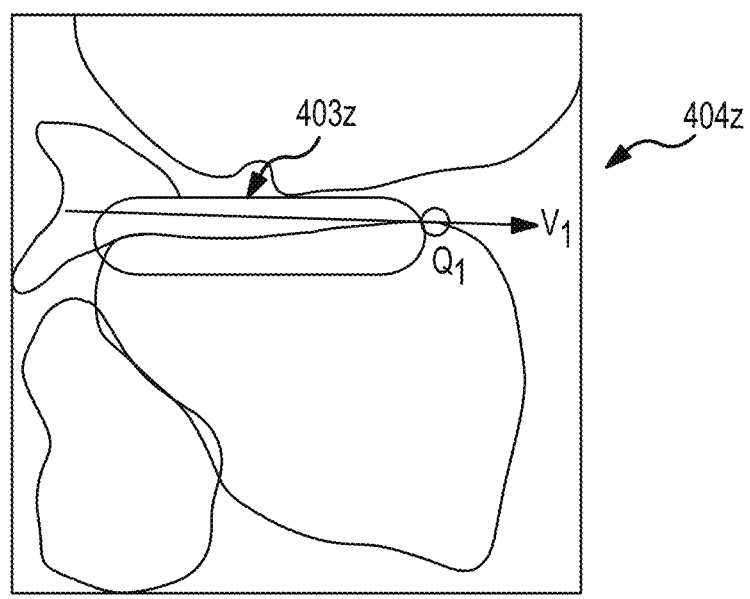

FIG. 73D is a sagittal cross section through a damaged lateral tibia plateau of the 2D tibia model.

Figure 74A:
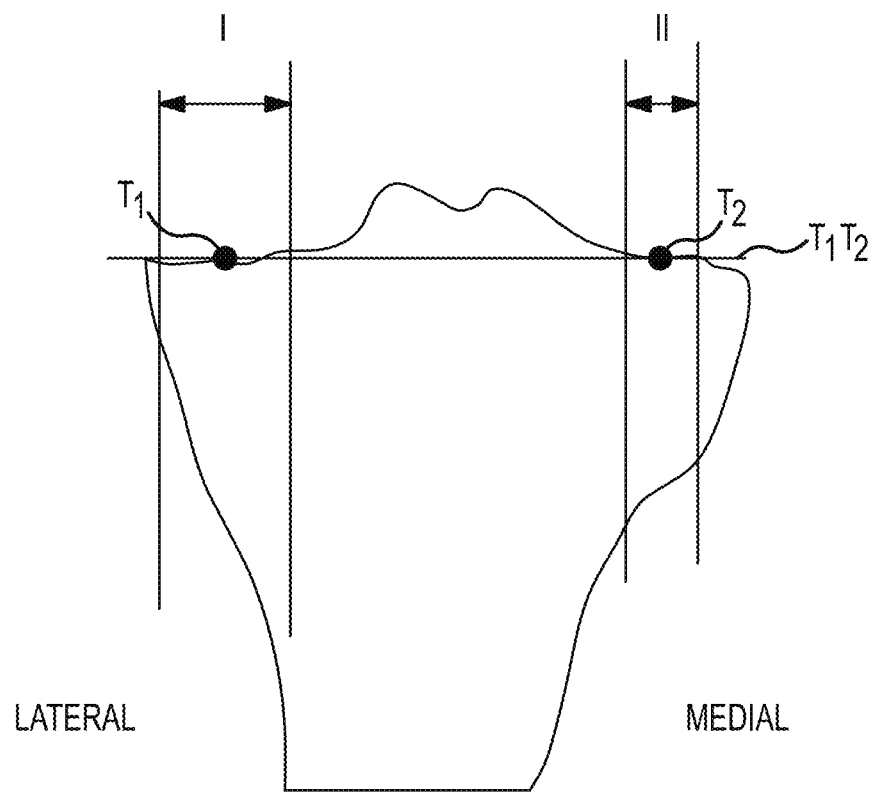

FIG. 74A is a coronal 2D imaging slice of the tibia.

Figure 74B:
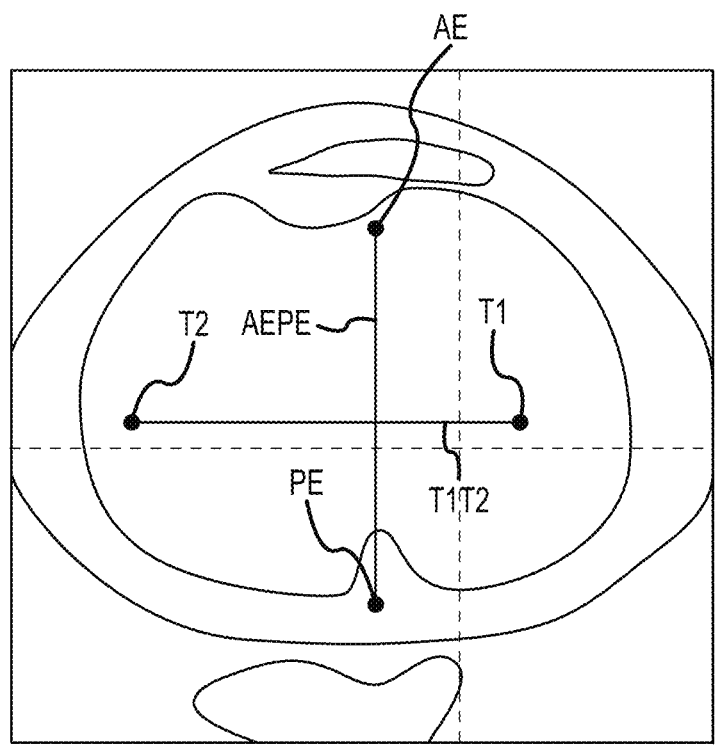

FIG. 74B is an axial 2D imaging slice of the tibia.

Figure 75A:
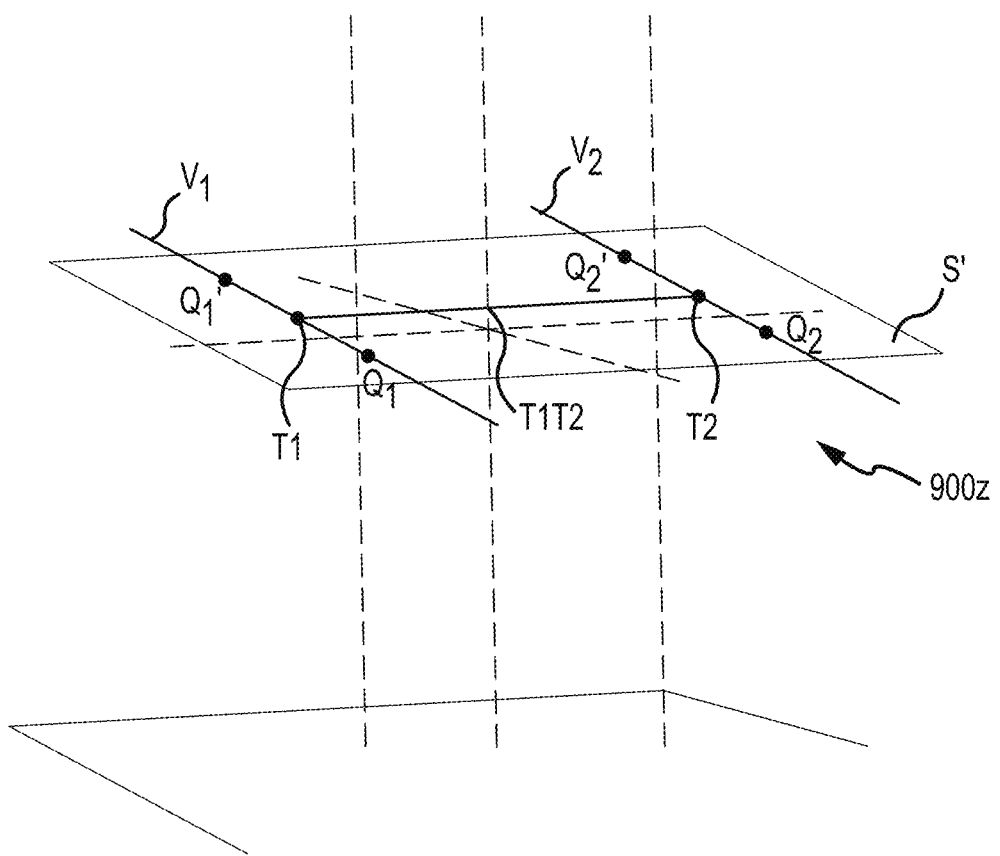

FIG. 75A depicts the tibia reference data on an x-y coordinate system.

Figure 75B:
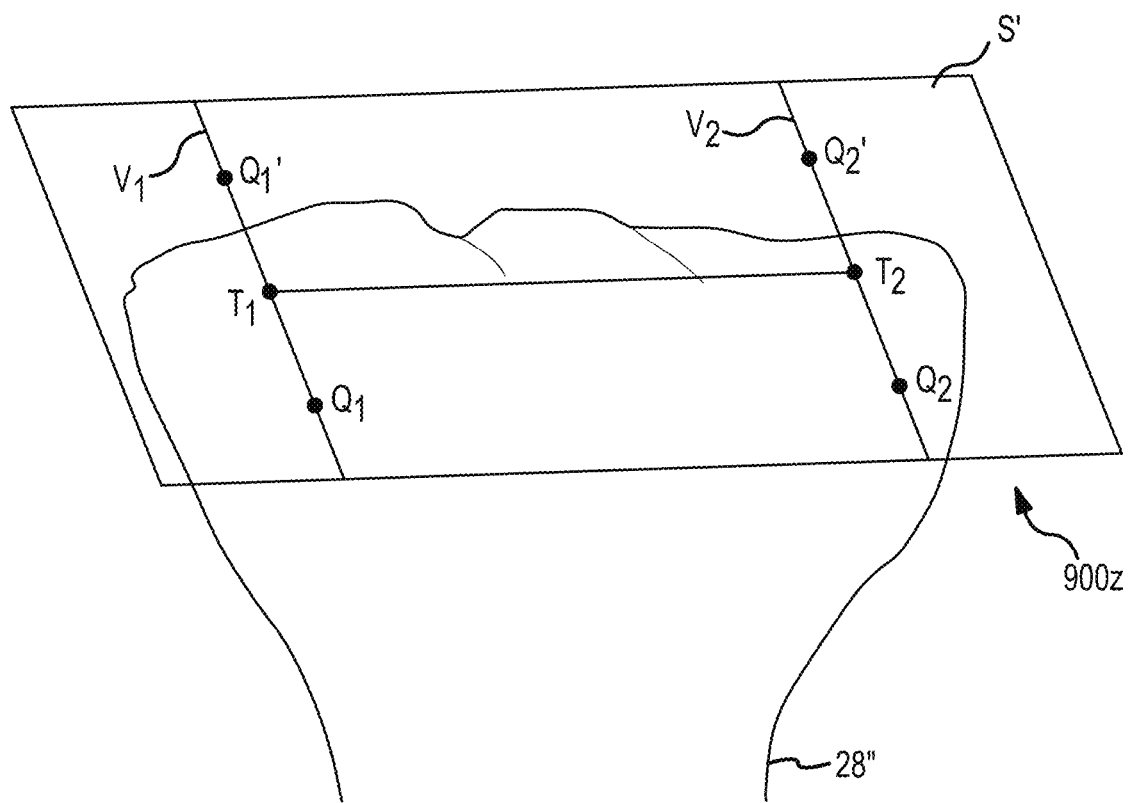

FIG. 75B depicts the tibia reference data on a proximal end of the tibia to aid in the selection of an appropriate tibia implant.

Figure 76A:
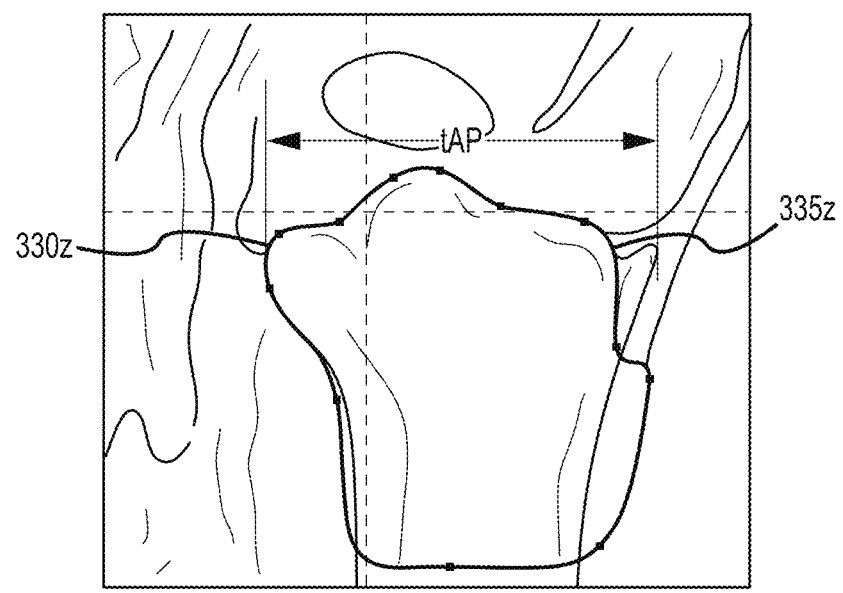

FIG. 76A is a 2D sagittal imaging slice of the tibia wherein a segmentation spline with an AP extant is shown.

Figure 76B:
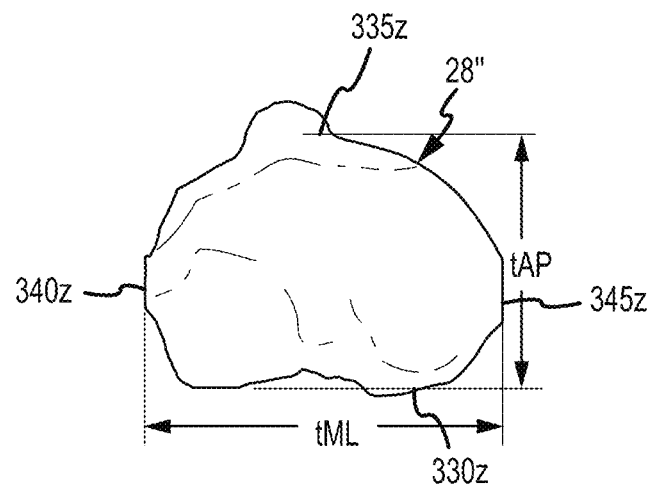

FIG. 76B is an axial end view of the tibia upper end of the tibia bone model depicted in FIG. 52A.

Figure 76C:
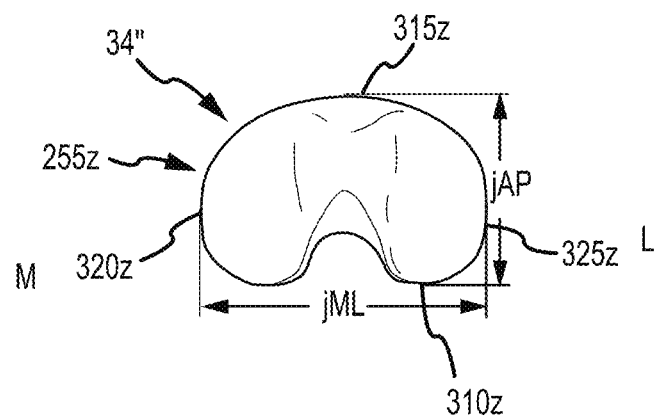

FIG. 76C is a plan view of the joint side of the tibia implant model depicted in FIG. 52B.

Figure 77:
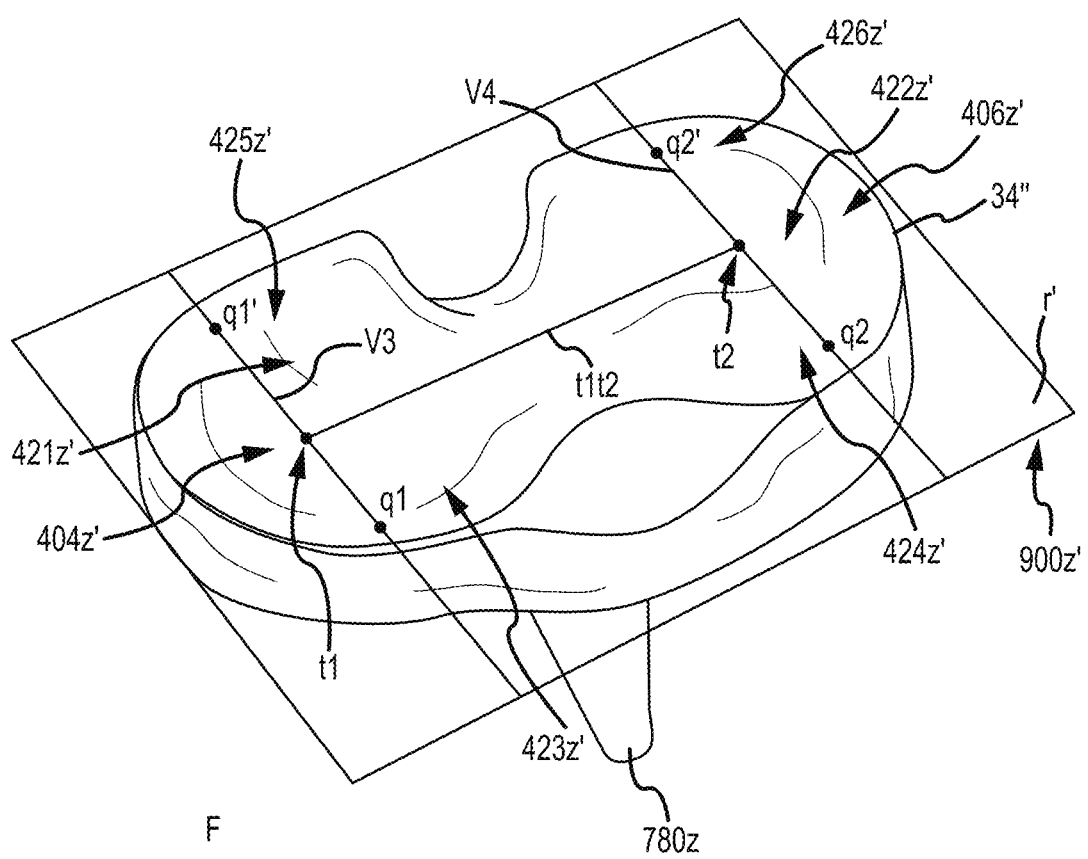

FIG. 77 is a top isometric view of the tibia plateaus of a tibia implant model.

Figure 78A:
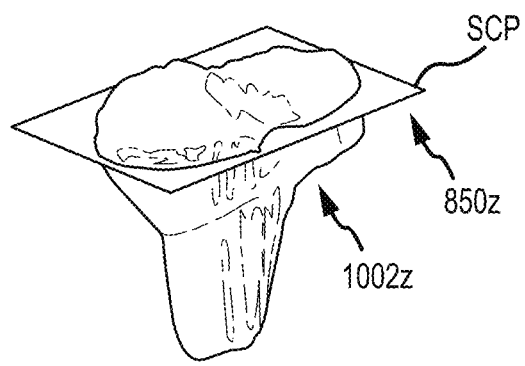

FIG. 78A is an isometric view of the 3D tibia bone model showing the surgical cut plane SCP design.

Figures 78B, 78C:
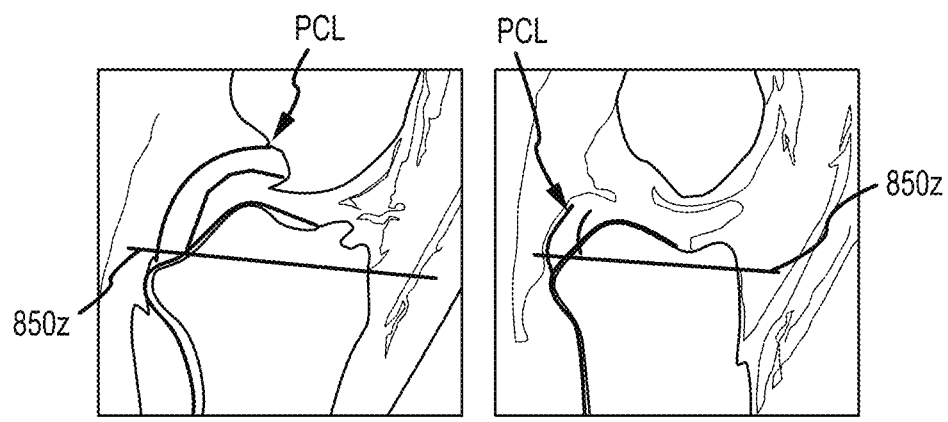

FIGS. 78B and 78C are sagittal MRI views of the surgical tibia cut plane SCP design with the posterior cruciate ligament PCL.

Figure 79A:
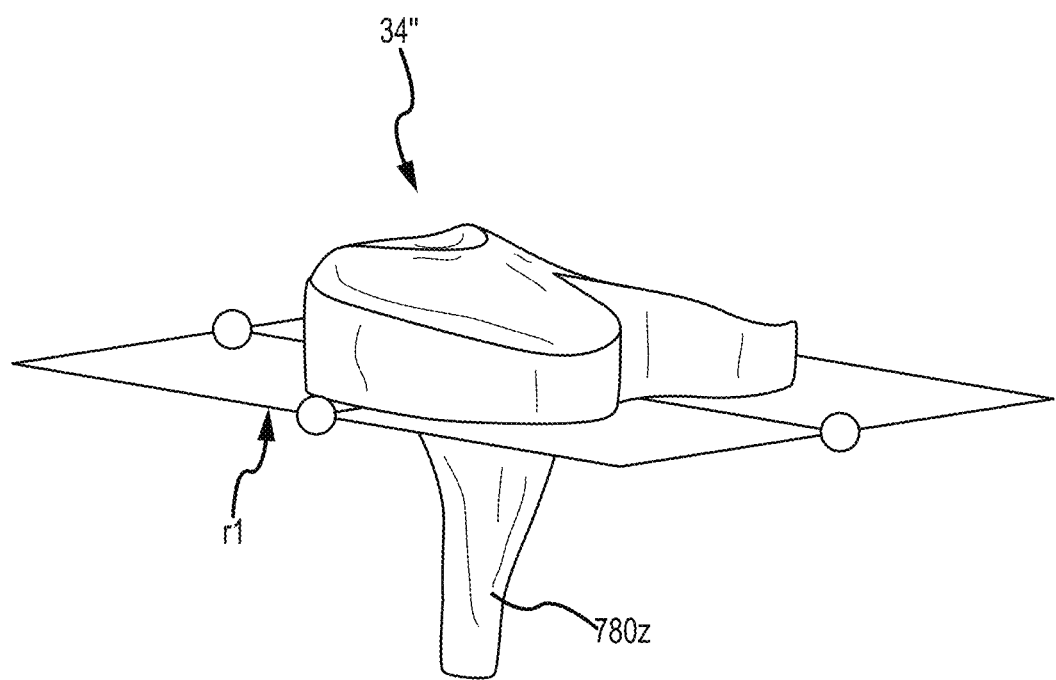

FIG. 79A is an isometric view of the tibia implant wherein a cut plane is shown.

Figure 79B:
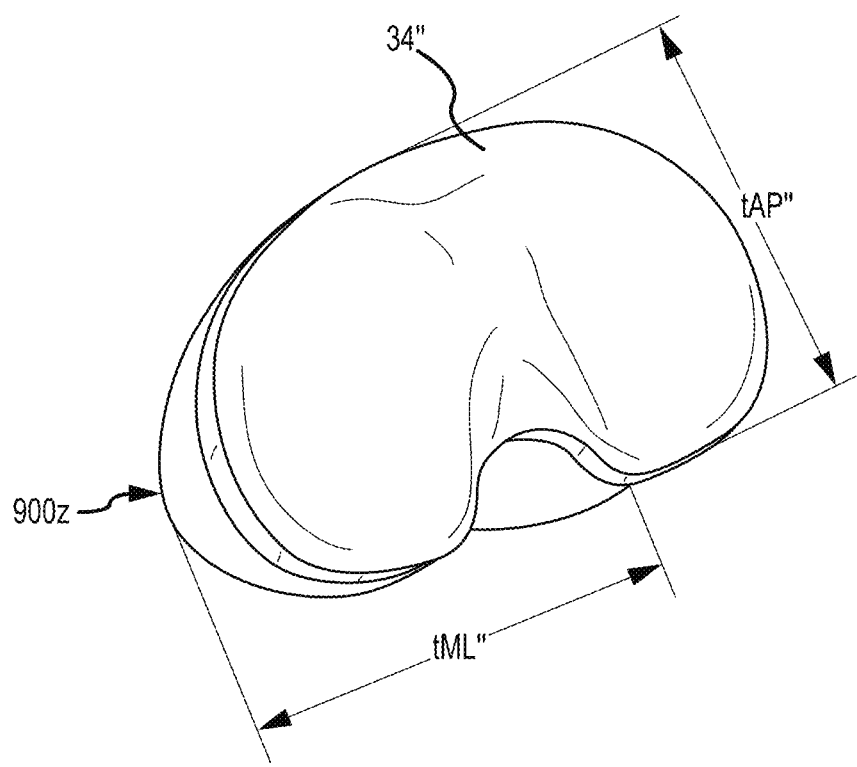

FIG. 79B is a top axial view of the implant superimposed on the tibia reference data.

Figure 79C:
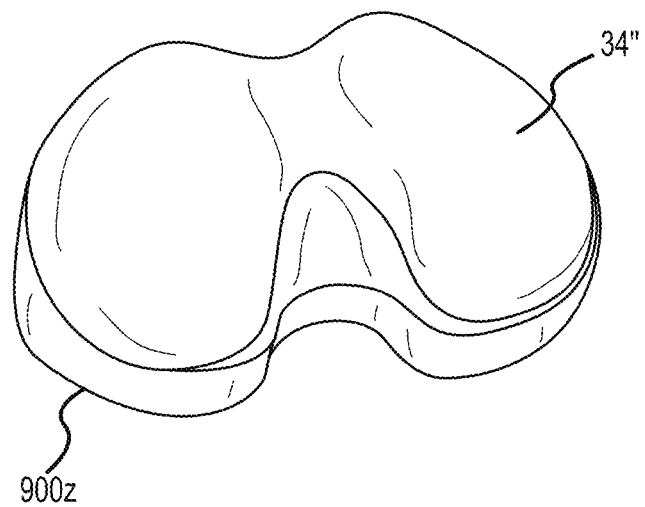

FIG. 79C is an axial view of the tibial implant aligned with the tibia reference data.

Figure 79D:
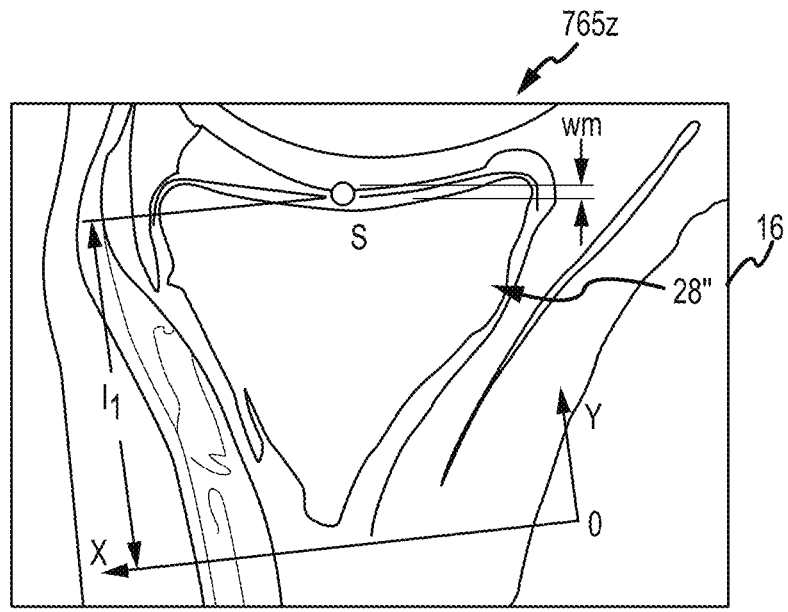

FIG. 79D is a MRI imaging slice of the medial portion of the proximal tibia and indicates the establishment of landmarks for the tibia POP design, as depicted in a sagittal view.

Figure 79E:
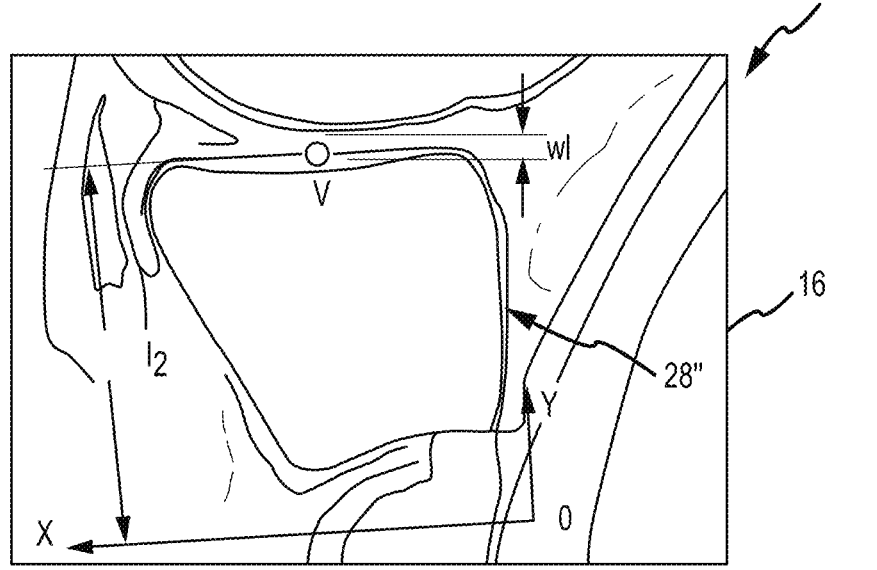

FIG. 79E is a MRI imaging slice of the lateral portion of the proximal tibia, as depicted in a sagittal view.

Figure 79F:
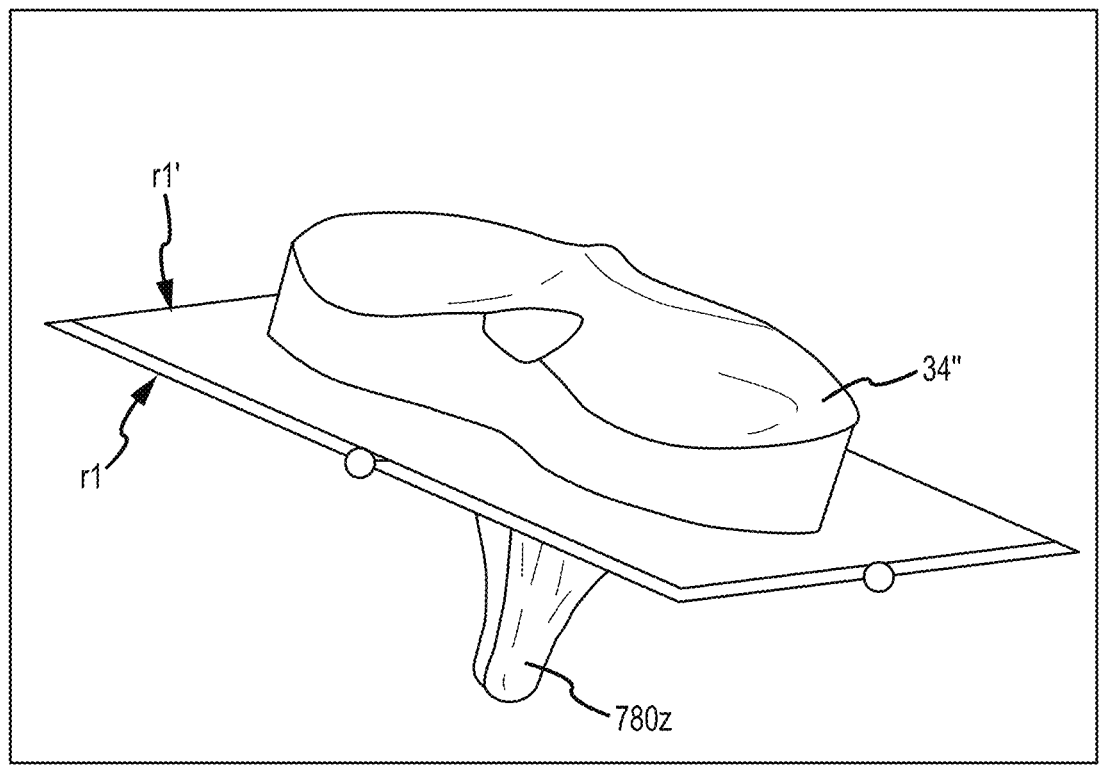

FIG. 79F is an isometric view of the 3D model of the tibia implant and the cut plane.

Figure 80A:
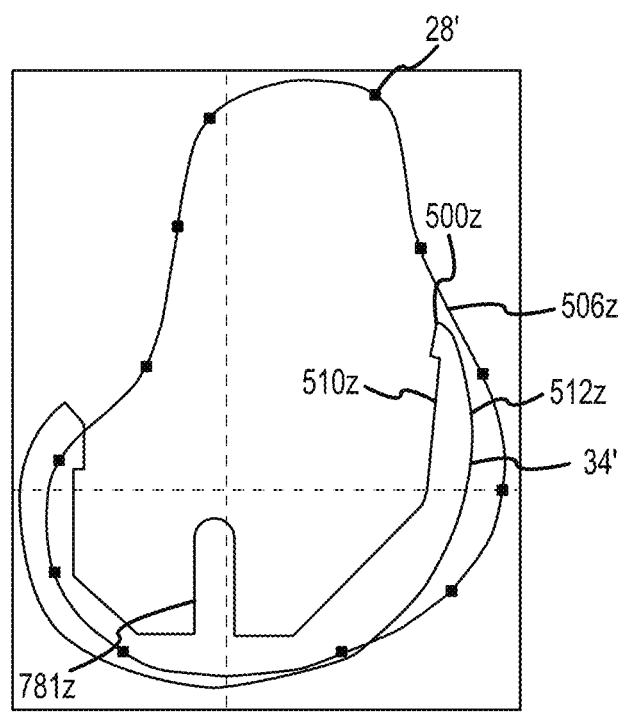
Figure 80B:
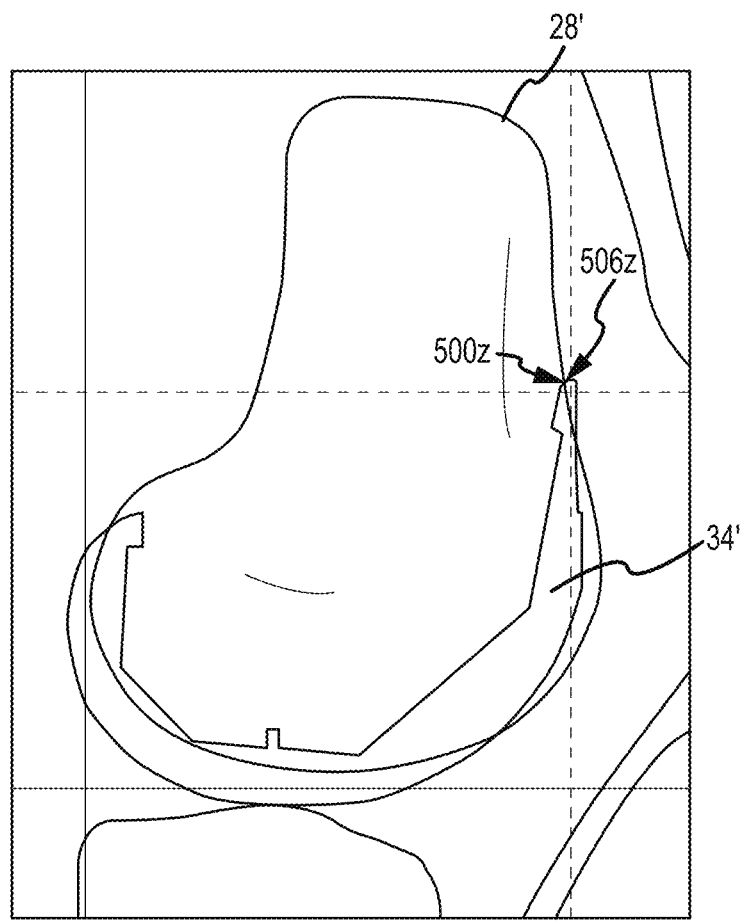

FIGS. 80A-80B are sagittal views of a 2D imaging slice of the femur wherein the 2D computer generated implant models are also shown.

Figure 80C:
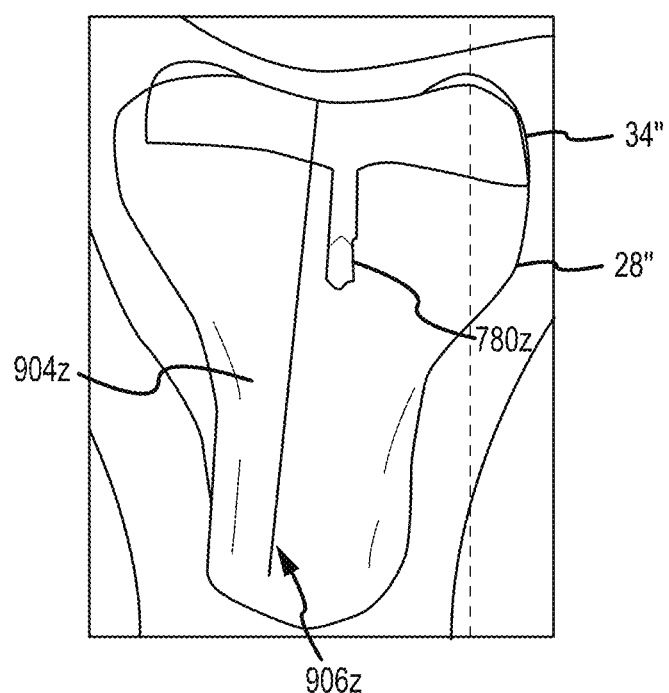

FIG. 80C is a sagittal view of a 2D imaging slice of the tibia wherein the 2D computer generated implant model is also shown.

Figures 81A, 81B, 81C:
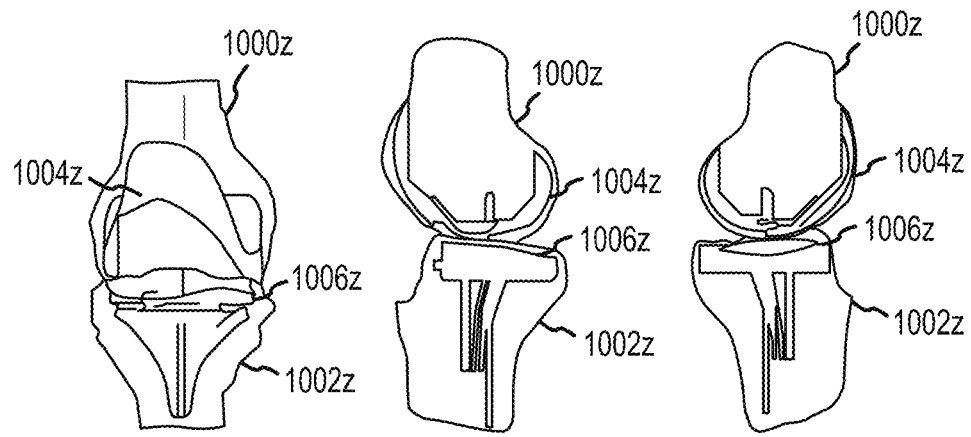

FIGS. 81A-81C are various views of the 2D implant models superimposed on the 2D bone models.

Figure 81D:
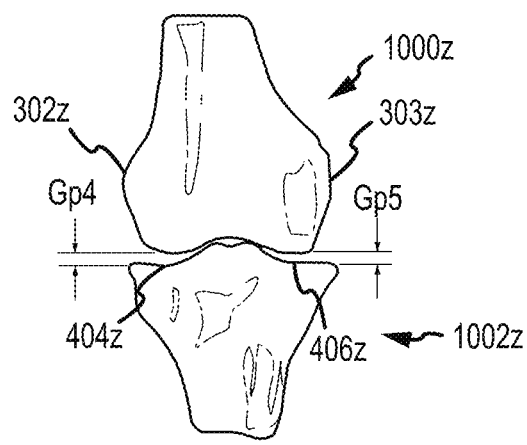

FIG. 81D is a coronal view of the 2D bone models.

Figure 81E:
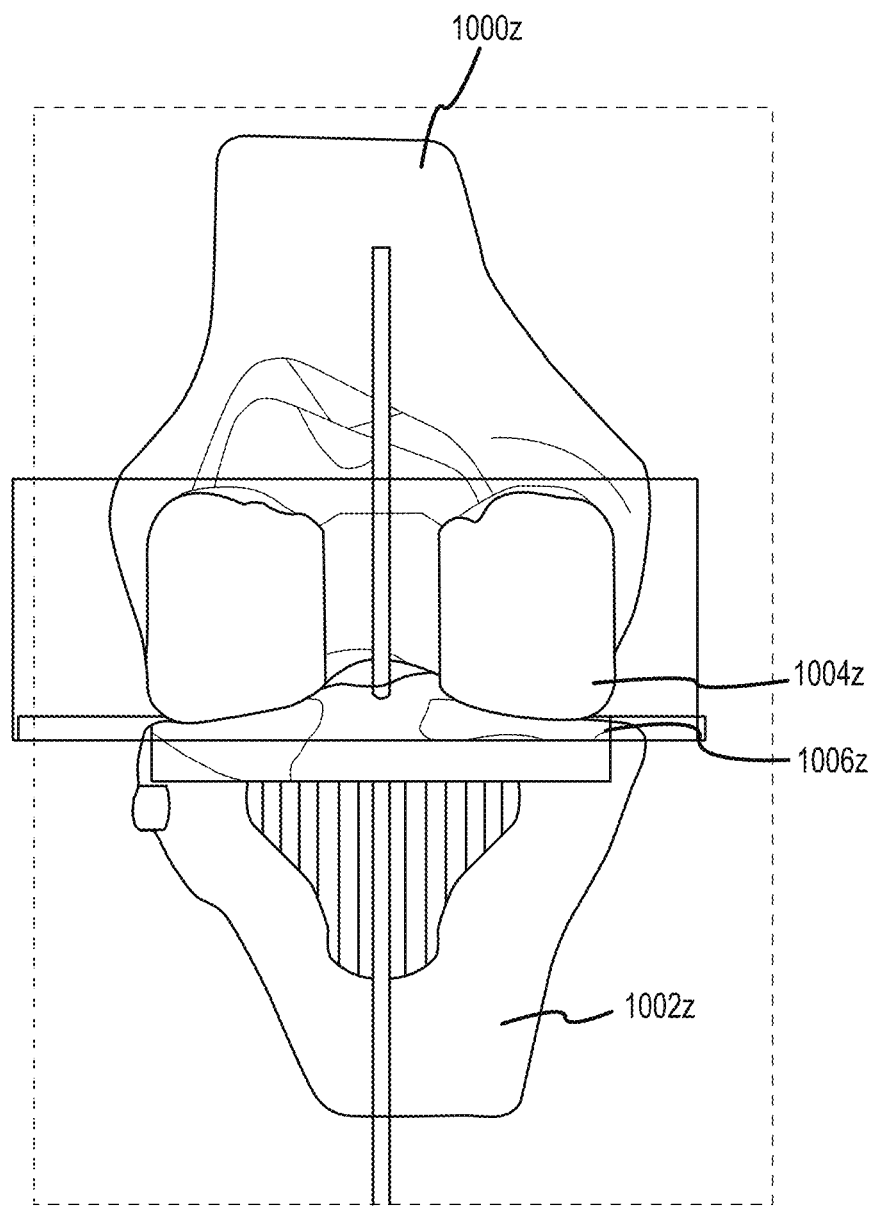
Figure 81F:
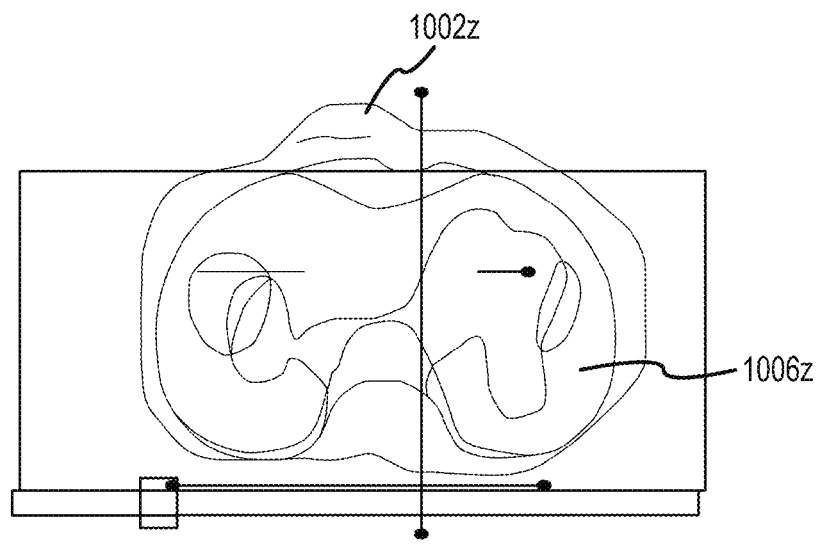
Figure 81G:
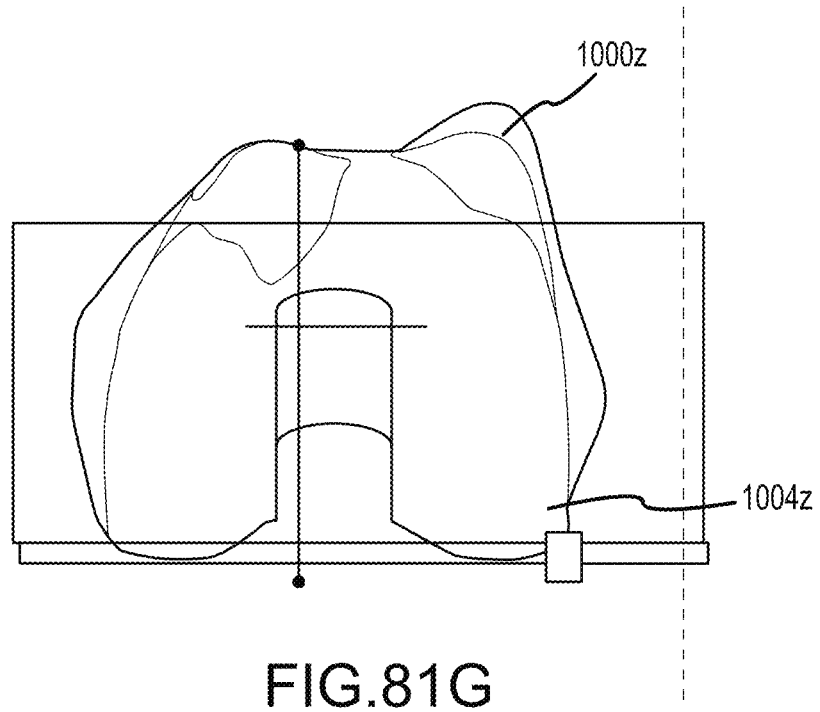

FIGS. 81E-81G are various views of the 2D implant models superimposed on the 2D bone models.

Figure 82A:
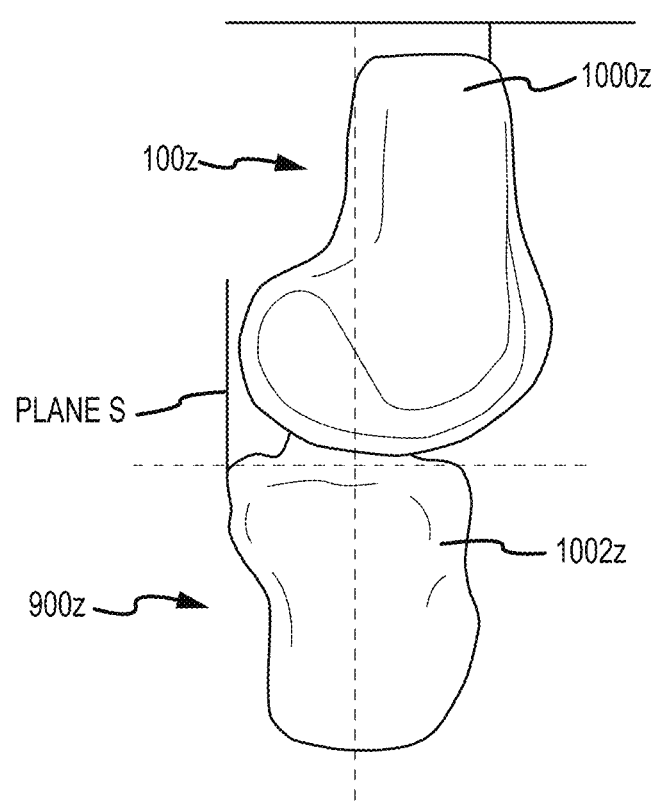

FIG. 82A is a medial view of the 3D bone models.

Figure 82B:
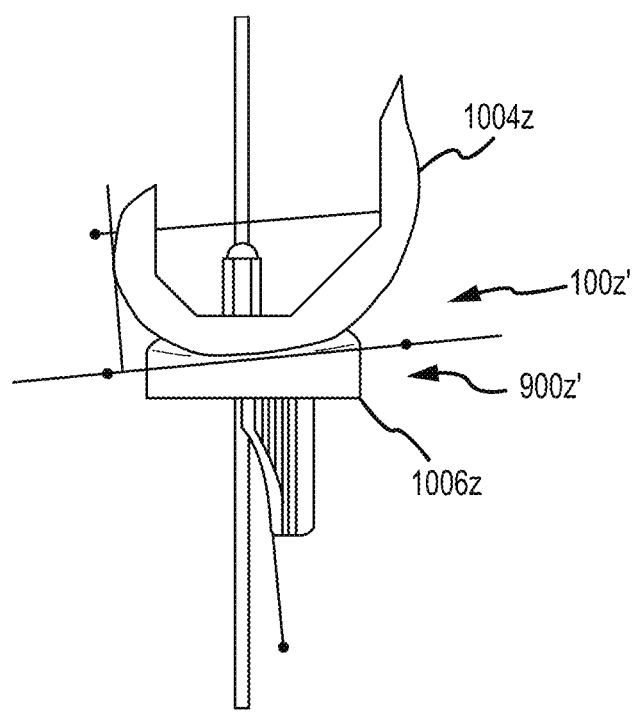

FIG. 82B is a medial view of the 3D implant models

Figure 82C:
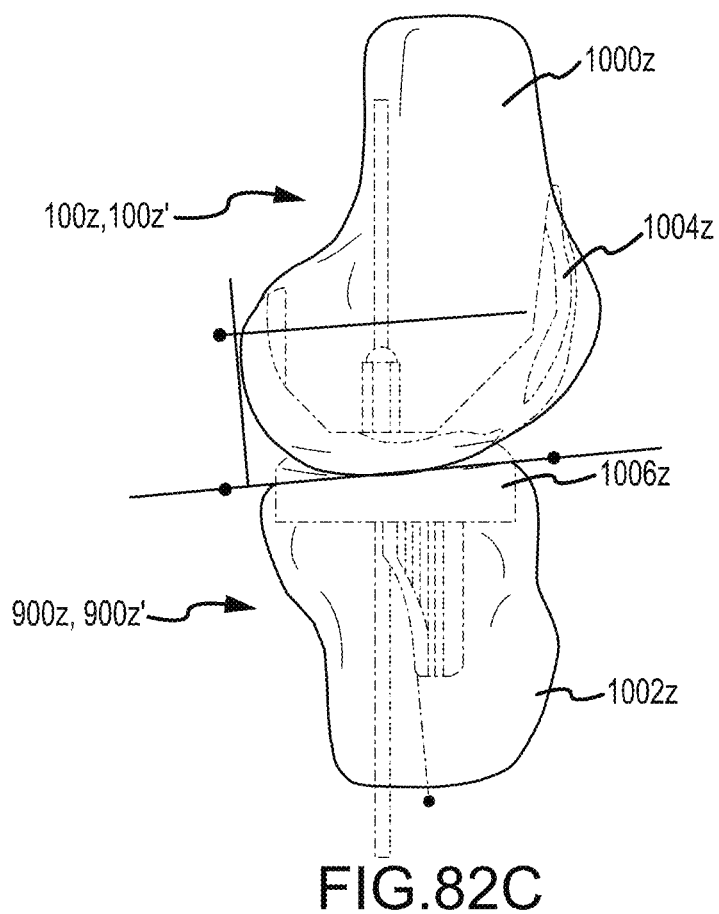

FIG. 82C is a medial view of the 3D implant models superimposed on the 3D bone models.

DETAILED DESCRIPTION

Disclosed herein are customized arthroplasty jigs 2 and systems 4 for, and methods of, producing such jigs 2. The jigs 2 are customized to fit specific bone surfaces of specific patients. Depending on the embodiment and to a greater or lesser extent, the jigs 2 are automatically planned and generated and may be similar to those disclosed in these three U.S. patent applications: U.S. patent application Ser. No. 11/656,323 to Park et al., titled "Arthroplasty Devices and Related Methods" and filed Jan. 19, 2007; U.S. patent application Ser. No. 10/146,862 to Park et al., titled "Improved Total Joint Arthroplasty System" and filed May 15, 2002; and U.S. patent Ser. No. 11/642,385 to Park et al., titled "Arthroplasty Devices and Related Methods" and filed Dec. 19, 2006. The disclosures of these three U.S. patent applications are incorporated by reference in their entireties into this Detailed Description.

As an overview, Section I. of the present disclosure provides a description of systems and methods of manufacturing custom arthroplasty cutting guides. Section II. of the present disclosure provides an overview of exemplary segmentation processes performed on medical images, and the generation of bone models representing bones of a joint in a deteriorated state. Section III. of the present disclosure describes an overview of a bone restoration process where image data of a patient's bones in a deteriorated state is restored to a pre-deteriorated state, and where the restored image data may be used to generate a restored bone model representing the patient bone in a pre-deteriorated or pre-degenerated state. And Section IV. of the present disclosure provides an overview of the pre-operative surgical planning process that may take place on the patient's image data (e.g., image data of deteriorated bone or restored image data).

Figure 1A:
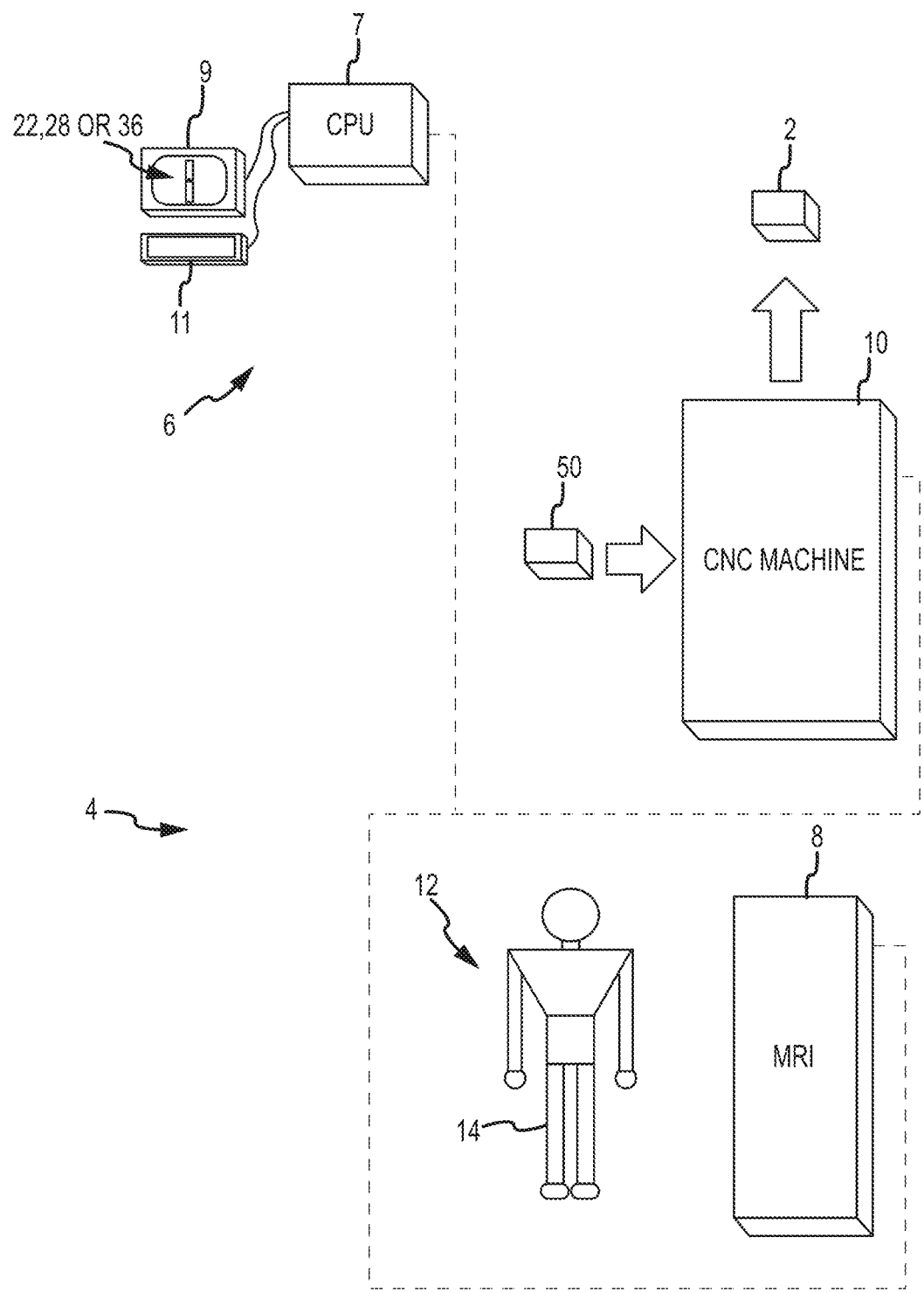
FIG. 1A is a schematic diagram of a system for employing the automated jig production method disclosed herein.

I. Overview of System and Method for Manufacturing Customized Arthroplasty Cutting Jigs For an overview discussion of the systems 4 for, and methods of, producing the customized arthroplasty jigs 2, reference is made to FIGS. 1A-1E. FIG. 1A is a schematic diagram of a system 4 for employing the automated jig production method disclosed herein. FIGS. 1B-1E are flow chart diagrams outlining the jig production method disclosed herein. The following overview discussion can be broken down into three sections.

The first section, which is discussed with respect to FIG. 1A and [blocks 100-125] of FIGS. 1B-1E, pertains to an example method of determining, in a three-dimensional ("3D") computer model environment, saw cut and drill hole locations 30, 32 relative to 3D computer models that are termed restored bone models 28 (also referenced as "planning models" throughout this submission.) In some embodiments, the resulting "saw cut and drill hole data" 44 is referenced to the restored bone models 28 to provide saw cuts and drill holes that will allow arthroplasty implants to restore the patient's joint to its pre-degenerated state. In other words, in some embodiments, the patient's joint may be restored to its natural alignment, whether valgus, varus or neutral.

While many of the embodiments disclosed herein are discussed with respect to allowing the arthroplasty implants to restore the patient's joint to its pre-degenerated or natural alignment state, many of the concepts disclosed herein may be applied to embodiments wherein the arthroplasty implants restore the patient's joint to a zero mechanical axis alignment such that the patient's knee joint ends up being neutral, regardless of whether the patient's predegenerated condition was varus, valgus or neutral. For example, as disclosed in U.S. patent application Ser. No. 12/760,388 to Park et al., titled "Preoperatively Planning An Arthroplasty Procedure And Generating A Corresponding Patient Specific Arthroplasty Resection Guide", filed Apr. 14, 2010, and incorporated by reference into this Detailed Description in its entirety, the system 4 for producing the customized arthroplasty jigs 2 may be such that the system initially generates the preoperative planning ("POP") associated with the jig in the context of the POP resulting in the patient's knee being restored to its natural alignment. Such a natural alignment POP is provided to the physician, and the physician determines if the POP should result in (1) natural alignment, (2) mechanical alignment, or (3) something between (1) and (2). The POP is then adjusted according to the physician's determination, the resulting jig 2 being configured such that the arthroplasty implants will restore the patient's joint to (1), (2) or (3), depending on whether the physician elected (1), (2) or (3), respectively. Accordingly, this disclosure should not be limited to methods resulting in natural alignment only, but should, where appropriate, be considered as applicable to methods resulting in natural alignment, zero mechanical axis alignment or an alignment somewhere between natural and zero mechanical axis alignment.

The second section, which is discussed with respect to FIG. 1A and [blocks 100-105 and 130-145] of FIGS. 1B-1E, pertains to an example method of importing into 3D computer generated jig models 38 3D computer generated surface models 40 of arthroplasty target areas 42 of 3D computer generated arthritic models 36 of the patient's joint bones. The resulting "jig data" 46 is used to produce a jig customized to matingly receive the arthroplasty target areas of the respective bones of the patient's joint.

The third section, which is discussed with respect to FIG. 1A and [blocks 150-165] of FIG. 1E, pertains to a method of combining or integrating the "saw cut and drill hole data" 44 with the "jig data" 46 to result in "integrated jig data" 48. The "integrated jig data" 48 is provided to the CNC machine 10 for the production of customized arthroplasty jigs 2 from jig blanks 50 provided to the CNC machine 10. The resulting customized arthroplasty jigs 2 include saw cut slots and drill holes positioned in the jigs 2 such that when the jigs 2 matingly receive the arthroplasty target areas of the patient's bones, the cut slots and drill holes facilitate preparing the arthroplasty target areas in a manner that allows the arthroplasty joint implants to generally restore the patient's joint line to its pre-degenerated state.

As shown in FIG. 1A, the system 4 includes one or more computers 6 having a CPU 7, a monitor or screen 9 and an operator interface controls 11. The computer 6 is linked to a medical imaging system 8, such as a CT or MRI machine 8, and a computer controlled machining system 10, such as a CNC milling machine 10.

In another embodiment, rather than using a single computer for the whole process, multiple computers can perform separate steps of the overall process, with each respective step managed by a respective technician skilled in that particular aspect of the overall process. The data generated in one process step on one computer can be then transferred for the next process step to another computer, for instance via a network connection.

As indicated in FIG. 1A, a patient 12 has a joint 14 (e.g., a knee, elbow, ankle, wrist, hip, shoulder, skull/vertebrae or vertebrae/vertebrae interface, etc.) to be replaced. The patient 12 has the joint 14 scanned in the imaging machine 8. The imaging machine 8 makes a plurality of scans of the joint 14, wherein each scan pertains to a thin slice of the joint 14.

As can be understood from FIG. 1B, the plurality of scans is used to generate a plurality of two-dimensional ("2D") images 16 of the joint 14 [block 100]. Where, for example, the joint 14 is a knee 14, the 2D images will be of the femur 18 and tibia 20. The imaging may be performed via CT or MRI. In one embodiment employing MRI, the imaging process may be as disclosed in U.S. patent application Ser. No. 11/946,002 to Park, which is entitled "Generating MRI Images Usable For The Creation Of 3D Bone Models Employed To Make Customized Arthroplasty Jigs," was filed Nov. 27, 2007 and is incorporated by reference in its entirety into this Detailed Description.

As can be understood from FIG. 1A, the 2D images are sent to the computer 6 for creating computer generated 3D models. As indicated in FIG. 1B, in one embodiment, point P is identified in the 2D images 16 [block 105]. In one embodiment, as indicated in [block 105] of FIG. 1A, point P may be at the approximate medial-lateral and anterior-posterior center of the patient's joint 14. In other embodiments, point P may be at any other location in the 2D images 16, including anywhere on, near or away from the bones 18, 20 or the joint 14 formed by the bones 18, 20.

As described later in this overview, point P may be used to locate the computer generated 3D models 22, 28, 36 created from the 2D images 16 and to integrate information generated via the 3D models. Depending on the embodiment, point P, which serves as a position and/or orientation reference, may be a single point, two points, three points, a point plus a plane, a vector, etc., so long as the reference P can be used to position and/or orient the 3D models 22, 28, 36 generated via the 2D images 16.

As discussed in detail below, the 2D images 16 are segmented along bone boundaries to create bone contour lines. Also, the 2D images 16 are segmented along bone and cartilage boundaries to create bone and cartilage lines.

Figure 1C:
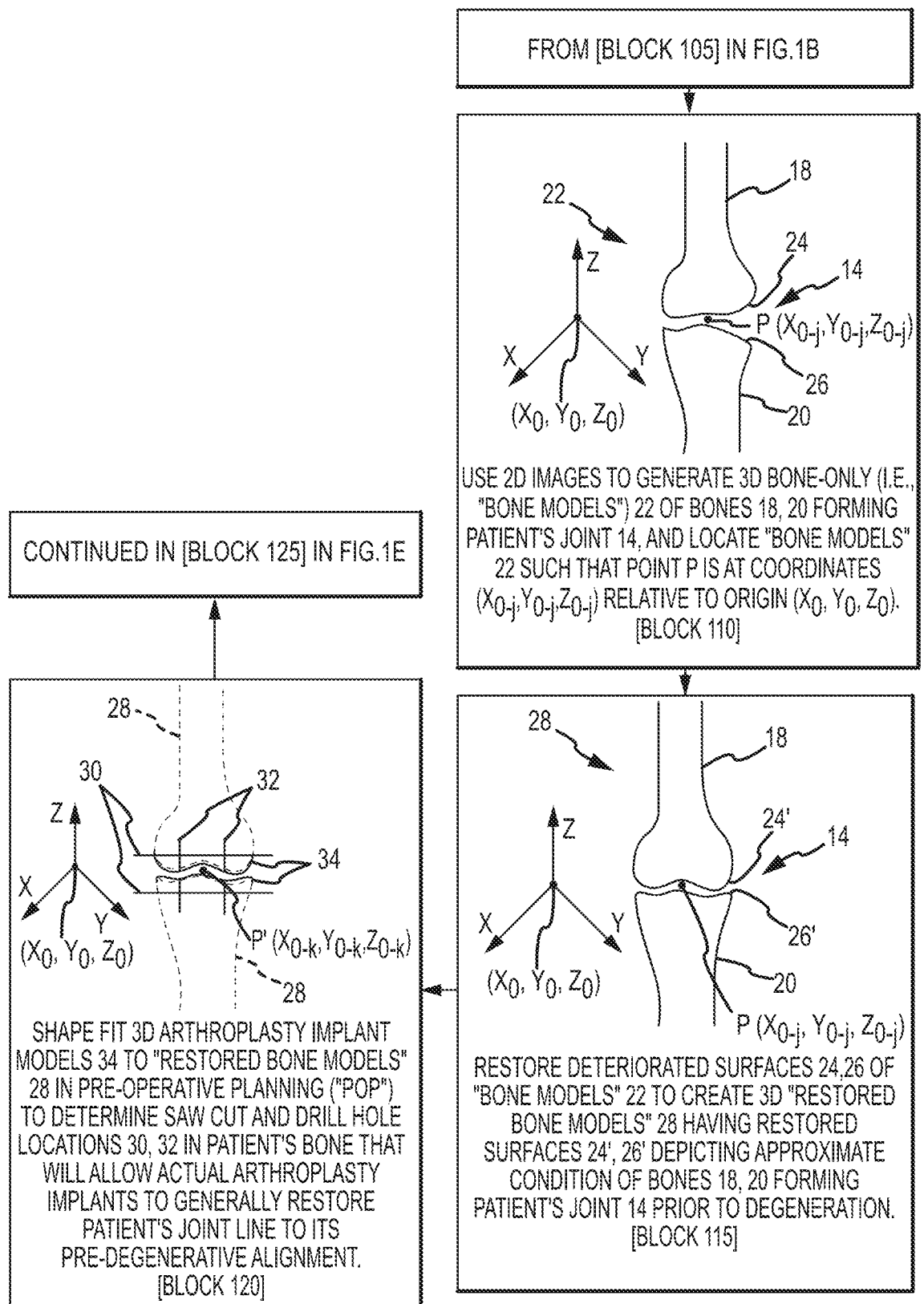

As shown in FIG. 1C, the segmented 2D images 16 (i.e., bone contour lines) are employed to create computer generated 3D bone-only (i.e., "bone models") 22 of the bones 18, 20 forming the patient's joint 14 [block 110]. The bone models 22 are located such that point P is at coordinates ($X_P$, $Y_P$, $Z_P$) relative to an origin ($X_O$, $Y_O$, $Z_O$) of an X-Y-Z coordinate system [block 110]. The bone models 22 depict the bones 18, 20 in the present deteriorated condition with their respective degenerated joint surfaces 24, 26, which may be a result of osteoarthritis, injury, a combination thereof, etc.

Computer programs for creating the 3D computer generated bone models 22 from the segmented 2D images 16 (i.e., bone contour lines) include: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org. Further, some embodiments may use customized software such as OMSegmentation (renamed "PerForm" in later versions), developed by OtisMed, Inc. The OMSegmentation software may extensively use "ITK" and/or "VTK" (Visualization Toolkit from Kitware, Inc, available at www.vtk.org.) Some embodiments may include using a prototype of OMSegmentation, and as such may utilize InsightSNAP software.

As indicated in FIG. 1C, the 3D computer generated bone models 22 are utilized to create 3D computer generated "restored bone models" or "planning bone models" 28 wherein the degenerated surfaces 24, 26 are modified or restored to approximately their respective conditions prior to degeneration [block 115]. Thus, the bones 18, 20 of the restored bone models 28 are reflected in approximately their condition prior to degeneration. The restored bone models 28 are located such that point P is at coordinates ($X_P$, $Y_P$, $Z_P$) relative to the origin ($X_0$, $Y_0$, $Z_0$). Thus, the restored bone models 28 share the same orientation and positioning relative to the origin ($X_0$, $Y_0$, $Z_0$) as the bone models 22.

In one embodiment, the restored bone models 28 are manually created from the bone models 22 by a person sitting in front of a computer 6 and visually observing the bone models 22 and their degenerated surfaces 24, 26 as 3D computer models on a computer screen 9. The person visually observes the degenerated surfaces 24, 26 to determine how and to what extent the degenerated surfaces 24, 26 surfaces on the 3D computer bone models 22 need to be modified to restore them to their pre-degenerated condition. By interacting with the computer controls 11, the person then manually manipulates the 3D degenerated surfaces 24, 26 via the 3D modeling computer program to restore the surfaces 24, 26 to a state the person believes to represent the pre-degenerated condition. The result of this manual restoration process is the computer generated 3D restored bone models 28, wherein the surfaces 24', 26' are indicated in a non-degenerated state.

In one embodiment, the bone restoration process is generally or completely automated. In other words, a computer program may analyze the bone models 22 and their degenerated surfaces 24, 26 to determine how and to what extent the degenerated surfaces 24, 26 surfaces on the 3D computer bone models 22 need to be modified to restore them to their pre-degenerated condition. The computer program then manipulates the 3D degenerated surfaces 24, 26 to restore the surfaces 24, 26 to a state intended to represent the pre-degenerated condition. The result of this automated restoration process is the computer generated 3D restored bone models 28, wherein the surfaces 24', 26' are indicated in a non-degenerated state. For more detail regarding a generally or completely automated system for the bone restoration process, see U.S. patent application Ser. No. 12/111,924 to Park, which is titled "Generation of a Computerized Bone Model Representative of a Pre-Degenerated State and Usable in the Design and Manufacture of Arthroplasty Devices", was filed Apr. 29, 2008, and is incorporated by reference in its entirety into this Detailed Description.

As depicted in FIG. 1C, the restored bone models 28 are employed in a pre-operative planning ("POP") procedure to determine saw cut locations 30 and drill hole locations 32 in the patient's bones that will allow the arthroplasty joint implants to generally restore the patient's joint line to it pre-degenerative alignment [block 120].

In one embodiment, the POP procedure is a manual process, wherein computer generated 3D implant models 34 (e.g., femur and tibia implants in the context of the joint being a knee) and restored bone models 28 are manually manipulated relative to each other by a person sitting in front of a computer 6 and visually observing the implant models 34 and restored bone models 28 on the computer screen 9 and manipulating the models 28, 34 via the computer controls 11. By superimposing the implant models 34 over the restored bone models 28, or vice versa, the joint surfaces of the implant models 34 can be aligned or caused to correspond with the joint surfaces of the restored bone models 28. By causing the joint surfaces of the models 28, 34 to so align, the implant models 34 are positioned relative to the restored bone models 28 such that the saw cut locations 30 and drill hole locations 32 can be determined relative to the restored bone models 28.

In one embodiment, the POP process is generally or completely automated. For example, a computer program may manipulate computer generated 3D implant models 34 (e.g., femur and tibia implants in the context of the joint being a knee) and restored bone models or planning bone models 28 relative to each other to determine the saw cut and drill hole locations 30, 32 relative to the restored bone models 28. The implant models 34 may be superimposed over the restored bone models 28, or vice versa. In one embodiment, the implant models 34 are located at point P' ($X_{P'}$, $Y_{P'}$, $Z_{P'}$) relative to the origin ($X_0$, $Y_0$, $Z_0$), and the restored bone models 28 are located at point P ($X_P$, $Y_P$, $Z_P$). To cause the joint surfaces of the models 28, 34 to correspond, the computer program may move the restored bone models 28 from point P ($X_P$, $Y_P$, $Z_P$) to point P' ($X_{P'}$, $Y_{P'}$, $Z_{P1}$), or vice versa. Once the joint surfaces of the models 28, 34 are in close proximity, the joint surfaces of the implant models 34 may be shape-matched to align or correspond with the joint surfaces of the restored bone models 28. By causing the joint surfaces of the models 28, 34 to so align, the implant models 34 are positioned relative to the restored bone models 28 such that the saw cut locations 30 and drill hole locations 32 can be determined relative to the restored bone models 28. For more detail regarding a generally or completely automated system for the POP process, see U.S. patent application Ser. No. 12/563,809 to Park, which is titled Arthroplasty System and Related Methods, was filed Sep. 21, 2009, and is incorporated by reference in its entirety into this Detailed Description.

While the preceding discussion regarding the POP process is given in the context of the POP process employing the restored bone models as computer generated 3D bone models, in other embodiments, the POP process may take place without having to employ the 3D restored bone models, but instead taking placing as a series of 2D operations. For more detail regarding a generally or completely automated system for the POP process wherein the POP process does not employ the 3D restored bone models, but instead utilizes a series of 2D operations, see U.S. patent application Ser. No. 12/546,545 to Park, which is titled Arthroplasty System and Related Methods, was filed Aug. 24, 2009, and is incorporated by reference in its entirety into this Detailed Description.

As indicated in FIG. 1E, in one embodiment, the data 44 regarding the saw cut and drill hole locations 30, 32 relative to point P' ($X_{P'}$, $Y_{P'}$, $Z_{P'}$) is packaged or consolidated as the "saw cut and drill hole data" 44 [block 145]. The "saw cut and drill hole data" 44 is then used as discussed below with respect to [block 150] in FIG. 1E.

Figure 1D:
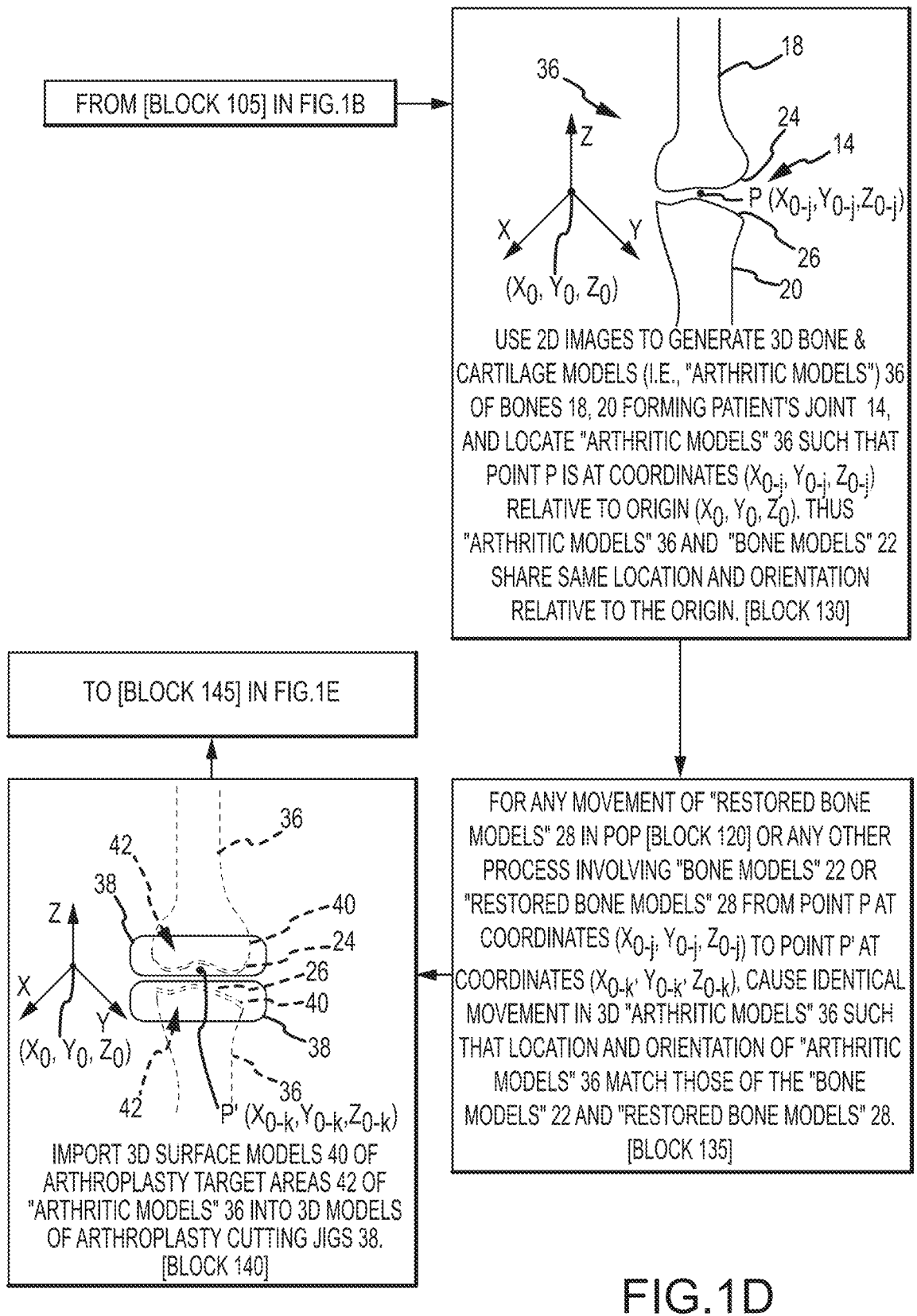

As can be understood from FIG. 1D, the 2D images 16 employed to generate the bone models 22 discussed above with respect to [block 110] of FIG. 1C are also segmented along bone and cartilage boundaries to form bone and cartilage contour lines that are used to create computer generated 3D bone and cartilage models (i.e., "arthritic models") 36 of the bones 18, 20 forming the patient's joint 14 [block 130]. Like the above-discussed bone models 22, the arthritic models 36 are located such that point P is at coordinates ($X_P$, $Y_P$, $Z_P$) relative to the origin ($X_0$, $Y_0$, $Z_0$) of the X-Y-Z axis [block 130]. Thus, the bone and arthritic models 22, 36 share the same location and orientation relative to the origin ($X_0$, $Y_0$, $Z_0$). This position/orientation relationship is generally maintained throughout the process discussed with respect to FIGS. 1B-1E. Accordingly, movements relative to the origin ($X_0$, $Y_0$, $Z_0$) of the bone models 22 and the various descendants thereof (i.e., the restored bone models 28, bone cut locations 30 and drill hole locations 32) are also applied to the arthritic models 36 and the various descendants thereof (i.e., the jig models 38). Maintaining the position/orientation relationship between the bone models 22 and arthritic models 36 and their respective descendants allows the "saw cut and drill hole data" 44 to be integrated into the "jig data" 46 to form the "integrated jig data" 48 employed by the CNC machine 10 to manufacture the customized arthroplasty jigs 2.

Computer programs for creating the 3D computer generated arthritic models 36 from the segmented 2D images 16 (i.e., bone and cartilage contour lines) include: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org. Some embodiments may use customized software such as OMSegmentation (renamed "PerForm" in later versions), developed by OtisMed, Inc. The OMSegmentation software may extensively use "ITK" and/or "VTK" (Visualization Toolkit from Kitware, Inc, available at www.vtk.org.). Also, some embodiments may include using a prototype of OMSegmentation, and as such may utilize InsightSNAP software.

Similar to the bone models 22, the arthritic models 36 depict the bones 18, 20 in the present deteriorated condition with their respective degenerated joint surfaces 24, 26, which may be a result of osteoarthritis, injury, a combination thereof, etc. However, unlike the bone models 22, the arthritic models 36 are not bone-only models, but include cartilage in addition to bone. Accordingly, the arthritic models 36 depict the arthroplasty target areas 42 generally as they will exist when the customized arthroplasty jigs 2 matingly receive the arthroplasty target areas 42 during the arthroplasty surgical procedure.

As indicated in FIG. 1D and already mentioned above, to coordinate the positions/orientations of the bone and arthritic models 36, 36 and their respective descendants, any movement of the restored bone models 28 from point P to point P' is tracked to cause a generally identical displacement for the "arthritic models" 36 [block 135].

As depicted in FIG. 1D, computer generated 3D surface models 40 of the arthroplasty target areas 42 of the arthritic models 36 are imported into computer generated 3D arthroplasty jig models 38 [block 140]. Thus, the jig models 38 are configured or indexed to matingly receive the arthroplasty target areas 42 of the arthritic models 36. Jigs 2 manufactured to match such jig models 38 will then matingly receive the arthroplasty target areas of the actual joint bones during the arthroplasty surgical procedure.

In one embodiment, the procedure for indexing the jig models 38 to the arthroplasty target areas 42 is a manual process. The 3D computer generated models 36, 38 are manually manipulated relative to each other by a person sitting in front of a computer 6 and visually observing the jig models 38 and arthritic models 36 on the computer screen 9 and manipulating the models 36, 38 by interacting with the computer controls 11. In one embodiment, by superimposing the jig models 38 (e.g., femur and tibia arthroplasty jigs in the context of the joint being a knee) over the arthroplasty target areas 42 of the arthritic models 36, or vice versa, the surface models 40 of the arthroplasty target areas 42 can be imported into the jig models 38, resulting in jig models 38 indexed to matingly receive the arthroplasty target areas 42 of the arthritic models 36. Point P' ($X_{P'}$, $Y_{P'}$, $Z_{P'}$) can also be imported into the jig models 38, resulting in jig models 38 positioned and oriented relative to point P' ($X_{P'}$, $Y_{P'}$, $Z_{P'}$) to allow their integration with the bone cut and drill hole data 44 of [block 125].

In one embodiment, the procedure for indexing the jig models 38 to the arthroplasty target areas 42 is generally or completely automated, as disclosed in U.S. patent application Ser. No. 11/959,344 to Park, which is entitled System and Method for Manufacturing Arthroplasty Jigs, was filed Dec. 18, 2007 and is incorporated by reference in its entirety into this Detailed Description. For example, a computer program may create 3D computer generated surface models 40 of the arthroplasty target areas 42 of the arthritic models 36. The computer program may then import the surface models 40 and point P' ($X_{P'}$, $Y_{P'}$, $Z_{P'}$) into the jig models 38, resulting in the jig models 38 being indexed to matingly receive the arthroplasty target areas 42 of the arthritic models 36. The resulting jig models 38 are also positioned and oriented relative to point P' ($X_{P'}$, $Y_{P'}$, $Z_{P'}$) to allow their integration with the bone cut and drill hole data 44 of [block 125].

In one embodiment, the arthritic models 36 may be 3D volumetric models as generated from a closed-loop process. In other embodiments, the arthritic models 36 may be 3D surface models as generated from an open-loop process.

As indicated in FIG. 1E, in one embodiment, the data regarding the jig models 38 and surface models 40 relative to point P' ($X_{P'}$, $Y_{P'}$, $Z_{P'}$) is packaged or consolidated as the "jig data" 46 [block 145]. The "jig data" 46 is then used as discussed below with respect to [block 150] in FIG. 1E.

As can be understood from FIG. 1E, the "saw cut and drill hole data" 44 is integrated with the "jig data" 46 to result in the "integrated jig data" 48 [block 150]. As explained above, since the "saw cut and drill hole data" 44, "jig data" 46 and their various ancestors (e.g., models 22, 28, 36, 38) are matched to each other for position and orientation relative to point P and P', the "saw cut and drill hole data" 44 is properly positioned and oriented relative to the "jig data" 46 for proper integration into the "jig data" 46. The resulting "integrated jig data" 48, when provided to the CNC machine 10, results in jigs 2: (1) configured to matingly receive the arthroplasty target areas of the patient's bones; and (2) having cut slots and drill holes that facilitate preparing the arthroplasty target areas in a manner that allows the arthroplasty joint implants to generally restore the patient's joint line to its pre-degenerated state.

As can be understood from FIGS. 1A and 1E, the "integrated jig data" 44 is transferred from the computer 6 to the CNC machine 10 [block 155]. Jig blanks 50 are provided to the CNC machine 10 [block 160], and the CNC machine 10 employs the "integrated jig data" to machine the arthroplasty jigs 2 from the jig blanks 50.

Figure 1F:
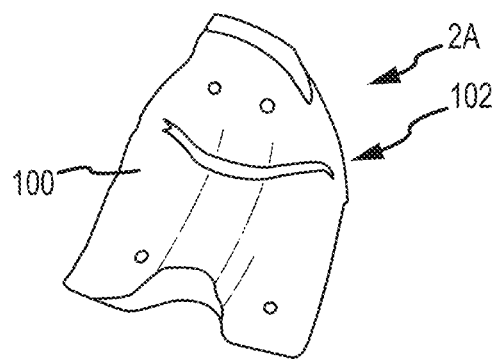
FIGS. 1F and 1G are, respectively, bottom and top perspective views of an example customized arthroplasty femur jig.
Figure 9:
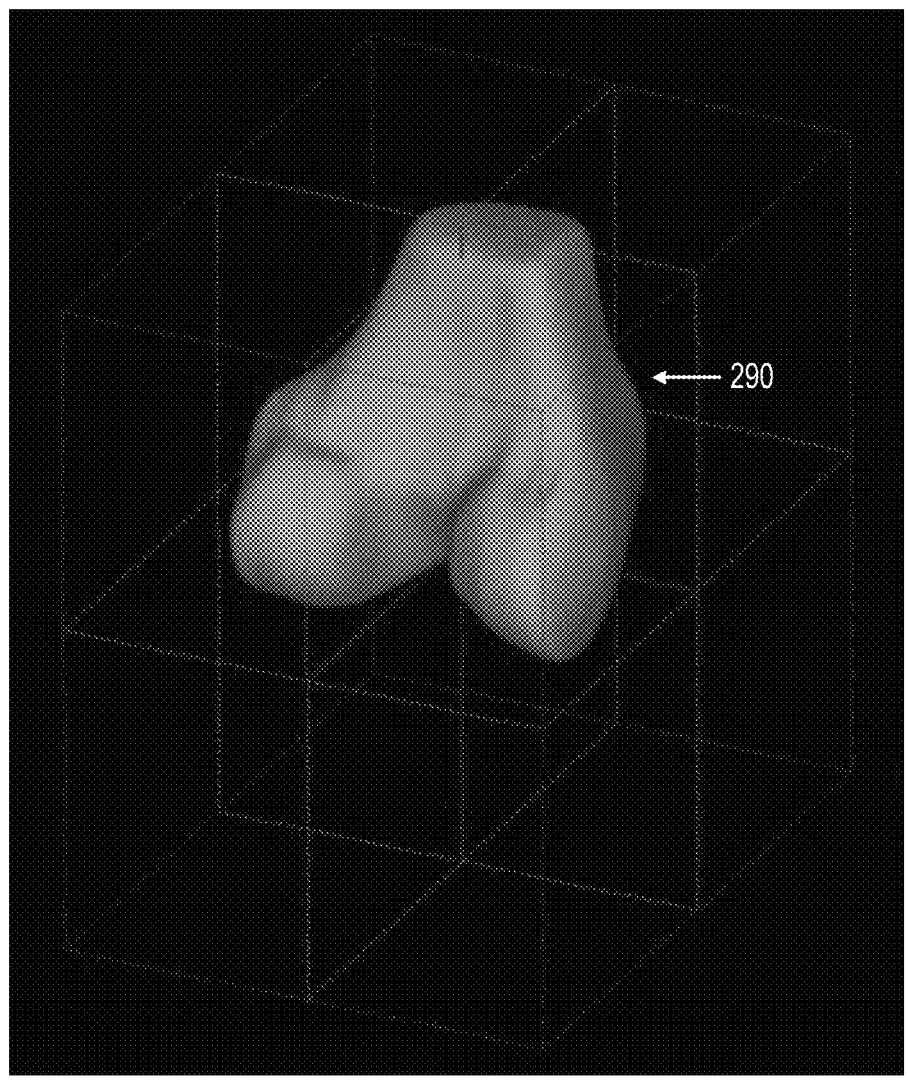
FIG. 9 depicts a 3D mesh geometry of a femur.
Figure 10:
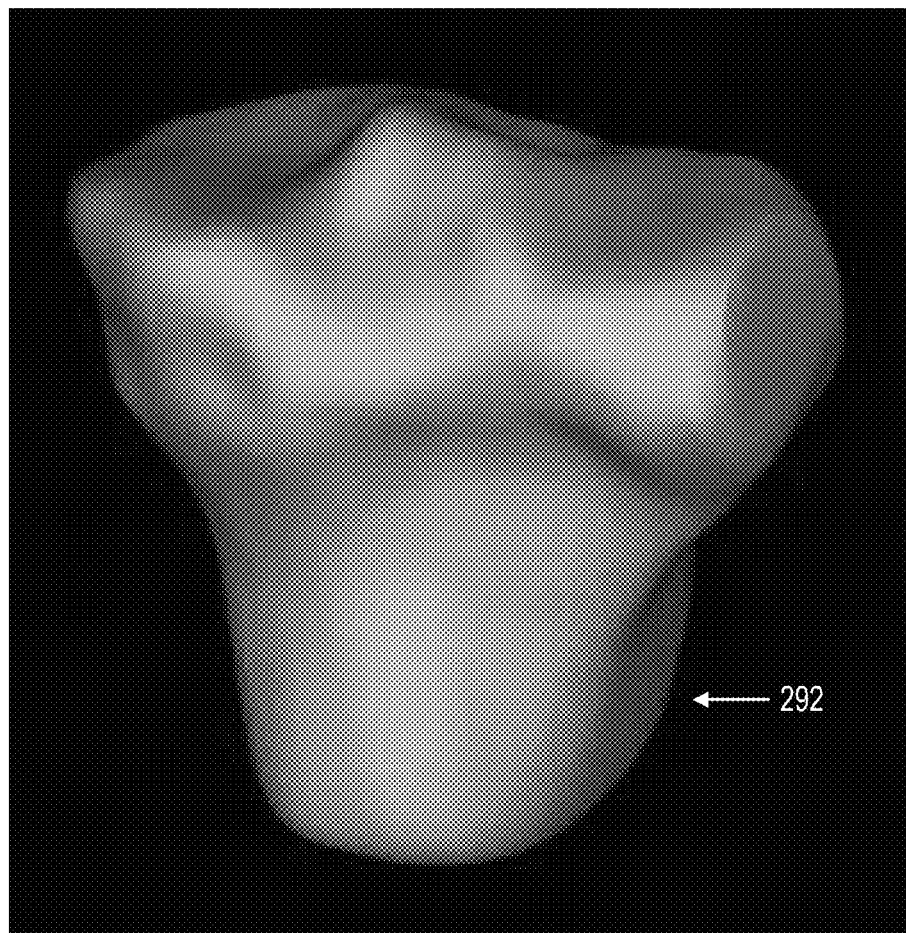
FIG. 10 depicts a 3D mesh geometry of a tibia.
Figure 11:
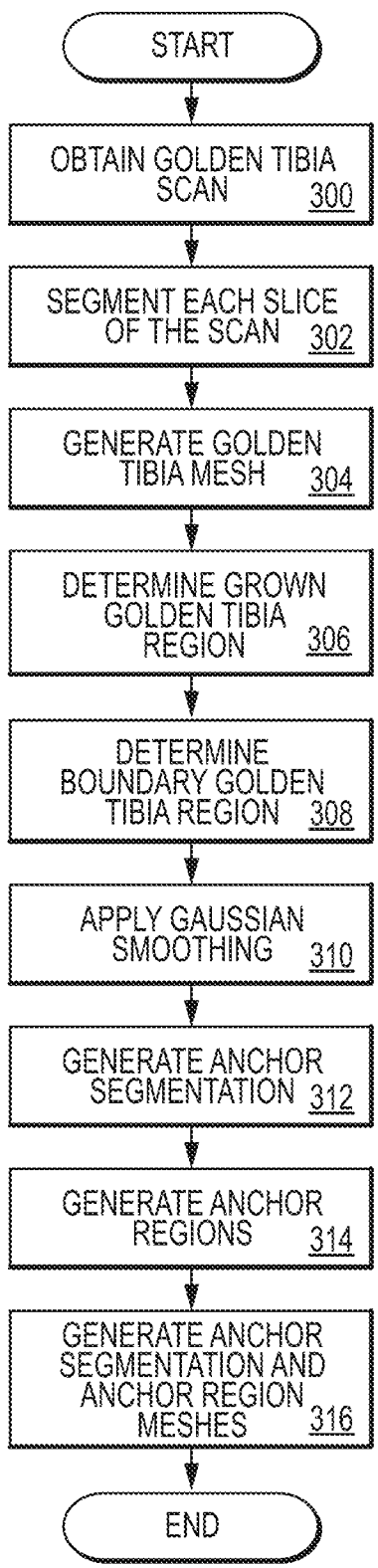
FIG. 11 depicts a flowchart illustrating one method for generating a golden template.

For a discussion of example customized arthroplasty cutting jigs 2 capable of being manufactured via the above-discussed process, reference is made to FIGS. 1F-11. While, as pointed out above, the above-discussed process may be employed to manufacture jigs 2 configured for arthroplasty procedures involving knees, elbows, ankles, wrists, hips, shoulders, vertebra interfaces, etc., the jig examples depicted in FIGS. 1F-1I are for total knee replacement ("TKR") or partial knee replacement ("PKR") procedures. Thus, FIGS. 1F and 1G are, respectively, bottom and top perspective views of an example customized arthroplasty femur jig 2A, and FIGS. 1H and 11 are, respectively, bottom and top perspective views of an example customized arthroplasty tibia jig 2B.

Figure 1G:
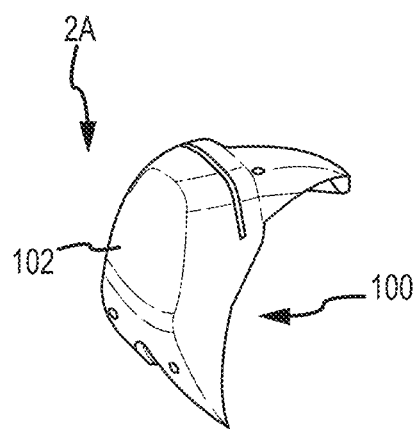

As indicated in FIGS. 1F and 1G, a femur arthroplasty jig 2A may include an interior side or portion 100 and an exterior side or portion 102. When the femur cutting jig 2A is used in a TKR or PKR procedure, the interior side or portion 100 faces and matingly receives the arthroplasty target area 42 of the femur lower end, and the exterior side or portion 102 is on the opposite side of the femur cutting jig 2A from the interior portion 100.

The interior portion 100 of the femur jig 2A is configured to match the surface features of the damaged lower end (i.e., the arthroplasty target area 42) of the patient's femur 18. Thus, when the target area 42 is received in the interior portion 100 of the femur jig 2A during the TKR or PKR surgery, the surfaces of the target area 42 and the interior portion 100 match.

The surface of the interior portion 100 of the femur cutting jig 2A is machined or otherwise formed into a selected femur jig blank 50A and is based or defined off of a 3D surface model 40 of a target area 42 of the damaged lower end or target area 42 of the patient's femur 18.

Figure 1H:
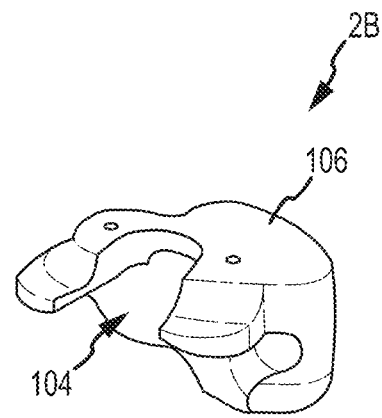
FIGS. 1H and 1I are, respectively, bottom and top perspective views of an example customized arthroplasty tibia jig.
Figure 1I:
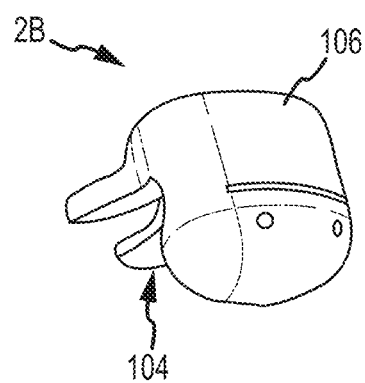

As indicated in FIGS. 1H and 11, a tibia arthroplasty jig 2B may include an interior side or portion 104 and an exterior side or portion 106. When the tibia cutting jig 2B is used in a TKR or PKR procedure, the interior side or portion 104 faces and matingly receives the arthroplasty target area 42 of the tibia upper end, and the exterior side or portion 106 is on the opposite side of the tibia cutting jig 2B from the interior portion 104.

The interior portion 104 of the tibia jig 2B is configured to match the surface features of the damaged upper end (i.e., the arthroplasty target area 42) of the patient's tibia 20. Thus, when the target area 42 is received in the interior portion 104 of the tibia jig 2B during the TKR or PKR surgery, the surfaces of the target area 42 and the interior portion 104 match.

The surface of the interior portion 104 of the tibia cutting jig 2B is machined or otherwise formed into a selected tibia jig blank 50B and is based or defined off of a 3D surface jig model 40 of a target area 42 of the damaged upper end or target area 42 of the patient's tibia 20.

II. Overview of Segmentation Process

A. Automatic Segmentation of Scanner Modality Image Data to Generate 3D Surface Model of a Patient's Bone In one embodiment as mentioned above, the 2D images 16 of the patient's joint 14 as generated via the imaging system 8 (see FIG. 1A and [block 100] of FIG. 1B) are segmented or, in other words, analyzed to identify the contour lines of the bones and/or cartilage surfaces that are of significance with respect to generating 3D models 22, 36, as discussed above with respect to [blocks 110 and 130] of FIGS. 1C and 1D. Specifically, a variety of image segmentation processes may occur with respect to the 2D images 16 and the data associated with such 2D images 16 to identify contour lines that are then compiled into 3D bone models, such as bone models 22 and arthritic models 36. A variety of processes and methods for performing image segmentation are disclosed in the remainder of this Detailed Description.

Figure 2A:
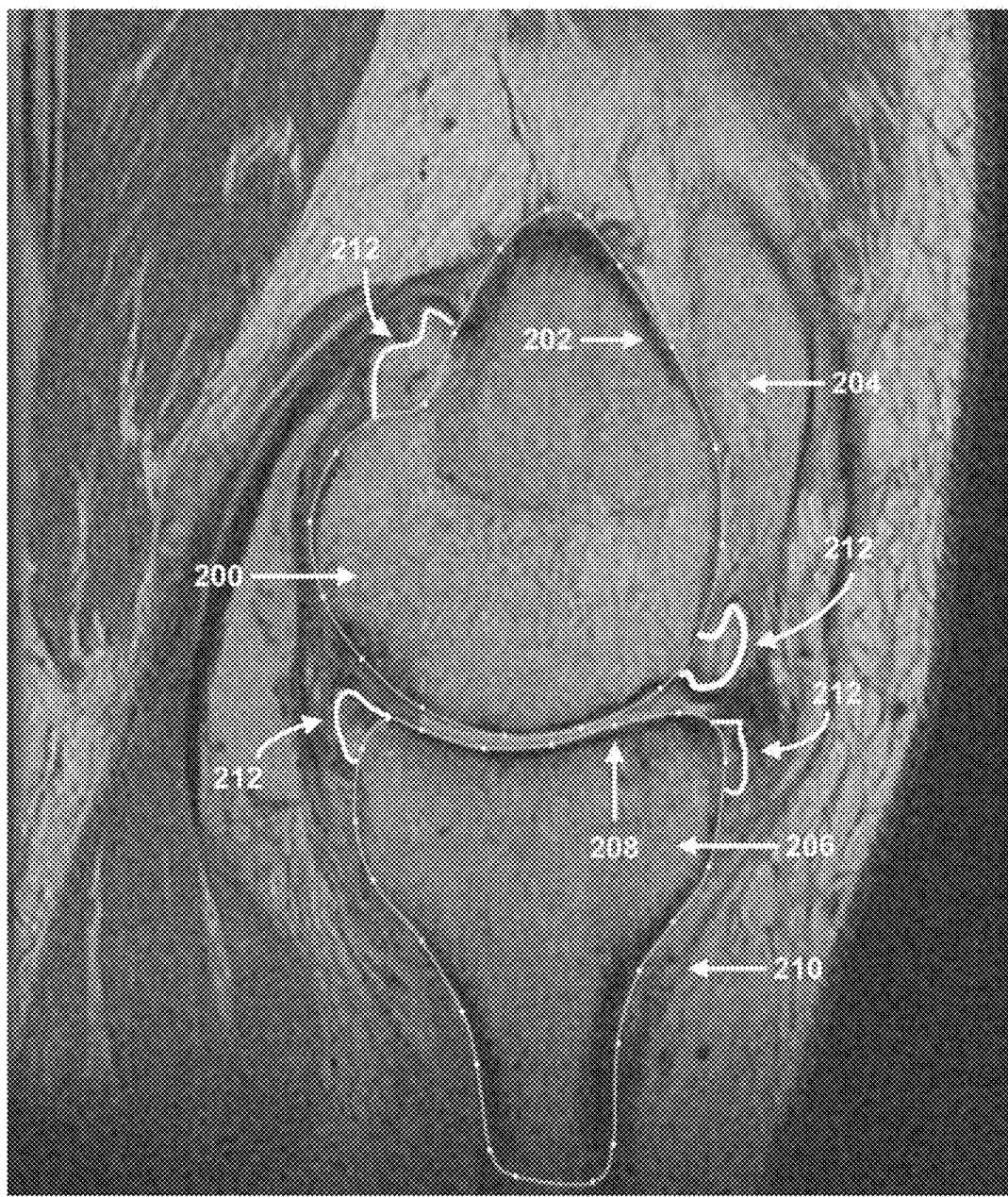
FIG. 2A is a sagittal plane image slice depicting a femur and tibia and neighboring tissue regions with similar image intensity.

The imager 8 typically generates a plurality of image slices 16 via repetitive imaging operations. Depending on whether the imager 8 is a MRI or CT imager, each image slice will be a MRI or CT slice. As shown in FIG. 2A, the image slice may depict the cancellous bone 200, the cortical bone 202 surrounding the cancellous bone, and the articular cartilage lining portions of the cortical bone 202 of an object of interest of a joint, e.g., a femur 204 in a patient's knee joint 14. The image may further depict the cancellous bone 206, the cortical bone 208 of another object of interest in the joint, e.g., a tibia 210 of the knee joint 14. In one embodiment, each image slice 16 may be a two-millimeter 2D image slice.

One embodiment may automatically segment one or more features of interest (e.g., bones) present in MRI or CT scans of a patient joint, e.g., knee, hip, elbow, etc. A typical scan of a knee joint may represent approximately a 100-millimeter by 150-millimeter by 150-millimeter volume of the joint and may include about 40 to 80 slices taken in sagittal planes. A sagittal plane is an imaginary plane that travels from the top to the bottom of the object (e.g., the human body), dividing it into medial and lateral portions. It is to be appreciated that a large inter-slice spacing may result in voxels (volume elements) with aspect ratios of about one to seven between the resolution in the sagittal plane (e.g., the y z plane) and the resolution along the x axis (i.e., each scan slice lies in the yz plane with a fixed value of x). For example, a two-millimeter slice that is 150-millimeters by 150-millimeters may be comprised of voxels that are approximately 0.3-millimeter by 0.3-millimeter by 2-millimeters (for a 512 by 512 image resolution in the sagittal plane).

In one embodiment, each slice may be a gray scale image with a resolution of 512 by 512 voxels where the voxel value represents the brightness (intensity) of the voxel. The intensity may be stored as a 16-bit integer resulting in an intensity range from 0 to 65,535, where 0 may represent black and 65,535 may represent white. The intensity of each voxel typically represents the average intensity of the voxel volume. Other embodiments may employ scans having higher or lower resolutions in the sagittal plane, different inter-slice spacing, or images where the intensity may be represented by a 24 bit vector (e.g., eight bits each for a red component, green component and blue component). Additionally, other embodiments may store intensity values as 32-bit signed integers or floating point values.

Figure 2B:
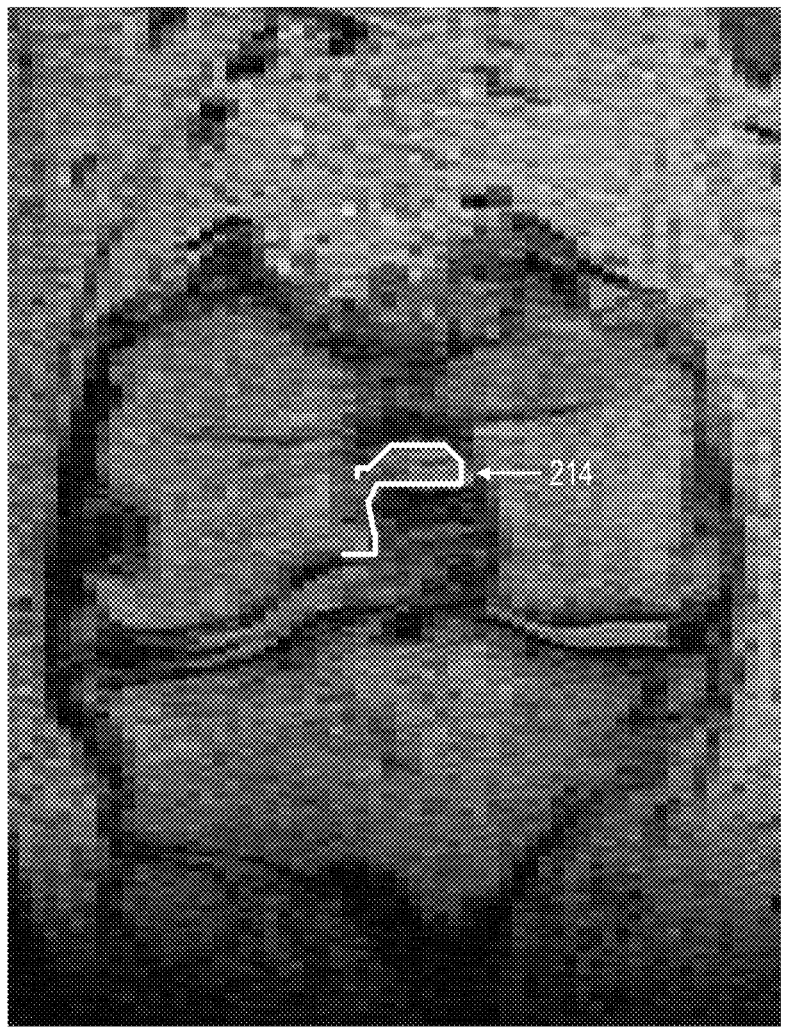
FIG. 2B is a sagittal plane image slice depicting a region extending into the slice from an adjacent image slice.
Figure 2C:
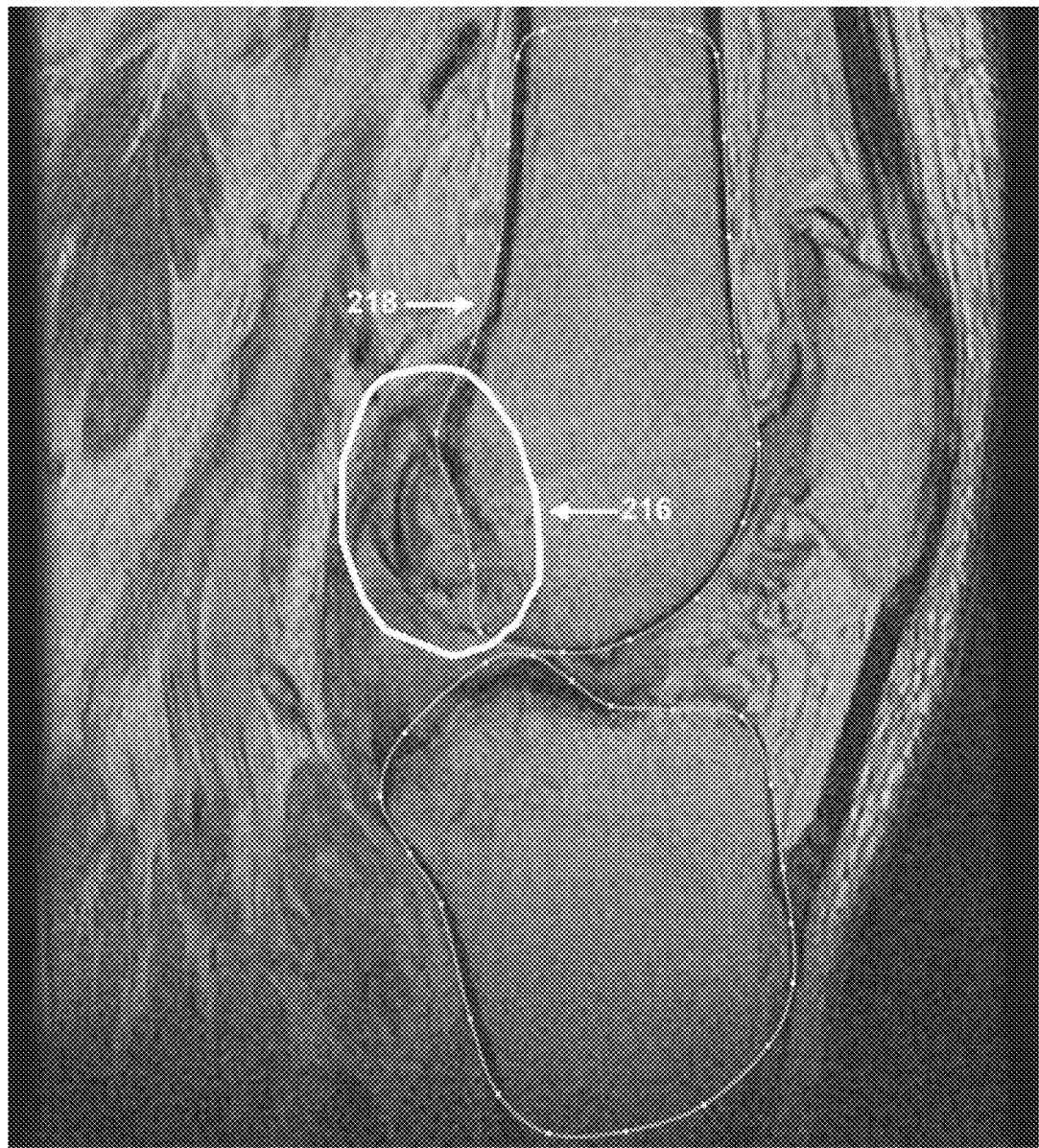
FIG. 2C is a sagittal plane image slice depicting a region of a femur that is approximately tangent to the image slice.

Typical MRI and CT scan data generally provide images where parts of a bone boundary of interest may be well defined while other parts of the bone boundary may be difficult to determine due to voxel volume averaging, the presence of osteophyte growth, the presence of tissue having similar image intensities in neighboring areas to the object to be segmented, amongst other things. Such poor definition of parts of the bone boundary in the images may cause traditional automated segmentation techniques to fail. For example, FIG. 2A depicts regions 212 within a slice where an object boundary may not be visible due to neighboring tissue having about the same intensity as the feature of interest. Depicted in FIG. 2B are regions 214 that may be extended into the slice from adjacent slices due to a high voxel aspect ratio. Depicted in FIG. 2C is a region 216 of the bone boundary 218 that may disappear or lose regularity when the bone boundary 218 is approximately tangent to the slice.

One embodiment may employ image segmentation techniques using a golden template to segment bone boundaries and provide improved segmentation results over traditional automated segmentation techniques. Such techniques may be used to segment an image when similarity between pixels within an object to be identified may not exist. That is, the pixels within a region to be segmented may not be similar with respect to some characteristic or computed property such as a color, intensity or texture that may be employed to associate similar pixels into regions. Instead, a spatial relationship of the object with respect to other objects may be used to identify the object of interest. In one embodiment, a 3D golden template of a feature of interest to be segmented may be used during the segmentation process to locate the target feature in a target scan. For example, when segmenting a scan of a knee joint, a typical 3D image of a known good femur (referred to as a golden femur template) may be used to locate and outline (i.e., segment) a femur in a target scan.

Generally, much of the tissues surrounding the cancellous and cortical matter of the bone to be segmented may vary from one MRI scan to another MRI scan. This may be due to disease and/or patient joint position (e.g., a patient may not be able to straighten the joint of interest because of pain). By using surrounding regions that have a stable connection with the bone (e.g., the grown golden and boundary golden regions of the template as described in more detail below), the registration may be improved. Additionally, use of these regions allows the bone geometry of interest to be captured during the segmentation rather than other features not of interest. Further, the segmentation takes advantage of the higher resolution of features of interest in certain directions of the scan data through the use of a combination of 2D and 3D techniques, that selectively increases the precision of the segmentation as described in more detail below with respect to refining the bone registration using an artificially generated image.

Figure 3A:
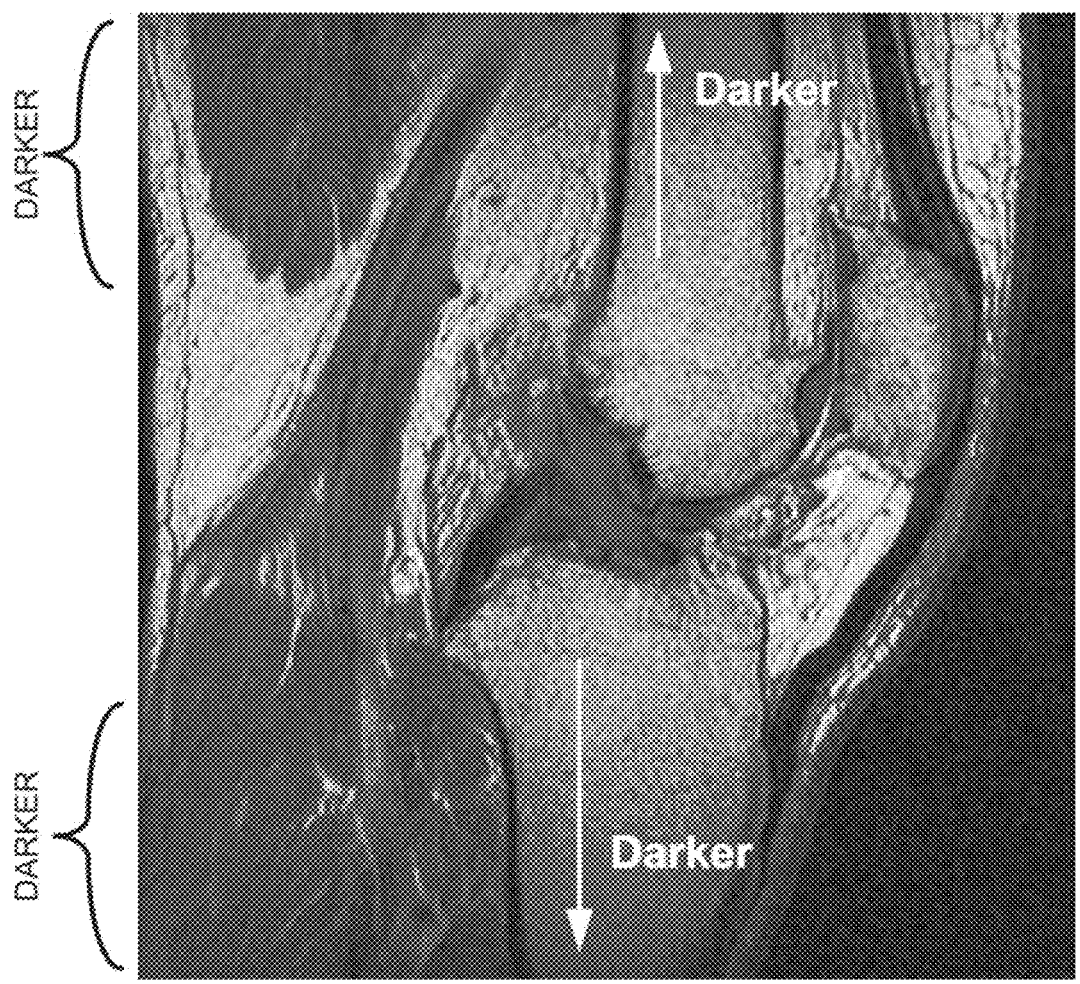
FIG. 3A is a sagittal plane image slice depicting an intensity gradient across the slice.
Figure 3B:
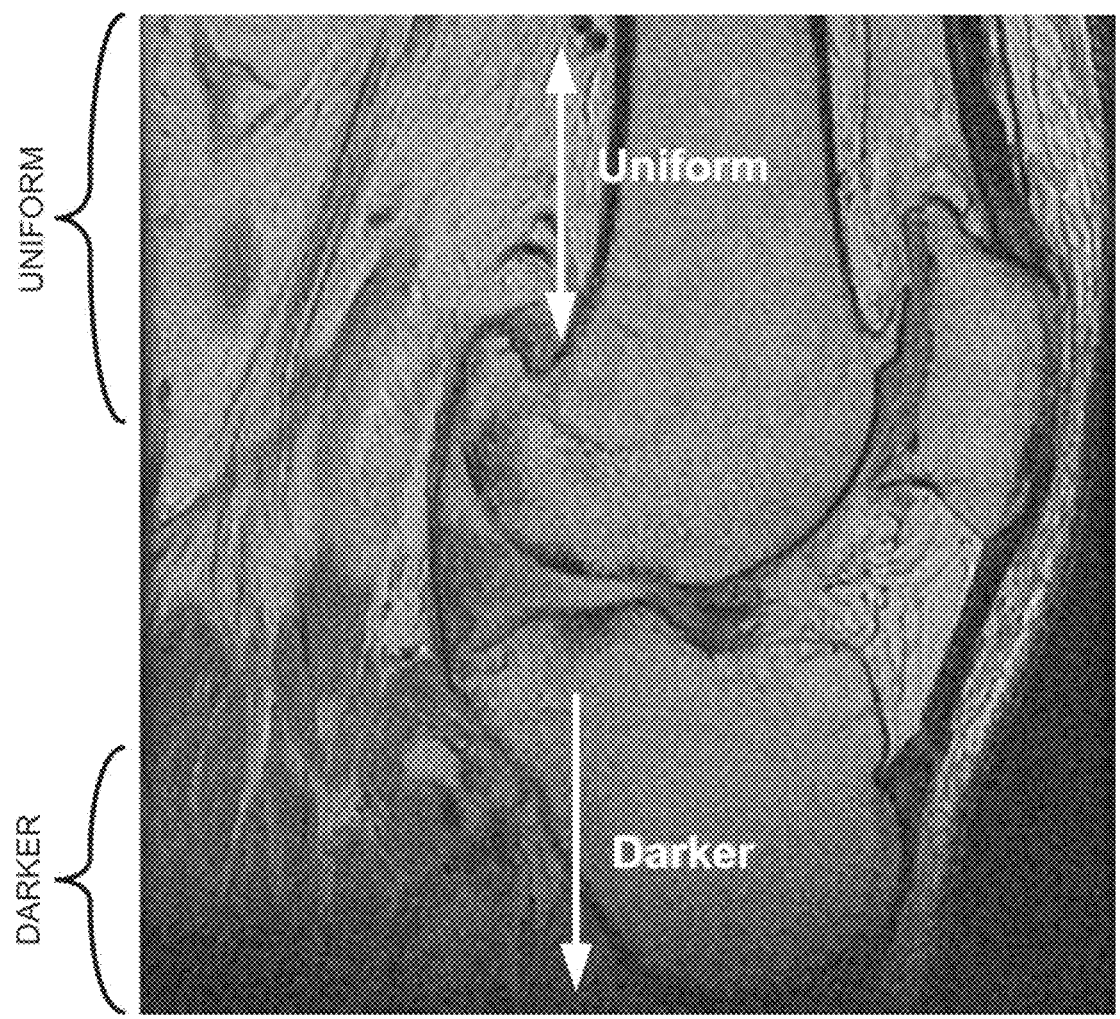
FIG. 3B is a sagittal plane image slice depicting another intensity gradient across the slice.
Figure 3C:
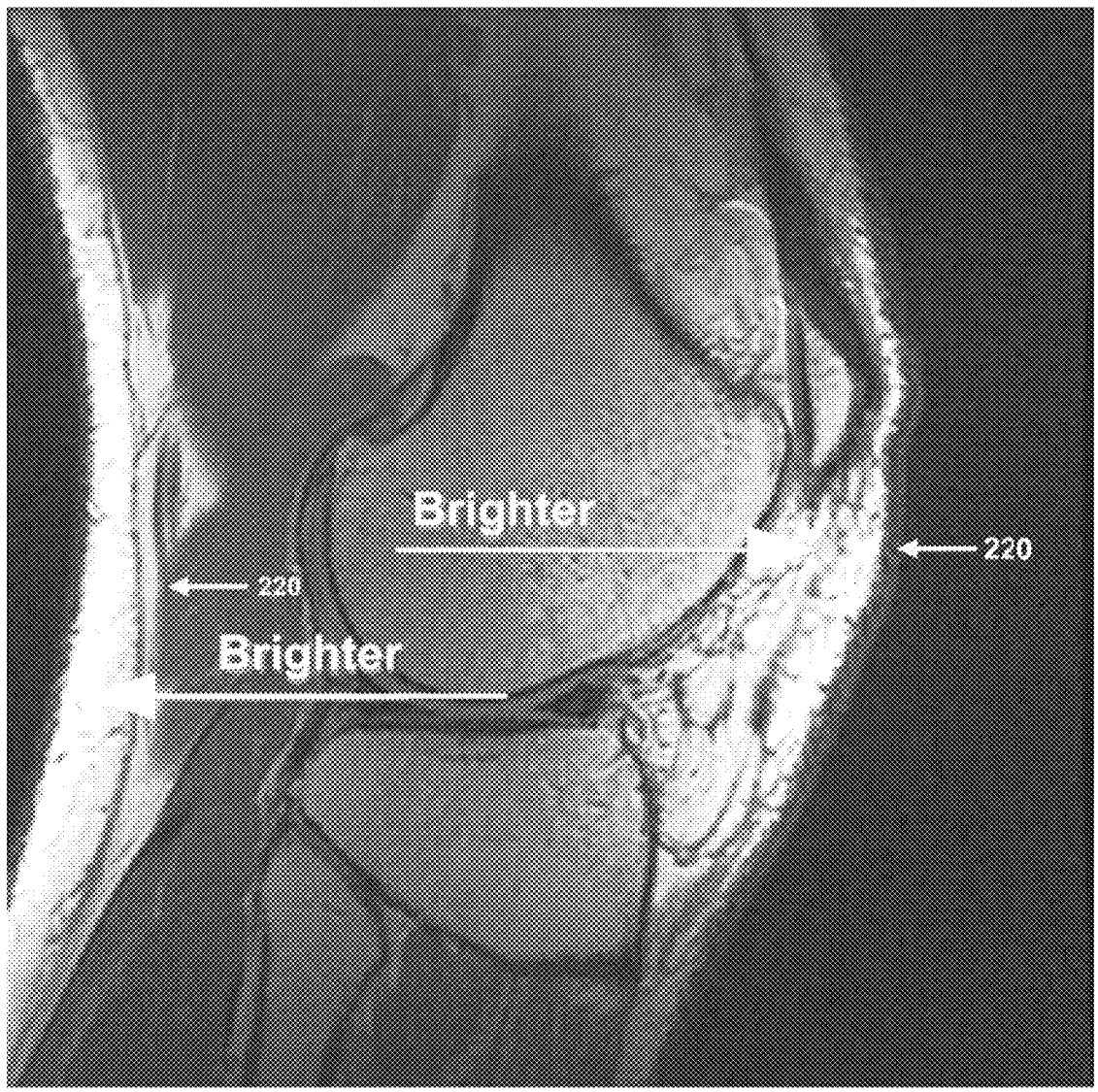
FIG. 3C is a sagittal plane image slice depicting another intensity gradient across the slice.
Figure 4A:
FIG. 4A depicts a sagittal plane image slice with a high noise level.
Figure 4B:
FIG. 4B depicts a sagittal plane image slice with a low noise level.

The segmentation method employed by one embodiment may accommodate a variety of intensity gradients across the scan data. FIGS. 3A-C depict intensity gradients (i.e., the intensity varies non-uniformly across the image) in slices (an intensity gradient that is darker on the top and bottom as depicted in FIG. 3A, an intensity gradient that is darker on the bottom as depicted in FIG. 3B, and an intensity gradient 220 that is brighter on the sides as depicted in FIG. 3C) that may be segmented by one embodiment. Further, the embodiment generally does not require approximately constant noise in the slices to be segmented. The embodiment may accommodate different noise levels, e.g., high noise levels as depicted in FIG. 4A as well as low noise levels as depicted in FIG. 4B. The decreased sensitivity to intensity gradients and noise level typically is due to image registration techniques using a golden template, allowing features of interest to be identified even though the feature may include voxels with differing intensities and noise levels.

Segmentation generally refers to the process of partitioning a digital image into multiple regions (e.g., sets of pixels for a 2D image or sets of voxels in a 3D image). Segmentation may be used to locate features of interest (bones, cartilage, ligaments, etc.) and boundaries (lines, curves, etc. that represent the bone boundary or surface) in an image. In one embodiment, the output of the automatic segmentation of the scan data may be a set of images (scan slices 16) where each image 16 includes a set of extracted closed contours representing bone outlines that identify respective bone location and shape for bones of interest (e.g., the shape and location of the tibia and femur in the scan data of a knee joint). The generation of a 3D model correspondent to the above closed contours may be additionally included into the segmentation process. The automatic or semi-automatic segmentation of a joint, using image slices 16 to create 3D models (e.g., bone models 22 and arthritic models 36) of the surface of the bones in the joint, may reduce the time required to manufacture customized arthroplasty cutting jigs 2. It is to be appreciated that certain embodiments may generate open contours of the bone shapes of interest to further reduce time associated with the process.

In one embodiment, scan protocols may be chosen to provide good definition in areas where precise geometry reconstruction is required and to provide lower definition in areas that are not as important for geometry reconstruction. The automatic or semi-automatic image segmentation of one embodiment employs components whose parameters may be tuned for the characteristics of the image modality used as input to the automatic segmentation and for the features of the anatomical structure to be segmented, as described in more detail below.

In one embodiment, a General Electric 3T MRI scanner may be used to obtain the scan data. The scanner settings may be set as follows: pulse sequence: FRFSE-XL Sagittal PD; 3 Pane Locator-Scout Scan Thickness: 4-millimeters; Imaging Options: TRF, Fast, FR; Gradient Mode: Whole; TE: approximately 31; TR: approximately 2100; Echo Train Length: 8; Bandwidth: 50 Hz; FOV: 16 centimeters, centered at the joint line; Phase FOV: 0.8 or 0.9; Slice Thickness: 2 millimeters; Spacing: Interleave; Matrix: 384×192; NEX: 2; Frequency: SI; and Phase Correct: On. It is to be appreciated that other scanners and settings may be used to generate the scan data.

Typically, the voxel aspect ratio of the scan data is a function of how many scan slices may be obtained while a patient remains immobile. In one embodiment, a two-millimeter inter-slice spacing may be used during a scan of a patient's knee joint. This inter-slice spacing provides sufficient resolution for constructing 3D bone models of the patient's knee joint, while allowing sufficiently rapid completion of scan before the patient moves.

Figure 5:
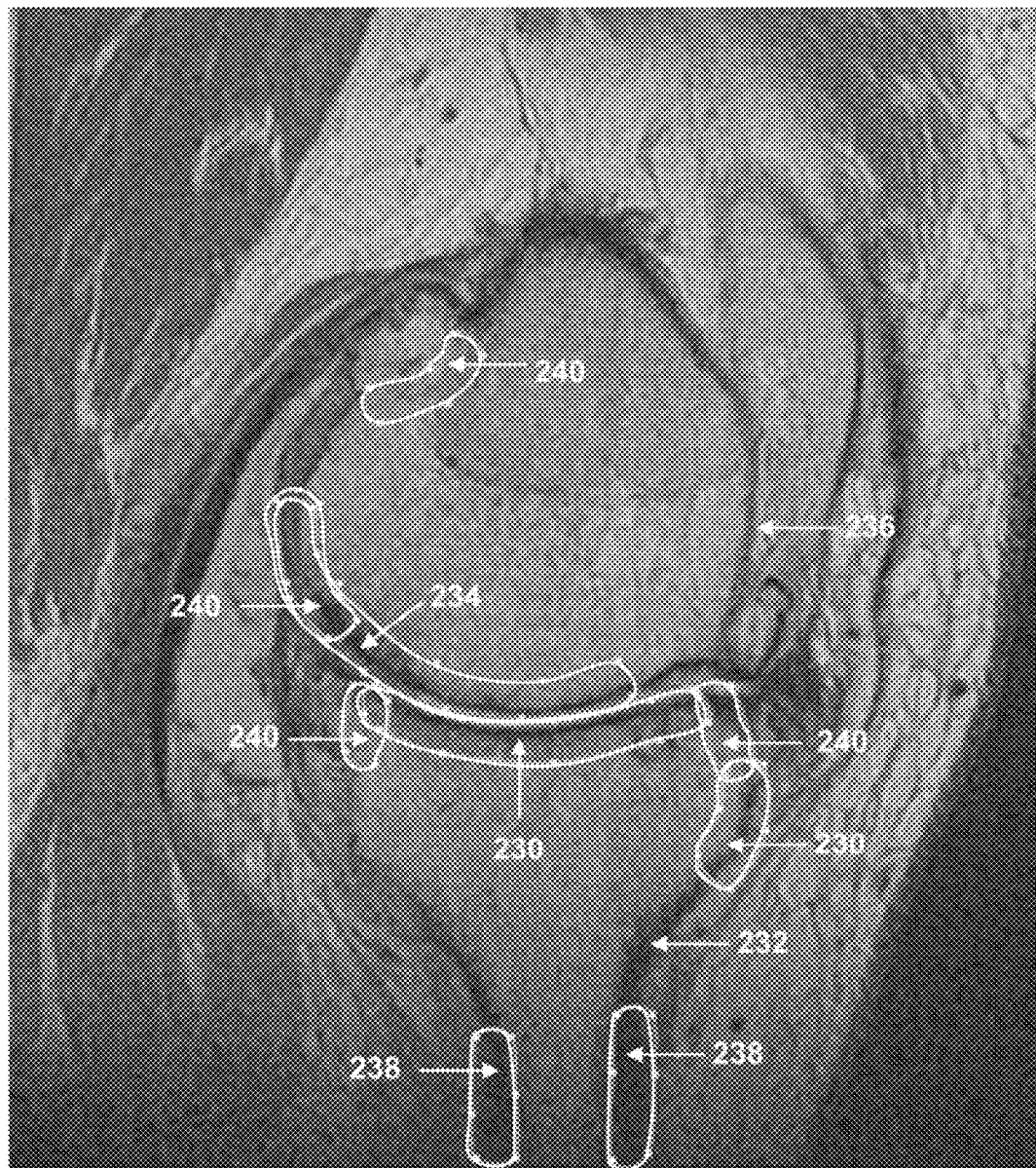
FIG. 5 is a sagittal plane image slice of a femur and tibia depicting regions where good definition may be needed during automatic segmentation of the femur and tibia.

FIG. 5 depicts a MRI scan slice that illustrates image regions where good definition may be needed during automatic segmentation of the image. Typically, this may be areas where the bones come in contact during knee motion, in the anterior shaft area next to the joint and areas located at about a 10- to 30-millimeter distance from the joint. Good definition may be needed in regions 230 of the tibia 232 and regions 234 of the femur 236. Regions 238 depict areas where the tibia is almost tangent to the slice and boundary information may be lost due to voxel volume averaging.

Voxel volume averaging may occur during the data acquisition process when the voxel size is larger than a feature detail to be distinguished. For example, the detail may have a black intensity while the surrounding region may have a white intensity. When the average of the contiguous data enclosed in the voxel is taken, the average voxel intensity value may be gray. Thus, it may not be possible to determine in what part of the voxel the detail belongs.

Regions 240 depict areas where the interface between the cortical bone and cartilage is not clear (because the intensities are similar), or where the bone is damaged and may need to be restored, or regions where the interface between the cancellous bone and surrounding region may be unclear due to the presence of a disease formation (e.g., an osteophyte growth which has an image intensity similar to the adjacent region).

Figure 6:
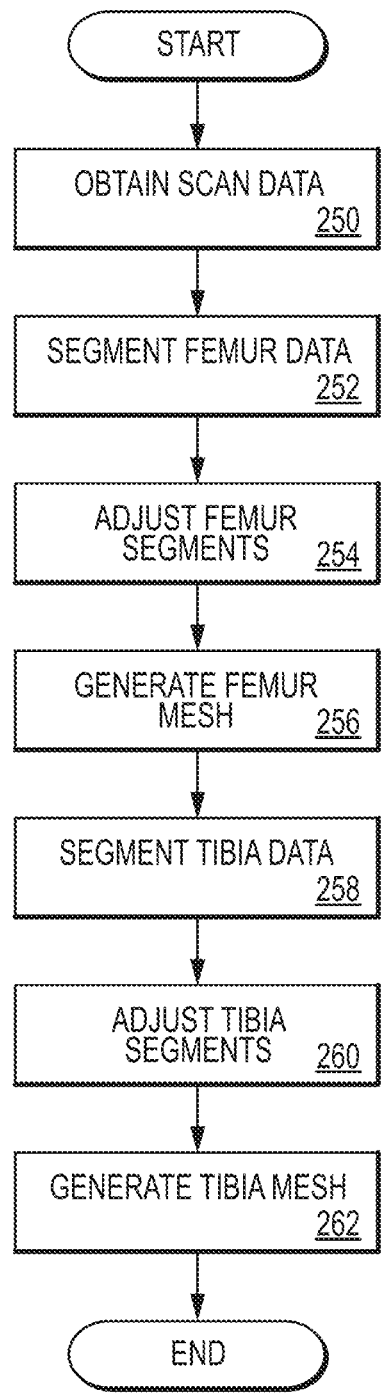
FIG. 6 depicts a flowchart illustrating one method for automatic segmentation of an image modality scan of a patient's knee joint.
Figure 7A:
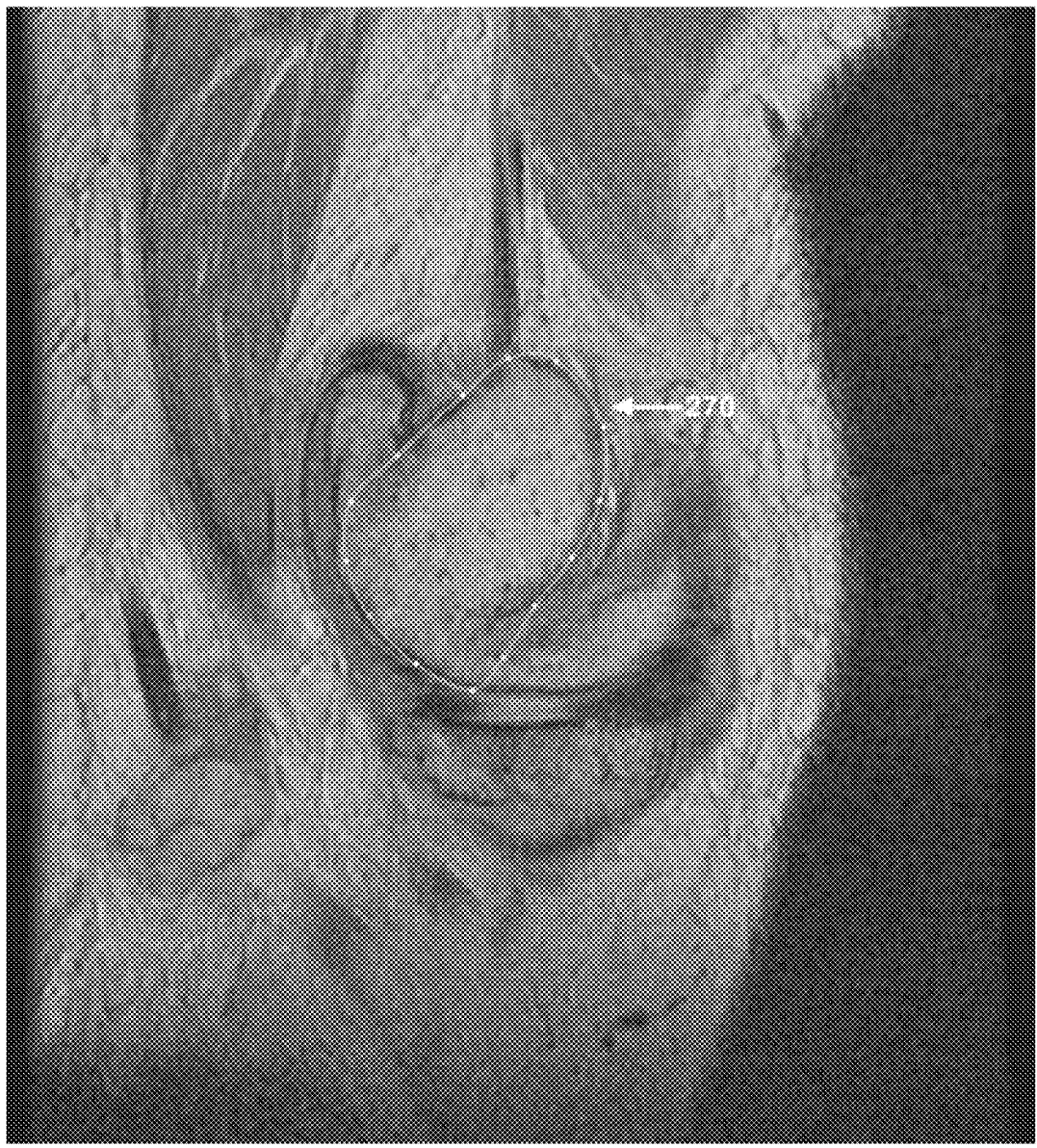
FIG. 7A is a sagittal plane image slice of a segmented femur.
Figure 7B:
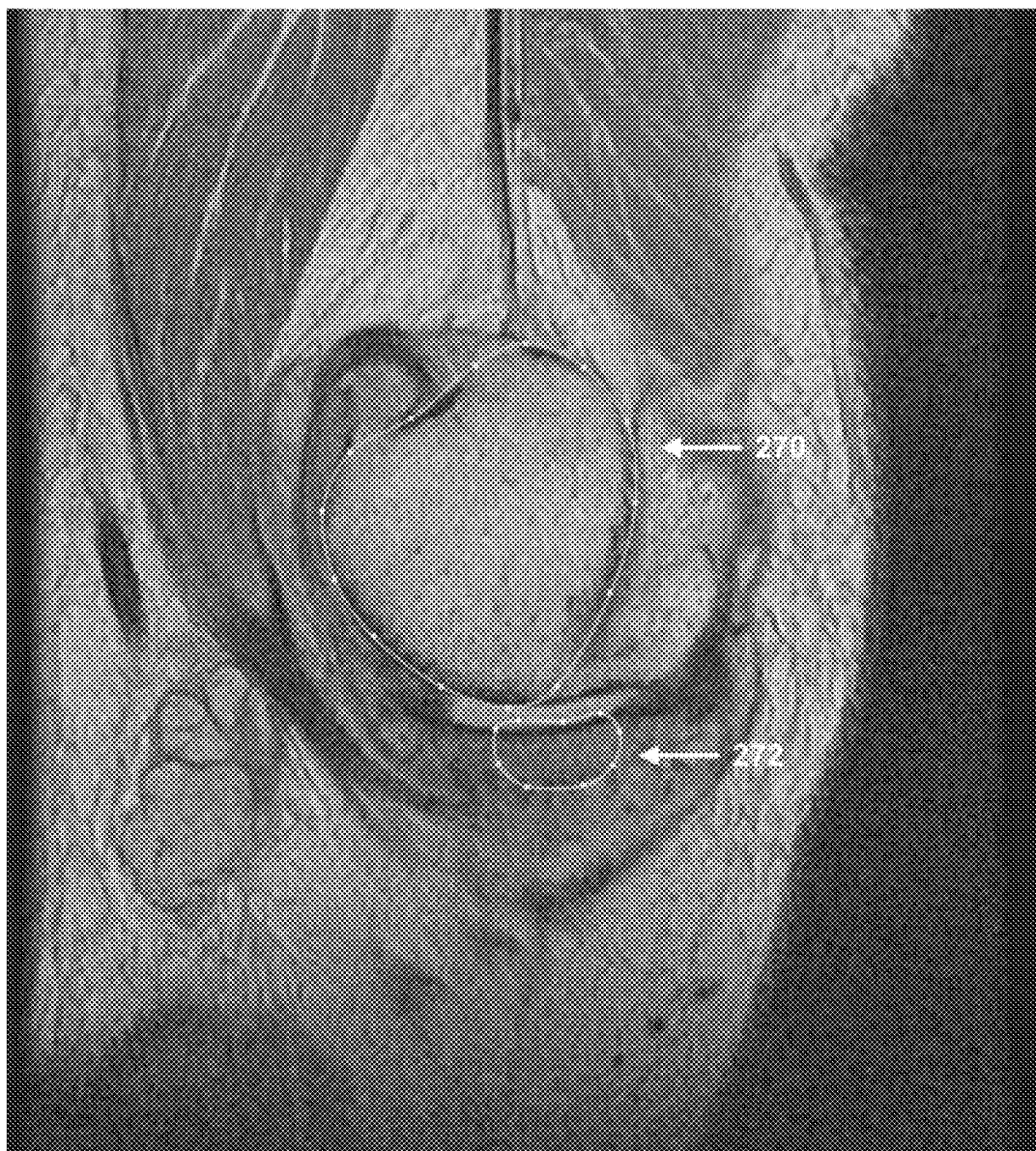
FIG. 7B is a sagittal plane image slice of a segmented femur and tibia.
Figure 7C:
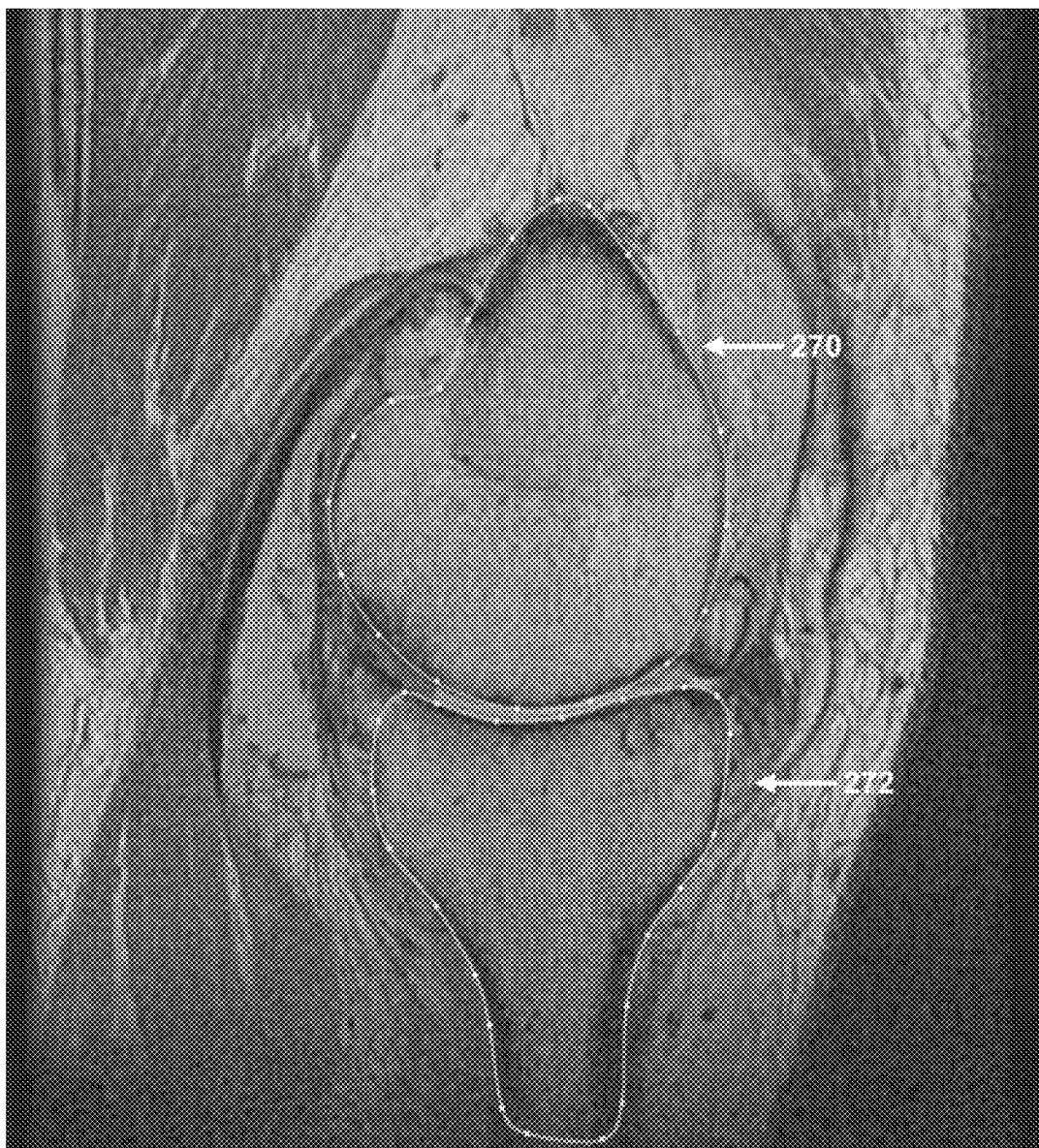
FIG. 7C is another sagittal plane image slice of a segmented femur and tibia.
Figure 7D:
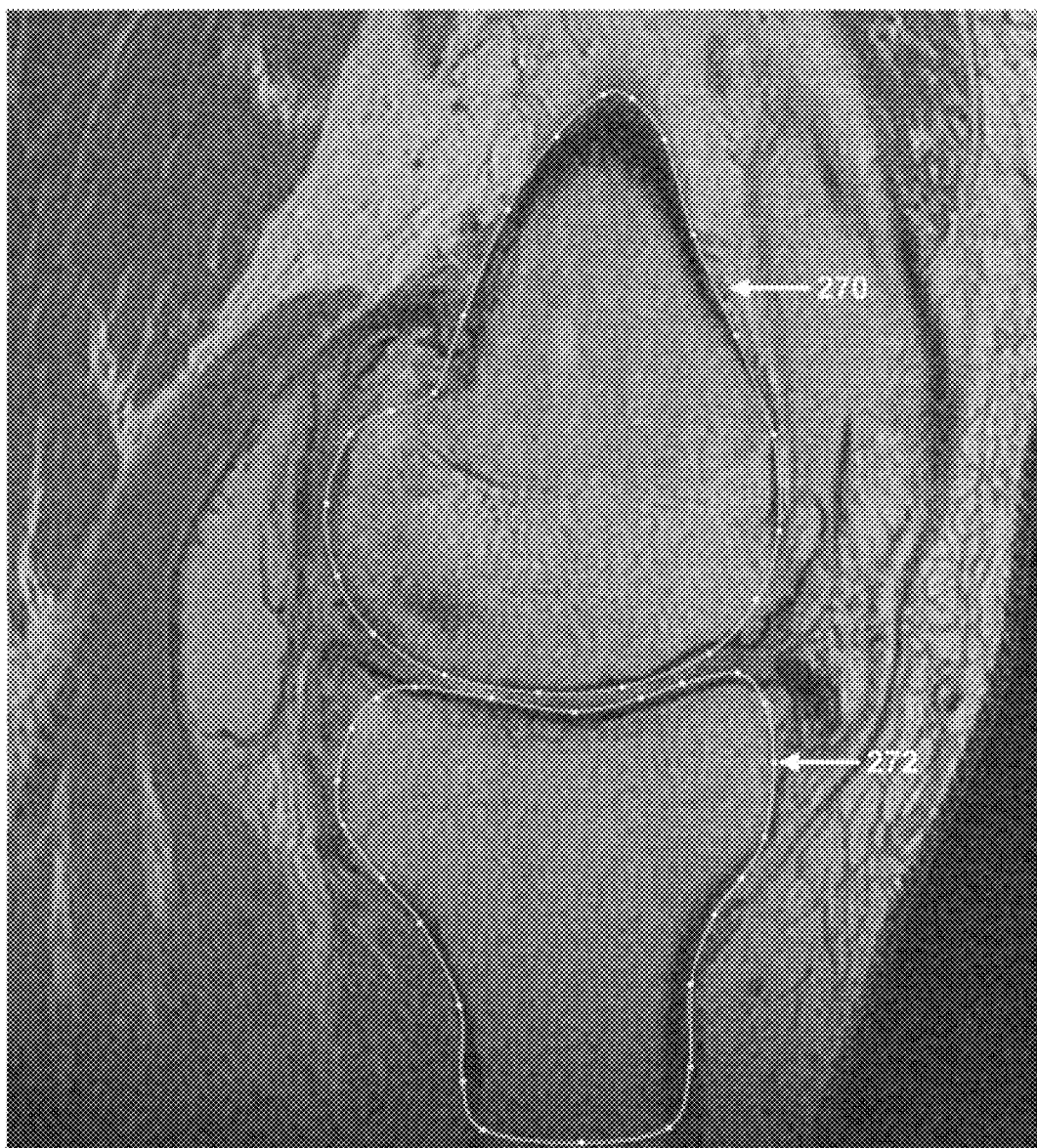
FIG. 7D is another sagittal plane image slice of a segmented femur and tibia.
Figure 7E:
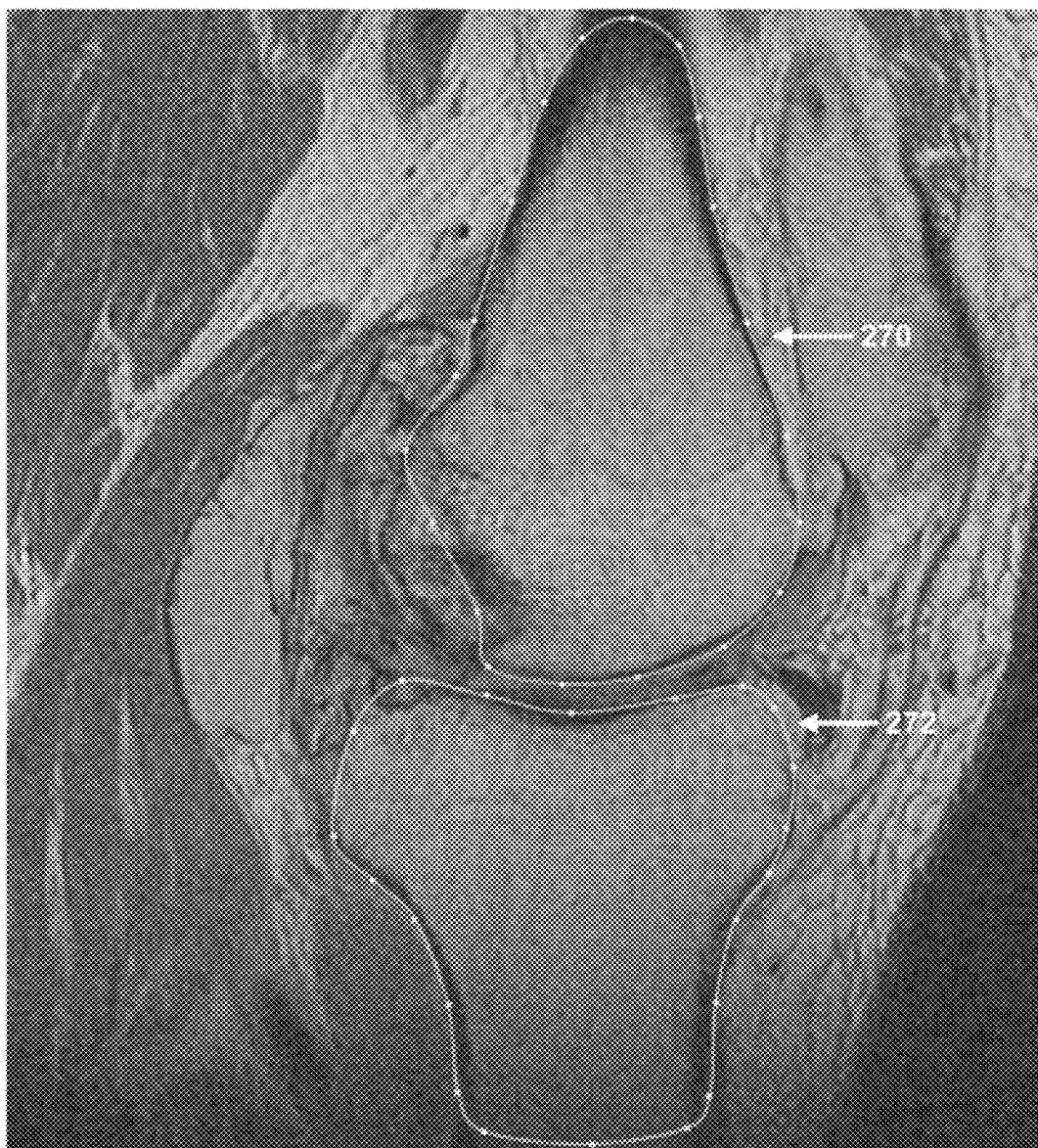
FIG. 7E is another sagittal plane image slice of a segmented femur and tibia.
Figure 7F:
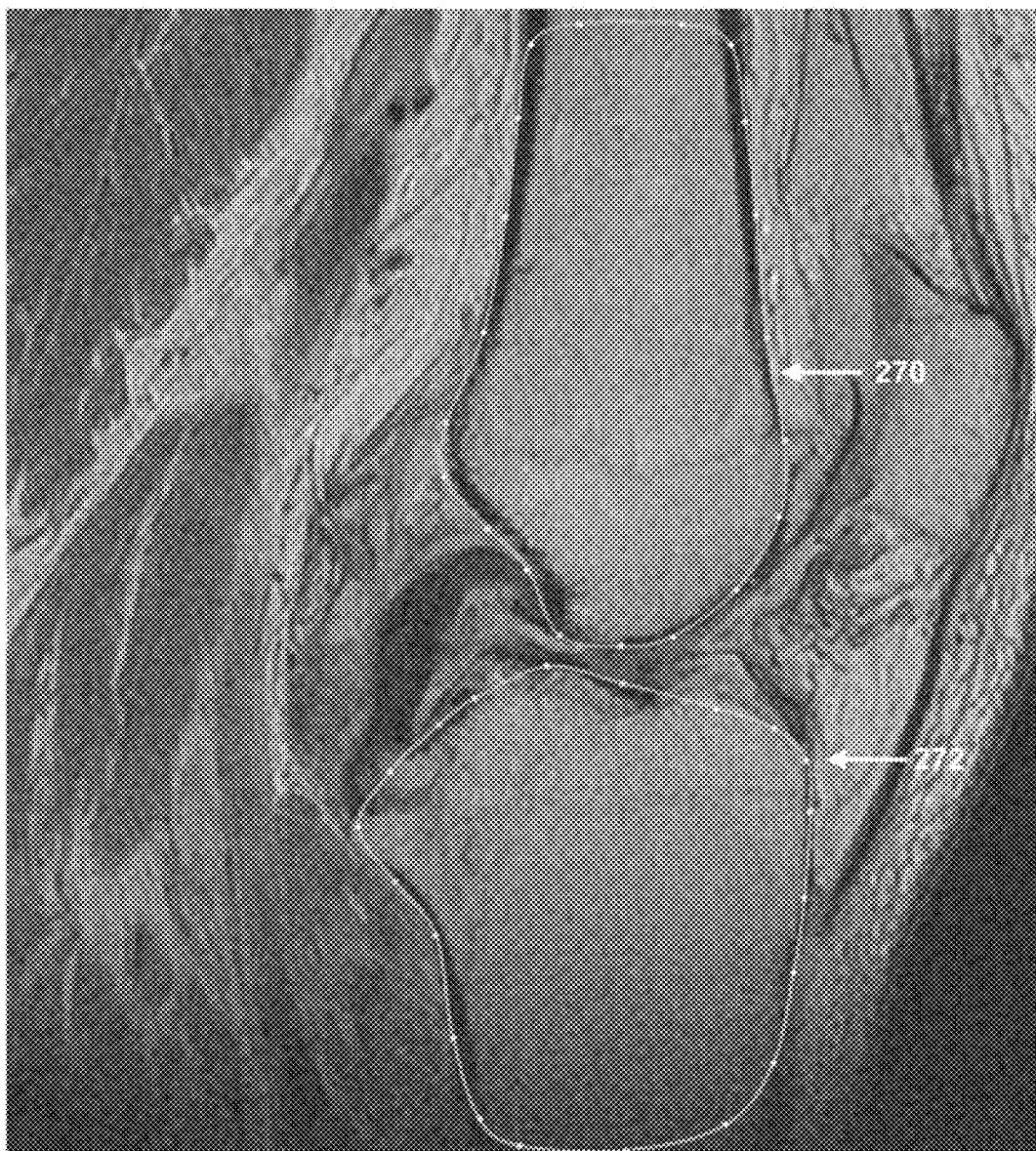
FIG. 7F is another sagittal plane image slice of a segmented femur and tibia.
Figure 7G:
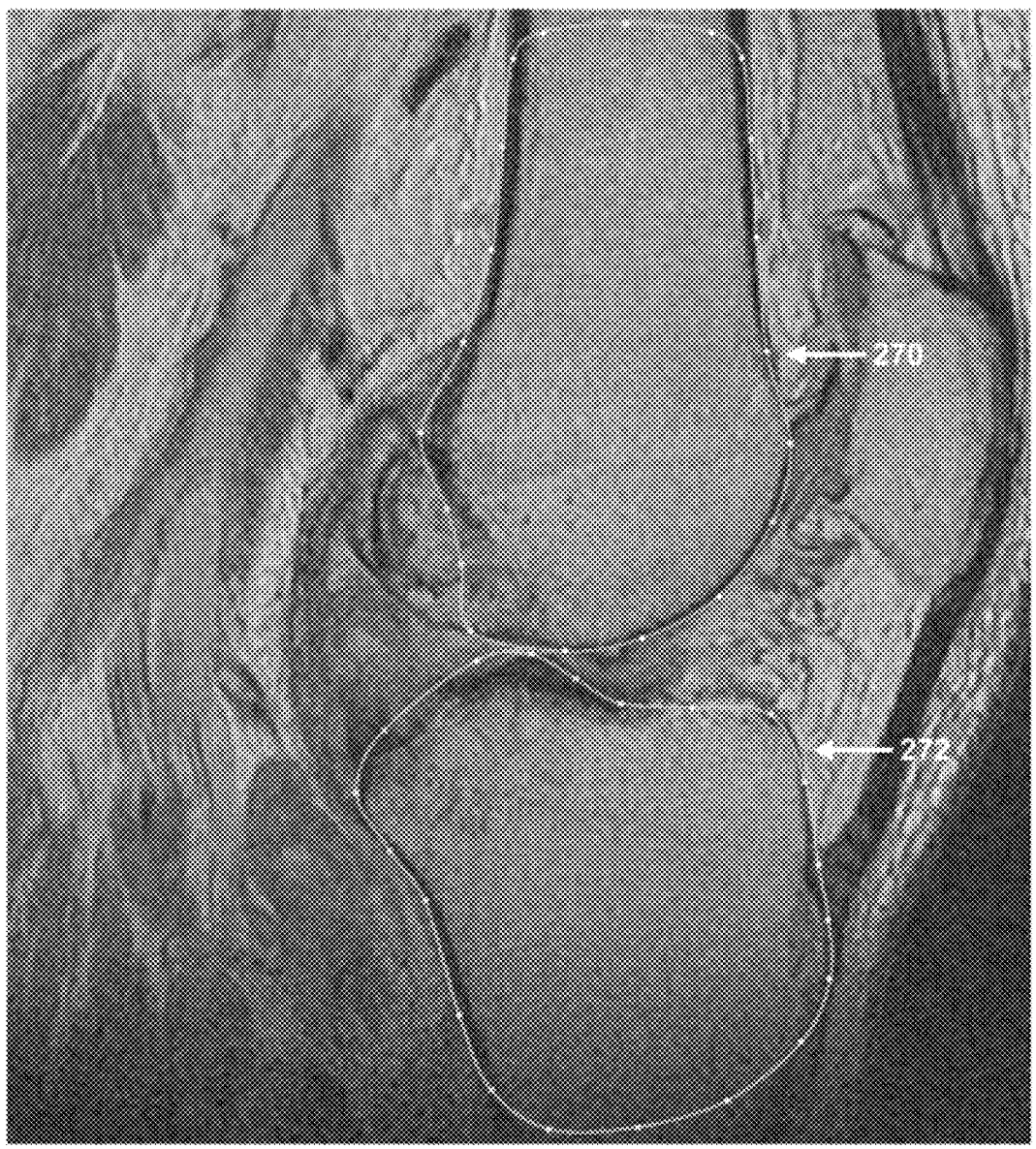
FIG. 7G is another sagittal plane image slice of a segmented femur and tibia.
Figure 7H:
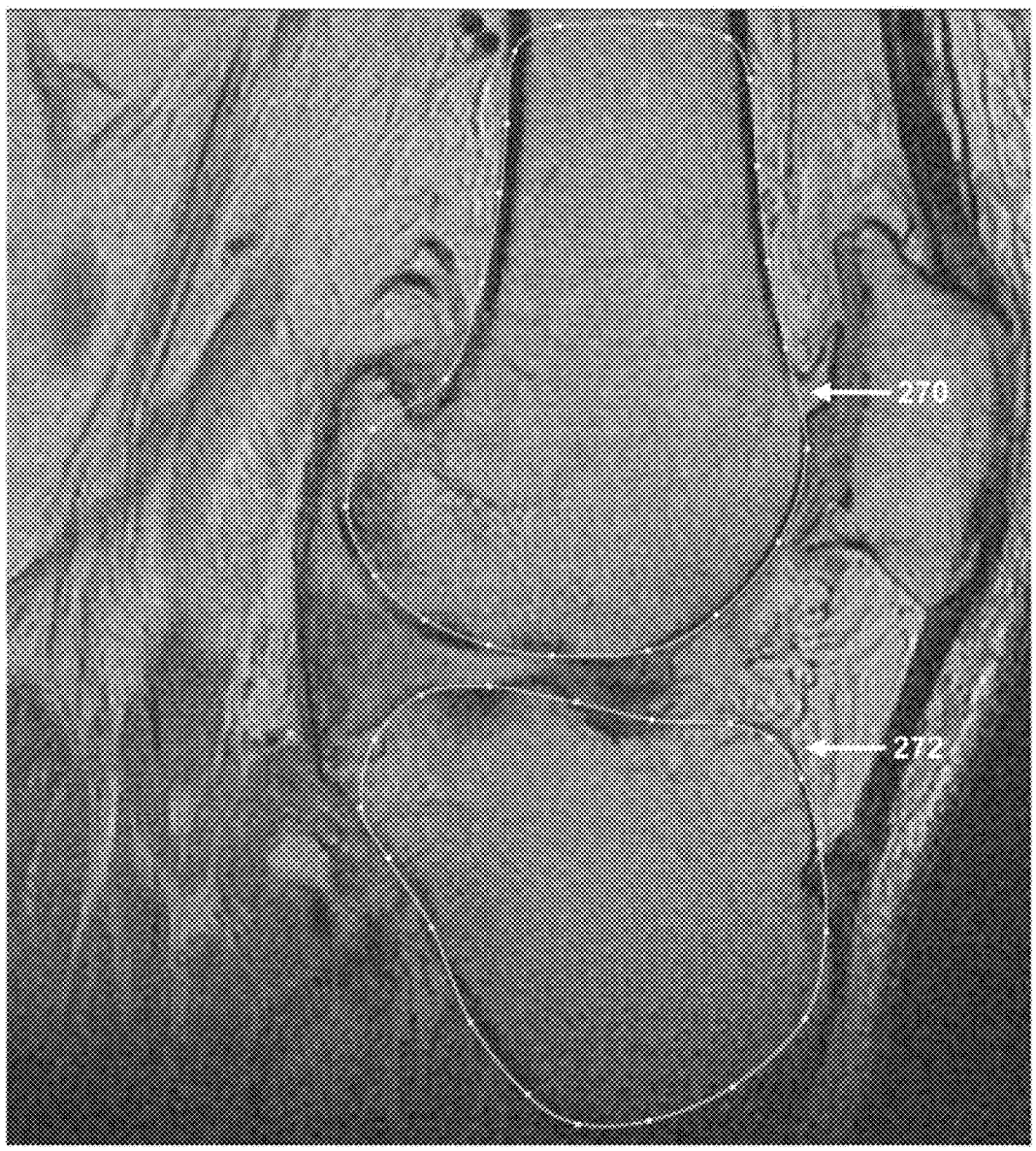
FIG. 7H is another sagittal plane image slice of a segmented femur and tibia.
Figure 71:
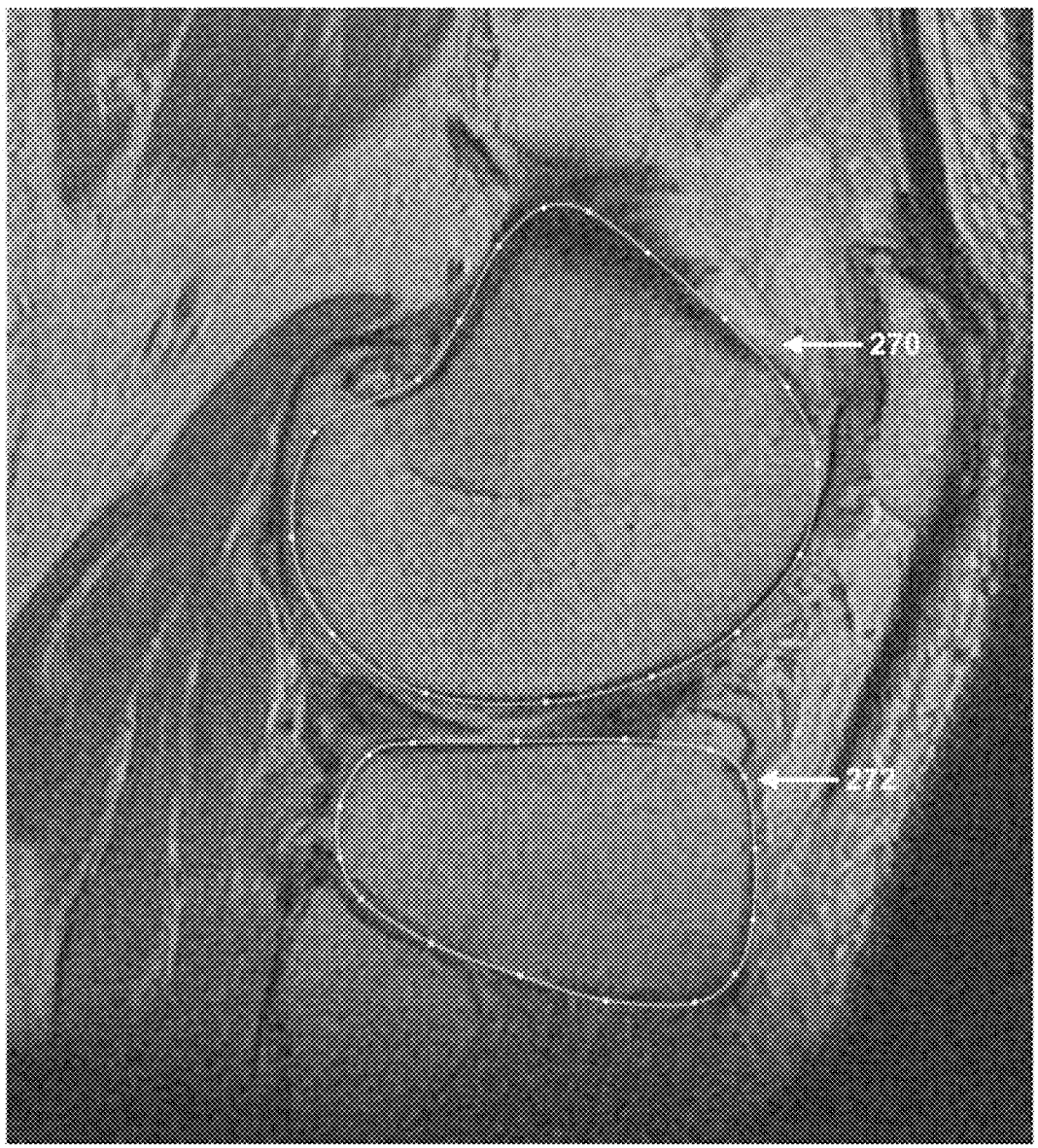
Figure 7J:
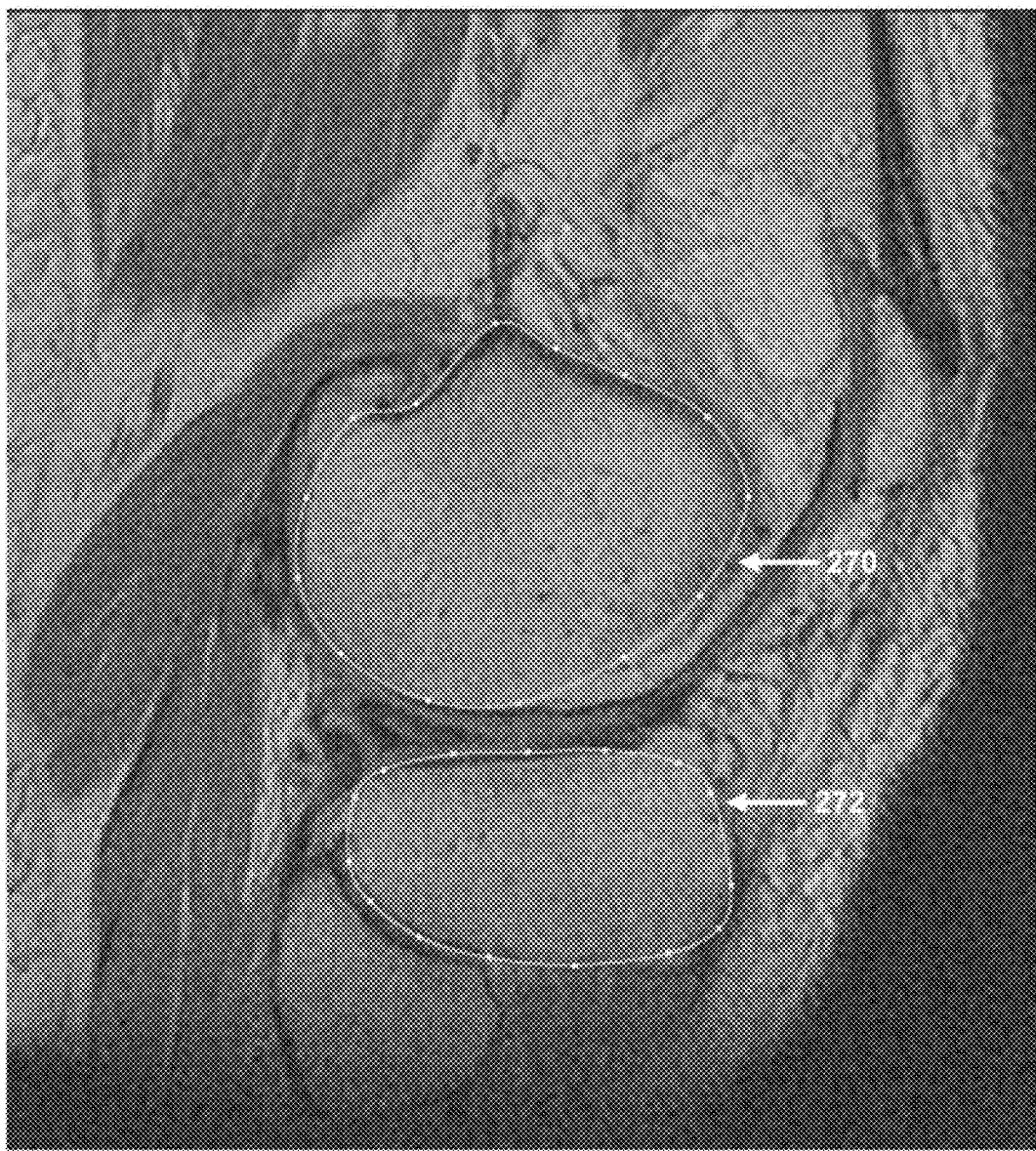
FIG. 7J is another sagittal plane image slice of a segmented femur and tibia.
Figure 7K:
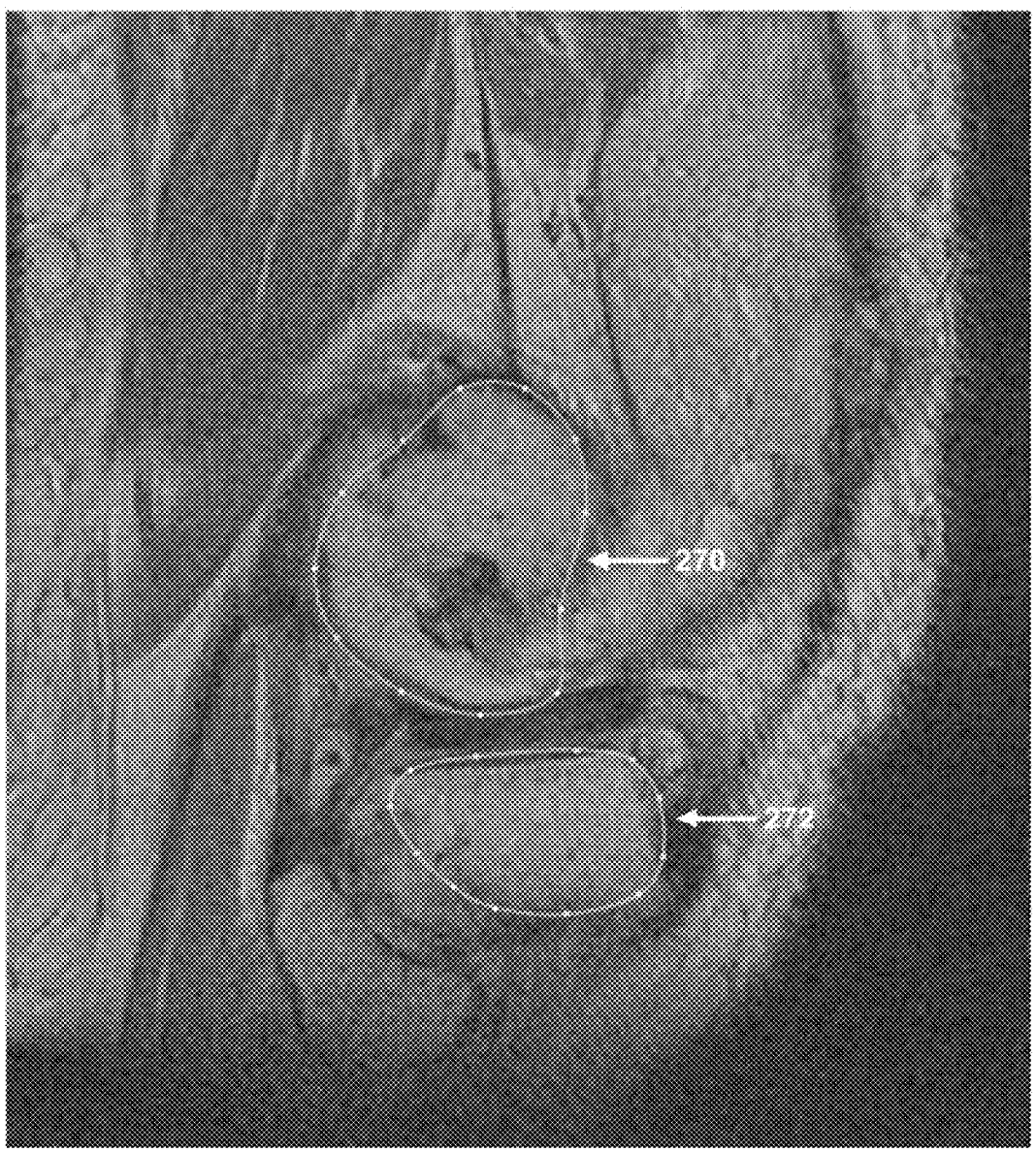
FIG. 7K is another sagittal plane image slice of a segmented femur and tibia.

FIG. 6 depicts a flowchart illustrating one method for automatic or semi-automatic segmentation of Femur and Tibia Planning models of an image modality scan (e.g., an MRI scan) of a patient's knee joint. Initially, operation 250 obtains a scan of the patient's knee joint. In one embodiment, the scan may include about 50 sagittal slices. Other embodiments may use more or fewer slices. Each slice may be a gray scale image having a resolution of 512 by 512 voxels. The scan may represent approximately a 100-millimeter by 150-millimeter by 150-millimeter volume of the patient's knee. While the invention will be described for an MRI scan of a knee joint, this is by way of illustration and not limitation. The invention may be used to segment other types of image modality scans such as computed tomography (CT) scans, ultrasound scans, positron emission tomography (PET) scans, etc., as well as other joints including, but not limited to, hip joints, elbow joints, etc. Further, the resolution of each slice may be higher or lower and the images may be in color rather than gray scale. It is to be appreciated that transversal or coronal slices may be used in other embodiments.

After operation 250 obtains scan data (e.g., scan images 16) generated by imager 8, operation 252 may be performed to segment the femur data of the scan data. During this operation, the femur may be located and spline curves 270 may be generated to outline the femur shape or contour lines in the scan slices, as depicted in FIGS. 7A-7K. It should be appreciated that one or more spline curves may be generated in each slice to outline the femur contour depending on the shape and curvature of the femur as well as the femur orientation relative to the slice direction.

Figure 8:
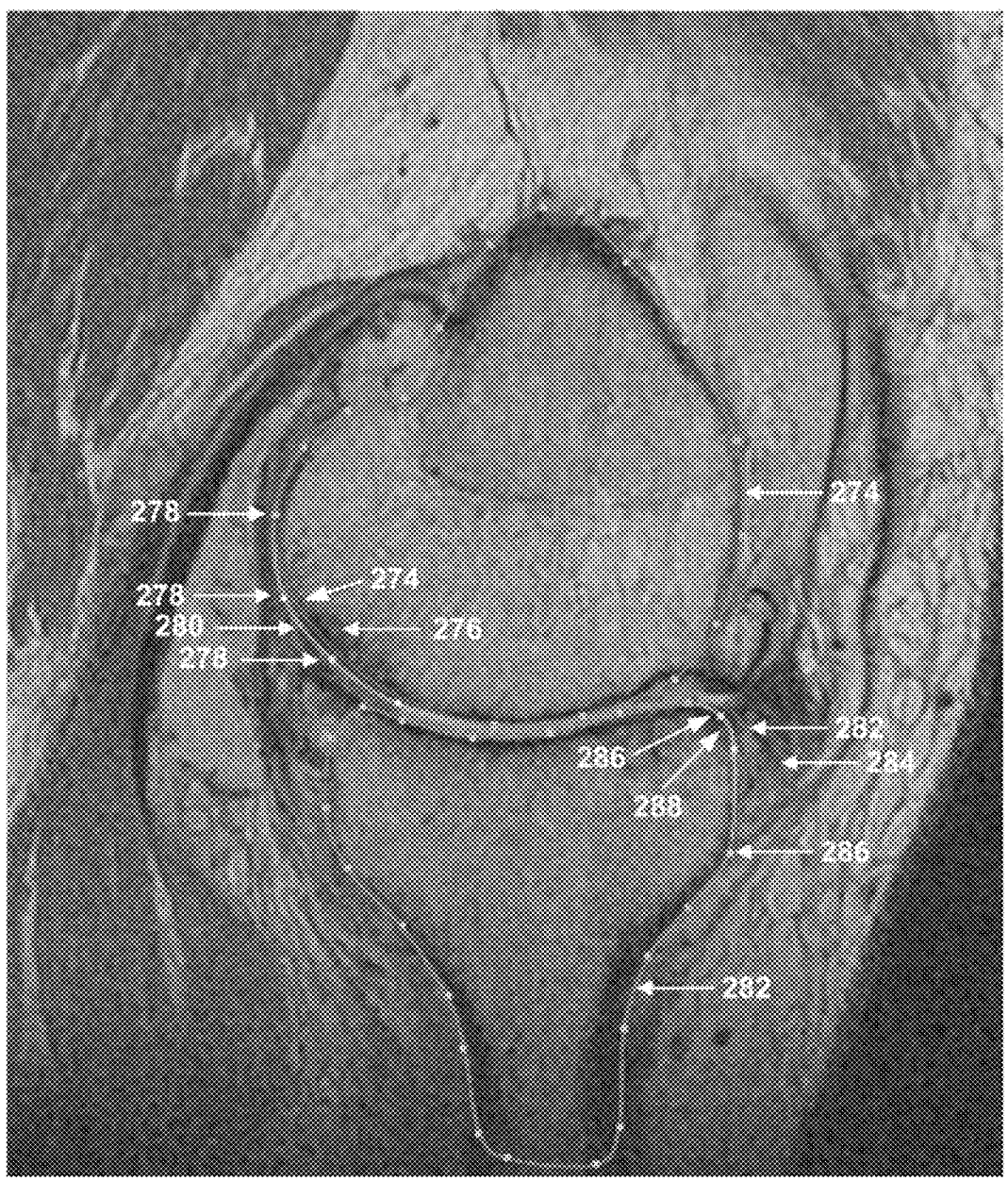
FIG. 8 is a sagittal plane image slice depicting automatically generated slice curves of a femur and a tibia.

Next, in operation 254, a trained technician may verify that the contours of the femur spline curves generated during operation 252 follow the surface of the femur bone. The technician may determine that a spline curve does not follow the bone shape in a particular slice. For example, FIG. 8 depicts an automatically generated femur spline curve 274. The technician may determine that the curve should be enlarged in the lower left part 276 of the femur. There may be various reasons why the technician may decide that the curve needs to be modified. For example, a technician may want to generate a pre-deteriorated bone shape, yet the bone may be worn out in this region and may need reconstruction. The technician may determine this by examining the overall 3D shape of the segmented femur and also by comparing lateral and medial parts of the scan data. The segmented region of the slice may be enlarged by dragging one or more control points 278 located on the spline curve 274 to adjust the curve to more closely follow the femur boundary as determined by the technician, as shown by adjusted curve 280. The number of control points on a spline curve may be dependent on the curve length and curvature variations. Typically, 10-25 control points may be associated with a spline curve for spline modification.

Once the technician is satisfied with all of the femur spline curves in the scan slices, operation 256 generates a watertight triangular mesh geometry from the femur segmentation that approximates the 3D surface of the femur. The mesh closely follows the femur spline curves 270 and smoothly interpolates between them to generate a 3D surface model of the femur. FIG. 9 depicts typical 3D mesh geometry 290 of a target femur generated by one embodiment. Such a 3D model may be a 3D surface model or 3D volume model resulting from open-loop contour lines or closed loop contour lines, respectively. In one embodiment, such a 3D model as depicted in FIG. 9 may be a bone model 22 or an arthritic model 36.

After operation 256, operation 258 may be performed to segment the tibia data in the scan data. During this operation, the tibia is located and spline curves may be generated to locate and outline the shape of the tibia found in the scan slices, as depicted by tibia spline curves 272 in FIGS. 7A-7K. It should be appreciated that one or more spline curves may be generated in each slice to outline the tibia depending on the shape and curvature of the tibia as well as the tibia orientation relative to the slice direction.

Next, in operation 260, the technician may verify the tibia spline curves generated during operation 258. The technician may determine that a spline curve does not follow the tibia in a particular slice. For example, referring back to FIG. 8, an automatically generated tibia spline curve 282 is depicted that may not follow the tibia in the right part of the tibia due to the presence of an osteophyte growth 284. The presence of the osteophyte growth 284 may be determined by examining neighboring slices. In this case, the segmented region may be reduced by dragging one or more control points 286 located on the spline curve to modify the tibia spline curve 282 to obtain the adjusted tibia spline curve 288. As previously discussed, each spline curve may have approximately 10-25 control points depending on the length and curvature variation of the spline curve.

When the purpose of the segmentation is generating bone models that will be shown to a surgeon in the images where they are overlapped by implants, a technician will not need to restore the segmentation model to its pre-deteriorated bone shape, and thus will not need to spend time on adjusting splines to follow the pre-deteriorated bone shape. Also there is no need to get highly precise segmentation in the bone areas that are to be replaced with implant. So there is no need to spend time on adjusting the non-perfect curves in the "to be replaced" areas.

Once the technician is satisfied with all of the tibia spline curves in the scan slices, operation 262 generates a watertight triangular mesh geometry from the tibia segmentation. The mesh closely follows the spline curves and smoothly interpolates between them to generate a 3D surface model of the tibia. FIG. 10 depicts a typical 3D mesh geometry 292 of a target tibia generated by one embodiment. Such a 3D model may be a 3D surface model or 3D volume model resulting from open-loop contour lines or closed loop contour lines, respectively. In one embodiment, such a 3D model as depicted in FIG. 10 may be a bone model 22 or an arthritic model 36.

Because the objects to be located in the scan data typically cannot be segmented by grouping similar voxels into regions, a golden template representative of a typical size and shape of the feature of interest may be employed during the segmentation process to locate the target feature of interest.

FIG. 11 depicts a flowchart illustrating one method for generating a golden template. The method will be described for generating a golden template of a tibia by way of illustration and not limitation. The method may be used to generate golden templates of other bones including, but not limited to a femur bone, a hip bone, etc.

Initially, operation 300 obtains a scan of a tibia that is not damaged or diseased. The appropriate tibia scan may be chosen by screening multiple MRI tibia scans to locate a MRI tibia scan having a tibia that does not have damaged cancellous and cortical matter (i.e., no damage in tibia regions that will be used as fixed images to locate a corresponding target tibia in a target scan during segmentation), which has good MRI image quality, and which has a relatively average shape, e.g., the shaft width relative to the largest part is not out of proportion (which may be estimated by eye-balling the images). This tibia scan data, referred to herein as a golden tibia scan, may be used to create a golden tibia template. It is to be appreciated that several MRI scans of a tibia (or other bone of interest) may be selected, a template generated for each scan, statistics gathered on the success rate when using each template to segment target MRI scans, and the one with the highest success rate selected as the golden tibia template.

In other embodiments, a catalog of golden models may be generated for any given feature, with distinct variants of the feature depending on various patient attributes, such as (but not limited to) weight, height, race, gender, age, and diagnosed disease condition. The appropriate golden mesh would then be selected for each feature based on a given patient's characteristics.

Figure 12A:
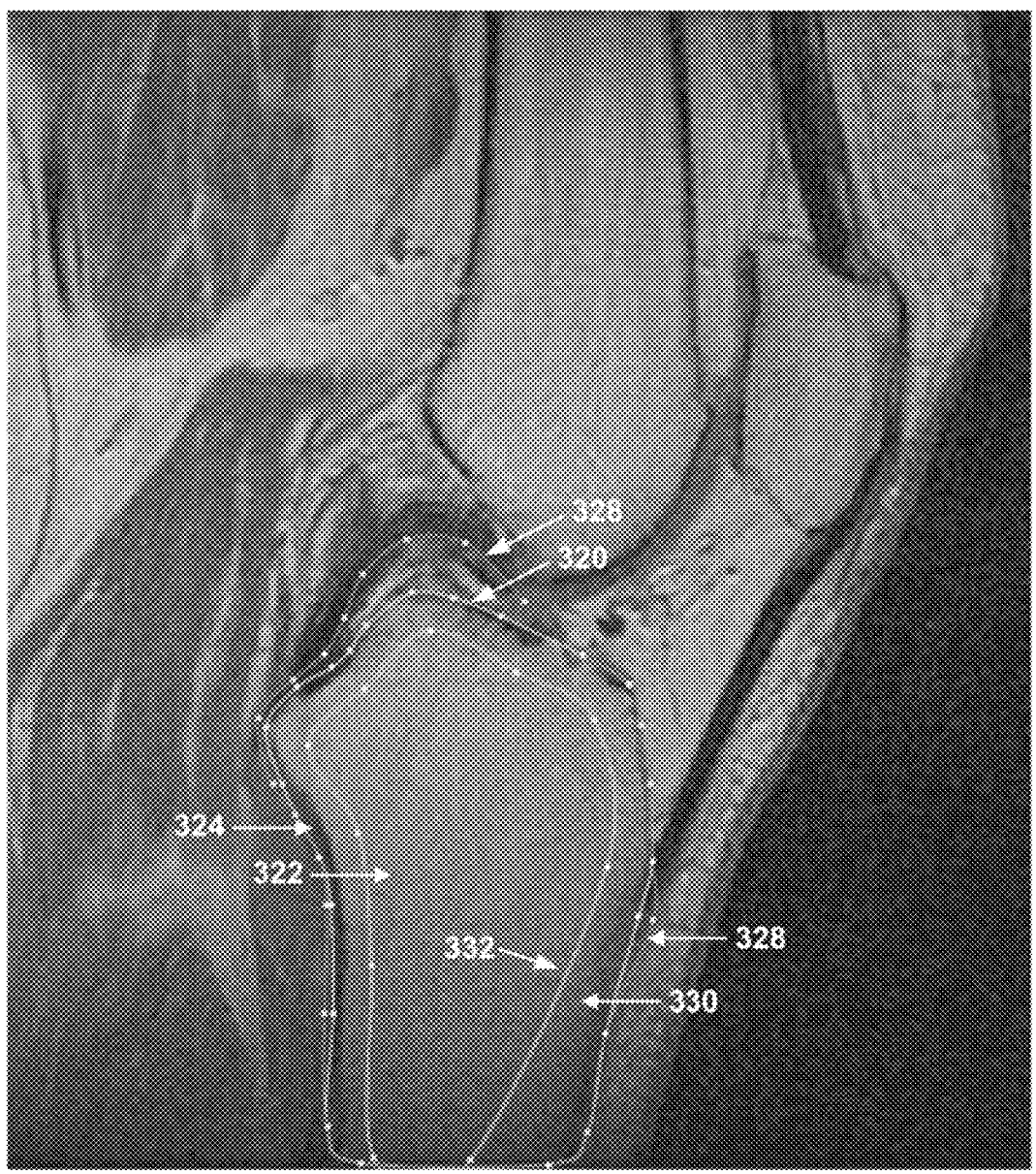
FIG. 12A is a sagittal plane image slice depicting a contour curve outlining a golden tibia region, a contour curve outlining a grown tibia region and a contour curve outlining a boundary golden tibia region.

Then, in operation 302 the tibia is segmented in each scan slice. Each segmentation region includes the cancellous matter 322 and cortical matter 324 of the tibia, but excludes any cartilage matter to form a golden tibia region, outlined by a contour curve 320, as depicted in FIG. 12A.

Figure 13A:
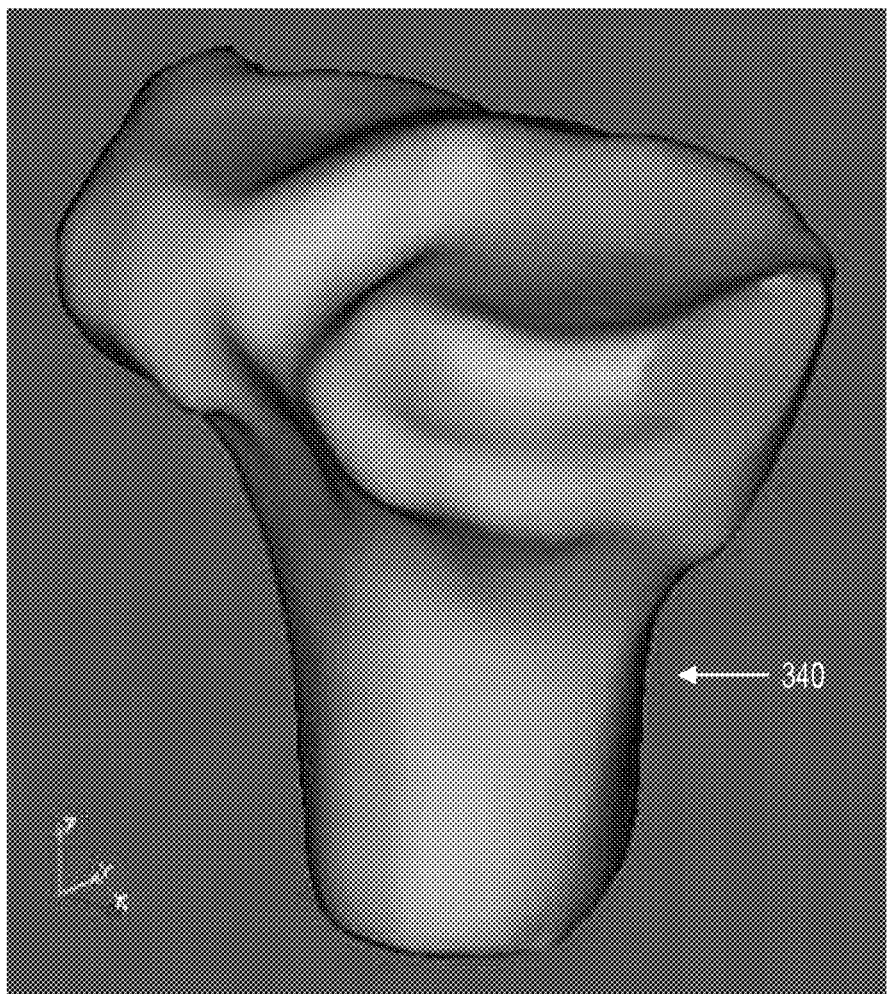
FIG. 13A depicts a golden tibia 3D mesh.

Next, operation 304 generates a golden tibia mesh 340 from the accumulated golden tibia contours of the image slices, as illustrated in FIG. 13A.

Next, operation 306 increases the segmented region in each slice by growing the region to include boundaries between the tibia and adjacent structures where the contact area is generally relatively stable from one MRI scan to another MRI scan. This grown region may be referred to herein as a grown golden tibia region, outlined by contour curve 328, as depicted in FIG. 12A.

The grown golden region may be used to find the surface that separates the hard bone (cancellous and cortical) from the outside matter (cartilage, tendons, water, etc.). The changes in voxel intensities when going from inside the surface to outside of the surface may be used to define the surface. The grown golden region may allow the registration process to find intensity changes in the target scan that are similar to the golden template intensity changes near the surface. Unfortunately, the golden segmentation region does not have stable intensity changes (e.g., near the articular surface) or may not have much of an intensity change. Thus, the grown region typically does not include such regions because they do not provide additional information and may slow down the registration due to an increased number of points to be registered.

Finally, use of a grown golden region may increase the distance where the metric function detects a feature during the registration process. When local optimization is used, the registration may be moved in a particular direction only when a small movement in that direction improves the metric function. When a golden template feature is farther away from the corresponding target bone feature (e.g., when there is a significant shape difference), the metric typically will not move toward that feature. Use of the larger grown region may allow the metric to detect the feature and move toward it.

Next, operation 308 cuts off most of the inner part of the grown golden tibia region to obtain a boundary golden tibia region 330 depicted in FIG. 12A. The boundary golden tibia region 330 is bounded on the inside by contour curve 332 and the outside by contour curve 328.

The boundary region may be used to obtain a more precise registration of the target bone by using the interface from the cancellous bone to the cortical bone. This may be done so that intensity variations in other areas (e.g., intensity variations deep inside the bone) that may move the registration toward wrong features and decrease the precision of locating the hard bone surface are not used during the registration.

Then, operation 310 applies Gaussian smoothing with a standard deviation of two pixels to every slice of the golden tibia scan. In one embodiment, a vtkImageGaussianSmooth filter (part of Visualization Toolkit, a free open source software package) may be used to perform the Gaussian smoothing by setting the parameter "Standard Deviation" to a value of two.

Then, operation 312 generates an anchor segmentation. The anchor segmentation typically follows the original segmentation where the tibia boundary is well defined in most MRI scans. In areas where the tibia boundary may be poorly defined, but where there is another well-defined feature close to the tibia boundary, the anchor segmentation may follow that feature instead. For example, in an area where a healthy bone normally has cartilage, a damaged bone may or may not have cartilage. If cartilage is present in this damaged bone region, the bone boundary separates the dark cortical bone from the gray cartilage matter. If cartilage is not present in this area of the damaged bone, there may be white liquid matter next to the dark cortical bone or there may be another dark cortical bone next to the damaged bone area. Thus, the interface from the cortical bone to the outside matter in this region of the damaged bone typically varies from MRI scan to MRI scan. In such areas, the interface between the cortical and the inner cancellous bone may be used. These curves may be smoothly connected together in the remaining tibia areas to obtain the tibia anchor segmentation curve 358, depicted in FIG. 14A.

Figure 14A:
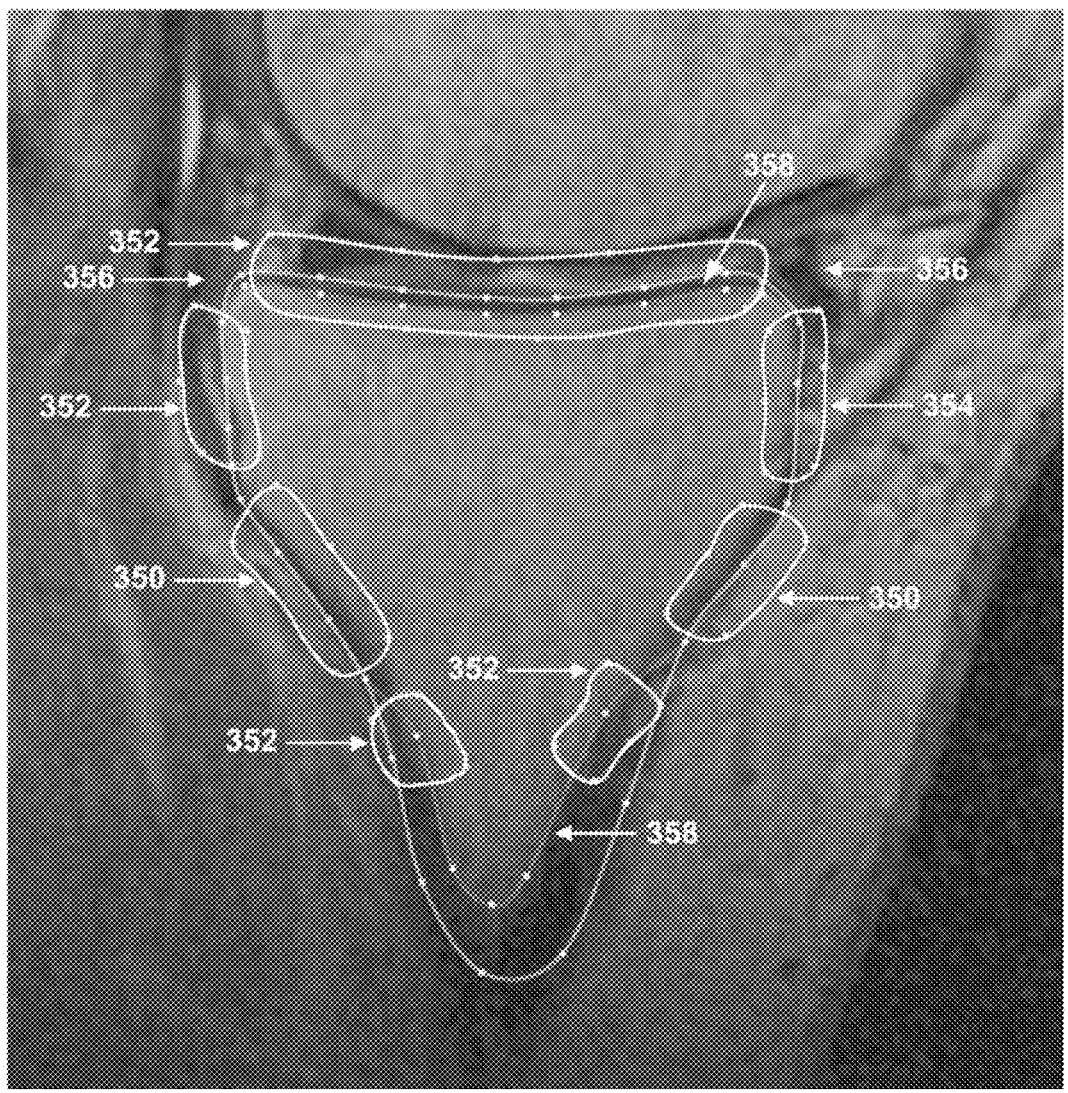
FIG. 14A is a sagittal plane image slice depicting anchor segmentation regions of a tibia.

Then, operation 314 may determine three disjoint regions along the anchor segmentation boundary. Each of these regions is generally well defined in most MRI scans. FIG. 14A depicts these three disjoint regions for a particular image slice. The first region 350, referred to herein as the tibia InDark-OutLight region, depicts a region where the anchor segmentation boundary separates the inside dark intensity cortical matter voxels from the outside light intensity voxels. The second region 352, referred to herein as the tibia InLight-OutDark region, depicts a region where the boundary separates the inside light intensity cancellous matter voxels from the outside dark intensity cortical matter voxels. Finally, region 354, referred to herein as the tibia Dark-in-Light region, depicts a region that has a very thin layer of dark intensity cortical matter voxels along the boundary, but which has light intensity matter voxels away from the boundary (i.e., on both sides of the boundary). Generally, the other regions along the anchor segmentation boundary vary from scan to scan or may not be clear in most of the scans, as depicted by regions 356. Such regions may be an osteophyte growth with an arbitrary shape but which has about the same intensity as the region next to it. Thus, such regions typically are not used as anchor regions in one embodiment of the invention.

Figure 15A:
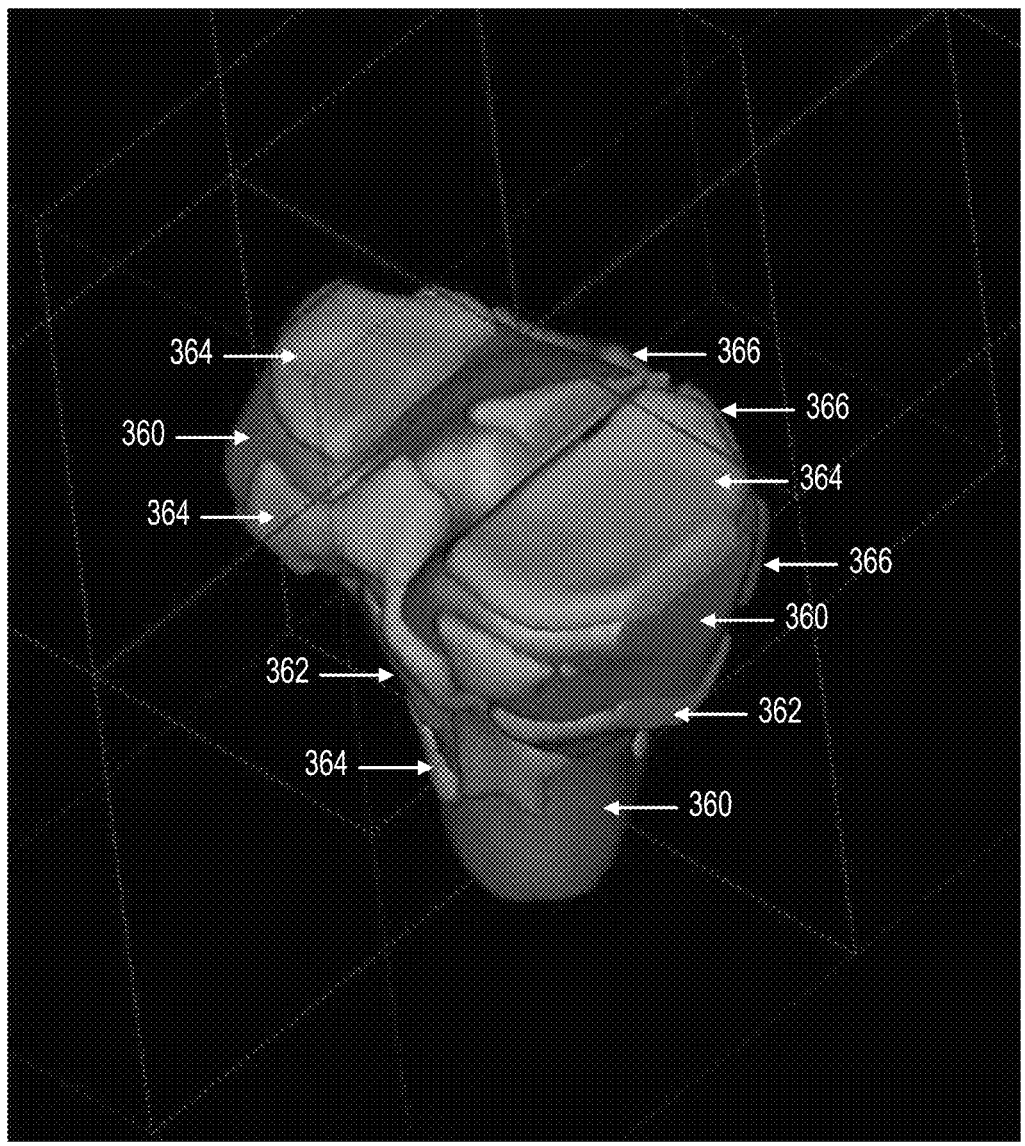
FIG. 15A is a 3D mesh geometry depicting the anchor segmentation mesh, the InDark-OutLight anchor mesh, the InLight-OutDark anchor mesh, and the Dark-In-Light anchor mesh of a tibia.

Finally, operation 316 generates a mesh corresponding to the anchor segmentation and also generates a mesh for each anchor region. FIG. 15A depicts the anchor segmentation mesh 360, the InDark-OutLight anchor region mesh 362, the InLight-OutDark anchor region mesh 364 and the Dark-in-Light anchor region mesh 366 for the tibia. These 3D meshes model the surface of the golden tibia in the specified regions. It is to be appreciated that the 3D meshes are distinct and generally are not combined to create a composite mesh. These meshes may be used to create an artificial fixed image that is used during the registration process as described in more detail below.

Figure 12B:
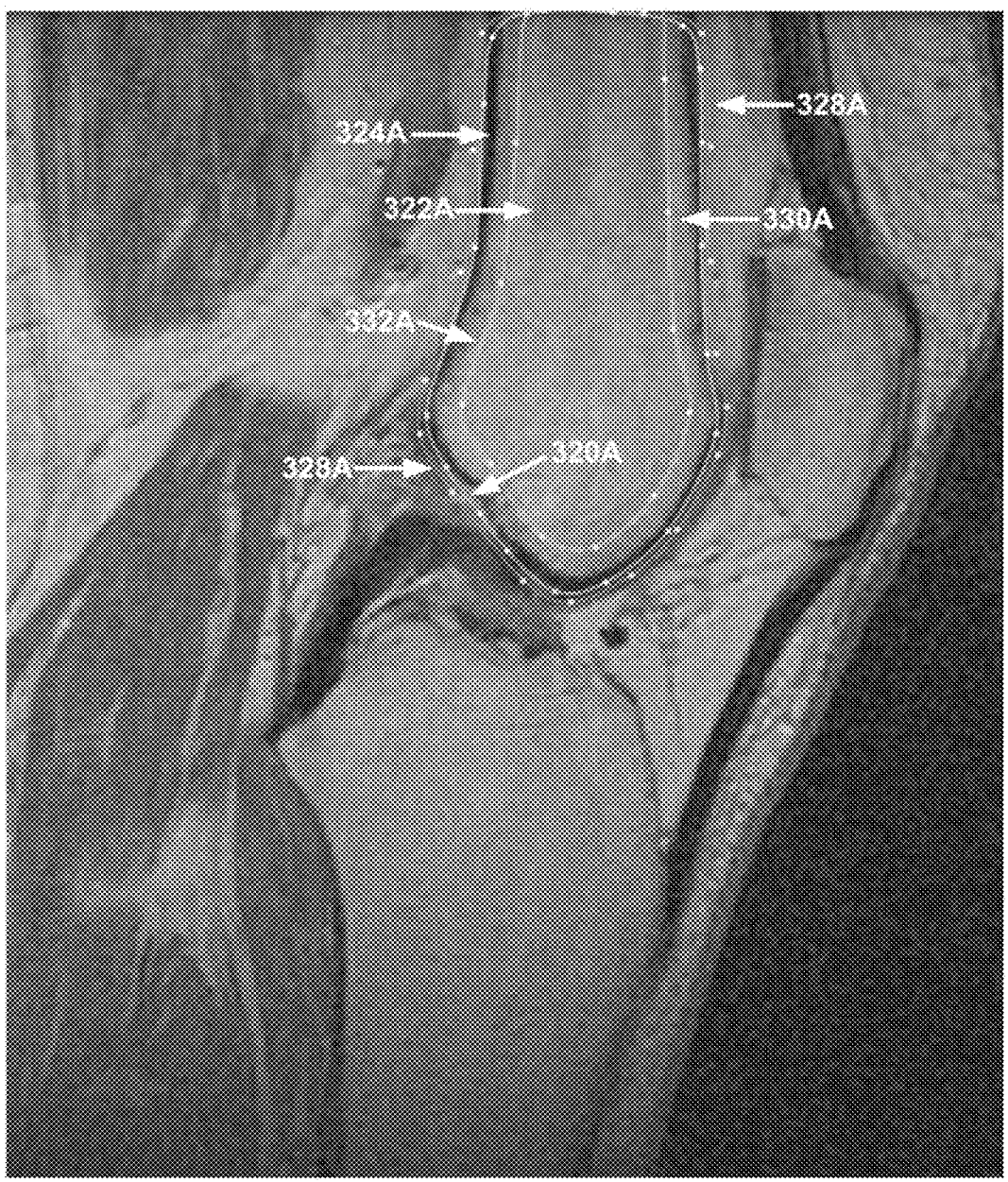
FIG. 12B is a sagittal plane image slice depicting a contour curve outlining a golden femur region, a contour curve outlining a grown femur region and a contour curve outlining a boundary golden femur region.
Figure 13B:
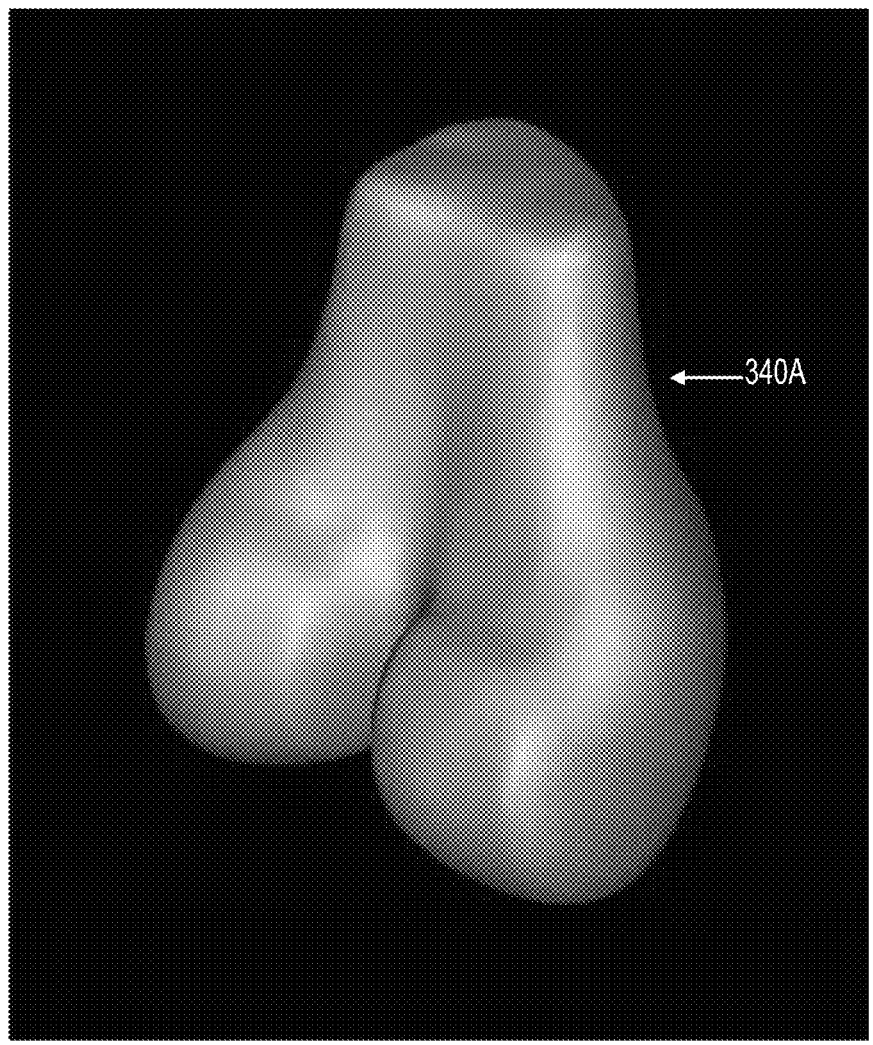
FIG. 13B depicts a golden femur 3D mesh.
Figure 14B:
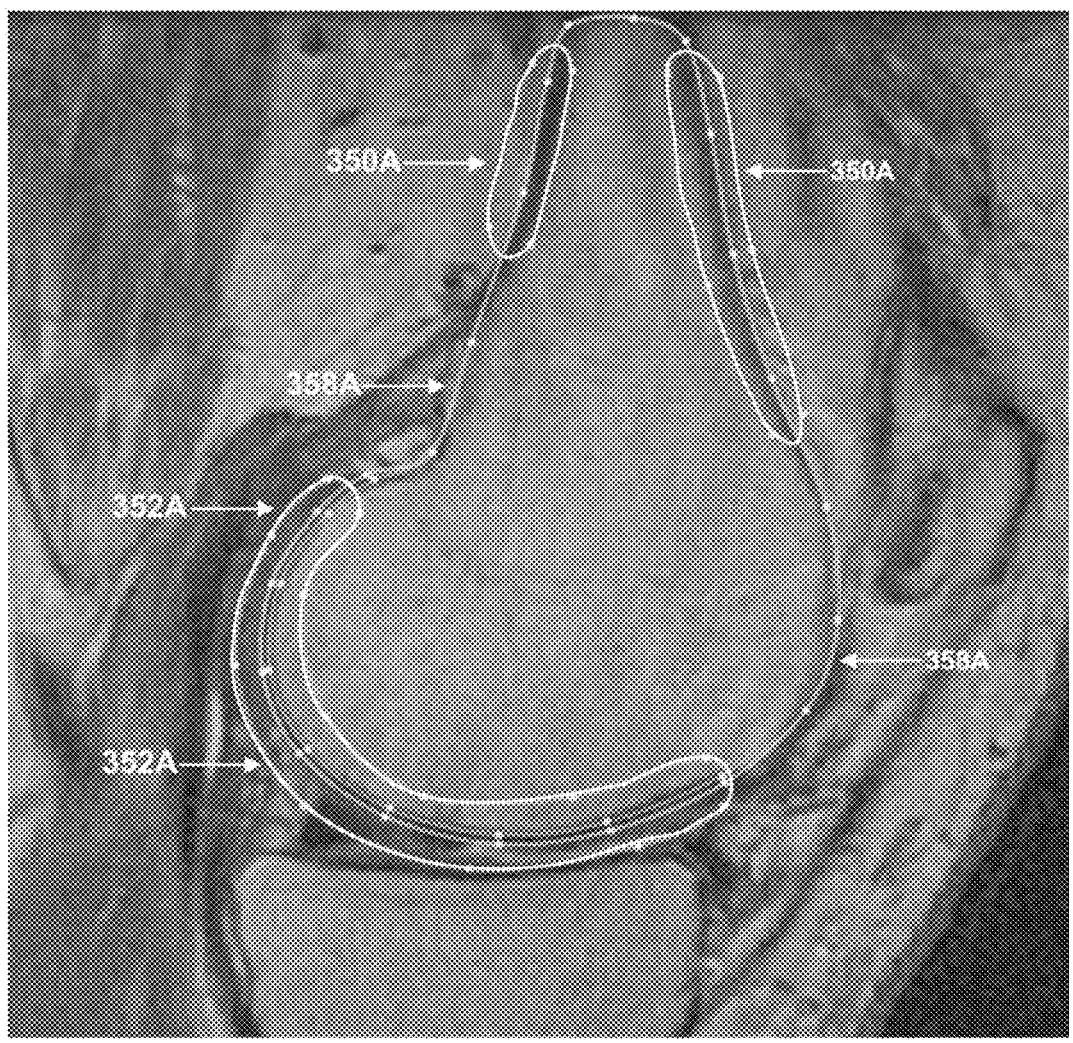
FIG. 14B is a sagittal plane image slice depicting anchor segmentation regions of a femur.
Figure 15B:
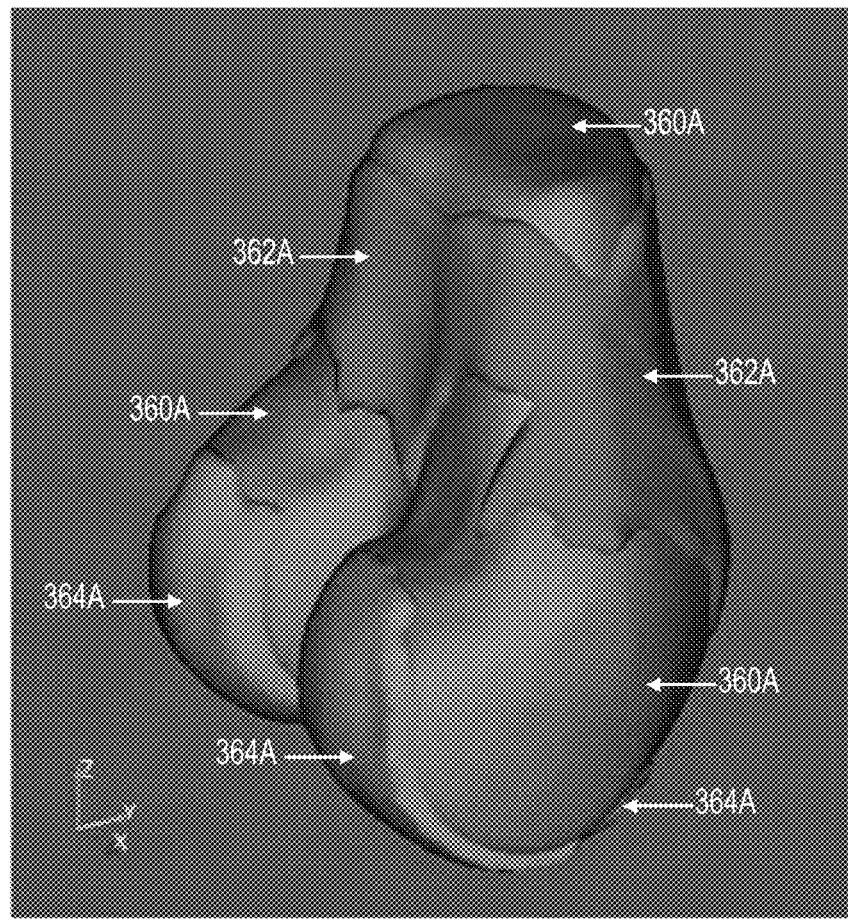
FIG. 15B is a 3D mesh geometry depicting the anchor segmentation mesh, the InDark-OutLight anchor mesh and the InLight-OutDark anchor mesh of a femur.

A golden template of a femur may also be generated in a similar manner using the method depicted by FIG. 11. FIG. 12B depicts the golden femur region, outlined by a contour curve 320A, the grown femur region, outlined by contour curve 328A, and the boundary golden femur region 330A bounded on the inside by contour curve 332A and the outside by contour curve 328A. FIG. 13B depicts the golden femur mesh 340A. FIG. 14B depicts the femur anchor segmentation curve 358A, the femur InDark-OutLight region 350A and the femur InLight-OutDark region 352A. Finally, FIG. 15B depicts the anchor segmentation mesh 360A, the InDark-OutLight anchor region mesh 362A and the InLight-OutDark anchor region mesh 364A for the femur.

Figure 16:
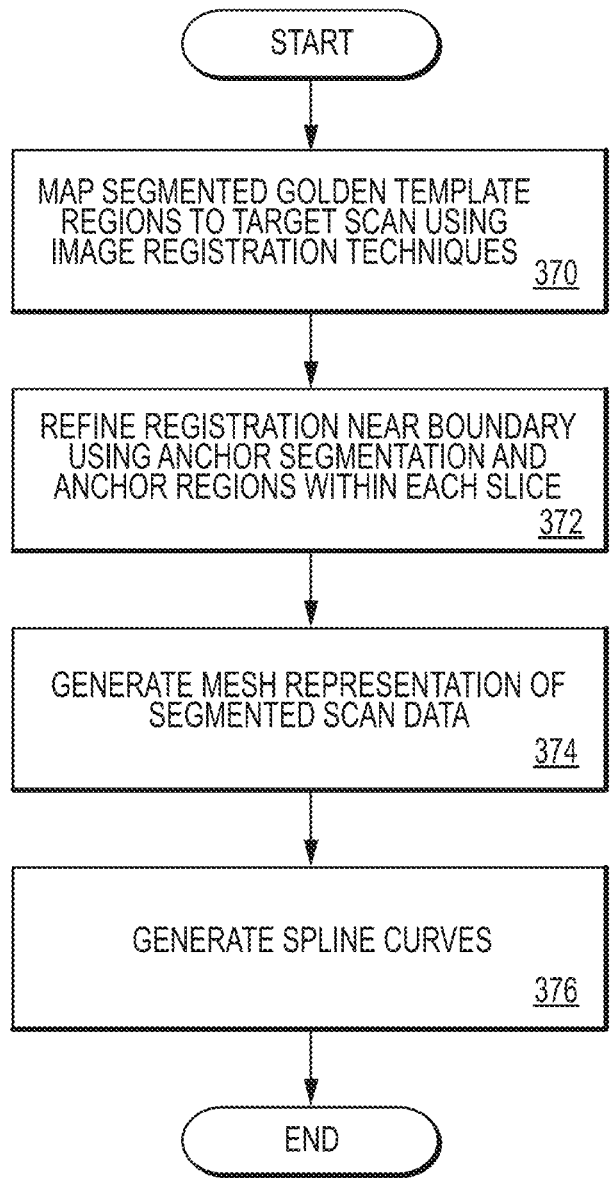
FIG. 16 depicts a flowchart illustrating one method for performing automatic segmentation of scan data using golden template registration.

FIG. 16 depicts a flowchart illustrating one method for performing automatic segmentation (e.g., operation 252 or operation 258 of FIG. 6) of the scan data of a joint (e.g., a MRI scan of a knee joint) using golden template registration. The segmentation method may be used to segment the femur (operation 252 of FIG. 6) and/or the tibia (operation 258 of FIG. 6) in either the left or right knee. Different golden template data may be used to segment the left tibia, right tibia, left femur or right femur. Additionally, other embodiments may segment other joints, including but not limited to, hip joints, elbow joints, by using an appropriate golden template of the feature of interest to be segmented.

Initially, operation 370 maps the segmented 3D golden template and marked regions (e.g., grown and boundary regions) to the target scan data using image registration techniques. This may be done to locate the corresponding feature of interest in the target scan (e.g., a target femur or tibia). Registration transforms the template image coordinate system into the target coordinate system. This allows the template image to be compared and/or integrated with the target image.

Next, operation 372 refines the registration near the feature (e.g., a bone) boundary of interest. Anchor segmentation and anchor regions may be used with a subset of 3D free-form deformations to move points within the plane of the slices (e.g., the yz plane) but not transversal (along the x axis) to the slices. Refinement of the initial registration operation may be necessary to correct errors caused by a high voxel aspect ratio. When a point from a golden template is mapped onto the target scan, it generally maps to a point between adjacent slices of the scan data. For example, if a translation occurs along the x direction, then the point being mapped may only align with a slice when the translation is a multiple of the inter-slice scan distance (e.g., a multiple of two-millimeters for an inter-slice spacing of two-millimeters). Otherwise, the point will be mapped to a point that falls between slices. In such cases, the intensity of the target scan point may be determined by averaging the intensities of corresponding points (voxels) in the two adjacent slices. This may further reduce image resolution. Additionally, refinement of the initial registration operation may correct for errors due to unhealthy areas and/or limited contrast areas. That is, the golden template may be partially pulled away from the actual bone boundary in diseased areas and/or minimal contrast areas (e.g., toward a diseased area having a different contrast) during the initial registration operation.

Next, operation 374 generates a polygon mesh representation of the segmented scan data. A polygon mesh typically is a collection of vertices, edges, and faces that may define the surface of a 3D object. The faces may consist of triangles, quadrilaterals or other simple convex polygons. In one embodiment, a polygon mesh may be generated by applying the registration transform found during operation 372 to all the vertices of a triangle golden template mesh (i.e., the surface of the mesh is composed of triangular faces). It is to be appreciated that the cumulative registration transform typically represents the transform that maps the golden template into the target MRI scan with minimal misalignment error.

Finally, operation 376 generates spline curves that approximate the intersection of the mesh generated by operation 374 with the target MRI slices. Note that these spline curves may be verified by the technician (during operation 254 or operation 260 of FIG. 6).

Figure 17:
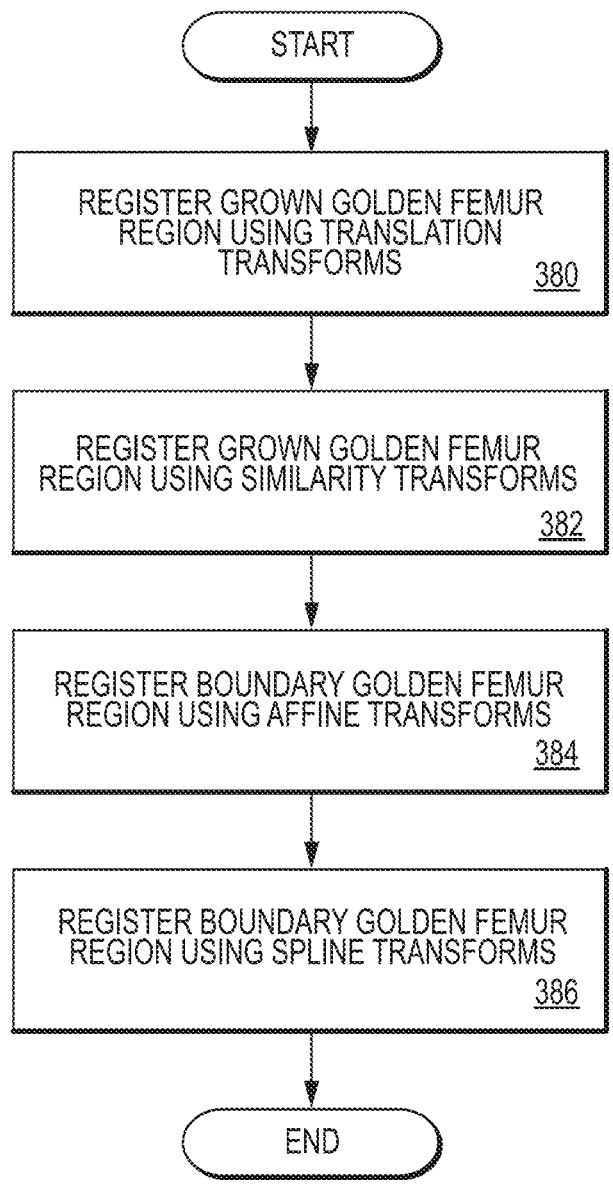
FIG. 17 depicts a flowchart illustrating one method for mapping the segmented golden femur template regions into the target scan data using image registration techniques.

FIG. 17 depicts a flowchart illustrating one method for mapping the segmented golden femur template regions into the target scan using image registration techniques. Registration may be thought of as an optimization problem with a goal of finding a spatial mapping that aligns a fixed image with a target image. Generally several registration operations may be performed, first starting with a coarse image approximation and a low-dimensional transformation group to find a rough approximation of the actual femur location and shape. This may be done to reduce the chance of finding wrong features instead of the femur of interest. For example, if a free-form deformation registration was initially used to register the golden femur template to the target scan data, the template might be registered to the wrong feature, e.g., to a tibia rather than the femur of interest. A coarse registration may also be performed in less time than a fine registration, thereby reducing the overall time required to perform the registration. Once the femur has been approximately located using a coarse registration, finer registration operations may be performed to more accurately determine the femur location and shape. By using the femur approximation determined by the prior registration operation as the initial approximation of the femur in the next registration operation, the next registration operation may find a solution in less time.

Figure 18:
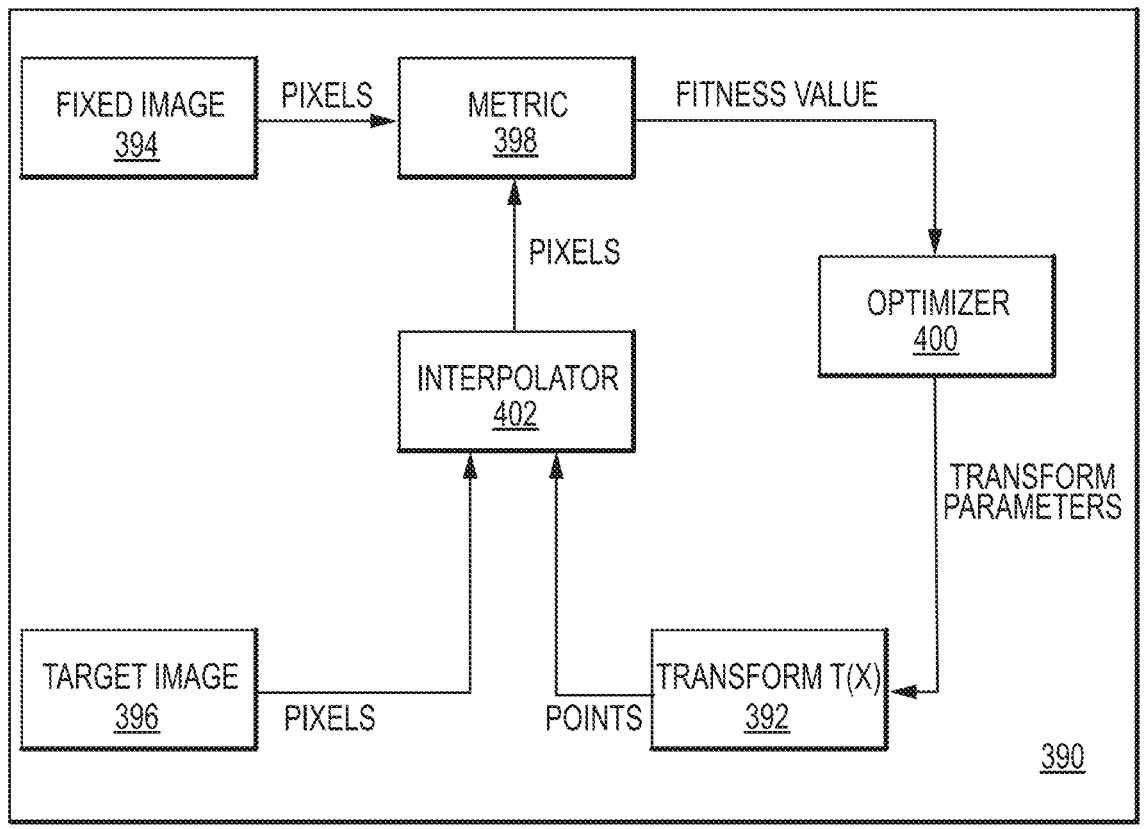
FIG. 18 depicts a registration framework that may be employed by one embodiment.

In one embodiment, each registration operation may employ a registration framework 390 as depicted in FIG. 18. The registration framework 390 may employ an image similarity-based method. Such a method generally includes a transformation model T(X) 392, which may be applied to coordinates of a fixed (or reference) image 394 (e.g., a golden femur template) to locate their corresponding coordinates in a target image 396 space (e.g., a MRI scan), an image similarity metric 398, which quantifies the degree of correspondence between features in both image spaces achieved by a given transformation, and an optimizer 400, which tries to maximize image similarity (or minimize an opposite function) by changing the parameters of the transformation model 392. An interpolator 402 may be used to evaluate target image intensities at non-grid locations (e.g., reference image points that are mapped to target image points that lie between slices). Thus, a registration framework typically includes two input images, a transform, a metric, an interpolator and an optimizer.

Referring again to FIG. 17, operation 380 may approximately register a grown femur region in a MRI scan using a coarse registration transformation. In one embodiment, this may be done by performing an exhaustive translation transform search on the MRI scan data to identify the appropriate translation transform parameters that minimizes translation misalignment of the reference image femur mapped onto the target femur of the target image. This coarse registration operation typically determines an approximate femur position in the MRI scan.

A translational transform, translates (or shifts) all elements of an image by the same 3D vector. That is, the reference femur may be mapped into the target image space by shifting the reference femur along one or more axes in the target image space to minimize misalignment. During this operation the reference femur is not rotated, scaled or deformed. In one embodiment, three parameters for the translation transformation may be generated: one parameter for each dimension that specifies the translation for that dimension. The final parameters of the translation transform minimizing the misalignment of the mapped reference femur image coordinates into the target image space may be stored.

Next, operation 382 further refines the image registration determined by operation 380. This may be done by approximately registering the grown femur region of the reference golden template femur into the target MRI scan data using a similarity transformation. In one embodiment, a similarity transformation may be performed in 3D space. The reference golden femur region may be rotated in 3D, translated in 3D and homogeneously scaled to map its coordinates into the target MRI scan data to minimize misalignment between the reference golden femur region and the corresponding region in the target MRI scan. In some embodiments, a center of rotation may be specified so that both the rotation and scaling operations are performed with respect to the specified center of rotation. In one embodiment, a 3D similarity transformation, specified by seven parameters, may be used. One parameter specifies the scaling factor, three parameters specify a versor that represents the 3D rotation and three parameters specify a vector that represents the 3D translation in each dimension. A versor is a unit quaternion that provides a convenient mathematical notation for representing orientations and rotations of objects in three dimensions.

In one embodiment, local minimization techniques may be employed with the similarity transformation to obtain a refined registration of the reference golden femur region onto the target MRI scan that is not far from the registration of the reference golden femur region onto the target MRI scan found in the previous operation 190 and used as the initial starting approximation. Registering the grown golden femur region may increase the distance where the metric function detects a feature during the registration process. When local optimization is used, the registration may be moved in a particular direction only when a small movement in that direction improves the metric function. When a golden femur template feature is farther away from the corresponding target femur feature (e.g., when there is a significant shape difference), the metric typically will not move toward that feature. Use of the larger grown femur region may allow the metric to detect the feature and move toward it.

After operation 382, operation 384 further refines the image registration of the golden femur into the target scan. In one embodiment, an affine transformation may be used to register coordinates of a boundary golden femur region of a golden femur template into the target MRI scan data. In one embodiment, the approximate femur registration found during operation 382 may be used as the initial starting approximation for the affine transformation.

An affine transformation typically is a linear transformation followed by a translation. The affine transformation preserves collinearity between points (i.e., three points which lie on a line continue to be collinear after the transformation) and ratios of distances along a line. In one embodiment, a 3D affine transformation, specified by 12 parameters, may be utilized. Nine parameters of the affine transformation specify the linear transformation (which may be represented by a three by three matrix) and three parameters of the affine transformation specify the 3D translation in each dimension. The parameters of the affine transform that minimizes the misalignment of the boundary golden femur region mapped into the target MRI scan data may be stored.

Finally, operation 386 further refines the image registration of the boundary golden femur region. In one embodiment, a spline transformation may be used to register the coordinates of the boundary golden femur region into the MRI scan data (target image space). In one embodiment, a 3D B-Spline deformable transformation may be employed and the transformation found in operation 384 may be used as the initial transformation values for the 3D B-Spline deformable transformation.

A B-Spline deformable transformation typically is a free form deformation of an object using a deformation field where a deformation vector is assigned to every point in space. For example, a 3D B-spline deformable transform T may specify a 3D vector V(P) for every point P in the original 3D space that is moved by T such that T:P→P+V (P).

In one embodiment, a B-Spline transformation may be specified with M×N parameters, where M is the number of nodes in the B-Spline grid and N is the dimension of the space. In one embodiment, a 3D B-Spline deformable transformation of order three may be used to map every reference image 3D point into the target MRI scan by a different 3D vector. The field of the vectors may be modeled using B-splines. Typically a grid J×K×L of control points may be specified where J, K, and L are parameters of the transformation.

In one embodiment, splines of order three may be used with a grid 9×6×6 of control points. That is, the transformation employs nine control points in the medial/lateral direction (i.e., the x direction), and six control points in the other directions (i.e., y and z directions). Two control points in each dimension (i.e., 2 of 9 in the x direction, 2 of 6 in the y direction and 2 of 6 in the z direction) may be used to specify boundary conditions. As such, the inner spline nodes may form a grid of size 7 by 4 by 4 and the boundary conditions increase the grid to size 9 by κ by 6. The parametric set for this transformation has a dimension of 3×9×6×6=972 (i.e., each dimension may have a 9×6×6 grid of control points). The final parameters of the spline transformation that minimizes the misalignment between the reference golden femur template and the target MRI scan data may be stored. This may be referred to as the cumulative femur registration transform herein.

Figure 19:
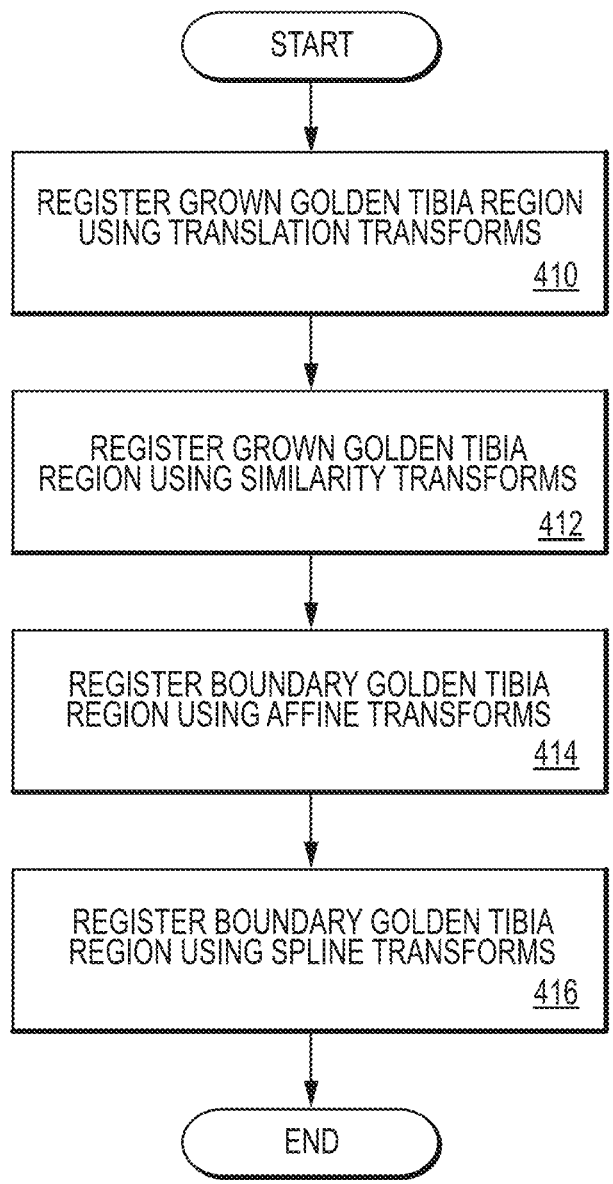
FIG. 19 depicts a flowchart illustrating one method for mapping the segmented golden tibia template regions into the target scan data using image registration techniques.

FIG. 19 depicts a flowchart illustrating one method for mapping the segmented golden tibia template regions into the target scan using image registration techniques. Generally several registration operations may be performed, first starting with a coarse image approximation and a low-dimensional transformation group to find a rough approximation of the actual tibia location and shape. This may be done to reduce the chance of finding wrong features instead of the tibia of interest. For example, if a free-form deformation registration was initially used to register the golden tibia template to the target scan data, the template might be registered to the wrong feature, e.g., to a femur rather than the tibia of interest. A coarse registration may also be performed in less time than a fine registration, thereby reducing the overall time required to perform the registration. Once the tibia has been approximately located using a coarse registration, finer registration operations may be performed to more accurately determine the tibia location and shape. By using the tibia approximation determined by the prior registration operation as the initial approximation of the tibia in the next registration operation, the next registration operation may find a solution in less time.

In one embodiment, each registration operation may employ a registration framework 390 as depicted in FIG. 18. The registration framework 390 may employ an image similarity-based method. Such a method generally includes a transformation model T(X) 392, which may be applied to coordinates of a fixed (or reference) image 394 (e.g., a golden tibia template) to locate their corresponding coordinates in a target image 396 space (e.g., a MRI scan), an image similarity metric 398, which quantifies the degree of correspondence between features in both image spaces achieved by a given transformation, and an optimizer 400, which tries to maximize image similarity by changing the parameters of the transformation model 392. An interpolator 402 may be used to evaluate target image intensities at non-grid locations (i.e., reference image points that are mapped to target image points that lie between slices). Thus, a registration framework typically includes two input images, a transform, a metric, an interpolator and an optimizer.

The automatic segmentation registration process will be described using scan data that includes a right tibia bone. This is by way of illustration and not limitation. Referring again to FIG. 19, operation 410 may approximately register a grown tibia region in a MRI scan using a coarse registration transformation. In one embodiment, this may be done by performing an exhaustive translation transform search on the MRI scan data to identify the appropriate translation transform parameters that minimizes translation misalignment of the reference image tibia mapped onto the target tibia of the target image. This coarse registration operation typically determines an approximate tibia position in the MRI scan. During this operation, the tibia of the reference image may be overlapped with the target tibia of the target image using a translation transformation to minimize translational misalignment of the tibias.

A translational transform, translates (or shifts) an image by the same 3D vector. That is, the reference tibia may be mapped into the target image space by shifting the reference tibia along one or more axes in the target image space to minimize misalignment. During this operation the reference tibia is not rotated, scaled or deformed. In one embodiment, three parameters for the translation transformation may be generated, one parameter for each dimension that specifies the translation for that dimension. The final parameters of the translation transform minimizing the misalignment of the mapped reference tibia image coordinates into the target image space may be stored.

Next, operation 412 further refines the image registration determined by operation 410. This may be done by approximately registering the grown tibia region of the reference golden tibia template into the target MRI scan data using a similarity transformation. In one embodiment, a similarity transformation may be performed in 3D space. The reference golden tibia region may be rotated in 3D, translated in 3D and homogeneously scaled to map its coordinates into the target MRI scan data to minimize misalignment between the reference golden tibia region and the corresponding region in the target MRI scan. In some embodiments, a center of rotation may be specified so that both the rotation and scaling operations are performed with respect to the specified center of rotation. In one embodiment, a 3D similarity transformation, specified by seven parameters, may be used. One parameter specifies the scaling factor, three parameters specify a versor that represents the 3D rotation and three parameters specify a vector that represents the 3D translation in each dimension. A versor is a unit quaternion that provides a convenient mathematical notation for representing orientations and rotations of objects in three dimensions.

In one embodiment, local minimization techniques may be employed with the similarity transformation to obtain a refined registration of the reference golden tibia region onto the target MRI scan that is not far from the registration of the reference golden tibia region onto the target MRI scan found in the previous operation 410 and used as the initial starting approximation. Registering the grown golden tibia region may increase the distance where the metric function detects a feature during the registration process. When local optimization is used, the registration may be moved in a particular direction only when a small movement in that direction improves the metric function. When a golden tibia template feature is farther away from the corresponding target tibia feature (e.g., when there is a significant shape difference), the metric typically will not move toward that feature. Use of the larger grown tibia region may allow the metric to detect the feature and move toward it.

After operation 412, operation 414 further refines the image registration. In one embodiment, an affine transformation may be used to register coordinates of a boundary golden tibia region of a golden tibia template into the target MRI scan data. In one embodiment, the approximate tibia registration found during operation 412 may be used as the initial starting approximation for the affine transformation.

An affine transformation typically is a linear transformation followed by a translation. The affine transformation preserves collinearity between points (i.e., three points which lie on a line continue to be collinear after the transformation) and ratios of distances along a line. In one embodiment, a 3D affine transformation, specified by 12 parameters, may be utilized. Nine parameters of the affine transformation specify the linear transformation (which may be represented by a three by three matrix) and three parameters of the affine transformation specify the 3D translation in each dimension. The parameters of the affine transform that minimizes the misalignment of the boundary golden tibia region mapped into the target MRI scan data may be stored.

Finally, operation 416 further refines the image registration of the boundary golden tibia region. In one embodiment, a spline transformation may be used to register the coordinates of the boundary golden tibia region into the MRI scan data (target image space). In one embodiment, a 3D B-Spline deformable transformation may be employed and the transformation found in operation 414 may be used as the initial transformation values for the 3D B-Spline deformable transformation.

A B-Spline deformable transformation typically is a free form deformation of an object using a deformation field where a deformation vector is assigned to every point in space. In one embodiment, a B-Spline transformation may be specified with M×N parameters, where M is the number of nodes in the B-Spline grid and N is the dimension of the space. In one embodiment, a 3D B-Spline deformable transformation of order three may be used to map every reference image 3D point into the target MRI scan by a different 3D vector. The field of the vectors may be modeled using B-splines. Typically a grid J×K×L of control points may be specified where J, K, and L are parameters of the transformation.

In one embodiment, splines of order three may be used with a grid 9×6×6 of control points. That is, the transformation employs nine control points in the medial/lateral direction (i.e., the x direction, and six control points in the other directions (i.e., the y and z directions). Two control points in each dimension (i.e., 2 of 9 in the x direction, 2 of 6 in the y direction and 2 of 6 in the z direction) may be used to specify boundary conditions. As such, the inner spline nodes may form a grid of size 7 by 4 by 4 and the boundary conditions increase the grid to size 9 by 6 by 6. The parametric set for this transformation has a dimension of 3×9×6×6=972. The final parameters of the spline transformation that minimizes the misalignment between the reference golden tibia template and the target MRI scan data may be stored. This may be referred to as the cumulative tibia registration transform herein.

The shape of the tibia may vary more from patient to patient than does the shape of the femur. As a result, the affine transformation may not provide a close enough registration of the golden tibia template to the target tibia in the target scan. This may cause the Spline transformation to find a local optimum that may be far from the actual tibia in some areas. In one embodiment, an additional registration operation between the affine transform and spline transform operations may be performed to more closely align the golden tibia and the target tibia, allowing the spline transform to converge to the correct local optimum rather than a nearby (but wrong) local optimum.

The class of transforms utilized generally should allow more flexibility (or degrees of freedom) than the Affine transform and less flexibility than the B-spline transforms. The number of degrees of freedom generally is equal to the number of transform parameters. In one embodiment, a class of transforms with more than 12 parameters and less than 3×9×6×6 parameters may be used. For example, a B-spline transform with fewer control points (than used in the subsequent spline transform) may be used for the additional transform operation. Alternatively, the deformations may be modeled using quadric rather than cubic functions.

In another embodiment, several golden tibia templates may be used that represent typical tibia variations, e.g., golden tibia templates for varum, valgum and normal tibia. In one embodiment, each of the golden tibia templates may be used during the translation, similarity and affine transform registration operations to find the template that provides the best match (e.g., best correlation) in the affine transform registration operation. This template may then be used in the remaining registration operations.

Finally, in one embodiment, the tibia registration may be improved by performing the tibia segmentation after the femur segmentation and adding a restriction on the tibia registration transformations such that the tibia may not penetrate the femur. In one embodiment, this may be implemented by introducing a penalty for the penetration. In the target MRI all the voxels that lie inside the femur splines may be marked. The metric functions, described in more detail below, that are used in the registration operations may be modified to include a penalty term. The penalty term may be computed by selecting a set of points on the boundary of the golden template segmentation, applying a transform to the set of points (in a similar way as the transform is applied to the sample points used in the correlation computations), determining if a transformed sample point falls into any of the marked voxels, and adding a large value to the penalty term for each transformed sample point that falls into any of the marked voxels.

In each of the above registration operations, a metric may be used to quantify the degree of correspondence between features in both the reference image and target image achieved by a given transformation. In one embodiment, the metric quantitatively measures how well the transformed golden template image fits the target image (e.g., a target MRI scan) and may compare the gray-scale intensity of the images using a set of sample points in the golden template region to be registered.

Figure 20:
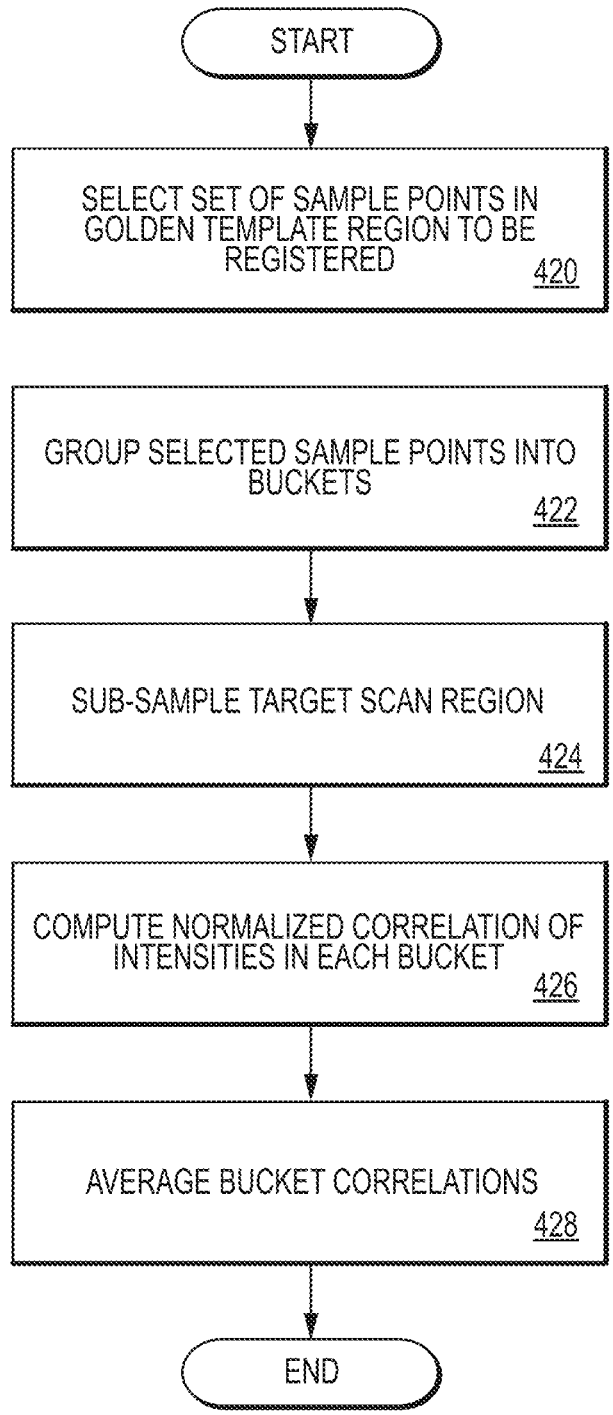
FIG. 20 depicts a flowchart illustrating one method for computing a metric for the registration framework of FIG. 18.

FIG. 20 depicts a flowchart illustrating one method for computing the metric used by the registration operations described above. For a particular registration operation, the metric may be computed in the same way, but the metric may have different parameters specified for the particular registration operation. The metric may be referred to herein as "local correlation in sample points." Initially, operation 420 selects a set of sample points in the golden template region to be registered.

For the translation and similarity transformations, the sample points may be selected as follows. Initially, a rectilinear grid of L×M×N that covers the whole bone in 3D space may be used. L, M, and N may vary from one to 16. In one embodiment, an eight by eight grid in every image slice may be used to select uniform sample points in the grown golden region of the golden template. For each grid cell, the first sample point is selected. If the sample point falls within the grown golden region, it is used. If the sample point falls outside the golden region, it is discarded.

For the affine and spline transformations, the sample points may be determined by randomly selecting one out of every 32 points in the boundary golden region of the MRI slice.

Next, operation 422 groups the selected points into buckets. In one embodiment, buckets may be formed as follows. First, the 3D space may be subdivided into cells using a rectilinear grid. Sample points that belong to the same cell are placed in the same bucket. It should be noted that sample points may be grouped into buckets to compensate for non-uniform intensities in the MRI scan.

For example, MRI scan data may be brighter in the middle of the image and darker towards the edges of the image. This brightness gradient typically is different for different scanners and may also depend on other parameters including elapsed time since the scanner was last calibrated. Additionally, high aspect ratio voxels typically result in voxel volume averaging. That is, cortical bone may appear very dark in areas where its surface is almost perpendicular to the slice and generally will not be averaged with nearby tissues. However, cortical bone may appear as light gray in the areas where its surface is almost tangent to the slice and generally may be averaged with a large amount of nearby tissues.

Next, operation 424 sub-samples the target MRI slice. Sub-sampling the target space generally has the effect of smoothing the metric function. This may remove tiny local minima such that the local minimization algorithm converges to a deeper minimum. In one embodiment, during operations 410 and 412 (of FIG. 19), each slice may be sub-sampled with an eight by eight grid. During operations 414 and 416 (of FIG. 19), each slice may be sub-sampled with a four by four grid. That is, during the sub-sampling, one point from every grid cell may be selected (e.g., the first point) and the remaining points in the grid cells may be discarded.

Next, operation 426 computes a correlation of the intensities of the points in each bucket and their corresponding points in the target MRI scan (after mapping). The correlation (NC) metric may be expressed as:

$$NC(A, B) = \frac{\sum_{i=1}^{N} A_i B_i}{\sqrt{\left(\sum_{i=1}^{N} A_i^2\right)\left(\sum_{i=1}^{N} B_i^2\right)}} \frac{N\sum A_i B_i - \sum A_i \sum B_i}{\sqrt{N\sum A_i^2 - \left(\sum A_i\right)^2} \sqrt{N\sum B_i^2 - \left(\sum B_i\right)^2}}$$

where $A_i$ is the intensity in the $i^{th}$ voxel of image A, $B_i$ is the intensity in the corresponding $i^{th}$ voxel of image B and N is the number of voxels considered, and the sum is taken from i equals one to N. It should be appreciated that the metric may be optimal when image differences are minimized (or when the correlation of image similarities is maximized). The NC metric generally is insensitive to intensity shifts and to multiplicative factors between the two images and may produce a cost function with sharp peaks and well defined minima.

Finally, operation 428 averages the correlations computed in every bucket with weights proportional to the number of sample points in the bucket.

It is to be appreciated that the above process for computing the metric may compensate for non-uniform intensities, for example, those described above with respect to FIGS. 3A-3C, in the MRI scan data.

During the registration process, an optimizer may be used to maximize image similarity between the reference image and target image by adjusting the parameters of a given transformation model to adjust the location of reference image coordinates in the target image. In one embodiment, the optimizer for a registration operation may use the transformed image (e.g., the transformed golden template) from the previous registration operation as its initial approximation. Then, local optimization techniques may be used to search for a local optimum near the initial starting approximation. This may be done so that any potential matches farther away from the feature of interest (e.g., the femur or tibia in a knee joint) reliably found in an earlier operation may be eliminated.

For the translation transformation, an exhaustive search may be performed using a grid 10×10×10 of size 5-millimeter translation vectors. A translation for every vector in the grid may be performed and the translation providing a maximum local correlation in sample points may be selected as the optimum translation.

For the similarity transformation, a regular step gradient descent optimizer may be used by one embodiment. A regular step gradient descent optimizer typically advances transformation parameters in the direction of the gradient and a bipartition scheme may be used to compute the step size. The gradient of a function typically points in the direction of the greatest rate of change and whose magnitude is equal to the greatest rate of change.

For example, the gradient for a three dimensional space may be given by:

$$\nabla f(x, y, z) = \left(\frac{\partial f}{\partial x}, \frac{\partial f}{\partial y}, \frac{\partial f}{\partial z}\right).$$

That is, the gradient vector may be composed of partial derivatives of the metric function over all the parameters defining the transform. In one embodiment the metric function may be a composition of an outer and N inner functions. The outer function may compute a metric value according to operations 426 and 428 given the vectors $\{A_i\}$ and $\{B_i\}$. The N inner functions may map N sample points from the fixed (reference) image $A_i$ into the target image $B_i$ using the transform and evaluate intensities of the target image $B_i$ in the mapped points. Each of the inner functions generally depends on the transform parameters as well as on the point in the "from" space to which the transform is applied. When computing the partial derivatives, the chain rule for computing a derivative of the function composition may be used.

To find a local minimum, parameter steps may be taken in the direction of the negative of the metric gradient (or the approximate gradient) over the transform parameter space at the current point. This generally optimizes the metric which typically has a local minimum when features of the reference image mapped into corresponding features of the target image have minimal misalignment).

The initial center of rotation for the similarity transformation (e.g., operation 382 of FIG. 17) may be specified as the center of a bounding box (or minimum sized cuboid with sides parallel to the coordinate planes) that encloses the feature (e.g., a bone) registered in the translation registration (e.g., operation 380 of FIG. 17). Scaling coefficients of approximately 40-millimeters may be used for the scaling parameters when bringing them together with translation parameters. It is to be appreciated that the gradient computation generally relies on a customized metric function in the parameter space, due to the fact that with a similarity transformation, the transform parameters do not have the same dimensionality. The translation parameters have a dimension of millimeters, while the parameters for rotational angles and scaling do not have a dimension of millimeters. In one embodiment, a metric ρ may be defined as ρ=SQRT($X^2+Y^2+Z^2$+(40-millimeter*$A1$)$^2$+ . . . )

where X is the translation along the x axis, Y is the translation along the y axis, Z is the translation along the z axis, A1 is the first rotation angle, etc. A scaling coefficient of approximately 40-millimeters may be used because it is approximately half the size of the bone (in the anterior/posterior and medial/lateral directions) of interest and results in a point being moved approximately 40-millimeters when performing a rotation of one radian angle.

In one embodiment, a maximum move of 1.5-millimeters may be specified for every point, a relaxation factor may be set to 0.98 and a maximum of 300 iterations may be performed to determine the parameters of the similarity transformation that results in minimal misalignment between the reference image and target MRI scan.

For the affine transformation, a regular step gradient optimizer may be used by one embodiment. Scaling coefficients of approximately 40-millimeters may be used for the matrix coefficients variations when bringing them together with translation parameters. A maximum 1.0-millimeter move for every point may be set for each iteration, the relaxation factor may be set to 0.98 and a maximum of 300 iterations may be performed to determine the parameters of the affine transformation that results in minimal misalignment.

For the B-spline transformation, a modified regular step gradient descent optimizer may be used by one embodiment when searching for the best B-spline deformable transformation. An MRI image gradient may often follow the bone surface in diseased areas (e.g., where the bone contact surface is severely damaged and/or where osteophytes have grown). Such a gradient may cause deformations of the golden template that would introduce large distortions in the segmented bone shape.

In one embodiment, the MRI image gradient may be corrected for such deformations by computing a normal to golden boundary vector field where every vector points towards the closest point in the golden template shape found during the affine transformation (e.g., operation 384 of FIG. 17). This may be done using a distance map (also referred to as a distance transform). A distance map supplies each voxel of the image with the distance to the nearest obstacle voxel (e.g., a boundary voxel in a binary image). In one embodiment, the gradient of the signed distance map of the golden tibia region may be mapped using the affine transformation found in operation 384 of FIG. 17. In one embodiment, a signed Danielsson distance map image filter algorithm may be used. Then, the MRI image gradient may be projected onto the vector field to obtain the corrected gradient field. This corrected gradient field is parallel to the normal to golden boundary field and typically defines a very thin subset of the set of B-spline transformations that may be spanned during the optimization.

Additionally, rather than computing one gradient vector for the transform space and taking a step along it, a separate gradient may be computed for every spline node. In one embodiment, order three B-splines (with J×K×L control nodes) may be used and J×K×L gradients may be computed, one for each control point. At every iteration, each of the spline nodes may be moved along its respective gradient. This may allow the spline curve to be moved in low contrast areas at the same time it is moved in high contrast areas. A relaxation factor of 0.95 may be used for each spline node. A maximum move of one-millimeter may be set for every point during an iteration and a maximum of 20 iterations may be performed to find the parameters of the B-spline transformation that provides minimal misalignment of the golden tibia region mapped into the target MRI scan.

Figure 21:
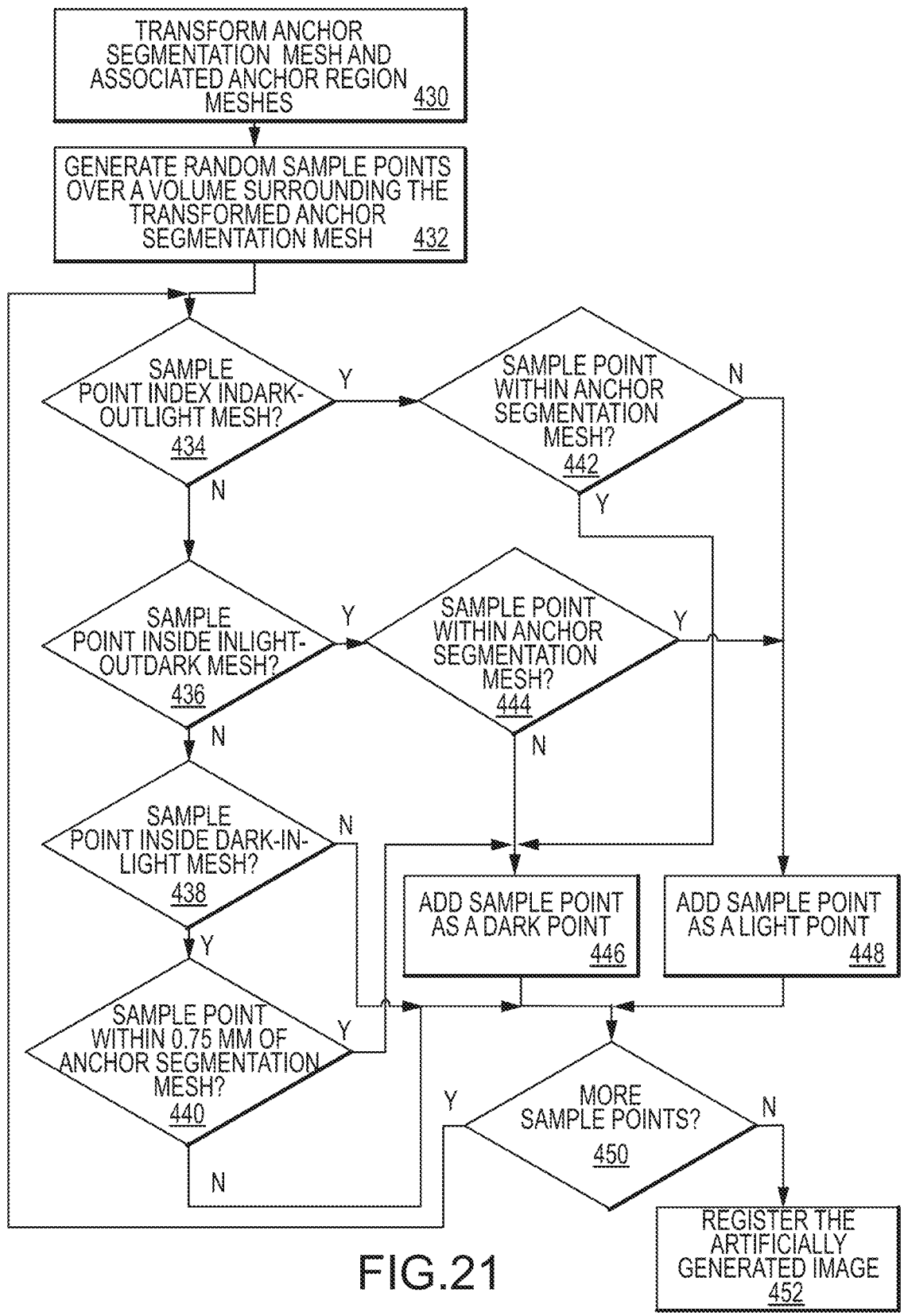
FIG. 21 depicts a flowchart illustrating one method for refining the registration results using anchor segmentation and anchor regions.

Once the position and shape of the feature of interest of the joint has been determined using image registration (operation 370 of FIG. 16), the registration results may be refined using anchor segmentation and anchor regions (operation 372 of FIG. 16). FIG. 21 depicts a flowchart illustrating one method for refining the registration results using anchor segmentation and anchor regions. Typically, during this operation, one more registration may be done using an artificially generated image for the fixed image 394 of the registration framework 390. Use of an artificial image may improve the overall segmentation by registering known good regions that typically do not change from scan to scan to correct for any errors due to diseased and/or low contrast areas that otherwise may distort the registration.

Additionally, the artificial image may be used to increase surface detection precision of articular surfaces and shaft middle regions. The image slices typically have higher resolution in two dimensions (e.g., 0.3-millimeter in the y and z dimensions) and lower resolution in the third dimension (e.g., 2-millimeters in the x dimension). The articular surfaces and shaft middle regions typically are well defined in the image slices due to these surfaces generally being perpendicular to the slices. The surface detection precision may be improved using a combination of 2D and 3D techniques that preserves the in-slice precision by only moving points within slices rather than between slices. Further, a 3D B-spline transform may be used such that the slices are not deformed independently of one another. Since each slice may not contain enough information, deforming each slice independently may result in the registration finding the wrong features. Instead, the slices as a whole may be deformed such that the registration remains near the desired feature. While each slice may be deformed differently, the difference in deformation between slices generally is small such that the changes from one slice to the next are gradual.

In one embodiment, the artificial image may comprise a set of dark and light sample points that may be used by the metric. All dark points in the artificial image may have the same intensity value (e.g., 100) and all light points in the artificial image may have the same intensity value (e.g., 200). It should be appreciated that the correlations are generally insensitive to scaling and zero shift. Thus, any intensity values may be used as long as the dark intensity value is less than the light intensity value.

Initially, operation 430 may apply the cumulative registration transform (computed by operation 370 of FIG. 16) to an anchor segmentation mesh and its three associated anchor region meshes (e.g., InDark-OutLight mesh, InLight-OutDark mesh and Dark-in-Light mesh) to generate a transformed anchor segmentation mesh and associated transformed anchor region meshes (transformed InDark-OutLight anchor mesh, transformed InLight-OutDark anchor mesh and transformed Dark-in-Light anchor mesh) that lie in a space identical to the target image space.

Then, operation 432 generates random sample points lying within a thin volume surrounding the transformed anchor segmentation mesh surface. In one embodiment, this may be a volume having an outer boundary defined by the anchor segmentation mesh surface plus 1.5-millimeters and an inner boundary defined by the anchor segmentation mesh surface minus 1.5-millimeters, which may be referred to herein as the 1.5-millimeter neighborhood. The random sample points may be generated such that they are within the image slices of the target scan but not between the slices. For example, the image slices may be transversal to the x-axis with a spacing of 2-millimeters (at x-axis locations 0.0, 2.0, 4.0, . . . ). When a sample point is selected, its x-coordinate may be one of 0.0, 2.0, 4.0, etc. but may not be 1.7, 3.0, or some non-multiple of 2.0.

In one embodiment, voxels may be marked in every image slice that belong to the 1.5-millimeter neighborhood as follows. First, the intersection of the transformed anchor mesh with every image slice may be found. It should be appreciated that the intersection of the anchor mesh with an image slice may be a polyline(s). Then, in each image slice, the polyline segments may be traversed and all pixels that intersect with the mesh may be marked. Next, a Dilate filter may be applied to the marked pixels of each image slice using a radius of 1.5-millimeters. The Dilate filter typically enlarges the marked region by adding all the points that lie within a 1.5-millimeter distance from the originally marked points.

After operation 432, operation 434 determines if a sample point lies inside the transformed InDark-OutLight mesh surface. If operation 434 determines that the sample point lies inside the transformed InDark-OutLight mesh surface, then operation 442 is performed. If operation 434 determines that the sample point does not lie inside the transformed InDark-OutLight mesh surface, then operation 436 is performed.

Operation 442 determines if the sample point lies inside the transformed anchor segmentation mesh surface. If operation 442 determines that the sample point lies inside the transformed anchor segmentation mesh surface, then operation 446 is performed. If operation 442 determines that the sample point does not lie inside the transformed anchor segmentation mesh surface, then operation 448 is performed.

Operation 436 determines if the sample point lies inside the transformed InLight-OutDark mesh surface. If operation 436 determines that the sample point lies inside the transformed InLight-OutDark mesh surface, then operation 444 is performed. If operation 436 determines that the sample point does not lie inside the transformed InLight-OutDark mesh surface, then operation 438 is performed.

Operation 444 determines if the sample point lies inside the transformed anchor segmentation mesh surface. If operation 444 determines that the sample point lies inside the transformed anchor segmentation mesh surface, then operation 448 is performed. If operation 444 determines sample point does not lie within the transformed anchor segmentation mesh surface, then operation 446 is performed.

Operation 438 determines if the sample point lies inside the transformed Dark-In-Light mesh surface. If operation 438 determines that the sample point lies inside the transformed Dark-In-Light mesh surface, then operation 440 is performed. If operation 438 determines that the sample point does not lie inside the transformed Dark-In-Light mesh surface, then operation 450 is performed.

Operation 440 determines if the sample point is within 0.75-millimeter of the surface of the transformed anchor segmentation mesh. If operation 440 determines that the sample point is within 0.75-millimeter of the surface of the transformed anchor segmentation mesh, then operation 446 is performed. If operation 440 determines that the sample point is not within 0.75-millimeter of the surface of the anchor segmentation mesh, then operation 450 is performed.

Operation 446 adds the sample point to the artificial image as a dark point. Then, operation 450 is performed.

Operation 448 adds the sample point to the artificial image as a light sample point. Then, operation 450 is performed.

Operation 450 determines if there are more randomly generated samples points to be added to the artificial image. If operation 450 determines that there are more randomly generated sample points to be added to the artificial image, then operation 434 is performed. If operation 450 determines that there are no more randomly generated sample points to be added to the artificial image, then operation 452 is performed.

Figure 22:
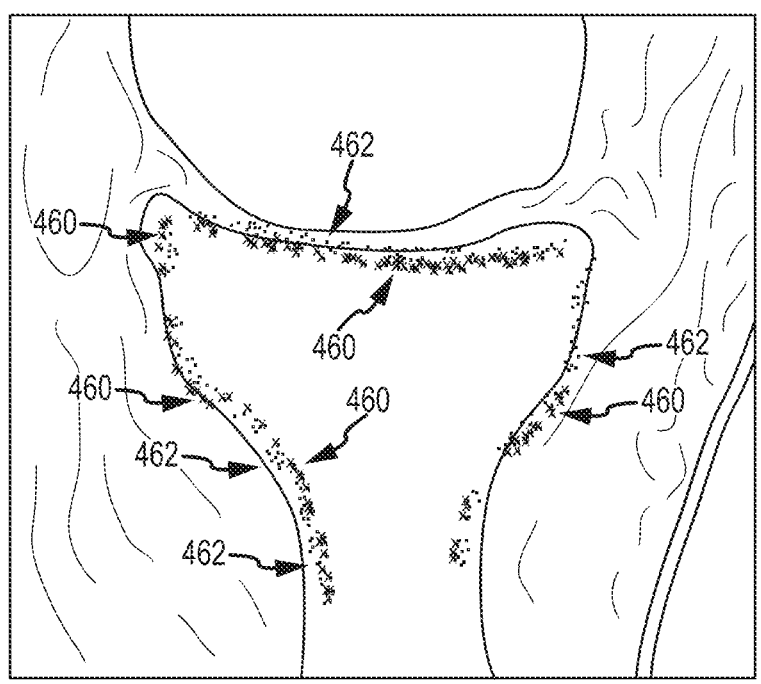
FIG. 22 depicts a set of randomly generated light sample points and dark sample points of a tibia.

FIG. 22 depicts a set of randomly generated light sample points 460 and dark sample points 462 over the target MRI 464. In one embodiment, approximately 8,000 sample points (light and dark) may be generated over the entire artificial image.

Referring again to FIG. 21, if operation 450 determines that there are no more randomly generated sample points to be added to the artificial image, operation 452 registers the set of dark and light points to the target MRI scan. This operation may perform a registration similar to the registration operation 196 (depicted in FIG. 17). In this transformation, a subset of B-spline deformable transformations may be performed that move points along their respective slices, but not transversal to their respective slices.

In a B-spline deformable transform, a translation vector for every control point (e.g., in the set of J×K×L control points) may be specified. To specify a transform that moves any point in 3D space along the y and z slice coordinates but not along the x coordinate, a restriction on the choice of translation vectors in the control points may be introduced. In one embodiment, only translation vectors with the x coordinate set equal to zero may be used to move points in the plane of the slice (e.g., the y and z directions) but not transversal to the slice (e.g., the x direction).

The use of anchor region meshes which typically are well pronounced in most image scans may reduce registration errors due to unhealthy areas and/or areas with minimal contrast differences between the feature to be segmented and surrounding image areas. For example, in the area where a healthy bone normally has cartilage, a damaged bone may or may not have cartilage. If cartilage is present in this damaged bone region, the bone boundary separates the dark cortical bone from the gray cartilage matter. If cartilage is not present in this area of the damaged bone, there may be white liquid matter next to the dark cortical bone or there may be another dark cortical bone next to the damage bone area. Thus, the interface from the cortical bone to the outside matter in this region of the damaged bone typically varies from MRI scan to MRI scan. In such areas, the interface between the cortical and the inner cancellous bone may be used as an anchor region.

The use of a subset of B-Spline deformable transforms may reduce errors due to the 2-millimeter spacing between image slices.

Figure 23:
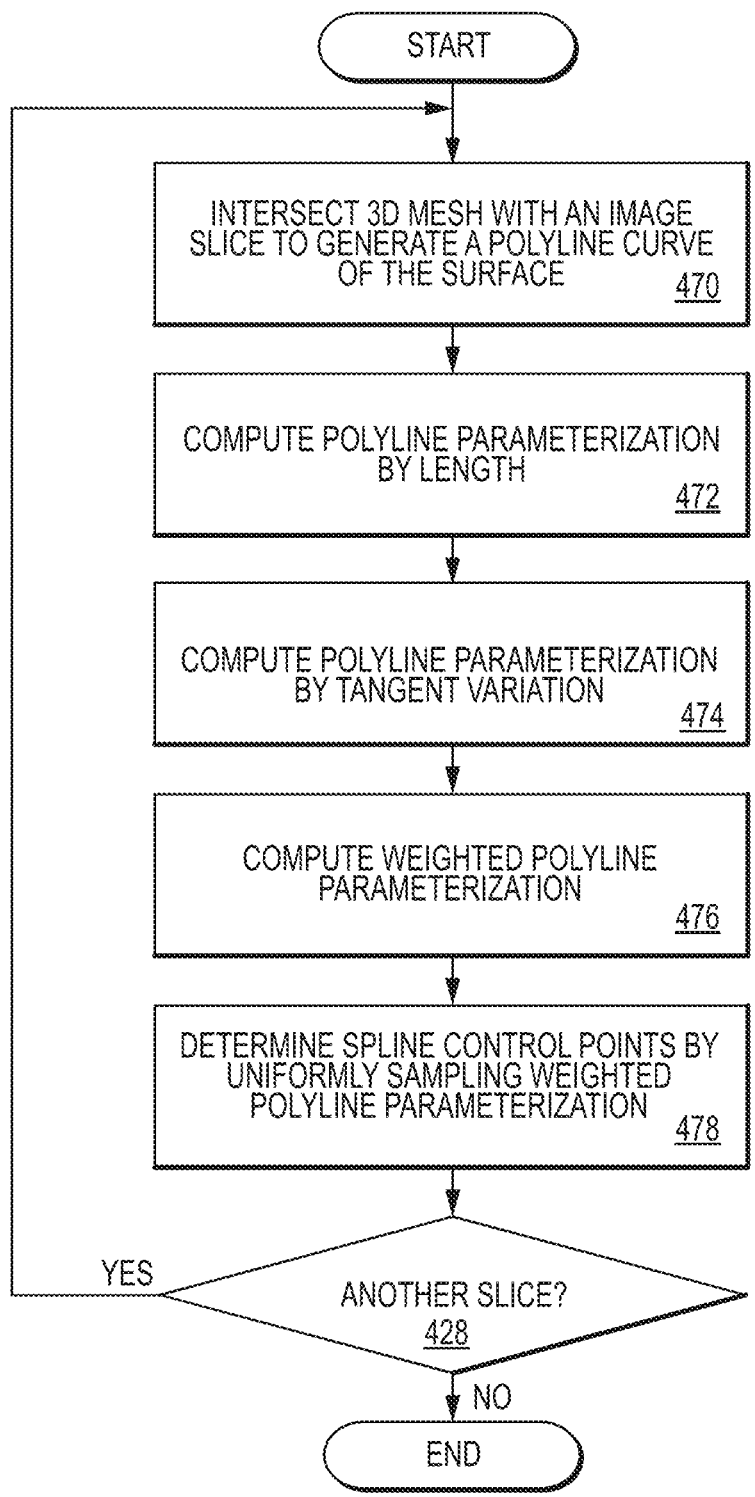
FIG. 23 depicts a flowchart illustrating one method for generating spline curves to outline features of interest in each target MRI slice.

FIG. 23 depicts a flowchart illustrating one method for generating spline curves outlining the surface of a feature of interest in each target MRI slice (e.g., operation 376 of FIG. 16). Initially, operation 470 intersects the generated 3D mesh model of the feature surface with a slice of the target scan data. The intersection defines a polyline curve of the surface of the feature (e.g., bone) in each slice. Two or more polyline curves may be generated in a slice when the bone is not very straightly positioned with respect to the slice direction.

A polyline curve is a piecewise linear approximation to a curved feature shape. Generally, this curve should be easy to manipulate with a set of control points. The polyline curve may have many segments, making it more difficult to manipulate the polyline curve (e.g., during operation 254 or 260 of FIG. 6). One embodiment may generate one or more Kochanek splines from the polyline curve. Each spline typically has a smaller number of control points and typically fits the polyline curve with about 0.2-millimeter deviation. Generally, a Kochanek spline may have more control points along the high curvature regions of the polyline curve and fewer control points along low curvature regions (i.e., where the curve tends to be flatter) of the polyline curve.

Figure 24:
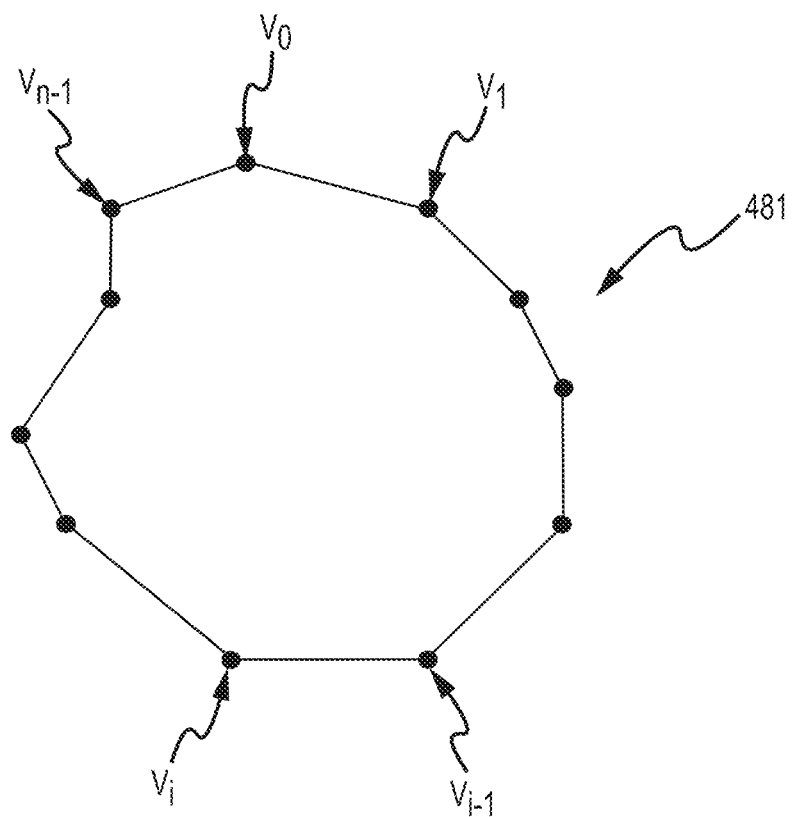
FIG. 24 depicts a polyline curve with n vertices.

Once a polyline curve has been generated, operation 472 may compute a polyline parameterization, $L_i$, as a function of the polyline's length. FIG. 24 depicts a polyline curve 481 with n vertices, $V_0, V_1, \ldots V_{i-1}, V_i \ldots V_{n-1}$. Note that vertex $V_0$ follows vertex $V_{n-1}$ to form a closed contour curve. The length of a segment connecting vertices Vi−1 and Vi may be denoted by $\Delta L_i$ such that the length parameterization, $L_i$, of the polyline at vertex $V_i$ may be expressed as:

$$L_i = \Delta L_0 + \Delta L_1 + \ldots + \Delta L_i.$$

Next, operation 474 may compute a polyline parameterization, $A_i$, as a function of the polyline's tangent variation.

The absolute value of the angle between a vector connecting vertices $V_{i-1}$ and $V_i$ and a vector connecting vertices $V_i$ and $V_{i+1}$ may be denoted by $\Delta A_i$ such that the tangent variation parameter $A_i$ at vertex $V_i$ may be expressed as:

$$A_i = \Delta A_0 + \Delta A_1 + \ldots + \Delta A_i.$$

Then, operation 476 determines a weighted sum parameterization of the polyline length and tangent variation parameterizations. In one embodiment the weighted sum parameterization, $W_i$, at vertex $V_i$ may be computed as:

$$W_i = \alpha * L_i + \beta * A_i$$

where $\alpha$ may be set to 0.2 and $\beta$ may be set to 0.8 in one embodiment.

Then, operation 478 may perform a uniform sampling of the polyline using the W parameterization results determined by operation 476. In one embodiment, a spacing interval of approximately 3.7 of the W parameter value may be used for positioning K new sample points. First, K may be computed as follows:

$$K = \text{ROUND}(W_n/3.7).$$

That is, the W parameter value, which is the last computed value $W_n$, may be divided by 3.7 and the result rounded to the nearest integer to get the number of new sample points. Then, the spacing of the sample points, $\Delta W$ may be computed as:

$$\Delta W = W_n/K.$$

Finally, the K new sample points, which are uniformly spaced, may be positioned at intervals $\Delta W$ of the parameter W. The resulting sample points may be used as control points for the Kochanek splines to convert the polyline into a spline. A Kochanek spline generally has a tension, a bias and a continuity parameter that may be used to change the behavior of the tangents. That is, a closed Kochanek spline with K control points typically is interpolated with K curve segments. Each segment has a starting point, an ending point, a starting tangent and an ending tangent. Generally, the tension parameter changes the length of the tangent vectors, the bias parameter changes the direction of the tangent vectors and the continuity parameter changes the sharpness in change between tangents. In certain embodiments, the tension, bias and continuity parameters may be set to zero to generate a Catmull-Rom spline.

In one embodiment, operation 478 may perform a linear interpolation of $W_i$ and $W_{i+1}$ to locate a sample point that lies between $W_i$ and $W_{i+1}$. The interpolated value of W may be used to determine the corresponding sample location in the segment connecting vertices $V_i$ and $V_{i+1}$.

In certain embodiments, operation 478 may divide the W parameter value by six to obtain the new number of sample points K. That is, $$K = \text{ROUND}(W_n/6).$$

Then, a measure of closeness (i.e., how closely the spline follows the polyline) may be computed as follows. First, the spline is sampled such that there are seven sample points in every arc of the spline (i.e., 7*K sample points). Then, the sum of the squared distances of the sample points to the polyline may be computed. Next, the coordinates of the K control points are varied (i.e., two*K parameters). Then, a local optimization algorithm is used to find the closest spline. If the closest spline found during the optimization is not within a certain precision (e.g., within approximately 0.4-millimeter of the polyline), then the number of control points, K, may be increased by one. The new number of control points may be uniformly distributed along the W parameter, and another optimization performed to find the new closest spline. Generally one to two optimizations provide a spline that follows the polyline with the desired degree of precision (e.g., within approximately 0.2-millimeter).

Finally, operation 480 determines if a spline curve(s) should be generated for another image slice. If operation 480 determines that a spline curve should be generated for another slice, then operation 472 is performed. If operation 480 determines that there are no more image slices to be processed, the method terminates.

As discussed above, in one embodiment, the output of the segmentation may be a triangular mesh (e.g., a 3D surface model) of the segmented bone(s) of a joint (e.g., the femur and tibia of a knee joint). The mesh generated generally represents a watertight surface that closely follows the segmentation contour curves of the slices, smoothly interpolates between the segmentation contour curves, and may have a low triangular count.

In one embodiment, a triangular mesh may be generated as follows. The segmentation data may be represented in 3D using (x, y, z) coordinates with the image slices transversal to the x direction. Thus, the segmentation contours lie in yz planes with fixed values of x. Initially, an in-slice distance image may be computed for each segmented slice. The value of each (y, z) pixel in an in-slice distance image is the distance to the closest point in the contours when the point is located inside one of the contours and is the inverse (i.e., negative) of the distance to the closest point in the contours when the point is outside all of the contours.

Then, a marching cubes algorithm may be applied to the in-slice distance images to generate the mesh. The marching cubes algorithm is a computer algorithm for extracting a polygonal mesh of an isosurface (i.e., the contours) from a three-dimensional scalar field (or voxels). The algorithm typically proceeds through the voxels, taking eight neighbor voxels at a time (thus forming an imaginary cube) and determines the polygon(s) needed to represent the part of the isosurface (i.e., contour) that passes through the imaginary cube. The individual polygons are then fused into the desired surface. The generated mesh generally passes through the zero level of the signed distance function in each slice such that the mesh lies close to the contours.

It is to be appreciated that the image resolution in the y and z directions typically determines how well the zero level of the signed distance function approximates the original contours and may also determine the triangular count in the resulting mesh. In one embodiment, a voxel size of 1.5-millimeters in the y and z directions may be used. This typically yields deviations within 0.1-millimeter of the original contours and produces a smooth mesh.

In one embodiment, a smoothing operation may be performed in the x direction (i.e., transversal to the image slices) to compensate for surface waviness that may have been introduced when the automatically generated contours were adjusted (e.g., during operation 260 of FIG. 6). Such waviness may occur in regions of an image slice where there is minimal contrast variation and the curve is positioned by the technician. Typically a smooth best guess mesh in uncertain areas may be desired when generating a planning model that may be used to locate the position of an implant. Alternatively, a smooth overestimation may be desired in uncertain areas such as in an arthritic model used to create a jig.

In one embodiment, simple smoothing may be used and the amount of smoothing (i.e., how much a voxel value may be modified) may be controlled by two user specified parameters, MaxUp and MaxDown. After an average is computed for a voxel, it is clamped using these values to limit the amount of smoothing. The smoothing operation typically does not change the image much in areas where the image contrast is good. For smooth best guess averaging in uncertain areas, MaxUp and MaxDown may each be set to 1 millimeter. For smooth overestimation averaging in uncertain regions, MaxUp may be set to 2-millimeters and MaxDown may be set to 0-millimeter.

Figure 25:
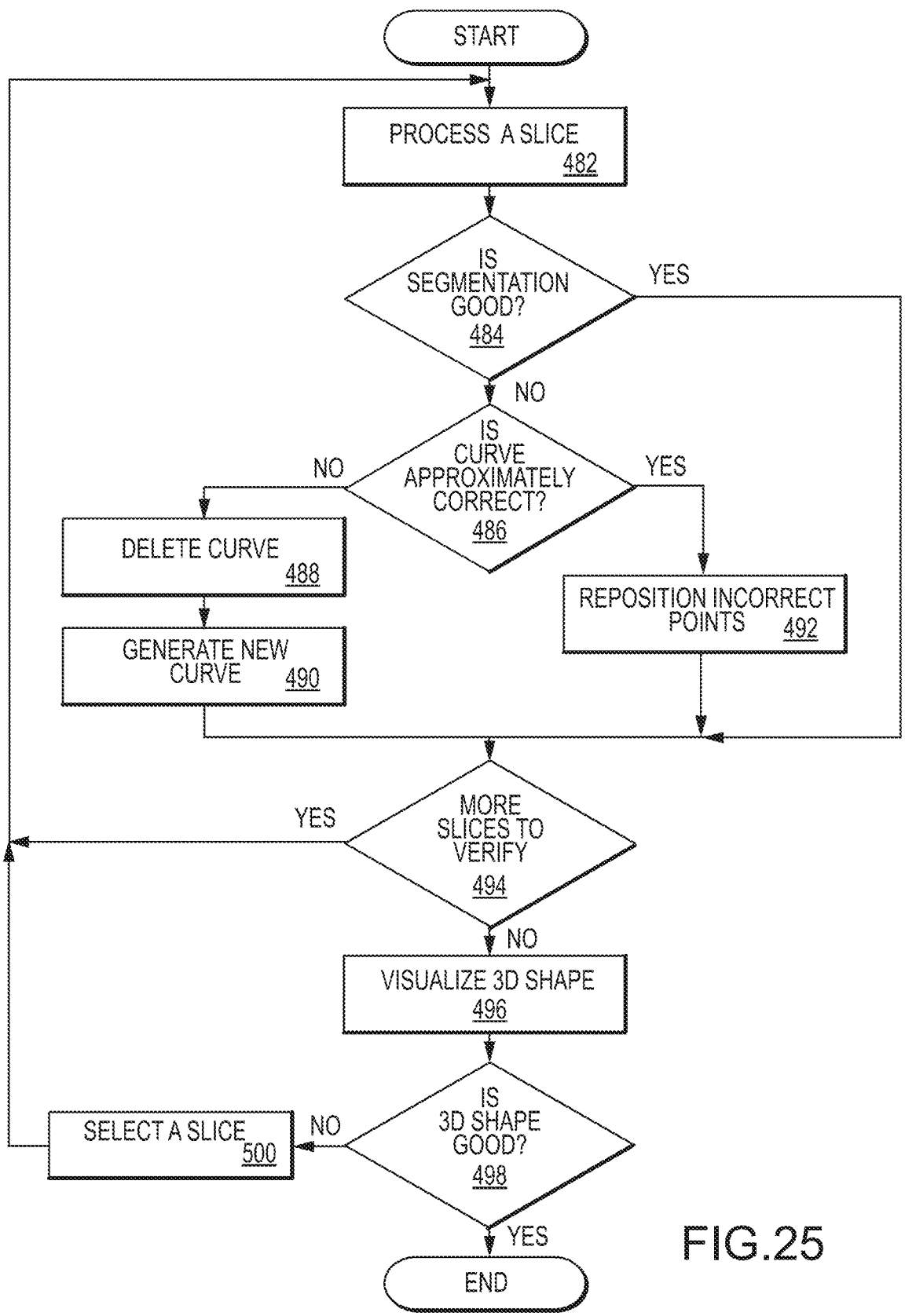
FIG. 25 depicts a flowchart illustrating one method for adjusting segments.

The operation of adjusting segments of the segmentation process will now be described with reference to FIG. 25, which depicts a flowchart for one method of adjusting segments (e.g., operation 254 or operation 260 of the flowchart depicted in FIG. 6). In one embodiment, the segmentation data may be manually adjusted by a trained technician sitting in front of a computer 6 and visually observing the automatically generated contour curves in the image slices on a computer screen 9. By interacting with computer controls 11, the trained technician may manually manipulate the contour curves. The trained technician may visually observe all of the contours as a 3D surface model to select an image slice for further examination.

Initially, in operation 482 a slice is selected for verification. In one embodiment, the slice may be manually selected by a technician.

Next, operation 484 determines if the segmentation contour curve in the selected slice is good. If operation 484 determines that the segmentation contour curve is good, then operation 494 is performed. If operation 484 determines that the segmentation contour curve is not good, then operation 486 is performed.

Operation 486 determines if the segmentation contour curve is approximately correct. If operation 486 determines that the contour curve is approximately correct, then operation 492 is performed.

Figure 26:
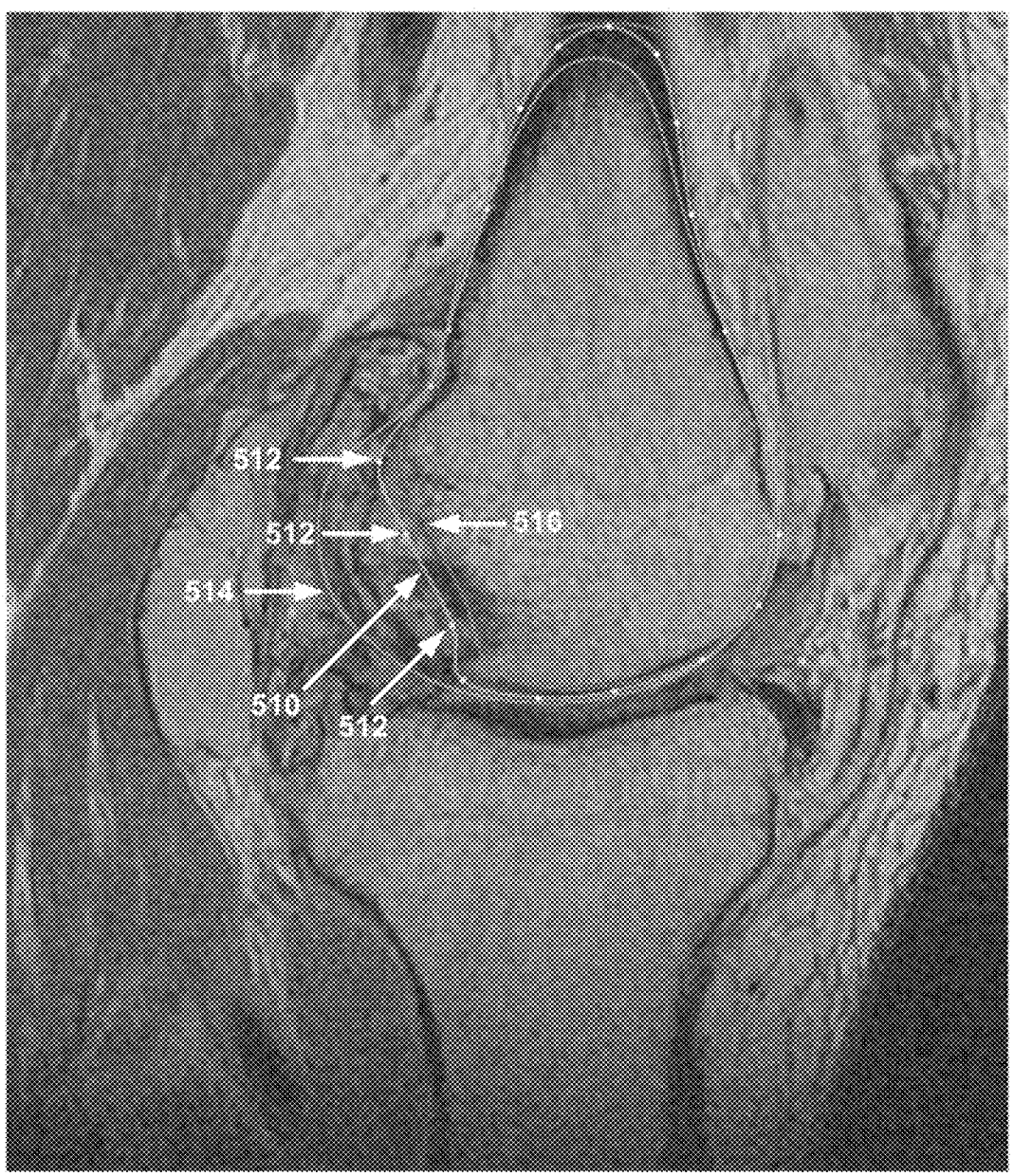
FIG. 26 is a sagittal plane image slice depicting a contour curve with control points outlining a femur with superimposed contour curves of the femur from adjacent image slices.

In operation 492 incorrect points of the segmentation contour curve may be repositioned. In one embodiment this may be performed manually by a trained technician. It is to be appreciated that it may be difficult for the technician to determine where the correct contour curve should be located in a particular slice. This may be due to missing or unclear bone boundaries and/or areas with little contrast to distinguish image features. In one embodiment, a compare function may be provided to allow the technician to visually compare the contour curve in the current slice with the contour curves in adjacent slices. FIG. 26 depicts an image showing the contour curve 510 (e.g., a spline curve) with control points 512 of the contour curve 510 for the current image slice as well the contour curves 514, 516 of the previous and next image slices, respectively, superimposed on the current image slice.

It may be difficult to determine where the correct segmentation contour curve should be located due to missing or unclear bone boundaries due to the presence of unhealthy areas, areas with limited contrast differences, and/or voxel volume averaging. When visually comparing adjacent slices, the technician may visualize the data in 2D planes (xy, yz, and xz) and in 3D. In one embodiment, the technician may select an area for examination by positioning a crosshair on a location in any window and clicking a mouse button to select that image point. The crosshair will be placed at the desired point and may be used to indicate the same location when the data is visualized in each window.

The technician may use the spline control points to manipulate the shape of the curve. This may be done by using a mouse to click on a control point and dragging it to a desired location. Additionally, the technician may add or delete spline curve control points. This may be done by using a mouse to select two existing control points between which a control point will be inserted or deleted. Alternatively, the technician may use a mouse cursor to point to the location on the curve where a control point is to be inserted. In one embodiment, by pressing the letter I on a keyboard and then positioning the cursor at the desired location, clicking the left mouse button will insert the control point. A control point may be deleted by pressing the letter D on the keyboard and then positioning the cursor over the desired control point to be deleted. The selected control point will change color. The selected control point will be deleted when the left mouse button is clicked.

Referring again to FIG. 25, if operation 486 determines that the contour curve is not approximately correct, operation 488 is performed to delete the curve. Then, operation 490 is performed.

Operation 490 generates a new segmentation contour curve for the image slice. In one embodiment, a technician may use a spline draw tool to insert a new spline curve. With the spline draw tool, the technician may click on consecutive points in the current slice to indicate where the spline curve should be located and a spline curve is generated that passes through all of the indicated points. A right mouse click may be used to connect the first and last points of the new spline curve. Alternatively, the technician may use a paste command to copy the spline curve(s) from the previous slice into the current slice. The spline control points may then be manipulated to adjust the spline curves to follow the feature in the current image slice.

In another embodiment, a paste similar command may be used by the technician to copy the spline curve from the previous slice into the current slice. Rather than pasting a copy of the spline curve from the previous slice, the spline curve may be automatically modified to pass through similar image features present in both slices. This may be done by registering a region around the spline curve in the previous slice that is from about 0.7-millimeter outside of the curve to about 5.0-millimeter within the curve. Initially, this region is registered using an affine transformation. Then, the result of the affine transform may be used as a starting value for a B-Spline deformable transformation. The metric used for the transform may be the local correlation in sample points metric described previously. Typically, more sample points may be taken closer to the curve and fewer sample points taken farther away from the curve. Next, the spline control points may be modified by applying the final transformation found to the spline control points. Additionally, the trained technician may adjust from zero to a few control points in areas where the bone boundary changes a lot from the slice due to the bone being tangent to the slice or in areas of limited contrast (e.g., where there is an osteophyte growth). Then, operation 492 is performed.

Operation 494 determines if there are additional slices to be verified. If operation 494 determines that there are additional slices to be verified, operation 482 is performed.

If operation 494 determines that there are no more slices to be verified, then operation 496 is performed. Operation 496 generates a 3D surface model of the segmented bone.

Figure 27:
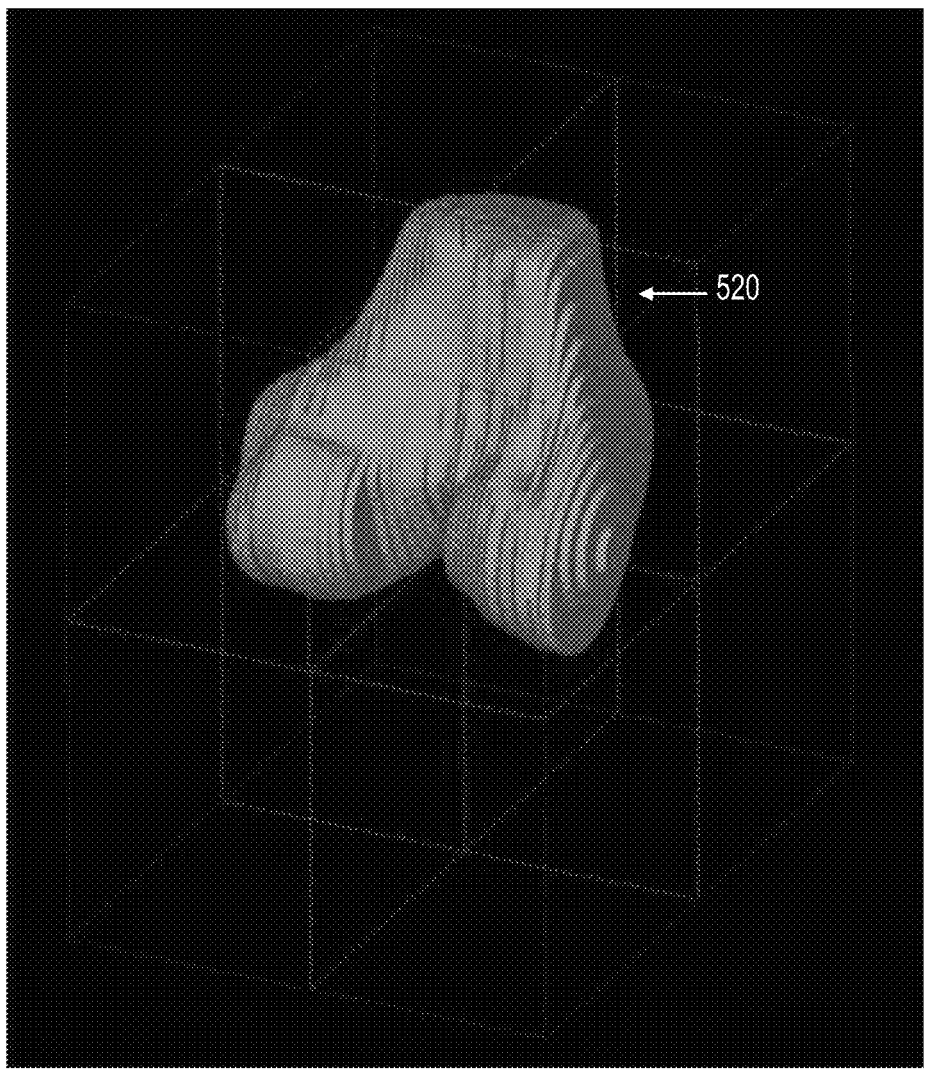
FIG. 27 depicts a 3D slice visualization of a femur showing the voxels inside of the spline curves.

Then, operation 498 determines if the 3D surface model is good. In one embodiment, a technician may manually determine if the 3D surface model is good. The technician may use a spline 3D visualization tool that generates a slice visualization showing the voxels inside all of the splines in 3D, as illustrated by the 3D shape 520 depicted in FIG. 27. This spline 3D visualization tool typically may be generated in real time to provide interactive updates to the technician as the spline curves are manually edited. Alternatively, a mesh visualization may be generated in response to a technician command. The mesh visualization typically generates a smooth mesh that passes close to all the spline curves, e.g., mesh 290 depicted in FIG. 9.

If operation 498 determines that the 3D model is not good, then operation 500 is performed. Operation 500 selects a slice lying in an area where the 3D shape is not good.

In one embodiment, a technician may manually select the slice. Then, operation 482 is performed.

If operation 498 determines that the 3D model is good, then the method terminates.

The 3D surface models of the lower end of the femur and the upper end of the tibia of a patient's knee may be used to create arthroplasty jigs and/or implants. For example, the models may be used to create femur and tibia jigs that can be used with a patient's femur and tibia as disclosed in the various U.S. Patent applications incorporated by reference herein in this Detailed Description and filed by Park and Park et al. Automatic segmentation of image data to generate 3D bone models may reduce the overall time required to perform a reconstructive surgery to repair a dysfunctional joint and may also provide improved patient outcomes.

B. Segmentation Using Landmarks of Scanner Modality Image Data to Generate 3D Surface Model of a Patient's Bone Now begins a discussion of an alternative embodiment of image segmentation. The alternative embodiment includes placing landmarks 777 (in FIG. 35A-FIG. 35H) on image contours. The landmarks 777 are then used to modify a golden bone model (e.g., golden femur or golden tibia), the resulting modified golden bone model being the output of segmentation.

Similar to the embodiment of image segmentation discussed above in section b. of this Detailed Discussion, in one version of the alternative embodiment of image segmentation, the 2D images 16 of the patient's joint 14 are generated via the imaging system 8 (see FIG. 1A and [block 100] of FIG. 1B). These images 16 are analyzed to identify the contour lines of the bones and/or cartilage surfaces that are of significance with respect to generating 3D models 22, 36, as discussed above in section a. of this Detailed Discussion with respect to [blocks 110 and 130] of FIGS. 1C and 1D. Specifically, a variety of image segmentation processes may occur with respect to the 2D images 16 and the data associated with such 2D images 16 to identify contour lines that are then compiled into 3D bone models, such as bone models 22, restored bone models 28, and arthritic models 36.

Algorithms and software are described in this Detailed Discussion for automatic and semi-automatic image segmentation. In the Detailed Description, alternative software tools and underlying methods are described, such alternative tools and methods helping a user to quickly generate bone models. Because the alternative software requires some user input such as, for example, initial Landmark positions, final verification and, in some instances, adjustment, this alternative segmentation process can be considered a semi-automatic segmentation process.

In some cases the alternative embodiment described in section c. of this Detailed Discussion may significantly reduce the user time spent on segmentation. In particular, compared to manual segmentation (where the user draws contour(s) by hand on each applicable slice for each applicable bone), the user time may be reduced by approximately five times when a user segments a planning model intended for communicating a preoperative planning model to a surgeon. For that purpose, a user may generate 3D bone models with high precision in particular areas and less precision in other areas. In some implementations, a user may get high precision (e.g., 0.5 mm) at well-defined bone contours in MRI images outside the implant regions and less precision (e.g., up to 2 mm) in the regions that will be replaced with implants by spending approximately 3-4 minutes in the user interface ("UI") setting landmarks for the algorithm. If improved precision is desired, the user may position more landmarks and thus spend more time in the UI.

In one embodiment, the software tool described in section c. of the Detailed Discussion is called "Segmentation using Landmarks". This tool may be implemented inside software application PerForm 1.0. A variety of processes and methods for performing image segmentation using landmarks are disclosed herein.

The imager 8 typically generates a plurality of image slices 16 via repetitive imaging operations. Depending on whether the imager 8 is a MRI or CT imager, each image slice will be a MRI or CT slice. As shown in FIG. 2A, the image slice may depict the cancellous bone 200, the cortical bone 202 surrounding the cancellous bone, and the articular cartilage lining portions of the cortical bone 202 of an object of interest of a joint, e.g., a femur 204 in a patient's knee joint 14. The image may further depict the cancellous bone 206, the cortical bone 208 of another object of interest in the joint, e.g., a tibia 210 of the knee joint 14. In one embodiment, each image slice 16 may be a two-millimeter 2D image slice.

One embodiment may segment one or more features of interest (e.g., bones) present in MRI or CT scans of a patient joint, e.g., knee, hip, elbow, etc. A typical scan of a knee joint may represent approximately a 100-millimeter by 150-millimeter by 150-millimeter volume of the joint and may include about 40 to 80 slices taken in sagittal planes. A sagittal plane is an imaginary plane that travels from the top to the bottom of the object (e.g., the human body), dividing it into medial and lateral portions. It is to be appreciated that a large inter-slice spacing may result in voxels (volume elements) with aspect ratios of about one to seven between the resolution in the sagittal plane (e.g., the y z plane) and the resolution along the x axis (i.e., each scan slice lies in the yz plane with a fixed value of x). For example, a two-millimeter slice that is 150-millimeters by 150-millimeters may be comprised of voxels that are approximately 0.3-millimeter by 0.3-millimeter by 2-millimeters (for a 512 by 512 image resolution in the sagittal plane).

In one embodiment, each slice may be a gray scale image with a resolution of 512 by 512 voxels where the voxel value represents the brightness (intensity) of the voxel. The intensity may be stored as a 16-bit integer resulting in an intensity range from 0 to 65,535, where 0 may represent black and 65,535 may represent white. The intensity of each voxel typically represents the average intensity of the voxel volume. Other embodiments may employ scans having higher or lower resolutions in the sagittal plane, different inter-slice spacing, or images where the intensity may be represented by a 24 bit vector (e.g., eight bits each for a red component, green component and blue component). Additionally, other embodiments may store intensity values as 8-bit or 32-bit signed or unsigned integers or floating point values.

Typical MRI and CT scan data generally provide images where parts of a bone boundary of interest may be well defined while other parts of the bone boundary may be difficult to determine due to voxel volume averaging, the presence of osteophyte growth, the presence of tissue having similar image intensities in neighboring areas to the object to be segmented, amongst other things. Such poor definition of parts of the bone boundary in the images may cause fully automated segmentation techniques to fail. For example, FIG. 2A depicts regions 212 within a slice where an object boundary may not be visible due to neighboring tissue having about the same intensity as the feature of interest. Depicted in FIG. 2B are regions 214 that may be extended into the slice from adjacent slices due to a high voxel aspect ratio. Depicted in FIG. 2C is a region 216 of the bone boundary 218 that may disappear or lose regularity when the bone boundary 218 is approximately tangent to the slice.

In one embodiment, a user may provide some additional input to the auto-segmentation algorithm, and the algorithm could use the additional user input for more accurate and faster segmentation of features of interest. For example, the additional user input may be a set of points on the boundary of the feature of interest. In the context of a knee procedure, the points might be on the Femur knee bone boundary or on the Tibia knee bone boundary. These can be called landmark points or simply landmarks 777.

In order for a user to provide particular landmark points, the software may allow loading MRI or CT image data, viewing and scrolling over image slices, specifying landmark points in the slices and editing them. The software may also allow visualization of the segmentation results (i.e., segmentation curves drawn in the image slices). The software may also generate a 3D model from 2D outlining curves in 2D slices.

In one embodiment, PerForm software may be used to provide functionality for loading MRI or CT scanned data, visualizing sagittal, coronal and axial slices and scrolling over them, drawing spline curves in slices, and generating a 3D mesh model passing through a set of spline curves. In one embodiment, a 3D mesh typically is a collection of vertices, edges, and faces that may define the surface of a 3D object. The faces may consist of triangles, quadrilaterals or other simple convex polygons. It should be appreciated that any other curve types may be employed instead of spline curves. For example, polyline curves may be used.

In one embodiment, a tool called "Segmentation using Landmarks" is added to PerForm software. Such a tool provides a UI for landmarks positioning and editing. The tool also provides a button "Segment", which invokes the segmentation algorithm. The algorithm uses 3D image and landmarks and generates spline curves outlining the required bone.

Figure 28:
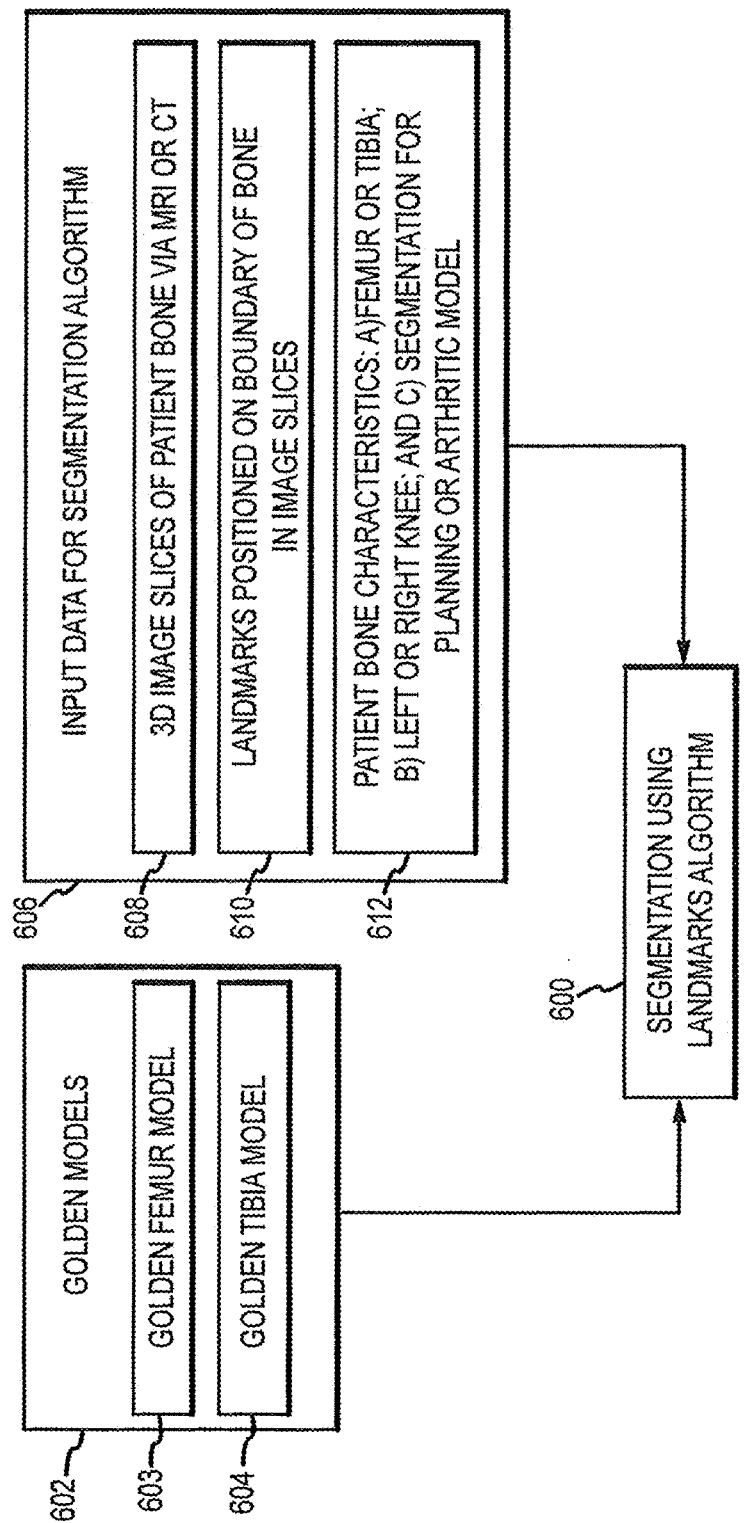
FIG. 28 is a diagram depicting types of data employed in the image segmentation algorithm that uses landmarks.

To begin the detailed discussion of the alternative embodiment of image segmentation described in this section c. of the Detailed Description, wherein landmarks 777 placed on image contours are used to modify a golden bone model (e.g., golden femur or golden tibia), the resulting modified golden bone model being segmented, reference is made to FIG. 28, which is a diagram depicting types of data employed in the image segmentation algorithm that uses landmarks. As shown in FIG. 28, the data employed in the segmentation algorithm 600 may be characterized as being two types of data. The first type of data exists in the system once generated and is for use with multiple patients and is not generated specifically for the patient for which the current image segmentation is being undertaken. This type of data may be called golden model data 602 and is derived similar to as discussed above with respect to FIG. 11, etc. and as generally reiterated below. The golden model data 602 may include, for example, one or more golden femur models 603 and one or more golden tibia models 604. If the joint being treated is something other than a knee, for example, the patient's arm, then the golden model data 602 may include another type of golden bone model, for example, a golden radius or golden ulna.

The second type of data is specific to the patient for which the current image segmentation is being undertaken. This type of data may be called input data for segmentation algorithm 606. The input data 606 includes 3D image slices data 608, which is 3D image slice data of the patient bone via MRI, CT or another type of medical imaging. The input data 606 also includes landmark data 610, which is landmarks 777 positioned on boundaries of the patient bone in the image slices. The input data 606 further includes patient bone characteristics 612 such as bone type (e.g., whether the bone is a tibia or femur), bone right or left handedness, and whether the segmentation is being done to generate an arthritic model 36 (see FIG. 1D) or a planning or restored bone model 28 (see FIG. 1C). As explained below, the golden model data 602 and the input data 606 are used in the segmentation algorithm 600 to segment the 3D image employing landmarks 777.

Figure 29:
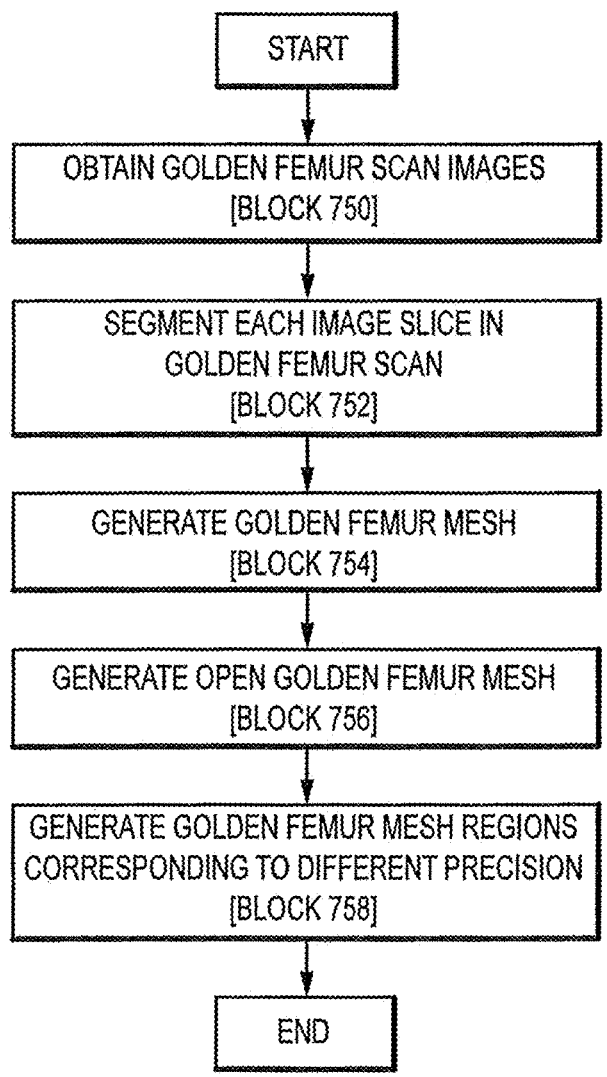
FIG. 29 is a flowchart illustrating the overall process for generating a golden femur model of FIG. 28.

As shown in FIG. 29, which is a flowchart illustrating the overall process for generating a golden femur model 603 of FIG. 28, golden femur scan image slices 616 are obtained in operation 750. For example, as discussed above with respect to FIG. 11 above, a representative femur 618 that is free of damage and disease may be scanned via medical imaging, such as, for example, MRI or CT. Where the golden femur model 603 is to be employed in generating a bone model 22 (see block 110 of FIG. 1C) and cartilage geometry is not of interest, the golden femur scan images slices 616 may be of a femur having damaged cartilage as long as the bone shape is otherwise desirable (e.g., normal) and free of deterioration or damage. Where the golden femur model 603 is to be employed in generating an arthritic model 36 (see block 130 of FIG. 1D) and cartilage geometry is of interest, the golden femur scan images slices 616 may be of a femur having both cartilage and bone shape that are desirable (e.g., normal) and free of deterioration or damage.

The appropriate femur scan may be selected by screening multiple MRI femur scans to locate an MRI femur scan having a femur that does not have damaged cancellous and cortical matter (i.e., no damage in femur regions that should be present in this particular model), which has good MRI image quality, and which has a relatively average shape, e.g., the shaft width relative to the largest part is not out of proportion (which may be estimated by eye-balling the images). This femur scan data, referred to herein as a golden femur scan, may be used to create a golden femur template.

It is to be appreciated that several MRI scans of a femur (or other bone of interest) may be selected, a template generated for each scan, statistics gathered on the success rate when using each template to segment target MRI scans, and selecting the one with the highest success rate as the golden femur template.

In other embodiments, a catalog of golden models may be generated for any given feature, with distinct variants of the feature depending on various patient attributes, such as (but not limited to) weight, height, race, gender, age, and diagnosed disease condition. The appropriate golden mesh would then be selected for each feature based on a given patient's characteristics.

Figure 30:
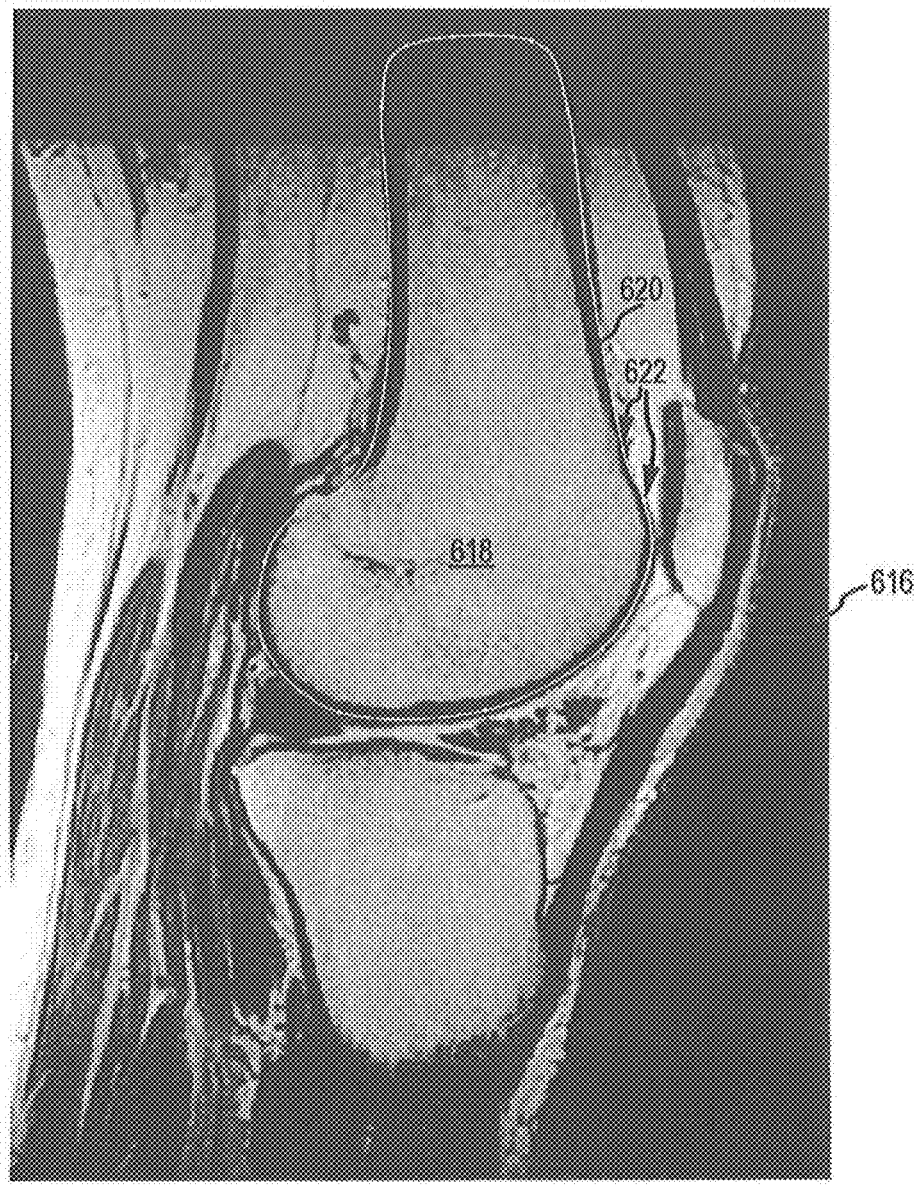
FIG. 30 is an image slice of the representative femur to be used to generate a golden femur mesh.

In operation 752 and as indicated in FIG. 30, each of the image slices 616 of the representative femur 618 are segmented with a contour curve or spline 620 having control points 622 and in a manner similar to that discussed above with respect to FIG. 12A, etc. For example and as shown in FIG. 30, where the golden model is to be used in the generation of a bone model 22 (see block 110 of FIG. 1C)

and cartilage geometry is not of interest, each segmentation region includes cancellous matter and cortical matter of the femur in a manner similar to that discussed above with respect to the cancellous matter 322 and cortical matter 324 of the tibia depicted in FIG. 12A, etc. Thus, as shown in FIG. 30, the contour curve 620 excludes any cartilage matter in outlining a golden femur region.

On the other hand, where the golden model is to be used in the generation of an arthritic model 36 (see block 130 of FIG. 1D) and cartilage geometry is of interest, each segmentation region the contour curve would include cartilage matter in outlining a golden femur region.

If the golden femur scan does not contain a sufficiently long shaft of the femur bone (e.g., it may be desired to segment a femur in a target MRI that may have a longer shaft), then the image segmentation can be extrapolated beyond the image to approximate a normal bone shape. This can be done because the femoral shaft is quite straight and, generally, all that is needed is to continue the straight lines beyond the MRI image, as can be understood from the extension of the contour line 620 proximal of the proximal edge of the femur image 616 of FIG. 30.

In operation 754 and as illustrated in FIG. 31A, the contour curves or splines 620 are compiled and smoothed into a golden femur mesh 624 as discussed above with respect to FIG. 13A, etc. As indicated in FIG. 30, in one embodiment, the segmentation curve 620 is a closed curve. Thus, the resulting golden femur mesh 624 is a closed mesh as depicted in FIG. 31A.

In operation 756 and as shown in FIG. 31B, the golden femur mesh 624 is converted into an open golden femur mesh 626, wherein the proximal portion of the golden femur mesh 624 is removed to create the open surface model called the open golden femur mesh 626. In other words, in operation 756 the artificial part of the femur mesh 626 is cut off, namely the proximally extending shaft portion that results from the proximal extrapolated extension of the contour line 620, so as to obtain the open golden femur mesh 626 of FIG. 31B.

In operation 758 and as indicated in FIG. 31C, regions 628, 629 of a different precision are generated for the golden femur mesh 626. For example, when segmenting the image slices 16 for the purpose of generating a golden femur mesh 626 that is used to create a 3D computer generated bone model used to show the preoperative planning ("POP") images to a surgeon, it is desirable that the bone geometry of the mesh 626 be generated with a relatively high degree of accuracy in certain regions 628 of the mesh 626 such that the resulting 3D computer generated bone model allows the physician to verify the POP with a desired degree of accuracy, while other regions 629 of the mesh 626 may not be generated to such a high degree of accuracy. For example, such a degree of accuracy in the certain regions 628 of the mesh 626 can be achieved via relatively precise image segmentation. The certain regions 628 of the mesh 626 having the relatively high degree of accuracy could include, among others, the lower shaft area, as depicted in FIG. 31C. In one embodiment, the relatively high accuracy of the certain regions 628 of the mesh 626 should allow the physician to verify the POP within 0.5 mm accuracy.

As can be understood from FIG. 31C, in one embodiment, the high precision region(s) 628 of the mesh 626 represent a portion of the distal anterior femoral shaft that would be contacted by the anterior flange of a candidate femoral implant. The rest of the mesh 626 may form the region 629 that has an accuracy that is not as precise as the high precision region 628. Such a lower precision region 629 of the mesh 626 may include the entire distal femur excluding the distal anterior region of the shaft included within the high precision region 628. Where the golden femur mesh 626 is employed to form other 3D computer generated bone models, such as, for example, the bone model 22 or arthritic model 36, the mesh 626 may have a different number of high precision regions 628 (e.g., none, one, two, three, or more such regions 628). Also, such regions 628 may have precisions that are greater or less than stated above. Finally, such regions 628 may correspond to different regions of the bone, encompass generally the entirety of the mesh surface, or include other regions in addition to the region 628 depicted in FIG. 31C.

Figure 32A:
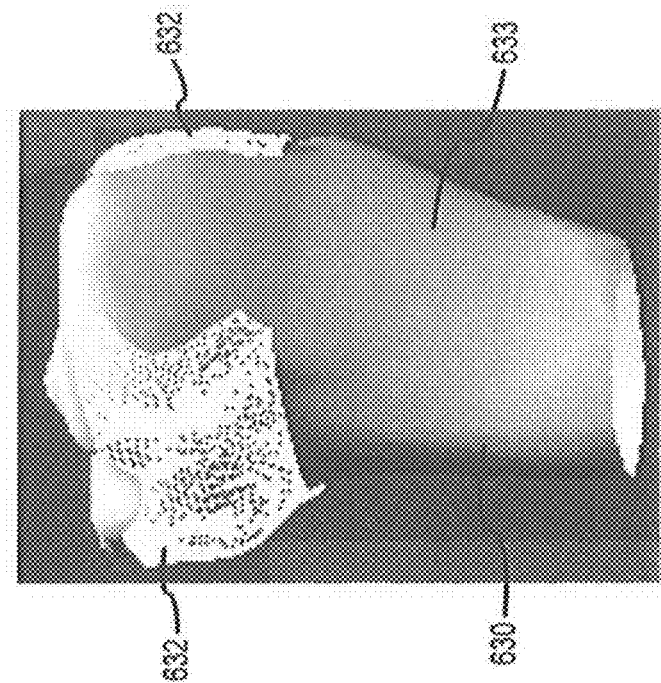
FIGS. 32A-32B are isometric views of an open golden tibia mesh with regions of a different precision indicated.
Figure 32B:
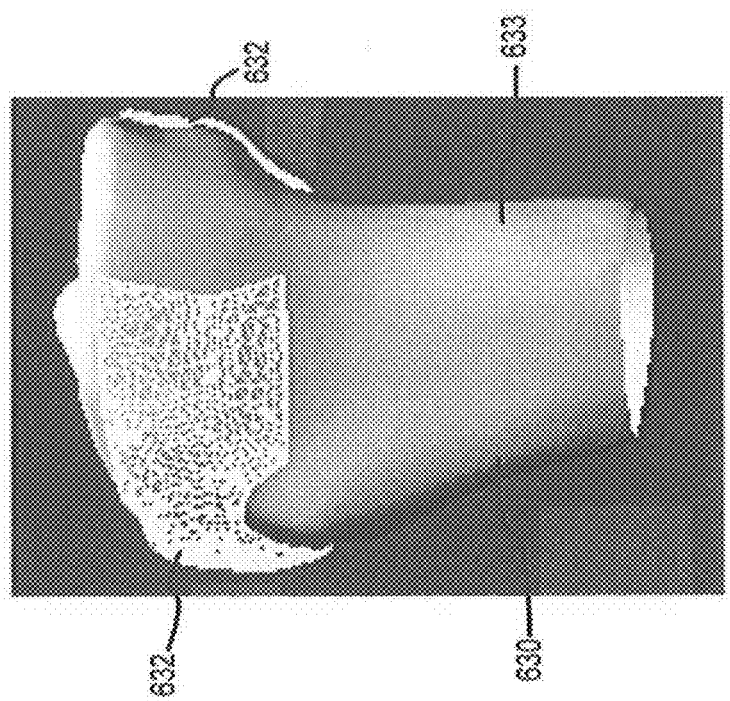

While the preceding discussion regarding the open golden bone mesh is given in the context of the open golden bone mesh being an open golden femur mesh 626, as can be understood from FIG. 32A-B, the open golden bone mesh may be an open golden tibia mesh 630 having regions 632, 633 of a different precision, all of which are generated in a manner similar to that discussed with respect to FIGS. 28-31C above.

For example, as can be understood from FIGS. 32A-32B, in one embodiment, the high precision region(s) 632 of the open golden tibia mesh 630 represent a portion of the proximal anterior tibial shaft immediately distal the tibial plateau and running medial to lateral generally proximal the tibial tuberosity. Another high precision region 632 may occupy a space similar in location and size, except on the posterior of the tibial shaft. The rest of the mesh 630 may form the region 633 that has an accuracy that is not as precise as the high precision region 632. Such a lower precision region 633 of the mesh 630 may include the entire proximal tibia excluding the regions of the shaft included within the high precision regions 632. Where the golden tibia mesh 630 is employed to form other 3D computer generated bone models, such as, for example, the bone model 22 or arthritic model 36, the mesh 630 may have a different number of high precision regions 632 (e.g., none, one, two, three, or more such regions 632). Also, such regions 630 may have precisions that are greater or less than stated above. Finally, such regions 630 may correspond to different regions of the bone, encompass generally the entirety of the mesh surface, or include other regions in addition to the regions 632 depicted in FIGS. 32A-32B.

Figure 33:
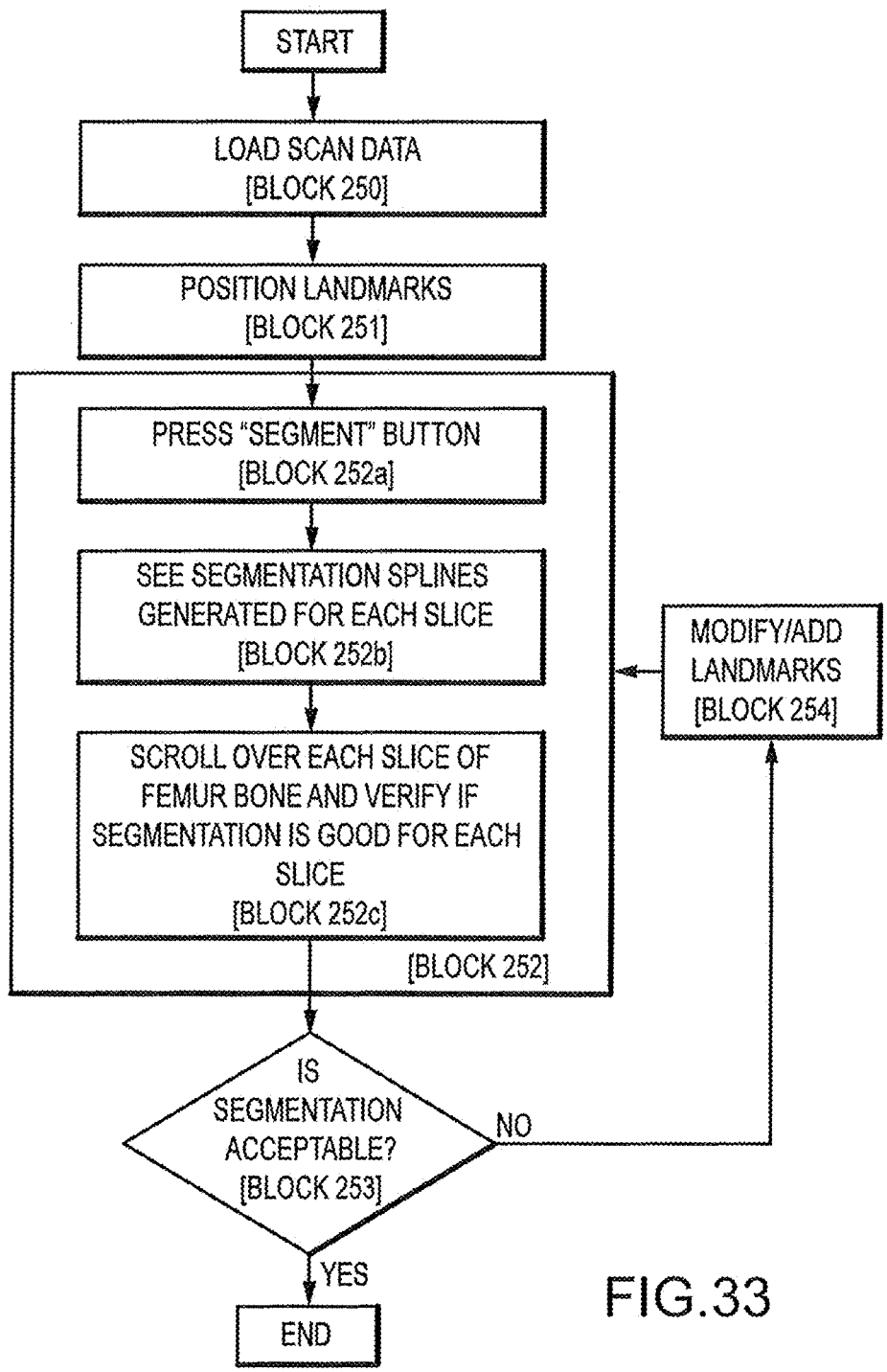
FIG. 33 is a flow chart illustrating an alternative method of segmenting an image slice, the alternative method employing landmarks.

For a discussion of an alternative embodiment of operations 250-254 of FIG. 6, reference is first made to FIG. 33, which is a flowchart illustrating the alternative embodiment of segmenting a target bone. In this example, the target bone is a femur 204, but may be a tibia 210 or any other type of bone.

Figure 34:
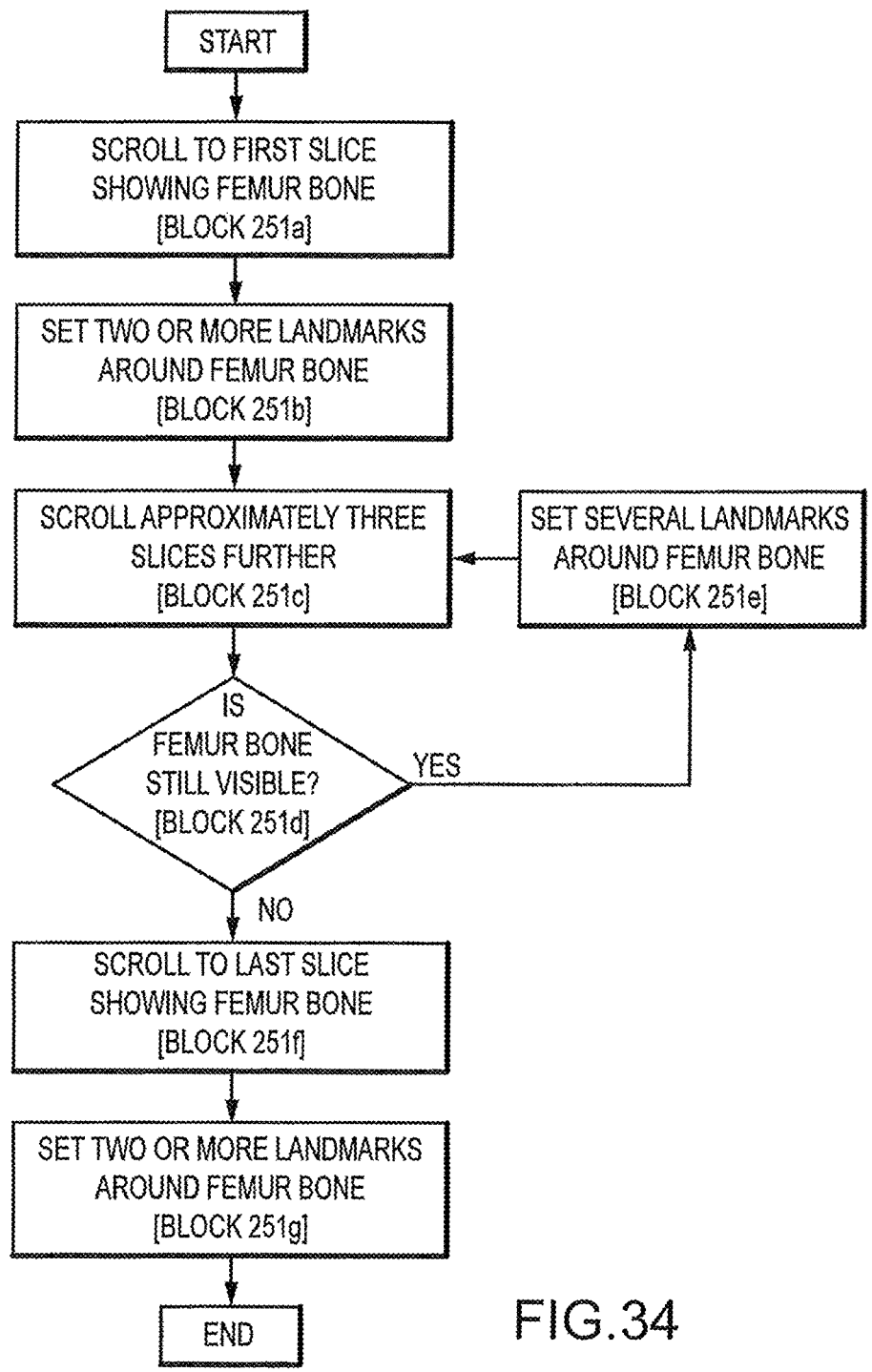
FIG. 34 is a flow chart illustrating the process involved in operation "position landmarks" of the flow chart of FIG. 33.
Figure 35A:
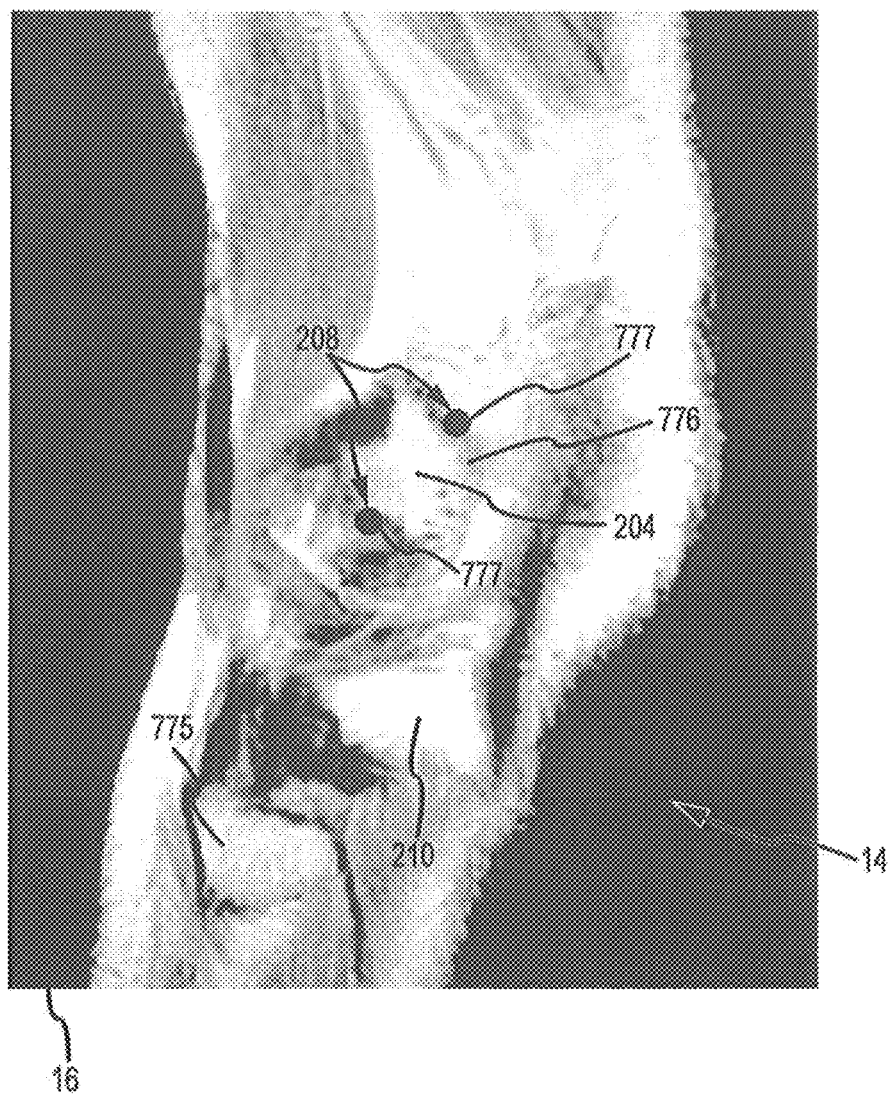
FIGS. 35A-35H are a series of sagittal image slices wherein landmarks have been placed according the process of FIG. 34.

As indicated in FIG. 33, operation 250 obtains or, more specifically, loads the scan data (e.g., scan images 16) generated by imager 8 of the patient's joint 14 to be analyzed. In operation 251 the landmarks are positioned in the scan images. In other words, as can be understood from FIG. 34, which is a flowchart illustrating the steps of operation 251, operation 251 begins with operation 251a, wherein the images 16 are scrolled through (e.g., medial to lateral or lateral to medial) to the most medial or lateral image slice were the femur bone 204 first appears, as shown in FIG. 35A, which, in this example, is a most lateral sagittal MRI image slice 16 where the femur bone 204 or, more specifically, the lateral epicondyle 776 first appears. Since the slice 16 of FIG. 35A is the most lateral image where bone has begun to appear, the fibula 775 can be seen adjacent the tibia 210 in such instances where the image slice is positioned so as to show both the femur 204 and the tibia 210.

In operation 251*b*, two or more landmarks 777 are positioned on the outer rim of the black cortical bone 208 of the image slice 16 depicted in FIG. 35A. As is the case with all of the images depicted in FIGS. 35A-35H, in one embodiment, the landmarks are placed via an operator sitting at a work station. In one embodiment, the operator or user is able to add landmarks by simply clicking onto the slice image, the landmark (point) being created at the exact coordinates where the click has occurred. The operator is able to move existing landmarks within the slice by selecting them and moving them with the mouse, a keyboard, a pen-and-tablet system, or similar. The user is able to delete existing landmarks by selecting them and indicating to the software that they should be deleted.

In another embodiment, a touch-screen surface may be used to provide input and display for interactive editing of landmarks and segmentation curves. Specialized gestures may be adopted for various editing operations.

In another embodiment, a spatial input device may be used for manipulation of landmarks, segmentation curves, and other operations involving POP and jig design activities.

Figure 35B:
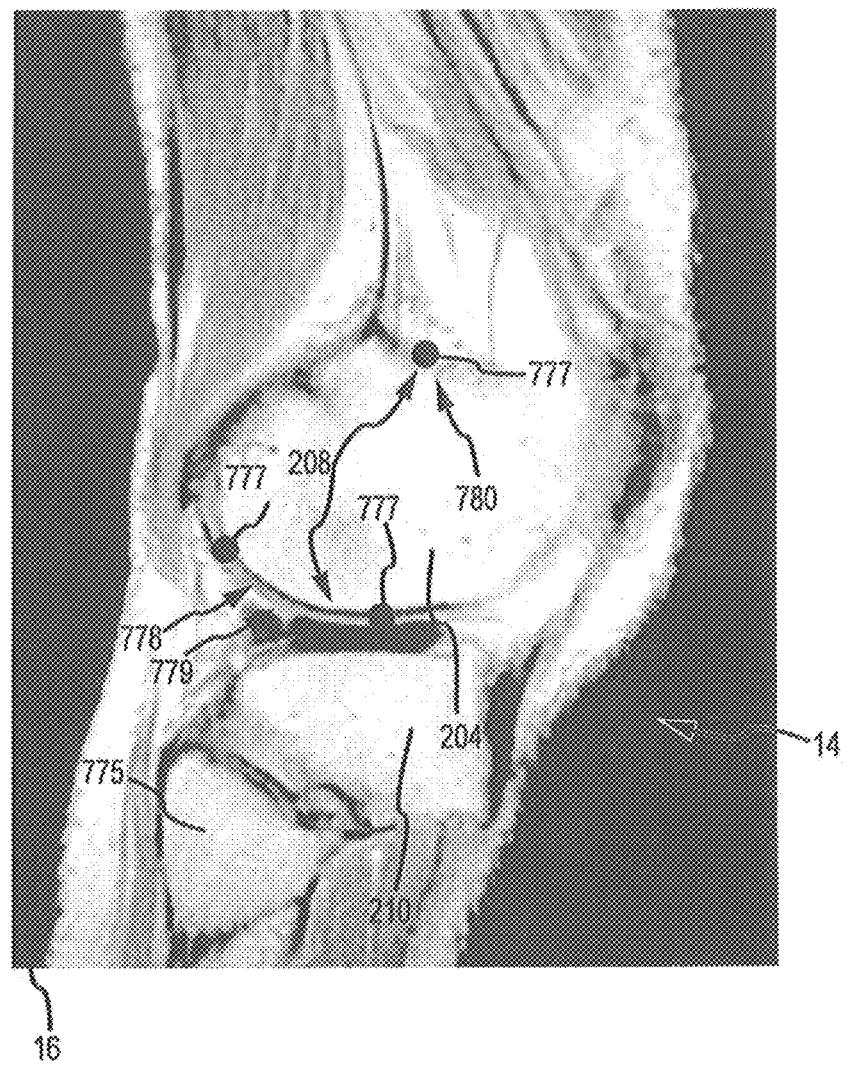

In operation 251*c*, the image slices 16 are scrolled lateral to medial through approximately three slices 16 further to a new image slice 16 and, at operation 251*d*, it is determined if the femur bone 204 is still visible in the new image slice 16, which is depicted in FIG. 35B. If so, then operation 251*e* adds landmarks 777 to the new image slice 16 as indicated in FIG. 35B. Specifically, as indicated in FIG. 35B, this new image slice 16 may show the femur lateral condyle 778 and be the first image slice having a clear boundary 779 of the femur lateral condyle. As can be seen in FIG. 35B, the fibula 775 and tibia 210 are also more fully shown. Landmarks 777 are set on the clear boundary 779 of the outer rim of the dark cortical bone of the femur lateral condyle, and an additional landmark 777 is set on the opposite side 780 on the rim of the black cortical bone 208. As is the case with the placement of landmarks 777 in any of the images 16, more or fewer landmarks 777 may be placed along the rim of the black cortical bone depicted in the image 16, including landmarks being placed on the rim of the black cortical cone of the entirety of the distal femur, including the distal femur condyle and distal femur shaft.

Figure 35C:
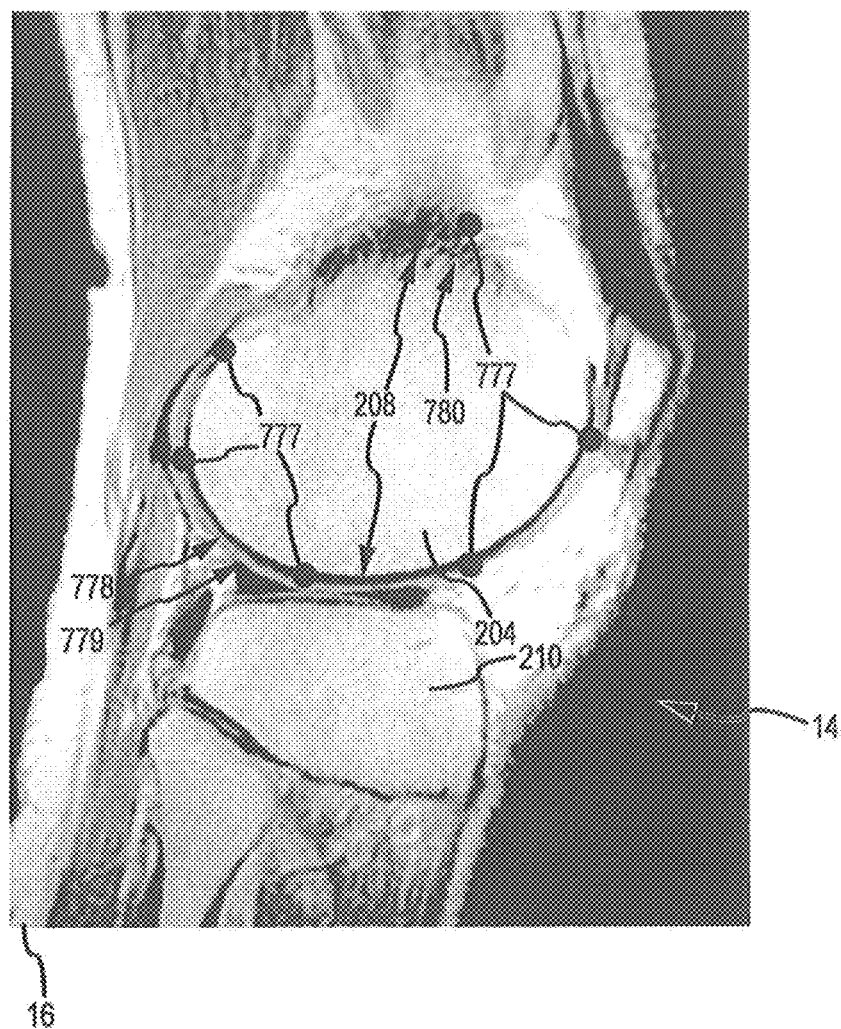

Operations 251*c* through 251*e* are repeated to set landmarks 777 at the bone contour boundaries of approximately every third image slice 16 moving lateral to medial until eventually at operation 251*d* it is determined that bone no longer appears in the present image slice. Thus, as operation 251 of FIG. 33 loops through operations 251*c*-251*e* of FIG. 34, landmarks 777 are set at the bone contour boundaries in each of the sagittal image slices 16 depicted in FIGS. 35C-35H, which are, respectively, approximately every third sagittal image slice 16 tabbing lateral to medial through all the sagittal image slices 16 loaded in operation 250 of FIG. 33. Thus, as shown in FIG. 35C, which represents a sagittal image slice 16 approximately three slices more medial than the image slice 16 of FIG. 35B, the femur lateral condyle 778 has a clear bone contour boundary 779, and landmarks 777 are set along the boundary 779 on the rim of the dark cortical bone 208. A landmark 777 is also set on the top region 780 of the cortical bone boundary 779 where the bone contour boundary is less clear, the landmark being positioned on the rim of the dark cortical bone 208.

Figure 35D:
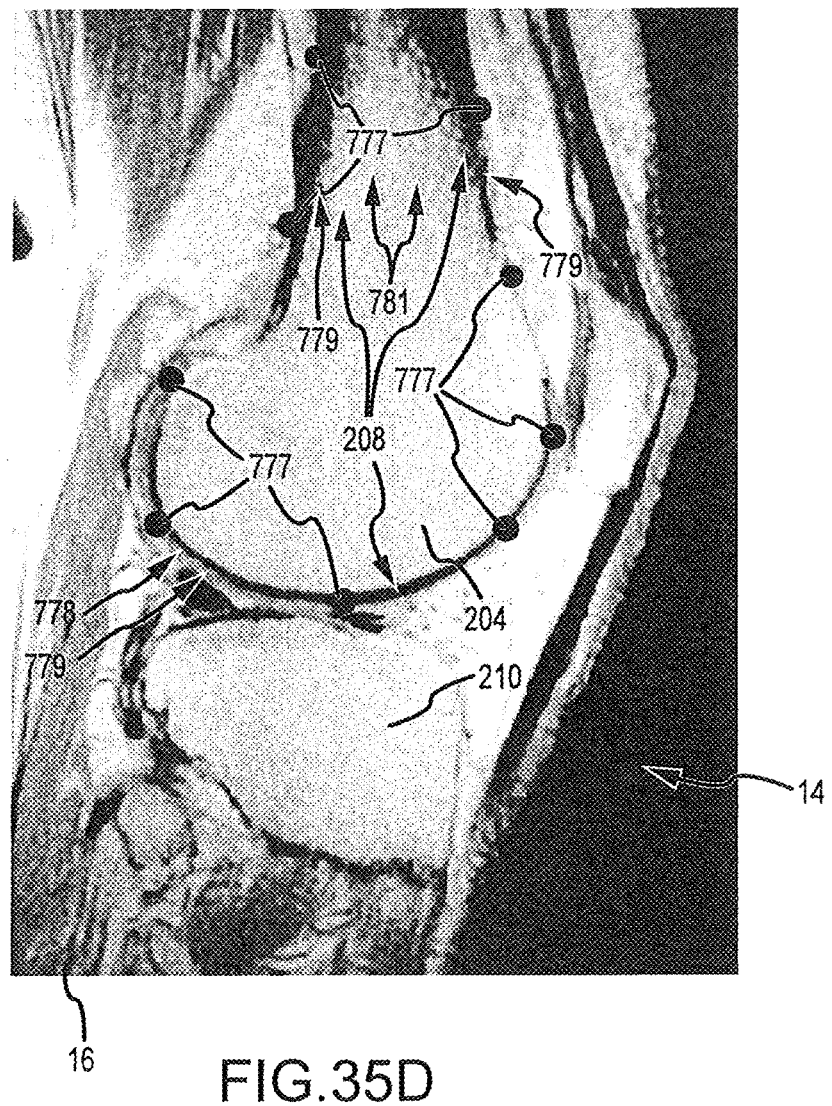

As illustrated in FIG. 35D, which represents a sagittal image slice 16 approximately three slices 16 more medial than the image slice 16 of FIG. 35C, the femur shaft 781 has now appeared in an image slice 16 and both the femur shaft 781 and femur lateral condyle 778 have clear bone contour boundaries 779. Landmarks 777 are set along the bone contour boundaries 779 on the rim of the dark cortical bone 208.

Figure 35E:
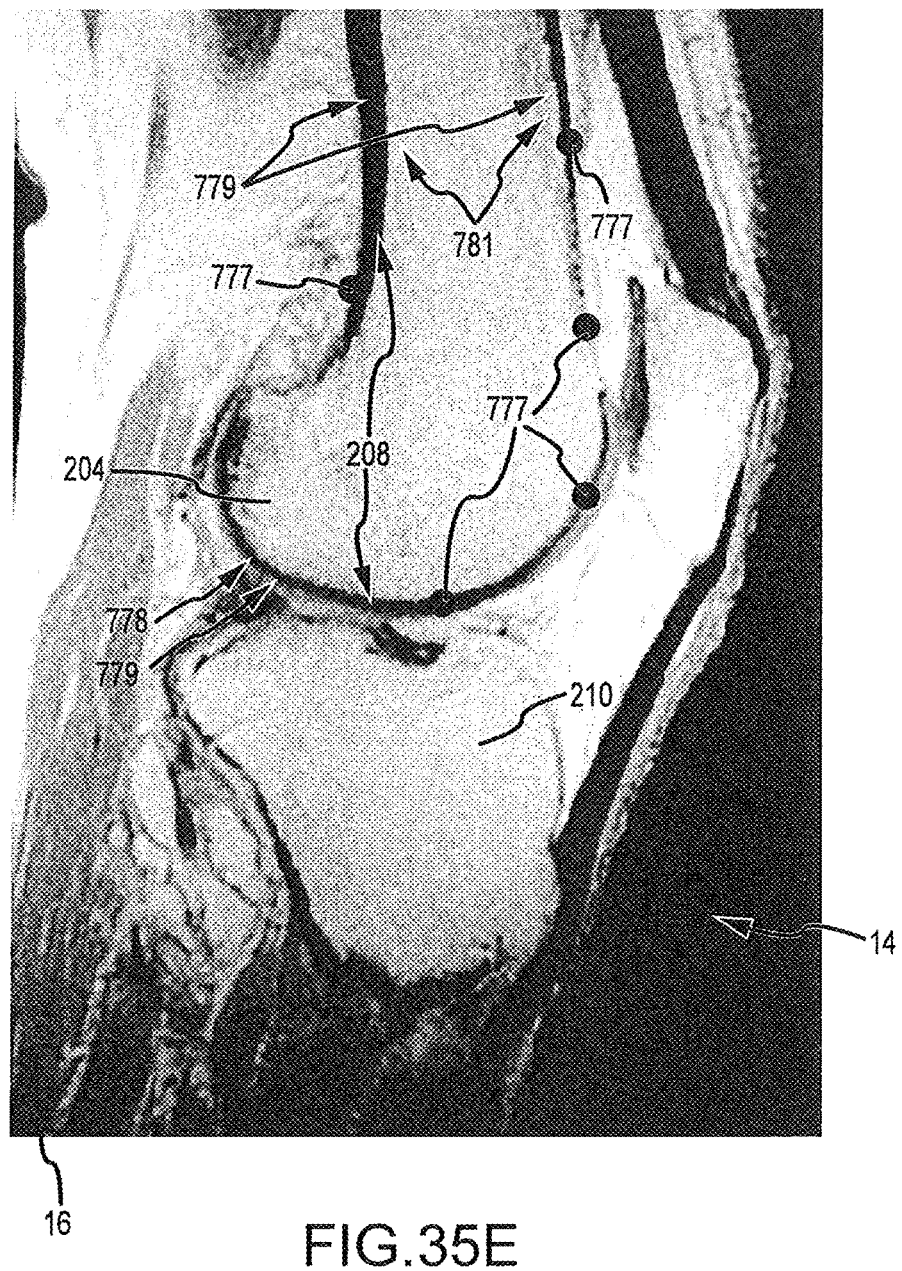

As shown in FIG. 35E, which represents a sagittal image slice 16 approximately three slices 16 more medial than the image slice 16 of FIG. 35D, the femur lateral condyle 778 is starting to disappear, and part of its cortical bone contour boundary 779 is not clear. Landmarks 777 are only set outside the dark cortical bone 208 in the regions where the contour boundary 779 is clear.

Figure 35F:
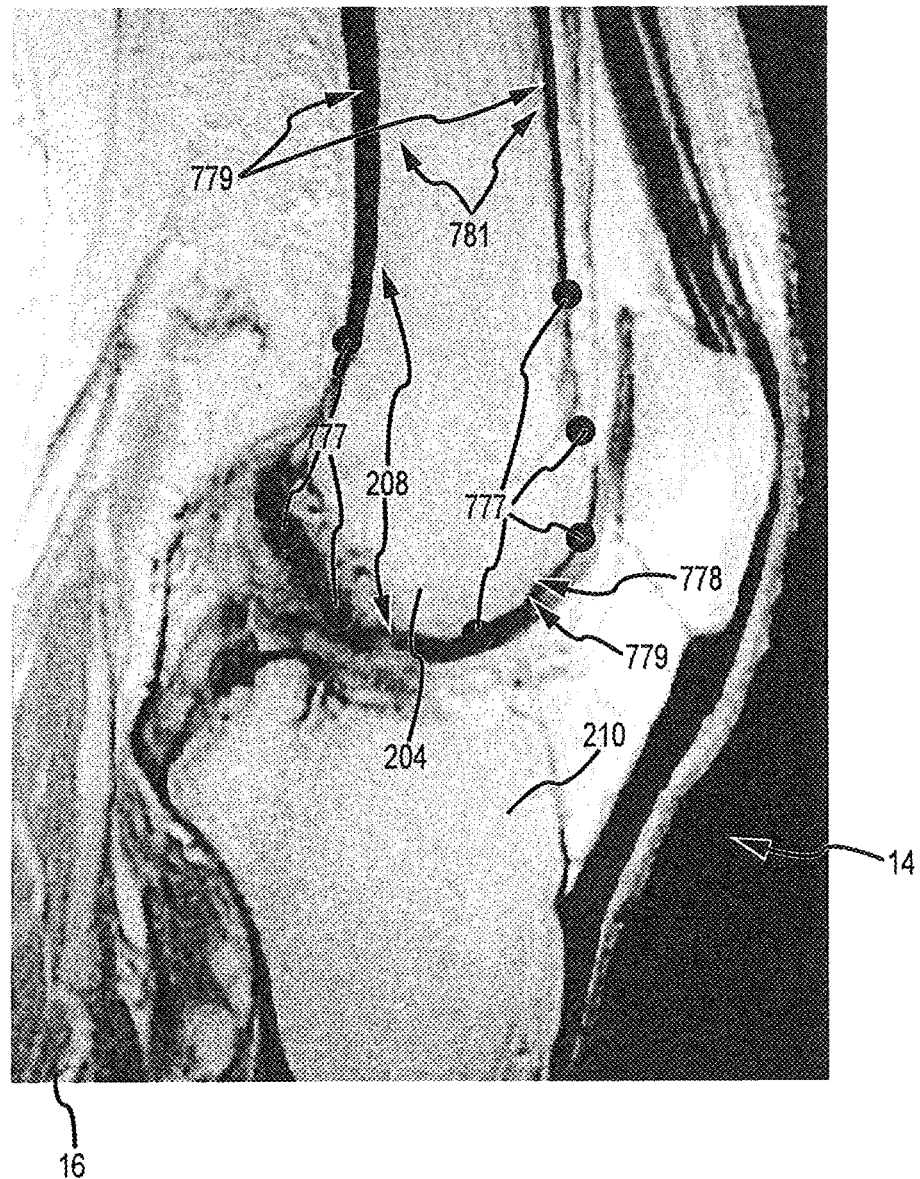

As illustrated in FIG. 35F, which represents a sagittal image slice 16 approximately three slices 16 more medial than the image slice 16 of FIG. 35E, the bone contour boundary 779 has become less clear as the femur lateral condyle 778 has decreased in size as compared to the femur lateral condyle 778 of slice 16 in FIG. 35E. The slice 16 of FIG. 30F is just lateral of the trochlear groove 782 between the femur lateral condyle 778 and femur medial condyle 783. The bone contour boundary 779 is clear in the anterior region of the femur lateral condyle 778 and two landmarks 777 are placed there. Additional landmarks 777 are set along the bone contour boundaries 779 on the rim of the dark cortical bone 208.

Figure 35G:
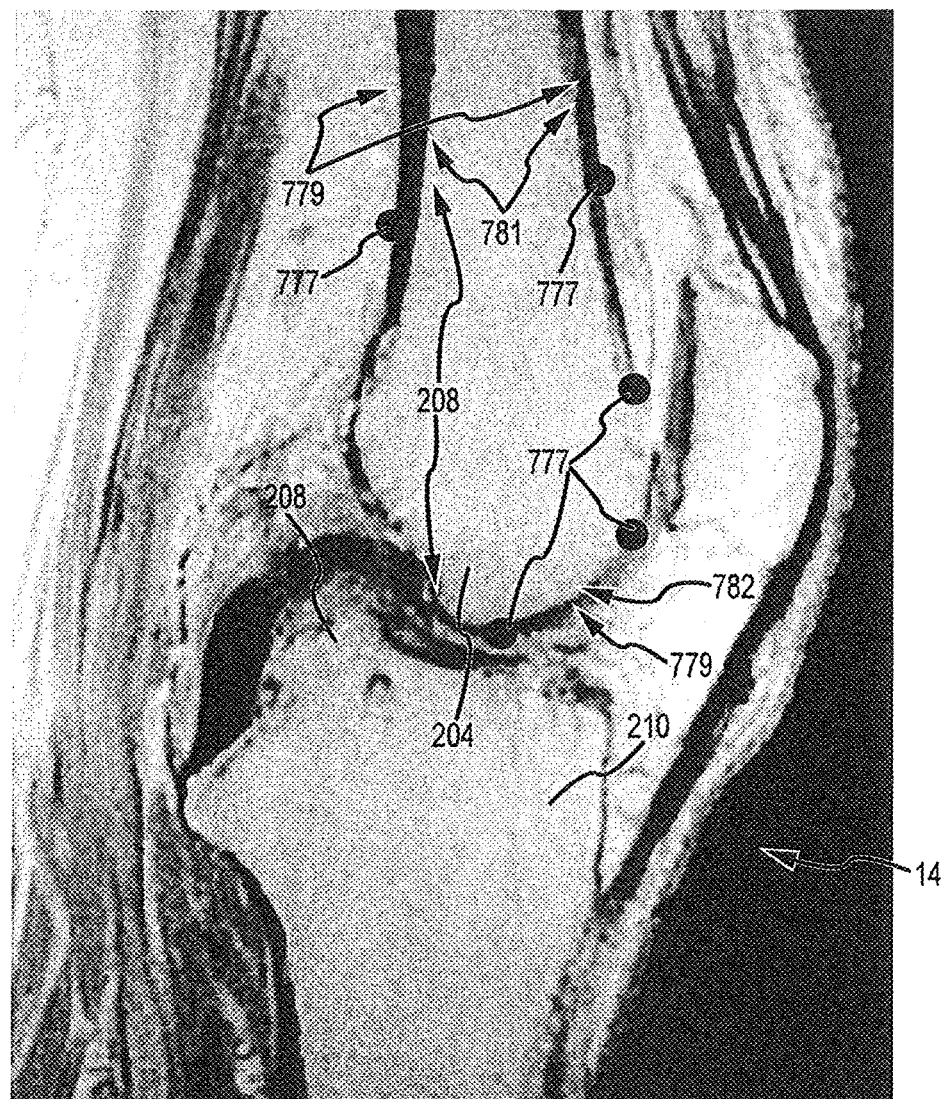

As indicated in FIG. 35G, which represents a sagittal image slice 16 approximately three slices 16 more medial than the image slice 16 of FIG. 35F, landmarks 777 are set along the bone contour boundaries 779 on the rim of the dark cortical bone 208. The slice 16 of FIG. 35G is in the trochlear groove 782 between the femur lateral condyle 778 and femur medial condyle 783. The intercondylar eminence 784 of the tibia 210 can be seen in the slice 16 of FIG. 35G.

Figure 35H:
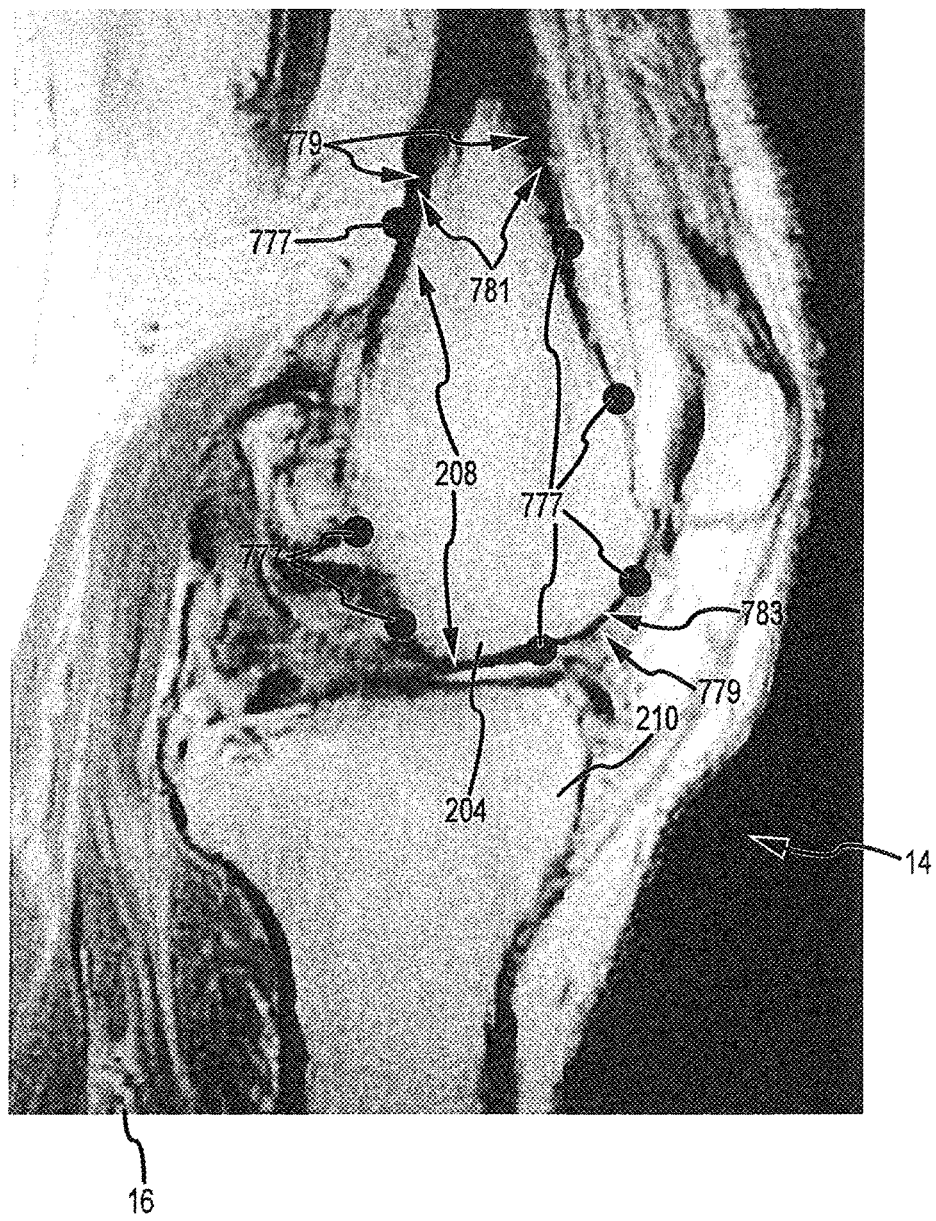

As indicated in FIG. 35H, which represents a sagittal image slice 16 approximately three slices 16 more medial than the image slice 16 of FIG. 35G, the femur shaft 781 has begun to disappear and the femur medial condyle 783 has begun to appear as the slice of FIG. 35H is medial of the trochlear groove 782 depicted in the slice of FIG. 35G. The bone contour boundary 779 is clear in the anterior region of the femur medial condyle 783 and two landmarks 777 are placed there. Additional landmarks 777 are set along the bone contour boundaries 779 on the rim of the dark cortical bone 208.

As stated above, operations 251*c* through 251*e* continue to be repeated as the slices 16 continue to be tabbed through lateral to medial to set landmarks 777 at the bone contour boundaries of approximately every third image slice 16 until eventually at operation 251*d* it is determined that bone no longer appears in the present image slice. Operation 251*f* then scrolls medial to lateral through the image slices 16 until arriving at the image slice 16 where the most medial portion of the femur is depicted. Operation 251*g* then sets two or more landmarks 777 around the bone (e.g., the medial epicondyle) in a manner similar to that depicted in FIG. 35A with respect to the lateral epicondyle 776. This is the end of operation 251 and, as can be understood from FIG. 33, operation 252 begins by pressing the "segment" button (operation 252*a*), which causes segmentation lines to be generated for each slice 16 with landmarks 777 (operation 252*b*) in a manner similar to that illustrated and discussed above with respect to FIGS. 7A-7K or as now will be discussed below beginning with FIG. 36.

When positioning landmarks, a user needs to distribute them over the cortical bone outer surface, favoring areas where the cortical bone boundary is sharp and is more orthogonal to the slice plane, particularly favoring certain "important" areas of the bone surface (where importance is dictated by eventual contact between bone and implant or by other requirements from POP procedure.) The user should only sparsely mark up the remaining parts of the bone, particularly where there is a lot of volume averaging (and/or the bone surface is more parallel to slice plane.) While the image slices depicted in FIGS. 35A-35H are MRI generated image slices, in other embodiments the imaging slices may be via other medical imaging methods, such as, for example, CT.

In one embodiment, the landmark-driven segmentation algorithm described below is deliberately sensitive to the number of landmarks (points) placed at a given area of the bone. So for instance, if the user desires the auto-generated bone mesh to very accurately pass through particular spots on the slice, the user can place more than one landmark on that same spot or very near that spot. When there is a high concentration of landmarks in a small area of the bone, the auto-generated mesh will be biased to more accurately model that area. The software indicates to the user, making it visible at a glance whenever more than one landmark is located within the same small area of the image.

In one embodiment, instead of putting landmarks in every three slices, a user may position landmarks in every slice but use three times fewer landmarks in each slice. The result of the segmentation usually varies very little depending on how a user distributes landmarks around the bone surface as long as the entire surface is covered.

While much of the following discussion takes place in reference to the segmentation of a femur (operation 252 of FIG. 6), the concepts discussed herein are readily applicable to the segmentation of a tibia (operation 258 of FIG. 6). Additionally, the concepts discussed herein are readily applicable to both the left or right knee. Different golden template data may be used to segment the left tibia, right tibia, left femur or right femur for bone models 22 or planning models 28. Additionally, other embodiments may segment other models and or joints, including but not limited to, arthritic models 36, hip joints, elbow joints, etc. by using an appropriate golden template of the feature of interest to be segmented.

Figure 36:
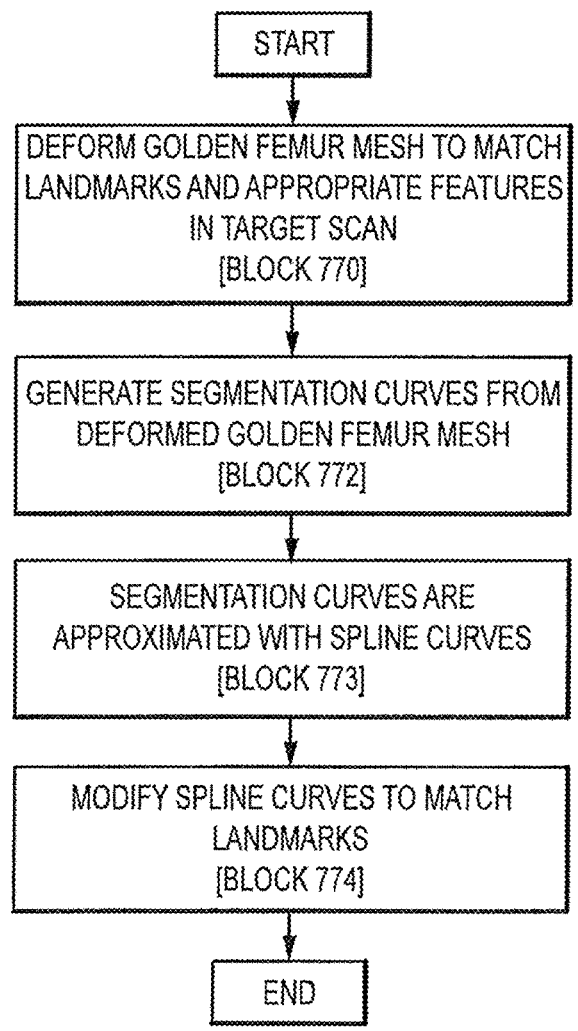
FIG. 36 is a flowchart illustrating the process of segmenting the target images that were provided with landmarks in operation "position landmarks" of the flow chart of FIG. 33.

As shown in FIG. 36, which is a flowchart illustrating the process of segmenting the target images 16 that were provided with landmarks 777 in operation 251, the full or entire golden femur mesh 626, including its regions 628, 629 in FIG. 31C, is deformed in operation 770 to match landmarks 777 and appropriate features, such as, for example, the outer edges of dark cortical bone, in the target scan images 16.

As discussed below with respect to FIG. 37, a method is provided for mapping the golden femur mesh into the target scan using registration techniques. Registration may be thought of as an optimization problem with a goal of finding a spatial mapping that aligns a fixed object with a target object. Generally, several registration operations may be performed, first starting with a low-dimensional transformation group to find a rough approximation of the actual femur location and shape in the target image. This may be done to reduce the chance of finding wrong features instead of the femur of interest. For example, if a free-form deformation registration was initially used to register the golden femur mesh to the target scan data, the template might be registered to the wrong feature, e.g., to a tibia rather than the femur of interest. A coarse registration may also be performed in less time than a fine registration, thereby reducing the overall time required to perform the registration. Once the femur has been approximately located using a coarse registration, finer registration operations may be performed to more accurately determine the femur location and shape. By using the femur approximation determined by the prior registration opera-tion as the initial approximation of the femur in the next registration operation, the next registration operation may find a solution in less time. It is to be understood that similar considerations apply to segmentation of other entities (and not just the femur.)

In one embodiment, each registration operation may employ a registration framework. The registration framework may be based on three general blocks. The first block defines a transformation model (or a class of transforms) T(X), which may be applied to coordinates of a fixed (or reference) object (e.g., a golden femur template) to locate their corresponding coordinates in a target image space (e.g., an MRI scan). The second block defines a metric, which quantifies the degree of correspondence or similarity between features of a fixed (or reference) object and the target object (that is landmarks and appropriate target image features) achieved by a given transformation. It should be noted that instead of a metric that defines the degree of correspondence, an opposite to it function is defined, which is call the defect function. The third block defines an optimization algorithm (optimizer), which tries to maximize the reference and the target objects similarity (or minimize the opposite defect function) by changing the parameters of the transformation model. Thus, as discussed below in detail with reference to FIG. 37, in every registration operation 770a-770c and 770e there is a need to specify three blocks: (1) class of transforms; (2) metric (or defect) function; and (3) optimization algorithm. In one embodiment, the same third block may be used in all four registration steps. For instance, a gradient descent optimizer or conjugate gradient descend optimizer may be used. Alternatively, any other appropriate optimization algorithm, such as Monte Carlo, simulated annealing, genetic algorithms, neural networks, and so on, may be used.

Figure 37:
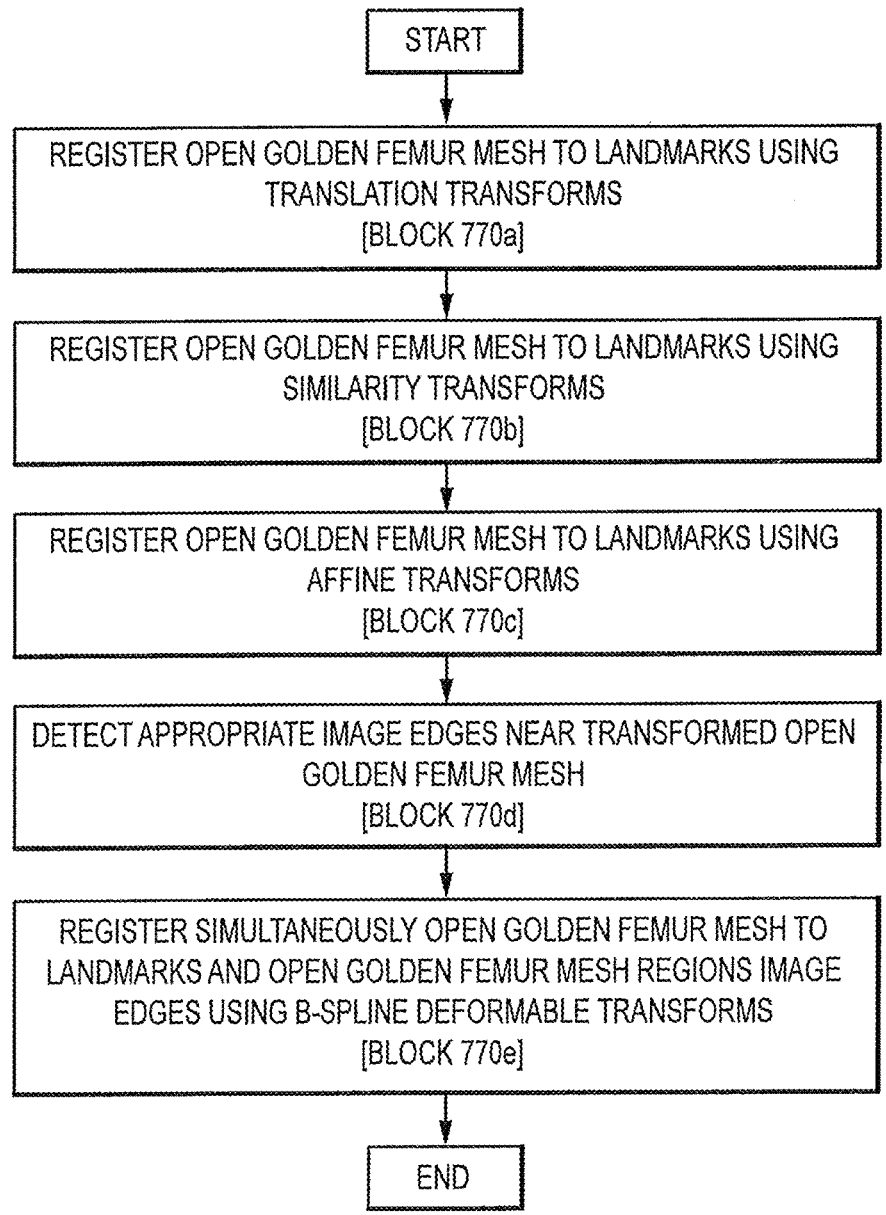
FIG. 37 is a flowchart illustrating the process of operation "Deform Golden Femur Mesh" of FIG. 36, the process including mapping the golden femur mesh into the target scan using registration techniques.

As shown in FIG. 37, which is a flowchart illustrating the process of operation 770 of FIG. 36, in operation 770a translation transforms are used to register the full or entire open golden femur mesh 626 to the landmarks 777. More specifically, in operation 770a, the open golden femur mesh 626 may be approximately registered to landmarks 777 using a coarse registration transformation. In one embodiment, this may be done by finding appropriate translation transform parameters that minimize translation misalignment with landmarks of the reference open golden femur mesh mapped onto the target femur of the target image, where landmarks 777 are positioned. This coarse registration operation typically determines an approximate femur position in the MRI scan. During this operation, the reference open golden femur mesh 626 may be overlapped with the target femur of the target image using a translation transformation to minimize translational misalignment of the femurs. A translation transform, translates (or shifts) all the points in 3D space by the same 3D vector. That is, the reference femur may be mapped into the target image space by shifting the reference open golden femur mesh along one or more axes in the target image space to minimize misalignment. During this operation the reference object is not rotated, scaled or deformed. In one embodiment, three parameters for the translation transformation may be generated: one parameter for each dimension that specifies the translation for that dimension. In one embodiment, the final parameters of the translation transform minimizing the misalignment of the mapped reference femur image coordinates into the target image space may be found using a gradient descent optimizer. In other embodiments, other types of optimizers may be utilized, such as for instance an Iterative Closest Point (ICP) algorithm.

Optimization of mesh alignment with respect to landmarks is based on minimizing a cost function D, which in one embodiment can be the sum, across all landmarks, of the squared distance from each landmark point 777 to the transformed open golden mesh. The same cost function may be used for steps 770a-770c. Methods for computing this cost function and its gradient are covered in more detail later in this disclosure.

After an optimal transform has been found, it is applied to all the golden femur data (i.e., the closed golden femur mesh 624, open golden femur mesh 626, and golden femur mesh regions 628, 629. The next operation (i.e., operation 770b of FIG. 37, which is discussed immediately below) is then started with transformed golden femur data. As can be understood from the following discussion, after every consecutive operation 770a, 770b, 770c and 770e of FIG. 37, the transform found during the registration step is applied to all the golden femur data. As a result, after each operation the golden femur data is successively made more closely aligned with the femur in the target image.

In operation 770b of FIG. 37 similarity transforms are used to register the full or entire open golden femur mesh 626 to the landmarks 777. Specifically, operation 770b further refines the object's registration determined by operation 770a. This may be done by approximately registering the open golden femur mesh 626 to landmarks 777 using a similarity transformation. In one embodiment, a similarity transformation may be performed in 3D space. The reference open golden femur mesh may be rotated in 3D, translated in 3D and homogeneously scaled to map its coordinates into the target MRI scan data to minimize misalignment between the open golden femur mesh and the landmarks in the target MRI scan. In some embodiments, a center of rotation may be specified so that both the rotation and scaling operations are performed with respect to the specified center of rotation. In one embodiment, a 3D similarity transformation, specified by seven parameters, may be used. One parameter specifies the scaling factor, three parameters specify a versor that represents the 3D rotation, and three parameters specify a vector that represents the 3D translation in each dimension. A versor is a unit quaternion that provides a convenient mathematical notation for representing rotations of objects in three dimensions.

In one embodiment, local minimization techniques may be employed with the similarity transformation to obtain a refined registration of the reference open golden femur mesh onto the target MRI scan that is not far from the registration of the reference open golden femur mesh onto the target MRI scan found in previous operation 770a and used as the initial starting approximation. For instance, gradient descent, conjugate gradient descent, or ICP optimization may be used. After the best transform is found for operation 770b of FIG. 37, the transform is applied to the golden femur data in a manner similar to that of operation 770a.

In operation 770c of FIG. 37 affine transforms are used to register the full or entire open golden femur mesh 626 to the landmarks 777. Specifically, operation 770c further refines the image registration determined by operation 770b. In one embodiment, an affine transformation may be used to register the open golden femur mesh 626 to landmarks 777 in the target MRI scan data. In one embodiment, the approximate femur registration found during operation 770b may be used as the initial starting approximation for the affine transformation of operation 770c.

An affine transformation typically is a linear transformation followed by a translation. The affine transformation preserves collinearity between points (i.e., three points which lie on a line continue to be collinear after the transformation) and ratios of distances along a line. In one embodiment, a 3D affine transformation, specified by 12 parameters, may be utilized. Nine parameters of the affine transformation specify the linear transformation (which may be represented by a three by three matrix) and three parameters of the affine transformation specify the 3D translation in each dimension. The parameters of the affine transform that minimizes the misalignment of the open golden femur mesh with landmarks may be found using again local minimization techniques, such as gradient descent or conjugate gradient descent optimization.

After the best transform is found for operation 770c of FIG. 37, the transform is applied to the golden femur data. The transformed golden femur data from operation 770c is then employed in the preparatory step of detecting appropriate image edges, namely, operation 770d, which is discussed below. Those edges will be later used in operation 770e of FIG. 37, as discussed below. The transformed golden femur data from operation 770c is used as reference data similar to the previous operations.

A discussion of image edges is now provided before discussing the details of operation 770d of FIG. 37. Image edges consist of those points in the image where the image contrast significantly changes between neighbor pixels (or voxels) and this contrast change is consistent along several neighboring points distributed over a smooth curve. For example, points that lie between the light cancellous bone pixels and dark cortical bone pixels form an image edge. Similarly, the points that lie between the dark cortical bone pixels and the grayish cartilage pixels form an image edge. Yet a configuration involving a one-pixel black spot and the surrounding light pixels does not form an image edge because the light points represent a curve with too much curvature, whereas the dark point represents a curve that is too discontinuous (spanning only a single voxel.) Usually there is an image edge that separates one type of the body tissue from a neighboring different type of body tissue.

The purpose of segmenting an image is to be able to separate in the image certain body tissues from the surrounding tissues. Ideally, the segmentation boundaries (or curves) should lie mostly in the image edges. A general MRI or CT image contains lots of edges separating various body tissues from the neighboring tissues. Yet when segmenting, there is only interest in certain tissues and thus particular edges only. Operation 770d is intended to find those edges that are of interest for segmenting a particular body object.

In particular in case of the segmentation of any of the versions of the femur planning model 22, 28 (shown in blocks 110 and 115, respectively, of FIG. 1C), operation 770d of FIG. 37 will find the edges that separate the cortical femur bone from the outside knee tissues (i.e., the tendons, ligaments, cartilage, fluid, etc.). In some embodiments, operation 770d will not find the edges that separate the femur cancellous bone from the femur cortical bone. In other embodiments, operation 770d will find the edges that separate the femur cancellous bone form the cortical bone.

Operation 770d may also find some edges that are of no interest to the femur planning segmentation. Most of those edges of no interest will lie at significant distance from the femur boundary surface and, as a result, the edges of no interest will not influence the next operation in the algorithm, namely, operation 770e of FIG. 37.

In some cases, some of the edges of no interest might happen to be very close to the edges of interest. Such nearby edges of no interest are likely to be the edges separating the cartilage tissue from the other tissues outside the bone. Such edges might adversely influence the next operation in the algorithm, namely, operation 770e of FIG. 37, and lead to inaccurate segmentation. In some embodiments, this inaccuracy can be remedied by the user providing extra landmarks 777 in the area that is likely to cause such inaccuracies or manually fixing the spline curves during the verification and adjustment operations.

The result of the operation 770e of FIG. 37 will be a 3D image of the same size as the target scan data. The resulting 3D image can be called an edges image. The voxels in the edges image correspondent to strong edges will have highest intensities, the non-edge voxels will have low intensities, and the voxels correspondent to weak edges will have intermediate intensities. Discussion of the operation 770d of FIG. 37 is now provided.

Figure 38A:
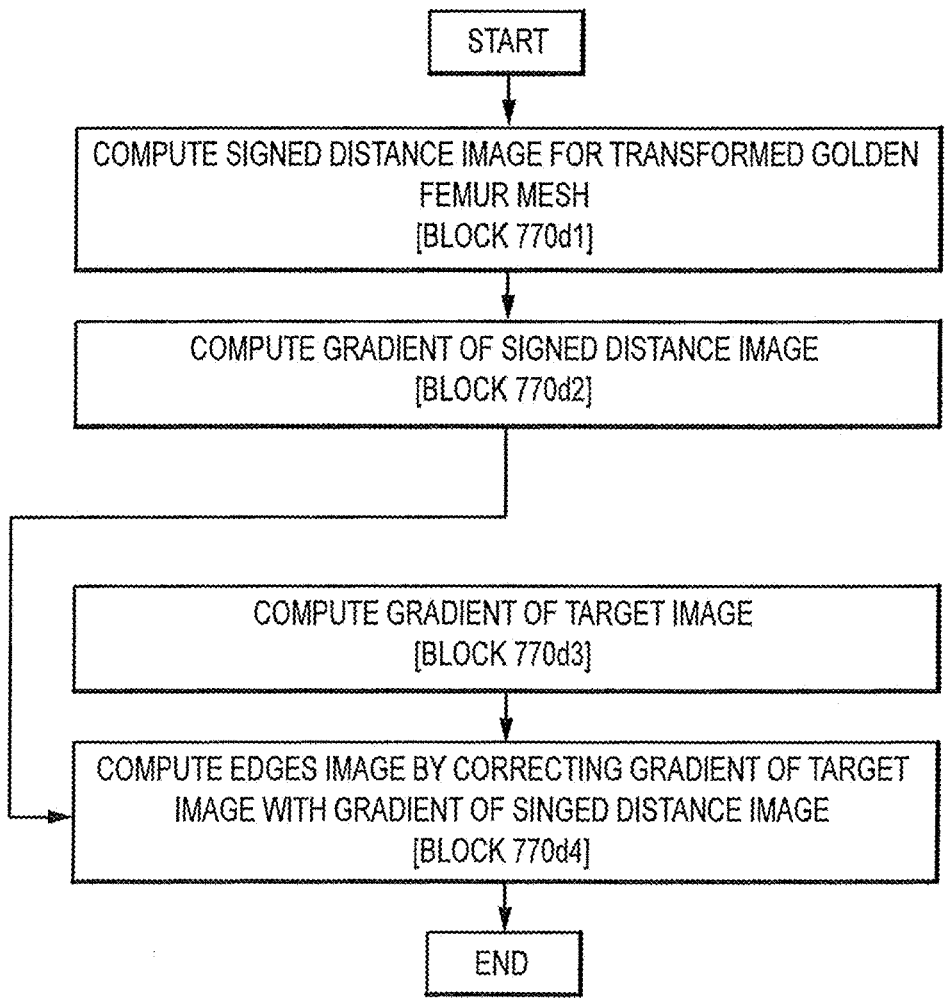
FIG. 38A is a flowchart illustrating the process of operation "Detect Appropriate Image Edges" of FIG. 37.

In operation 770d of FIG. 37 appropriate edges of the target images are detected near the transformed open golden femur mesh 626. For example, as indicated in FIG. 38A, which is a flowchart illustrating the process of operation 770d of FIG. 37, in operation 770d1 the signed distance image is computed for the transformed golden femur mesh 626. A signed distance map is a distance map of a region in 2D (or 3D) and is a function in 2D (or 3D). The signed distance value for a point equals the distance from the point to the boundary of a region. A signed distance value can have a positive or negative value. For example, when a point is inside the region, the signed distance value of the point is the distance from the point to the boundary of the region in the form of a negative value. When a point is outside the region, the signed distance value of the point is the distance from the point to the boundary of the region in the form of a positive value. If the signed distance map function is computed in a regular grid of points in 2D (or 3D) correspondent to image pixels (or voxels) and stored as a 2D (or 3D) image representation, the result can be said to be a 2D (or 3D) signed distance image.

Thus, from the preceding discussion, it can be understood that the signed distance for a watertight surface is a function that has absolute values equal to the regular (Euclidean) distance, but the values also have a sign. The sign is negative for the points inside the surface, and the sign is positive for the points outside the surface. The open golden femur mesh 626 transformed in operations 770a-770c of FIG. 37 is used in operation 770d1 of FIG. 38A. By the time of operation 770d1, the open golden femur mesh 626 may quite closely match the landmarks 777 positioned in the target image and, as a result, the open golden femur mesh 626 also matches quite closely the target femur bone in the target image. Since the golden femur mesh 626 is a watertight mesh, the mask image marking may be computed as "1" for all voxels that lie inside the open golden femur mesh 626 and as "0" for all the voxels that lie outside the mesh. The Signed Danielsson Distance Map Image Filter from the ITK library can then be used to compute the signed distance to the mask boundary, which is approximately the same as the signed distance to the mesh. It may be desired to have greater accuracy close to the mesh. If so, then for the voxels where the absolute value of the signed distance is small, the distance to the mesh may be recomputed by finding the closest points via a more exact method, as detailed later in this specification.

In operation 770d2 the gradient of the signed distance image is computed. As can be understood from FIG. 38B, the gradient of the signed distance image contains a vector 1000 in every voxel. The vector 1000 represents the gradient of the signed distance image at the particular point of the voxel. Because the signed distance image represents the signed distance to the transformed open golden femur mesh 626, which follows closely the boundary of the femur bone in the target image, the gradient image has gradient vectors nearly orthogonal to the boundary of the target femur in the voxels close to the boundary.

Figure 38B:
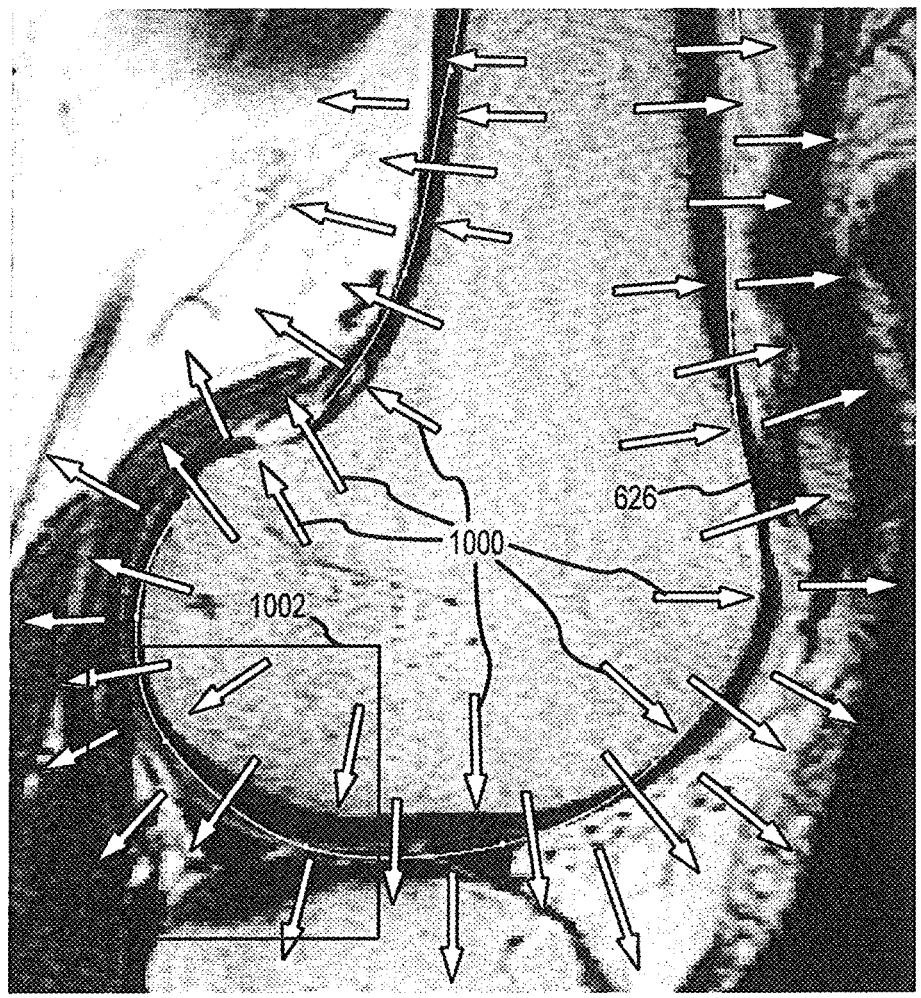
FIG. 38B is an image slice with a contour line representing the approximate segmentation mesh surface found in operation 770c of FIG. 37, the vectors showing the gradient of the signed distance for the contour.

The contour line 626 in FIG. 38B represents the approximate segmentation mesh surface found in the previous registration step of operation 770c of FIG. 37. The vectors 1000 show the gradient of the signed distance for the contour 626. The starting end of the vector 1000 is the point or voxel where the vector 1000 is computed. The gradient of a signed distance has a vector direction in every point or voxel toward the closest point in the contour 626. Vectors 1000 are oriented from inside to outside the contour 626. Each vector 1000 has a unit length.

In operation 770d3 the gradient of the target image is computed. As can be understood from FIG. 38C, which is an enlarged view of the area in FIG. 38B enclosed by the square 1002, the gradient of the target image has gradient vectors 1004 orthogonal to the edges 1006, 1008 in the target image, and the length of those vectors 1004 is larger for stronger edges and smaller for weaker edges. Such vectors 1004 are always oriented from the darker image region to the lighter image region or, in other words, from darker pixels towards brighter pixels. The vectors 1004 are longer where the contrast is higher. For purposes of illustration in FIG. 38C, the vectors 1004 illustrated are only long vectors corresponding to high contrast pixels associated with strong edges. The gradient vectors 1004 can be used to identify the outer cortical bone boundary 1006 and other edges 1008, 1010 that are not of interest for the analysis.

Figure 38C:
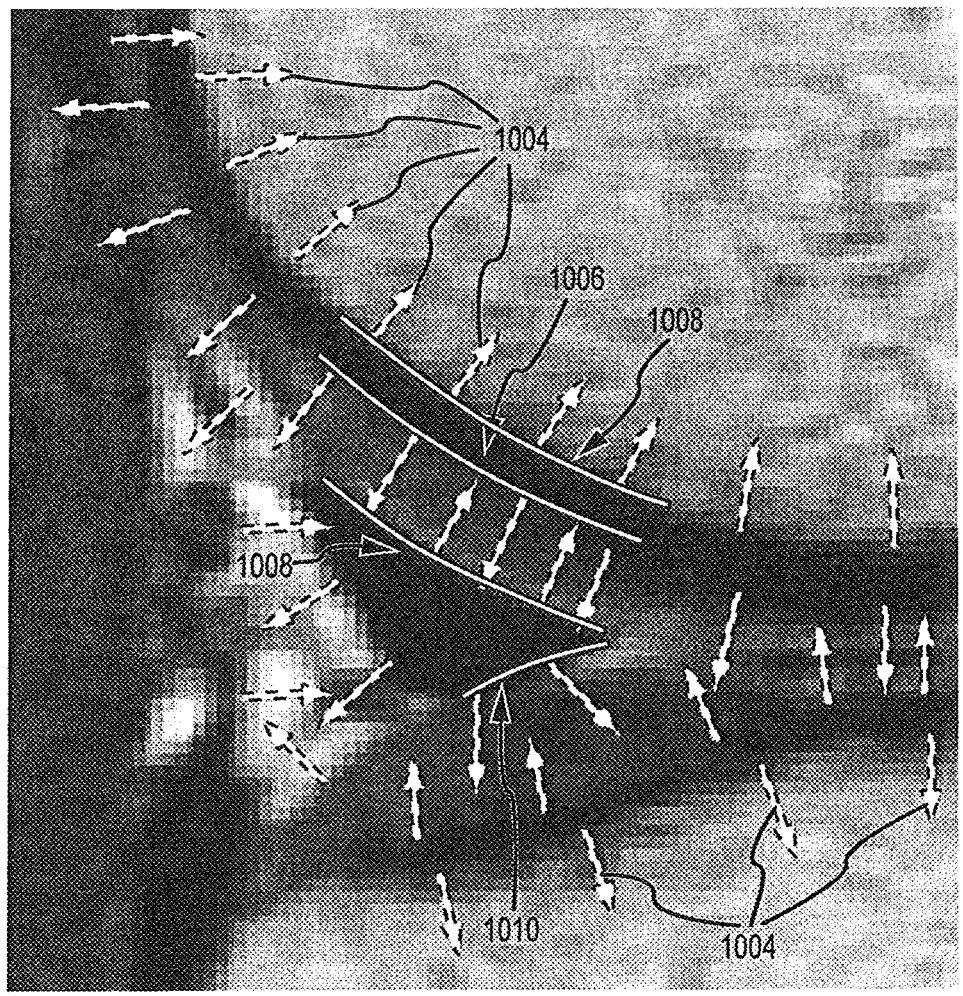
FIG. 38C is an enlarged view of the area in FIG. 38B enclosed by the square 1002, the vectors showing the computed gradient of the target image.

Finally, operation 770d of FIG. 37 is completed via operation 770d4 of FIG. 38A, wherein the edges image is computed by correcting the gradient of the target image with the gradient of the signed distance image. As can be understood from FIG. 38D, the edges image is computed by combining the results from operations 770d2 and 770d3. Depending on the type of 3D computer generated bone model being generated from the segmented images, different boundary edges may be of relevance. For example, if the images are being segmented to generate a bone model 22, the boundary edges that are of interest contain dark cortical voxels inside and lighter cartilage or other voxels outside. As a result, the voxels that are of interest are those voxels that have similarly oriented gradients 1000, 1004 computed in operations 770d2 and 770d3 as shown in FIGS. 38B and 38C, respectively. In every voxel the vector 1004 from operation 770d3 is projected onto the vector 1000 from operation 770d2. When the projection of image gradient vector onto a signed distance gradient vector points in the same direction as the signed distance vector, its magnitude is taken as the voxel value for the resulting edges image. When it points in the opposite direction (or has no magnitude at all), "0" is taken as the voxel value for the resulting edges image.

The resulting edges image has high values in the target femur cortical bone outer boundary 1006. However, the edges image does not have many other high values close to the transformed open golden femur mesh with one exception, namely, the voxels on the boundary between the target femur cartilage and the outsight bright voxels (for example fluid voxels) might have high values.

Figure 38D:
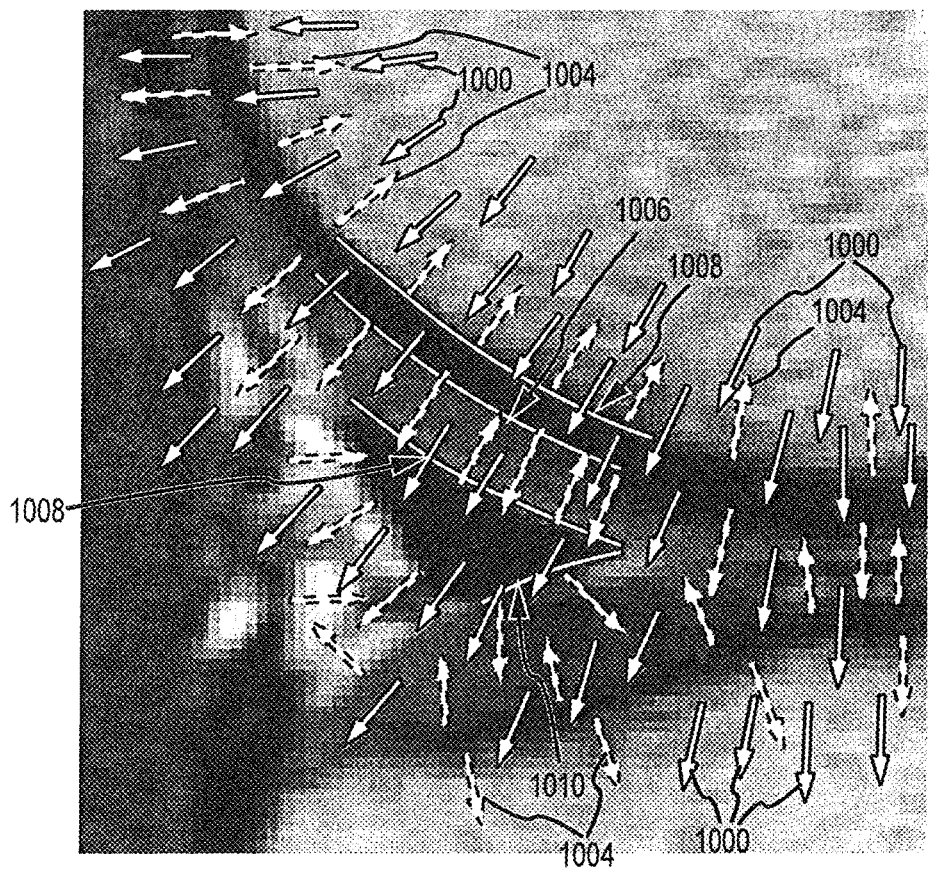
FIG. 38D is the same view as FIG. 38C, except the vectors of FIGS. 38B and 38C are superimposed.

As can be understood from FIG. 38D, the gradient of the signed distance vectors 1000 are uniformly oriented orthogonal to the bone surface and go from inside to outside of the bone. The image gradient vectors 1004 are oriented differently near different image details. For the points in the bone outer boundary 1006, the vectors 1004 are almost parallel to the vectors 1000. For two of the other boundaries 1008, the vectors 1000, 1004 are generally oppositely oriented. Finally, for the last boundary 1010, the vectors 1000, 1004 are quite differently oriented from each other. As a result of the combination of the vectors 1000, 1004 and an analysis of their directional relationships to each other, the edges image will be for FIG. 38D as follows. For points associated with the bone contour line 1006, the edges image will reflect the length of the image gradient vector. For points associated with contour lines 1008, the edges image will be zero. For points associated with the contour line 1010, the edges image values will be smaller than the length of the image gradient vector associated with the bone contour line 1006. Thus, the edges image will tend to have the largest values for the points of the bone contour line 1006.

The high values correspondent to a cartilage/fluid boundary might negatively impact operation 770e of the registration in FIG. 37. Consequently, it may be desirable to suppress those values. This can be done in the beginning of operation 770d3 of FIG. 38A. Specifically, a windowing filter may be applied to the whole target image. A window [w0, w1] may be used, where w0 will be the minimum value in the image, and w1 will be approximately the value correspondent to the cartilage intensity. The filter will replace the high intensity values in the image with w1 value, and thus the boundary between the cartilage and the lighter matters will disappear. For the type of MRI images that may be used, the w1 value correspondent to the median of all the values in the image works quite well. Although such a filter may not always suppress the cartilage boundary entirely, it makes cartilage outer boundary very much weaker in the image and, as a result, the cartilage has less of an impact in operation 770e of FIG. 37.

In one embodiment, a more sophisticated method for suppressing the cartilage boundary may be employed. The cartilage intensity values may be estimated by comparing the voxel values near landmarks 777 along the signed distance gradient direction. The values before a landmark correspond to the cortical bone intensities, while the values after the landmark correspond to the cartilage intensity. Thus for every landmark, a value may be found that represents an "Out of cortical bone" intensity. Such values may be interpolated into the whole image and this windowing function may be applied rather than the constant windowing value w1.

It should be appreciated that a lesser resolution than the target image resolution may be used in all the images participating in the edges image computation. For example, an in-slice voxel size of 1 mm may be used rather than ~0.3 mm in the target image. Using coarser resolution in effect smoothes out the data, allowing a more stable edges computation. It also significantly speeds up the computation. In case of very noisy target images, an additional smoothing step may be applied.

Operation 770 of FIG. 36 is completed via operation 770e of FIG. 37, wherein the full or entire golden femur mesh 626, including its regions 628, 629, are simultaneously registered to landmarks 777 and image edges respectively using B-spline deformable transforms. Specifically, operation 770e of FIG. 37 further refines the image registration of the boundary golden femur region. In one embodiment, a spline transformation may be used to register the open golden femur mesh 626 into the MRI scan data (target image space). In one embodiment, 3D B-Spline deformable transforms may be employed.

A B-Spline deformable transformation typically is a free form deformation of an object using a deformation field where a deformation vector is assigned to every point in space. For example, a 3D B-spline deformable transform T may specify a 3D vector V(P) for every point P in the original 3D space that is moved by T such that T:P→P+V (P).

In one embodiment, a B-Spline transformation may be specified with M×N parameters, where M is the number of nodes in the B-Spline grid and N is the dimension of the space. In one embodiment, a 3D B-Spline deformable transformation of order three may be used to map every reference image 3D point into the target MRI scan by a different 3D vector. The field of vectors may be modeled using B-splines. Typically a grid J×K×L of control points may be specified where J, K, and L are parameters of the transformation.

In one embodiment, splines of order three may be used with a grid 27×9×11 of control points. That is, the transformation employs 27 control points in the medial/lateral direction (i.e., the x direction), 9 control points in posterior/anterior direction, and 11 control points in distal/proximal direction. Two control points in each dimension (i.e., 2 of 27 in the x direction, 2 of 9 in the y direction and 2 of 11 in the z direction) may be used to specify boundary conditions. As such, the inner spline nodes may form a grid of size 25 by 7 by 9 and the boundary conditions increase the grid to size 27 by 9 by 11. The parametric set for this transformation has a dimension of 3×27×9×11=8019 (i.e., at each node of a 27×9×11 grid of control points, there is specified a 3-dimensional transformation vector; a nonlinear interpolation of transformation vectors for points located between adjacent nodes, is governed by spline equations.) The final parameters of the spline transformation that minimizes the misalignment between the reference golden femur template and the target MRI scan data may be found.

In operation 770e of FIG. 37 a different metric (or defect function) may be used as compared to what was used in operations 770a, 770b, and 770c. Specifically, a combined defect function may be used. The combined defect function may be defined as a linear combination of the defect function D (same as in operations 770a, 770b, and 770c) and defect functions D_i that evaluate the discrepancy between the golden mesh regions 628, 629 and the scan image edges defined in operation 770d of FIG. 37.

The defect function D_i, or rather its opposite metric function M_i=−D_i, for a given Golden Mesh Region R_i may be defined as follows. All the vertices in the golden mesh region R_i, are taken, a transform is applied to them, and the correspondent intensities are evaluated in the edges image. M_i may be set to be the sum of those intensities. Thus, when more vertices from the transformed golden mesh region R_i come close to the image edges, a higher metric value is the result.

When defining the combined metric or defect, that is when taking the linear combination of D and all the D_i, the coefficients in the linear combination need to be specified. It may be desirable to use a very high coefficient with D because we want to follow very precisely the landmarks 777 provided by a user. Smaller coefficients may be employed with D_i. The latter coefficients might be also different. The higher coefficients may be used for those regions of the bone that require a greater degree of precision, the associated image segmentation needing to result in more clearly defined regions. The lower coefficients may be used for those regions of the bone that do not require a high degree of precision, the associated image segmentation resulting in less clearly defined regions.

Some bones may have a higher degree of shape variations across the population than is found with the knee region of the femur. For example, the shape of the tibia may vary more from patient to patient than does the shape of the femur. As a result, the affine transformation may not provide a close enough registration of the golden tibia template to the target tibia in the target scan. This may cause the Spline transformation to find a local optimum that may be far from the actual tibia in some areas. In one embodiment, an additional registration operation between the affine transform and spline transform operations may be performed to more closely align the golden tibia and the target tibia, allowing the spline transform to converge to the correct local optimum rather than a nearby, but wrong, local optimum.

The class of transforms utilized generally should allow more flexibility (or degrees of freedom) than the Affine transform and less flexibility than the B-spline transforms. The number of degrees of freedom generally is equal to the number of transform parameters. In one embodiment, a class of transforms with more than 12 parameters and less than 3×27×9×11 parameters may be used. For example, a B-spline transform with fewer control points than used in the subsequent spline transform may be used for the additional transform operation. Alternatively, the deformations may be modeled using quadric rather than cubic functions.

In another embodiment, several golden tibia templates may be used that represent typical tibia variations, e.g., golden tibia templates for varus, valgus, and normal tibia. In one embodiment, each of the golden tibia templates may be used during the translation, similarity and affine transform registration operations to find the template that provides the best match (e.g., best correlation) in the affine transform registration operation. This template may then be used in the remaining registration operations.

Finally, in one embodiment, the tibia registration may be improved by performing the tibia segmentation after the femur segmentation and adding a restriction on the tibia registration transformations such that the tibia may not penetrate the femur. In one embodiment, this may be implemented by introducing a penalty for the penetration. In the target MRI all the voxels that lie inside the femur segmentation curves may be marked. The metric functions, described in more detail below, that are used in the registration operations may be modified to include a penalty term. The penalty term may be computed by taking points in the golden tibia mesh, applying a transform to the set of points, determining if a transformed sample point falls into any of the marked voxels, and adding a large value to the penalty term for each transformed sample point that falls into any of the marked voxels.

In each of the above registration operations, a metric may be used to quantify the degree of correspondence between the reference objects and target image achieved by a given transformation. In one embodiment, the metric quantitatively measures how well the transformed golden femur data fits the target image (e.g., a target MRI scan) and landmarks positioned there.

As discussed above, metrics M=−D, M_i=−D_i, and their linear combination are used in operations 770a-770d of the registration. An explanation is now given regarding the details on how to compute those metrics. As far as using those metrics with optimizers that require computations of the gradient of the metric, it is also explained how to compute the gradient of those metrics.

When computing the metric M or rather the defect D, such a computation can include finding the sum of the squared distances from each landmark point 777 to the transformed open golden mesh. In order to make this computation as quickly and efficiently as possible, the following can be done. First, a B-Spline transformation of a mesh is no longer a mesh. The plane triangles forming the original mesh get curved over the transformation, and the triangles are no longer planar. Rather than computing distances to curved triangles, which would be very computationally expensive, planar triangles connecting the transformed vertices are used. Very little precision is lost with this substitution because the triangles are very small.

Next, after finding the transformed mesh, it is desirable for every Landmark point to find the closest point in the transformed mesh triangles and take the squared distance to it. A spatial subdivision scheme is used to sort all the triangles by spatial location. An octree subdivision is used, although other schemes (kd-tree, fixed size grid, etc.) would work as well. The spatial subdivision helps to find a closest mesh triangle and a closest point in it using an order of LOG(n) operations where n is the number of triangles in the mesh.

The optimizers used in the registration steps require the computation of the gradient of the metric function, which depends on the applied transform, over the transform parameters.

In one embodiment the metric function may be a composition of several functions. For the metric M (or cost function D), for example, the following functions are used in the composition: a) mesh transformation, b) distance from a Landmark point to the transformed mesh, c) squared distance, d) sum of squares, e) inverse of the sum.

For a composition of functions, determining the gradient involves finding partial derivatives for each function and then applying the chain rule. The derivatives of the algebraic functions are computed by standard formulae. The only non-trivial computation in the above functions is the computation of the partial derivative of a distance from a point to the transformed mesh.

For the latter computation, it may involve using an approximate method. Namely, take the closest triangle found in the metric computation followed by taking the plane containing that triangle. This plane approximates the transformed mesh surface in some small neighborhood of the closest point. One of the transform parameters is changed by a very small amount. It is observed where the former closest triangle is mapped after the variation.

The plane containing the varied triangle is taken. This plane approximates the varied transformed mesh surface in some small neighborhood of the varied closest point. The distance from the landmark point to this varied plane is taken. It is approximately the distance from the landmark point to the whole varied transformed mesh surface. Now the difference between the varied distance and the original distance is taken and divided by the value of the parameters variation. This gives approximately the partial derivative for this parameter.

In order to compute the gradient of the metric D_i with respect to the transform parameters, the gradient image of the edges image is computed right after the computation of the edges image itself. To compute the partial derivative of D_i over a transform parameter, the computation may take place for the derivative of every transformed vertex motion over that parameter using the chain rule. This derivative will be a 3D vector. Its dot product is taken with the correspondent Gradient vector of the Gradient Image of the Edges Image and the values are summed all over the vertices.

Finally, since the combined defect function is a linear combination of defect functions D and D_i, then the gradient of the combined defect function with respect to a given transform, is correspondingly a linear combination (with the same coefficients) of the gradients of D and D_i with respect to that same transform.

In summary and as can be understood from the immediately preceding discussion regarding operations 770a-770c and 770e of FIG. 37, translation transforms (operation 770a), similarity transforms (operation 770b), affine transforms (operation 770c), and B-Spline deformable transforms (operation 770e) are employed as part of accomplishing operation 770 of FIG. 36. Because in operations 770a-770c of FIG. 37 it is intended to register the open golden femur mesh to landmarks, the metric (or defect) function should evaluate how close the transformed open golden femur mesh is to landmarks. Thus, in operations 770a-770c, there is a selection of the defect function D to be the sum of squared distances from landmarks to the deformed open golden mesh. In the operation 770e, a simultaneous registering of several parameters may be defined as a combined metric that will take into account all the parameters. The combined defect function may be defined as a linear combination of the defect function D (same as in operations 770a-770c) and defect functions D_i that evaluate the discrepancy between the golden mesh regions and the scan image edges defined in operation 770d of FIG. 37.

Once operation 770 of FIG. 36 is completed, the process of FIG. 36 then continues with operation 772, wherein the deformed open golden femur mesh 626 and associated regions 628, 629 are segmented followed by operation 773, wherein the resulting segmentation curves are approximated with splines. The process continues with operation 774, wherein the contour lines or splines generated in operation 773 are modified to match landmarks.

In other words, in operation 774 the segmentation curves are refined to more precisely match the landmarks. Typically, the segmentation curves created via the above-described algorithms match the landmarks quite closely. Accordingly, most any simple algorithm for a local curve adjustment can work to further refine the precision of the match of the segmentation curves with the landmarks.

In one embodiment of operation 774 when further refining the segmentation curves to match landmarks, only those curves that belong to slices that contain landmarks are considered. When a curve belongs to a slice with landmarks, it is assumed that it should rather precisely go through all the Landmarks. In one embodiment, a curve may be considered to be precisely enough located relative to a landmark if its distance from the landmark ("Tol") is Tol=0.3 mm or less. Most often all the landmarks are within the Tol distance from the curve. However, sometimes a few of the landmarks are further than the Tol distance from the curve. As can be understood from the following discussion regarding operation 774, for every curve generated via the above-described algorithms, each landmark in a slice is iterated. If a landmark is not within Tol distance from the curve, a correction algorithm is applied to the curve as described below with respect to operation 774.

Operation 774 locally modifies the spline curve to fit a selected landmark. Specifically, as can be understood from FIG. 39, which is a flowchart illustrating the process of operation 774 of FIG. 36 in the context of a particular image slice containing landmarks and a segmentation contour, in operation 774a a landmark 777 is identified. In operation 774b, the distance of the identified landmark 777 to the spline generated from the golden femur mesh 626 is computed. More specifically, the algorithm of operation 774 first computes distances for all the other landmarks in the same slice to avoid making the distance relationships of the landmarks and curve worse.

In operation 774c, an arc of the contour line or spline that is the closest to the landmark is identified. Specifically, the closest spline arc [A, B] to the selected landmark L is located, where A and B are consecutive vertices in the spline curve.

In operation 774d, the arc is modified to include the identified landmark, resulting in a modified contour line or spline. Specifically, the vertices A and B are moved iteratively so that the arc [A, B] fits L. For each iteration, the closest point C in [A, B] to L is found. The ratio $\alpha:(1-\alpha)$ is then found in which C divides [A, B]. Next, A is moved by $(1-\alpha)*(L-C)$, and B is moved by $\alpha*(L-C)$. The process stops when 0.5*Tol distance is achieved.

Figure 39:
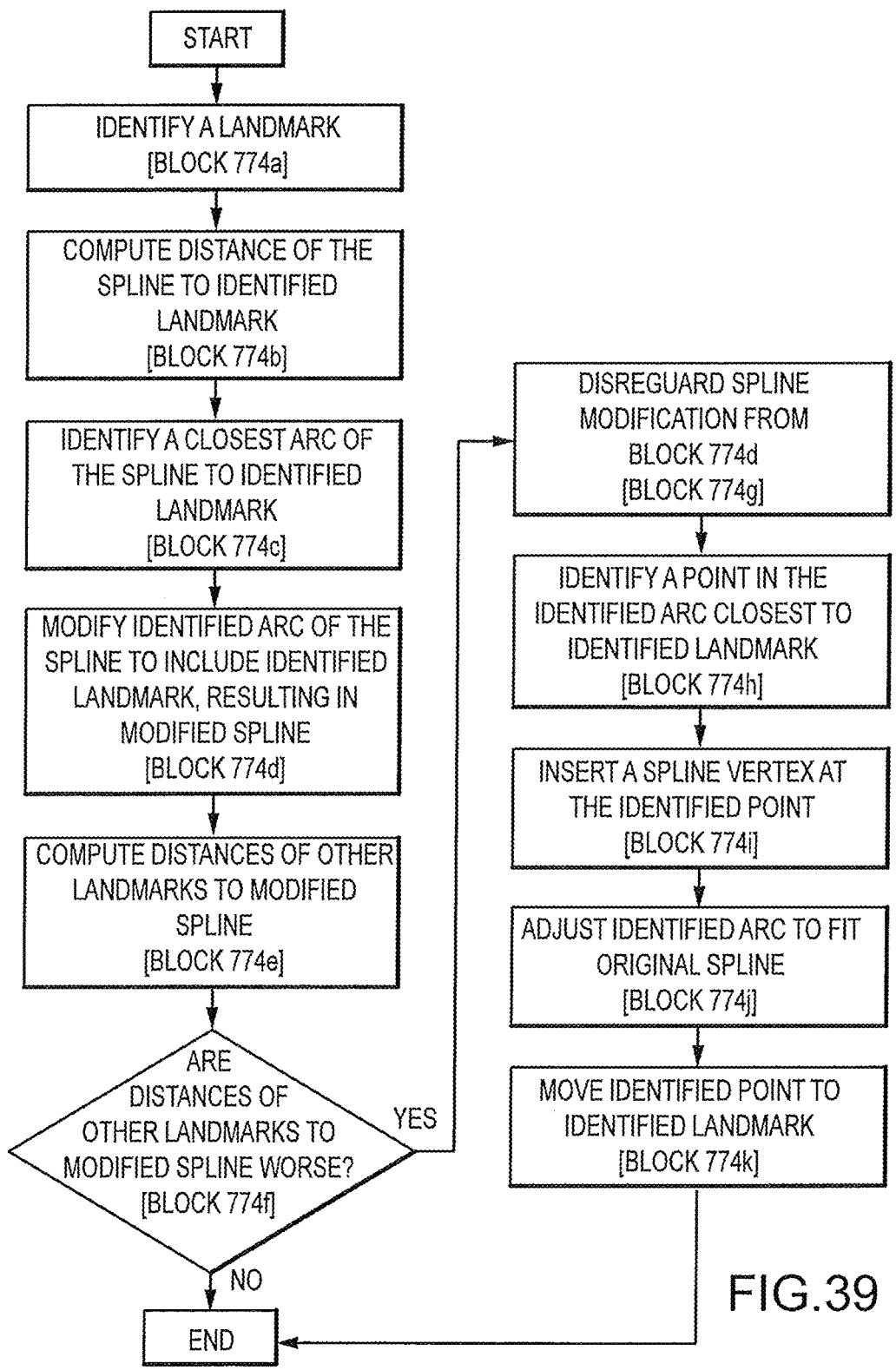
FIG. 39 is a flowchart illustrating the process of operation "Modify Splines" of FIG. 36.

In operation 774e, distances of other landmarks to the modified spline are computed and reviewed in operation 774f to verify operations 774a-774d have not made the fit between the spline and other landmarks worse. In other words, the following is checked for every landmark. First, it is checked to see if the new distance between the spline and landmark is within Tol and, if it is, then the relationship between the spline and landmark is acceptable. Second, it is checked to see if the new distance between the spline and landmark is smaller than the old distance and, if it is, then the relationship between the spline and landmark is acceptable. Third, it is checked to see if the new distance is higher than Tol, the old distance was higher than Tol, and the new distance increased by less than 0.5*Tol. If the answer is yes with respect to all three of the elements of the third check, then the relationship between the spline and landmark is acceptable. For all the other cases, the relationship between the spline and landmark is not acceptable. If the distance relationships between the spline and all of the landmarks are considered acceptable, the process outlined in FIG. 39 is completed for the identified landmark, and the process of FIG. 39 can then be run for another identified landmark until all landmarks have gone through the process of FIG. 39.

If any of the distance relationships between any landmark and the spline are found to be unacceptable in operation 774f due to a modification of the spline with respect to a selected landmark according to operations 774a-774d, then per operation 774g the spline modification from operation 774d is disregarded and a more local modification is employed, as described below with respect to operations 774h-774k of FIG. 39. The more local modification will add a new vertex into the spline making the spline more flexible in this region. The more local modification will then move the new vertex to L, and this will affect a very small area of the spline. Thus, the chance of decreasing the fit to other landmarks will be very small. The more local modification occurs as follows.

In operation 774h, a point in the identified arc closest to the identified landmark is identified. Specifically, the point C in arc [A, B] that is the closest to landmark L is found.

In operation 774i, a spline vertex is inserted at the identified point C. With the insertion of a new vertex, the spline shape usually changes in the two immediately adjacent neighbor arcs on both sides of the arc [A, B]. As a result, the arc spline can become too wavy in the vicinity of the arc [A, B].

To remedy the situation, the arc [A, B] is adjusted to fit the original spline in operation 774j. Specifically, the vertices A and B are modified to try to fit the new spline as closely as possible to the original spline. In doing so, a measure of closeness (i.e., how closely the new spline follows the original spline in the six neighboring arcs—three to each side of the new control point C) may be computed as follows. In one embodiment, the six spline arcs are sampled such that there are twenty or so sample points in every arc of the spline (i.e., 20*6 sample points). Then, the sum of the squared distances from the sample points to the original spline may be computed. Next, the coordinates of the A and B vertices (control points) are varied (i.e., two parameters for each of A and B, that is four parameters). Then, a local optimization algorithm is used to find the closest spline. This process may be similar to the process of fitting a spline to a polyline, as described elsewhere in this Detailed Description.

Per operation 774k, the identified point is moved to the identified landmark. Specifically, the spline vertex C is moved into the landmark point L.

The process outlined in FIG. 39 is completed for the identified landmark, and the process of FIG. 39 can then be run for another identified landmark until all landmarks have gone through the process of FIG. 39.

Once the process of FIG. 39 is completed for all landmarks and the associated contour lines or splines, the process of operation 774 of FIG. 36 is considered complete, which completes the process of FIG. 36 for the operation 252a of FIG. 33. The process of operation 252a in FIG. 33 is now complete. The image slices 16 are then scrolled over to verify if the segmentation results are acceptable, as indicated by operation 252c. In operation 253, if the segmentation is acceptable, then the segmentation process of FIG. 33 ends.

As can be understood from FIG. 33, if in operation 253 the segmentation is not acceptable, then the segmentation of each offending slice 16 is modified by adding additional landmarks 777 and/or modifying the locations of existing landmarks 777 per operation 254 of FIG. 33. For example and as can be understood from FIG. 40, a first spline 800, which is generated via a first run through operation 252 of FIG. 33, has control points 802 and extends along first landmarks 777a placed in the slice 16 of FIG. 40 during operation 251 of FIG. 33.

Figure 40:
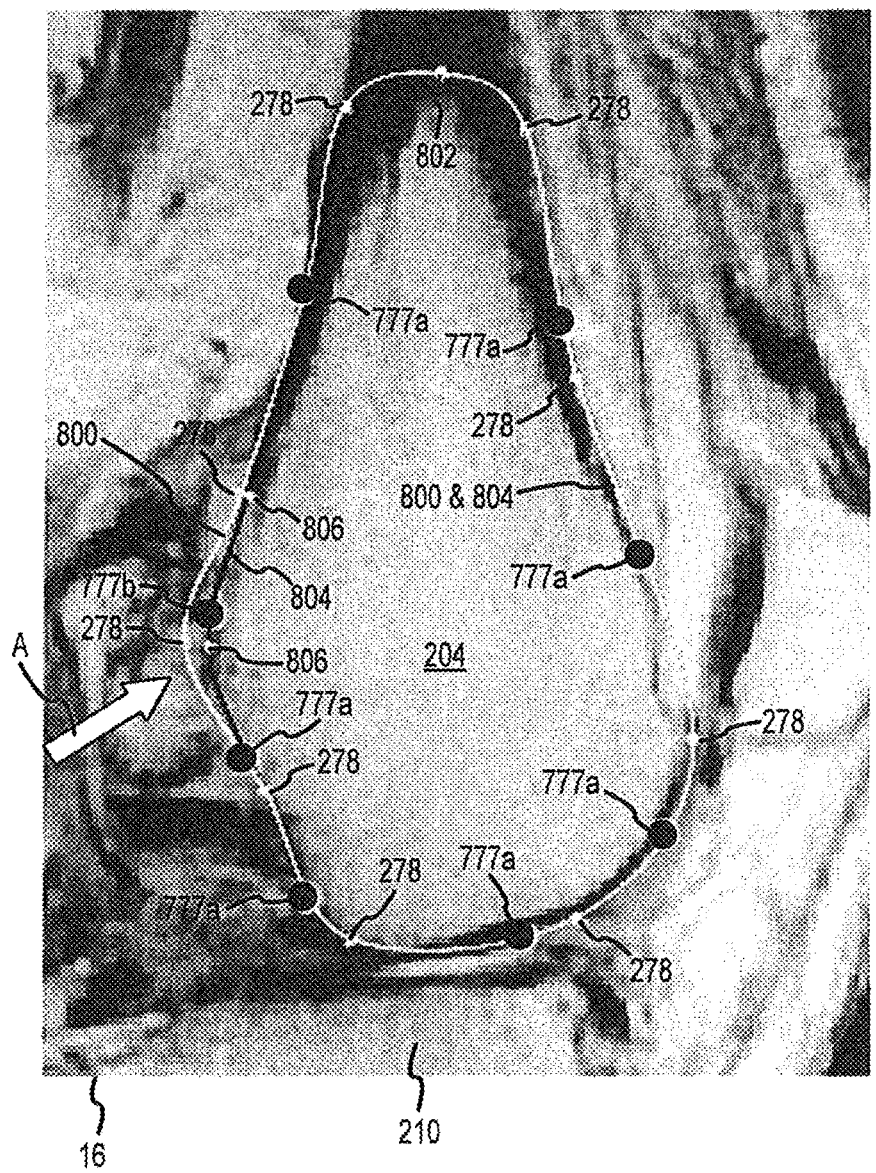
FIG. 40 is an image slice with a spline being modified according to the operations of the flow chart of FIG. 39.

During operation 253 of FIG. 33 the segmentation of the slice 16 of FIG. 40 is identified as being unsatisfactory in the location called out by arrow A in FIG. 40. A new landmark 777b is added in the location called out by arrow A per operation 254 and operation 252, or more specifically, operations 774b-774e of the algorithm of FIG. 39, are repeated to generate a second spline 804, which has control points 806 and extends along both the first landmarks 777a and the second landmark 777b. As can be understood from FIG. 40, the first spline 800 and the second spline 804 are generally identical and coextensive, except in the region identified by arrow A. The segmentation of the second spline 804 is then approved or disapproved per operation 253. If approved, then the segmentation process of FIG. 33 ends. If disapproved, then the second spline 804 is further modified per operation 254 in a manner similar to as discussed above with respect to FIG. 40.

In one embodiment of operation 254 of FIG. 33, the spline may be simultaneously modified near a new added landmark or near moving landmarks to fit the moving landmarks. In doing so, it may be the case that the user is satisfied with the corrected splines. As a result, the process of FIG. 33 may simply end at operation 254 as if the entirety of operation 252 had been completed and the segmentation was found acceptable at operation 253.

In one embodiment, when a user adds a new landmark into a slice with a spline, the spline is immediately modified using precisely the same algorithm of FIG. 39, namely operations 774b-774e. When a user moves a landmark, the spline is updated during the motion using operations 774b-774e of the algorithm of FIG. 39. Adding landmarks (operations 774g-774k of the algorithm of FIG. 39) is avoided during the motion phase as it may lead to multiple updates during motions, resulting in too many points.

Once the contour lines or splines are successfully segmented from each target image slice, the contour lines or splines are compiled as discussed above into a 3D mesh that may be used as an arthritic bone model 36 (see FIG. 1D) or bone models 22 (see FIG. 1C).

In one embodiment of the registration process discussed above, an optimizer may be used during the registration process to maximize similarity between the open golden mesh and landmarks in the target image (and possibly edges image) by adjusting the parameters of a given transformation model to adjust the location of reference image coordinates in the target image. In one embodiment, the optimizer for a registration operation may use the transformed golden femur data from the previous registration operation as its initial approximation. Then, local optimization techniques may be used to search for a local optimum near the initial starting approximation. This may be done so that any potential matches farther away from the feature of interest (e.g., the femur or tibia in a knee joint) reliably found in an earlier operation may be eliminated.

In operation 770a of FIG. 37, when optimizing the translation transformation, a regular step gradient descent optimizer may be used by one embodiment. Other embodiments may use different optimization techniques.

To find a local minimum, parameter steps may be taken in the direction of the negative of the metric gradient (or the approximate gradient) over the transform parameter space at the current point. This generally optimizes the metric which typically has a local minimum when features of the reference image mapped into corresponding features of the target image have minimal misalignment).

In one embodiment, initial gradient step of 3 millimeters may be specified, a relaxation factor may be set to 0.95 and a maximum of 50 iterations may be used in the regular step gradient descent optimization method to determine the parameters of the translation transformation that results in minimal misalignment between the reference Open Golden Femur mesh and the Landmarks in the target MRI scan.

In operation 770b of FIG. 37, when optimizing the similarity transformation, a regular step gradient descent optimizer may be used again by one embodiment. When applying the regular step gradient descent optimizer to similarity transformation, the result and the convergence rate depend on the proper choice of parameters representing the similarity transforms. A good choice of parameters when used with gradient computations is such that a variation of every parameter by one unit leads to approximately equal displacement of object points. In order to ensure similar displacement of points with respect to three rotational parameters in the similarity transform, the initial center of rotation for the similarity transformation may be specified as the center of a bounding box (or minimum sized cuboid with sides parallel to the coordinate planes) that encloses the feature (e.g., a bone) registered in the translation registration (e.g., operation 770a in FIG. 37). For knee segmentation, scaling coefficients of approximately 40-millimeters may be used for the scaling parameters when bringing the rotational angle parameters together with translation parameters. A scaling coefficient of approximately 40-millimeters may be used because it is approximately half the size of the bone (in the anterior/posterior and medial/lateral directions) of interest and results in a point being moved approximately 40-millimeters when performing a rotation of one radian angle. By the same reason a scaling coefficient of 40 millimeters may be used in the similarity transform scaling parameter together with its translational parameters.

In one embodiment, an initial gradient step of 1.5 millimeters may be specified, a relaxation factor may be set to 0.95 and a maximum of 50 iterations may be performed in the regular step gradient descent optimization method to determine the parameters of the similarity transformation that results in minimal misalignment between the reference open golden template mesh and landmarks in the target MRI scan.

In operation 770c of FIG. 37, when optimizing the affine transformation, a regular step gradient optimizer may be used again by one embodiment. For knee bones, scaling coefficients of approximately 40 millimeters may be used for the matrix coefficients variations when bringing them together with translation parameters. An initial gradient step of 1 millimeter may be specified, the relaxation factor may be set to 0.95 and a maximum of 50 iterations may be performed to determine the parameters of the affine transformation that results in minimal misalignment.

In operation 770e of FIG. 37, when optimizing the B-spline transformation, a modified regular step gradient descent optimizer may be used by one embodiment when searching for the best B-spline deformable transformation. Namely, a combination of regular step gradient descent optimizer with by coordinate descent may be used here.

Rather than computing one gradient vector for the transform space and taking a step along it, a separate gradient may be computed for every B-spline transform node. In one embodiment, order three B-splines (with J×K×L control nodes) may be used and J×K×L gradients may be computed, one for each control point. At every iteration, each of the spline nodes may be moved along its respective gradient. This may enable faster convergence of the optimization scheme. A relaxation factor of 0.95 may be used for each spline node. A an initial gradient step of one-millimeter may be set for every B-spline grid node, and a maximum of 50 iterations may be used in the regular step gradient descent optimization method to find the parameters of the B-spline transformation that provides minimal misalignment of the open golden femur mesh and landmarks and feature edges in the target MRI scan.

FIG. 23 depicts a flowchart illustrating one method for generating spline curves outlining the surface of an object of interest in each target MRI slice (e.g., as discussed above with respect to operation 772 of FIG. 36) after the transformed golden femur mesh is found in operation 770e in FIG. 37. Initially, operation 470 intersects the transformed golden femur mesh with a slice of the target scan data. The intersection defines a polyline curve of the surface of the feature (e.g., bone) in each slice. Two or more polyline curves may be generated in a slice when the bone is not very straightly positioned with respect to the slice direction.

A polyline curve is a piecewise linear approximation to a curved feature shape. Generally, this curve should be easy to manipulate with a set of control points. The polyline curve may have many segments, making it more difficult to manipulate the polyline curve (e.g., during operation 254 or 260 of FIG. 6). One embodiment may generate one or more Kochanek splines from the polyline curve. Each spline typically has a smaller number of control points and typically fits the polyline curve with about 0.3-millimeter deviation. See previous description in this Detailed Description for a detailed discussion regarding spline generation.

As discussed above, in one embodiment, the output of the segmentation may be a triangular mesh (e.g., a 3D surface model) of the segmented bone(s) of a joint (e.g., the femur and tibia of a knee joint). The mesh generated generally represents a watertight surface that closely follows the segmentation contour curves of the slices, smoothly interpolates between the segmentation contour curves, and may have a low triangular count. See previous description in this Detailed Description for a detailed discussion regarding mesh generation and the manual adjustment of segmentation splines.

The 3D surface models of the lower end of the femur and the upper end of the tibia of a patient's knee may be used to create arthroplasty jigs and/or implants. For example, the models may be used to create femur and tibia jigs that can be used with a patient's femur and tibia as disclosed in the various U.S. Patent applications incorporated by reference herein in this Detailed Description and filed by Park and Park et al. The automatic or semi-automatic processes described herein for segmentation of image data to generate 3D bone models may reduce the overall time required to perform a reconstructive surgery to repair a dysfunctional joint and may also provide improved patient outcomes.

III. Overview of Bone Model Restoration or Modification Process

The description in Section II. focused on the acquisition of medical images, the segmentation or auto-segmentation of the medical images, and the generation of a patient bone model from the segmented images that is representative of the bones of the patient in a deteriorated or degenerated state. Beginning in Section III., the present disclosure includes a description of exemplary methods of modifying image data (e.g., 2D image slices) into restored image data (e.g., restored 2D image data), and then generating a restored bone model representing a patient's bone in a pre-deteriorated or pre-degenerated state. The restored bone model or the restored image data (e.g., restored 2D image data) may then be used in implant planning (e.g., determining coordinate locations for resections, implant sizes), as will be described in Section IV.

As mentioned above with respect to [block 115] of FIG. 1C, the process for restoring damaged regions of 3D "bone models" 22 to generate 3D "restored bone models" 28 can be automated to be carried out to a greater or lesser extent by a computer. A discussion of various examples of such an automated process will be described, beginning with an overview of various automated bone restoration processes.

As can be understood from FIG. 1A and [blocks 100-105] of FIG. 1B, a patient 12 has a joint 14 (e.g., a knee, elbow, ankle, wrist, shoulder, hip, vertebra interface, etc.) to be replaced (e.g., partially or totally) or resurfaced. The patient 12 has the joint 14 scanned in an imaging machine 10 (e.g., a CT, MRI, etc. machine) to create a plurality of 2D scan images 16 of the bones (e.g., femur 18 and tibia 20) forming the patient's joint 14 (e.g., knee). The process of creating the 2D scan images or slices 16 may occur as disclosed in Ser. No. 11/946,002, which was filed by Park Nov. 27, 2007 and is incorporated by reference in its entirety into this Detailed Description. Each scan image 16 is a thin slice image of the targeted bone(s) 18, 20. The scan images 16 are sent to the CPU 7, which may employ an open-loop or closed-loop image analysis along targeted features 42 of the scan images 16 of the bones 18, 20 to generate a contour line for each scan image 16 along the profile of the targeted features 42. The process of generating contour lines for each scan image 16 may occur as disclosed in Ser. No. 11/959,344, which is incorporated by reference in its entirety into this Detailed Description.

As can be understood from FIG. 1A and [block 110] of FIG. 1C, the CPU 7 compiles the scan images 16 and, more specifically, the contour lines to generate 3D computer surface or volumetric models ("bone models") 22 of the targeted features 42 of the patient's joint bones 18, 20. In the context of total knee replacement ("TKR") or partial knee replacement surgery, the targeted features 42 may be the lower or knee joint portions of the patient's femur 18 and the upper or knee joint portions of the patient's tibia 20. More specifically, for the purposes of generating the femur bone models 22, the targeted features 42 may include the condyle portion of the femur and may extend upward to include at least a portion of the femur shaft. Similarly, for purposes of generating the tibia bone models 22, the targeted features 42 may include the plateau portion of the tibia and may extend downward to include at least a portion of the tibia shaft.

In some embodiments, the "bone models" 22 may be surface models or volumetric solid models respectively formed via an open-loop or closed-loop process such that the contour lines are respectively open or closed loops. Regardless, the bone models 22 are bone-only 3D computer generated models of the joint bones that are the subject of the arthroplasty procedure. The bone models 22 represent the bones in the deteriorated condition in which they existed at the time of the medical imaging of the bones.

To allow for the POP procedure, wherein the saw cut and drill hole locations 30, 32 are determined as discussed with respect to [block 120] of FIG. 1C, the "bone models" 22 and/or the image slices 16 (see [block 100] of FIG. 1B) are modified to generate a 3D computer generated model that approximates the condition of the patient's bones prior to their degeneration. In other words, the resulting 3D computer generated model, which is termed a "restored bone model" 28, approximates the patient's bones in a non-degenerated or healthy state and can be used to represent the patient's joint in its natural alignment prior to degeneration.

Figure 41:
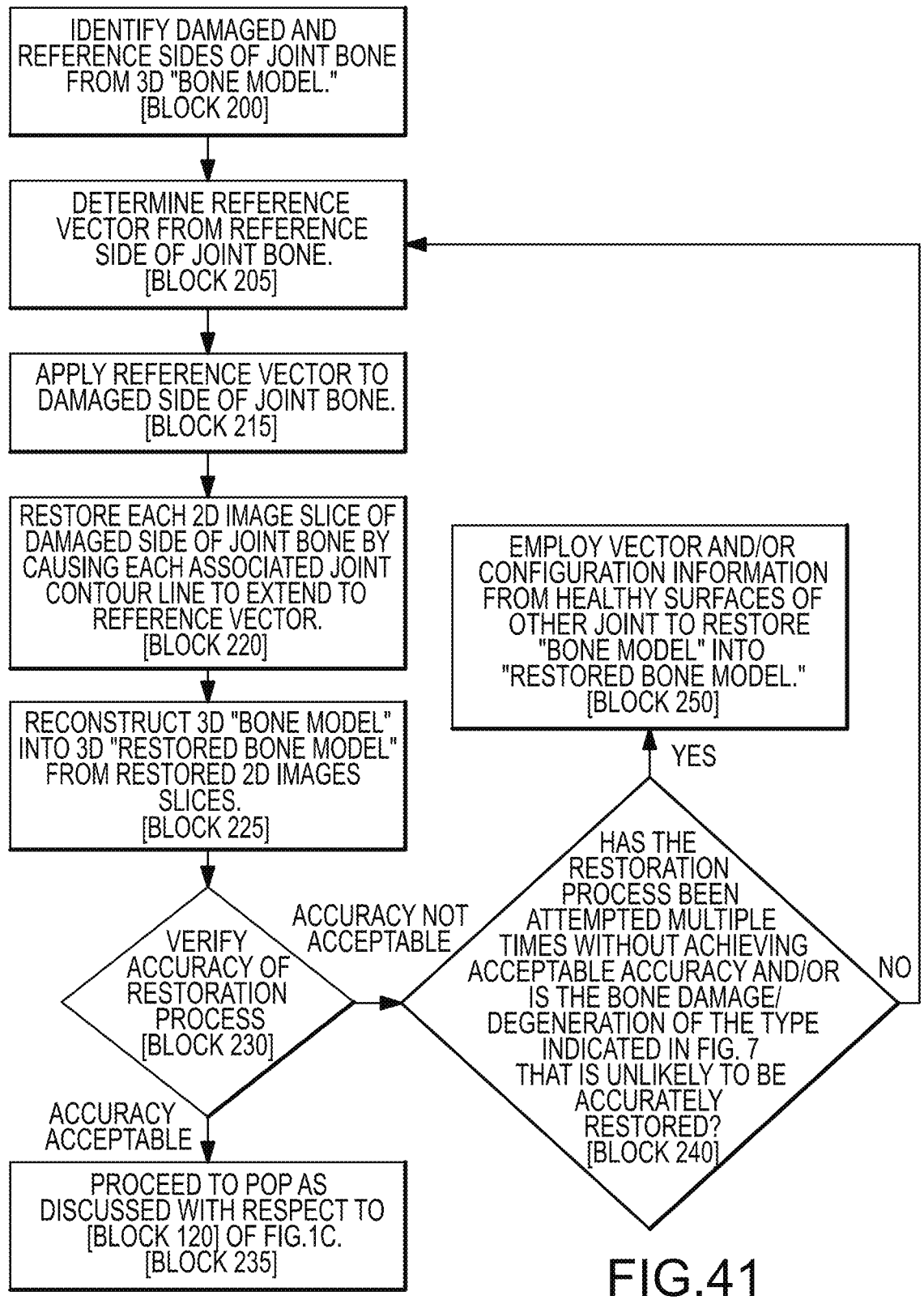
FIG. 41 is a diagram generally illustrating a bone restoration process for restoring a 3D computer generated bone model into a 3D computer generated restored bone model.

In one embodiment, the bone restoration process employed to generate the restored bone model 28 from the bone model 22 or image slices 16 may be as indicated in the process diagram depicted in FIG. 41. As shown in FIG. 41, the damaged and reference sides of a joint bone to undergo an arthroplasty procedure are identified from the 3D computer generated "bone model" [block 200]. The damaged side is the side or portion of the joint bone that needs to be restored in the bone model 22, and the reference side is the side of the joint bone that is generally undamaged or at least sufficiently free of deterioration that it can serve as a reference for restoring the damaged side.

As can be understood from FIG. 41, reference data or information (e.g., in the form of ellipses, ellipse axes, and/or vectors in the form of lines and/or planes) is then determined from the reference side of the joint bone [block 205]. The reference information or data is then applied to the damaged side of the joint bone [block 215]. For example, in a first embodiment and in the context of a knee joint, a vector associated with a femur condyle ellipse of the reference side is determined and applied to the damaged side femur condyle and damaged side tibia plateau. In a second embodiment and in the context of a knee joint, a vector associated with the highest anterior and posterior points of a tibia plateau of the reference side is determined and applied to the damaged side femur condyle and damaged side tibia plateau. These vectors are generally parallel with the condyle ellipse and generally parallel with the knee joint line.

As indicated in FIG. 41, each joint contour line associated with a 2D image slice of the damaged side of the joint bone is caused to extend to the reference vector or ellipse [block 220]. This restoration process is carried out slice-by-slice for the joint contour lines of most, if not all, image slices associated with the damaged side of the joint. The 3D "bone model" is then reconstructed into the 3D "restored bone model" from the restored 2D images slices [block 225].

Once generated from the "bone model" 22, the "restored bone model" 28 can then be employed in the POP process discussed with respect to [block 120] of FIG. 1C. As discussed with respect to [blocks 125 and 150], "saw cut and drill hole data" resulting from the POP process is indexed into "jig data" 46 to create "integrated jig data" 48. As discussed with respect to [blocks 155-165] of FIG. 1E, the "integrated jig data" 48 is utilized by a CNC machine 10 to produce customized arthroplasty jigs 2.

The systems 4 and methods disclosed herein allow for the efficient manufacture of arthroplasty jigs 2 customized for the specific bone features of a patient. Each resulting arthroplasty jig 2 includes an interior portion dimensioned specific to the surface features of the patient's bone that are the focus of the arthroplasty. Each jig 2 also includes saw cut slots and drill holes that are indexed relative to the interior portion of the jig such that saw cuts and drill holes administered to the patient's bone via the jig will result in cuts and holes that will allow joint implants to restore the patient's joint line to a pre-degenerated state or at least a close approximation of the pre-degenerated state.

Where the arthroplasty is for TKR or partial knee replacement surgery, the jigs will be a femur jig and/or a tibia jig. The femur jig will have an interior portion custom configured to match the damaged surface of the lower or joint end of the patient's femur. The tibia jig will have an interior portion custom configured to match the damaged surface of the upper or joint end of the patient's tibia.

The jigs 2 and systems 4 and methods of producing such jigs are illustrated herein in the context of knees and TKR or partial knee replacement surgery. However, those skilled in the art will readily understand the jigs 2 and system 4 and methods of producing such jigs can be readily adapted for use in the context of other joints and joint replacement or resurfacing surgeries, e.g., surgeries for elbows, shoulders, hips, etc. Accordingly, the disclosure contained herein regarding the jigs 2 and systems 4 and methods of producing such jigs should not be considered as being limited to knees and TKR or partial knee replacement surgery, but should be considered as encompassing all types of joint surgeries.

A. Overview of the Mechanics of an Accurate Restored Bone Model

An overview discussion of the mechanics of an accurate restored bone model 28 will first be given before discussing any of the bone restoration procedures disclosed herein. While this overview discussion is given in the context of a knee joint 14 and, more particularly, a femur restored bone model 28A and a tibia restored bone model 28B, it should be remembered that this discussion is applicable to other joints (e.g., elbows, ankles, wrists, hips, spine, etc.) and should not be considered as being limited to knee joints 14, but to include all joints.

Figure 42A:
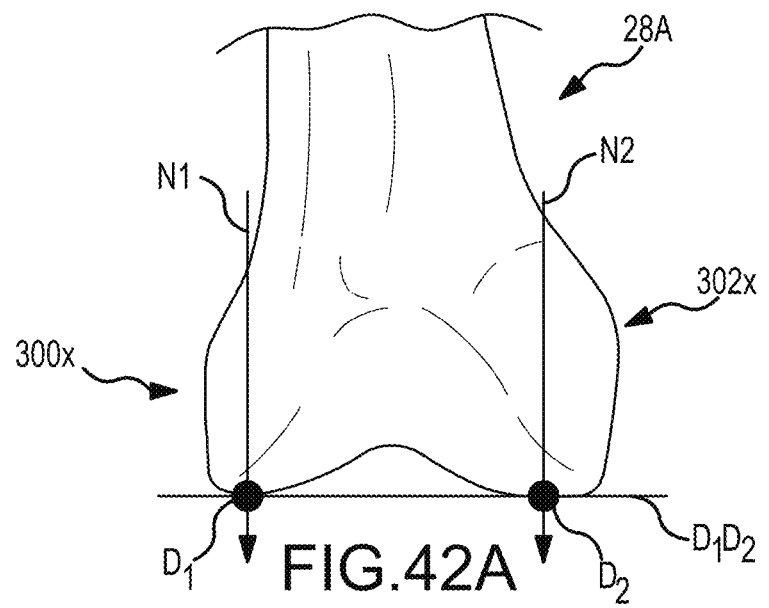
FIG. 42A is a coronal view of a distal or knee joint end of a femur restored bone model.

As shown in FIG. 42A, which is a coronal view of a distal or knee joint end of a femur restored bone model 28A, points $D_1$, $D_2$ represent the most distal tangent contact points of each of the femoral lateral and medial condyles 300x, 302x, respectively. In other words, points $D_1$, $D_2$ represent the lowest contact points of each of the femoral lateral and medial condyles 300x, 302x when the knee is in zero degree extension. Line $D_1D_2$ can be obtained by extending across the two tangent contact points $D_1$, $D_2$. In this femur restored bone model 28A, line $D_1D_2$ is parallel or nearly parallel to the joint line of the knee when the knee is in zero degree extension.

The reference line $N_1$ is perpendicular to line $D_1D_2$ at point $D_1$ and can be considered to represent a corresponding 2D image slice 16 taken along line $N_1$. The reference line $N_2$ is perpendicular to line $D_1D_2$ at point $D_2$ and can be considered to represent a corresponding 2D image slice 16 taken along line $N_2$. The cross-sectional 2D image slices 16 taken along lines $N_1$, $N_2$ are perpendicular or nearly perpendicular to the tangent line $D_1D_2$ and joint line.

Figure 42B:
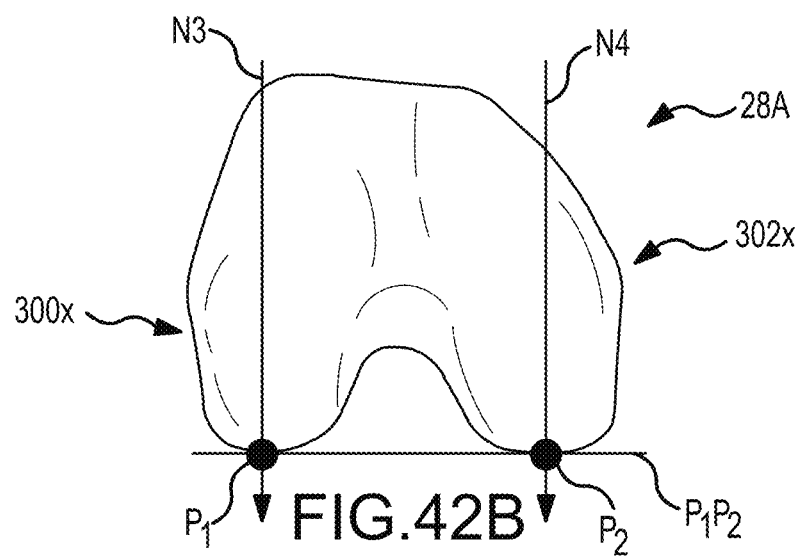
FIG. 42B is an axial view of a distal or knee joint end of a femur restored bone model.

As shown in FIG. 42B, which is an axial view of a distal or knee joint end of a femur restored bone model 28A, points $P_1$, $P_2$ represent the most posterior tangent contact points of each of the femoral lateral and medial condyles 300x, 302x, respectively. In other words, points $P_1$, $P_2$ represent the lowest contact points of each of the femoral lateral and medial condyles 300x, 302x when the knee is in 90 degree extension. Line $P_1P_2$ can be obtained by extending across the two tangent contact points $P_1$, $P_2$. In this femur restored bone model 28A, line $P_1P_2$ is parallel or nearly parallel to the joint line of the knee when the knee is in 90 degree flexion.

The reference line $N_3$ is perpendicular to line $P_1P_2$ at point $P_1$ and can be considered to represent a corresponding 2D image slice 16 taken along line $N_3$. In some instances, the lines $N_1$, $N_3$ may occupy generally the same space on the femur restored bone model 28A or lines $N_1$, $N_3$ may be offset to a greater or lesser extent from each other along the joint line of the knee. The reference line $N_4$ is perpendicular to line $P_1P_2$ at point $P_2$ and can be considered to represent a corresponding 2D image slice 16 taken along line $N_4$. In some instances, the lines $N_2$, $N_4$ may occupy generally the same space on the femur restored bone model 28A or lines $N_2$, $N_4$ may be offset to a greater or lesser extent from each other along the joint line of the knee. The cross-sectional 2D image slices 16 taken along lines $N_3$, $N_4$ are perpendicular or nearly perpendicular to the tangent line $P_1P_2$ and joint line.

Figure 42C:
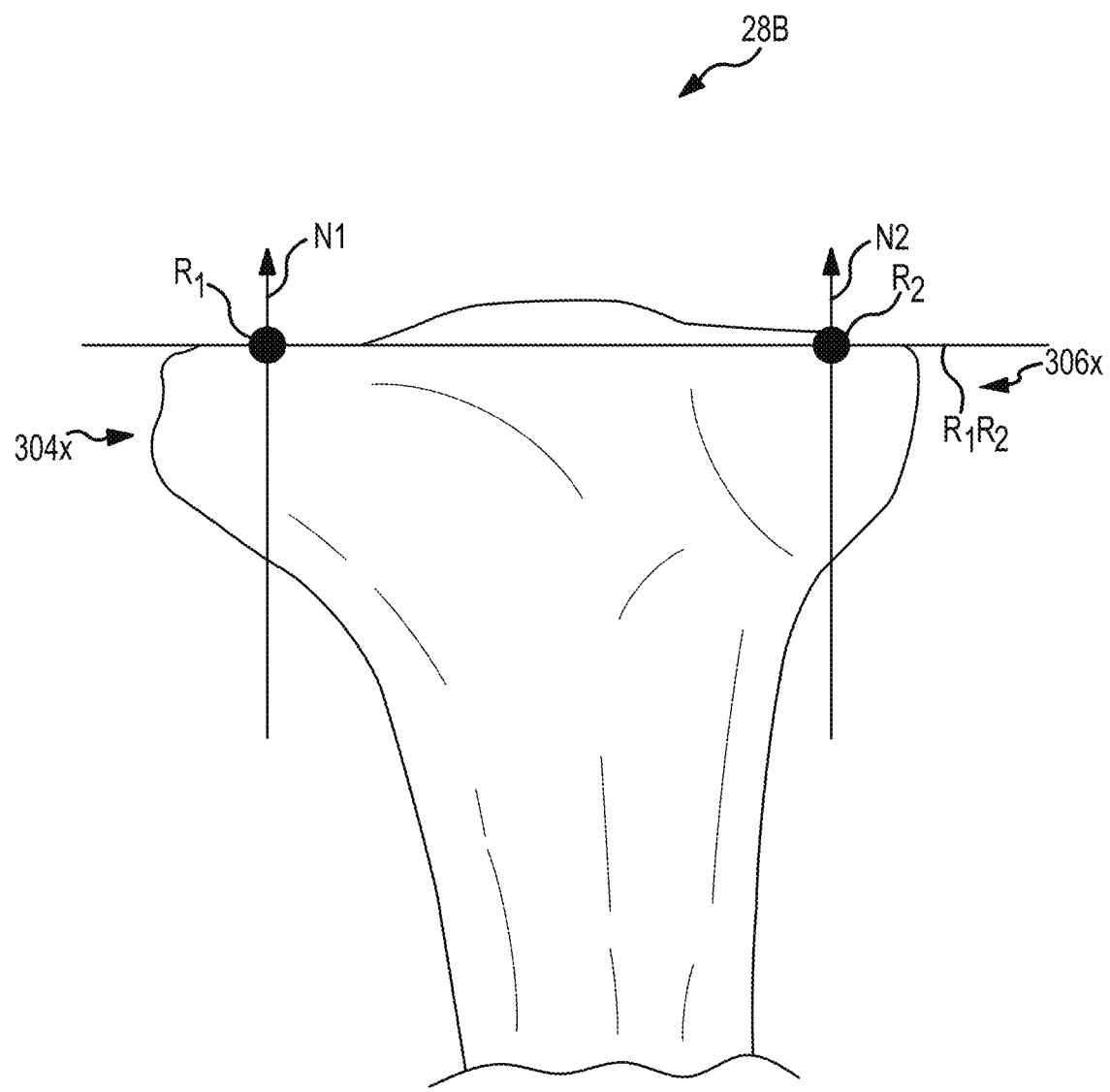
FIG. 42C is a coronal view of a proximal or knee joint end of a tibia restored bone model.

As shown in FIG. 42C, which is a coronal view of a proximal or knee joint end of a tibia restored bone model 28B, points $R_1$, $R_2$ represent the lowest tangent contact points of each of the tibial lateral and medial plateaus 304x, 306x, respectively. In other words, points $R_1$, $R_2$ represent the lowest points of contact of the tibia plateau with the femur condyles when the knee is in zero degree extension. Line $R_1R_2$ can be obtained by extending across the two tangent contact points $R_1$, $R_2$. In this tibia restored bone model 28B, line $R_1R_2$ is parallel or nearly parallel to the joint line of the knee when the knee is in zero degree extension. Also, when the knee joint is in zero degree extension, line $R_1R_2$ is parallel or nearly parallel to line $D_1D_2$. When the knee joint is in 90 degree extension, line $R_1R_2$ is parallel or nearly parallel to line $P_1P_2$.

The reference line $N_1$ is perpendicular to line $R_1R_2$ at point $R_1$ and can be considered to represent a corresponding 2D image slice 16 taken along line $N_1$. The reference line $N_2$ is perpendicular to line $R_1R_2$ at point $R_2$ and can be considered to represent a corresponding 2D image slice 16 taken along line $N_2$. The cross-sectional 2D image slices 16 taken along lines $N_1$, $N_2$ are perpendicular or nearly perpendicular to the tangent line $R_1R_2$ and joint line. Because both the femur and tibia restored bone models 28A, 28B represent the knee joint 14 prior to degeneration or damage, lines $N_1$, $N_2$ of the femur restored model 28A in FIG. 1A align with and may be the same as lines $N_1$, $N_2$ of the tibia restored bone model 28B when the knee joint is in zero degree extension. Thus, points $D_1$, $D_2$ align with points $R_1$, $R_2$ when the knee joint is in zero degree extension.

Figure 42D:
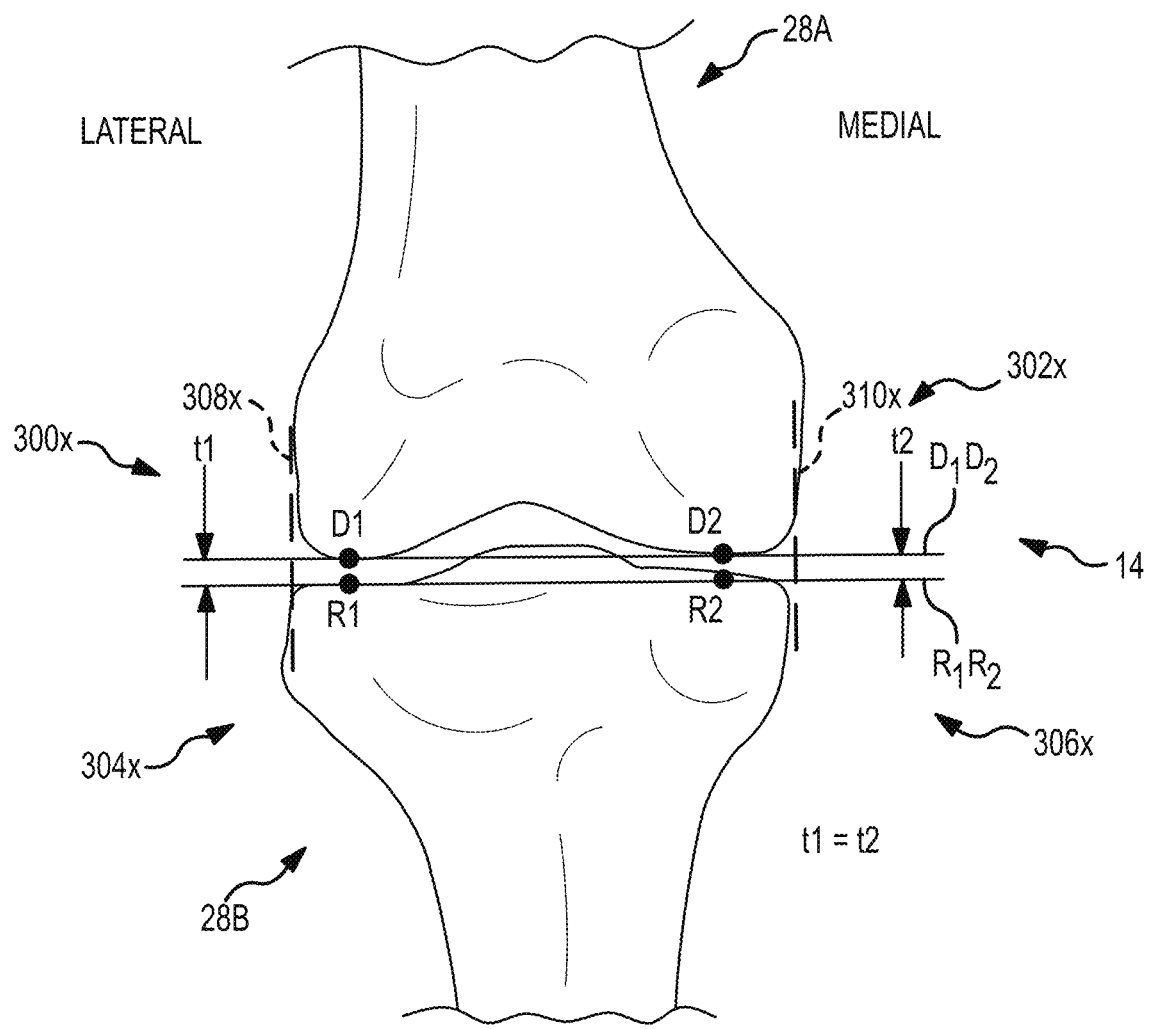
FIG. 42D represents the femur and tibia restored bone models in the views depicted in FIGS. 42A and 42C positioned together to form a knee joint.

FIG. 42D represents the femur and tibia restored bone models 28A, 28B in the views depicted in FIGS. 42A and 42C positioned together to form a knee joint 14. FIG. 42D shows the varus/valgus alignment of the femur and tibia restored bone models 28A, 28B intended to restore the patient's knee joint 14 back to its pre-OA or pre-degenerated state, wherein the knee joint 14 is shown in zero degree extension and in its natural alignment (e.g., neutral, varus or valgus) as the knee joint existed prior to degenerating. The respective locations of the lateral collateral ligament ("LCL") 308x and medial collateral ligament ("MCL") 310x are indicated in FIG. 42D by broken lines and serve as stabilizers for the side-to-side stability of the knee joint 14.

As can be understood from FIGS. 42A, 42C and 42D, when the knee joint 14 is in zero degree extension, lines $N_1$, $N_2$ are parallel or nearly parallel to the LCL 308x and MCL 310x. Gap t1 represents the distance between the tangent contact point $D_1$ of the femoral lateral condyle 300x and the tangent contact point $R_1$ of the tibia lateral plateau 304x. Gap t2 represents the distance between the tangent contact point $D_2$ of the femoral medial condyle 302x and the tangent contact point R2 of the medial tibia plateau 306x. For a properly restored knee joint 14, as depicted in FIG. 42D, in one embodiment, with respect to varus/valgus rotation and alignment, t1 is substantially equal to t2 such that the difference between t1 and t2 is less than one millimeter (e.g., [t1−t2]<<1 mm). Accordingly, line $D_1 D_2$ is parallel or nearly parallel to the joint line and line $R_1R_2$.

Figure 42E:
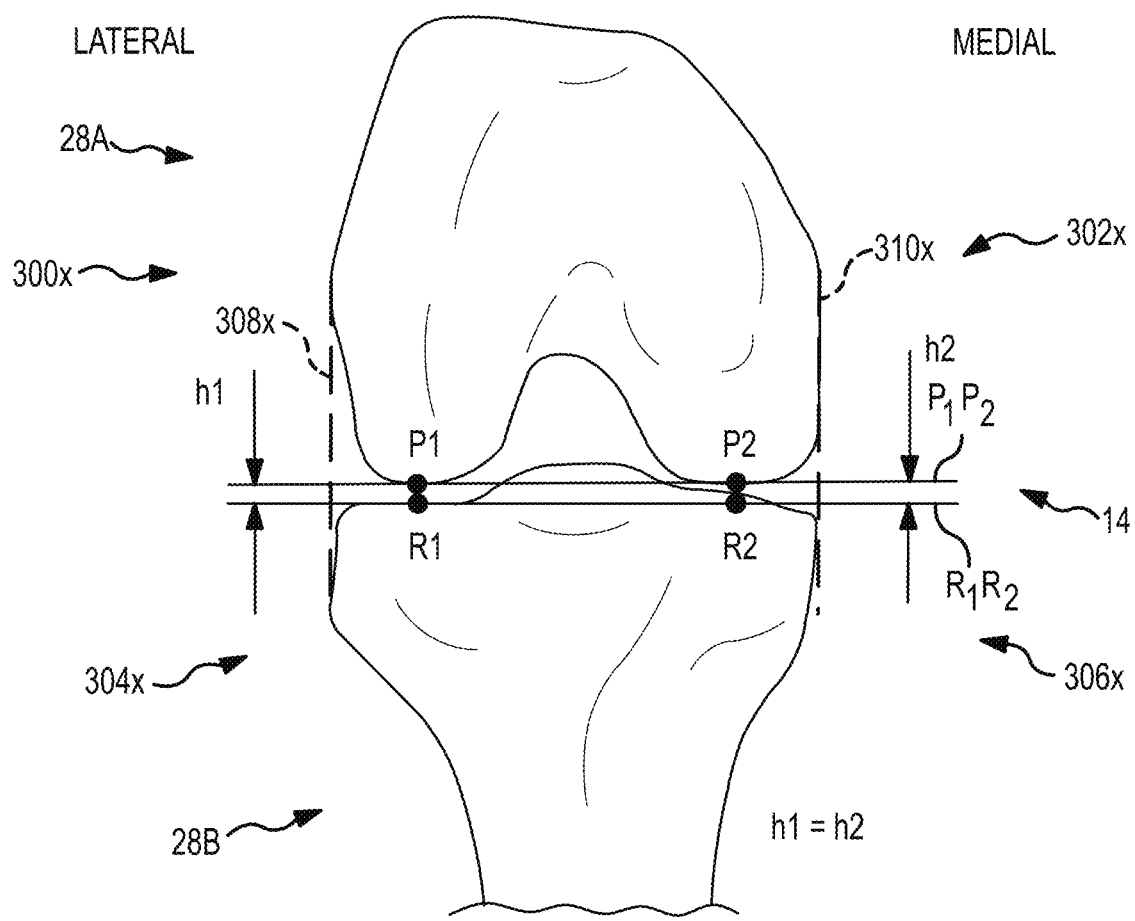
FIG. 42E represents the femur and tibia restored bone models in the views depicted in FIGS. 42B and 42C positioned together to form a knee joint.

FIG. 42E represents the femur and tibia restored bone models 28A, 28B in the views depicted in FIGS. 42B and 42C positioned together to form a knee joint 14. FIG. 42E shows the varus/valgus alignment of the femur and tibia restored bone models 28A, 28B intended to restore the patient's knee joint 14 back to its pre-OA or pre-degenerated state, wherein the knee joint 14 is shown in 90 degree flexion and in its natural alignment (e.g., neutral, varus or valgus) as the knee joint existed prior to degenerating. The respective locations of the lateral collateral ligament ("LCL") 308x and medial collateral ligament ("MCL") 310x are indicated in FIG. 42E by broken lines and serve as stabilizers for the side-to-side stability of the knee joint 14.

As can be understood from FIGS. 42B, 42C and 42E, when the knee joint 14 is in 90 degree flexion, lines $N_3$, $N_4$ are parallel or nearly parallel to the LCL 308x and MCL 310x. Gap h1 represents the distance between the tangent contact point $P_1$ of the femoral lateral condyle 300x and the tangent contact point $R_1$ of the tibia lateral plateau 304x. Gap h2 represents the distance between the tangent contact point $P_2$ of the femoral medial condyle 302x and the tangent contact point R2 of the medial tibia plateau 306x. For a properly restored knee joint 14, as depicted in FIG. 42E, in one embodiment, with respect to varus/valgus rotation and alignment, h1 is substantially equal to h2 such that the difference between h1 and h2 is less than one millimeter (e.g., [h1−h2]<<1 mm). Accordingly, line $P_1P_2$ is parallel or nearly parallel to the joint line and line $R_1R_2$.

Figure 42F:
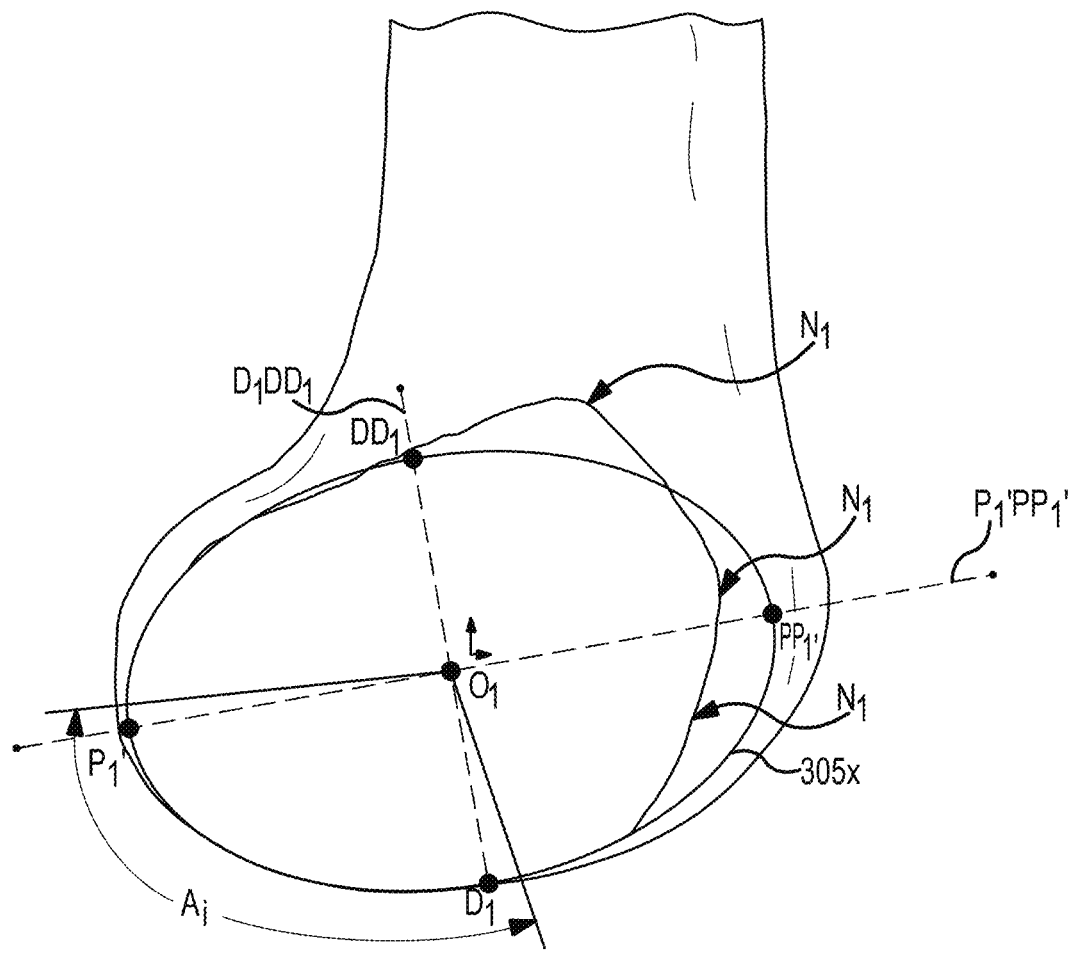
FIG. 42F is a sagittal view of the femoral medial condyle ellipse and, more specifically, the $N_1$ slice of the femoral medial condyle ellipse as taken along line $N_1$ in FIG. 42A.

FIG. 42F is a sagittal view of the femoral medial condyle ellipse 300x and, more specifically, the $N_1$ slice of the femoral medial condyle ellipse 300x is taken along line $N_1$ in FIG. 42A. The contour line $N_1$ in FIG. 42F represents the $N_1$ image slice of the femoral medial condyle 300x. The $N_1$ image slice may be generated via such imaging methods as MRI, CT, etc. An ellipse contour 305x of the medial condyle 300x can be generated along contour line $N_1$. The ellipse 305x corresponds with most of the contour line $N_1$ for the $N_1$ image slice, including the posterior and distal regions of the contour line $N_1$ and portions of the anterior region of the contour line $N_1$. As can be understood from FIG. 42F and discussed in greater detail below, the ellipse 305x provides a relatively close approximation of the contour line $N_1$ in a region of interest or region of contact $A_i$ that corresponds to an region of the femoral medial condyle surface that contacts and displaces against the tibia medial plateau.

As can be understood from FIGS. 42A, 42B and 42F, the ellipse 305x can be used to determine the distal extremity of the femoral medial condyle 300x, wherein the distal extremity is the most distal tangent contact point $D_1$ of the femoral medial condyle 300x of the $N_1$ slice. Similarly, the ellipse 305x can be used to determine the posterior extremity of the femoral medial condyle 300x, wherein the posterior extremity is the most posterior tangent contact point $P_1'$ of the femoral medial condyle 300x of the $N_1$ slice. The ellipse origin point $O_1$, the ellipse major axis $P_1'PP_1'$ and ellipse minor axis $D_1DD_1$ can be obtained based on the elliptical shape of the $N_1$ slice of the medial condyle 300x in conjunction with well-known mathematical calculations for determining the characteristics of an ellipse.

As can be understood from FIG. 42F and as mentioned above, the region of contact A represents or corresponds to the overlapping surface region between the medial tibia plateau 304x and the femoral medial condyle 300x along the $N_1$ image slice. The region of contact $A_i$ for the $N_1$ image slice is approximately 120° of the ellipse 305x of the $N_1$ image slice from just proximal the most posterior tangent contact point $P_1'$ to just anterior the most distal tangent contact point $D_1$.

Figure 42G:
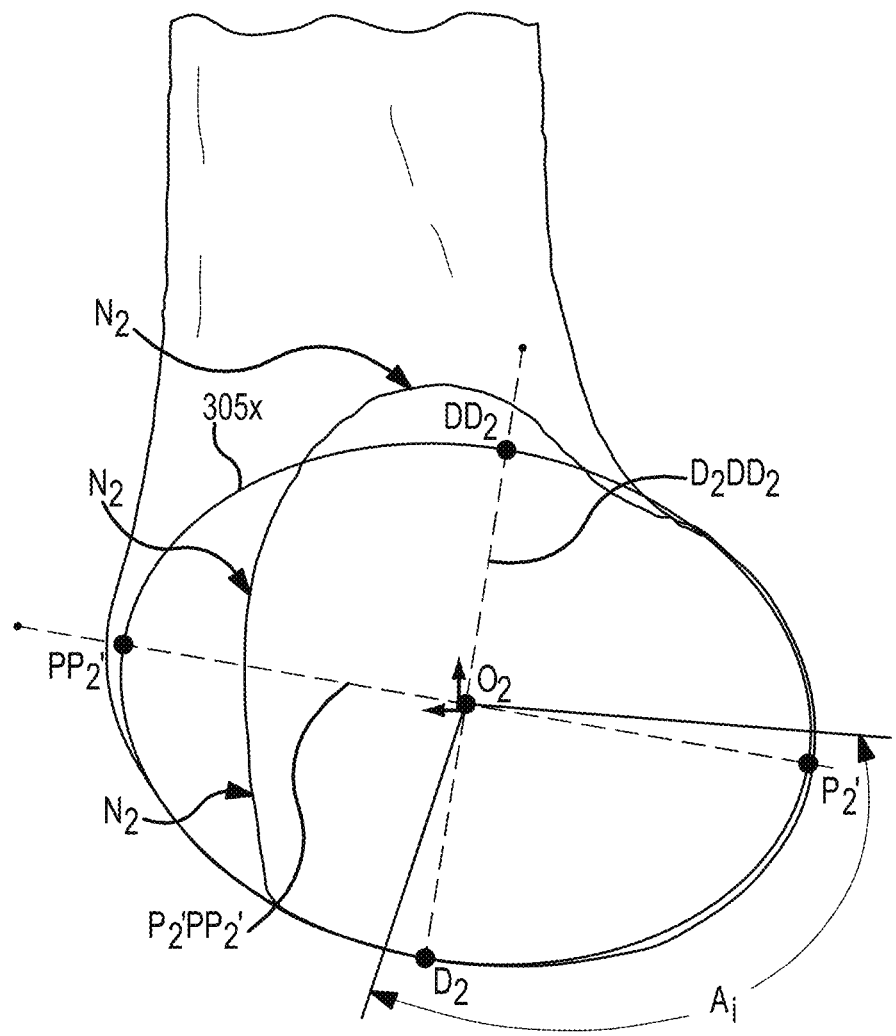
FIG. 42G is a sagittal view of the femoral lateral condyle ellipse and, more specifically, the $N_2$ slice of the femoral lateral condyle ellipse as taken along line $N_2$ in FIG. 42A.

FIG. 42G is a sagittal view of the femoral lateral condyle ellipse 302x and, more specifically, the $N_2$ slice of the femoral lateral condyle ellipse 302x is taken along line $N_2$ in FIG. 42A. The contour line $N_2$ in FIG. 42G represents the $N_2$ image slice of the femoral lateral condyle 302x. The $N_2$ image slice may be generated via such imaging methods as MRI, CT, etc. An ellipse contour 305x of the lateral condyle 302x can be generated along contour line $N_2$. The ellipse 305x corresponds with most of the contour line $N_2$ for the $N_2$ image slice, including the posterior and distal regions of the contour line $N_2$ and portions of the anterior region of the contour line $N_2$. As can be understood from FIG. 42G and discussed in greater detail below, the ellipse 305x provides a relatively close approximation of the contour line $N_2$ in a region of interest or region of contact $A_i$ that corresponds to an region of the femoral lateral condyle surface that contacts and displaces against the tibia lateral plateau.

As can be understood from FIGS. 42A, 42B and 42G, the ellipse 305x can be used to determine the distal extremity of the femoral lateral condyle 302x, wherein the distal extremity is the most distal tangent contact point $D_2$ of the femoral lateral condyle 302x of the $N_2$ slice. Similarly, the ellipse 305x can be used to determine the posterior extremity of the femoral lateral condyle 302x, wherein the posterior extremity is the most posterior tangent contact point $P_2'$ of the femoral lateral condyle 302x of the $N_2$ slice. The ellipse origin point $O_2$, the ellipse major axis $P_2'PP_2'$ and ellipse minor axis $D_2DD_2$ can be obtained based on the elliptical shape of the $N_2$ slice of the lateral condyle 302x in conjunction with well-known mathematical calculations for determining the characteristics of an ellipse.

As can be understood from FIG. 42G and as mentioned above, the region of contact A represents or corresponds to the overlapping surface region between the lateral tibia plateau 306x and the femoral lateral condyle 302x along the $N_2$ image slice. The region of contact $A_i$ for the $N_2$ image slice is approximately 120° of the ellipse 305x of the $N_2$ image slice from just proximal the most posterior tangent contact point $P_2'$ to just anterior the most distal tangent contact point $D_2$.

Figure 42H:
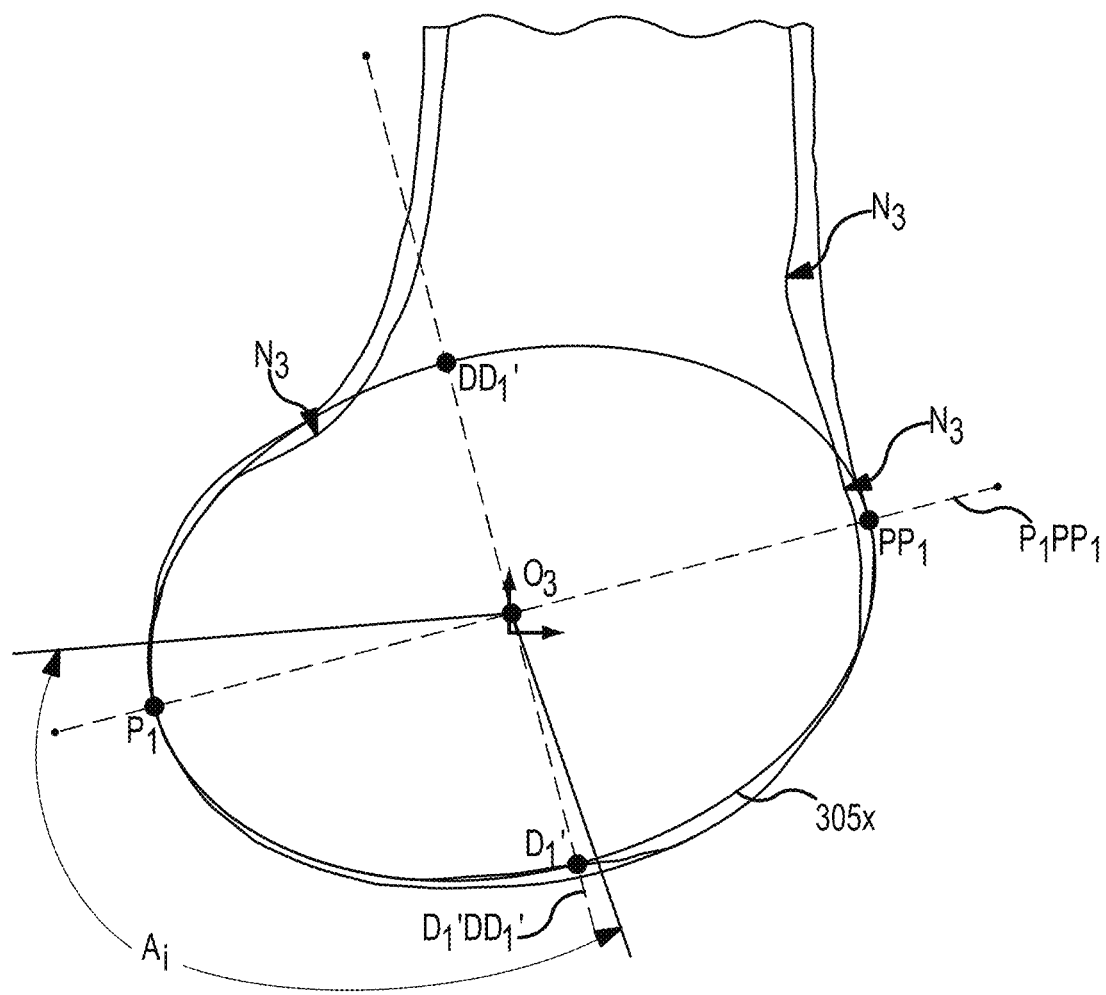
FIG. 42H is a sagittal view of the femoral medial condyle ellipse and, more specifically, the $N_3$ slice of the femoral medial condyle ellipse as taken along line $N_3$ in FIG. 42B.

FIG. 42H is a sagittal view of the femoral medial condyle ellipse 300x and, more specifically, the $N_3$ slice of the femoral medial condyle ellipse 300x is taken along line $N_3$ in FIG. 42B. The contour line $N_3$ in FIG. 42H represents the $N_3$ image slice of the femoral medial condyle 300x. The $N_3$ image slice may be generated via such imaging methods as MRI, CT, etc. An ellipse contour 305x of the medial condyle 300x can be generated along contour line $N_3$. The ellipse 305x corresponds with most of the contour line $N_3$ for the $N_3$ image slice, including the posterior and distal regions of the contour line $N_3$ and portions of the anterior region of the contour line $N_3$. As can be understood from FIG. 42H and discussed in greater detail below, the ellipse 305x provides a relatively close approximation of the contour line $N_3$ in a region of interest or region of contact $A_i$ that corresponds to an region of the femoral medial condyle surface that contacts and displaces against the tibia medial plateau.

As can be understood from FIGS. 42A, 42B and 42H, the ellipse 305x can be used to determine the distal extremity of the femoral medial condyle 300x, wherein the distal extremity is the most distal tangent contact point $D_1'$ of the femoral medial condyle 300x of the $N_3$ slice. Similarly, the ellipse 305x can be used to determine the posterior extremity of the femoral medial condyle 300x, wherein the posterior extremity is the most posterior tangent contact point $P_1$ of the femoral medial condyle 300x of the $N_3$ slice. The ellipse origin point $O_3$, the ellipse major axis $P_1PP_1$ and ellipse minor axis $D_1'DD_1'$ can be obtained based on the elliptical shape of the $N_3$ slice of the medial condyle 300x in conjunction with well-known mathematical calculations for determining the characteristics of an ellipse.

As can be understood from FIG. 42H and as mentioned above, the region of contact A represents or corresponds to the overlapping surface region between the medial tibia plateau 304x and the femoral medial condyle 300x along the $N_3$ image slice. The region of contact $A_i$ for the $N_3$ image slice is approximately 120° of the ellipse 305x of the $N_3$ image slice from just proximal the most posterior tangent contact point $P_1$ to just anterior the most distal tangent contact point $D_1'$.

Figure 42I:
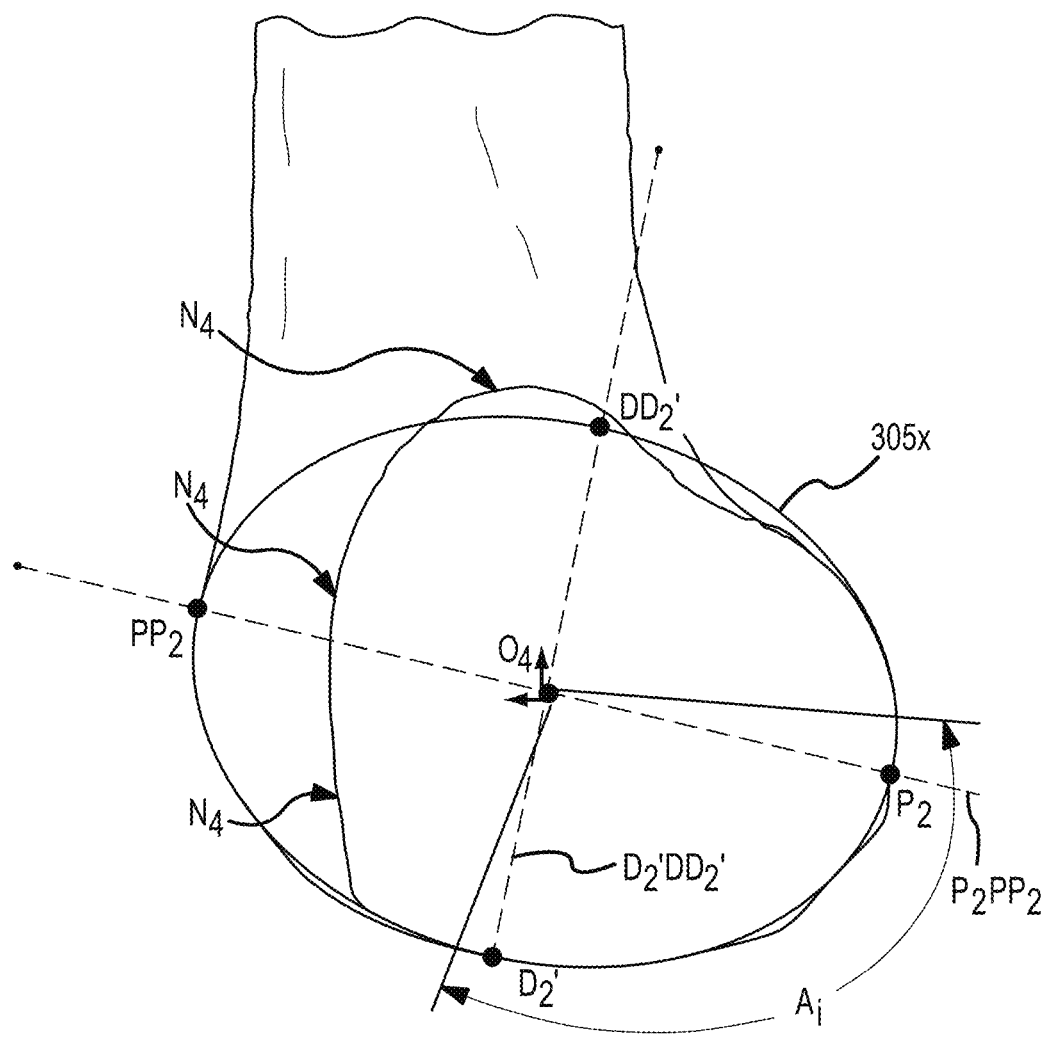
FIG. 42I is a sagittal view of the femoral lateral condyle ellipse and, more specifically, the $N_4$ slice of the femoral lateral condyle ellipse as taken along line $N_4$ in FIG. 42B.

FIG. 42I is a sagittal view of the femoral lateral condyle ellipse 302x and, more specifically, the $N_4$ slice of the femoral lateral condyle ellipse 302x is taken along line $N_4$ in FIG. 42B. The contour line $N_4$ in FIG. 42I represents the $N_4$ image slice of the femoral lateral condyle 302x. The $N_4$ image slice may be generated via such imaging methods as MRI, CT, etc. An ellipse contour 305x of the lateral condyle 302x can be generated along contour line $N_4$. The ellipse 305x corresponds with most of the contour line $N_4$ for the $N_4$ image slice, including the posterior and distal regions of the contour line $N_4$ and portions of the anterior region of the contour line $N_4$. As can be understood from FIG. 42G and discussed in greater detail below, the ellipse 305x provides a relatively close approximation of the contour line $N_4$ in a region of interest or region of contact $A_i$ that corresponds to an region of the femoral lateral condyle surface that contacts and displaces against the tibia lateral plateau.

As can be understood from FIGS. 42A, 42B and 42I, the ellipse 305x can be used to determine the distal extremity of the femoral lateral condyle 302x, wherein the distal extremity is the most distal tangent contact point $D_2'$ of the femoral lateral condyle 302x of the $N_4$ slice. Similarly, the ellipse 305x can be used to determine the posterior extremity of the femoral lateral condyle 302x, wherein the posterior extremity is the most posterior tangent contact point $P_2$ of the femoral lateral condyle 302x of the $N_4$ slice. The ellipse origin point $O_4$, the ellipse major axis $P_2PP_2$ and ellipse minor axis $D_2'DD_2'$ can be obtained based on the elliptical shape of the $N_4$ slice of the lateral condyle 302x in conjunction with well-known mathematical calculations for determining the characteristics of an ellipse.

As can be understood from FIG. 42I and as mentioned above, the region of contact A represents or corresponds to the overlapping surface region between the lateral tibia plateau 306x and the femoral lateral condyle 302x along the $N_4$ image slice. The region of contact $A_i$ for the $N_4$ image slice is approximately 120° of the ellipse 305x of the $N_4$ image slice from just proximal the most posterior tangent contact point $P_2$ to just anterior the most distal tangent contact point $D_2'$.

While the preceding discussion is given in the context of image slices $N_1$, $N_2$, $N_3$ and $N_4$, of course similar elliptical contour lines, ellipse axes, tangent contact points and contact regions may be determined for the other image slices generated during the imaging of the patient's joint and which are parallel to image slices $N_1$, $N_2$, $N_3$ and $N_4$.

B. Employing Vectors from a Reference Side of a Joint to a Damaged Side of a Joint and Extending the Contour Lines of the Damaged Side to Meet the Vectors to Restore the Damaged Side A discussion of methods for determining reference vectors from a reference side of a joint bone for use in restoring a damaged side of the joint bone is first given, followed by specific examples of the restoration process in the context of MRI images. While this overview discussion is given in the context of a knee joint 14 and, more particularly, femur and tibia bone models 22A, 22B being converted image slice by slice into femur and tibia restored bone models 28A, 28B, it should be remembered that this discussion is applicable to other joints (e.g., elbows, ankles, wrists, hips, spine, etc.) and should not be considered as being limited to knee joints 14, but to include all joints. Also, while the image slices are discussed in the context of MRI image slices, it should be remembered that this discussion is applicable to all types of medical imaging, including CT scanning.

Figure 43A:
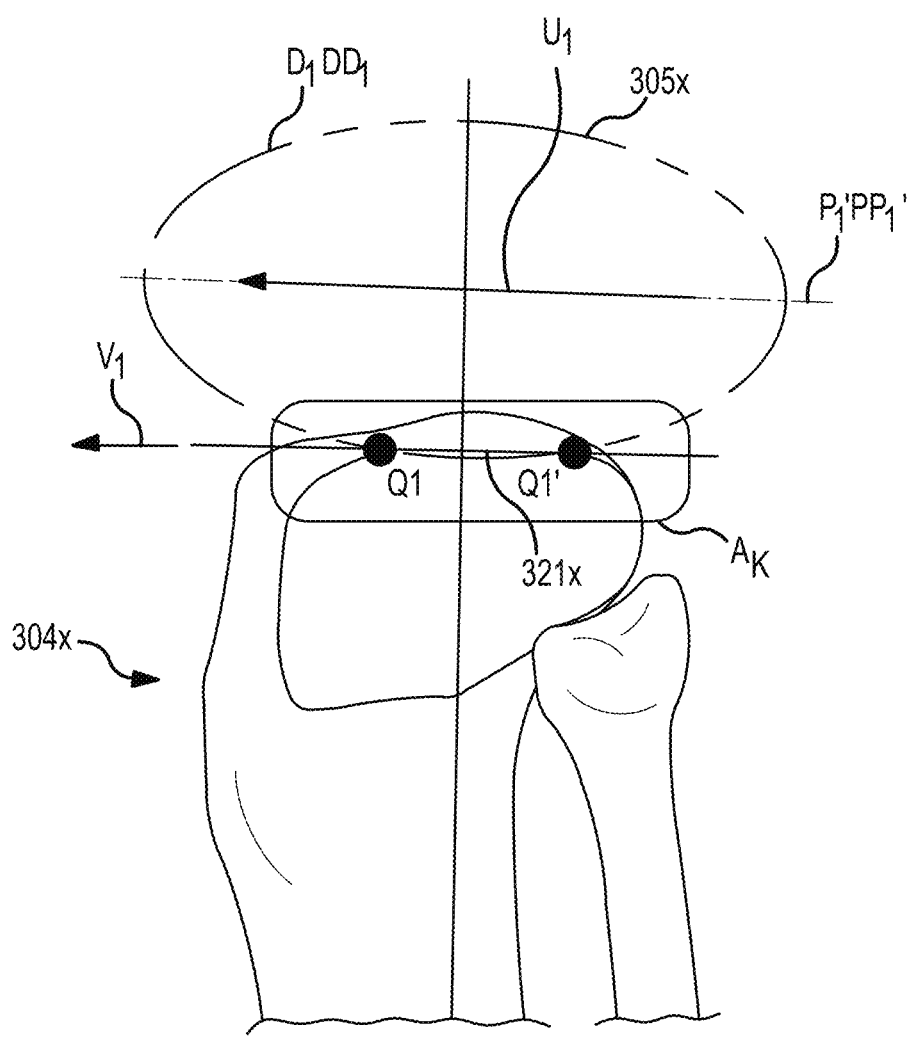
FIG. 43A is a sagittal view of the lateral tibia plateau with the lateral femur condyle ellipse of the $N_1$ slice of FIG. 42F superimposed thereon.
Figure 43B:
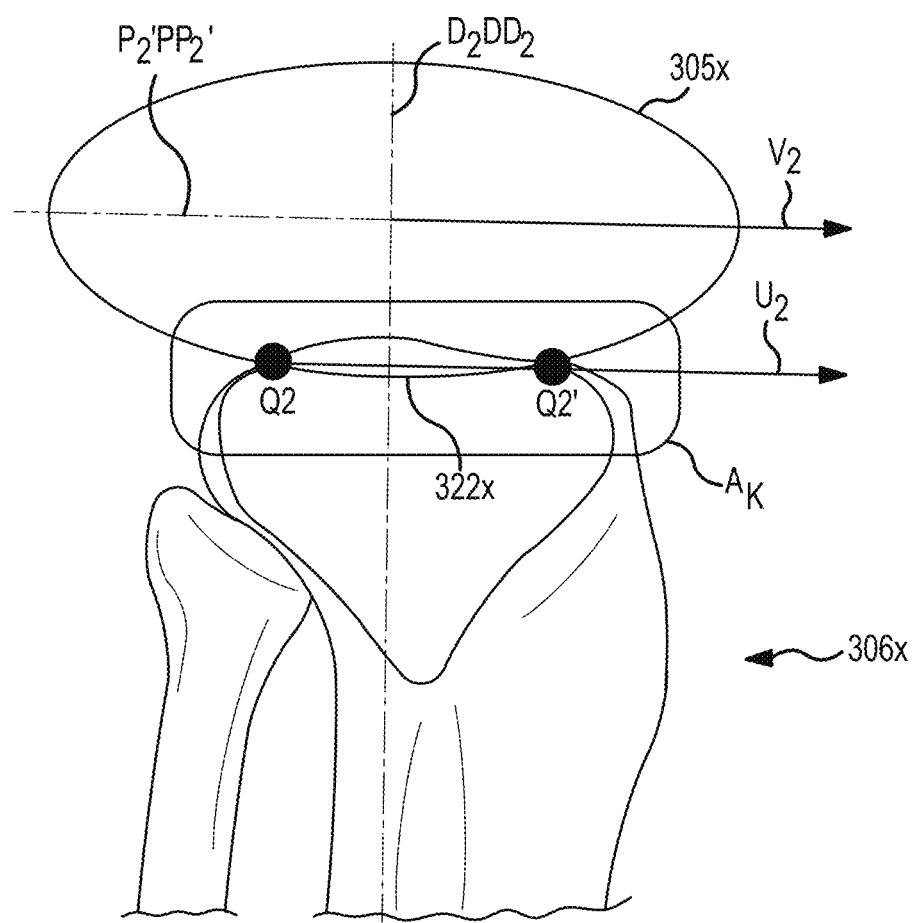
FIG. 43B is a sagittal view of the medial tibia plateau with the lateral femur condyle ellipse of the $N_2$ slice of FIG. 42G superimposed thereon.

For a discussion of the motion mechanism of the knee and, more specifically, the motion vectors associated with the motion mechanism of the knee, reference is made to FIGS. 43A and 43B. FIG. 43A is a sagittal view of the lateral tibia plateau 304x with the lateral femur condyle ellipse 305x of the $N_1$ slice of FIG. 42F superimposed thereon. FIG. 43B is a sagittal view of the medial tibia plateau 306x with the lateral femur condyle ellipse 305x of the $N_2$ slice of FIG. 42G superimposed thereon.

The motion mechanism for a human knee joint operates as follows. The femoral condyles glide on the corresponding tibia plateaus as the knee moves, and in a walking theme, as a person's leg swings forward, the femoral condyles and the corresponding tibia plateaus are not under the compressive load of the body. Thus, the knee joint movement is a sliding motion of the tibia plateaus on the femoral condyles coupled with a rolling of the tibia plateaus on the femoral condyles in the same direction. The motion mechanism of the human knee as the femur condyles and tibia plateaus move relative to each other between zero degree flexion and 90 degree flexion has associated motion vectors. As discussed below, the geometrical features of the femur condyles and tibia plateaus can be analyzed to determine vectors $U_1$, $U_2$, $V_1$, $V_2$, $V_3$, $V_4$ that are associated with image slices $N_1$, $N_2$, $N_3$ and $N_4$. These vectors $U_1$, $U_2$, $V_1$, $V_2$, $V_3$, $V_4$ correspond to the motion vectors of the femur condyles and tibia plateaus moving relative to each other. The determined vectors $U_1$, $U_2$, $V_1$, $V_2$, $V_3$, $V_4$ associated with a healthy side of a joint 14 can be applied to a damaged side of a joint 14 to restore the bone model 22 to create a restored bone model 28.

In some embodiments of the bone restoration process disclosed herein and as just stated, the knee joint motion mechanism may be utilized to determine the vector references for the restoration of bone models 22 to restored bone models 28. As can be understood from a comparison of FIGS. 42F and 42G to FIGS. 43A and 43B, the $U_1$ and $U_2$ vectors respectively correspond to the major axes $P_1'PP_1'$ and $P_2'PP_2'$ of the ellipses 305x of the $N_1$ and $N_2$ slices. Since the major axes $P_1'PP_1'$ and $P_2'PP_2'$ exist in the $N_1$ and $N_2$ slices, which are planes generally perpendicular to the joint line, the $U_1$ and $U_2$ vectors may be considered to represent both vector lines and vector planes that are perpendicular to the joint line.

The $U_1$ and $U_2$ vectors are based on the joint line reference between the femur and the tibia from the zero degree flexion (full extension) to 90 degree flexion. The $U_1$ and $U_2$ vectors represent the momentary sliding movement force from zero degree flexion of the knee to any degree of flexion up to 90 degree flexion. As can be understood from FIGS. 43A and 43B, the $U_1$ and $U_2$ vectors, which are the vectors of the femoral condyles, are generally parallel to and project in the same direction as the $V_1$ and $V_2$ vectors of the tibia plateaus 321x, 322x. The vector planes associated with these vectors $U_1$, $U_2$, $V_1$, $V_2$ are presumed to be parallel or nearly parallel to the joint line of the knee joint 14 represented by restored bone model 28A, 28B such as those depicted in FIGS. 42D and 42E.

As shown in FIGS. 43A and 43B, the distal portion of the ellipses 305x extend along and generally correspond with the curved surfaces 321x, 322x of the tibia plateaus. The curved portions 321x, 322x of the tibia plateaus that generally correspond with the distal portions of the ellipses 305x represent the tibia contact regions $A_k$, which are the regions that contact and displace along the femur condyles and correspond with the condyle contact regions $A_i$ discussed with respect to FIGS. 42F-42I.

Figure 43C:
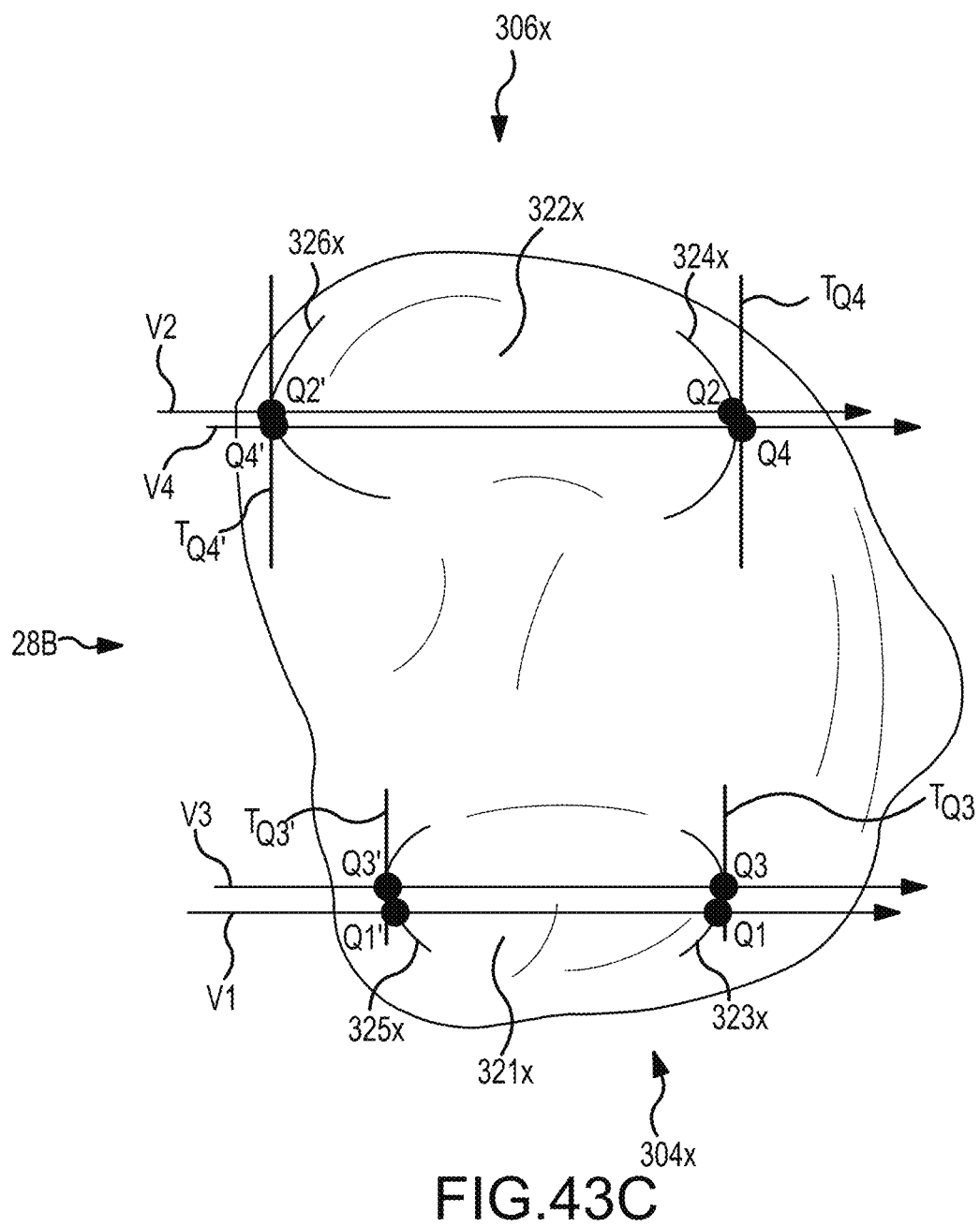
FIG. 43C is a top view of the tibia plateaus of a restored tibia bone model.
Figure 43D:
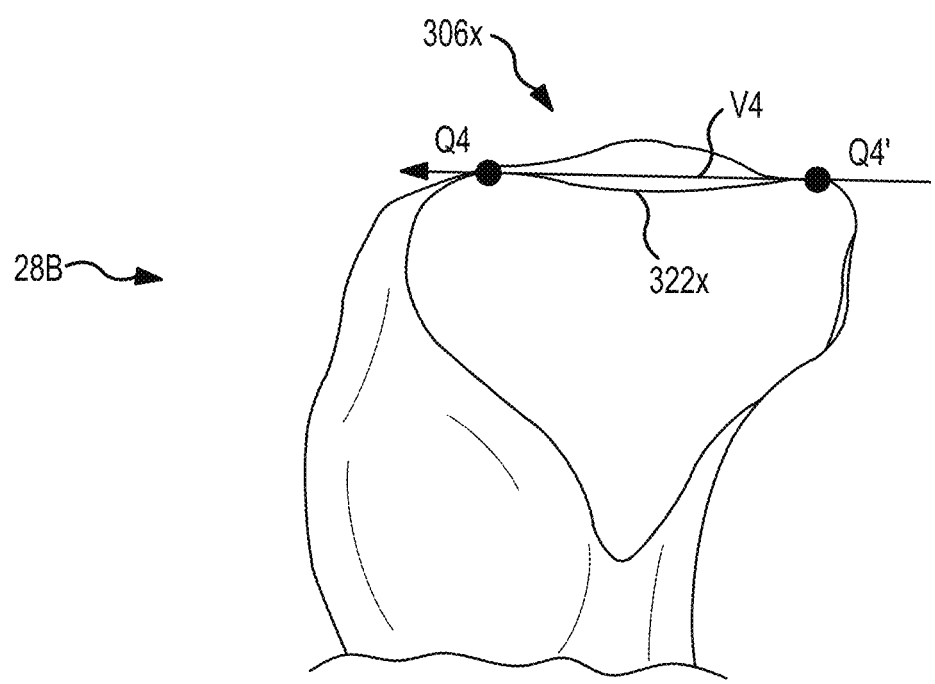
FIG. 43D is a sagittal cross section through a lateral tibia plateau of the restored bone model 28B of FIG. 43C and corresponding to the $N_3$ image slice of FIG. 42B.
Figure 43E:
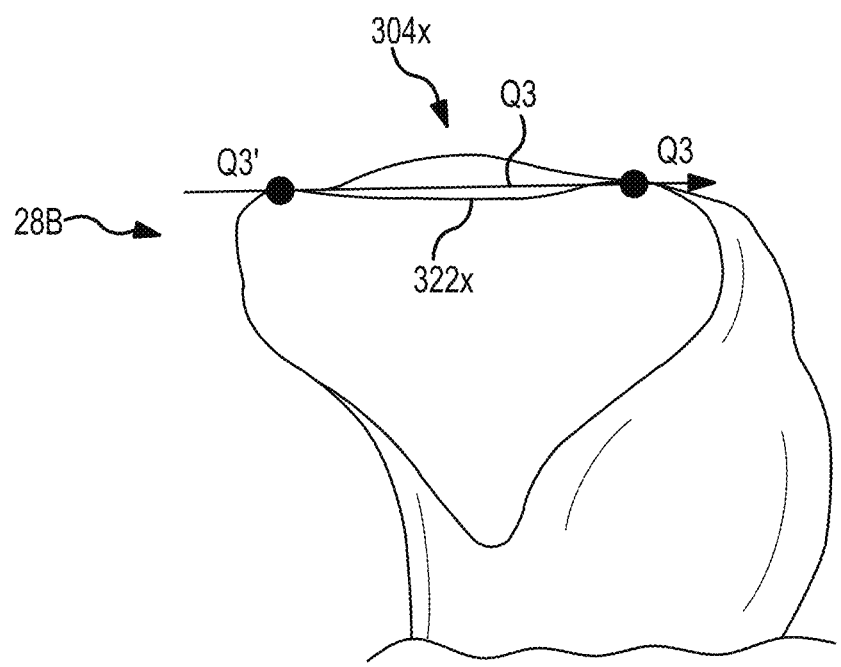
FIG. 43E is a sagittal cross section through a medial tibia plateau of the restored bone model of FIG. 43C and corresponding to the $N_4$ image slice of FIG. 42B.

For a discussion of motion vectors associated with the tibia plateaus, reference is made to FIGS. 43C-43E. FIG. 43C is a top view of the tibia plateaus 304x, 306x of a restored tibia bone model 28B. FIG. 43D is a sagittal cross section through a lateral tibia plateau 304x of the restored bone model 28B of FIG. 43C and corresponding to the $N_3$ image slice of FIG. of FIG. 42B. FIG. 43E is a sagittal cross section through a medial tibia plateau 306x of the restored bone model 28B of FIG. 43C and corresponding to the $N_4$ image slice of FIG. of FIG. 42B.

As shown in FIGS. 43C-43E, each tibia plateau 304x, 306x includes a curved recessed condyle contacting surface 321x, 322x that is generally concave extending anterior/posterior and medial/lateral. Each curved recessed surface 321x, 322x is generally oval in shape and includes an anterior curved edge 323x, 324x and a posterior curved edge 325x, 326x that respectively generally define the anterior and posterior boundaries of the condyle contacting surfaces 321x, 322x of the tibia plateaus 304x, 306x. Depending on the patient, the medial tibia plateau 306x may have curved edges 324x, 326x that are slightly more defined than the curved edges 323x, 325x of the lateral tibia plateau 304x.

Anterior tangent lines $T_{Q3}$, $T_{Q4}$ can be extended tangentially to the most anterior location on each anterior curved edge 323x, 324x to identify the most anterior points Q3, Q4 of the anterior curved edges 323x, 324x. Posterior tangent lines $T_{Q3}'$, $T_{Q4}'$ can be extended tangentially to the most posterior location on each posterior curved edge 325x, 326x to identify the most posterior points Q3', Q4' of the posterior curved edges 325x, 326x. Such anterior and posterior points may correspond to the highest points of the anterior and posterior portions of the respective tibia plateaus.

Vector line V3 extends through anterior and posterior points Q3, Q3', and vector line V4 extends through anterior and posterior points Q4, Q4'. Each vector line V3, V4 may align with the lowest point of the anterior-posterior extending groove/valley that is the elliptical recessed tibia plateau surface 321x, 322x. The lowest point of the anterior-posterior extending groove/valley of the elliptical recessed tibia plateau surface 321x, 322x may be determined via simple ellipsoid calculus. Each vector V3, V4 will be generally parallel to the anterior-posterior extending valleys of its respective elliptical recessed tibia plateau surface 321x, 322x and will be generally perpendicular to it respective tangent lines $T_{Q3}$, $T_{Q4}$, $T_{Q3}'$, $T_{Q4}'$. The anterior-posterior extending valleys of the elliptical recessed tibia plateau surfaces 321x, 322x and the vectors V3, V4 aligned therewith may be generally parallel with and even exist within the $N_3$ and $N_4$ image slices depicted in FIG. 42B.

As can be understood from FIGS. 43A-43E, the $V_3$ and $V_4$ vectors, which are the vectors of the tibia plateaus, are generally parallel to and project in the same direction as the other tibia plateau vectors $V_1$ and $V_2$ and, as a result, the femur condyle vectors $U_1$, $U_2$. The vector planes associated with these vectors $U_1$, $U_2$, $V_1$, $V_2$, $V_3$ and $V_4$ are presumed to be parallel or nearly parallel to the joint line of the knee joint 14 represented by restored bone models 28A, 28B such as those depicted in FIGS. 42D and 42E.

As indicated in FIGS. 43A-43C, tibia plateau vectors $V_1$ and $V_2$ in the $N_1$ and $N_2$ image slices can be obtained by superimposing the femoral condyle ellipses 305x of the $N_1$ and $N_2$ image slices onto their respective tibia plateaus. The ellipses 305x correspond to the elliptical tibia plateau surfaces 321x, 322x along the condyle contact regions $A_k$ of the tibia plateaus 304x, 306x. The anterior and posterior edges 323x, 324x, 325x, 326x of the elliptical tibia plateau surfaces 321x, 322x can be determined at the locations where the ellipses 305x cease contact with the plateau surfaces 321x. 322x. These edges 323x, 324x, 325x, 326x are marked as anterior and posterior edge points Q1, Q1', Q2, Q2' in respective image slices $N_1$ and $N_2$. Vector lines V1 and V2 are defined by being extended through their respective edge points Q1, Q1', Q2, Q2'.

As can be understood from FIG. 43C, image slices $N_1$, $N_2$, $N_3$ and $N_4$ and their respective vectors $V_1$, $V_2$, $V_3$ and $V_4$ may be medially-laterally spaced apart a greater or lesser extent, depending on the patient. With some patients, the $N_1$ and $N_3$ image slices and/or the $N_2$ and $N_4$ image slices may generally medially-laterally align.

While the preceding discussion is given with respect to vectors $U_1$, $U_2$, $V_1$, $V_2$, $V_3$ and V4, contact regions $A_j$, $A_k$, and anterior and posterior edge points Q1, Q1', Q2, Q2', Q3, Q3', Q4, Q4' associated with image slices $N_1$, $N_2$, $N_3$ and $N_4$, similar vectors, contact regions, and anterior and posterior edge points can be determined for the other image slices 16 used to generate the 3D computer generated bone models 22 (see [block 100]-[block 110] of FIGS. 1A-1C).

As illustrated via the following examples given with respect to MRI slices, vectors similar to the $U_1$, $U_2$, $V_1$, $V_2$, $V_3$, $V_4$ vectors of FIGS. 43A-43E can be employed in restoring image slice-by-image slice the bone models 22A, 22B into restored bone models 28A, 28B. For example, a bone model 22 includes a femur bone model 22A and a tibia bone model 22B. The bone models 22A, 22B are 3D bone-only computer generated models compiled via any of the above-mentioned 3D computer programs from a number of image slices 16, as discussed with respect to [blocks 100]-[block 110] of FIGS. 1A-1C. Depending on the circumstances and generally speaking, either the medial side of the bone models will be generally undamaged and the lateral side of the bone models will be damaged, or vice versa.

Figure 43F:
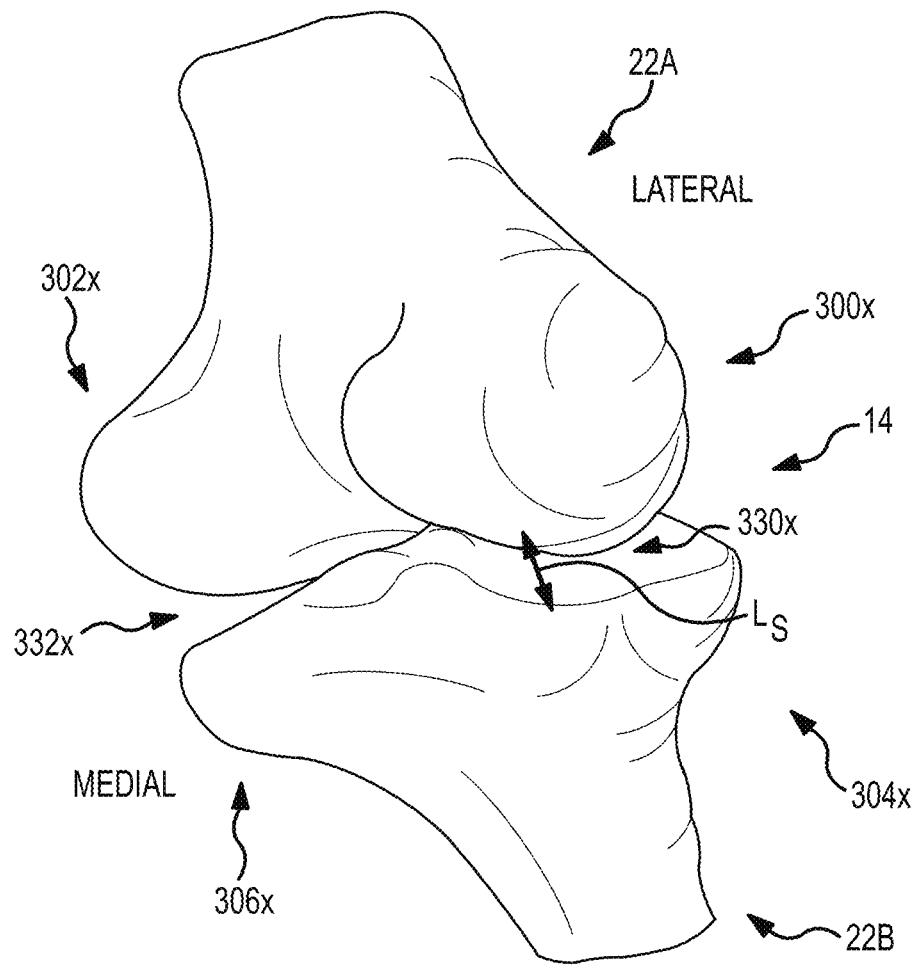
FIG. 43F is a posterior-lateral perspective view of femur and tibia bone models forming a knee joint.

For example, as indicated in FIG. 43F, which is a posterior-lateral perspective view of femur and tibia bone models 22A, 22B forming a knee joint 14, the medial sides 302x, 306x of the bone models 22A, 22B are in a generally non-deteriorated condition and the lateral sides 300x, 304x of the bone models 22A, 22B are in a generally deteriorated or damaged condition. The lateral sides 300x, 304x of the femur and tibia bone models 22A, 22B depict the damaged bone attrition on the lateral tibia plateau and lateral femoral condyle. The lateral sides 300x, 304x illustrate the typical results of OA, specifically joint deterioration in the region of arrow $L_S$ between the femoral lateral condyle 300x and the lateral tibia plateau 304x, including the narrowing of the lateral joint space 330x as compared to medial joint space 332x. As the medial sides 302x, 306x of the bone models 22A, 22B are generally undamaged, these sides 302x, 306x will be identified as the reference sides of the 3D bone models 22A, 22B (see [block 200] of FIG. 41). Also, as the lateral sides 300x, 304x of the bone models 22A, 22B are damaged, these sides 300x, 304x will be identified as the damaged sides of the 3D bone models 22A, 22B (see [block 200] of FIG. 41) and targeted for restoration, wherein the images slices 16 associated with the damaged sides 300x, 304x of the bone models 22A, 22B are restored slice-by-slice.

Reference vectors like the $U_1$, $U_2$, $V_1$, $V_2$, $V_3$, $V_4$ vectors may be determined from the reference side of the bone models 22A, 22B (see [block 205] of FIG. 41). Thus, as can be understood from FIGS. 43B and 43F, since the medial sides 302x, 306x are the reference sides 302x, 306x, the reference vectors $U_2$, $V_2$ $V_4$ may be applied to the damaged sides 300x, 304x to restore the damaged sides 300x, 304x 2D image slice by 2D image slice (see [block 215]-[block 220] of FIG. 41). The restored image slices are then recompiled into a 3D computer generated model, the result being the 3D computer generated restored bone models 28A, 28B (see [block 225] of FIG. 41).

Figure 43G:
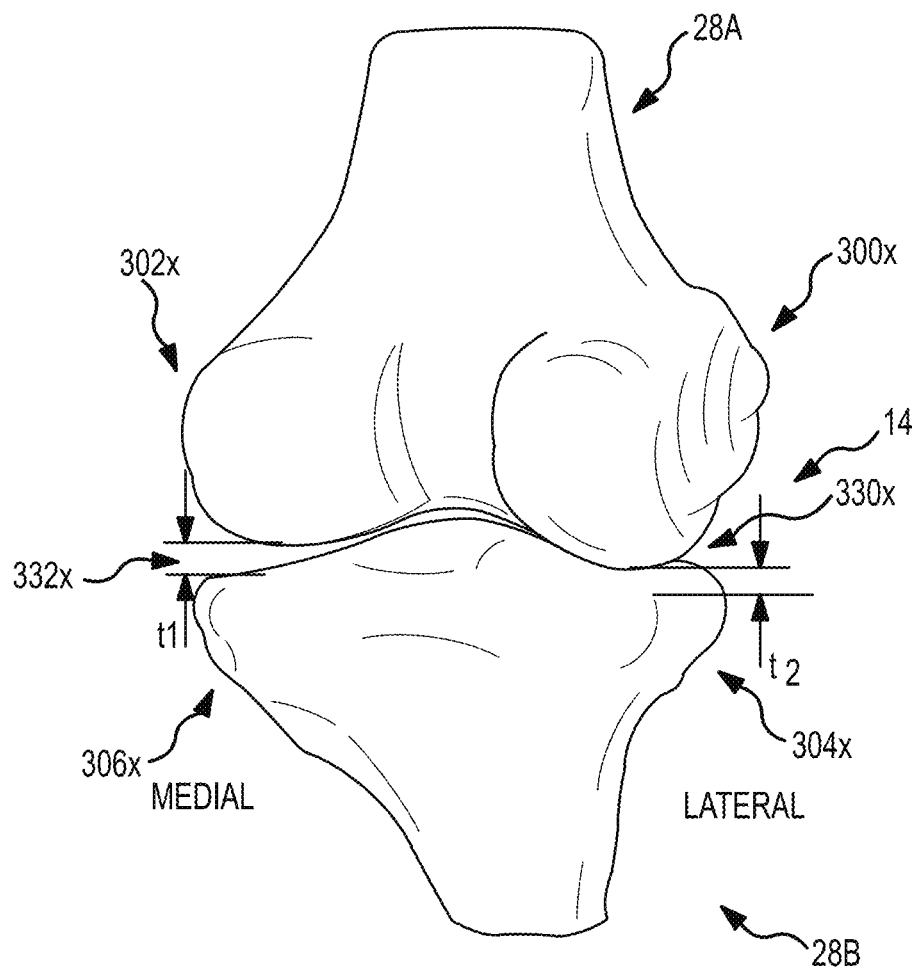
FIG. 43G is a posterior-lateral perspective view of femur and tibia restored bone models forming a knee joint.

As shown in FIG. 43G, which is a posterior-lateral perspective view of femur and tibia restored bone models 28A, 28B forming a knee joint 14, the lateral sides 300x, 304x of the restored bone models 28A, 28B have been restored such that the lateral and medial joint spaces 330x, 332x are generally equal. In other words, the distance t1 between the lateral femur condyle and lateral tibia plateau is generally equal to the distance t2 between the medial femur condyle and the medial tibia plateau.

The preceding discussion has occurred in the context of the medial sides 302x, 306x being the reference sides and the lateral sides 300x, 304x being the damaged sides; the reference vectors $U_2$, $V_2$ and $V_4$ of the medial sides 302x, 306x being applied to the damaged sides 300x, 304x in the process of restoring the damaged sides 300x, 304x. Of course, as stated above, the same process could occur in a reversed context, wherein the lateral sides 300x, 304x are generally undamaged and are identified as the reference sides, and the medial sides 302x, 306x are damaged and identified as the damaged sides. The reference vectors $U_1$, $V_1$ and $V_3$ of the lateral sides 300x, 304x can then be applied to the damaged sides 302x, 306x in the process of restoring the damaged sides 302x, 306x.

Multiple approaches are disclosed herein for identifying reference vectors and applying the reference vectors to a damaged side for the restoration thereof. For example, as can be understood from FIGS. 43B and 43F, where the medial sides 302x, 306x are the undamaged reference sides 302x, 304x and the lateral sides 300x, 304x the damaged sides 300x, 304x, in one embodiment, the ellipses and vectors associated with the reference side femur condyle 302x (e.g., the ellipse 305x of the $N_2$ slice and the vector $U_2$) can be applied to the damaged side femur condyle 300x and damaged side tibia plateau 304x to restore the damaged condyle 300x and damaged plateau 304x. Alternatively or additionally, the ellipses and vectors associated with the reference side femur condyle 302x as applied to the reference side tibia plateau 306x (e.g., the ellipse 305x of the $N_2$ slice and the vector $V_2$) can be applied to the damaged side femur condyle 300x and damaged side tibia plateau 304x to restore the damaged condyle 300x and damaged plateau 304x. In another embodiment, as can be understood from FIGS. 43C, 43E and 43F, the vectors associated with the reference side tibia plateau 306x (e.g., the vector $V_4$) can be applied to the damaged side femur condyle 300x and damaged side tibia plateau 304x to restore the damaged condyle 300x and damaged plateau 304x. Of course, if the conditions of the sides 300x, 302x, 304x, 306x were reversed in FIG. 43F, the identification of the reference sides, the damaged sides, the reference vectors and the application thereof would be reversed from examples given in this paragraph.

Figure 44A:
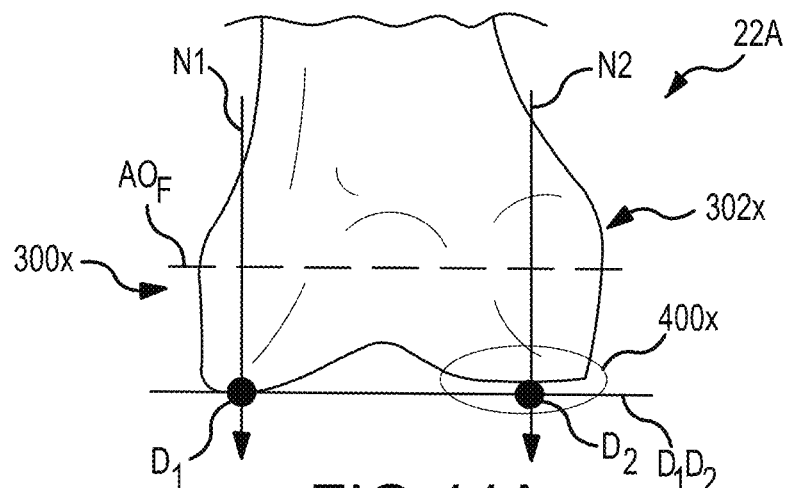
FIG. 44A is a coronal view of a femur bone model.
Figure 44B:
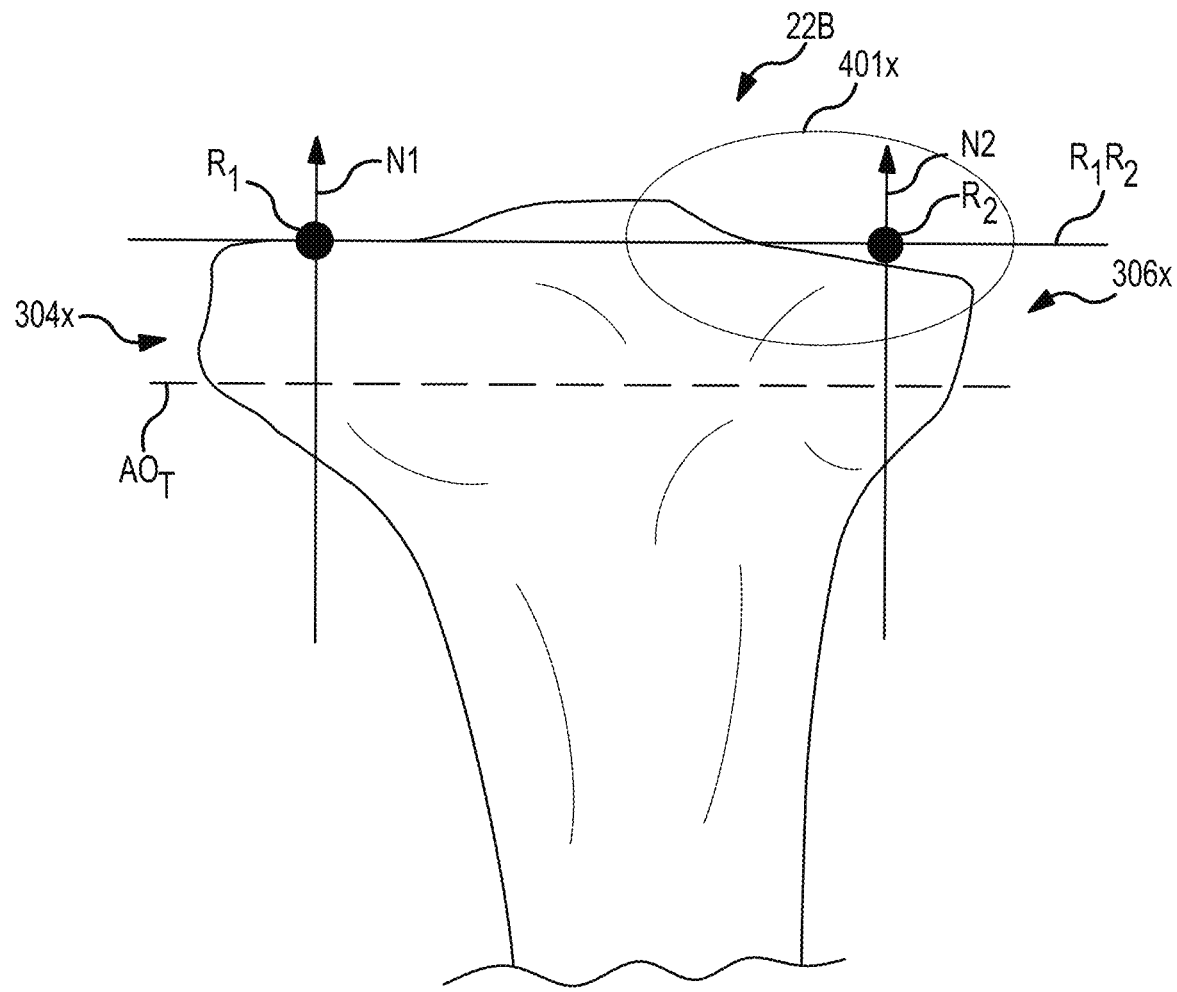
FIG. 44B is a coronal view of a tibia bone model.

1. Employing Vectors from a Femur Condyle of a Reference Side of a Knee Joint to Restore the Femur Condyle and Tibia Plateau of the Damaged Side For a discussion of a first scenario, wherein the medial sides 302x, 306x are the damaged sides and the lateral sides 300x, 304x are the reference sides, reference is made to FIGS. 44A-44B. FIG. 44A is a coronal view of a femur bone model 22A, and FIG. 44B is a coronal view of a tibia bone model 22B.

As shown in FIG. 44A, the medial femur condyle 302x is deteriorated in region 400x such that the most distal point of the medial condyle 302x fails to intersect point $D_2$ on line $D_1D_2$, which will be corrected once the femur bone model 22A is properly restored to a restored femur bone model 28A such as that depicted in FIG. 42A. As illustrated in FIG. 44B, the medial tibia plateau 306x is deteriorated in region 401x such that the lowest point of the medial plateau 306x fails to intersect point $R_2$ on line $R_1R_2$, which will be corrected once the tibia bone model 22B is properly restored to a restored tibia bone model 28B such as that depicted in FIG. 42C. Because the medial condyle 302x and medial plateau 306x of the bone models 22A, 22B are deteriorated, they will be identified as the damaged sides and targeted for restoration ([block 200] of FIG. 41).

As illustrated in FIG. 44A, the lateral condyle 300x and lateral plateau 304x of the bone models 22A, 22B are in a generally non-deteriorated state, the most distal point $D_1$ of the lateral condyle 300x intersecting line $D_1 D_2$, and the lowest point $R_1$ of the lateral plateau 304x intersecting line $R_1R_2$. Because the lateral condyle 300x and lateral plateau 304x of the bone models 22A, 22B are generally in a non-deteriorated state, they will be identified as the reference sides and the source of information used to restore the damaged sides 302x, 306x ([block 200] of FIG. 41).

As can be understood from FIGS. 42F, 43A and 44A, for most if not all of the image slices 16 of the lateral condyle 300x, image slice information or data such as ellipses and vectors can be determined. For example, an ellipse 305x and vector $U_1$ can be determined for the $N_1$ slice ([block 205] of FIG. 41). The data or information associated with one or more of the various slices 16 of the lateral condyle 300x is applied to or superimposed on one or more image slices 16 of the medial condyle 302x ([block 215] of FIG. 41). For example, as shown in FIG. 44C1, which is an $N_2$ image slice of the medial condyle 302x as taken along the $N_2$ line in FIG. 44A, data or information pertaining to the $N_1$ slice is applied to or superimposed on the $N_2$ image slice to determine the extent of restoration needed in deteriorated region 400x. For example, the data or information pertaining to the $N_1$ slice may be in the form of the $N_1$ slice's ellipse $305x$-$N_1$, vector $U_1$, ellipse axes $P_1'PP_1'$, $D_1DD_1$, etc. The ellipse $305x$-$N_1$ will inherently contain its major and minor axis information, and the vector $U_1$ of the $N_1$ slice will correspond to the major axis of the $305x$-$N_1$ ellipse and motion vector of the femur condyles relative to the tibia plateaus. The major axis of the $305x$-$N_1$ and the vector $U_1$ of the $N_1$ slice are generally parallel to the joint line plane.

In a first embodiment, the $N_1$ slice information may be applied only to the contour line of the $N_2$ slice or another specific slice. In other words, information of a specific reference slice may be applied to a contour line of a single specific damaged slice with which the specific reference slice is coordinated with via manual selection or an algorithm for automatic selection. For example, in one embodiment, the $N_1$ slice information may be manually or automatically coordinated to be applied only to the $N_2$ slice contour line, and the $N_3$ slice information may be manually or automatically coordinated to be applied only to the $N_4$ slice contour line. Other reference side slice information may be similarly coordinated with and applied to other damaged side slice contours in a similar fashion. Coordination between a specific reference slice and a specific damaged slice may be according to various criteria, for example, similarity of the function and/or shape of the bone regions pertaining to the specific reference slice and specific damaged slice and/or similarity of accuracy and dependability for the specific reference slice and specific damaged slice.

In a second embodiment, the $N_1$ slice information or the slice information of another specific slice may be the only image slice used as a reference slice for the contour lines of most, if not all, of the damaged slices. In other words, the $N_1$ image slice information may be the only reference side information used (i.e., to the exclusion of, for example, the $N_3$ image slice information) in the restoration of the contour lines of most, if not each, damaged side image slice (i.e., the $N_1$ image slice information is applied to the contour lines of the $N_2$ and $N_4$ image slices and the $N_3$ image slice information is not used). In such an embodiment, the appropriate single reference image slice may be identified via manual identification or automatic identification via, for example, an algorithm. The identification may be according to certain criteria, such as, for example, which reference image slice is most likely to contain the most accurate and dependable reference information.

While the second embodiment is discussed with respect to information from a single reference image being applied to the contour lines of most, if not all, damaged side image slices, in other embodiments, the reference information applied to the contour lines of the damaged image slices may be from more than one image slice. For example, information from two or more reference image slices (e.g., $N_1$ image slice and $N_3$ image slice) are applied individually to the contour lines of the various damage image slices. In one embodiment, the information from the two or more reference image slices may be combined (e.g., averaged) and the combined information then applied to the contour lines of individual damaged image slices.

In some embodiments, the reference side data or information may include a distal tangent line DTL and a posterior tangent line PTL. The distal tangent line DTL may tangentially intersect the extreme distal point of the reference image slice and be parallel to the major axis of the reference image slice ellipse. For example, with respect to the $N_1$ image slice serving as a reference side image slice, the distal tangent line DTL may tangentially intersect the extreme distal point $D_1$ of the reference $N_1$ image slice and be parallel to the major axis $P_1'PP_1'$ of the reference $N_1$ image slice ellipse $305x\text{-}N_1$.

The posterior tangent line PTL may tangentially intersect the extreme posterior point of the reference image slice and be parallel to the major axis of the reference image slice ellipse. For example, with respect to the $N_1$ image slice serving as a reference side image slice, the posterior tangent line PTL may tangentially intersect the extreme posterior point $P_1$ of the reference $N_1$ image slice and be parallel to the minor axis $D_1DD_1$ of the reference $N_1$ image slice ellipse $305x\text{-}N_1$.

As can be understood from FIGS. 42F-42I, most, if not all, femur condyle image slices $N_1$, $N_2$, $N_3$, $N_4$ will have an origin $O_1$, $O_2$, $O_3$, $O_4$ associated with the ellipse $305x$ used to describe or define the condyle surfaces of each slice $N_1$, $N_2$, $N_3$, $N_4$. When these image slices are combined together to form the 3D computer generated bone models 22, the various origins $O_1$, $O_2$, $O_3$, $O_4$ will generally align to form a femur axis $AO_F$ extending medial-lateral through the femur bone model 22A as depicted in FIG. 44A. This axis $AO_F$ can be used to properly orient reference side data (e.g., the ellipse $305x\text{-}N_1$ and vector $U_1$ of the $N_1$ slice in the current example) when being superimposed onto a damaged side image slice (e.g., the $N_2$ image slice in the current example). The orientation of the data or information of the reference side does not change as the data or information is being superimposed or otherwise applied to the damaged side image slice. For example, the orientation of the ellipse $305x\text{-}N_1$ and vector $U_1$ of the $N_1$ slice is maintained or held constant during the superimposing of such reference information onto the $N_2$ slice such that the reference information does not change with respect to orientation or spatial ratios relative to the femur axis $AO_F$ when being superimposed on or otherwise applied to the $N_2$ slice. Thus, as described in greater detail below, since the reference side information is indexed to the damaged side image slice via the axis $AO_F$ and the orientation of the reference side information does not change in the process of being applied to the damaged side image slice, the reference side information can simply be adjusted with respect to size, if needed and as described below with reference to FIGS. 44C2 and 44C3, to assist in the restoration of the damaged side image slice.

While the reference side information may be positionally indexed relative to the damaged side image slices via the femur reference axis $AO_F$ when being applied to the damaged side image slices, other axes may be used for indexing besides an AO axis that runs through or near the origins of the respective image slice ellipses. For example, a reference axis similar to the femur reference axis $AO_F$ and running medial-lateral may pass through other portions of the femur bone model 22A or outside the femur bone model 22A and may be used to positionally index the reference side information to the respective damaged side image slices.

The contour line $N_2$ of the $N_2$ image slice, as with any contour line of any femur or tibia image slice, may be generated via an open or closed loop computer analysis of the cortical bone of the medial condyle $302x$ in the $N_2$ image slice, thereby outlining the cortical bone with an open or closed loop contour line $N_2$. Where the contour lines are closed loop, the resulting 3D models 22, 28 will be 3D volumetric models. Where the contour lines are open loop, the resulting 3D models 22, 28 will be 3D surface models.

Figure 44D:
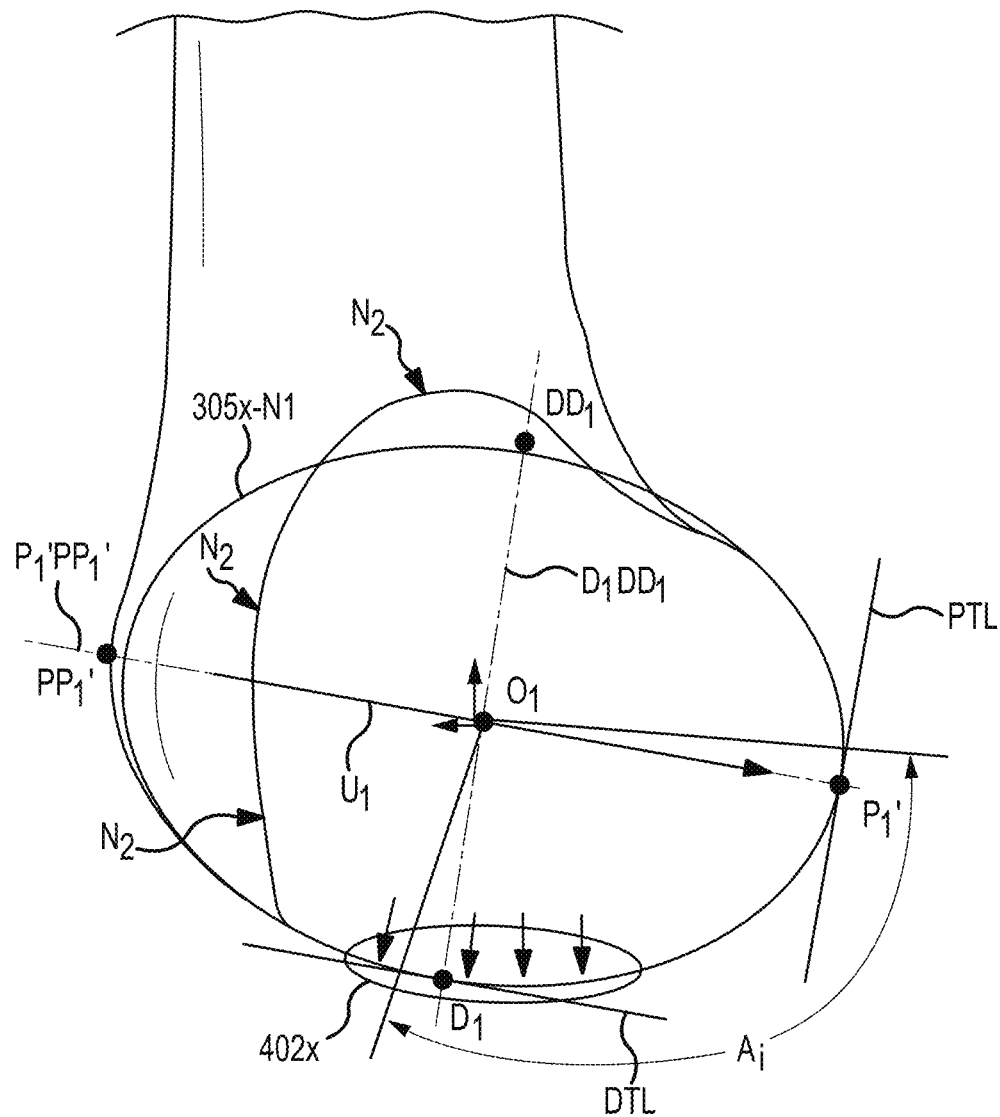
FIG. 44D is the $N_2$ image slice of FIG. 44C1 subsequent to restoration.

While in some cases the reference information from a reference image slice may be substantially similar in characteristics (e.g., size and/or ratios) to the damaged image slice contour line to be simply applied to the contour line, in many cases, the reference information may need to be adjusted with respect to size and/or ratio prior to using the reference information to restore the damaged side contour line as discussed herein with respect to FIGS. 44C1 and 44D. For example, as indicated in FIG. 44C2, which is the same view as FIG. 44C1, except illustrating the reference information is too small relative to the damaged side contour line, the reference information should be increased prior to being used to restore the damaged side contour line. In other words, the $N_1$ information (e.g., the $N_1$ ellipse, vector and tangent lines PTL, DTL), when applied to the contour line of the $N_2$ image slice based on the AO axis discussed above, is too small for at least some of the reference information to match up with at least some of the damaged contour line at the most distal or posterior positions. Accordingly, as can be understood from a comparison of FIGS. 44C1 and 44C2, the $N_1$ information may be increased in size as needed, but maintaining its ratios (e.g., the ratio of the major/minor ellipse axes to each other and the ratios of the offsets of the PTL, DTL from the origin or AO axis), until the $N_1$ information begins to match a boundary of the contour line of the $N_2$ image slice. For example, as depicted in FIG. 44C2, the $N_1$ ellipse is superimposed over the $N_2$ image slice and positionally coordinated with the $N_2$ image slice via the AO axis. The $N_1$ ellipse is smaller than needed to match the contour line of the $N_2$ image slice and is expanded in size until a portion (e.g., the PTL and $P_1'$ of the $N_1$ ellipse) matches a portion (e.g., the most posterior point) of the elliptical contour line of the $N_2$ image slice. A similar process can also be applied to the PTL and DTL, maintaining the ratio of the PTL and DTL relative to the AO axis. As illustrated in FIG. 44C1, the $N_1$ information now corresponds to at least a portion of the damaged image side contour line and can now be used to restore the contour line as discussed below with respect to FIG. 44D.

As indicated in FIG. 44C3, which is the same view as FIG. 44C1, except illustrating the reference information is too large relative to the damaged side contour line, the reference information should be decreased prior to being used to restore the damaged side contour line. In other words, the $N_1$ information (e.g., the $N_1$ ellipse, vector and tangent lines PTL, DTL), when applied to the contour line of the $N_2$ image slice based on the AO axis discussed above, is too large for at least some of the reference information to match up with at least some of the damaged contour line at the most distal or posterior positions. Accordingly, as can be understood from a comparison of FIGS. 44C1 and 44C3, the $N_1$ information may be decreased in size as needed, but maintaining its ratios (e.g., the ratio of the major/minor ellipse axes to each other and the ratios of the offsets of the PTL, DTL from the origin or AO axis), until the $N_1$ information begins to match a boundary of the contour line of the $N_2$ image slice. For example, as depicted in FIG. 44C3, the $N_1$ ellipse is superimposed over the $N_2$ image slice and positionally coordinated with the $N_2$ image slice via the AO axis. The $N_1$ ellipse is larger than needed to match the contour line of the $N_2$ image slice and is reduced in size until a portion (e.g., the PTL and $P_1'$ of the $N_1$ ellipse) matches a portion (e.g., the most posterior point) of the elliptical contour line of the $N_2$ image slice. A similar process can also be applied to the PTL and DTL, maintaining the ratio of the PTL and DTL relative to the AO axis. As illustrated in FIG. 44C1, the $N_1$ information now corresponds to at least a portion of the damaged image side contour line and can now be used to restore the contour line as discussed below with respect to FIG. 44D.

As can be understood from FIG. 44D, which is the $N_2$ image slice of FIG. 44C1 subsequent to restoration, the contour line $N_2$ of the $N_2$ image slice has been extended out to the boundaries of the ellipse $305x$-$N_1$ in the restored region $402x$ ([block 220] of FIG. 41). This process of applying information (e.g., ellipses $305x$ and vectors) from the reference side to the damaged side is repeated slice-by-slice for most, if not all, image slices 16 forming the damaged side of the femur bone model 22A. Once most or all of the image slices 16 of the damaged side have been restored, the image slices used to form the femur bone model 22A, including the recently restored images slices, are recompiled via 3D computer modeling programs into a 3D femur restored bone model 28A similar to that depicted in FIG. 42A ([block 225] of FIG. 41).

As can be understood from FIGS. 44C1 and 44D, in one embodiment, the damaged contour line $N_2$ of the $N_2$ image slice is adjusted based on the ratio of the reference side major axis major axis $P_1'PP_1'$ to the reference side minor axis $D_1DD_1$. In one embodiment, the damaged contour line $N_2$ of the $N_2$ image slice is adjusted based on reference side ellipse $305x$-$N_1$. Therefore, the damaged contour lines of the damaged side image slices can be assessed to be enlarged according to the ratios pertaining to the ellipses of the reference side image slices.

Depending on the relationship of the joint contour lines of the damaged side image slice relative to the ratios obtained from the reference side information or data, the joint contour lines of the damaged side image slice may be manipulated so the joint contour line is increased along its major axis and/or its minor axis. Depending on the patient's knee shape, the major axis and minor axis of the condyle ellipse varies from person to person. If the major axis is close to the minor axis in the undamaged condyle, then the curvature of the undamaged condyle is close to a round shape. In such configured condyles, in the restoration procedure, the contour of the damaged condyle can be assessed and increased in a constant radius in both the major and minor axis. For condyles of other configurations, such as where the undamaged condyle shows an ellipse contour with a significantly longer major axis as compared to its minor axis, the bone restoration may increase the major axis length in order to modify the damaged condyle contour.

A damaged side tibia plateau can also be restored by applying data or information from the reference side femur condyle to the damaged side tibia plateau. In this continued example, the damaged side tibia plateau will be the medial tibia plateau $306x$, and the reference side femur condyle will be the lateral femur condyle $300x$. In one embodiment, the process of restoring the damaged side tibia plateau $306x$ begins by analyzing the damaged side tibia plateau $306x$ to determine at least one of a highest anterior point or a highest posterior point of the damaged side tibia plateau $306x$.

In one embodiment, as can be understood from FIG. 43C as viewed along the $N_4$ image slice and assuming the damage to the medial tibia plateau $306x$ is not so extensive that at least one of the highest anterior or posterior points Q4, Q4' still exists, the damaged tibia plateau $306x$ can be analyzed via tangent lines to identify the surviving high point Q4, Q4'. For example, if the damage to the medial tibia plateau $306x$ was concentrated in the posterior region such that the posterior highest point Q4' no longer existed, the tangent line TQ4 could be used to identify the anterior highest point Q4. Similarly, if the damage to the medial tibia plateau $306x$ was concentrated in the anterior region such that the anterior highest point Q4 no longer existed, the tangent line TQ4' could be used to identify the posterior highest point Q4'. In some embodiments, a vector extending between the highest points Q4, Q4' may be generally perpendicular to the tangent lines $T_{Q4}$, $T_{Q4}'$.

Figure 44E:
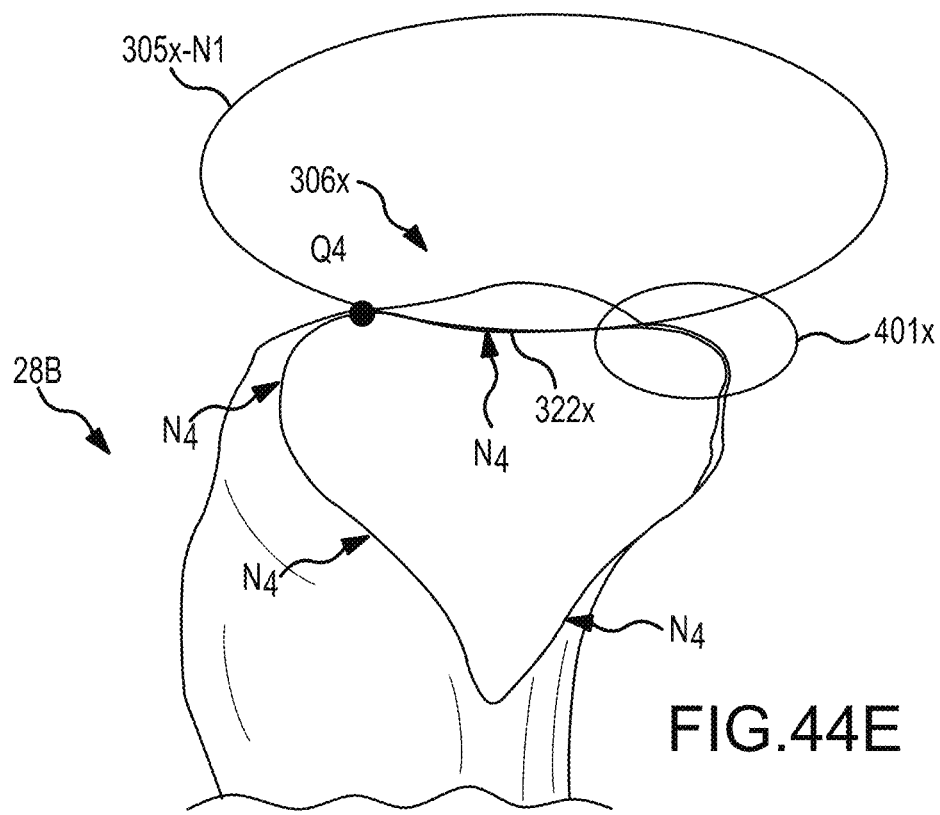
FIG. 44E is a sagittal view of the medial tibia plateau along the $N_4$ image slice, wherein damage to the plateau is mainly in the posterior region.

In another embodiment, the reference side femur condyle ellipse $305x$-$N_1$ can be applied to the damaged medial tibia plateau $306x$ to determine at least one of the highest anterior or posterior points Q4, Q4' along the $N_4$ image slice. This process may be performed assuming the damage to the medial tibia plateau $306x$ is not so extensive that at least one of the highest anterior or posterior points Q4, Q4' still exists. For example, as illustrated by FIG. 44E, which is a sagittal view of the medial tibia plateau $306x$ along the $N_4$ image slice, wherein damage $401x$ to the plateau $306x$ is mainly in the posterior region, the reference side femur condyle ellipse $305x$-$N_1$ can be applied to the damaged medial tibia plateau $306x$ to identify the anterior highest point Q4 of the tibia plateau $306x$. Similarly, in another example, as illustrated by FIG. 44F, which is a sagittal view of the medial tibia plateau $306x$ along the $N_4$ image slice, wherein damage $401x$ to the plateau $306x$ is mainly in the anterior region, the reference side femur condyle ellipse $305x$-$N_1$ can be applied to the damaged medial tibia plateau $306x$ to identify the posterior highest point Q4' of the tibia plateau $306x$.

In one embodiment in a manner similar to that discussed above with respect to FIGS. 44C2 and 44C3, the reference information (e.g., $N_1$ information such as the $N_1$ ellipse) may be applied to the damaged contour line via the AO axis and adjusted in size (e.g., made smaller or larger) until the $N_1$ ellipse matches a portion of the damaged contour line in order to find the highest point, which may be, for example, Q4 or Q4'. As explained above with respect to FIGS. 44C2 and 44C3, the adjustments in size for reference information may be made while maintaining the ratio of the $N_1$ information.

Figure 44F:
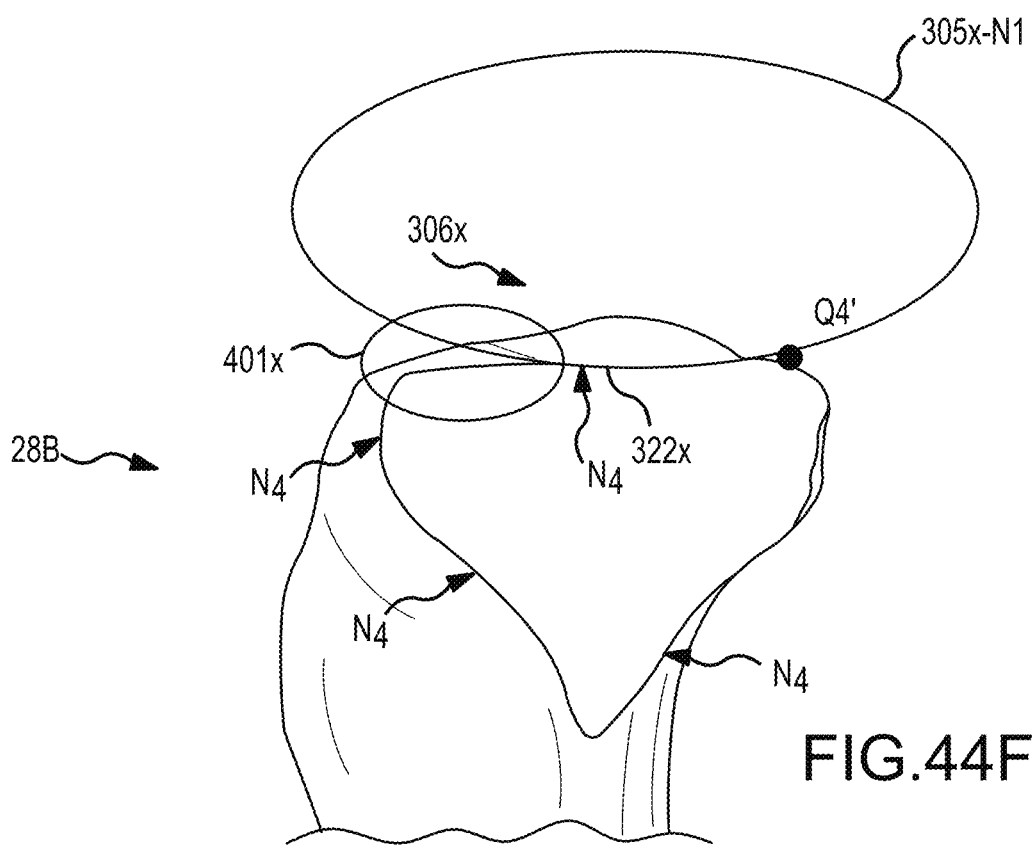
FIG. 44F is a sagittal view of the medial tibia plateau along the $N_4$ image slice, wherein damage to the plateau is mainly in the anterior region.
Figure 44G:
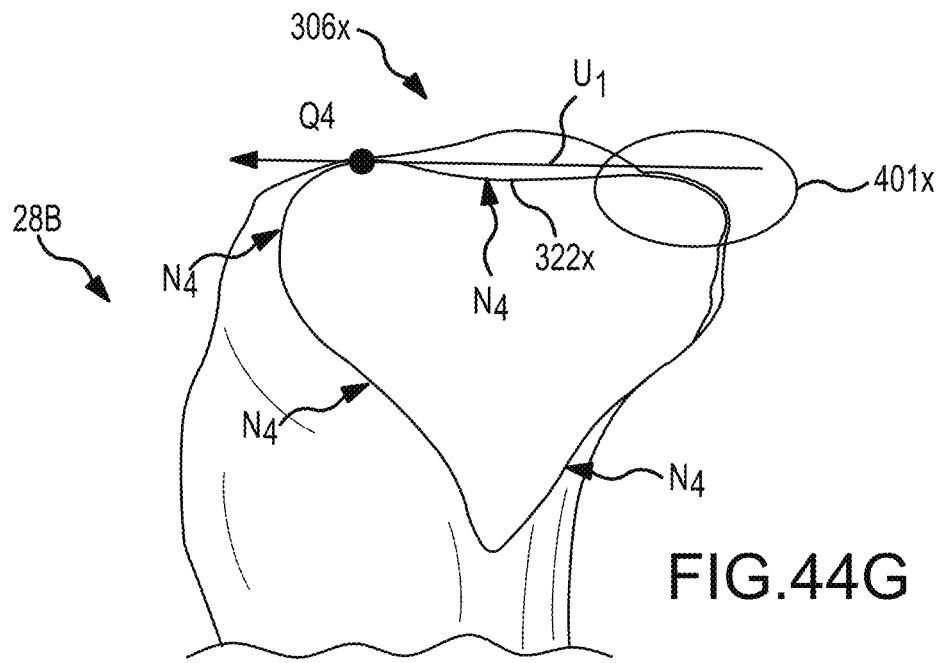
FIG. 44G is the same view as FIG. 44E, except showing the reference side femur condyle vector extending through the anterior highest point of the tibia plateau.
Figure 44H:
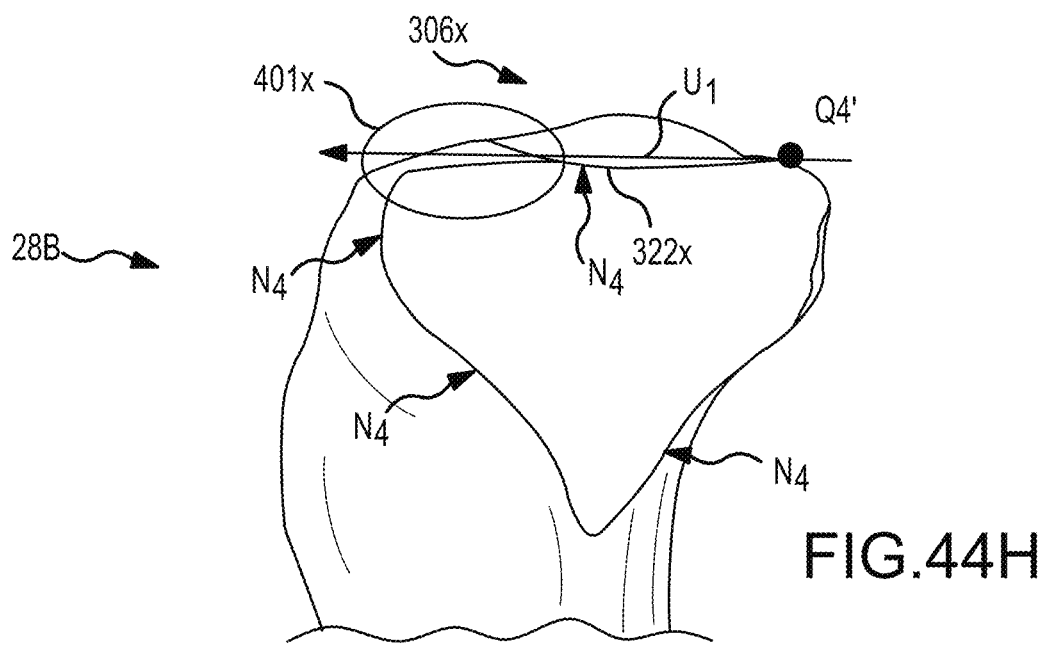
FIG. 44H is the same view as FIG. 44F, except showing the reference side femur condyle vector extending through the posterior highest point of the tibia plateau.

Once the highest point is determined through any of the above-described methods discussed with respect to FIGS. 43C, 44E and 44F, the reference side femur condyle vector can be applied to the damaged side tibia plateau to determine the extent to which the tibia plateau contour line $322x$ needs to be restored ([block 215] of FIG. 41). For example, as illustrated by FIGS. 44G and 44H, which are respectively the same views as FIGS. 44E and 44F, the vector from the reference side lateral femur condyle $300x$ (e.g., the vector $U_1$ from the $N_1$ image slice) is applied to the damaged side medial tibia plateau $306x$ such that the vector $U_1$ intersects the existing highest point. Thus, as shown in FIG. 44G, where the existing highest point is the anterior point Q4, the vector $U_1$ will extend through the anterior point Q4 and will spaced apart from damage $401x$ in the posterior region of the tibia plateau contour line $322x$ by the distance the posterior region of the tibia plateau contour line $322x$ needs to be restored. Similarly, as shown in FIG. 44H, where the existing highest point is the posterior point Q4', the vector $U_1$ will extend through the posterior point Q4' and will spaced apart from the damage $401x$ of the anterior region of the tibia plateau contour line 322x by the distance the anterior region of the tibia plateau contour line 322x needs to be restored.

Figure 44I:
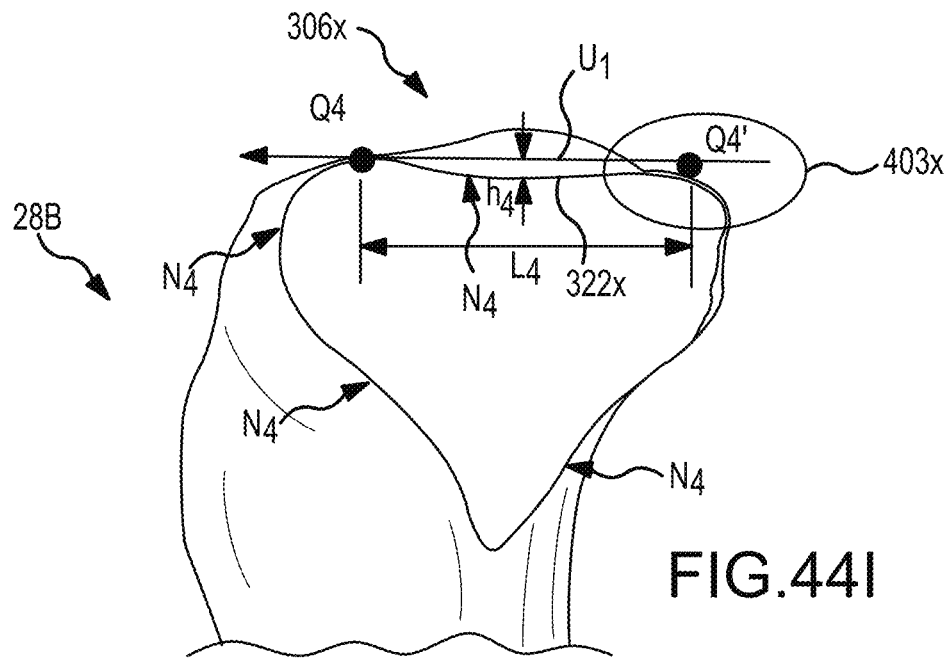
FIG. 44I is the same view as FIG. 44G, except showing the anterior highest point of the tibia plateau restored.
Figure 44J:
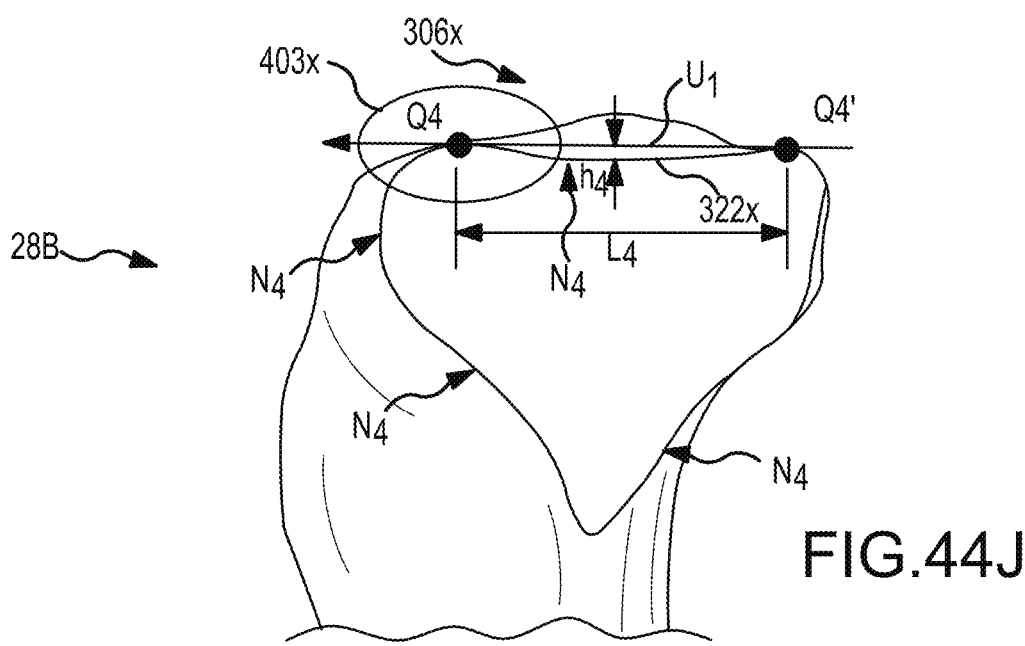
FIG. 44J is the same view as FIG. 44H, except showing the posterior highest point of the tibia plateau restored.

As shown in FIGS. 44I and 44J, which are respectively the same views as FIGS. 44G and 44H, the damaged region 401x of the of the tibia plateau contour line 322x is extended up to intersect the reference vector $U_1$, thereby restoring the missing posterior high point Q4' in the case of FIG. 44I and the anterior high point Q4 in the case of and FIG. 44J, the restoring resulting in restored regions 403x. As can be understood from FIGS. 44E, 44F, 44I and 44J, in one embodiment, the reference side femur condyle ellipse 305x-$N_1$ may be applied to the damaged side tibia plateau 306x to serve as a guide to locate the proper offset distance L4 between the existing high point (i.e., Q4 in FIG. 44I and Q4' in FIG. 44J) and the newly restored high point (i.e., Q4' in FIG. 44I and Q4 in FIG. 44J) of the restored region 403x. Also, in one embodiment, the reference side femur condyle ellipse 305x-$N_1$ may be applied to the damaged side tibia plateau 306x to serve as a guide to achieve the proper curvature for the tibia plateau contour line 322x. The curvature of the tibia plateau contour line 322x may such that the contour line 322x near the midpoint between the anterior and posterior high points Q4, Q4' is offset from the reference vector $U_1$ by a distance $h_4$. In some embodiments, the ratio of the distances $h_4/L_4$ after the restoration is less than approximately 0.01. As discussed above, the reference ellipse may be applied to the damaged contour line and adjusted in size, but maintaining the ratio, until the ellipse matches a portion of the damaged contour line.

As discussed above with respect to the femur condyle image slices being positionally referenced to each other via a femur reference axis $AO_F$, and as can be understood from FIG. 44B, each tibia image slice $N_1$, $N_2$, $N_3$, $N_4$ will be generated relative to a tibia reference axis $AO_T$, which may be the same as or different from the femur reference axis $AO_F$. The tibia reference axis $AO_T$ will extend medial-lateral and may pass through a center point of each area defined by the contour line of each tibia image slice $N_1$, $N_2$, $N_3$, $N_4$. The tibia reference axis $AO_T$ may extend through other regions of the tibia image slices $N_1$, $N_2$, $N_3$, $N_4$ or may extend outside of the tibia image slices, even, for example, through the origins $O_1$, $O_2$, $O_3$, $O_4$ of the respective femur images slices $N_1$, $N_2$, $N_3$, $N_4$ (in such a case the tibia reference axis $AO_F$ and femur reference axis $AO_F$ may be the same or share the same location).

The axis $AO_T$ can be used to properly orient reference side data (e.g., the ellipse 305x-$N_1$ and vector $U_1$ of the $N_1$ slice in the current example) when being superimposed onto a damaged side image slice (e.g., the $N_4$ image slice in the current example). The orientation of the data or information of the reference side does not change as the data or information is being superimposed or otherwise applied to the damaged side image slice. For example, the orientation of the ellipse 305x-$N_1$ and vector $U_1$ of the $N_1$ slice is maintained or held constant during the superimposing of such reference information onto the $N_4$ slice such that the reference information does not change when being superimposed on or otherwise applied to the $N_4$ slice. Thus, since the reference side information is indexed to the damaged side image slice via the axis $AO_T$ and the orientation of the reference side information does not change in the process of being applied to the damaged side image slice, the reference side information can simply be adjusted with respect to size to assist in the restoration of the damaged side image slice.

The contour line $N_4$ of the $N_4$ image slice, as with any contour line of any femur or tibia image slice, may be generated via an open or closed loop computer analysis of the cortical bone of the medial tibia plateau 306x in the $N_4$ image slice, thereby outlining the cortical bone with an open or closed loop contour line $N_4$. Where the contour lines are closed loop, the resulting 3D models 22, 28 will be 3D volumetric models. Where the contour lines are open loop, the resulting 3D models 22, 28 will be 3D surface models.

The preceding example discussed with respect to FIGS. 44A-44J is given in the context of the lateral femur condyle 300x serving as the reference side and the medial femur condyle 302x and medial tibia condyle 306x being the damaged sides. Specifically, reference data or information (e.g., ellipses, vectors, etc.) from lateral femur condyle 300x is applied to the medial femur condyle 302x and medial tibia plateau 306x for the restoration thereof. The restoration process for the contour lines of the damaged side femur condyle 302x and damaged side tibia plateau 306x take place slice-by-slice for the image slices 16 forming the damaged side of the bone models 22A, 22B ([block 220] of FIG. 41). The restored image slices 16 are then utilized when a 3D computer modeling program recompiles the image slices 16 to generate the restored bone models 28A, 28B ([block 225] of FIG. 41).

While a specific example is not given to illustrate the reversed situation, wherein the medial femur condyle 302x serves as the reference side and the lateral femur condyle 300x and lateral tibia condyle 304x are the damaged sides, the methodology is the same as discussed with respect to FIGS. 44A-44J and need not be discussed in such great detail. It is sufficient to know that reference data or information (e.g., ellipses, vectors, etc.) from the medial femur condyle 302x is applied to the lateral femur condyle 300x and lateral tibia plateau 304x for the restoration thereof, and the process is the same as discussed with respect to FIGS. 44A-44J.

2. Employing Vectors from a Tibia Plateau of a Reference Side of a Knee Joint to Restore the Tibia Plateau of the Damaged Side A damaged side tibia plateau can also be restored by applying data or information from the reference side tibia plateau to the damaged side tibia plateau. In this example, the damaged side tibia plateau will be the medial tibia plateau 306x, and the reference side tibia plateau will be the lateral tibia plateau 304x.

In one embodiment, the process of restoring the damaged side tibia plateau 306x begins by analyzing the reference side tibia plateau 304x to determine the highest anterior point and a highest posterior point of the reference side tibia plateau 304x. Theses highest points can then be used to determine the reference vector.

In one embodiment, as can be understood from FIG. 43C as viewed along the $N_3$ image slice, the reference side tibia plateau 304x can be analyzed via tangent lines to identify the highest points Q3, Q3'. For example, tangent line $T_{Q3}$ can be used to identify the anterior highest point Q3, and tangent line $T_{Q3}'$ can be used to identify the posterior highest point Q3'. In some embodiments, a vector extending between the highest points Q3, Q3' may be generally perpendicular to the tangent lines $T_{Q3}$, $T_{Q3}'$.

In another embodiment, the reference side femur condyle ellipse 305x-$N_1$ can be applied to the reference side lateral tibia plateau 304x to determine the highest anterior or posterior points Q3, Q3' along the $N_3$ image slice. For example, as can be understood from FIG. 43A, the reference side femur condyle ellipse 305x-$N_1$ (or ellipse 305x-$N_3$ if analyzed in the $N_3$ image slice) can be applied to the reference side lateral tibia plateau 304x to identify the anterior highest point Q1 of the tibia plateau 304x, and the reference side femur condyle ellipse 305x-$N_1$ (or ellipse 305x-$N_3$ if analyzed in the $N_3$ image slice) can be applied to the reference side lateral tibia plateau 304x to identify the posterior highest point Q1' of the tibia plateau 306x. Where the ellipse 305x-$N_3$ of the $N_3$ image slice is utilized, the highest tibia plateau points may be Q3, Q3'.

As can be understood from FIG. 43A, once the highest points are determined, a reference vector can be determined by extending a vector through the points. For example, vector $V_1$ can be found by extending the vector through highest tibia plateau points Q1, Q1' in the $N_1$ slice.

In one embodiment, the process of restoring the damaged side tibia plateau 306x continues by analyzing the damaged side tibia plateau 306x to determine at least one of a highest anterior point or a highest posterior point of the damaged side tibia plateau 306x.

In one embodiment, as can be understood from FIG. 43C as viewed along the $N_4$ image slice and assuming the damage to the medial tibia plateau 306x is not so extensive that at least one of the highest anterior or posterior points Q4, Q4' still exists, the damaged tibia plateau 306x can be analyzed via tangent lines to identify the surviving high point Q4, Q4'. For example, if the damage to the medial tibia plateau 306x was concentrated in the posterior region such that the posterior highest point Q4' no longer existed, the tangent line $T_{Q4}$ could be used to identify the anterior highest point Q4. Similarly, if the damage to the medial tibia plateau 306x was concentrated in the anterior region such that the anterior highest point Q4 no longer existed, the tangent line $T_{Q4'}$ could be used to identify the posterior highest point Q4'.

In another embodiment, the reference side femur condyle ellipse 305x-$N_1$ can be applied to the damaged medial tibia plateau 306x to determine at least one of the highest anterior or posterior points Q4, Q4' along the $N_4$ image slice. This process may be performed assuming the damage to the medial tibia plateau 306x is not so extensive that at least one of the highest anterior or posterior points Q4, Q4' still exists. For example, as illustrated by FIG. 44E, which is a sagittal view of the medial tibia plateau 306x along the $N_4$ image slice, wherein damage 401x to the plateau 306x is mainly in the posterior region, the reference side femur condyle ellipse 305x-$N_1$ can be applied to the damaged medial tibia plateau 306x to identify the anterior highest point Q4 of the tibia plateau 306x. Similarly, in another example, as illustrated by FIG. 44F, which is a sagittal view of the medial tibia plateau 306x along the $N_4$ image slice, wherein damage 401x to the plateau 306x is mainly in the anterior region, the reference side femur condyle ellipse 305x-$N_1$ can be applied to the damaged medial tibia plateau 306x to identify the posterior highest point Q4' of the tibia plateau 306x.

In one embodiment in a manner similar to that discussed above with respect to FIGS. 44C2 and 44C3, the reference information (e.g., $N_1$ information such as the $N_1$ ellipse) may be applied to the damaged contour line via the AO axis and adjusted in size (e.g., made smaller or larger) until the $N_1$ ellipse matches a portion of the damaged contour line in order to find the highest point, which may be, for example, Q4 or Q4'. As explained above with respect to FIGS. 44C2 and 44C3, the adjustments in size for reference information may be made while maintaining the ratio of the $N_1$ information.

Figure 44K:
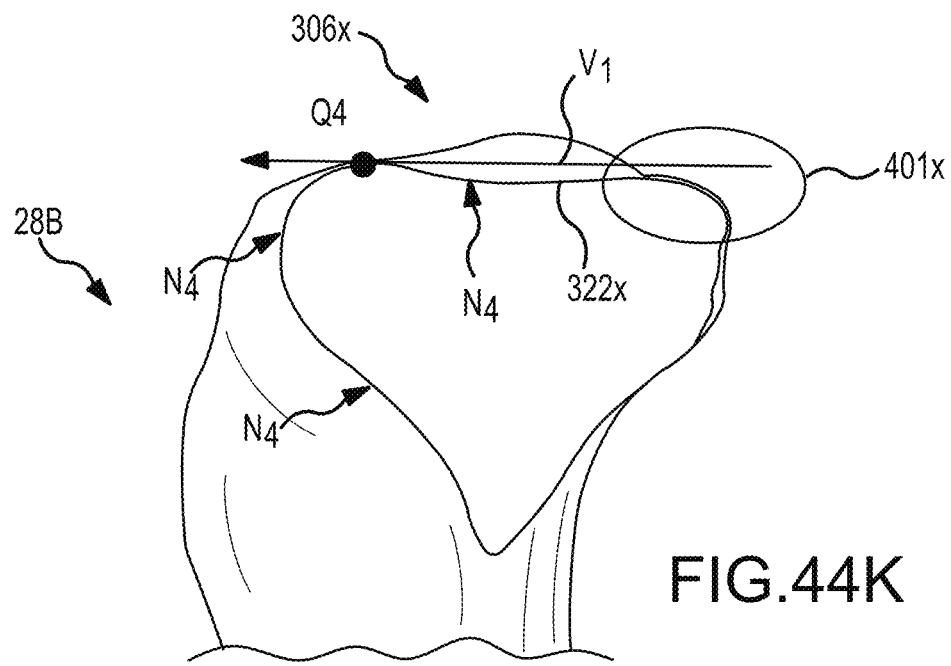
FIG. 44K is the same view as FIG. 44G, except employing reference vector $V_1$ as opposed to $U_1$.
Figure 44L:
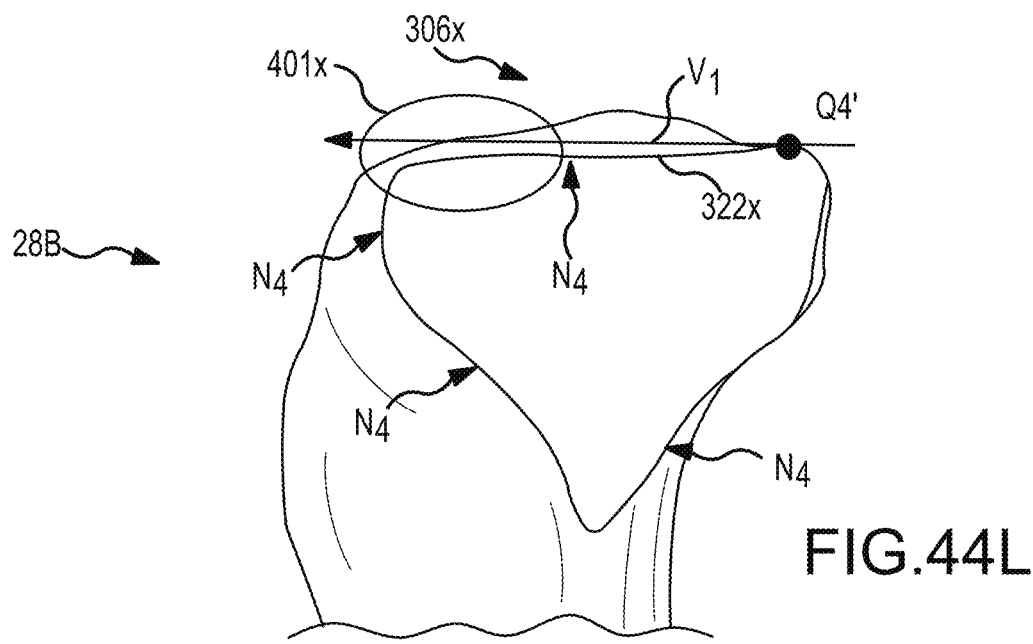
FIG. 44L is the same view as FIG. 44H, except employing reference vector $V_1$ as opposed to $U_1$.

Once the highest point is determined through any of the above-described methods discussed with respect to FIGS. 43C, 44E and 44F, the reference side tibia plateau vector can be applied to the damaged side tibia plateau to determine the extent to which the tibia plateau contour line 322x needs to be restored ([block 215] of FIG. 41). For example, as can be understood from FIGS. 44K and 44L, which are respectively the same views as FIGS. 44G and 44H, the vector from the reference side lateral tibia plateau 304x (e.g., the vector $V_1$ from the $N_1$ image slice) is applied to the damaged side medial tibia plateau 306x such that the vector $V_1$ intersects the existing highest point. Thus, as shown in FIG. 44K, where the existing highest point is the anterior point Q4, the vector $V_1$ will extend through the anterior point Q4 and will spaced apart from damage 401x in the posterior region of the tibia plateau contour line 322x by the distance the posterior region of the tibia plateau contour line 322x needs to be restored. Similarly, as shown in FIG. 44L, where the existing highest point is the posterior point Q4', the vector $V_1$ will extend through the posterior point Q4' and will spaced apart from the damage 401x of the anterior region of the tibia plateau contour line 322x by the distance the anterior region of the tibia plateau contour line 322x needs to be restored.

Figure 44M:
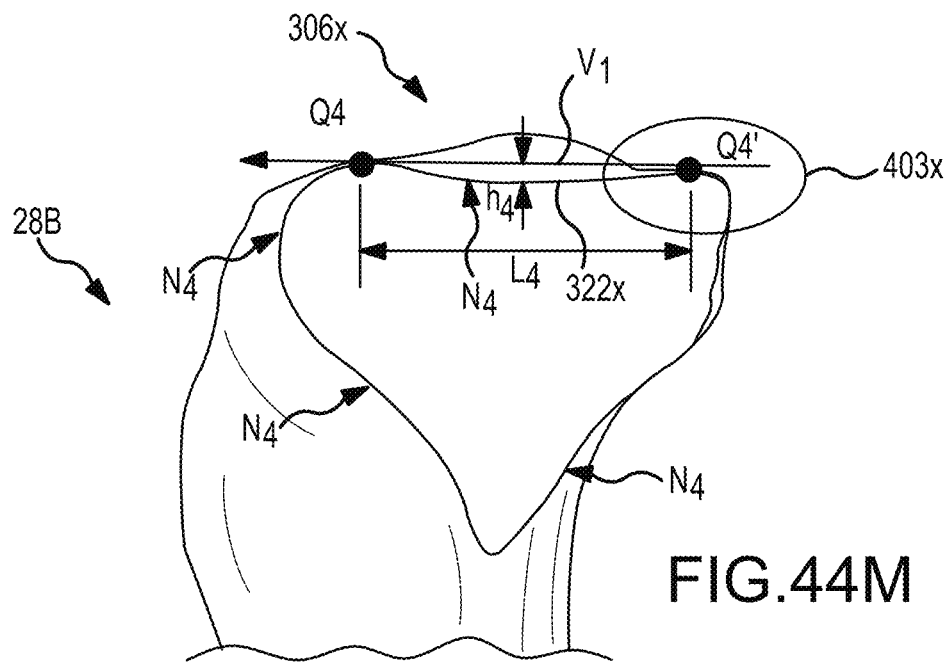
FIG. 44M is the same view as FIG. 44I, except employing reference vector $V_1$ as opposed to $U_1$.
Figure 44N:
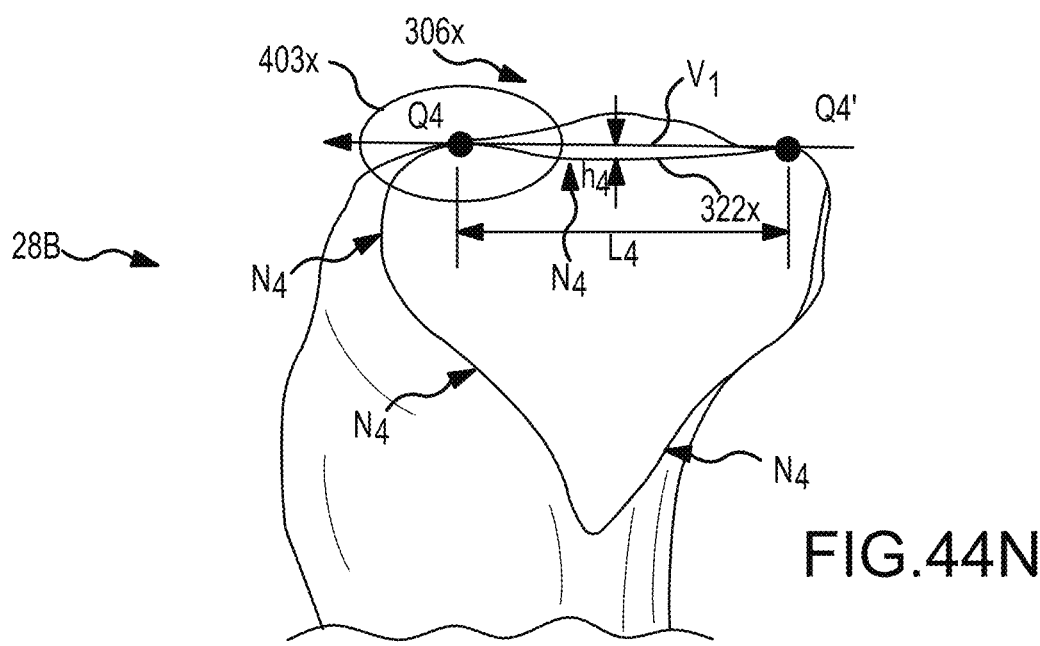
FIG. 44N is the same view as FIG. 44J, except employing reference vector $V_1$ as opposed to $U_1$.

As shown in FIGS. 44M and 44N, which are respectively the same views as FIGS. 44I and 44J, the damaged region 401x of the of the tibia plateau contour line 322x is extended up to intersect the reference vector $V_1$, thereby restoring the missing posterior high point Q4' in the case of FIG. 44M and the anterior high point Q4 in the case of and FIG. 44N, the restoring resulting in restored regions 403x. As can be understood from FIGS. 44E, 44F, 44M and 44N, in one embodiment, the reference side femur condyle ellipse 305x-$N_1$ may be applied to the damaged side tibia plateau 306x to serve as a guide to locate the proper offset distance L4 between the existing high point (i.e., Q4 in FIG. 44M and Q4' in FIG. 44N) and the newly restored high point (i.e., Q4' in FIG. 44M and Q4 in FIG. 44N) of the restored region 403x. Also, in one embodiment, the reference side femur condyle ellipse 305x-$N_1$ may be applied to the damaged side tibia plateau 306x to serve as a guide to achieve the proper curvature for the tibia plateau contour line 322x. The curvature of the tibia plateau contour line 322x may such that the contour line 322x near the midpoint between the anterior and posterior high points Q4, Q4' is offset from the reference vector $U_1$ by a distance h4. In some embodiments, the ratio of the distances $h_4/L_4$ after the restoration is less than approximately 0.01. As discussed above, the reference ellipse may be applied to the damaged contour line and adjusted in size, but maintaining the ratio, until the ellipse matches a portion of the damaged contour line.

As discussed above with respect to the femur condyle image slices being positionally referenced to each other via a femur reference axis $AO_F$, and as can be understood from FIG. 44B, each tibia image slice $N_1$, $N_2$, $N_3$, $N_4$ will be generated relative to a tibia reference axis $AO_T$, which may be the same as or different from the femur reference axis $AO_F$. The tibia reference axis $AO_T$ will extend medial-lateral and may pass through a center point of each area defined by the contour line of each tibia image slice $N_1$, $N_2$, $N_3$, $N_4$. The tibia reference axis $AO_T$ may extend through other regions of the tibia image slices $N_1$, $N_2$, $N_3$, $N_4$ or may extend outside of the tibia image slices, even, for example, through the origins $O_1$, $O_2$, $O_3$, $O_4$ of the respective femur images slices $N_1$, $N_2$, $N_3$, $N_4$ (in such a case the tibia reference axis $AO_F$ and femur reference axis $AO_F$ may be the same or share the same location).

The axis $AO_T$ can be used to properly orient reference side data (e.g., the ellipse 305x-$N_1$ and vector $V_1$ of the $N_1$ slice in the current example) when being superimposed onto a damaged side image slice (e.g., the $N_4$ image slice in the current example). The orientation of the data or information of the reference side does not change as the data or information is being superimposed or otherwise applied to the damaged side image slice. For example, the orientation of the ellipse 305x-$N_1$ and vector $V_1$ of the $N_1$ slice is maintained or held constant during the superimposing of such reference information onto the $N_4$ slice such that the reference information does not change when being superimposed on or otherwise applied to the $N_4$ slice. Thus, since the reference side information is indexed to the damaged side image slice via the axis $AO_T$ and the orientation of the reference side information does not change in the process of being applied to the damaged side image slice, the reference side information can simply be adjusted with respect to size to assist in the restoration of the damaged side image slice.

The contour line $N_4$ of the $N_4$ image slice, as with any contour line of any femur or tibia image slice, may be generated via an open or closed loop computer analysis of the cortical bone of the medial tibia plateau 306x in the $N_4$ image slice, thereby outlining the cortical bone with an open or closed loop contour line $N_4$. Where the contour lines are closed loop, the resulting 3D models 22, 28 will be 3D volumetric models. Where the contour lines are open loop, the resulting 3D models 22, 28 will be 3D surface models.

In the current example discussed with respect to FIGS. 44K-44N, the information from the reference side tibia plateau 304x is employed to restore the damaged side tibia plateau 306x. However, the information from the reference side femur condyle 300x is still used to restore the damaged side femur condyle 302x as discussed above in the preceding example with respect to FIGS. 44A-44D.

The preceding example discussed with respect to FIGS. 44K-44N is given in the context of the lateral tibia plateau 304x and lateral femur condyle 300x serving as the reference sides and the medial femur condyle 302x and medial tibia condyle 306x being the damaged sides. Specifically, reference data or information (e.g., vectors from the lateral tibia plateau 304x and ellipses, vectors, etc. from the lateral femur condyle 300x) are applied to the medial femur condyle 302x and medial tibia plateau 306x for the restoration thereof. The restoration process for the contour lines of the damaged side femur condyle 302x and damaged side tibia plateau 306x take place slice-by-slice for the image slices 16 forming the damaged side of the bone models 22A, 22B ([block 220] of FIG. 41). The restored image slices 16 are then utilized when a 3D computer modeling program recompiles the image slices 16 to generate the restored bone models 28A, 28B ([block 225] of FIG. 41).

While a specific example is not given to illustrate the reversed situation, wherein the medial tibia plateau 306x and medial femur condyle 302x serve as the reference sides and the lateral femur condyle 300x and lateral tibia condyle 304x are the damaged sides, the methodology is the same as discussed with respect to FIGS. 44A-5D and 44K-44N and need not be discussed in such great detail. It is sufficient to know that reference data or information (e.g., ellipses, vectors, etc.) from the medial tibia plateau 306x and medial femur condyle 302x are applied to the lateral femur condyle 300x and lateral tibia plateau 304x for the restoration thereof, and the process is the same as discussed with respect to FIGS. 44A-44D and 44K-44N.

C. Verifying Accuracy of Restored Bone Model

Once the bone models 22A, 22B are restored into restored bone models 28A, 28B as discussed in the preceding sections, the accuracy of the bone restoration process is checked ([block 230] of FIG. 41). Before discussion example methodology of conducting such accuracy checks, the following discussion regarding the kinetics surround a knee joint is provided.

The morphological shape of the distal femur and its relation to the proximal tibia and the patella suggests the kinetics of the knee (e.g., see Eckhoff et al., "Three-Dimensional Mechanics, Kinetics, and Morphology of the Knee in Virtual Reality", JBJS (2005); 87:71-80). The movements that occur at the knee joint are flexion and extension, with some slight amount of rotation in the bent position. During the movement, the points of contact of the femur with the tibia are constantly changing. Thus, in the flexed position (90° knee extension), the hinder part of the articular surface of the tibia is in contact with the rounded back part of the femoral condyles. In the semiflexed position, the middle parts of the tibia facets articulate with the anterior rounded part of the femoral condyles. In the fully extended position (0° knee extension), the anterior and the middle parts of the tibia facets are in contact with the anterior flattened portion of the femoral condyles.

With respect to the patella, in extreme flexion, the inner articular facet rests on the outer part of the internal condyle of the femur. In flexion, the upper part of facets rest on the lower part of the trochlear surface of the femur. In midflexion, the middle pair rest on the middle of the trochlear surface. However, in extension, the lower pair of facets on the patella rest on the upper portion of the trochlear surface of the femur. The difference may be described as the shifting of the points of contact of the articulate surface.

The traditional knee replacement studies focus mainly around the tibial-femoral joint. The methods disclosed herein employ the patella in a tri-compartmental joint study by locating the patella groove of the knee. The posterior surface of patella presents a smooth oval articular area divided into two facets by a vertical ridge, the facets forming the medial and lateral parts of the same surface.

The vertical ridge of the posterior patella corresponds to the femoral trochlear groove. In the knee flexion/extension motion movement, the patella normally moves up and down in the femoral trochlear grove along the vertical ridge and generates quadriceps forces on the tibia. The patellofemoral joint and the movement of the femoral condyles play a major role in the primary structure/mechanics across the joint. When the knee is moving and not fully extended, the femoral condyle surfaces bear very high load or forces. In a normal knee, the patella vertical ridge is properly aligned along the femoral trochlear groove so this alignment provides easy force generation in the sliding movement. If the patella is not properly aligned along the trochlear groove or tilted in certain angles, then it is hard to initiate the sliding movement so it causes difficulty with respect to walking. Further, the misaligned axis along the trochlear groove can cause dislocation of the patella on the trochlear groove, and uneven load damage on the patella as well.

The methods disclosed herein for the verification of the accuracy of the bone restoration process employ a "trochlear groove axis" or the "trochlear groove reference plane" as discussed below. This axis or reference plane extend across the lowest extremity of trochlear groove in both the fully-extended and 90° extension of the knee. Moreover, in relation to the joint line, the trochlear groove axis is perpendicular or generally perpendicular to the joint line of the knee.

Because the vertical ridge of the posterior patella is generally straight (vertical) in the sliding motion, the corresponding trochlear groove axis should be straight as well. The trochlear groove axis is applied into the theory that the joint line of the knee is parallel to the ground. In a properly aligned knee or normal knee, the trochlear groove axis is presumed to be perpendicular or nearly perpendicular to the joint line.

For the OA, rarely is there bone damage in the trochlear groove, typically only cartilage damage. Thus, the femoral trochlear groove can serve as a reliable bone axis reference for the verification of the accuracy of the bone restoration when restoring a bone model 22 into a restored bone model 28.

Figure 45A:
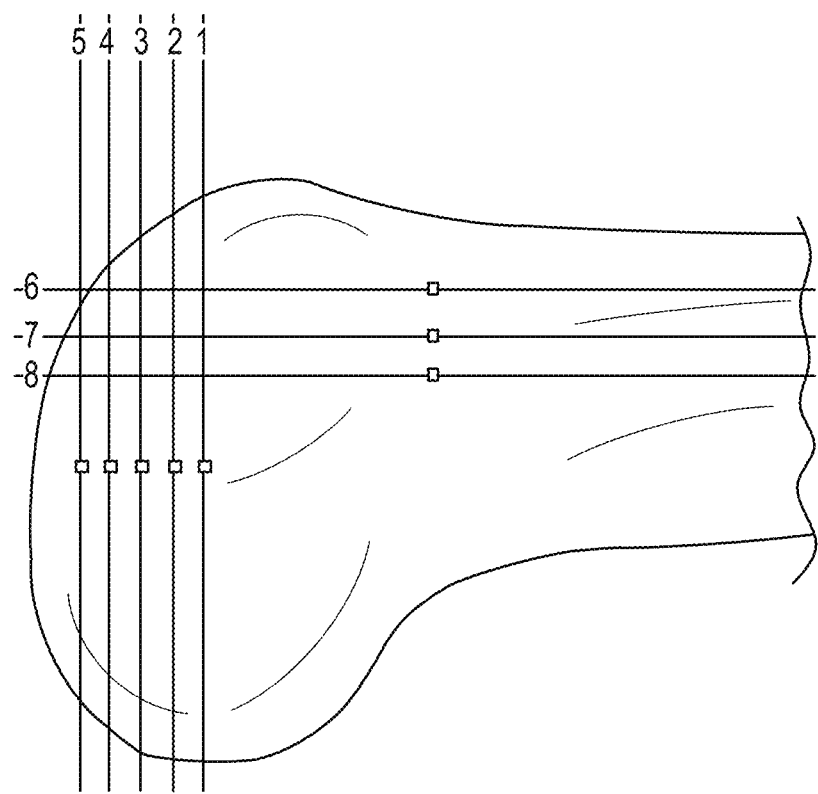
FIG. 45A is a sagittal view of a femur restored bone model illustrating the orders and orientations of imaging slices (e.g., MRI slices, CT slices, etc.) forming the femur restored bone model.
Figures 45B, 45C:
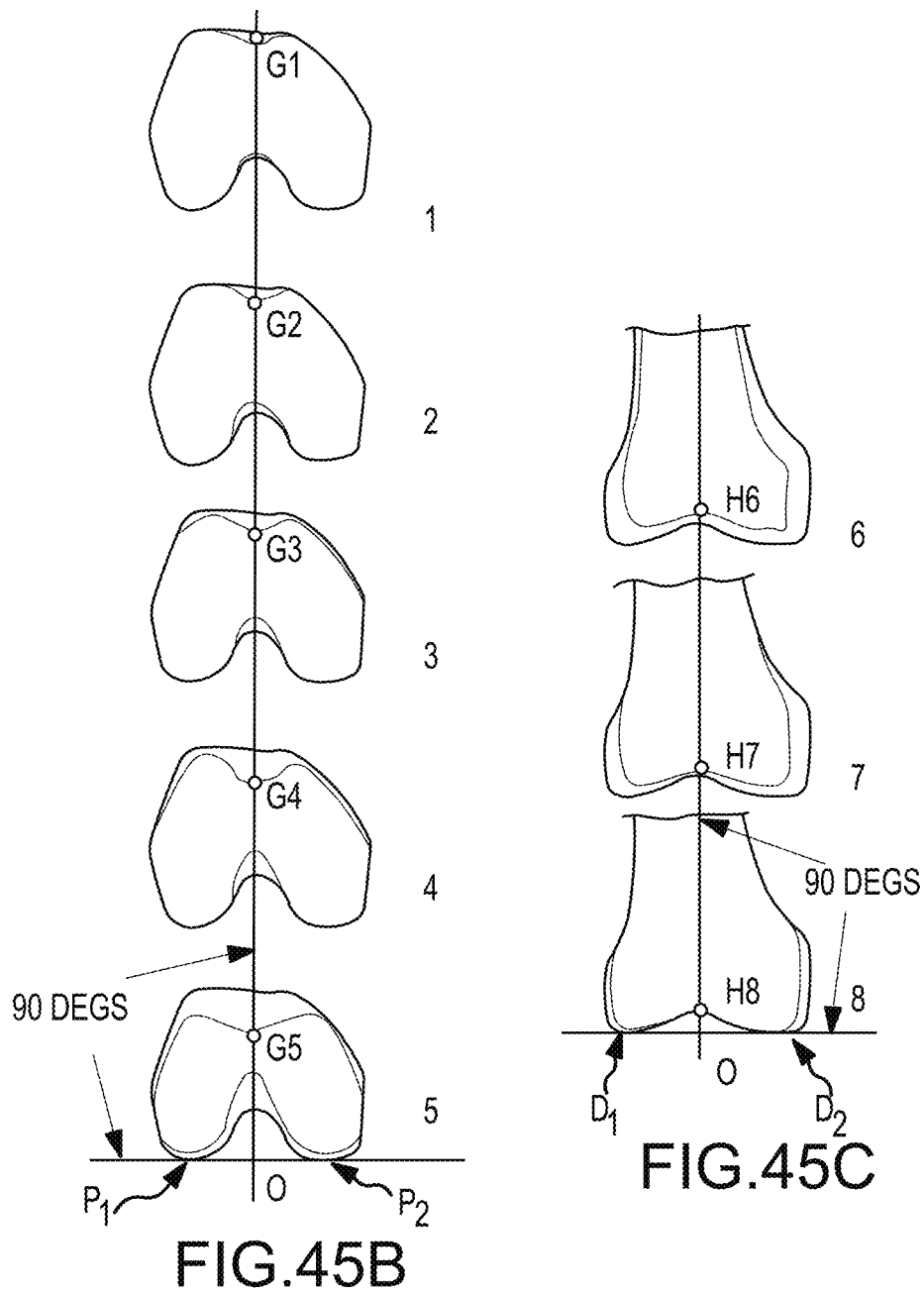
FIG. 45B is the distal images slices 1-5 taken along section lines 1-5 of the femur restored bone model in FIG. 45A.
FIG. 45C is the coronal images slices 6-8 taken along section lines 6-8 of the femur restored bone model in FIG. 45A.
Figure 45D:
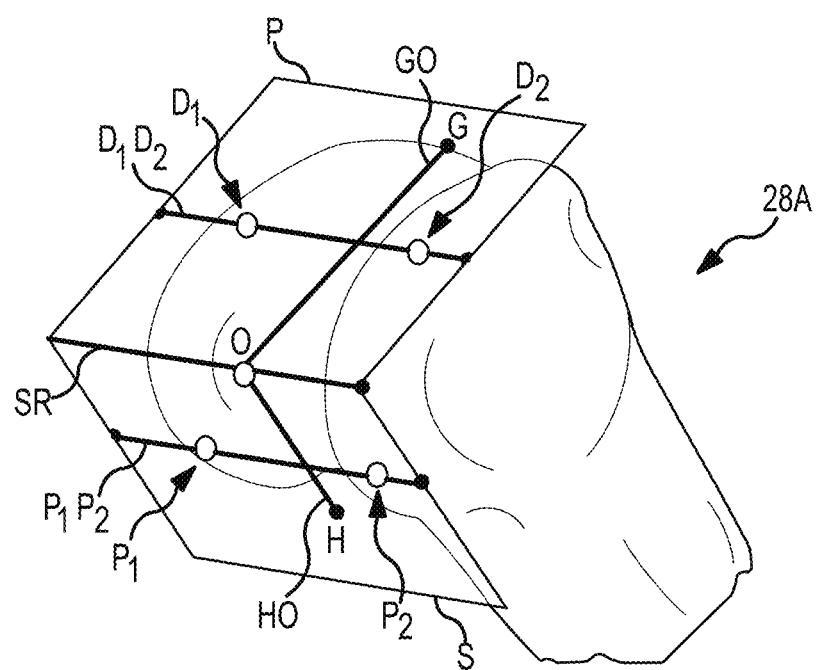
FIG. 45D is a perspective view of the distal end of the femur restored bone model.

For a detailed discussion of the methods for verifying the accuracy of the bone restoration process, reference is made to FIGS. 45A-45D. FIG. 45A is a sagittal view of a femur restored bone model 28A illustrating the orders and orientations of imaging slices 16 (e.g., MRI slices, CT slices, etc.) forming the femur restored bone model 28A. FIG. 45B is the distal images slices 1-5 taken along section lines 1-5 of the femur restored bone model 28A in FIG. 45A. FIG. 45C is the coronal images slices 6-8 taken along section lines 6-8 of the femur restored bone model 28A in FIG. 45A. FIG. 45D is a perspective view of the distal end of the femur restored bone model 28A.

As shown in FIG. 45A, a multitude of image slices are compiled into the femur restored bone model 28A from the image slices originally forming the femur bone model 22A and those restored image slices modified via the above-described methods. Image slices may extend medial-lateral in planes that would be normal to the longitudinal axis of the femur, such as image slices 1-5. Image slices may extend medial-lateral in planes that would be parallel to the longitudinal axis of the femur, such as image slices 6-8. The number of image slices may vary from 1-50 and may be spaced apart in a 2 mm spacing.

As shown in FIG. 45B, each of the slices 1-5 can be aligned vertically along the trochlear groove, wherein points G1, G2, G3, G4, G5 respectively represent the lowest extremity of trochlear groove for each slice 1-5. By connecting the various points G1, G2, G3, G4, G5, a point O can be obtained. As can be understood from FIGS. 42B and 45D, resulting line GO is perpendicular or nearly perpendicular to tangent line $P_1P_2$. In a 90° knee extension in FIG. 42B, line GO is perpendicular or nearly perpendicular to the joint line of the knee and line $P_1P_2$.

As shown in FIG. 45C, each of the slices 6-8 can be aligned vertically along the trochlear groove, wherein points H6, H7, H8 respectively represent the lowest extremity of the trochlear groove for each slice 6-8. By connecting the various points H6, H7, H8, the point O can again be obtained. As can be understood from FIGS. 42A and 45D, resulting line HO is perpendicular or nearly perpendicular to tangent line $D_1D_2$. In a 0° knee extension in FIG. 42A, line HO is perpendicular or nearly perpendicular to the joint line of the knee and line $D_1D_2$.

As illustrated in FIG. 45D, the verification of the accuracy of the restoration process includes determining if the reference lines GO and HO are within certain tolerances with respect to being parallel to certain lines and perpendicular to certain lines. The line GO, as the reference across the most distal extremity of the trochlear groove of the femur and in a 90° knee extension, should be perpendicular to tangent line $D_1D_2$. The line HO, as the reference across the most posterior extremity of trochlear groove of the femur and in a 0° knee extension, should be perpendicular to tangent line $P_1P_2$.

Line HO and line $P_1P_2$ may form a plane S, and lines GO and line $D_1 D_2$ may form a plane P that is perpendicular to plane S and forms line SR therewith. Line HO and line GO are parallel or nearly parallel to each other. Lines $P_1P_2$, $D_1$ $D_2$ and SR are parallel or nearly parallel to each other. Lines $P_1P_2$, $D_1D_2$ and SR are perpendicular or nearly perpendicular to lines HO and GO.

As can be understood from FIG. 45D, in one embodiment, lines HO and GO must be within approximately three degrees of being perpendicular with lines $P_1P_2$, and $D_1D_2$ or the restored bones models 28A, 28B will be rejected and the restoration process will have to be repeated until the resulting restored bone models 28A, 28B meet the stated tolerances, or there has been multiple failed attempts to meet the tolerances ([block 230]-[block 240] of FIG. 41). Alternatively, as can be understood from FIG. 45D, in another embodiment, lines HO and GO must be within approximately six degrees of being perpendicular with lines $P_1P_2$, and $D_1D_2$ or the restored bones models 28A, 28B will be rejected and the restoration process will have to be repeated until the resulting restored bone models 28A, 28B meet the stated tolerances, or there has been multiple failed attempts to meet the tolerances ([block 230]-[block 240] of FIG. 41). If multiple attempts to provide restored bone models 28A, 28B satisfying the tolerances have been made without success, then bone restoration reference data may be obtained from another similar joint that is sufficiently free of deterioration. For example, in the context of knees, if repeated attempts have been made without success to restore a right knee medial femur condyle and tibia plateau from reference information obtained from the right knee lateral sides, then reference data could be obtained from the left knee lateral or medial sides for use in the restoration process in a manner similar to described above.

In some embodiments, as depicted in the table illustrated in FIG. 46, some OA knee conditions are more likely to be restored via the methods disclosed herein than other conditions when it comes to obtaining the reference data from the same knee as being restored via the reference data. For example, the damaged side of the knee may be light (e.g., no bone damage or bone damage less than 1 mm), medium (e.g., bone damage of approximately 1 mm) or severe (e.g., bone damage of greater than 1 mm). As can be understood from FIG. 46, the bone restoration provided via some of the above-described embodiments may apply to most OA patients having light-damaged knees and medium-damaged knees and some OA patients having severe-damaged knees, wherein restoration data is obtained from a reference side of the knee having the damaged side to be restored. However, for most OA patients having severe-damaged and some OA patients having medium-damaged knees, in some embodiments as described below, bone restoration analysis entails obtaining restoration data from a good first knee of the patient for application to, and restoration of, a bad second knee of the patient.

It should be understood that the indications represented in the table of FIG. 46 are generalities for some embodiments disclosed herein with respect to some patients and should not be considered as absolute indications of success or failure with respect to whether or not any one or more of the embodiments disclosed herein may be successfully applied to an individual patient having any one of the conditions (light, medium, severe) reflected in the table of FIG. 46. Therefore, the table of FIG. 46 should not be considered to limit any of the embodiments disclose herein.

D. Further Discussion of Bone Model Restoration Methods

Figure 47A:
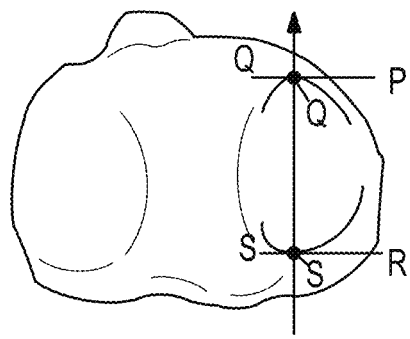
FIGS. 47A-47D are various views of the tibia plateau with reference to restoration of a side thereof.

For further discussion regarding embodiments of bone model restoration methods, reference is made to FIGS. 47A-47D. FIG. 47A shows the construction of reference line SQ in a medial portion of the tibia plateau. In one embodiment, the reference line SQ may be determined by superimposing an undamaged femoral condyle ellipse onto the medial tibia plateau to obtain two tangent points Q and S. In another embodiment, the tangent points Q and S may be located from the image slices by identifying the highest points at the posterior and anterior edges of the medial tibia plateau. By identifying tangent points Q and S, the tangent lines QP and SR may be determined by extending lines across each of the tangent points Q and S, wherein the tangent lines QP and SR are respectively tangent to the anterior and posterior curves of the medial tibia plateau. Reference line SQ may be obtained where tangent line QP is perpendicular or generally perpendicular to reference line SQ and tangent line SR is perpendicular or generally perpendicular to reference line SQ.

Figure 47B:
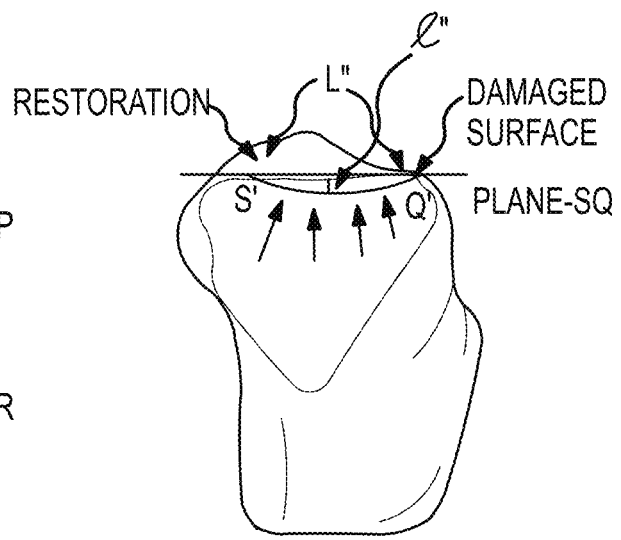

FIG. 47B shows the restoration of a damaged anterior portion of the lateral tibia plateau. The reference vector line or the vector plane is obtained from FIG. 47A, as line SQ or plane SQ. The reference vector plane SQ from the medial side may be applied as the reference plane in the damaged lateral side of the tibia plateau surface. In FIG. 47B, the contour of the damaged anterior portion of the lateral tibia plateau may be adjusted to touch the proximity of the reference vector plane SQ from the undamaged medial side. That is, points S' and Q' are adjusted to reach the proximity of the plane SQ. The outline between points S' and Q' are adjusted and raised to the reference plane SQ. By doing this adjustment, a restored tangent point Q' may be obtained via this vector plane SQ reference.

Figure 47C:
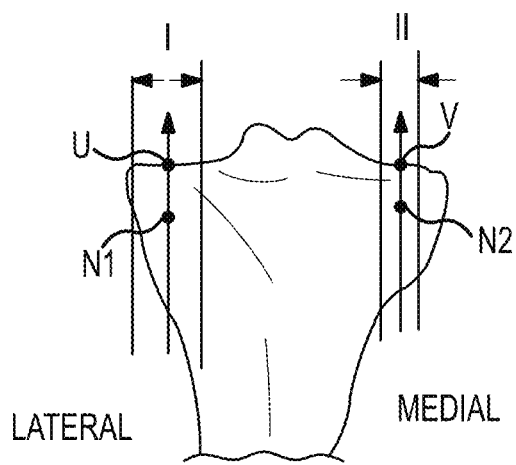
Figure 47D:
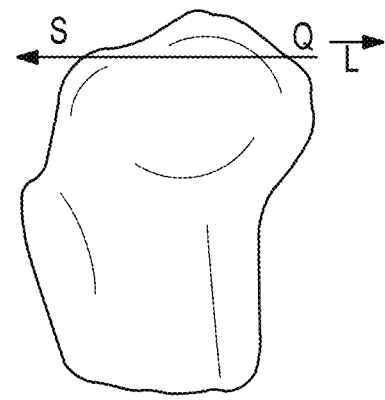

As shown in FIG. 47D, the reference vector plane SQ in the medial side is parallel or nearly parallel to the restored vector plane S'Q' in the lateral side. In FIG. 47B, the length L" represents the length of line S'Q'. The length l" is the offset from the recessed surface region of the tibia plateau to the plane S'Q' after the restoration. In the bone restoration assessment, the ratio of l"/L" may be controlled to be less than 0.01.

FIG. 47C is the coronal view of the restored tibia after 3D reconstruction, with a 0° knee extension model. The points U and V represent the lowest extremity of tangent contact points on each of the lateral and medial tibia plateau, respectively. In one embodiment, tangent points U and V are located within the region between the tibia spine and the medial and lateral epicondyle edges of the tibia plateau, where the slopes of tangent lines in this region are steady and constant. In one embodiment, the tangent point U in the lateral plateau is in area I between the lateral side of lateral intercondylar tubercule to the attachment of the lateral collateral ligament. For the medial portion, the tangent point V is in area II between the medial side of medial intercondylar tubercule to the medial condyle of tibia, as shown in FIG. 47C.

As previously stated, FIG. 47C represents the restored tibia models and, therefore, the reference lines $N_1$ and $N_2$ can apply to the restored tibia model in FIG. 47C, when the knee is at 0° extension. As can be understood from FIG. 47C, line $N_1$ when extended across point U is perpendicular or generally perpendicular to line-UV, while line $N_2$ when extended across point V is perpendicular or generally perpendicular to line UV. In restored the tibia model, line UV may be parallel or nearly parallel to the joint line of the knee. Within all these reference lines, in one embodiment, the tolerable range of the acute angle between nearly perpendicular or nearly parallel lines or planes may be within an absolute 6-degree angle, $|X-X'|<6°$. If the acute angle difference from FIG. 47C is less than 6°, the numerical data for the femur and/or tibia restoration is acceptable. This data may be transferred to the further assess the varus/valgus alignment of the knee models.

Figure 48A:
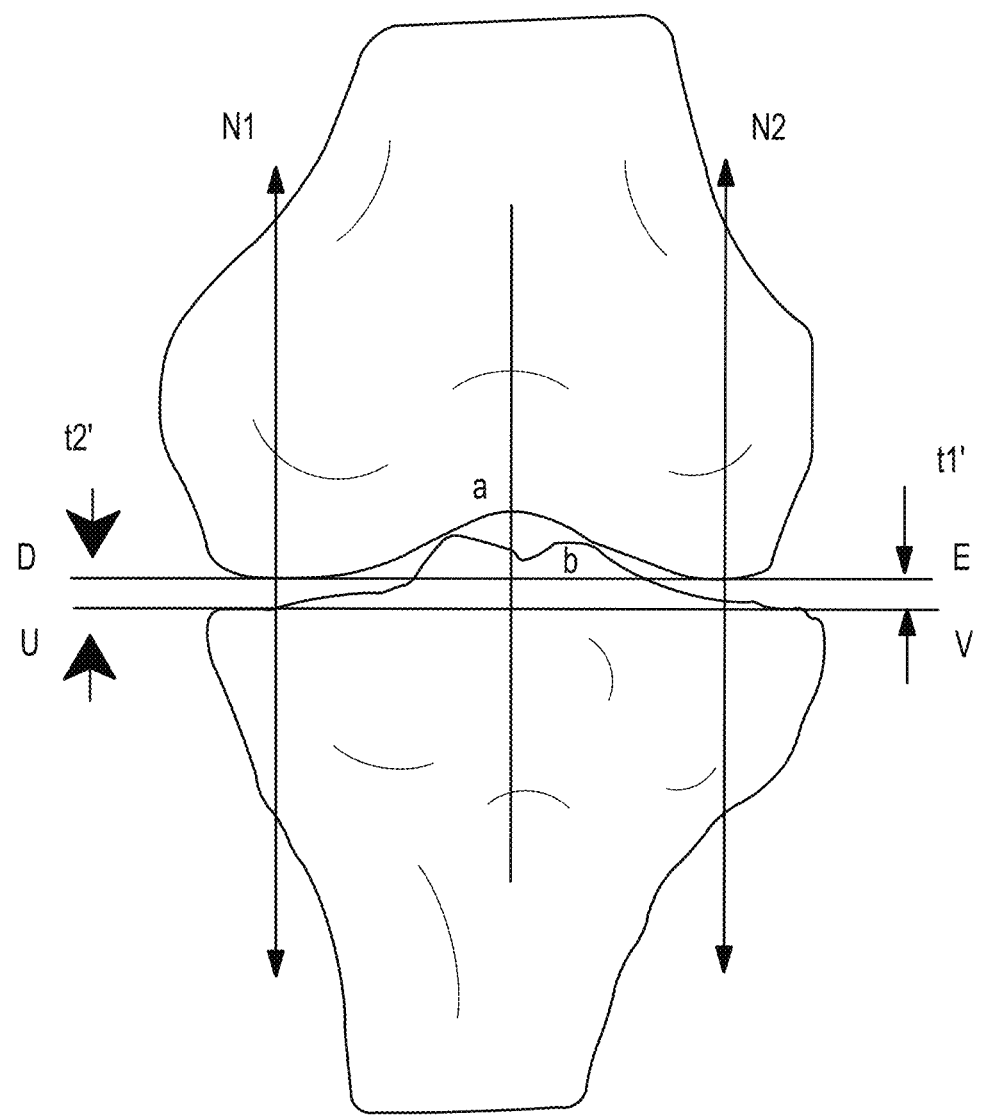
FIGS. 48A and 48B are, respectively, coronal and sagittal views of the restored bone models.

FIG. 48A is a coronal view of the restored knee models of proximal femur and distal tibia with 0° extension of the knee. Line ab extends across the lowest extremity of trochlear groove of the distal femur model. Reference lines $N_1$ and $N_2$ are applied to the restored knee model of varus/valgus alignment, where line-$N_1$ is parallel or generally parallel to line $N_2$ and line ab. Depending on the embodiment, the acute angles between these lines may be controlled within a 3 degree range or a 5 degree range. The tangent points D and E represent the lowest extremities of the restored proximal femur model. The tangent points U and V are obtained from the restored distal tibia plateau surface. In the medial portion, t1' represents the offset of the tangent lines between the medial condyle and medial tibia plateau. In the lateral portion, t2' represents the offset of the tangent lines between the lateral condyle and lateral tibia plateau. In the varus/valgus rotation and alignment, t1' is substantially equal to t2', or $|t1'-t2'|<<1$ mm. Therefore, line DE may be generally parallel to the joint line of the knee and generally parallel to line UV.

Figure 48B:
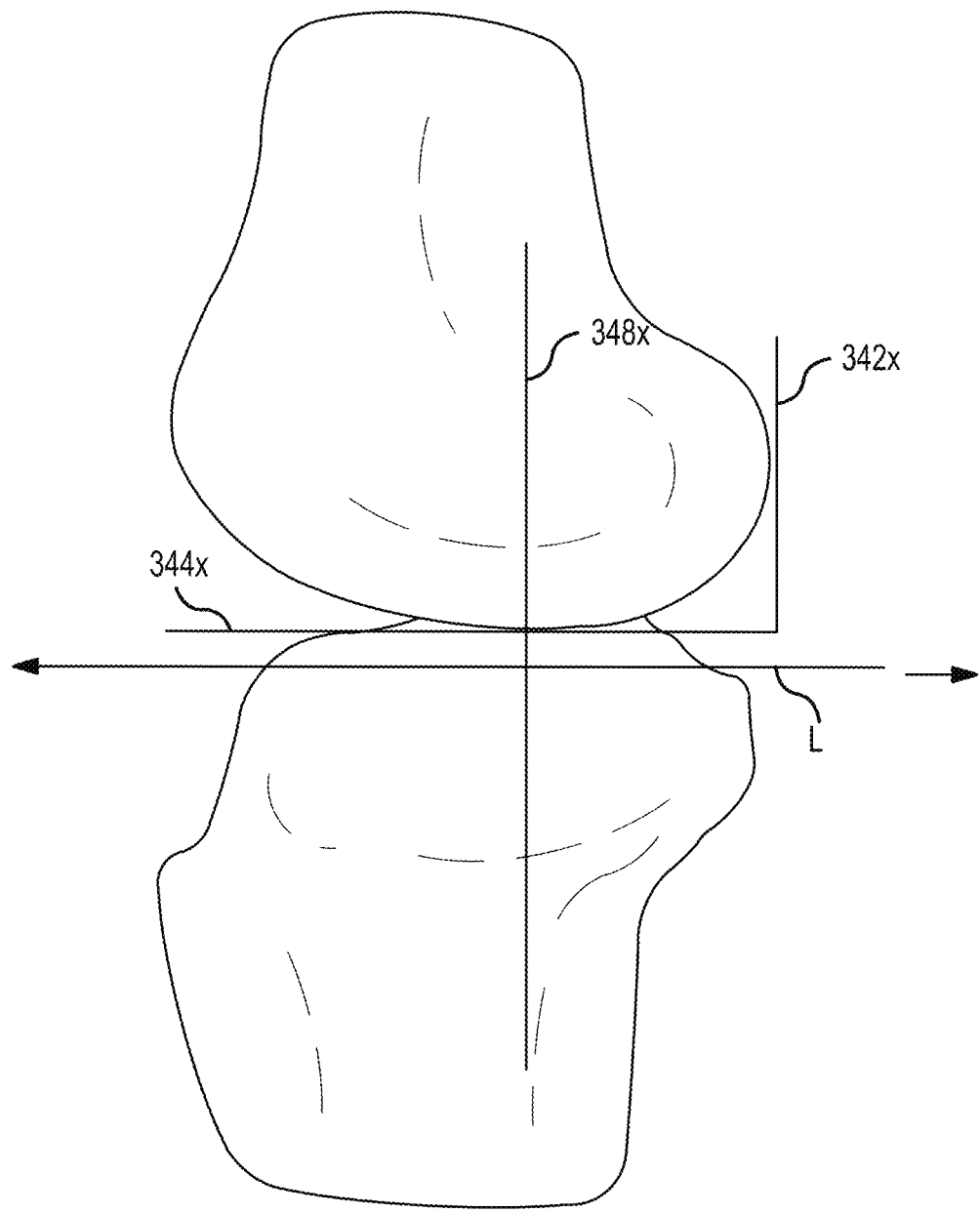

FIG. 48B is a sagittal view of the restored knee models. Line 348 represents the attachment location of lateral collateral ligament which lies on the lateral side of the joint. Line 342 represents the posterior extremity portion of the lateral femoral condyle. Line 344 represents the distal extremity portion of the lateral condyle. In this restored knee model, line 344 may be parallel or generally parallel to line L. That is, plane 344 is parallel or generally parallel to plane L and parallel or generally parallel to the joint plane of the knee. In one embodiment, the tolerable range of acute angle between these planes may be controlled within an absolute 6 degrees. If the angle is less than an absolute 6 degrees, the information of the femur and tibia model will then be forwarded to the preoperative design for the implant modeling. If the acute angle is equal or larger than an absolute 6 degrees, the images and 3D models will be rejected. In this situation, the procedure will be returned to start all over from the assessment procedure of reference lines/planes.

E. Using Reference Information from a Good Joint to Create a Restored Bone Model for a Damaged Joint As mentioned above with respect to the table of FIG. 46, the knee that is the target of the arthroplasty procedure may be sufficiently damaged on both the medial and lateral sides such that neither side may adequately serve as a reference side for the restoration of the other side. In a first embodiment and in a manner similar to that discussed above with respect to FIGS. 41-45D, reference data for the restoration of the deteriorated side of the target knee may be obtained from the patient's other knee, which is often a healthy knee or at least has a healthy side from which to obtain reference information. In a second embodiment, the image slices of the healthy knee are reversed in a mirrored orientation and compiled into a restored bone model representative of the deteriorated knee prior to deterioration, assuming the patient's two knees where generally mirror images of each other when they were both healthy. These two embodiments, which are discussed below in greater detail, may be employed when the knee targeted for arthroplasty is sufficiently damaged to preclude restoration in a manner similar to that described above with respect to FIGS. 41-45D. However, it should be noted that the two embodiments discussed below may also be used in place of, or in addition to, the methods discussed above with respect to FIGS. 41-45D, even if the knee targeted for arthroplasty has a side that is sufficiently healthy to allow the methods discussed above with respect to FIGS. 41-45D to be employed.

Figure 49A:
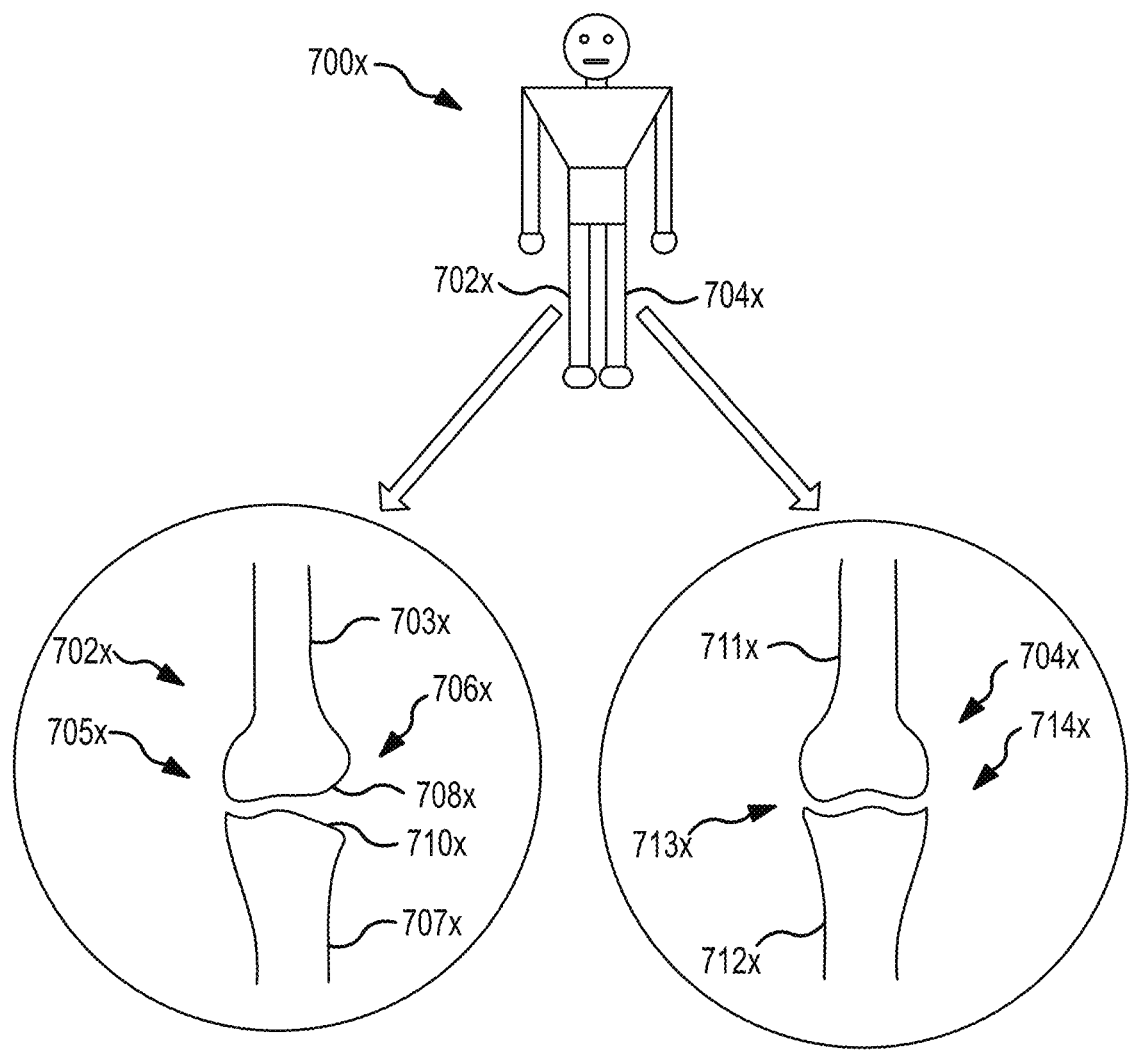
FIG. 49A is a diagram illustrating the condition of a patient's right knee, which is in a deteriorated state, and left knee, which is generally healthy.
Figure 49B:
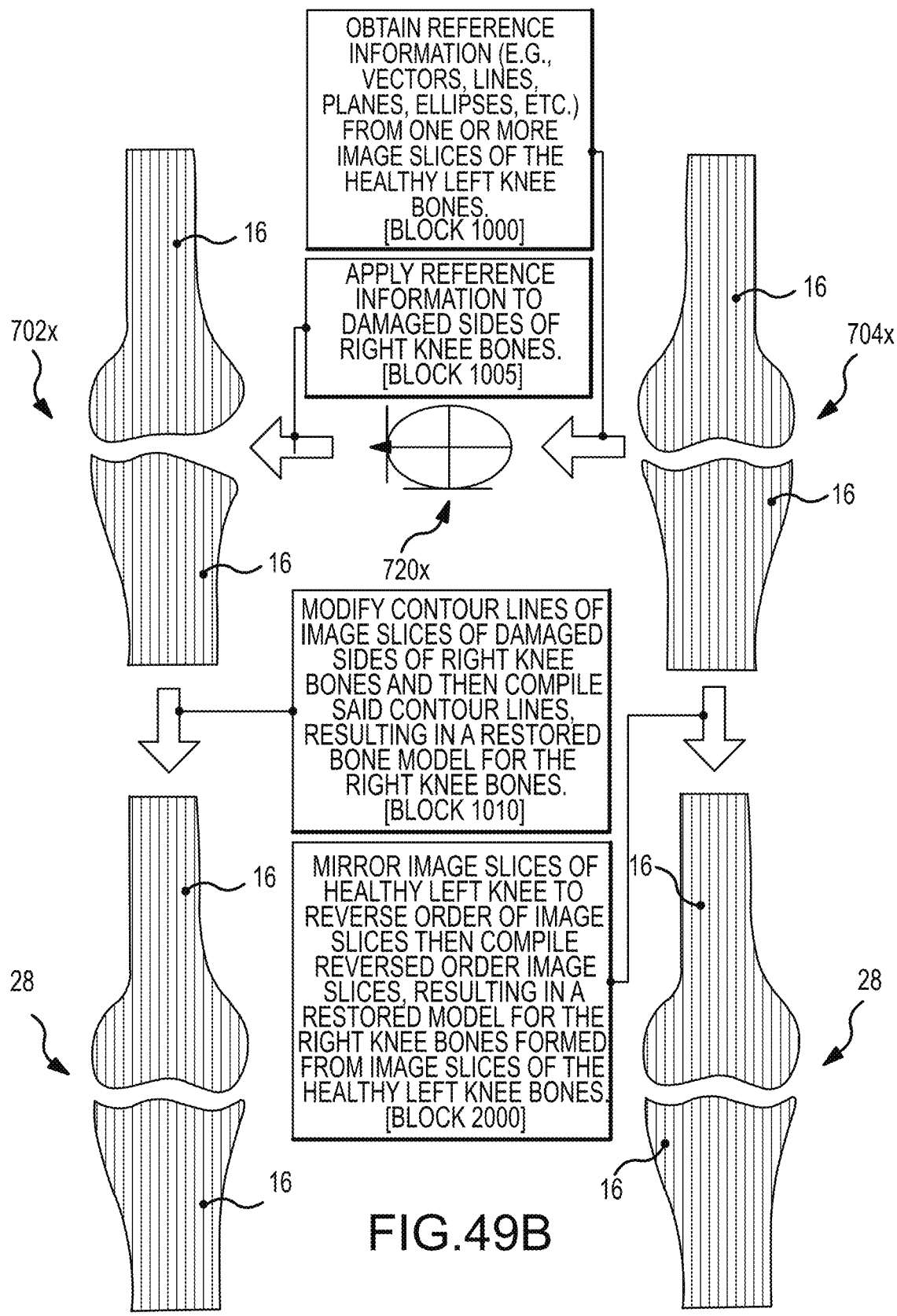
FIG. 49B is a diagram illustrating two options for creating a restored bone model for a deteriorated right knee from image slices obtained from a healthy left knee.

For a discussion of the two embodiments for creating a restored bone model for a deteriorated knee targeted for arthroplasty from image slices obtained from a healthy knee, reference is made to FIGS. 49A and 49B. FIG. 49A is a diagram illustrating the condition of a patient's right knee, which is in a deteriorated state, and left knee, which is generally healthy. FIG. 49B is a diagram illustrating the two embodiments. While in FIGS. 49A and 49B and the following discussion the right knee 702x of the patient 700x is designated as the deteriorate knee 702x and the left knee 704x of the patient 700x is designated as the healthy knee 704x, of course such designations are for example purposes only and the conditions of the knees could be the reverse.

As indicated in FIG. 49A, the patient 700x has a deteriorated right knee 702x formed of a femur 703x and a tibia 707x and which has one or both of sides in a deteriorated condition. In this example, the lateral side 705x of the right knee 702x is generally healthy and the medial side 706x of the right knee 702x is deteriorated such that the right medial condyle 708x and right medial tibia plateau 710x will need to be restored in any resulting restored bone model 28. As can be understood from FIG. 49A, the patient also has a left knee 704x that is also formed of a femur 711x and a tibia 712x and which has a medial side 713x and a lateral side 714x. In FIG. 49A, both sides 713x, 714x of the left knee 704x are generally healthy, although, for one of the following embodiments, a single healthy side is sufficient to generate a restored bone model 28 for the right knee 702x.

As indicated in FIG. 49B, image slices 16 of the deteriorated right knee 702x and healthy left knee 704x are generated as discussed above with respect to FIGS. 1A and 1B. In the first embodiment, which is similar to the process discussed above with respect to FIGS. 41-45D, except the process takes place with a deteriorated knee and a health knee as opposed to the deteriorated and healthy sides of the same knee, reference information (e.g., vectors, lines, planes, ellipses, etc. as discussed with respect to FIGS. 41-45D) 720x is obtained from a healthy side of the healthy left knee 704x [block 1000 of FIG. 49B]. The reference information 720x obtained from the image slices 16 of the health left knee 704x is applied to the deteriorated sides of the right knee 702x [block 1005 of FIG. 49B]. Specifically, the applied reference information 720x is used to modify the contour lines of the images slices 16 of the deteriorated sides of the right knee 702x, after which the modified contour lines are compiled, resulting in a restored bone model 28 that may be employed as described with respect to FIG. 1C. The reference information 720x obtained from the healthy left knee image slices 16 may be coordinated with respect to position and orientation with the contour lines of the deteriorated right knee image slices 16 by identifying a similar location or feature on each knee joint that is generally identical between the knees and free of bone deterioration, such as a point or axis of the femur trochlear groove or tibia plateau spine.

In the second embodiment, image slices 16 are generated of both the deteriorate right knee 702x and healthy left knee 704x as discussed above with respect to FIG. 1B. The image slices 16 of the deteriorated right knee 702x may be used to generate the arthritic model 36 as discussed above with respect to FIG. 1D. The image slices 16 of the healthy left knee 704x are mirrored medially/laterally to reverse the order of the image slices 16 [block 2000 of FIG. 49B]. The mirrored/reversed order image slices 16 of the healthy left knee 704x are compiled, resulting in a restored bone model 28 for the right knee 702x that is formed from the image slices 16 of the left knee 704x [block 2000 of FIG. 49B]. In other words, as can be understood from [block 2000] and its associated pictures in FIG. 49B, by medially/laterally mirroring the image slices 16 of left knee 704x to medially/laterally reverse their order and then compiling them in such a reversed order, the image slices 16 of the left knee 704x may be formed into a bone model that would appear to be a bone model of the right knee 702x in a restored condition, assuming the right and left knees 702x, 704x were generally symmetrically identical mirror images of each other when both were in a non-deteriorated state.

To allow for the merger of information (e.g., saw cut and drill hole data 44 and jig data 46) determined respectively from the restored bone model 28 and the arthritic model 28 as discussed above with respect to FIG. 1E, the restored bone model 28 generated from the mirrored image slices 16 of the healthy left knee 704x may be coordinated with respect to position and orientation with the arthritic model 36 generated from the image slices 16 of the deteriorated right knee 702x. In one embodiment, this coordination between the models 28, 36 may be achieved by identifying a similar location or feature on each knee joint that is generally identical between the knees and free of bone deterioration, such as a point or axis of the femur trochlear groove or tibia plateau spine. Such a point may serve as the coordination or reference point P' ($X_{0-k}$, $Y_{0-k}$, $Z_{0-k}$) as discussed with respect to FIG. 1E.

While the two immediately preceding embodiments are discussed in the context of knee joints, these embodiments, like the rest of the embodiments disclosed throughout this Detailed Description, are readily applicable to other types of joints including ankle joints, hip joints, wrist joints, elbow joints, shoulder joints, finger joints, toe joints, etc., and vertebrae/vertebrae interfaces and vertebrae/skull interfaces. Consequently, the content of this Detailed Description should not be interpreted as being limited to knees, but should be consider to encompass all types of joints and bone interfaces, without limitation.

IV. Overview of Pre-Operative Surgical Planning Process

Section II. of the present disclosure describes the acquisition of medical images, the segmentation or auto-segmentation of the medical images, and the generation of a patient bone model from the segmented images that is representative of the bones of the patient in a deteriorated or degenerated state. Section III. of the present disclosure describes exemplary methods of modifying image data (e.g., 2D image slices) of a patient's bone in a deteriorated state to restored image data (e.g., restored 2D image slices) that may be used to generate a restored bone model representing the patient's bone in a pre-deteriorated or pre-degenerated state. Beginning in Section IV., the present disclosure describes exemplary methods of implant planning (e.g., determining coordinate locations for resections, implant sizes) utilizing the bone models or image data (e.g., 2D image slices, restored 2D image slices) described previously. As described herein, the implant planning may take place utilizing the image data (e.g., 2D image slices) of the bone models representative of the patient's bones in a pre-deteriorated state (described in Section III) or a deteriorated state (described in Section II).

Disclosed herein are customized arthroplasty jigs 2 and systems 4 for, and methods of, producing such jigs 2. The jigs 2 are customized to fit specific bone surfaces of specific patients. Depending on the embodiment, the jigs 2 are automatically planned and generated and may be similar to those disclosed in these three U.S. patent applications: U.S.

patent application Ser. No. 11/656,323 to Park et al., titled "Arthroplasty Devices and Related Methods" and filed Jan. 19, 2007, now U.S. Pat. No. 9,017,336; U.S. patent application Ser. No. 10/146,862 to Park et al., titled "Improved Total Joint Arthroplasty System" and filed May 15, 2002; and U.S. patent Ser. No. 11/642,385 to Park et al., titled "Arthroplasty Devices and Related Methods" and filed Dec. 19, 2006. The disclosures of these three U.S. patent applications are incorporated by reference in their entireties into this Detailed Description.

A. Overview of System and Method for Manufacturing Customized Arthroplasty Cutting Jigs For an overview discussion of the systems 4 for, and methods of, producing the customized arthroplasty jigs 2, reference is made to FIGS. 1A-1I AND 50A-50E. FIG. 1A is a schematic diagram of a system 4 for employing the automated jig production method disclosed herein. FIGS. 50A-50E are flow chart diagrams outlining the jig production method disclosed herein. The following overview discussion can be broken down into three sections.

The first section, which is discussed with respect to FIG. 1A and [blocks 100-125] of FIGS. 50A, 50B, 50C, and 50E, pertains to an example method of determining, in a two-dimensional ("2D") computer model environment, saw cut and drill hole locations 30, 32 relative to 2D images 16 of a patient's joint 14. The resulting "saw cut and drill hole data" 44 is planned to provide saw cuts 30 and drill holes 32 that will allow arthroplasty implants to restore the patient's joint to its pre-degenerated or natural alignment state.

Figure 50A:
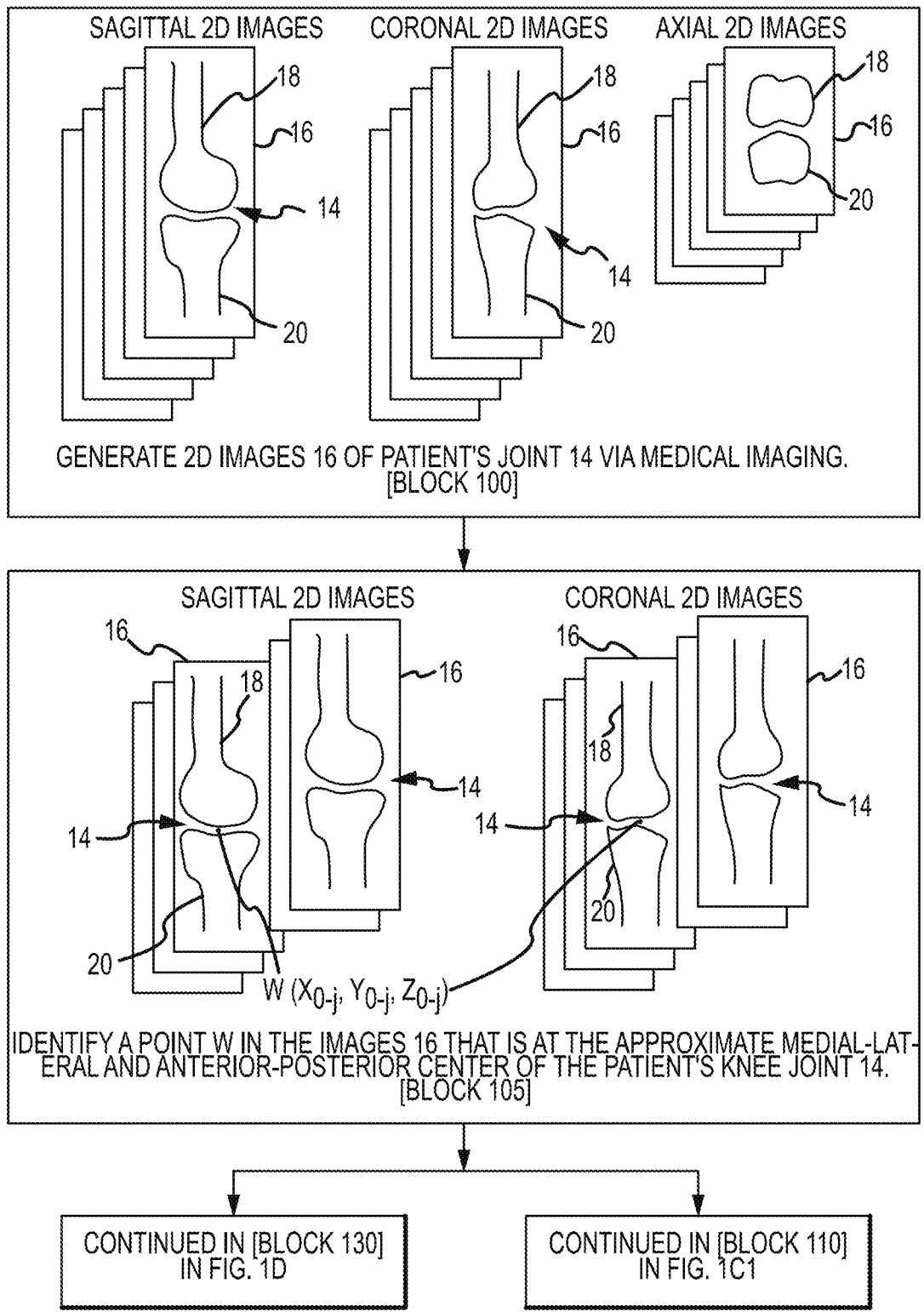
Figure 50D:
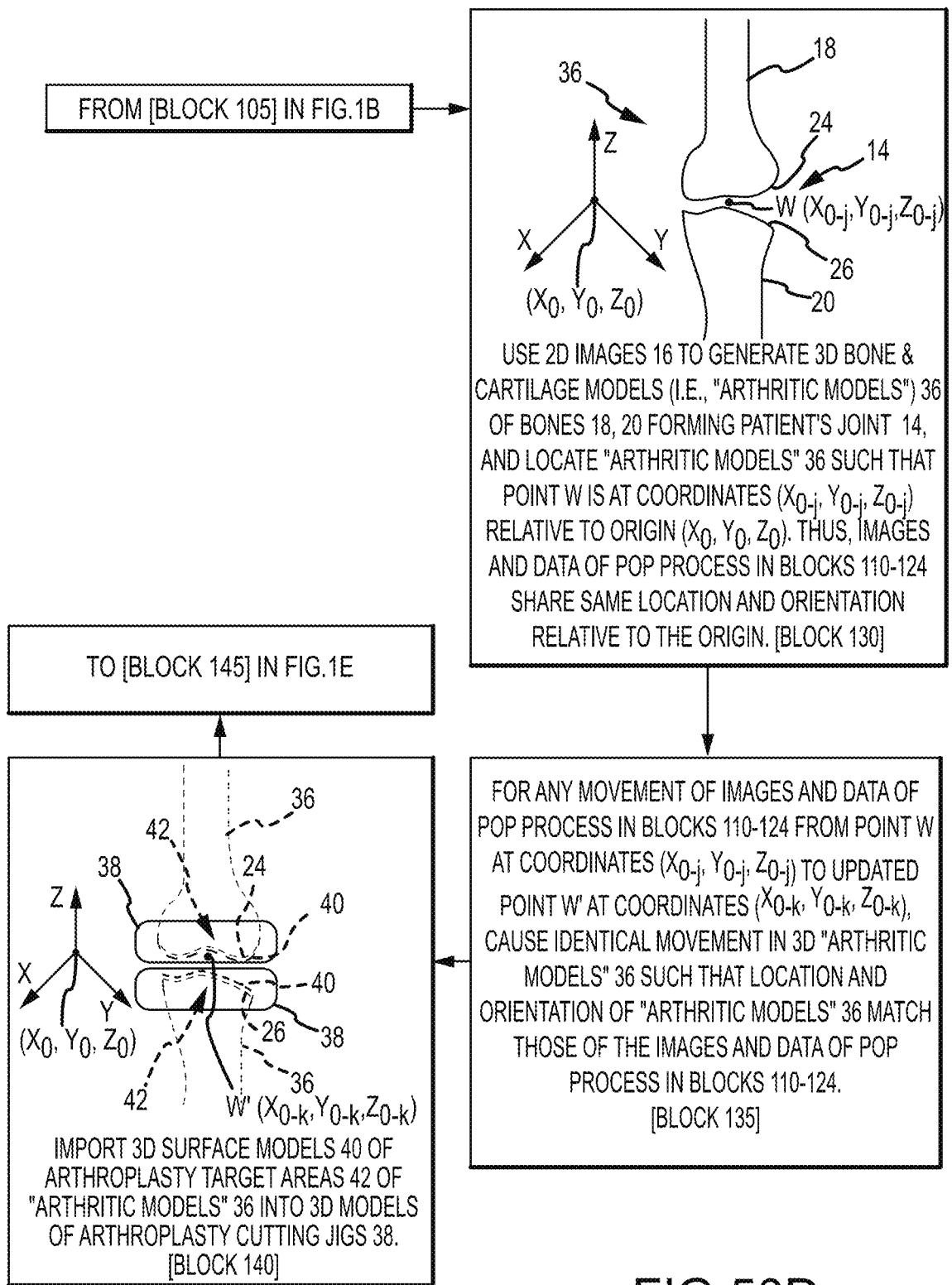
Figure 50E:
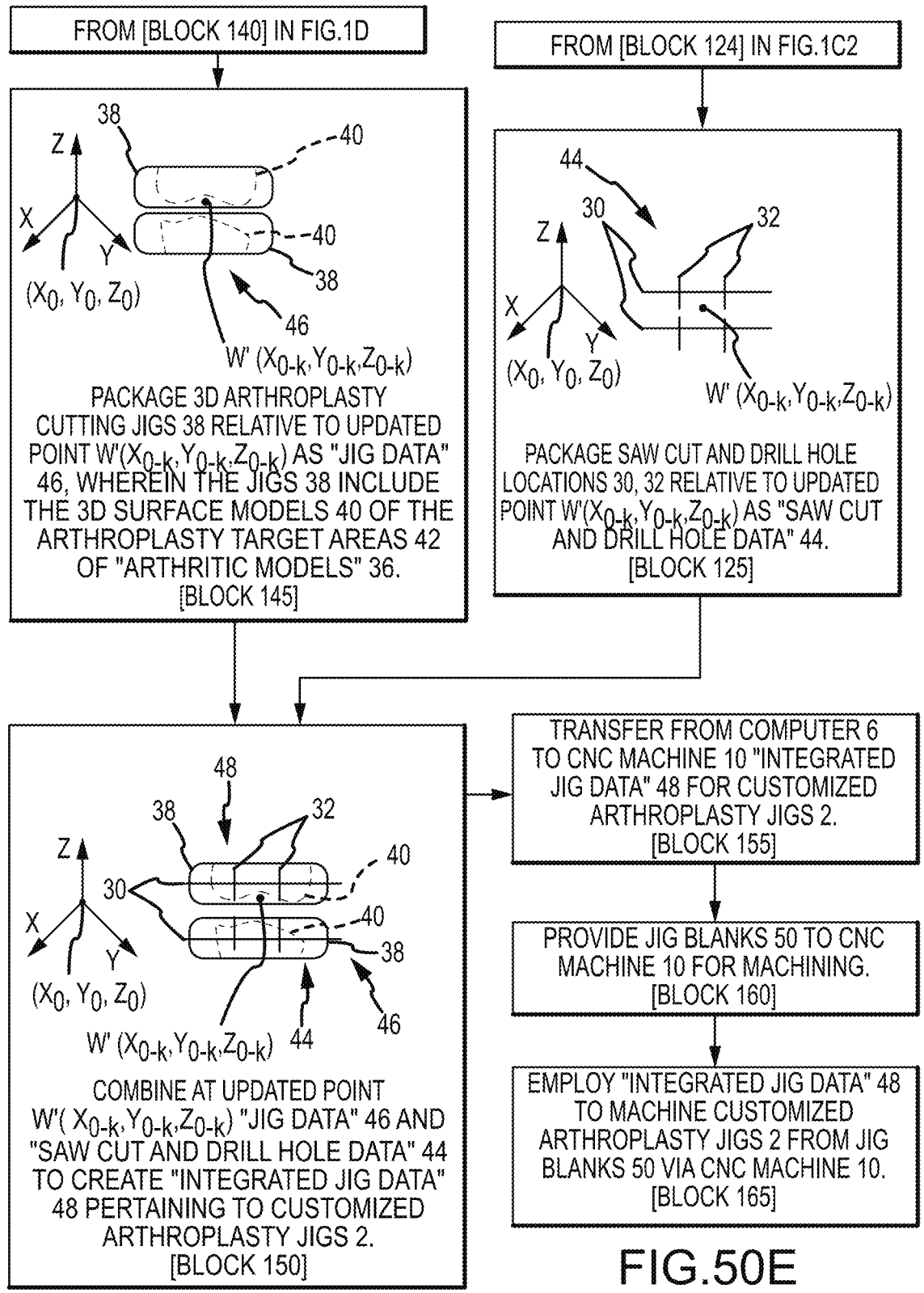

The second section, which is discussed with respect to FIG. 1A and [blocks 100-105 and 130-145] of FIGS. 50A, 50D, and 50E, pertains to an example method of importing into 3D computer generated jig models 38 3D computer generated surface models 40 of arthroplasty target areas 42 of 3D computer generated arthritic models 36 of the patient's joint bones. The resulting "jig data" 46 is used to produce a jig customized to matingly receive the arthroplasty target areas of the respective bones of the patient's joint.

The third section, which is discussed with respect to FIG. 1A and [blocks 150-165] of FIG. 50E, pertains to a method of combining or integrating the "saw cut and drill hole data" 44 with the "jig data" 46 to result in "integrated jig data" 48. The "integrated jig data" 48 is provided to the CNC machine 10 or other rapid production machine (e.g., a stereolithography apparatus ("SLA") machine) for the production of customized arthroplasty jigs 2 from jig blanks 50 provided to the CNC machine 10. The resulting customized arthroplasty jigs 2 include saw cut slots and drill holes positioned in the jigs 2 such that when the jigs 2 matingly receive the arthroplasty target areas of the patient's bones, the cut slots and drill holes facilitate preparing the arthroplasty target areas in a manner that allows the arthroplasty joint implants to generally restore the patient's joint line to its pre-degenerated state or natural alignment state.

As shown in FIG. 1A, the system 4 includes a computer 6 having a CPU 7, a monitor or screen 9 and an operator interface controls 11. The computer 6 is linked to a medical imaging system 8, such as a CT or MRI machine 8, and a computer controlled machining system 10, such as a CNC milling machine 10.

As indicated in FIG. 1A, a patient 12 has a joint 14 (e.g., a knee, elbow, ankle, wrist, hip, shoulder, skull/vertebrae or vertebrae/vertebrae interface, etc.) to be replaced. The patient 12 has the joint 14 scanned in the imaging machine 8. The imaging machine 8 makes a plurality of scans of the joint 14, wherein each scan pertains to a thin slice of the joint 14.

As can be understood from FIG. 50A, the plurality of scans is used to generate a plurality of two-dimensional ("2D") images 16 of the joint 14 [block 100z]. Where, for example, the joint 14 is a knee 14, the 2D images will be of the femur 18 and tibia 20. The imaging may be performed via CT or MRI. In one embodiment employing MRI, the imaging process may be as disclosed in U.S. patent application Ser. No. 11/946,002 to Park, which is entitled "Generating MRI Images Usable For The Creation Of 3D Bone Models Employed To Make Customized Arthroplasty Jigs," was filed Nov. 27, 2007 and is incorporated by reference in its entirety into this Detailed Description. The images 16 may be a variety of orientations, including, for example, sagittal 2D images, coronal 2D images and axial 2D images.

As can be understood from FIG. 1A, the 2D images are sent to the computer 6 for analysis and for creating computer generated 2D models and 3D models. In one embodiment, the bone surface contour lines of the bones 18, 20 depicted in the image slices 16 may be auto segmented via an image segmentation process as disclosed in U.S. Patent Application 61/126,102, which was filed Apr. 30, 2008, is entitled System and Method for Image Segmentation in Generating Computer Models of a Joint to Undergo Arthroplasty, and is hereby incorporated by reference into the present application in its entirety.

As indicated in FIG. 50A, in one embodiment, reference point W is identified in the 2D images 16 [block 105]. In one embodiment, as indicated in [block 105] of FIG. 1A, reference point W may be at the approximate medial-lateral and anterior-posterior center of the patient's joint 14. In other embodiments, reference point W may be at any other location in the 2D images 16, including anywhere on, near or away from the bones 18, 20 or the joint 14 formed by the bones 18, 20. Reference point W may be defined at coordinates (X0-$j$, Y0-$j$, Z0-$j$) relative to an origin (X0, Y0, Z0) of an X-Y-Z axis and depicted in FIGS. 50A-50D as W (X0-$j$, Y0-$j$, Z0-$j$). Throughout the processes described herein, to allow for correlation between the different types of images, models or any other data created from the images, movements of such images, models or any other data created form the images may be tracked and correlated relative to the origin.

As described later in this overview, point W may be used to locate the 2D images 16 and computer generated 3D model 36 created from the 2D images 16 respectively with the implant images 34 and jig blank model 38 and to integrate information generated via the POP process. Depending on the embodiment, point W, which serves as a position and/or orientation reference, may be a single point, two points, three points, a point plus a plane, a vector, etc., so long as the reference point W can be used to position and/or orient the 2D images 16, 34 and 3D models 36, 38 relative to each other as needed during the POP process.

As shown in FIG. 50B, the coronal and axial 2D images 16 of the femur 18 forming the patient's joint 14 are analyzed to determine femur reference data [block 110]. For example, the coronal 2D images are analyzed to determine the most distal femur point D1 on a healthy condyle and a joint line perpendicular to a trochlear groove line is used to estimate the location of a hypothetical most distal point D2 on the damaged condyle. Similarly, the axial 2D images are analyzed to determine the most posterior femur point P1 on a healthy condyle and a joint line perpendicular to a trochlear groove line is used to estimate the location of a hypothetical most posterior point $P_2$ on the damaged condyle. The femur reference data points D1, D2, P1, $P_2$ is mapped or otherwise imported to a sagittal or y-z plane in a computer environment and used to determine the sagittal or y-z plane relationship between the femur reference data points D1, D2, P1, $P_2$. The femur reference data D1, D2, P1, $P_2$ is then used to choose candidate femoral implant(s). [Block 112]. The femur reference data points D1, D2, P1, $P_2$ are respectively correlated with similar reference data points D1', D2', P1', $P_2$' of the selected femur implant 34 in a sagittal or y-z plane [block 114]. This correlation determines the locations and orientations of the cut plane 30 and drill holes 32 needed to cause the patient's joint to returned to a natural, pre-deteriorated alignment with the selected implant 34. The cut plane 30 and drill hole 32 locations determined in block 114 are adjusted to account for cartilage thickness [block 118].

As shown in FIG. 50C at block 120, tibia reference data is determined from the images in a manner similar to the process of block 110, except different image planes are employed. Specifically, sagittal and coronal images slices of the tibia are analyzed to identify the lowest (i.e., most distal) and most anterior and posterior points of the tibia recessed condylar surfaces. This tibia reference data is then projected onto an axial view. The tibia reference data is used to select an appropriate tibia implant [Block 121]. The tibia reference data is correlated to similar reference data of the selected tibia implant in a manner similar to that of block 114, except the correlation takes place in an axial view [Block 122]. The cut plane 30 associated with the tibia implant's position determined according to block 122 is adjusted to account for cartilage thickness [Block 123].

Once the saw cut locations 30 and drill hole locations 32 associated with the POP of the femur and tibia implants 34 has been completed with respect to the femur and tibia data 28 (e.g., the 2D femur and tibia images 16 and reference point W), the saw cut locations 30 and drill hole locations 32 are packaged relative to the reference point W(X0-$j$, Y0-$j$, Z0-$j$) [Block 124]. As the images 16 and other data created from the images or by employing the images may have moved during any of the processes discussed in blocks 110-123, the reference point W(X0-$j$, Y0-$j$, Z0-$j$) for the images or associated data may become updated reference point W' at coordinates (X0-$k$, Y0-$k$, Z0-$k$) relative to an origin (X0, Y0, Z0) of an X-Y-Z axis. For example, during the correlation process discussed in blocks 114 and 122, the implant reference data may be moved towards the bone image reference data or, alternatively, the bone image reference data may be moved towards the implant reference data. In the latter case, the location of the bone reference data will move from reference point W(X0-$j$, Y0-$j$, Z0-$j$) to updated reference point W'(X0-$k$, Y0-$k$, Z0-$k$), and this change in location with respect to the origin will need to be matched by the arthritic models 36 to allow for "saw cut and drill hole" data 44 obtained via the POP process of blocks 110-125 to be merged with "jig data" 46 obtained via the jig mating surface defining process of blocks 130-145, as discussed below.

As can be understood from FIG. 50E, the POP process may be completed with the packaging of the saw cut locations 30 and drill hole locations 32 with respect to the updated reference point W'(X0-$k$, Y0-$k$, Z0-$k$) as "saw cut and drill hole data" 44 [Block 125]. The "saw cut and drill hole data" 44 is then used as discussed below with respect to [block 150] in FIG. 50E.

In one embodiment, the POP procedure is a manual process, wherein 2D bone images 28 (e.g., femur and tibia 2D images in the context of the joint being a knee) are manually analyzed to determine reference data to aid in the selection of a respective implant 34 and to determine the proper placement and orientation of saw cuts and drill holes that will allow the selected implant to restore the patient's joint to its natural, pre-deteriorated state. (The reference data for the 2D bone images 28 may be manually calculated or calculated by a computer by a person sitting in front of a computer 6 and visually observing the images 28 on the computer screen 9 and determining the reference data via the computer controls 11. The data may then be stored and utilized to determine the candidate implants and proper location and orientation of the saw cuts and drill holes. In other embodiments, the POP procedure is totally computer automated or a combination of computer automation and manual operation via a person sitting in front of the computer.

In some embodiments, once the selection and placement of the implant has been achieved via the 2D POP processes described in blocks 110-125, the implant selection and placement may be verified in 2D by superimposing the implant models 34 over the bone images data, or vice versa. Alternatively, once the selection and placement of the implant has been achieved via the 2D POP processes described in blocks 110-125, the implant selection and placement may be verified in 3D by superimposing the implant models 34 over 3D bone models generated from the images 16. Such bone models may be representative of how the respective bones may have appeared prior to degeneration. In superimposing the implants and bones, the joint surfaces of the implant models can be aligned or caused to correspond with the joint surfaces of the 3D bone models. This ends the overview of the POP process. A more detailed discussion of various embodiments of the POP process is provided later in this Detailed Description As can be understood from FIG. 50D, the 2D images 16 employed in the 2D POP analysis of blocks 110-124 of FIGS. 50B-50C are also used to create computer generated 3D bone and cartilage models (i.e., "arthritic models") 36 of the bones 18, 20 forming the patient's joint 14 [block 130]. Like the above-discussed 2D images and femur and tibia reference data, the arthritic models 36 are located such that point W is at coordinates (X0-$j$, Y0-$j$, Z0-$j$) relative to the origin (X0, Y0, Z0) of the X-Y-Z axis [block 130]. Thus, the 2D images and femur and tibia data of blocks 110-125 and arthritic models 36 share the same location and orientation relative to the origin (X0, Y0, Z0). This position/orientation relationship is generally maintained throughout the process discussed with respect to FIGS. 50A-50E. Accordingly, movements relative to the origin (X0, Y0, Z0) of the 2D images and femur and tibia data of blocks 110-125 and the various descendants thereof (i.e., bone cut locations 30 and drill hole locations 32) are also applied to the arthritic models 36 and the various descendants thereof (i.e., the jig models 38). Maintaining the position/orientation relationship between the 2D images and femur and tibia data of blocks 110-125 and arthritic models 36 and their respective descendants allows the "saw cut and drill hole data" 44 to be integrated into the "jig data" 46 to form the "integrated jig data" 48 employed by the CNC machine 10 to manufacture the customized arthroplasty jigs 2, as discussed with respect to block 150 of FIG. 50E.

Computer programs for creating the 3D computer generated arthritic models 36 from the 2D images 16 include: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org.

The arthritic models 36 depict the bones 18, 20 in the present deteriorated condition with their respective degenerated joint surfaces 24, 26, which may be a result of osteoarthritis, injury, a combination thereof, etc. The arthritic models 36 also include cartilage in addition to bone. Accordingly, the arthritic models 36 depict the arthroplasty target areas 42 generally as they will exist when the customized arthroplasty jigs 2 matingly receive the arthroplasty target areas 42 during the arthroplasty surgical procedure.

As indicated in FIG. 50D and already mentioned above, to coordinate the positions/orientations of the 2D images and femur and tibia data of blocks 110-125 and arthritic models 36 and their respective descendants, any movement of the 2D images and femur and tibia data of blocks 110-125 from point W to point W' is tracked to cause a generally identical displacement for the "arthritic models" 36, and vice versa [block 135].

As depicted in FIG. 50D, computer generated 3D surface models 40 of the arthroplasty target areas 42 of the arthritic models 36 are imported into computer generated 3D arthroplasty jig models 38 [block 140]. Thus, the jig models 38 are configured or indexed to matingly receive the arthroplasty target areas 42 of the arthritic models 36. Jigs 2 manufactured to match such jig models 38 will then matingly receive the arthroplasty target areas of the actual joint bones during the arthroplasty surgical procedure.

In one embodiment, the procedure for indexing the jig models 38 to the arthroplasty target areas 42 is a manual process. The 3D computer generated models 36, 38 are manually manipulated relative to each other by a person sitting in front of a computer 6 and visually observing the jig models 38 and arthritic models 36 on the computer screen 9 and manipulating the models 36, 38 by interacting with the computer controls 11. In one embodiment, by superimposing the jig models 38 (e.g., femur and tibia arthroplasty jigs in the context of the joint being a knee) over the arthroplasty target areas 42 of the arthritic models 36, or vice versa, the surface models 40 of the arthroplasty target areas 42 can be imported into the jig models 38, resulting in jig models 38 indexed to matingly receive the arthroplasty target areas 42 of the arthritic models 36. Point W' (X0-$k$, Y0-$k$, Z0-$k$) can also be imported into the jig models 38, resulting in jig models 38 positioned and oriented relative to point W' (X0-$k$, Y0-$k$, Z0-$k$) to allow their integration with the bone cut and drill hole data 44 of [block 125].

In one embodiment, the procedure for indexing the jig models 38 to the arthroplasty target areas 42 is generally or completely automated, as disclosed in U.S. patent application Ser. No. 11/959,344 to Park, which is entitled System and Method for Manufacturing Arthroplasty Jigs, was filed Dec. 18, 2007, now U.S. Pat. No. 8,221,430 and is incorporated by reference in its entirety into this Detailed Description. For example, a computer program may create 3D computer generated surface models 40 of the arthroplasty target areas 42 of the arthritic models 36. The computer program may then import the surface models 40 and point W' (X0-$k$, Y0-$k$, Z0-$k$) into the jig models 38, resulting in the jig models 38 being indexed to matingly receive the arthroplasty target areas 42 of the arthritic models 36. The resulting jig models 38 are also positioned and oriented relative to point W' (X0-$k$, Y0-$k$, Z0-$k$) to allow their integration with the bone cut and drill hole data 44 of [block 125].

In one embodiment, the arthritic models 36 may be 3D volumetric models as generated from the closed-loop process discussed in U.S. patent application Ser. No. 11/959, 344 filed by Park. In other embodiments, the arthritic models 36 may be 3D surface models as generated from the open-loop process discussed in U.S. patent application Ser. No. 11/959,344 filed by Park.

In one embodiment, the models 40 of the arthroplasty target areas 42 of the arthritic models 36 may be generated via an overestimation process as disclosed in U.S. Provisional Patent Application 61/083,053, which is entitled System and Method for Manufacturing Arthroplasty Jigs Having Improved Mating Accuracy, was filed by Park Jul. 23, 2008, and is hereby incorporated by reference in its entirety into this Detailed Description.

As indicated in FIG. 50E, in one embodiment, the data regarding the jig models 38 and surface models 40 relative to point W' (X0-$k$, Y0-$k$, Z0-$k$) is packaged or consolidated as the "jig data" 46 [block 145]. The "jig data" 46 is then used as discussed below with respect to [block 150] in FIG. 50E.

As can be understood from FIG. 50E, the "saw cut and drill hole data" 44 is integrated with the "jig data" 46 to result in the "integrated jig data" 48 [block 150]. As explained above, since the "saw cut and drill hole data" 44, "jig data" 46 and their various ancestors (e.g., 2D images and femur and tibia data of blocks 110-125 and models 36, 38) are matched to each other for position and orientation relative to point W and W', the "saw cut and drill hole data" 44 is properly positioned and oriented relative to the "jig data" 46 for proper integration into the "jig data" 46. The resulting "integrated jig data" 48, when provided to the CNC machine 10, results in jigs 2: (1) configured to matingly receive the arthroplasty target areas of the patient's bones; and (2) having cut slots and drill holes that facilitate preparing the arthroplasty target areas in a manner that allows the arthroplasty joint implants to generally restore the patient's joint line to its pre-degenerated state or natural alignment state.

As can be understood from FIGS. 1A and 50E, the "integrated jig data" 44 is transferred from the computer 6 to the CNC machine 10 [block 155]. Jig blanks 50 are provided to the CNC machine 10 [block 160], and the CNC machine 10 employs the "integrated jig data" to machine the arthroplasty jigs 2 from the jig blanks 50 [block 165].

Figure 51A:
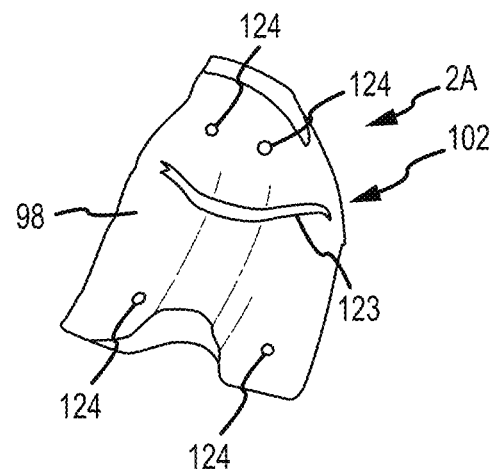
FIGS. 51A and 51B are, respectively, bottom and top perspective views of an example customized arthroplasty femur jig.
Figure 51B:
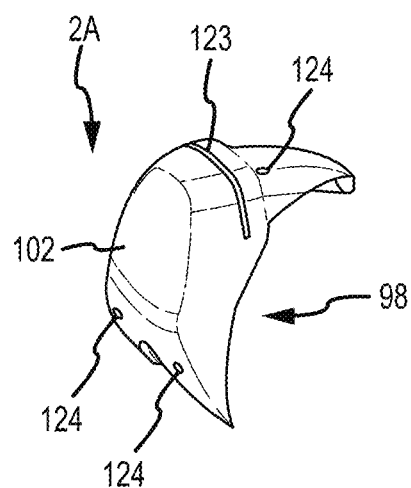
Figure 51C:
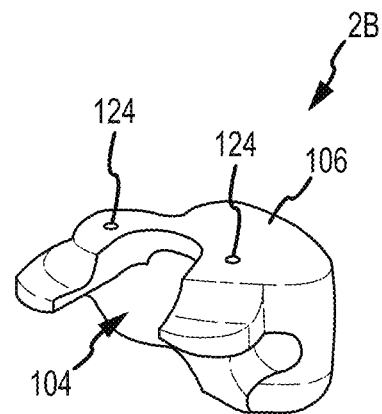
FIGS. 51C and 51D are, respectively, top/posterior and bottom/anterior perspective views of an example customized arthroplasty tibia jig.
Figure 51D:
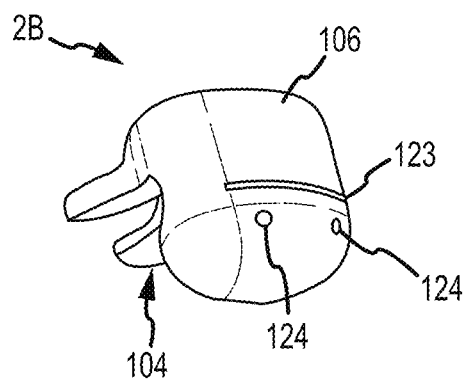

For a discussion of example customized arthroplasty cutting jigs 2 capable of being manufactured via the above-discussed process, reference is made to FIGS. 51A-51D. While, as pointed out above, the above-discussed process may be employed to manufacture jigs 2 configured for arthroplasty procedures involving knees, elbows, ankles, wrists, hips, shoulders, vertebra interfaces, etc., the jig examples depicted in FIGS. 51A-51D are for total knee replacement ("TKR") or partial knee ("uni-knee") replacement procedures. Thus, FIGS. 51A and 51B are, respectively, bottom and top perspective views of an example customized arthroplasty femur jig 2A, and FIGS. 51C and 51D are, respectively, bottom and top perspective views of an example customized arthroplasty tibia jig 2B.

As indicated in FIGS. 51A and 51B, a femur arthroplasty jig 2A may include an interior side or portion 98 and an exterior side or portion 102. When the femur cutting jig 2A is used in a TKR procedure, the interior side or portion 98 faces and matingly receives the arthroplasty target area 42 of the femur lower end, and the exterior side or portion 102 is on the opposite side of the femur cutting jig 2A from the interior portion 98.

The interior portion 98 of the femur jig 2A is configured to match the surface features of the damaged lower end (i.e., the arthroplasty target area 42) of the patient's femur 18. Thus, when the target area 42 is received in the interior portion 98 of the femur jig 2A during the TKR surgery, the surfaces of the target area 42 and the interior portion 98 match. The cutting jig 2A may include one or more saw guiding slots 123 and one or more drill holes 124.

The surface of the interior portion 98 of the femur cutting jig 2A is machined or otherwise formed into a selected femur jig blank 50A and is based or defined off of a 3D surface model 40 of a target area 42 of the damaged lower end or target area 42 of the patient's femur 18.

As indicated in FIGS. 51C and 51D, a tibia arthroplasty jig 2B may include an interior side or portion 104 and an exterior side or portion 106. When the tibia cutting jig 2B is used in a TKR procedure, the interior side or portion 104 faces and matingly receives the arthroplasty target area 42 of the tibia upper end, and the exterior side or portion 106 is on the opposite side of the tibia cutting jig 2B from the interior portion 104.

The interior portion 104 of the tibia jig 2B is configured to match the surface features of the damaged upper end (i.e., the arthroplasty target area 42) of the patient's tibia 20. Thus, when the target area 42 is received in the interior portion 104 of the tibia jig 2B during the TKR surgery, the surfaces of the target area 42 and the interior portion 104 match.

The surface of the interior portion 104 of the tibia cutting jig 2B is machined or otherwise formed into a selected tibia jig blank 50B and is based or defined off of a 3D surface model 40 of a target area 42 of the damaged upper end or target area 42 of the patient's tibia 20. The cutting jig 2B may include one or more saw guiding slots 123 and one or more drill holes 124.

While the discussion provided herein is given in the context of TKR and TKR jigs and the generation thereof, the disclosure provided herein is readily applicable to uni-compartmental or partial arthroplasty procedures in the knee or other joint contexts. Thus, the disclosure provided herein should be considered as encompassing jigs and the generation thereof for both total and uni-compartmental arthroplasty procedures.

The remainder of this Detailed Discussion will now focus on various embodiments for performing POP.

B. Overview of Preoperative Planning ("POP") Procedure

In one embodiment, as can be understood from [blocks 100-110] of FIGS. 50A-50C, medical images 16 of the femur and tibia 18, 20 are generated [blocks 100 and 105] and coronal, axial and sagittal image slices are analyzed to determine reference data 28, 100$z$, 900$z$. [Block 115]. The sizes of the implant models 34 are selected relative to the femur and tibia reference data. [Block 112, 114 and 121, 122]. The reference data 28, 100$z$, 900$z$ is utilized with the data associated with implant models 34 to determine the cut plane location. The joint spacing between the femur and the tibia is determined. An adjustment value tr is determined to account for cartilage thickness or joint gap of a restored joint. The implant models 34 are shifted or adjusted according to the adjustment value tr [blocks 118 and 123]. Two dimensional computer implant models 34 are rendered into the two dimensional imaging slice(s) of the bones 28 such that the 2D implant models 34 appear alongside the 2D imaging slices of the bones 28. In one embodiment, ITK software, manufactured by Kitware, Inc. of Clifton Park, N.Y. is used to perform this rendering. Once the 2D implant models 34 are rendered into the MRI/CT image, the proper selection, orientation and position of the implant models can be verified. An additional verification process may be used wherein 3D models of the bones and implants are created and proper positioning of the implant may be verified. Two dimensional computer models 34 and three dimensional computer models 1004$z$, 1006$z$ of the femur and tibia implants are generated from engineering drawings of the implants and may be generated via any of the above-referenced 2D and 3D modeling programs to confirm planning. If the implant sizing is not correct, then the planning will be amended by further analysis of the 2D images. If the implant sizing is accurate, then planning is complete. The process then continues as indicated in [block 125] of FIG. 50E.

This ends the overview of the POP process. The following discussions will address each of the aspects of the POP process in detail.

C. Femur and Tibia Images

FIG. 52A depicts 3D bone models or images 28', 28" of the femur and tibia 18, 20 from medical imaging scans 16. While FIG. 52A represents the patient's femur 18 and tibia 20 prior to injury or degeneration (such as, for example, in the case of the femur and tibia restored bone models 28A, 28B of FIGS. 42D and 42E), it can be understood that, in other embodiments, the images 28', 28" may also represent the patient's femur 18 and tibia 20 after injury or degeneration (such as, for example, the femur bone model 22A in FIG. 44A and the tibia bone model 22B in FIG. 44B). More specifically, FIG. 52A is a 3D bone model 28' of a femur lower end 200$z$ and an 3D bone model 28" of a tibia upper end 205$z$ representative of the corresponding patient bones 18, 20 in a non-deteriorated state and in position relative to each to form a knee joint 14. The femur lower end 200$z$ includes condyles 215$z$, and the tibia upper end 205$z$ includes a plateau 220$z$. The images or bone models 28', 28" are positioned relative to each other such that the curved articular surfaces of the condyles 215$z$, which would normally mate with complementary articular surfaces of the plateau 220$z$, are instead not mating, but roughly positioned relative to each other to generally approximate the knee joint 14.

As generally discussed above with respect to FIGS. 50A-50C, the POP begins by using a medical imaging process, such as magnetic resonance imaging (MRI), computed tomography (CT), and/or another other medical imaging process, to generate imaging data of the patient's knee. For example, current commercially available MRI machines use 8 bit (255 grayscale) to show the human anatomy. Therefore, certain components of the knee, such as the cartilage, cortical bone, cancellous bone, meniscus, etc., can be uniquely viewed and recognized with 255 grayscale. The generated imaging data is sent to a preoperative planning computer program. Upon receipt of the data, a user or the computer program may analyze the data (e.g., two-dimensional MRI images 16, and more specifically, the 2D femur image(s) 28' or 2D tibia image(s) 28") to determine various reference points, reference lines and reference planes. In one embodiment, the MRI imaging scans 16 may be analyzed and the reference data for POP may be generated by a proprietary software program called PerForm.

For greater detail regarding the methods and systems for computer modeling joint bones, such as the femur and tibia bones forming the knee, please see the following U.S. patent applications, which are all incorporated herein in their entireties: U.S. patent application Ser. No. 11/656,323 to Park et al., titled "Arthroplasty Devices and Related Methods" and filed Jan. 19, 2007, now U.S. Pat. No. 9,017,336;

U.S. patent application Ser. No. 10/146,862 to Park et al., titled "Improved Total Joint Arthroplasty System" and filed May 15, 2002; U.S. patent Ser. No. 11/642,385 to Park et al., titled "Arthroplasty Devices and Related Methods" and filed Dec. 19, 2006.

FIG. 52B is an isometric view of a computer model of a femur implant 34' and a computer model of a tibia implant 34" in position relative to each to form an artificial knee joint 14. The computer models 34', 34" may be formed, for example, via computer aided drafting or 3D modeling programs. As will be discussed later in this detailed description, the implant computer models may be in 2D or in 3D as necessary for the particular planning step.

The femur implant model 34' will have a joint side $240z$ and a bone engaging side $245z$. The joint side $240z$ will have a condyle-like surface for engaging a complementary surface of the tibia implant model 34". The bone engaging side $245z$ will have surfaces and engagement features $250z$ for engaging the prepared (i.e., sawed to shape) lower end of the femur 18.

The tibia implant model 34" will have a joint side $255z$ and a bone engaging side $260z$. The joint side $255z$ will have a plateau-like surface configured to engage the condyle-like surface of the femur implant model 34'. The bone engaging side $260z$ will have an engagement feature $265z$ for engaging the prepared (i.e., sawed to shape) upper end of the tibia 20.

As discussed in the next subsections of this Detailed Description, the reference data of the femur and tibia bone models or images 28', 28" may be used in conjunction with the implant models 34', 34" to select the appropriate sizing for the implants actually to be used for the patient. The resulting selections can then be used for planning purposes, as described later in this Detailed Description.

D. Femur Planning Process

For a discussion of the femur planning process, reference is now made to FIGS. 53-58. FIGS. 53-58 illustrate a process in the POP wherein the system 4 utilizes 2D imaging slices (e.g., MRI slices, CT slices, etc.) to determine femur reference data, such as reference points, lines and planes via their relationship to the trochlear groove plane-GHO of the femur. The resulting femur reference data $100z$ is then mapped or projected to a y-z coordinate system (sagittal plane). The femur reference data is then applied to a candidate femur implant model, resulting in femoral implant reference data $100z'$. The data $100z$, $100z'$ is utilized to select an appropriate set of candidate implants, from which a single candidate implant will be chosen, which selection will be discussed in more detail below with reference to FIGS. 59-71.

1. Determining Femur Reference Data

Figure 53:
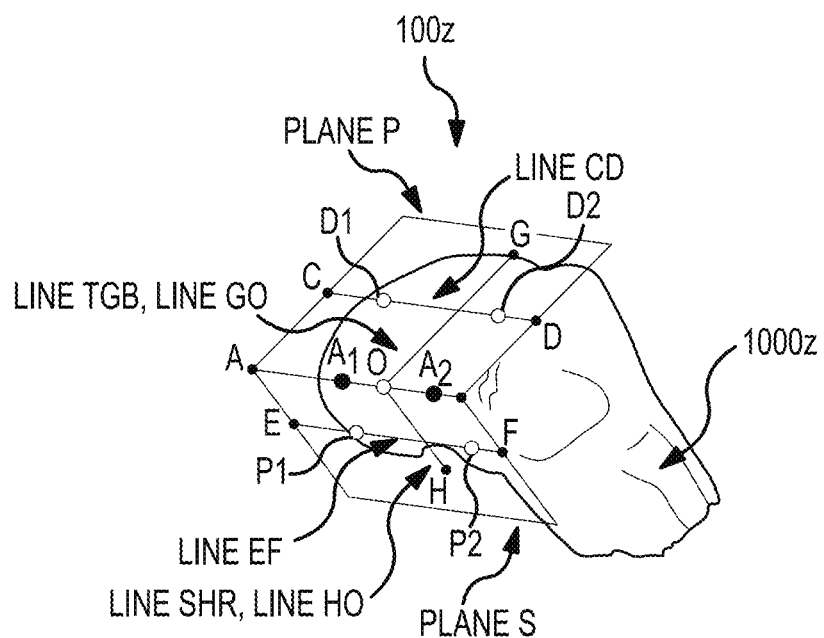
FIG. 53 is a perspective view of the distal end of 3D model of the femur wherein the femur reference data is shown.

For a discussion of a process used to determine the femur reference data, reference is now made to FIGS. 53-56C. FIG. 53 is a perspective view of the distal end of a 3D model $1000z$ of the femur image of FIG. 52A wherein the femur reference data $100z$ is shown. As will be explained in more detail below, the femur reference data is generated by an analysis of the 2D image scans and FIG. 53 depicts the relative positioning of the reference data on a 3D model. As shown in FIG. 53, the femur reference data $100z$ may include reference points (e.g. D1, D2), reference lines (e.g. GO, EF) and reference planes (e.g. P, S). The femur reference data $100z$ may be determined by a process illustrated in FIGS. 54A-56D and described in the next sections.

Figure 54A:
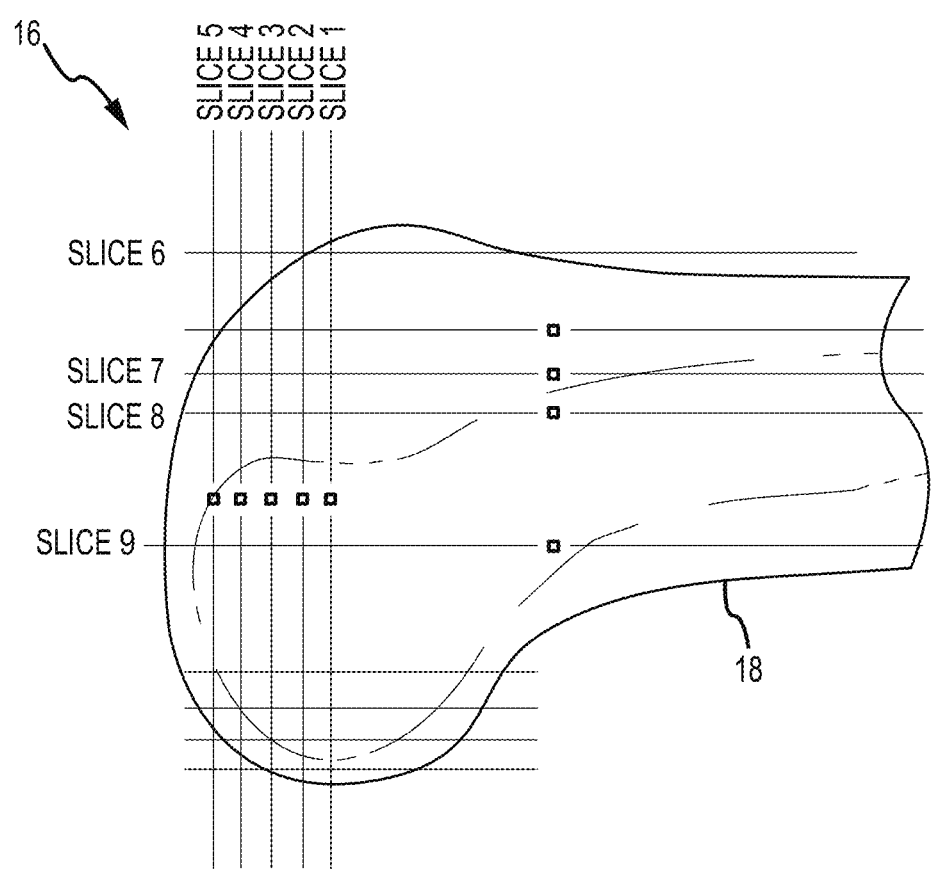
FIG. 54A is a sagittal view of a femur illustrating the orders and orientations of imaging slices utilized in the femur POP.
Figure 54B:
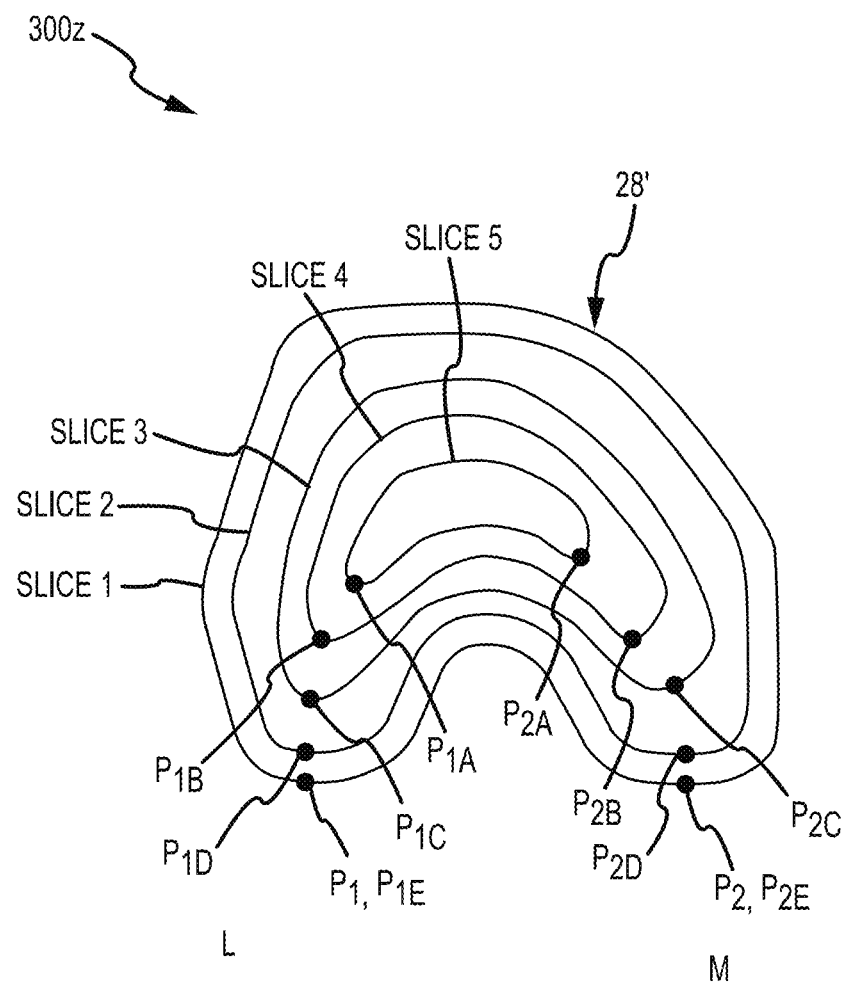
FIG. 54B depicts axial imaging slices taken along section lines of the femur of FIG. 54A.
Figure 54C:
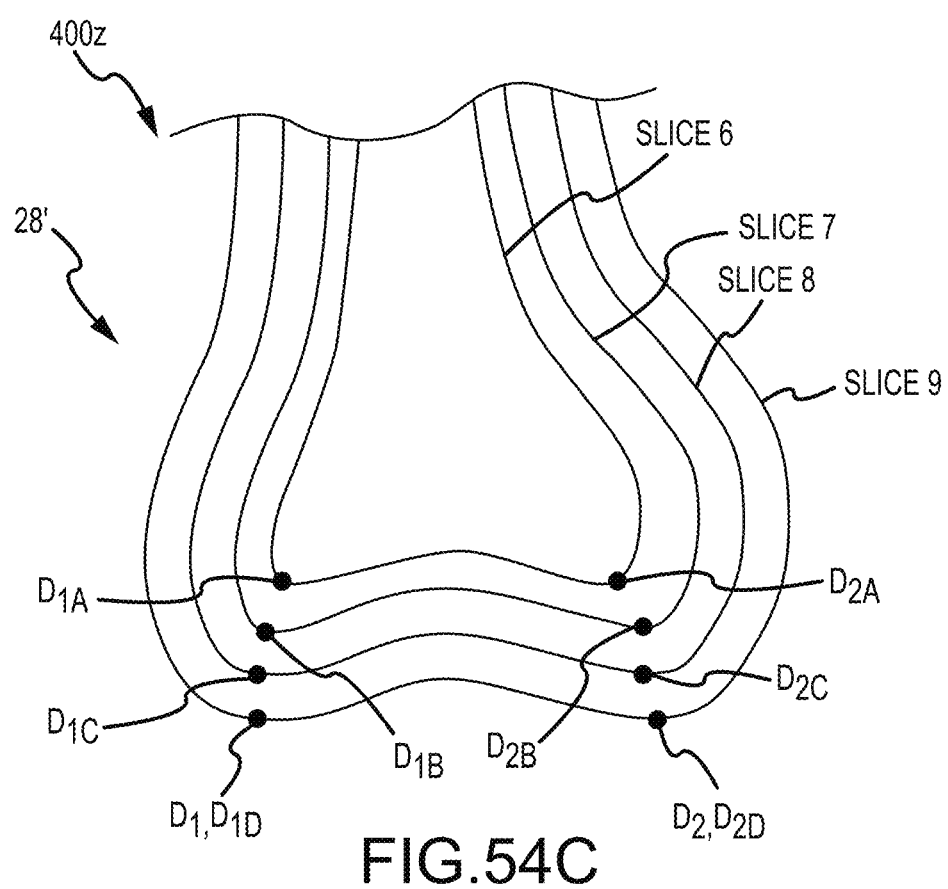
FIG. 54C depicts coronal imaging slices taken along section lines of the femur of FIG. 54A.

As shown in FIG. 54A, which is a sagittal view of a femur 18 illustrating the orders and orientations of imaging slices 16 that are utilized in the femur POP, a multitude of image slices may be compiled. In some embodiments, the image slices may be analyzed to determine, for example, distal contact points prior to or instead of being compiled into a bone model. Image slices may extend medial-lateral in planes that would be normal to the longitudinal axis of the femur, such as image slices 1-5 of FIGS. 54A and 55D. Image slices may extend medial-lateral in planes that would be parallel to the longitudinal axis of the femur, such as image slices 6-9 of FIGS. 54A and 56B. The number of image slices may vary from 1-50 and may be spaced apart in a 2 mm spacing or other spacing.

a. Determining Reference Points P1P2

In some embodiments, the planning process begins with the analysis of the femur slices in a 2D axial view. As can be understood from FIG. 54B, which depicts axial imaging slices of FIG. 54A, the series of 2D axial femur slices are aligned to find the most posterior point of each condyle. For example, the most posterior points of slice 5, P1A, P2A, are compared to the most posterior points of slice 4, P1B, P2B. The most posterior points of slice 4 are more posterior than those of slice 5. Therefore, the points of slice 4 will be compared to slice 3. The most posterior points of slice 3, P1C, P2C, are more posterior than the posterior points P1B, P2B of slice 4. Therefore, the points of slice 3 will be compared to slice 2. The most posterior points of slice 2, P1D, P2D, are more posterior than the posterior points P1C, P2C of slice 3. Therefore, the points of slice 2 will be compared to slice 1. The most posterior points of slice 1, P1E, P2E, are more posterior than the posterior points P1D, P2D of slice 2. In some embodiments, the points of slice 1 may be compared to slice 0 (not shown). The most posterior points of slice 0, P1F, P2F, are less posterior than the posterior points P1E, P2E of slice 1. Therefore, the points of slice 1 are determined to be the most posterior points $P1P_2$ of the femur. In some embodiments, points P1 and $P_2$ may be found on different axial slices. That is, the most posterior point on the medial side and most posterior point on the lateral side may lie in different axial slices. For example, slice 2 may include the most posterior point on the lateral side, while slice 1 may include the most posterior point on the medial side. It can be appreciated that the number of slices that are analyzed as described above may be greater than five slices or less than five slices. The points P1, $P_2$ are stored for later analysis.

b. Determining Reference Points D1, D2

The planning process continues with the analysis of the femur slices in a 2D coronal view. As can be understood from FIG. 54C, which depicts coronal imaging slices of FIG. 54A, the series of 2D coronal femur slices are aligned to find the most distal point of each condyle. For example, the most distal points of slice 6, D1A, D2A, are compared to the most distal points of slice 7, D1B, D2B. The most distal points of slice 7 are more distal than those of slice 6. Therefore, the points of slice 7 will be compared to slice 8. The most distal points of slice 8, D1C, D2C, are more distal than the distal points D1B, D2B of slice 7. Therefore, the points of slice 8 will be compared to slice 9. The most distal points of slice 9, D1D, D2D, are more distal than the distal points D1C, D2C of slice 8. In some embodiments, the points of slice 9 may be compared to slice 10 (not shown). The most distal points of slice 10, D1E, D2E, are less distal than the distal points D1D, D2D of slice 9. Therefore, the points of slice 9 are determined to be the most distal points D1, D2 of the femur. In some embodiments, points D1 and D2 may be found on different coronal slices. That is, the most distal point on the medial side and most distal point on the lateral side may lie in different coronal slices. For example, slice 9 may include the most distal point on the lateral side, while slice 8 may include the most distal point on the medial side. It can be appreciated that the number of slices that are analyzed as described above may be greater than four slices or less than four slices. The points D1, D2 are stored for future analysis.

c. Determining Reference Lines CD and GO

Figure 55A:
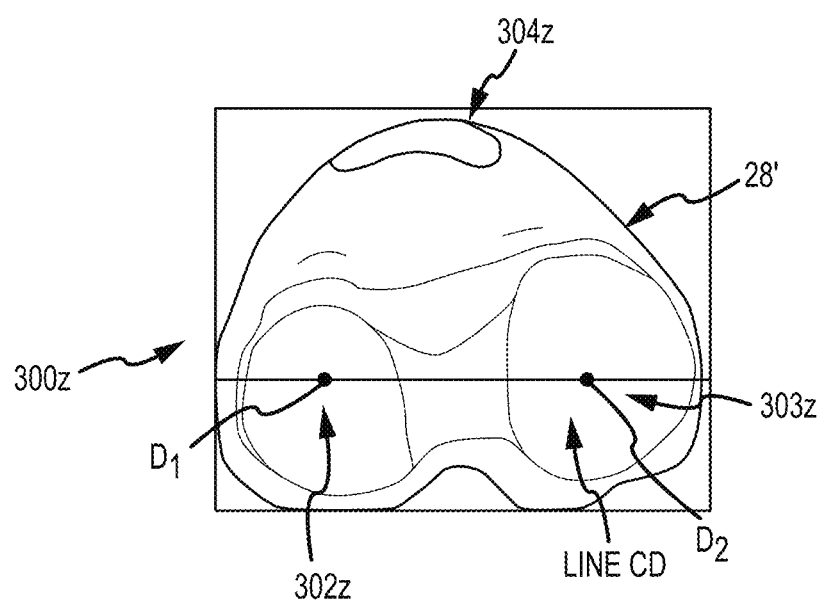
FIG. 55A is an axial imaging slice taken along section lines of the femur of FIG. 54A, wherein the distal reference points are shown.

Analysis of the 2D slices in the axial view aid in the determination of internal/external rotation adjustment. The points D1, D2 represent the lowest contact points of each of the femoral lateral and medial condyles 302z, 303z. Thus, to establish an axial-distal reference line, line CD, in 2D image slice(s), the analysis utilizes the most distal point, either D1 or D2, from the undamaged femoral condyle. For example, as shown in FIG. 55A, which is an axial imaging slice of the femur of FIG. 54A, when the lateral condyle 302z is undamaged but the medial condyle 303z is damaged, the most distal point D1 will be chosen as the reference point in establishing the axial-distal reference line, line CD. The line CD is extended from the lateral edge of the lateral condyle, through point D1, to the medial edge of the medial condyle. If the medial condyle was undamaged, then the distal point D2 would be used as the reference point through which line CD would be extended. The distal points D1, D2 and line CD are stored for later analysis.

A line CD is verified. A most distal slice of the series of axial views is chosen to verify the position of an axial-distal reference line, line CD. As shown in FIG. 55A, the most distal slice 300z of the femur (e.g., slice 5 in FIGS. 54A and 55D) is chosen to position line CD such that line CD is generally anteriorly-posteriorly centered in the lateral and medial condyles 302z, 303z. Line CD is generally aligned with the cortical bone of the undamaged posterior condyle. For example, if the medial condyle 303z is damaged, the line CD will be aligned with the undamaged lateral condyle, and vice versa. To verify the location of line CD and as can be understood from FIGS. 53 and 55C, the line CD will also connect the most distal points D1, D2. The geography information of line CD will be stored for future analysis.

Line GO is determined. The "trochlear groove axis" or the "trochlear groove reference plane" is found. In the knee flexion/extension motion movement, the patella 304z generally moves up and down in the femoral trochlear groove along the vertical ridge and generates quadriceps forces on the tibia. The patellofemoral joint and the movement of the femoral condyles play a major role in the primary structure and mechanics across the joint. In a normal knee model or properly aligned knee, the vertical ridge of the posterior patella is generally straight (vertical) in the sliding motion. For the OA patients' knees, there is rarely bone damage in the trochlear groove; there is typically only cartilage damage. Therefore, the trochlear groove of the distal femur can serve as a reliable bone axis reference. In relation to the joint line assessment, as discussed with reference to FIGS. 63A-63J, the trochlear groove axis of the distal femur is perpendicular or nearly perpendicular to the joint line of the knee. A detailed discussion of the trochlear groove axis or the trochlear groove reference plane may be found in co-owned U.S. patent application Ser. No. 12/111,924, now U.S. Pat. No. 8,480,679, which is incorporated by reference in its entirety.

Figure 55B:
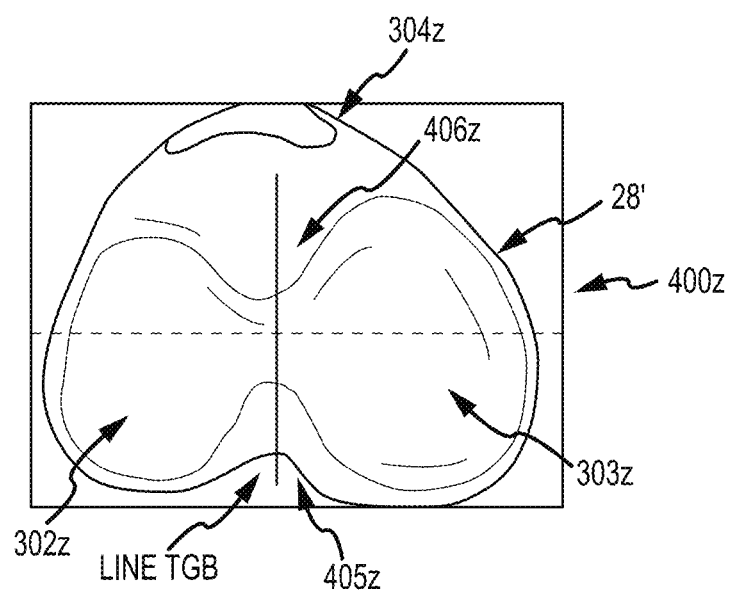
Figure 55C:
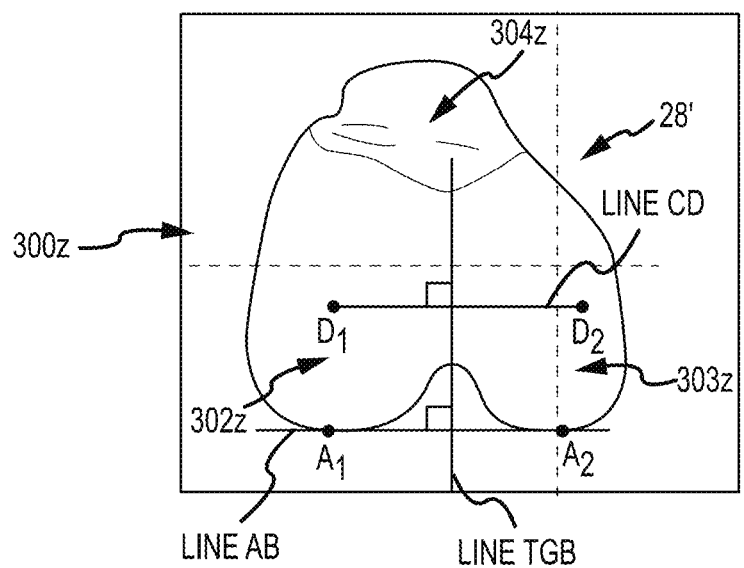
Figure 55D:
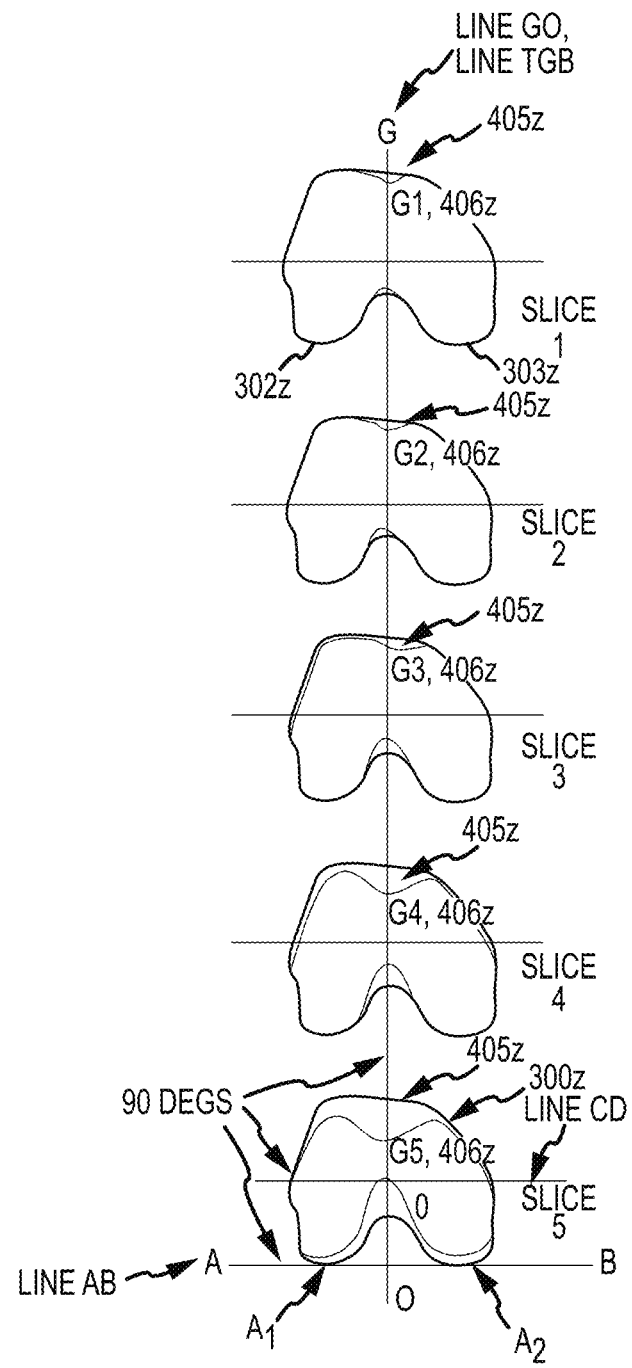

To perform the trochlear groove analysis, the MRI slice in the axial view with the most distinct femoral condyles (e.g., the slice with the largest condyles such as slice 400z of FIG. 55B) will be chosen to position the trochlear groove bisector line, line TGB. As shown in FIG. 55B, which is an axial imaging slice of the femur of FIG. 54A, the most distinct femoral condyles 302z, 303z are identified. The trochlear groove 405z is identified from image slice 400z. The lowest extremity 406z of the trochlear groove 405z is then identified. Line TGB is then generally aligned with the trochlear groove 405z across the lowest extremity 406z. In addition, and as shown in FIG. 55D, which is the axial imaging slices 1-5 taken along section lines 1-5 of the femur in FIG. 54A, each of the slices 1-5 can be aligned vertically along the trochlear groove 405z, wherein points G1, G2, G3, G4, G5 respectively represent the lowest extremity 406z of trochlear groove 405z for each slice 1-5. By connecting the various points G1, G2, G3, G4, G5, a point O can be obtained. As can be understood from FIGS. 53 and 55C, resulting line GO is perpendicular or nearly perpendicular to line D1 D2. In a 90° knee extension, line GO is perpendicular or nearly perpendicular to the joint line of the knee and line P1P2. Line GO is stored for later analysis.

d. Determining Reference Lines EF and HO

Figure 56A:
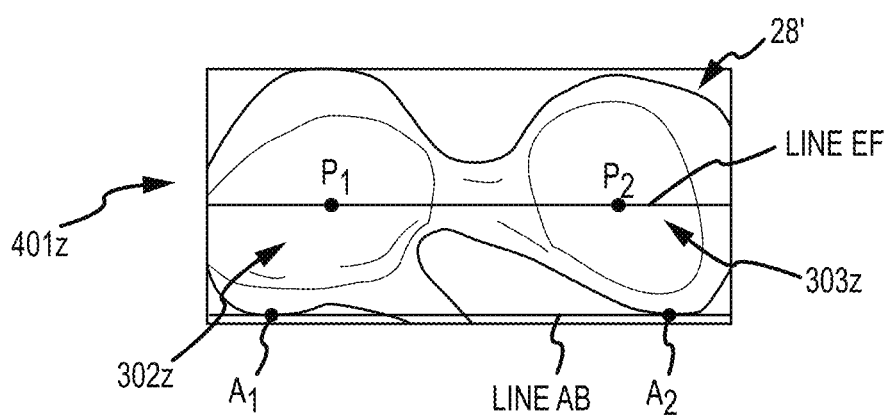

Analysis of the 2D slices in the coronal view aid in the determination of femoral varus/valgus adjustment. The points P1, $P_2$ determined above represent the most posterior contact points of each of the femoral lateral and medial condyles 302z, 303z. Thus, to establish a coronal posterior reference line, line EF, in 2D image slice(s), the analysis utilizes the most posterior point, either P1 or $P_2$, from the undamaged femoral condyle. For example, as shown in FIG. 56A, when the lateral condyle 302z is undamaged but the medial condyle 303z is damaged, the most posterior point P1 will be chosen as the reference point in establishing the coronal posterior reference line, line EF. The line EF is extended from the lateral edge of the lateral condyle, through point P1, to the medial edge of the medial condyle. If the medial condyle was undamaged, then the posterior point $P_2$ would be used as the reference point through which line EF would be extended. The posterior points P1, $P_2$ and line EF are stored for later analysis.

The points, P1$P_2$ were determined as described above with reference to FIG. 54B. Line EF is then verified. A most posterior slice of the series of coronal views is chosen to verify the position of a coronal posterior reference line, line EF. As shown in FIG. 56A, which is a coronal imaging slice of FIG. 54A, the most posterior slice 401 of the femur (e.g., slice 6 in FIGS. 54A and 56B) is chosen to position line EF such that line EF is generally positioned in the center of the lateral and medial condyles 302z, 303z. Line EF is generally aligned with the cortical bone of the undamaged posterior condyle. For example, if the medial condyle 303z is damaged, the line EF will be aligned with the undamaged lateral condyle, and vice versa. To verify the location of line EF and as can be understood from FIG. 53, the line EF will also connect the most posterior points P1, $P_2$. The geography information of line EF will be stored for future analysis.

Figure 56B:
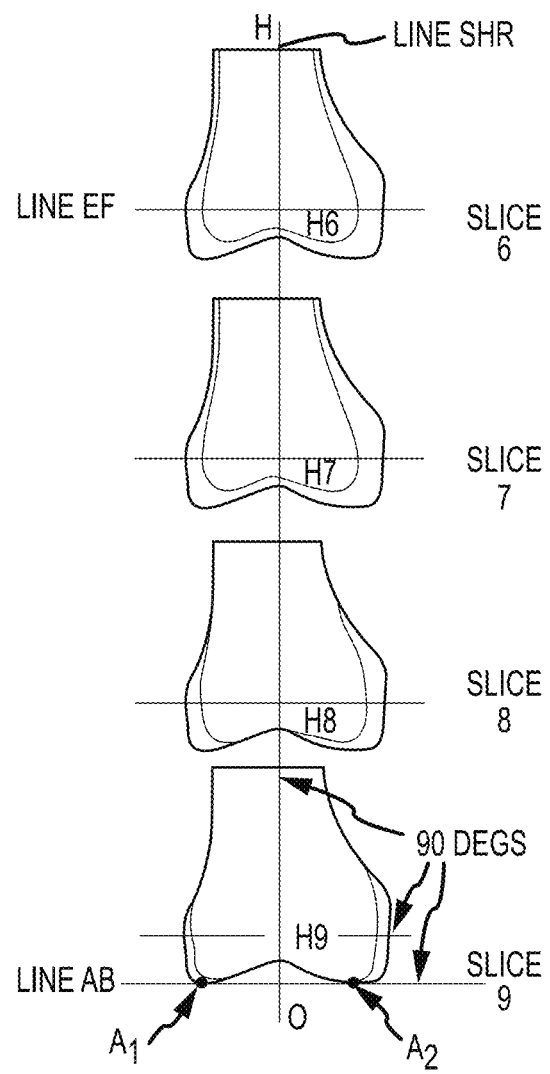

In some embodiments, line HO may be determined. As shown in FIG. 56B, which are coronal imaging slices 6-9 taken along section lines 6-9 of the femur in FIG. 54A, each of the image slices 6-9 taken from FIG. 54A can be aligned along the trochlear groove. The points H6, H7, H8, H9 respectively represent the lowest extremity of the trochlear groove for each of the image slices 6-8 from FIG. 54A. By connecting the various points H6, H7, H8, the point O can again be obtained. The resulting line HO is established as the shaft reference line-line SHR. The coronal-posterior reference line, line EF and coronal-distal reference line, line AB may be adjusted to be perpendicular or nearly perpendicular to the shaft reference line-line SHR (line HO). Thus, the shaft reference line, line SHR (line HO) is perpendicular or nearly perpendicular to the coronal-posterior reference line, line EF and to the coronal-distal reference line, line AB throughout the coronal image slices.

As can be understood from FIGS. 53 and 56B, the trochlear groove plane-GHO, as the reference across the most distal extremity of the trochlear groove of the femur and in a 90° knee extension, should be perpendicular to line AB. The line-HO, as the reference across the most posterior extremity of trochlear groove of the femur and in a 0° knee extension, should be perpendicular to line AB.

e. Determining Reference Line AB and Reference Planes P and S

As can be understood from FIG. 53, a posterior plane S may be constructed such that the plane S is normal to line GO and includes posterior reference points P1, $P_2$. A distal plane P may be constructed such that it is perpendicular to posterior plane S and may include distal reference points D1, D2 (line CD). Plane P is perpendicular to plane S and forms line AB therewith. Line HO and line GO are perpendicular or nearly perpendicular to each other. Lines CD, AB and EF are parallel or nearly parallel to each other. Lines CD, AB and EF are perpendicular or nearly perpendicular to lines HO and GO and the trochlear plane GHO.

f. Verification of the Femoral Reference Data

Figure 56C:
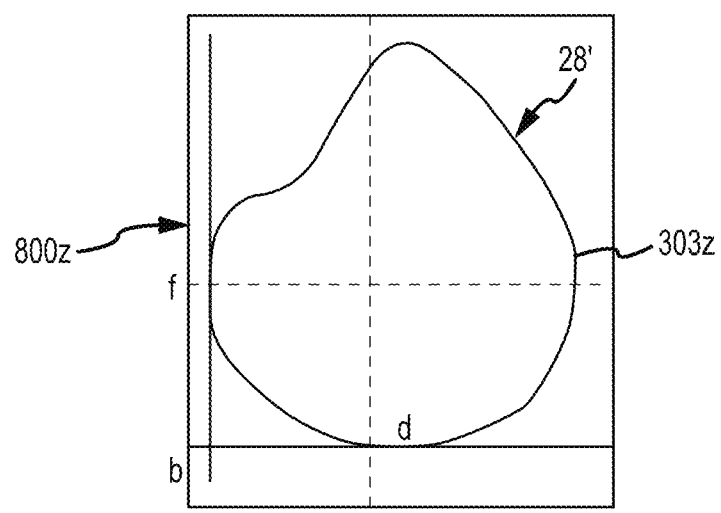

As shown in FIG. 56C, which is an imaging slice of the femur of FIG. 54A in the sagittal view, after the establishment of the reference lines from the axial and coronal views, the axial-distal reference line CD and coronal-posterior reference line EF and planes P, S are verified in the 2D sagittal view. The sagittal views provide the extension/flexion adjustment. Thus, as shown in FIG. 56C, slice 800z shows a sagittal view of the femoral medial condyle 303z. Line-bf and line-bd intersect at point-b. As can be understood from FIGS. 53 and 56C, line-bf falls on the coronal plane-S, and line-bd falls on the axial plane-P. Thus, in one embodiment of POP planning, axial and coronal views are used to generate axial-distal and coronal-posterior reference lines CD, EF. These two reference lines CD, EF can be adjusted (via manipulation of the reference data once it has been imported and opened on the computer) to touch in the black cortical rim of the femur. The adjustment of the two reference lines on the femur can also be viewed simultaneously in the sagittal view of the MRI slice, as displayed in FIG. 56C. Thus, the sagittal view in FIG. 56C provides one approach to verify if the two reference lines do touch or approximately touch with the femur cortical bone. In some embodiments, line-bf is perpendicular or nearly perpendicular to line-bd. In other embodiments, line bf may not be perpendicular to bd. This angle depends at least partially on the rotation of femoral bone within MRI.

With reference to FIGS. 53-56C, in one embodiment, lines HO and GO may be within approximately six degrees of being perpendicular with lines P1P2, D1D2 and A1A2 or the preoperative planning for the distal femur will be rejected and the above-described processes to establish the femoral reference data 100z (e.g. reference lines CD, EF, AB, reference points P1P2, D1D2) will be repeated until the femoral reference data meets the stated tolerances, or a manual segmentation for setting up the reference lines will be performed. In other embodiments, if there are multiple failed attempts to provide the reference lines, then the reference data may be obtained from another similar joint that is sufficiently free of deterioration. For example, in the context of knees, if repeated attempts have been made without success to determined reference data in a right knee medial femur condyle based on data obtained from the right knee lateral side, then reference data could be obtained from the left knee lateral or medial sides for use in the determination of the femoral reference data.

g. Mapping the Femoral Reference Data to a Y-Z Plane

Figure 56D:
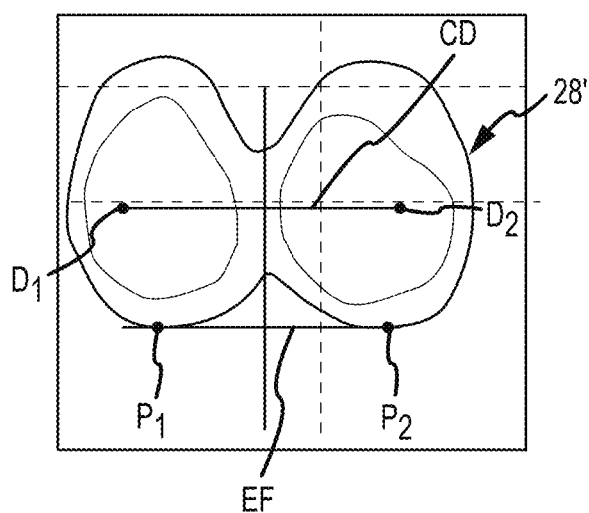
Figure 56E:
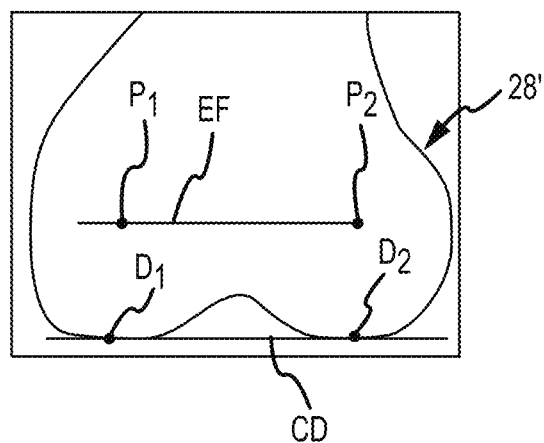

As can be understood from FIGS. 56D-58, the femoral reference data 100z will be mapped to a y-z coordinate system to aid in the selection of an appropriate implant. As shown in FIGS. 56D-56E, which are axial and coronal slices, respectively, of the femur, the points D1D2 of the distal reference line D1D2 or CD were determined from both a 2D axial view and a 2D coronal view and therefore are completely defined in 3D. Similarly, the points $P1P_2$ of the posterior reference line $P1P_2$ or EF were determined from both a 2D axial view and a 2D coronal view and therefore are completely defined in 3D.

Figure 57:
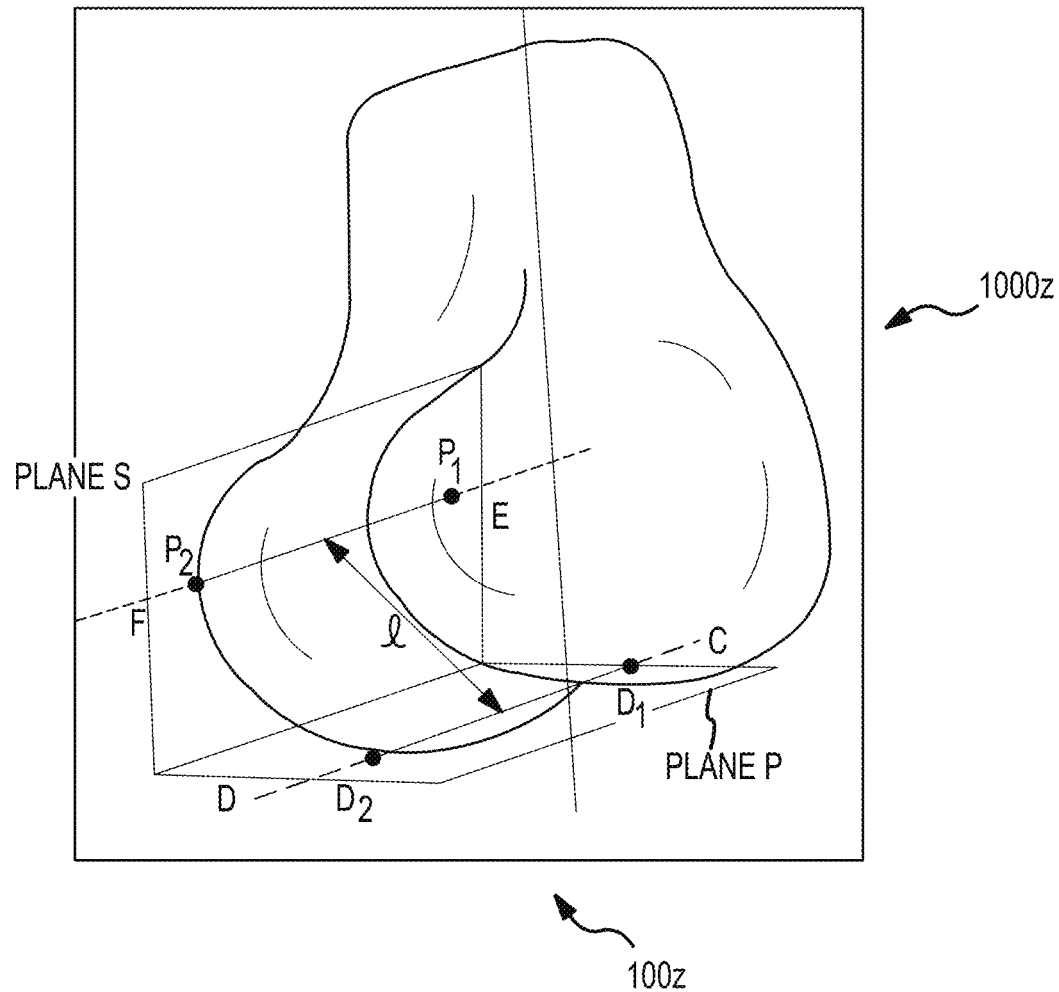

As shown in FIG. 57, which is a posterior view of a femur 3D model 1000z, the reference data 100z determined by an analysis of 2D images may be imported onto a 3D model of the femur for verification purposes. The distance L between line EF and line CD can be determined and stored for later analysis during the selection of an appropriate implant size.

Figure 58:
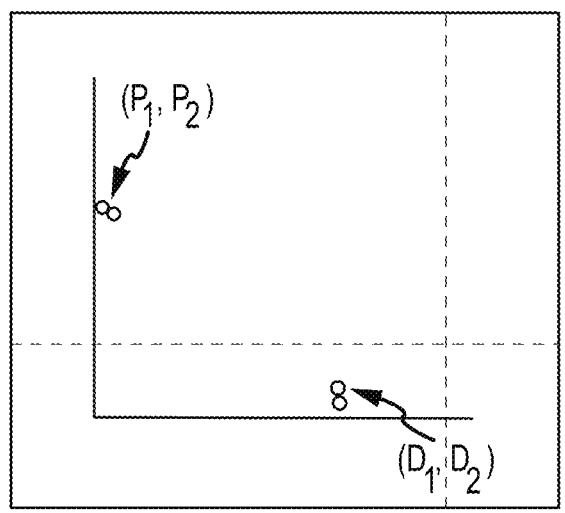

As indicated in FIG. 58, which depicts a y-z coordinate system, the posterior points $P1P_2$ and distal points D1D2 of the 2D images 28' may also be projected onto a y-z plane and this information is stored for later analysis.

2. Determining Femoral Implant Reference Data

Figure 59:
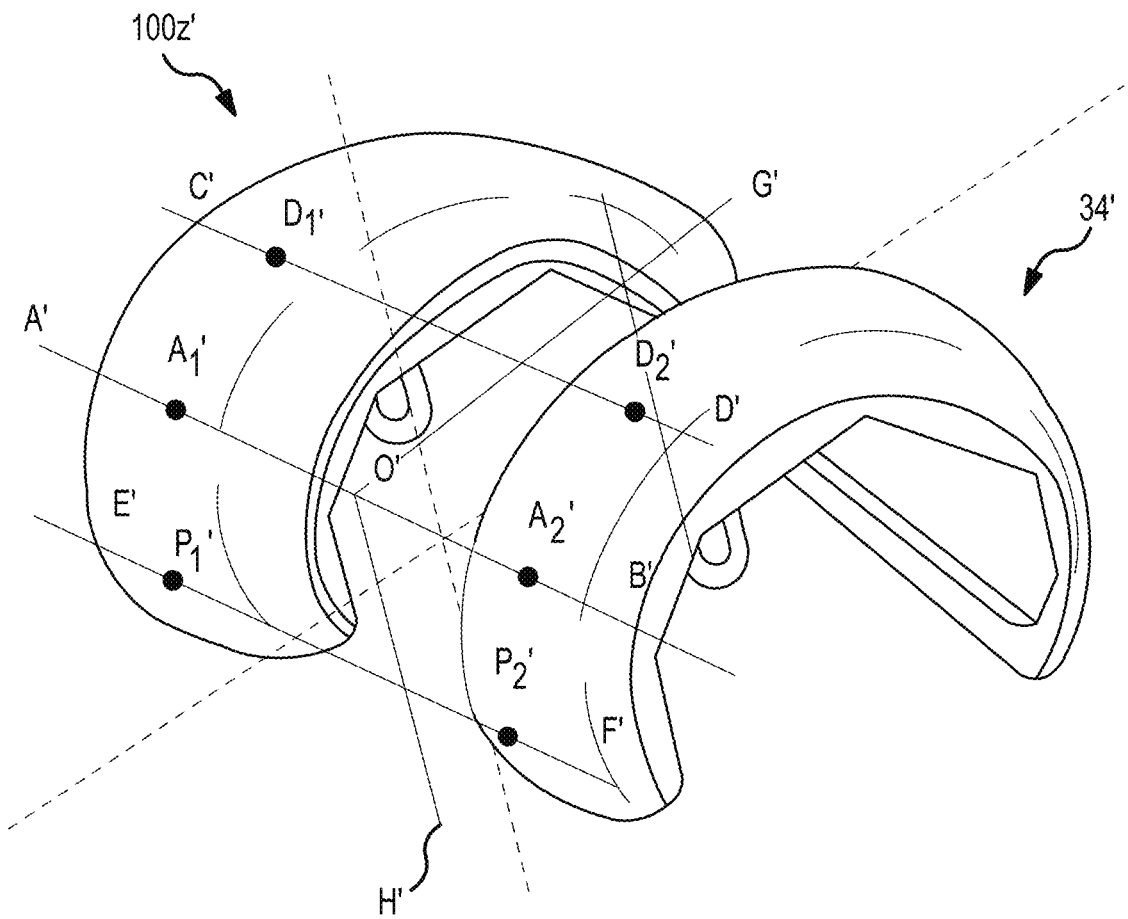
Figure 60:
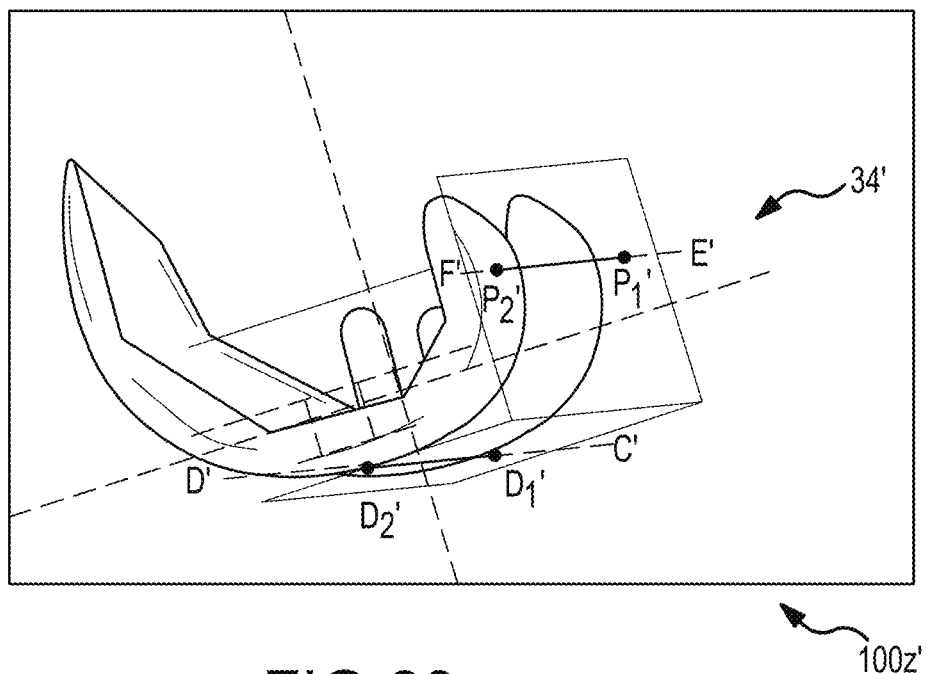

There are 6 degrees of freedom for a femoral implant to be moved and rotated for placement on the femoral bone. The femur reference data 100z (e.g. points P1P2, D1D2, reference lines EF, CD, reference planes P, S) is utilized in the selection and placement of the femoral implant. For a discussion of a process used to determine the implant reference data, reference is now made to FIGS. 59-71.

a. Map Femur Reference Data to Implant Model to Establish Femoral Implant Reference Data As shown in FIGS. 59 and 60, which are perspective views of a femoral implant model 34', the femur reference data 100z may be mapped to a 3D model of the femur implant model 34' in a process of POP. The femur reference data 100z and the femur implant model 34' are opened together. The femur implant model 34' is placed on a 3D coordinate system and the data 100z is also transferred to that coordinate system thereby mapping the data 100z to the model 34' to create femoral implant data 100z'. The femoral implant data 100z' includes an axial-distal reference line (line-C'D') and a coronal-posterior reference line (line-E'F').

As can be understood from FIGS. 59 and 60, distal line-D1'D2' represents the distance between the two most distal points D1', D2'. Posterior line-$P1'P_2'$ represents the distance between the two most posterior points P1', $P_2'$. The lines-D1'D2' $P1'P_2'$ of the implant model 34' can be determined and stored for further analysis.

Figure 61:
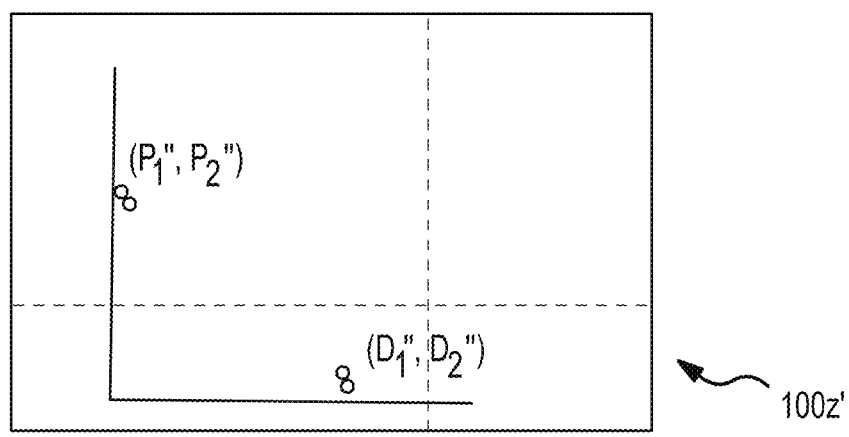

As shown in FIG. 61, which shows a coordinate system wherein some of the femoral implant reference data 100z' is shown, the endpoints D1'D2' and $P1'P_2'$ may also be projected onto a y-z plane and this information is stored for later analysis. As shown in FIG. 62, the implant reference data 100z' may also be projected onto the coordinate system. The distance L' between line E'F' and line C'D', and more specifically between lines D1'D2', $P1'P_2'$ can be determined and stored for later use during the selection of an implant.

3. Determining Joint Line and Adjustment to Implant that Allows Condylar Surfaces of Implant Model to Restore Joint to Natural Configuration In order to allow an actual physical arthroplasty implant to restore the patient's knee to the knee's pre-degenerated or natural configuration with the natural alignment and natural tensioning in the ligaments, the condylar surfaces of the actual physical implant generally replicate the condylar surfaces of the pre-degenerated joint bone. In one embodiment of the systems and methods disclosed herein, condylar surfaces of the 2D implant model 34' are matched to the condylar surfaces of the 2D bone model or image 28'. However, because the bone model 28' may be bone only and not reflect the presence of the cartilage that actually extends over the pre-degenerated condylar surfaces, the alignment of the implant 34' may be adjusted to account for cartilage or proper spacing between the condylar surfaces of the cooperating actual physical implants (e.g., an actual physical femoral implant and an actual physical tibia implant) used to restore the joint such that the actual physical condylar surfaces of the actual physical cooperating implants will generally contact and interact in a manner substantially similar to the way the cartilage covered condylar surfaces of the pre-degenerated femur and tibia contacted and interacted. Thus, in one embodiment, the implant models are modified or positionally adjusted to achieve the proper spacing between the femur and tibia implants.

a. Determine Adjustment Value tr

To achieve the correct adjustment, an adjustment value tr may be determined. In one embodiment, the adjustment value tr may be determined in 2D by a calipers measuring tool (a tool available as part of the software). The calipers tool is used to measure joint spacing between the femur and the tibia by selection of two points in any of the 2D MRI views and measuring the actual distance between the points. In another embodiment, the adjustment value tr that is used to adjust the implant during planning may be based off of an analysis associated with cartilage thickness. In another embodiment, the adjustment value tr used to adjust the implant during planning may be based off of an analysis of proper joint gap spacing. Both the cartilage thickness and joint gap spacing methods are discussed below in turn.

i. Determining Cartilage Thickness and Joint Line

FIG. 63A shows the femoral condyle 310z and the proximal tibia of the knee in a sagittal MRI image slice. The distal femur 28' is surrounded by the thin black rim of cortical bone. Due to the nature of irregular bone and cartilage loss in OA patients, it can be difficult to find the proper joint line reference for the models used during the POP.

The space between the elliptical outlining 325z', 325z" along the cortical bone represents the cartilage thickness of the femoral condyle 310z. The ellipse contour of the femoral condyle 310z can be seen on the MRI slice shown in FIG. 63A and obtained by a three-point tangent contact spot (i.e., point t1, t2, t3) method. In a normal, healthy knee, the bone joint surface is surrounded by a layer of cartilage. Because the cartilage is generally worn-out in OA and the level of cartilage loss varies from patient to patient, it may be difficult to accurately account for the cartilage loss in OA patients when trying to restore the joint via TKA surgery. Therefore, in one embodiment of the methodology and system disclosed herein, a minimum thickness of cartilage is obtained based on medical imaging scans (e.g., MRI, etc.) of the undamaged condyle. Based on the cartilage information, the joint line reference can be restored. For example, the joint line may be line 630z in FIG. 63B.

The system and method disclosed herein provides a POP method to substantially restore the joint line back to a "normal or natural knee" status (i.e., the joint line of the knee before OA occurred) and preserves ligaments in TKA surgery (e.g., for a total knee arthroplasty implant) or partial knee arthroplasty surgery (e.g., for a uni-knee implant).

FIG. 63B is a coronal view of a knee model in extension. As depicted in FIG. 63B, there are essentially four separate ligaments that stabilize the knee joint, which are the medial collateral ligament (MCL), anterior cruciate ligament (ACL), lateral collateral ligament (LCL), and posterior cruciate ligament (PCL). The MCL and LCL lie on the sides of the joint line and serve as stabilizers for the side-to-side stability of the knee joint. The MCL is a broader ligament, whereas the LCL is a distinct cord-like structure.

The ACL is located in the front part of the center of the joint. The ACL is a very important stabilizer of the femur on the tibia and serves to prevent the tibia from rotating and sliding forward during agility, jumping, and deceleration activities. The PCL is located directly behind the ACL and serves to prevent the tibia from sliding to the rear. The system and method disclosed herein provides POP that allows the preservation of the existing ligaments without ligament release during TKA surgery. Also, the POP method provides ligament balance, simplifying TKA surgery procedures and reducing pain and trauma for OA patients.

As indicated in FIG. 63B, the joint line reference 630z is defined between the two femoral condyles 302z, 303z and their corresponding tibia plateau regions 404z, 406z. Area A illustrates a portion of the lateral femoral condyle 302z and a portion of the corresponding lateral plateau 404z of tibia 205z. Area B illustrates the area of interest showing a portion of the medial femoral condyle 303z and a portion of the corresponding medial plateau 406z of tibia 205z.

FIGS. 63C, 63D and 63F illustrate MRI segmentation slices for joint line assessment. FIG. 63E is a flow chart illustrating the method for determining cartilage thickness used to determine proper joint line. The distal femur 200z is surrounded by the thin black rim of cortical bone 645z. The cancellous bone (also called trabecular bone) 650z is an inner spongy structure. An area of cartilage loss 655z can be seen at the posterior distal femur. For OA patients, the degenerative cartilage process typically leads to an asymmetric wear pattern that results in one femoral condyle with significantly less articulating cartilage than the other femoral condyle. This occurs when one femoral condyle is overloaded as compared to the other femoral condyle.

As can be understood from FIGS. 63C, 63E and 63F, the minimum cartilage thickness is observed and measured for the undamaged and damaged femoral condyle 302z, 303z [block 1170]. If the greatest cartilage loss is identified on the surface of medial condyle 303z, for example, then the lateral condyle 302z can be used as the cartilage thickness reference for purposes of POP. Similarly, if the greatest cartilage loss is identified on the lateral condyle 302z, then the medial condyle 303z can be used as the cartilage thickness reference for purposes of POP. In other words, use the cartilage thickness measured for the least damaged condyle cartilage as the cartilage thickness reference for POP [block 1175].

As indicated in FIG. 63D, the thickness of cartilage can be analyzed in order to restore the damaged knee compartment back to its pre-OA status. In each of the MRI slices taken in regions A and B in FIG. 63B, the reference lines as well as the major and minor axes 485z, 490z of ellipse contours 480z', 480z" in one femoral condyle 303z can be obtained.

As shown in FIG. 63F, for the three-point method, the tangents are drawn on the condylar curve at zero degrees and 90 degrees articular contact points. The corresponding tangent contact spots t1 and t2 are obtained from the tangents. The line 1450z perpendicular to the line 1455z determines the center of the ellipse curve, giving the origin of (0, 0). A third tangent contact spot t3 can be obtained at any point along the ellipse contour between the zero degree, t1 point and the 90 degree, t2 point. This third spot t3 can be defined as k, where k=1 to n points.

The three-point tangent contact spot analysis may be employed to configure the size and radius of the condyle $303z$ of the femur bone model $28'$. This provides the "x" coordinate and "y" coordinate, as the (x, y) origin (0, 0) shown in FIG. 63D. The inner ellipse model $480z'$ of the femoral condyle shows the femoral condyle surrounded by cortical bone without the cartilage attached. The minimum cartilage thickness tmmin outside the inner ellipse contour $480z'$ is measured. Based on the analysis of the inner ellipse contour $480z'$ (i.e., the bone surface) and outer ellipse contour $480z''$ (i.e., the cartilage surface) of the one non-damaged condyle of the femur bone model $28'$, the inner ellipse contour $480z'$ (i.e., the bone surface) and the outer ellipse contour $480z''$ (i.e., the cartilage surface) of the other condyle (i.e., the damage or deteriorated condyle) may be determined.

As can be understood from FIGS. 63B and 63D, ellipse contours $480z'$, $480z''$ are determined in areas A and B for the condyles $302z$, $303z$ of the femur bone model $28'$. The inner ellipse contour $480z'$, representing the bone-only surface, and the outer ellipse contour $480z''$, representing the bone-and-cartilage surface, can be obtained. The minimum cartilage thickness tmmin is measured based on the cartilage thickness tr between the inner ellipse $480z'$ and outer ellipse $480z''$. MRI slices of the two condyles $302z$, $303z$ of the femur bone model $28'$ in areas A and B are taken to compare the respective ellipse contours in areas A and B. If the cartilage loss is greatest at the medial condyle $303z$ in the MRI slices, the minimum thickness tmmin for the cartilage can be obtained from the lateral condyle $302z$. Similarly, if the lateral condyle $302z$ has the greatest cartilage loss, the cartilage thickness tmmin can be obtained from undamaged medial condyle $303z$ of the femur restored bone model $28'$. The minimum cartilage can be illustrated in the formula, tmmin=MIN (ti), where i=1 to k.

ii. Determining Joint Gap

As mentioned above, in one embodiment, the adjustment value tr may be determined via a joint line gap assessment. The gap assessment may serve as a primary estimation of the gap between the distal femur and proximal tibia of the bone images. The gap assessment may help achieve proper ligament balancing.

In one embodiment, an appropriate ligament length and joint gap may not be known from the 2D bone models or images $28'$, $28''$ (see, e.g. FIG. 52B) as the bone models or images may be oriented relative to each other in a fashion that reflects their deteriorated state. For example, as depicted in FIG. 63J, which is a coronal view of bone models $28'$, $28''$ oriented (e.g., tilted) relative to each other in a deteriorated state orientation, the lateral side $1487z$ was the side of the deterioration and, as a result, has a greater joint gap between the distal femur and the proximal tibia than the medial side $1485z$, which was the non-deteriorated side of the joint in this example.

In one embodiment, ligament balancing may also be considered as a factor for selecting the appropriate implant size. As can be understood from FIG. 63J, because of the big joint gap in the lateral side $1487z$, the presumed lateral ligament length (L1+L2+L3) may not be reliable to determine proper ligament balancing. However, the undamaged side, which in FIG. 63J is the medial side $1485z$, may be used in some embodiments as the data reference for a ligament balancing approach. For example, the medial ligament length (M1+M2+M3) of the undamaged medial side $1485z$ may be the reference ligament length used for the ligament balancing approach for implant size selection.

In one embodiment of the implant size selection process, it may be assumed that the non-deteriorated side (i.e., the medial side $1485z$ in FIG. 63J in this example) may have the correct ligament length for proper ligament balancing, which may be the ligament length of (M1+M2+M3). When the associated ligament length ("ALL") associated with a selected implant size equals the correct ligament length of (M1+M2+M3), then the correct ligament balance is achieved, and the appropriate implant size has been selected. However, when the ALL ends up being greater than the correct ligament length (M1+M2+M3), the implant size associated with the ALL may be incorrect and the next larger implant size may need to be selected for the design of the arthroplasty jig $2$.

For a discussion regarding the gap assessment, which may also be based on ligament balance off of a non-deteriorated side of the joint, reference is made to FIGS. 63G and 63H. FIGS. 63G and 63H illustrate coronal views of the bone models $28'$, $28''$ in their post-degeneration alignment relative to each as a result of OA or injury. As shown in FIG. 63G, the tibia model $28''$ is tilted away from the lateral side $1487z$ of the knee $1486z$ such that the joint gap between the femoral condylar surfaces $1490z$ and the tibia condylar surfaces $1491z$ on the lateral side $1487z$ is greater than the joint gap on the medial side $1485z$.

As indicated in FIG. 63H, which illustrates the tibia in a coronal cross section, the line $1495z$ may be employed to restore the joint line of the knee $1486z$. The line $1495z$ may be caused to extend across each of lowest extremity points $1496z$, $1497z$ of the respective femoral lateral and medial condyles $1498z$, $1499z$. In this femur bone model $28'$, line $1495z$ may be presumed to be parallel or nearly parallel to the joint line of the knee $1486z$.

As illustrated in FIG. 63H, the medial gap Gp2 represents the distance between the distal femoral medial condyle $1499z$ and the proximal tibia medial plateau $1477z$. The lateral gap Gp1 represents the distance between the distal femoral lateral condyle $1498z$ and the proximal tibia lateral plateau $1478z$. In this example illustrated in FIG. 63H, the lateral gap Gp1 is significantly larger than the medial gap Gp2 due to degeneration caused by injury, OA, or etc., that occurred in the lateral side $1487z$ of the knee $1486z$. It should be noted that the alignment of the bone models $28'$, $28''$ relative to each other for the example illustrated in FIGS. 63G and 63H depict the alignment the actual bones have relative to each other in a deteriorated state. To restore the joint line reference and maintain ligament balancing for the medial collateral ligament (MCL) and lateral collateral ligament (LCL), the joint line gap Gp3 that is depicted in FIG. 63I, which is the same view as FIG. 63G, except with the joint line gap Gp3 in a restored state, may be used for the joint spacing compensation adjustment as described below. As illustrated in FIG. 63I, the lines $1495z$ and $1476z$ respectively extend across the most distal contact points $1496z$, $1497z$ of the femur condyles $1498z$, $1499z$ and the most proximal contact points $1466z$, $1467z$ of the tibia plateau condyles $1477z$, $1478z$.

For calculation purposes, the restored joint line gap Gp3 may be whichever of Gp1 and Gp2 has the minimum value. In other words, the restored joint line gap Gp3 may be as follows: Gp3=MIN (Gp1, Gp2). For purposes of the adjustment for joint spacing compensation, the adjustment value tr may be calculated as being half of the value for Gp3, or in other words, tr=Gp3/2. As can be understood from FIGS. 63G-63H and 14J, in this example, the non-deteriorated side

1485z has Gp2, which is the smallest joint line gap and, therefore, Gp3=Gp2 in the example depicted in FIG. 63G-14J, and tr=Gp2/2.

In one embodiment, the joint line gap assessment may be at least a part of a primary assessment of the geometry relationship between the distal femur and proximal tibia. In such an embodiment, the joint gap assessment step may occur prior to the femur planning steps of the POP process. However, in other embodiments, the joint line gap assessment may occur at other points along the overall POP process.

b. Determine Compensation for Joint Spacing

Once the adjustment value tr is determined based off of cartilage thickness or joint line gap Gp3, the planning for the femoral implant model 34' can be modified or adjusted to compensate for the joint spacing in order to restore the joint line. As shown in FIG. 64, which is a 3D coordinate system wherein the femur reference data 100z is shown, the compensation for the joint spacing is performed both in distal and posterior approaches. Thus, the joint compensation points relative to the femur reference data are determined. As will be discussed later in this Detailed Description, the joint compensation points relative to the femur reference data will be used to determine the joint compensation relative to the femur implant.

As can be understood from FIG. 65, which is a y-z plane wherein the joint compensation points are shown, the posterior plane S and the distal plane P are moved away in the direction of normal of plane S and P respectively by the adjustment value tr. In one embodiment, the adjustment value tr is equal to the cartilage thickness. That is, the joint compensation points will be determined relative to the posterior plane S and the distal plane P which are moved away in the direction of normal of plane S and P, respectively, by an amount equal to the cartilage thickness. In some embodiments, the adjustment value tr is equal to one-half of the joint spacing. That is, the joint compensation points will be determined relative to the posterior plane S and the distal plane P which are moved away in the direction of normal of plane S and P, respectively, by an amount equal one-half the joint spacing. In other words, the femoral implant accounts for half of the joint spacing compensation, while the tibia implant will account for the other half of the joint spacing compensation.

As can be understood from FIG. 64, the femur reference data 100z was uploaded onto a coordinate system, as described above. To compensate for the joint spacing, the distal line-D1D2 is moved closer to the distal plane-P by an amount equal to the adjustment value tr, thereby resulting in joint spacing compensation points D1J, D2J and line D1JD2J. The distal plane P was previously moved by adjustment value tr. Similarly, posterior reference line $P1P_2$ is moved closer to the posterior plane-S by an amount equal to the adjustment value tr, thereby resulting in joint spacing compensation points P1J, P2J and line P1JP2J. The trochlear groove reference line-line GO does not move and remains as the reference line for the joint spacing compensation. Lines D1JD2J and P1JP2J will be stored and utilized later for an analysis related to the femoral implant silhouette curve.

4. Selecting the Sizes for the Femoral Implants

The next steps are designed to select an appropriate implant size such that the implant will be positioned within the available degrees of freedom and may be optimized by 2D optimization. There are 6 degrees of freedom for a femoral implant to be moved and rotated for placement on the femur. For example, the translation in the x direction is fixed based on the reference planes-S and P and sagittal slices of femur as shown in FIGS. 53 and 63C. Rotation around the y axis, which corresponds to the varus/valgus adjustment is fixed based on the reference lines determined by analysis of the coronal slices, namely, lines EF and AB, and coronal plane-S as shown in FIGS. 53 and 56B. Rotation around the z axis, which corresponds to internal/external rotation, is fixed by the trochlear groove reference line, line GO or TGB, axial-distal reference line, line CD, and axial-posterior reference line, line AB, as shown in the axial views in FIGS. 53 and 55A-55E. By fixing these three degrees of freedom, the position of the implant can be determined so that the outer silhouette line of the implant passes through both the distal reference line and posterior reference line. Optimization will search for a sub-optimal placement of the implant such that an additional angle of flange contact is greater than but relatively close to 7 degrees. Thus, by constraining the 3 degrees of freedom, the appropriate implant can be determined.

a. Overview of Selection of Femoral Implant

Based on previously determined femoral implant data 100z', as shown in FIGS. 60-62, a set of 3 possible sizes of implants are chosen. For each implant, the outer 2D silhouette curve of the articular surface of the candidate implant model is computed and projected onto a y-z plane, as shown in FIGS. 69A-69C. The calculated points of the silhouette curve are stored. Then, the sagittal slice corresponding to the inflection point 500z (see FIG. 70A) is found and the corresponding segmentation spline is considered and the information is stored. Then an iterative closest point alignment is devised to find the transform to match the implant to the femur.

The next sections of this Detailed Description will now discuss the process for determining the appropriate implant candidate, with reference to FIGS. 66-71.

i. Implant Selection

In one embodiment, there is a limited number of sizes of a candidate femoral implant. For example, one manufacturer may supply six sizes of femoral implants and another manufacturer may supply eight or another number of femoral implants. A first implant candidate 700z (see FIG. 66) may be chosen based on the distance L' between the posterior and distal reference lines $P1'P_2'$ and DIM' determined above in FIG. 62, with reference to the femoral implant reference data 100z'. The distance L' of the candidate implants may be stored in a database and can be retrieved from the implant catalogue. In some embodiments, a second and third implant candidate 702, 704 (not shown) may be chosen based on the distance L between the posterior and distal reference lines $P1P_2$ and D1D2 of the femur 28' determined above in FIG. 57, with reference to the femoral reference data 100z and distance L'. First implant candidate 700z has the same distance L as the patient femur. Second implant candidate 702 is one size smaller than the first implant candidate 700z. Third implant candidate 704 is one size larger than the first implant candidate 700z. In some embodiments, more than 3 implant candidates may be chosen.

The following steps 2-6 are performed for each of the implant candidates 700z, 702, 704 in order to select the appropriate femoral implant 34'.

ii. Gross Alignment of Implant onto Femur

In some embodiments, the gross alignment of the implant 34' onto the femur 28' may be by comparison of the implant reference data 100z' and the femur reference data 100z. In some embodiments, gross alignment may be via comparison of the medial-lateral extents of both the implant and the femur. In some embodiments, both gross alignment techniques may be used.

In some embodiments, as shown in FIG. 66, which shows the implant 34' placed onto the same coordinate plane with the femur reference data 100z, the implant candidate may be aligned with the femur. Alignment with the femur may be based on the previously determined implant reference lines D1'D2' and P1'P$_2$' and femur reference lines D1D2 and P1P2.

In some embodiments, and as can be understood from FIGS. 67A-67C and 68A-68C, the medial lateral extent of the femur and the implant can be determined and compared to ensure the proper initial alignment. FIG. 67A is a plan view of the joint side 240z of the femur implant model 34' depicted in FIG. 52B. FIG. 67B is an axial end view of the femur lower end 200z of the femur bone model 28' depicted in FIG. 52A. The views depicted in FIGS. 67A and 67B are used to select the proper size for the femoral implant model 34'.

As can be understood from FIG. 67A, each femoral implant available via the various implant manufacturers may be represented by a specific femoral implant 3D computer model 34' having a size and dimensions specific to the actual femoral implant. Thus, the representative implant model 34' of FIG. 67A may have an associated size and associated dimensions in the form of, for example, an anterior-posterior extent iAP and medial-lateral extent iML, which data can be computed and stored in a database. These implant extents iAP, iML may be compared to the dimensions of the femur slices from the patient's actual femur 18. For example, the femur bone 18 may have dimensions such as, for example, an anterior-proximal extent bAP and a medial-lateral extent bML, as shown in FIG. 67B. In FIG. 67A, the anterior-posterior extent iAP of the femoral implant model 34' is measured from the anterior edge 270z to the posterior edge 275z of the femoral implant model 34', and the medial-lateral extent iML is measured from the medial edge 280z to the lateral edge 285z of the femoral implant model 34'.

Each patient has femurs that are unique in size and configuration from the femurs of other patients. Accordingly, each femur slice will be unique in size and configuration to match the size and configuration of the femur medically imaged. As can be understood from FIG. 67B, the femoral anterior-posterior length bAP is measured from the anterior edge 290z of the patellofemoral groove to the posterior edge 295z of the femoral condyle, and the femoral medial-lateral length bML is measured from the medial edge 301z of the medial condyle to the lateral edge 305z of the lateral condyle. The implant extents iAP and iML and the femur extents bAP, bML may be aligned for proper implant placement as shown in FIG. 67C and along the direction of axial-distal reference line-CD.

As can be understood from FIGS. 68A-68C, these medial-lateral extents of the implant iML and femur bML can be measured from the 2D slices of the femur of FIG. 54A. For example, FIG. 68A, which shows the most medial edge of the femur in a 2D sagittal slice and FIG. 68B, which shows the most lateral edge of the femur in a 2D sagittal slice, can be used to calculate the bML of the femur 28'. The implant 34' will be centered between the medial and lateral edges, as shown in FIG. 68C, which is a 2D slice in coronal view showing the medial and lateral edges, thereby grossly aligning the implant with the femur.

iii. Determine Outer Silhouette Curve of Implant in Y-Z Plane

The silhouette of the femoral implant is the curve formed by farthest points from center in y-z plane projection of the femoral implant geometry. The points of the silhouette curve may be utilized to confirm placement of the implant onto the femur based on the femur reference lines that have been altered to account for the joint compensation.

For a discussion of the process for determining the points of the silhouette curve of the femoral implant, reference is now made to FIGS. 69A-69C. As can be understood from FIG. 69A, which is an implant 34' mapped onto a y-z plane, the points of a candidate implant are retrieved from the implant database. The points are then imported onto a y-z plane and the silhouette curve can be determined. The silhouette curve 34''' is determined by finding the points that are the farthest from the center along an outer circumference 35 of the articular surface of the implant 34'. FIG. 69B, which is the silhouette curve 34''' of the implant 34', shows the result of the silhouette curve calculations. The silhouette curve data is then imported into a y-z plane that includes the joint spacing compensation data, as shown in FIG. 69C, which is the silhouette curve 34''' aligned with the joint spacing compensation points D1JD2J and P1JP2J. The resulting joint spacing compensation and silhouette curve data 800z (e.g. D1'''D2''' P1'''P$_2$''') is stored for later analysis.

iv. Determination of Inflection Point, Flange Point, Femur Spline and Anterior Femur Cut Plane The flange point is determined and stored. As can be understood from FIG. 70A, which shows a distal femur 28' with an implant 34', the distal femur is analyzed and the flange point 500z of the implant 34' is determined relative to the anterior surface 502z of the distal end of a femur condyle 28'. FIG. 70B, which depicts a femur implant 34', illustrates the location of the flange point 500z on the implant 34' as determined by an analysis such as one illustrated in FIG. 70A.

The anterior cut plane 504z is determined and stored. The range of the anterior cut plane of the implant is determined such that the cut plane (and therefore the implant) is within certain tolerances. As shown in FIG. 70A, a cut plane 504z is determined based on the location of the implant 34' on the femur 28'. An angle A between the cut plane 504z and the flange point 500z is between approximately 7 and approximately 15 degrees. In some embodiments, the angle A is approximately 7 degrees. In some embodiments, the distal cut plane may be found as described below with respect to the final verification step. For each respective implant, the anterior cut plane and the distal cut plane are at a fixed angle for the implant. That is, once the anterior cut plane is found, the distal cut plane can be determined relative to the fixed angle and the anterior cut plane. Alternatively, once the distal cut plane is found, the anterior cut plane can be determined relative to the fixed angle and the distal cut plane.

The inflection point 506z is determined and stored. As shown in FIG. 70C, which shows a slice of the distal femur 28' in the sagittal view, the inflection point 506z is located on the anterior shaft of the spline 508 of femur 28' where the flange point 500z of the implant 34' is in contact with the femur 28'. An implant matching algorithm will match the flange point 500z of implant 34' to the spline 508 of the femur at approximately the inflection point 506z of the femur 28'. As can be understood from FIG. 70D, which shows the implant 34' positioned on the femur 28', the implant 34' should be aligned to touch the distal and posterior reference planes P, S respectively to reach proper alignment. In one embodiment, the implant matching algorithm is a customized extension of an algorithm known as iterative closest point matching.

The next section of the Detailed Description now discusses how the data and data points determined above and stored for future analysis will be used in the selection of an appropriate implant.

v. Determine Points of Set A and Set B

Determination of the data sets contained in Set A and Set B aid in determining the appropriate implant and ensuring that the chosen implant mates with the femur within certain tolerances.

The joint spacing compensation points D1JD2J and P1JP2J were determined as described with reference to FIG. 65 and are added to Set A. Next, the joint spacing compensation points D1JD2J and P1JP2J are matched to the closest respective points on the silhouette curve, as shown in FIG. 69C, thereby resulting in points $D1'''D2'''$ and $P1'''P_2'''$ or the joint spacing compensation and silhouette curve data $800z$. Points $D1'''D2'''$ and $P1'''P_2'''$ will be added to Set B.

The inflection point and flange point data are analyzed. An inflection point $506z'$ is found to represent the inflection point $506z$ that is closest in proximity to the flange point $500z$, which were both discussed with reference to FIGS. 70A-70D. The point $506z'$ is added to Set A. The flange point $500z$ is then projected to a y-z plane. The resulting flange point $500z'$ is added to Set B.

Thus, Set A contains the following points: the joint spacing compensation points D1JD2J and P1JP2J and the inflection point $506z'$. Set B contains the following points: Points $D1'''D2'''$ and $P1'''P_2'''$ (the joint spacing compensation and silhouette curve data $800z$) and the flange point $500z'$.

vi. Utilize the Data of Sets A and B

Find a rigid body transform. The data points of Set A and Set B are compared and a rigid body transform that most closely matches Set A to Set B is chosen. The rigid body transform will transform an object without scaling or deforming. That is, the rigid body transform will show a change of position and orientation of the object. The chosen transform will have rotation about the x-axis and translation in the y-z plane.

Find the inverse of the rigid body transform. The inverse of this rigid body transform is then imported into the y-z plane that also contains the femur reference lines D1D2 and $P1P_2$ and the femur spline 508 that corresponds to the flange point $500z$ of the implant 34'.

The steps described in this Detailed Description are repeated until the relative motion is within a small tolerance. In one embodiment, the steps are repeated fifty times. In some embodiments, the steps are repeated more than fifty times or less than fifty times.

In some embodiments, and as shown in FIG. 71A, an acceptable translation in y-z plane may be determined. FIG. 71A depicts an implant that is improperly aligned on a femur, but shows the range of the search for an acceptable angle A. Within this range for angle A, the translation in y-z leads to finding the rigid body transform as described above. In some embodiments, the process may optimize y-z translation and rotation around the x-axis in one step. This can be done by rotating the implant silhouette curve by several half degree increments and then, for each increment, performing the steps described in this Detailed Description. Translation in the y-z axis only occurs during the analysis utilizing the inverse of the rigid body transform.

vii. Additional Verification and Confirmation of Femur Cut Plane

By using the above outlined procedure, an appropriate implant is found by choosing the implant and transform combination that provides an inflection angle that is greater than 7 degrees but closest to 7 degrees, as explained with reference to FIG. 70A.

In some embodiments, an additional verification step is performed by placing the implant 34' in the MRI with the transform $28''''$ that is found by the above described method. As can be understood from FIG. 71B, which illustrates the implant positioned on the femur transform wherein a femur cut plane is shown, during the verification step, a user may determine the amount of bone that is cut J1 on the medial and lateral condyles by looking at the distal cut plane $514z$ of the implant 34'. J1 is determined such that the thickness of the bone cut on both the medial and lateral sides is such that the bone is flat after the cut. Multiple slices in both the distal and medial areas of the bone can be viewed to verify J1 is of proper thickness.

Once an appropriate femur implant is chosen, the preoperative planning process turns to the selection of an appropriate tibia implant. The tibia planning process includes a determination of the tibia reference lines to help determine the proper placement of the tibia implant. The candidate tibia implant is placed relative to the tibia reference lines and placement is confirmed based on comparison with several 2D segmentation splines.

E. Tibia Planning Process

For a discussion of the tibia planning process, reference is now made to FIGS. 72-81D. FIGS. 72-75B illustrate a process in the POP wherein the system 10 utilizes 2D imaging slices (e.g., MRI slices, CT slices, etc.) to determine tibia reference data, such as reference points and reference lines, relative to the undamaged side of the tibia plateau. The resulting tibia reference data $900z$ is then mapped or projected to an x-y plane (axial plane). A candidate tibia implant is chosen, which selection will be discussed with reference to FIGS. 76A-76C. The tibia implant placement is adjusted and confirmed relative to the tibia, as discussed in more detail below with reference to FIGS. 77-81D.

1. Determining Tibia Reference Data

For a discussion of a process used to determine the tibia reference data $900z$, reference is now made to FIGS. 72-76B. As can be understood from FIG. 72, which is a top view of the tibia plateaus $404z$, $406z$ of a tibia bone image or model 28'', the tibia reference data $900z$ may include reference points (e.g. Q1, Q1'), reference lines (e.g. T1T2, V1) and a reference plane (e.g. S') (see FIGS. 75A-75B). In some embodiments, the tibia reference data $900z$ may also include the anterior-posterior extant (tAP) and the medial-lateral extant (tML) of the tibia 28'' (see FIGS. 76A-76B). As shown in FIG. 72, each tibia plateau $404z$, $406z$ includes a curved recessed condyle contacting surface $421z$, $422z$ that is generally concave extending anterior/posterior and medial/lateral. Each curved recessed surface $421z$, $422z$ is generally oval in shape and includes an anterior curved edge $423z$, $424z$ and a posterior curved edge $425z$, $426z$ that respectively generally define the anterior and posterior boundaries of the condyle contacting surfaces $421z$, $422z$ of the tibia plateaus $404z$, $406z$. Depending on the patient, the medial tibia plateau $406z$ may have curved edges $424z$, $426z$ that are slightly more defined than the curved edges $423z$, $425z$ of the lateral tibia plateau $404z$.

a. Identify Points Q1, Q2 and Q1', Q2'

2D slices in the sagittal view are analyzed to determine the tibia flexion/extension adjustment. Anterior tangent lines TQ1, TQ2 can be extended tangentially to the most anterior location on each anterior curved edge 423z, 424z to identify the most anterior points Q1, Q2 of the anterior curved edges 423z, 424z. Posterior tangent lines TQ1', TQ2' can be extended tangentially to the most posterior location on each posterior curved edge 425z, 426z to identify the most posterior points Q1', Q2' of the posterior curved edges 425z, 426z. Thus, in one embodiment, the lateral side tibia plateau 404z can be analyzed via tangent lines to identify the highest points Q1, Q1'. For example, tangent line TQ1 can be used to identify the anterior highest point Q1, and tangent line TQ1' can be used to identify the posterior highest point Q1'. In some embodiments, a vector V1 extending between the highest points Q1, Q1' may be generally perpendicular to the tangent lines TQ1, TQ1'. Similarly, the medial side tibia plateau 406z can be analyzed via tangent lines to identify the highest points Q2, Q2'. For example, tangent line TQ2 can be used to identify the anterior highest point Q2, and tangent line TQ2' can be used to identify the posterior highest point Q2'. In some embodiments, a vector V2 extending between the highest points Q2, Q2' may be generally perpendicular to the tangent lines TQ2, TQ2'.

i. Confirm points Q1, Q2 and Q1', Q2'

As can be understood from FIGS. 73A-73D, the location of Q1, Q1', Q2 and Q2' may also be confirmed by an analysis of the appropriate sagittal slice. As shown in FIG. 73A, which is a sagittal cross section through a lateral tibia plateau 404z of the tibia model or image 28', points Q1 and Q1' can be identified as the most anterior and posterior points, respectively, of the curved recessed condyle contacting surface 421z of the lateral tibia plateau 404z. As shown in FIG. 73B, which is a sagittal cross section through a medial tibia plateau 406z of the tibia model 28", points Q2 and Q2' can be identified as the most anterior and posterior points, respectively, of the curved recessed condyle contacting surface 422z of the medial tibia plateau 406z. Such anterior and posterior points may correspond to the highest points of the anterior and posterior portions of the respective tibia plateaus.

b. Determine lines V1 and V2

As can be understood from FIGS. 72-73B, line V1 extends through anterior and posterior points Q1, Q1', and line V2 extends through anterior and posterior points Q2, Q2'. Line V1 is a lateral anterior-posterior reference line. Line V2 is a medial posterior-anterior reference line. Each line V1, V2 may align with the lowest point of the anterior-posterior extending groove/valley that is the elliptical recessed tibia plateau surface 421z, 422z. The lowest point of the anterior-posterior extending groove/valley of the elliptical recessed tibia plateau surface 421z, 422z may be determined via ellipsoid calculus. Each line V1, V2 will be generally parallel to the anterior-posterior extending valleys of its respective elliptical recessed tibia plateau surface 421z, 422z and will be generally perpendicular to its respective tangent lines TQ1, TQ1', TQ2, TQ2'. The anterior-posterior extending valleys of the elliptical recessed tibia plateau surfaces 421z, 422z and the lines V1, V2 aligned therewith may be generally parallel. The planes associated with lines V1 and V2 are generally parallel or nearly parallel to the joint line of the knee joint, as determined above.

Depending on the patient, the medial tibia plateau 406z may be undamaged or less damaged than the lateral tibia plateau 404z. In such a case, the reference points Q2, Q2' and reference line V2 of the medial plateau 406z may be used to establish one or more reference points and the reference line of the damaged lateral tibia plateau. FIG. 73C depicts a sagittal cross section through an undamaged or little damaged medial tibia plateau 406z of the tibia model 28", wherein osteophytes 432z are also shown. As indicated in FIG. 73C, the points Q2, Q2' can be located on the undamaged medial plateau and set as reference points. The anterior-posterior reference line, line V2, can be constructed by connecting the anterior and posterior reference points Q2, Q2'. The reference line V2 from the undamaged or little damaged medial side is saved for use in determining the reference line of the lateral tibia plateau in the case where the lateral tibia plateau is damaged. For example, as shown in FIG. 73D, which is a sagittal cross section through a damaged lateral tibia plateau 404z of the tibia model 28", the anterior point Q1 is found to be undamaged. In this case, the established reference line V2 from the medial plateau can be applied to the damaged lateral plateau by aligning the reference line V2 with point Q1. By doing so, the reference line V1 of the lateral plateau can be established such that line V1 touches the reference point Q1 and extends through the damaged area 403z. Thus, the reference line V1 in the lateral plateau is aligned to be parallel or nearly parallel to the reference line V2 in the medial plateau. While the above described process is described in terms of extrapolating one or more reference lines of a damaged lateral plateau from an analysis of the undamaged medial tibia plateau, it is understood that the same process can be undertaken where the lateral tibia plateau is undamaged and one or more reference lines of a damaged medial plateau can be extrapolated from the lateral tibia plateau.

In other embodiments, as can be understood from FIG. 73D and assuming the damage to the lateral tibia plateau 404z is not so extensive that at least one of the highest anterior or posterior points Q1, Q1' still exists, the damaged tibia plateau 404z can be analyzed via tangent lines to identify the surviving high point Q1, Q1'. For example, if the damage to the lateral tibia plateau 404z was concentrated in the posterior region such that the posterior highest point Q1' no longer existed, the tangent line TQ1 could be used to identify the anterior highest point Q1. Similarly, if the damage to the medial tibia plateau 406z was concentrated in the anterior region such that the anterior highest point Q1' no longer existed, the tangent line TQ1' could be used to identify the posterior highest point Q1'. In some embodiments, a vector extending between the highest points Q1, Q1' may be generally perpendicular to the tangent lines TQ1, TQ1'.

c. Determine Reference Points T1 and T2 and Reference Line T1T2

2D slices in both the axial and coronal views are analyzed to determine the varus/valgus adjustment by finding the reference points T1 and T2. As shown in FIGS. 74A-74B, which are coronal and axial 2D slices of the tibia, reference points T1 and T2 are determined by an analysis of the most proximal coronal slice (FIG. 74A) and the most proximal axial slice (FIG. 74B). As indicated in FIG. 74A, in which the tibia is shown in a 0° knee extension, reference points T1 and T2 are determined. The points T1 and T2 represent the lowest extremity of tangent contact points on each of the lateral and medial tibia plateaus, respectively. In one embodiment, tangent points T1 and T2 are located within the region between the tibia spine and the medial and lateral epicondyle edges of the tibia plateau, where the slopes of tangent lines in this region are steady and constant. For example, and as shown in FIG. 74A, the tangent point T1 is in the lateral plateau in Area I between the lateral side of the lateral intercondylar tubercle to the attachment of the lateral collateral ligament. For the medial portion, the tangent point T2 is in Area II between the medial side of the medial intercondylar tubercle to the medial condyle of the tibia.

As shown in FIG. 74B, the most proximal slice of the tibia in the axial view is analyzed to find reference points T1 and T2. As above, reference points T1 and T2 represent the lowest extremity of tangent contact points on each of the lateral and medial tibia plateaus. Once the reference points T1 and T2 are found in both the coronal and axial views, a line T1T2 is found.

A line T1T2 is created by extending a line between reference points T1 and T2. In some embodiments, the coronal and axial slices are viewed simultaneously in order to align the lateral and medial anterior-posterior reference lines V1 and V2. As shown in FIG. 72, the lateral and medial anterior-posterior reference lines V1 and V2 are generally perpendicular or nearly perpendicular to line T1T2.

d. Determine the Approximate ACL Attachment Point (AE) and the Approximate PCL Attachment Point (PE) of the Tibia and Reference Line AEPE As can be understood from FIGS. 72 and 74B, the reference points representing the approximate anterior cruciate ligament (ACL) attachment point of the tibia AE and the approximate posterior cruciate ligament (PCL) attachment point of the tibia PE are determined. The reference point AE can be determined by finding the approximate tibia attachment point for the ACL. The reference point PE can be determined by finding the approximate tibia attachment point for the PCL. The line AEPE connects through reference points AE and PE and may also be referred to as an ACL/PCL bisector line.

e. Confirm Location of Tibia Reference Data

As can be understood from FIG. 72, the tibia reference data $900z$ includes reference points and reference lines that help to define flexion/extension adjustment, varus/valgus adjustment and internal/external rotation. For example, the tibia flexion/extension adjustment is determined by an analysis of the sagittal images as shown in FIGS. 73A-D, which determine reference points Q1, Q1', Q2, Q2'. The tibia varus/valgus adjustment may be found by an analysis of FIG. 74A and finding reference points T1, T2 and reference line T1T2. As can be understood from FIG. 72, the proximal reference line, line T1T2, defines the internal/external rotation as shown in an axial view (line T1T2 in FIG. 74B) and the varus/valgus angle as shown in a coronal view (line T1T2 in FIG. 74A).

The location of the reference points and reference lines may also be confirmed based on their spatial relationship to each other. For example, as shown in FIGS. 72-73B, the anterior-posterior reference lines V1, V2 of the tibia plateau are generally parallel to the ACL/PCL bisector reference line, line AEPE. As indicated in FIGS. 72 and 74B, the axial-proximal reference line, line T1T2 is perpendicular or nearly perpendicular to anterior-posterior reference lines V1, V2. As shown in FIG. 72, the tangent lines TQ1, TQ2, TQ1', TQ2' are perpendicular or nearly perpendicular to the ACL/PCL bisector reference line, line AEPE.

f. Mapping the Tibia Reference Data to an x-y Plane

As can be understood from FIGS. 75A-75B, which depict the tibia reference data $900z$ on a coordinate system (FIG. 75A) and on a proximal end of the tibia (FIG. 75B), the tibia reference data $900z$ is mapped to an x-y coordinate system to aid in the selection of an appropriate tibia implant. As shown in FIG. 75A, the endpoints Q1, Q1', Q2, Q2' and their respective anterior posterior reference lines V1 and V2 and the endpoints T1, T2 and the proximal reference line T1T2 are each mapped to the reference plane. In addition, and as shown in FIG. 75B, the reference data $900z$ may be imported onto a 3D model of the tibia 28" for verification purposes. The tibia reference data $900z$ is stored for later analysis.

2. Selecting Tibia Implant Candidate

There are six degrees of freedom for placing the tibial implant onto the tibia. The reference points and reference lines determined above will constrain all but 2 degrees of freedom which are translated in the x-y plane. The sizing and positioning of the tibia implant (and the femoral component) will be verified with a 2D view of the knee and components.

As briefly discussed above with reference to FIGS. 1A and 50B-50C, when selecting the tibia implant model 34" corresponding to the appropriate tibia implant size to be used in the actual arthroplasty procedure, the system 4 may use one of at least two approaches to select the appropriate size for a tibia implant [block 115]. In one embodiment, the tibia implant is chosen based on the size of the femoral implant that was determined above. In some embodiments, as discussed with reference to FIGS. 76A-76C, the system 4 determines the tibial anterior-posterior length tAP and the tibial medial-lateral length tML and the tibia implant 34" can be selected based on the anterior-posterior extent tAP of the proximal tibia. In some embodiments, the tibia implant may be selected based on both the tibial anterior-posterior length tAP and the tibial medial-lateral length tML.

In one embodiment, there is a limited number of sizes of a candidate tibia implant. For example, one manufacturer may supply six sizes of tibia implants and another manufacturer may supply eight or another number of tibia implants. The anterior-posterior length jAP and medial-lateral length jML dimensions of these candidate implants may be stored in a database. The tAP and tML are compared to the jAP and jML of candidate tibia implants stored in the database.

FIG. 76A is a 2D sagittal image slice of the tibia wherein a segmentation spline with an AP extant is shown. FIG. 76B is an axial end view of the tibia upper end of the tibia bone image or model 28" depicted in FIG. 52A. FIG. 76C is a plan view of the joint side $255z$ of the tibia implant model 34" depicted in FIG. 52B. The views depicted in FIGS. 76A-76C are used to select the proper size for the tibial implant model 34". The tibia implant may be chosen based on the maximum tAP extent as measured in an analysis of the segmentation spine as shown in FIG. 76A.

Each patient has tibias that are unique in size and configuration from the tibias of other patients. Accordingly, each tibia bone model 28" will be unique in size and configuration to match the size and configuration of the tibia medically imaged. As can be understood from FIG. 76B, the tibial anterior-posterior length tAP is measured from the anterior edge $335z$ of the tibial bone model 28" to the posterior edge $330z$ of the tibial bone model 28", and the tibial medial-lateral length tML is measured from the medial edge $340z$ of the medial plateau of the tibia bone model 28" to the lateral edge $345z$ of the lateral plateau of the tibia bone model 28".

As can be understood from FIG. 76C, each tibial implant available via the various implant manufacturers may be represented by a specific tibia implant 3D computer model 34" having a size and dimensions specific to the actual tibia implant. Thus, the representative implant model 34" of FIG. 3D may have an associated size and associated dimensions in the form of, for example, anterior-proximal extent tAP and the medial-lateral extent tML of the tibia model 34", as shown in FIG. 76B. In FIG. 76C, the anterior-posterior extent jAP of the tibia implant model 34" is measured from the anterior edge $315z$ to the posterior edge $310z$ of the tibial implant model 34", and the medial-lateral extent jML is measured from the medial edge 320z to the lateral edge 325z of the tibial implant model 34". Once the tibia implant candidate 34" is chosen, the reference lines jML, jAP of the implant candidate 34" are stored by the system 4 for later analysis.

3. Determine Tibia Implant Reference Data

As can be understood from FIG. 77, which is a top view of the tibia plateaus 404z', 406z' of a tibia implant model 34", wherein the tibia implant reference data 900z' is shown, the tibia reference data 900z' may include tangent points q1, q1', q2, q2' and corresponding anterior-posterior reference lines V3, V4 and intersection points t1, t2 and its corresponding proximal reference line t1t2.

In order to define the implant reference data 900z' relative to the tibia model 28", the implant reference lines jML, jAP are imported into the same x-y plane with the tibia reference data 900z that was previously mapped to the x-y plane. For gross alignment purposes, the medial-lateral extent jML of the tibia implant 34" is aligned with the proximal reference line T1T2 of the tibia model 28". Then, the tibia reference data 900z' is determined. The implant 34" and the bone model 28" may then undergo additional alignment processes.

a. Determine Tangent Points q1, q1', q2, q2'

As shown in FIG. 77, each tibia plateau 404z', 406z' includes a curved recessed condyle contacting surface 421z', 422z' that is generally concave extending anterior/posterior and medial/lateral. Each curved recessed surface 421z', 422z' is generally oval in shape and includes an anterior curved edge 423z', 424z' and a posterior curved edge 425z', 426z' that respectively generally define the anterior and posterior boundaries of the condyle contacting surfaces 421z', 422z' of the tibia plateaus 404z', 406z'. Thus, the lateral tangent points q1, q1' can be identified as the most anterior and posterior points, respectively, of the curved recessed condyle contacting surface 421z' of the lateral tibia plateau 404z'. The medial tangent points q2, q2' can be identified as the most anterior and posterior points, respectively, of the curved recessed condyle contacting surface 422z' of the medial tibia plateau 406z'.

b. Determine Reference Lines V3 and V4

As can be understood from FIG. 77, line V3 extends through anterior and posterior points q1, q1', and line V4 extends through anterior and posterior points q2, q2'. Line V3 is a lateral anterior-posterior reference line. Line V4 is a medial posterior-anterior reference line. Each line V3, V4 may align with the lowest point of the anterior-posterior extending groove/valley that is the elliptical recessed tibia plateau surface 421z', 422z'. The lowest point of the anterior-posterior extending groove/valley of the elliptical recessed tibia plateau surface 421z', 422z' may be determined via ellipsoid calculus. Each line V3, V4 will be generally parallel to the anterior-posterior extending valleys of its respective elliptical recessed tibia plateau surface 421z', 422z'. The length of the reference lines V3, V4 can be determined and stored for later analysis.

c. Determine Intersection Points t1, t2 and Implant Proximal Reference Line t1t2

As shown in FIG. 77, the intersection or reference points t1, t2 represent the midpoints of the respective surfaces of the lateral tibia plateau 404z' and the medial tibia plateau 406z'. Also, each intersection point t1, t2 may represent the most distally recessed point in the respective tibia plateau 404z', 406z'. An implant proximal reference line t1t2 is created by extending a line between the lateral and medial lowest reference points t1, t2. The length of the reference line t1t2 can be determined and stored for later analysis. This line t1t2 is parallel or generally parallel to the joint line of the knee. Also, as indicated in FIG. 77, the tibia implant 34" includes a base member 780z for being secured to the proximal tibia 28".

d. Align Implant Reference Data 900z' with Tibia Reference Data 900z

As can be understood from FIGS. 77 and 75A, the implant reference data 900z' specifies the position and orientation of the tibia implant 34" and generally aligns with similar data 900z from the tibia bone model 28". Thus, the lateral tangent points q1, q1' and medial tangent points q2, q2' of the implant 34" generally align with the lateral tangent points Q1, Q1' and medial tangent points Q2, Q2' of the tibia 28". The anterior posterior reference lines V3, V4 of the implant 34" generally align with the anterior posterior reference lines V1, V2 of the tibia model 28". The intersection points t1, t2 of the implant 34" generally align with the reference points T1, T2 of the tibia 28". The proximal reference line t1t2 of the implant 34" generally aligns with the proximal reference line T1T2 of the tibia 28". Reference line t1t2 is approximately perpendicular to the anterior-posterior reference lines V3, V4.

The implant reference data 900z' lies on a coordinate frame, plane r'. The tibia reference data 900z lies on a coordinate frame, plane s'. Thus, the alignment of the implant 34" with the tibia 28" is the transformation between the two coordinate frames plane r', plane s'. Thus, the gross alignment includes aligning the proximal line t1t2 of the implant 34" to the proximal line T1T2 of the tibia 28". Then, in a further alignment process, the reference points t1, t2 of the implant and the reference points T1, T2 of the tibia 28" are aligned. The implant 34" is rotated such that the sagittal lines of the implant 34" (e.g. V3, V4) are parallel or generally parallel to the sagittal lines of the tibia 28" (e.g. V1, V2). Once the tibia 28" and the implant 34" are in alignment (via the reference data 900z, 900z'), the tibial cut plane can be determined.

4. Determine Surgical Cut Plane for Tibia a. Determine Cut Plane of the Tibia Implant The cut plane of the tibia implant is determined. The user may determine this cut plane by a method such as one described with respect to FIGS. 78A-78C. FIG. 78A is an isometric view of the 3D tibia bone model 1002z showing the surgical cut plane SCP design. FIGS. 78B and 78C are sagittal MRI views of the surgical tibia cut plane SCP design with the posterior cruciate ligament PCL.

During the TKA surgery, the damaged bone surface portions of the proximal tibia will be resected from the cut plane level 850z and be removed by the surgeon. As shown in FIGS. 78B and 78C, the surgical tibial cut plane 850z may be positioned above the surface where the PCL is attached, thereby providing for the maintenance of the PCL during TKA surgery.

FIG. 79A is an isometric view of the tibia implant 34" wherein a cut plane r1 is shown. As can be understood from FIG. 79A, the cut plane r1 of the implant 34" is the surgical tibial cut plane 850z and is a data point or set of data points that may be stored in the implant database. In order to determine whether an adjustment to the cut plane r1 must be made, the cut plane r1 of the tibia implant 34" is aligned with the tibia 28".

b. Determine Initial Cut Plane of the Tibia

As shown in FIG. 79B, which is a top axial view of the implant 34" superimposed on the tibia reference data 900z, the implant 34" is opened with the tibia reference data 900z and is generally aligned with the tibia reference data 900z at the level of the cut plane r1 by the system 4. However, the implant 34" is not centered relative to the tibia reference data 900z. The anterior/posterior extent tAP" and medial/lateral extent tML" of the tibia 28" at the cut level are found.

The implant 34" may be centered by the system (or manually by a user of the system). As indicated in FIG. 79C, which is an axial view of the tibial implant aligned with the tibia reference data 900z, the tibia implant 34" is then centered relative to the anterior posterior extent tAP" and the medial lateral extents tML" of the tibia 28".

c. Determine Joint Line and Adjustment

In order to allow an actual physical arthroplasty implant to restore the patient's knee to the knee's pre-degenerated or natural configuration with the its natural alignment and natural tensioning in the ligaments, the condylar surfaces of the actual physical implant generally replicate the condylar surfaces of the pre-degenerated joint bone. In one embodiment of the systems and methods disclosed herein, condylar surfaces of the bone model 28" are surface matched to the condylar surfaces of the implant model 34". However, because the bone model 28" may be bone only and not reflect the presence of the cartilage that actually extends over the pre-degenerated condylar surfaces, the surface matching of the modeled condylar surfaces may be adjusted to account for cartilage or proper spacing between the condylar surfaces of the cooperating actual physical implants (e.g., an actual physical femoral implant and an actual physical tibia implant) used to restore the joint such that the actual physical condylar surfaces of the actual physical cooperating implants will generally contact and interact in a manner substantially similar to the way the cartilage covered condylar surfaces of the pre-degenerated femur and tibia contacted and interacted.

i. Determine Adjustment Value tr

Thus, in one embodiment, the implant model is modified or positionally adjusted (via e.g. the tibia cut plane) to achieve the proper spacing between the femur and tibia implants. To achieve the correct adjustment or joint spacing compensation, an adjustment value tr may be determined. In one embodiment, the adjustment value tr that is used to adjust the implant location may be based off of an analysis associated with cartilage thickness. In another embodiment, the adjustment value used to adjust the implant location may be based off of an analysis of proper joint gap spacing, as described above with respect to FIGS. 63G and 63H. Both of the methods are discussed below in turn.

1. Determining Cartilage Thickness

FIG. 79D is a MRI image slice of the medial portion of the proximal tibia and indicates the establishment of landmarks for the tibia POP design. FIG. 79E is a MRI image slice of the lateral portion of the proximal tibia. The wm in FIG. 79D represents the cartilage thickness of the medial tibia meniscus, and the wl in FIG. 79E represents the cartilage thickness of the lateral tibia meniscus. In one embodiment, the cartilage thicknesses wl and wm are measured for the tibia meniscus for both the lateral and medial plateaus 760z, 765z via the MRI slices depicted in FIGS. 79D and 79E. The measured thicknesses may be compared. If the cartilage loss is observed for the medial plateau 765z, then the wlmin of lateral plateau 760z is selected as the minimum cartilage thickness. Similarly, if the lateral plateau 760z is damaged due to cartilage loss, then the wmmin of medial plateau 765z is selected as the minimum cartilage thickness. The minimum cartilage wr may be illustrated in the formula, wr=min (wm, wl). In one embodiment, for purposes of the adjustment to the tibia, the adjustment value tr may be may be equal to the minimum cartilage value wr.

2. Determining Joint Gap

In one embodiment, the joint gap is analyzed as discussed above with respect to FIGS. 63G and 63H to determine the restored joint line gap Gp3. In one embodiment, for purposes of the adjustment to the tibia shape matching, the adjustment value tr may be calculated as being half of the value for Gp3, or in other words, tr=Gp3/2.

d. Determine Compensation for Joint Spacing

After centering the implant 34" within the cut plane, joint spacing compensation is taken into account. As shown in FIG. 79F, which is an isometric view of the tibia implant and the cut plane, the implant 34" and cut plane-r1 are moved in a direction that is generally perpendicular to both the proximal and sagittal reference lines by an amount equal to adjustment value tr, thereby creating an adjusted cut plane r1'. In one embodiment, the adjustment value tr is equal to approximately one-half of the joint spacing. In other embodiments, the adjustment value tr is equal to the cartilage thickness.

Thus, the implant candidate may be selected relative to the joint spacing compensation that was determined previously with reference to FIGS. 63G, 63H, 79D and 79E. As discussed above, in one embodiment, once the joint spacing compensation is determined, one-half of the joint spacing compensation will be factored in to the femur planning process and one-half of the joint spacing compensation will be factored in to the tibia planning process. That is, the femur implant is adjusted by an amount equal to one-half of the joint spacing compensation. Thus, the candidate femur implant will be chosen such that when it is positioned on the femur relative to the joint spacing compensation, the candidate implant will approximate the pre-degenerated joint line. Similarly, the tibia implant is adjusted by an amount equal to one-half of the joint spacing compensation. Thus, the candidate tibia implant will be chosen such that when it is positioned on the tibia relative to the joint spacing compensation, the candidate implant will approximate the pre-degenerated joint line. Also, the tibia implant mounting post 780z (see FIG. 80B) and the femur implant mounting post 781z (see FIG. 31A) will be oriented at approximately the center of the tibia and femur.

F. Verification of Implant Planning Models and Generation of Surgical Jigs Based on Planning Model Information FIGS. 80A-81 illustrate one embodiment of a verification process that may be utilized for the preoperative planning process disclosed herein. FIGS. 80A-80C are sagittal views of a 2D image slice of the femur 28' (FIGS. 80A and 80B) and the tibia 28" (FIG. 80B) wherein the 2D computer generated implant models 34 are also shown. As can be understood from FIGS. 80A-80C, verification for both the distal femur and proximal tibia is performed by checking the reference lines/planes in 2D sagittal views. The reference lines/planes may also be checked in other views (e.g. coronal or axial). For example, and as can be understood from FIGS. 80A and 80B, for the femur planning model, the flexion-extension rotation is verified by checking whether the inflection point 506z of the anterior cortex of the femur 28' sufficiently contacts the interior surface 510z of the anterior flange 512z of implant 34'. That is, as can be understood from FIG. 80A2, when the implant 34' is properly aligned with the femur 28', the flange point 500z of the implant should touch the inflection point of the segmentation spline or femur 28'.

As can be understood with reference to FIG. 80B, the tibia planning may be verified by looking at a 2D sagittal slice. Depending on the initial planning choice made above, one of the following can be verified: 1) whether the size of the tibial implant 34" matches or corresponds with the size of the femoral implant 34', or 2) whether the tibial implant 34" is one size larger or one size smaller than the femoral implant 34' size (e.g., a size 2 femur, and a size 1 tibia; or a size 2 femur, and a size 2 tibia; or a size 2 femur, and a size 3 tibia). In other embodiments, the size of tibial implant may be chosen without taking into account the size of the femoral implant. One of skill in the art will recognize that different implant manufacturers may utilize a different naming convention to describe different sizes of implants. The examples provided herein are provided for illustrative purposes and are not intended to be limiting.

As indicated in FIG. 80B, the placement of the tibial implant can be verified by viewing the anterior and posterior positions of the implant 34" relative to the tibial bone 28". If the implant is properly positioned, the implant should not extend beyond the posterior or anterior edge of the tibia bone. The flexion-extension of the tibia 28" can be verified by checking that the tibial implant reference line 906z, which is a line segment approximating the normal direction of the implant's proximal surface, is at least parallel with the posterior surface 904z of the tibia 28" or converging with the posterior tibial surface 906z around the distal terminus of the tibial shaft.

In other embodiments, as shown in FIGS. 81A-81G and FIGS. 82A-82C, the planning can also be confirmed from generated 3D bone models 1000z, 1002z and 3D implant models 1004z, 1006z. If the planning is done incorrectly, the reference lines 100z, 100z', 900z, 900z' will be corrected in the 2D MRI views to amend the planning. FIGS. 81A-81C and FIGS. 81E-81G are various views of the implant 3D models 1004z, 1006z superimposed on the 3D bone models 1000z, 1002z. FIG. 81D is a coronal view of the bone models 1000z, 1002z.

FIGS. 81A-81G show an embodiment of the POP system disclosed herein. The alignment of the implant models 1004z, 1006z with the bone models 1000z, 1002z is checked in the anterior view (FIG. 81A), the posterior view (FIG. 81E), the lateral view (FIG. 81B), the medial view (FIG. 81C), the top view (FIG. 81F) and the bottom view (FIG. 81G).

The flexion/extension between the femur and tibia implant models 1004z, 1006z and the femur and tibia bone models 1000z, 1002z is examined in both the medial view and the lateral view. For example, FIG. 81B shows the lateral view wherein the knee is shown in full extension or 0 degree flexion and in its natural alignment similar to its pre-arthritis status (e.g., neutral, varus or valgus), and FIG. 81C shows the medial view of the knee in full extension or 0 degree flexion and in its natural alignment (e.g., neutral, varus or valgus).

FIG. 81D shows the varus/valgus alignment of the knee model 28 m', 28 m" with the absence of the implants 34 m', 34 m". The gaps Gp4, Gp5 between the lowermost portions of distal femoral condyles 302z, 303z and the lowermost portions of the tibia plateau 404z, 406z will be measured in the femoral and tibia bone models 28 m', 28 m". Gap Gp4 represents the distance between the distal lateral femoral condyle 302z and the lateral tibial plateau 404z. Gap Gp5 represents the distance between the distal medial femoral condyle 303z and the medial tibial plateau 406z. In the varus/valgus rotation and alignment, Gp4 is substantially equal to Gp5, or |Gp4-Gp5|<<1 mm. FIG. 81D shows the knee model 28 m', 28 m" that is intended to restore the patient's knee back to his pre-OA stage.

The IR/ER rotation between the femur and tibia implant models 1004z, 1006z and the femur and tibia bone models 1000z, 1002z is examined in both the top and bottom views. For example, FIG. 81F shows the top view of the tibia showing the IR/ER rotation between no flexion and high flexion, and FIG. 81G shows the bottom view of the femur showing the IR/ER rotation between no flexion and high flexion. The stem of the tibia implant model 1006z and the surgical cut plane of the tibia implant model 1006z provide the information for the IR/ER rotation.

FIGS. 82A-82C show another embodiment of the POP system disclosed herein. FIG. 82A is an medial view of the 3D bone models. FIG. 82B is an medial view of the 3D implant models. FIG. 82C is an medial view of the 3D implant models superimposed on the 3D bone models.

As shown in FIG. 82A, a 3D model of the femur bone 1000z and a 3D model of the tibia bone 1002z may be generated from the 2D segmentation splines of image slices and the reference data 100z, 900z determined above for verification of the POP. As shown in FIG. 82B, a 3D model of the femur implant 1004z and a 3D model of the tibia implant 1006z may be generated based on the reference lines 100z', 900z' determined above for verification of the POP. The implant models 1004z, 1006z and the bone models 1000z, 1002z are aligned based on the reference lines in a 3D computer modeling environment and the alignment is checked in the sagittal view as shown in FIG. 82C. If the alignment of the bone models 1000z, 1002z and the implant models 1004z, 1006z is not correct, the reference lines 100z, 100z', 900z, 900z' will be corrected in the 2D views to amend the planning.

The knee model 28', 28", 1000z, 1002z and associated implant models 34', 34", 1004z, 1006z developed through the above-discussed processes include dimensions, features and orientations that the system 10 depicted in FIG. 1A can be utilized to generate 3D models of femur and tibia cutting jigs 2. The 3D model information regarding the cutting jigs can then be provided to a CNC machine 10 to machine the jigs 2 from a polymer or other material.

G. Mechanical Axis Alignment

While much of the preceding disclosure is provided in the context of achieving natural alignment for the patient's knee post implantation of the actual physical femur and tibia implants, it should be noted that the systems and methods disclosed herein can be readily modified to produce an arthroplasty jig 2 that would achieve a zero degree mechanical axis alignment for the patient's knee post implantation.

For example, in one embodiment, the surgeon utilizes a natural alignment femoral arthroplasty jig 2A as depicted in FIGS. 51A and 51B to complete the first distal resection in the patient's femoral condylar region. Instead of utilizing a natural alignment tibia arthroplasty jig 2B as depicted in FIGS. 51C and 51D, the surgeon instead completes the first proximal resection in the patient's tibia plateau region via free hand or a mechanical axis guide to cause the patient's tibia implant to result in a mechanical axis alignment or an alignment based off of the mechanical axis (e.g., an alignment that is approximately one to approximately three degrees varus or valgus relative to zero degree mechanical axis).

In one embodiment of the POP systems and methods disclosed herein, instead of superposing the 3D bone models 1000z, 1002z to the 3D implant models 1004z, 1006z in a manner that results in the saw cut and drill hole data 44 that leads to the production of natural alignment arthroplasty jigs 2A, 2B, the superposing of the bone and implant models 1000z, 1002z, 1004z, 1006z may be conducted such that the resulting saw cut and drill hole data 44 leads to the production of zero degree mechanical axis alignment arthroplasty jigs or some other type of arthroplasty jig deviating in a desired manner from zero degree mechanical axis.

Thus, depending on the type of arthroplasty jig desired, the systems and methods disclosed herein may be applied to both the production of natural alignment arthroplasty jigs, zero degree mechanical axis alignment jigs, or arthroplasty jigs configured to provide a result that is somewhere between natural alignment and zero degree mechanical axis alignment.

Although the present invention has been described with respect to particular embodiments, it should be understood that changes to the described embodiments and/or methods may be made yet still embraced by alternative embodiments of the invention. For example, certain embodiments may operate in conjunction with a MRI or a CT medical imaging system. Yet other embodiments may omit or add operations to the methods and processes disclosed herein. Accordingly, the proper scope of the present invention is defined by the claims herein.

What is claimed is:

1. A method of performing an arthroplasty procedure, the method comprising:
   identify landmarks on first and second bone models, each bone model being a computer model representative of a patient bone in a pre-diseased or pre-injured state;
   utilize the landmarks to predict a position of a first healthy articular cartilage surface for the first bone model and a second healthy articular cartilage surface for the second bone model;
   position a computer model of a first implant relative to the first bone model such that an articular surface of the computer model of the first implant is located at a predicted position of the first healthy articular cartilage surface; and
   position a computer model of a second implant relative to the second bone model such that an articular surface of the computer model of the second implant is located at a predicted position of the second healthy articular cartilage surface.

2. The method of claim 1, wherein the first and second bone models are generated using medical imaging data of the patient bone.

3. The method of claim 2, wherein the medical imaging data includes data from at least one of MRI or CT.

4. The method of claim 1, wherein the position of the computer model of the first implant relative to the first bone model and the position of the computer model of the second implant relative to the second bone model are registered with corresponding bones of a patient.

5. The method of claim 4, wherein the position of the computer model of the first implant relative to the first bone model and the position of the computer model of the second implant relative to the second bone model are used to guide preparation of the corresponding bones of the patient to receive the first and second implants as part of the arthroplasty procedure.

6. The method of claim 1, wherein, when the landmarks are used to predict the positions of the first and second healthy articular cartilage surfaces, the landmarks are first used to predict a joint gap between the first and second bone models, and the predicted positions of the first and second healthy articular cartilage surfaces are determined from the predicted joint gap.

7. The method of claim 6, wherein the landmarks include a most distal point on a femoral condylar surface of the first bone model, and the landmarks include a most distal point on a tibial condylar surface of the second bone model.

8. The method of claim 7, wherein the most distal point on the femoral condylar surface of the first bone model and the most distal point on the tibial condylar surface of the second bone model are associated with a healthy side of a joint of a patient, and a distal-proximal distance between these two points is substantially mimicked between a same set of points on a diseased or injured side of the joint, thereby predicting the joint gap.

9. The method of claim 7, wherein the joint gap is a distal-proximal distance between the most distal point on the femoral condylar surface of the first bone model and the most distal point on the tibial condylar surface of the second bone model.

10. The method of claim 9, wherein a cartilage thickness of the femoral condylar surface or the tibial condylar surface is one half of the joint gap.

11. The method of claim 6, wherein the landmarks include a most posterior point on a femoral condylar surface of the first bone model, and the landmarks include a most distal point on a tibial condylar surface of the second bone model.

12. The method of claim 11, wherein, when the first and second bone models are oriented in approximately 90 degree flexion, the joint gap is a distal-proximal distance between the most posterior point on the femoral condylar surface of the first bone model and the most distal point on the tibial condylar surface of the second bone model.

13. The method of claim 6, wherein the landmarks include a most distal point on a medial femoral condylar surface of the first bone model and a most distal point on a lateral femoral condylar surface of the first bone model, and a first tangent line runs through the most distal point on the medial femoral condylar surface and the most distal point on the lateral femoral condylar surface.

14. The method of claim 13, wherein the first tangent line is at least substantially parallel to a joint line between the first and second bone models.

15. The method of claim 13, wherein the landmarks include a most distal point on a medial tibial condylar surface of the second bone model and a most distal point on a lateral tibial condylar surface of the second bone model, and a second tangent line runs through the most distal point on the medial tibial condylar surface and the most distal point on the lateral tibial condylar surface.

16. The method of claim 15, wherein the second tangent line is at least substantially parallel to the first tangent line and the joint gap is a distal-proximal distance between the first and second tangent lines.

17. The method of claim 16, wherein a cartilage thickness of the femoral condylar surface or the tibial condylar surface is one half of the joint gap.

18. The method of claim 6, wherein the landmarks include a most posterior point on a medial femoral condylar surface of the first bone model and a most posterior point on a lateral femoral condylar surface of the first bone model, and a first tangent line runs through the most posterior point on the medial femoral condylar surface and the most posterior point on the lateral femoral condylar surface, and wherein the landmarks include a most distal point on a medial tibial condylar surface of the second bone model and a most distal point on a lateral tibial condylar surface of the second bone model, and a second tangent line runs through the most distal point on the medial tibial condylar surface and the most distal point on the lateral tibial condylar surface.

19. The method of claim 18, wherein the second tangent line is at least substantially parallel to the first tangent line and the joint gap is a distal-proximal distance between the first and second tangent lines.

20. A method of performing an arthroplasty procedure, the method comprising:
generate first and second bone models using data taken from a patient bone, the first and second bone models being computer models, each bone model being representative of the patient bone in a pre-diseased or pre-injured state;
computer modeling at least one of a joint gap or cartilage thickness based off of landmark data associated with the first and second bone models; and
utilize the computer model of the at least one of the joint gap or cartilage thickness to computer model a position of an implant on the patient bone.

21. The method of claim 20, wherein the position of the implant is registered with the patient bone.

22. The method of claim 21, wherein the position of the implant is used to guide preparation of the patient bone to receive the implant as part of the arthroplasty procedure.

23. The method of claim 20, wherein, when the computer model of the at least one of the joint gap or cartilage thickness is used to computer model the position of the implant on the patient bone, an articular surface of a computer model of the implant is located at a predicted position of a healthy articular cartilage surface.

24. The method of claim 20, wherein the landmark data is associated with a most distal point on a femoral condylar surface of the first bone model, and the landmark data is associated with a most distal point on a tibial condylar surface of the second bone model.

25. The method of claim 24, wherein the most distal point on the femoral condylar surface of the first bone model and the most distal point on the tibial condylar surface of the second bone model are associated with a healthy side of a joint of the patient, and a distal-proximal distance between these two points is substantially mimicked between a same set of points on a diseased or injured side of the joint, thereby predicting the joint gap.

26. The method of claim 24, wherein the joint gap or cartilage thickness is computer modeled off of a distal-proximal distance between the most distal point on the femoral condylar surface of the first bone model and the most distal point on the tibial condylar surface of the second bone model.

27. The method of claim 20, wherein the landmark data is associated with a most posterior point on a femoral condylar surface of the first bone model, and the landmark data is associated with a most distal point on a tibial condylar surface of the second bone model.

28. The method of claim 27, wherein, when the first and second bone models are oriented in approximately 90 degree flexion, the joint gap or cartilage thickness is computer modeled off of a distal-proximal distance between the most posterior point on the femoral condylar surface of the first bone model and the most distal point on the tibial condylar surface of the second bone model.

\* \* \* \* \*